(12) United States Patent
Zhong et al.

(10) Patent No.: US 9,085,587 B2
(45) Date of Patent: *Jul. 21, 2015

(54) INHIBITORS OF HEPATITIS C VIRUS

(75) Inventors: Min Zhong, Palo Alto, CA (US); Leping Li, Burlingame, CA (US)

(73) Assignee: Presidio Pharmaceuticals, Inc., San Francisco, CA (US)

(*) Notice: Subject to any disclaimer, the term of this patent is extended or adjusted under 35 U.S.C. 154(b) by 327 days.

This patent is subject to a terminal disclaimer.

(21) Appl. No.: 13/456,181

(22) Filed: Apr. 25, 2012

(65) Prior Publication Data

US 2012/0251497 A1     Oct. 4, 2012

Related U.S. Application Data

(63) Continuation-in-part of application No. PCT/US2011/057398, filed on Oct. 21, 2011.

(60) Provisional application No. 61/524,220, filed on Aug. 16, 2011, provisional application No. 61/438,429, filed on Feb. 1, 2011, provisional application No. 61/406,972, filed on Oct. 26, 2010.

(51) Int. Cl.

| | |
|---|---|
| A61K 31/553 | (2006.01) |
| C07D 498/04 | (2006.01) |
| C07D 491/048 | (2006.01) |
| A61K 31/7056 | (2006.01) |
| A61K 38/21 | (2006.01) |
| A61K 45/06 | (2006.01) |
| C07D 487/04 | (2006.01) |
| A61K 31/343 | (2006.01) |
| A61K 31/407 | (2006.01) |
| A61K 31/4355 | (2006.01) |
| A61K 31/437 | (2006.01) |
| A61K 31/55 | (2006.01) |
| A61K 31/5513 | (2006.01) |
| C07D 307/84 | (2006.01) |
| C07D 471/14 | (2006.01) |
| C07D 491/14 | (2006.01) |

(52) U.S. Cl.
CPC .......... *C07D 491/048* (2013.01); *A61K 31/343* (2013.01); *A61K 31/407* (2013.01); *A61K 31/437* (2013.01); *A61K 31/4355* (2013.01); *A61K 31/55* (2013.01); *A61K 31/553* (2013.01); *A61K 31/5513* (2013.01); *A61K 31/7056* (2013.01); *A61K 38/212* (2013.01); *A61K 45/06* (2013.01); *C07D 307/84* (2013.01); *C07D 471/14* (2013.01); *C07D 487/04* (2013.01); *C07D 491/14* (2013.01); *C07D 498/04* (2013.01)

(58) Field of Classification Search
CPC ........................... A61K 31/553; C07D 498/04
USPC ...................... 514/211.1; 540/548
See application file for complete search history.

(56) References Cited

U.S. PATENT DOCUMENTS

| | | | |
|---|---|---|---|
| 6,350,741 B1 | 2/2002 | Golec et al. | |
| 7,265,152 B2 | 9/2007 | Saha et al. | |
| 7,666,863 B2 | 2/2010 | Saha et al. | |
| 7,772,271 B2 | 8/2010 | Karp et al. | |
| 7,781,478 B2 | 8/2010 | Karp et al. | |
| 7,868,037 B2 | 1/2011 | Karp et al. | |
| 7,973,069 B2 | 7/2011 | Karp et al. | |
| 7,994,171 B2 | 8/2011 | Yeung et al. | |
| 8,013,006 B2 | 9/2011 | Karp et al. | |
| 8,048,887 B2 | 11/2011 | Yeung et al. | |
| 8,071,797 B2 | 12/2011 | Labadie et al. | |
| 8,614,207 B2* | 12/2013 | Zhong et al. ............. | 514/211.1 |
| 2008/0275032 A1 | 11/2008 | Zhou et al. | |
| 2009/0047246 A1 | 2/2009 | Beigelman et al. | |
| 2009/0176778 A1 | 7/2009 | Schmitz et al. | |
| 2009/0208449 A1 | 8/2009 | Labadie et al. | |
| 2010/0063068 A1 | 3/2010 | Pracitto et al. | |
| 2010/0093694 A1 | 4/2010 | Yeung et al. | |
| 2010/0184800 A1 | 7/2010 | Pracitto et al. | |
| 2010/0260711 A1 | 10/2010 | Chen et al. | |
| 2010/0297073 A1 | 11/2010 | Chin et al. | |
| 2011/0104110 A1 | 5/2011 | Anikumar et al. | |
| 2012/0015907 A1 | 1/2012 | Barnes et al. | |
| 2012/0022046 A1 | 1/2012 | Byrd et al. | |
| 2012/0059019 A1 | 3/2012 | Yeung et al. | |
| 2012/0251497 A1 | 10/2012 | Zhong et al. | |
| 2013/0302282 A1* | 11/2013 | Zhong et al. ............. | 424/85.7 |
| 2014/0286899 A1 | 9/2014 | Zhong et al. | |

FOREIGN PATENT DOCUMENTS

| | | |
|---|---|---|
| CN | 103025738 A | 4/2013 |
| WO | WO-2004/099241 A1 | 11/2004 |
| WO | WO-2005/112640 A2 | 12/2005 |
| WO | WO-2005/112640 A3 | 12/2005 |
| WO | WO-2007/019674 A1 | 2/2007 |

(Continued)

OTHER PUBLICATIONS

Adityachaudhury, N. et al. (Feb. 1973). "A New Pterocarpan and Coumestan in the Roots of *Flemingia chappar*," *Phytochmistry* 12(2):425-428.

Chinese Office Action mailed on May 30, 2014, for Chinese Patent Application No. 201180061899.2, filed on Oct. 21, 2011, 10 pages.

Ding, M. et al. (2011). "The Synthesis of Novel Heteroaryl-fused 7,8,9,10--Tetrahydro-6H-Azepino[1,2-a]Indoles, 4-Oxo-2,3-Dihydro-1H-[1,4]Diazepino[1,7-a]Indoles and 1,2,4,5-Tetrahydro-[1,4]Oxazepino[4,5-a]indoles. Effective Inhibitors of HCV NS5B Polymerase," *Organic & Biomolecular Chemistry* 9(19):6654-6662.

European Office Action mailed on Mar. 3, 2014, for European Patent Application No. 11 836 903.2, filed on Oct. 21, 2011, 4 pages.

Extended European Search Report mailed on Oct. 25, 2013, for European Patent Application No. 11 836 903.2, filed on Oct. 21, 2011, 7 pages.

Eurasian Office Action mailed on Jun. 10, 2014, for Eurasian Patent Application No. 201390433, filed on Oct. 21, 2011, 3 pages.

European Examination Report, European Application No. 11836903.2, Jul. 9, 2014, 3 pages.

(Continued)

*Primary Examiner* — Brenda Coleman
(74) *Attorney, Agent, or Firm* — Morrison & Foerster LLP

(57) ABSTRACT

A class of compounds that inhibit Hepatitis C Virus (HCV) is disclosed, along with compositions containing the compound, and methods of using the composition for treating individuals infected with HCV.

8 Claims, No Drawings

(56) References Cited

FOREIGN PATENT DOCUMENTS

| WO | WO 2008/125874 | A1 | 10/2008 |
|---|---|---|---|
| WO | WO-2009/137493 | A1 | 11/2009 |
| WO | WO-2009/137500 | A1 | 11/2009 |
| WO | WO-2010/099166 | A1 | 9/2010 |
| WO | WO-2011/103063 | A1 | 8/2011 |
| WO | WO-2011/106929 | A1 | 9/2011 |
| WO | WO-2011/106986 | A1 | 9/2011 |
| WO | WO-2011/106992 | A1 | 9/2011 |
| WO | WO-2011/112186 | A1 | 9/2011 |
| WO | WO-2011/112191 | A1 | 9/2011 |
| WO | WO-2011/112429 | A1 | 9/2011 |
| WO | WO-2011/131709 | A1 | 10/2011 |
| WO | WO-2012/058125 | A1 | 5/2012 |
| WO | WO-2013/163466 | A1 | 10/2013 |

OTHER PUBLICATIONS

Final Office Action mailed on Jun. 12, 2013, for U.S. Appl. No. 13/544,261, filed Jul. 9, 2012, 6 pages.

Guo, X. et al. (2009). "Iron-Catalyzed Tandem Oxidative Coupling and Annulation: An Efficient Approach to Construct Polysubstituted Benzofurans," *J. of the American Chem. Society* 131(47):17387-17393.

International Search Report mailed on Mar. 12, 2012, for PCT Patent Application No. PCT/US2011/057398, filed on Oct. 21, 2011, 3 pages.

International Search Report mailed on Sep. 9, 2013, for PCT Patent Application No. PCT/US2013/038275, filed on Apr. 25, 2013, 3 pages.

Japanese Office Action mailed on Nov. 25, 2014, for Japanese Patent Application No. 2013-536688, filed on Oct. 21, 2011, 6 pages.

Kagechika, H. et al. (1989). "Retinobenzoic Acids. 3. Structure-Activity Relationships of Retinoidal Azobenzene-4-Carboxylic Acids and Stilbene-4-Carboxylic Acids," *J. of Med. Chem.* 32(5):1098-1108.

New Zealand Office Action mailed on Feb. 20, 2014, for New Zealand Patent Application No. 609564, filed on Oct. 21, 2011, 2 pages.

Non-Final Office Action mailed on Dec. 6, 2012, for U.S. Appl. No. 13/544,261, filed Jul. 9, 2012, 10 pages.

Written Opinion of the International Searching Authority mailed on Mar. 12, 2012, for PCT Patent Application No. PCT/US2011/057398, filed on Oct. 21, 2011, 10 pages.

Written Opinion of the International Searching Authority mailed on Sep. 9, 2013, for PCT Patent Application No. PCT/US2013/038275, filed on Apr. 25, 2013, 3 pages.

Zheng, X. et al. (Aug. 22-26, 2010). "Synthesis and SAR Studies on Highly Potent, Novel, N, 1-C2-Phenyl-Bridged 2-Phenyl-Indole-6-Carboxamide Based Hepatitis C Virus NS5B Inhibitors", 240th ACS National Meeting, Boston, MA, United States, MEDI-126, *American Chemical Society*, Washington, D.C., 5 Total Pages (Abstract Only).

\* cited by examiner

INHIBITORS OF HEPATITIS C VIRUS

CROSS REFERENCE TO RELATED APPLICATIONS

This application is a continuation-in-part of International Patent Application No. PCT/US2011/057398, filed Oct. 21, 2011, which claims the benefit of priority to U.S. Application No. 61/524,220, filed Aug. 16, 2011; U.S. Application No. 61/438,429, filed Feb. 1, 2011; and U.S. Application No. 61/406,972, filed Oct. 26, 2010, the contents each of which is incorporated herein by reference in its entirety.

FIELD OF THE INVENTION

The invention relates to compounds useful for inhibiting hepatitis C virus ("HCV") replication, particularly functions of the non-structural 5B ("NS5B") protein of HCV.

BACKGROUND OF THE INVENTION

HCV is a single-stranded RNA virus that is a member of the Flaviviridae family. The virus shows extensive genetic heterogeneity as there are currently seven identified genotypes and more than 50 identified subtypes. In HCV infected cells, viral RNA is translated into a polyprotein that is cleaved into ten individual proteins. At the amino terminus are structural proteins: the core (C) protein and the envelope glycoproteins, E1 and E2. p7, an integral membrane protein, follows E1 and E2. Additionally, there are six non-structural proteins, NS2, NS3, NS4A, NS4B, NS5A and NS5B, which play a functional role in the HCV life cycle. (see, for example, B. D. Lindenbach and C. M. Rice, Nature. 436:933-938, 2005). NS5B is the RNA polymerase or replicase of the virus and is responsible for replication of both positive- and negative-strand genomic RNA during the viral replicative cycle. NS5B plays an essential and critical role in viral replication, and a functional NS5B replicase is required for HCV replication and infection. Thus, inhibition of NS5B RNA-dependent polymerase activity is believed to be an effective way of treating HCV infection.

Infection by HCV is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The current standard of care treatment regimen for HCV infection involves interferon-alpha, alone, or in combination with ribavirin and a protease inhibtor. The treatment is cumbersome and sometimes has debilitating and severe side effects and many patients do not durably respond to treatment. New and effective methods of treating HCV infection are urgently needed.

SUMMARY OF THE INVENTION

Essential functions of the NS5B protein in HCV replication make it an attractive intervention target for treating HCV infection. The present disclosure describes a class of compounds targeting the NS5B protein and methods of their use to treat HCV infection in humans.

More particularly, the present disclosure describes a class of heterocyclic compounds targeting HCV NS5B polymerase and methods of their use to treat HCV infection in humans.

In a first aspect of the invention, compounds of formula I are provided:

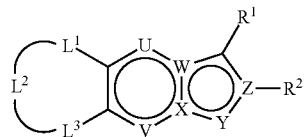

I wherein,
$L^1$, $L^2$ and $L^3$ together with the attached carbons of the aromatic ring form a 5-12 member ring containing 0-4 heteroatoms of N, O, S, P and/or Si;
$L^1$, $L^2$, or $L^3$ is independently selected from a group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;
n is 0, 1, or 2;
U or V is independently CH, N, CF, CCl, or CCN;
W, X, or Z is independently C or N;
Y is $NR^N$, N, O, S, Se, or —$CR^aR^b$;
$R^N$ is hydrogen, $C_{1-4}$ alkyl, $C_{3-6}$ cycloalkyl, $C_{4-5}$ heterocycle, aryl, heteroaryl, amide, sulfonamide, or carbamate;
$R^a$, $R^b$ is independently hydrogen, methyl, or together form a $C_{3-6}$ cycloalkyl bearing 0-1 heteroatom of O or $NR^3$;
$R^1$ is selected from hydrogen, halide, —$CF_3$, —CN, —C(O)H, —C(O)O$R^6$—, —C(O)NH$R^7$, —C(O)N(OH)$R^7$, —C(=N$R^7$)OMe, —C(=NOR')NH$R^7$, —CH(CF$_3$)NH$R^8$, —CH(CN)NH$R^9$, —S(O)$_2$NH$R^{10}$, —C(=NCN)NH$R^{11}$,

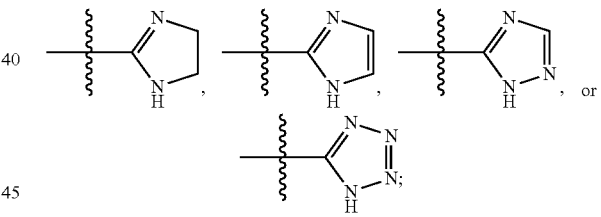

R' is selected from hydrogen, —(CH$_2$CH$_2$O)$_{0-8}$-Me, $C_{2-24}$ alkyl optionally containing 0-6 heteroatoms of O, $NR^N$ and/or S, and $C_{3-8}$ cycloalkyl optionally containing 0-2 heteroatoms of O, $NR^N$, and/or S;
$R^2$ is a substituted or unsubstituted aryl or heteroaryl;
$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;
$R^4$ and $R^5$ are independently methyl, ethyl, or cyclopropyl;
$R^6$ is hydrogen, allyl, $C_{1-4}$ alkyl, cyclopropyl, or benzyl;
$R^7$ is hydrogen, $C_{1-4}$ alkyl, cyclopropyl, $C_{1-4}$ alkoxy, cyclopropoxy, alkylsulfonyl, or cycloalkylsulfonyl;
$R^8$, $R^9$, $R^{10}$, or $R^{11}$ is independently hydrogen, $C_{1-4}$ alkyls, cyclopropyl, $C_{1-4}$ alkoxys, or cyclopropoxy; and
$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S.

The compounds may have an inhibitory activity with respect to HCV, as measured by the concentration of the compound effective to produce a half-maximal inhibition of HCV 1b replication ($EC_{50}$) in a 1b_Huh-Luc/Neo-ET cell line in culture, of 1 mM or less.

The compounds may have the structure wherein

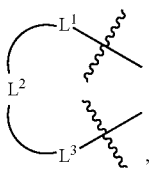

together with the attached carbons of the aromatic ring, is a seven- or eight-member ring.

The compounds may have the structure wherein

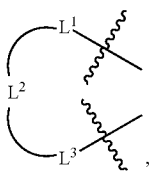

together with the attached carbons of the aromatic ring, form a 5-9 member ring, $L^1$ is —C($R^{15}R^{16}$)—, and $L^3$ is —N($SO_2$Me)— or —O—, where each of $R^{15}$ and $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S.

In a first embodiment of the first aspect,

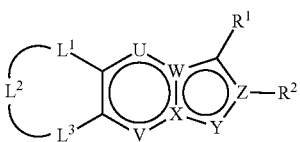

is selected from the group consisting of

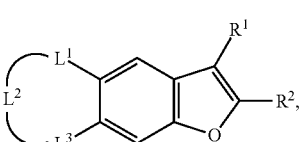

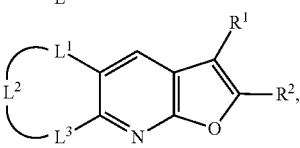

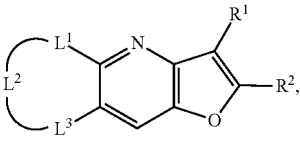

-continued

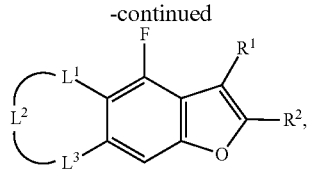

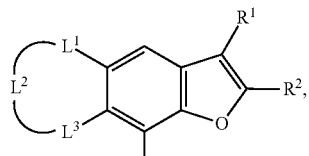

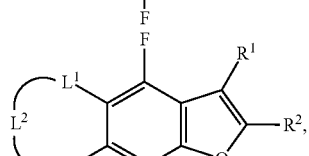

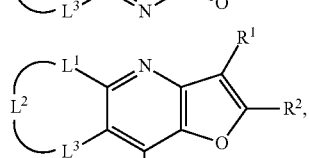

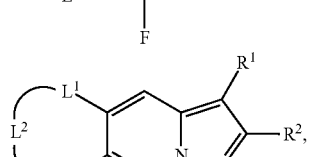

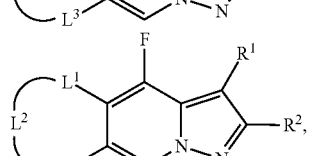

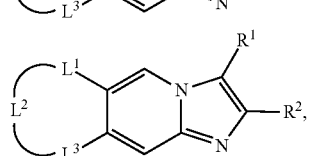

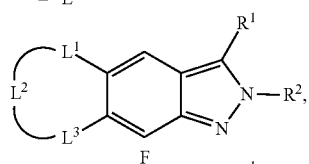

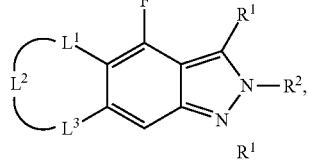

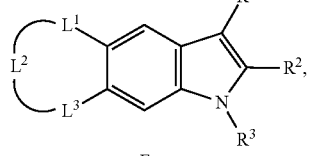

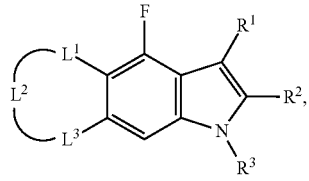

-continued

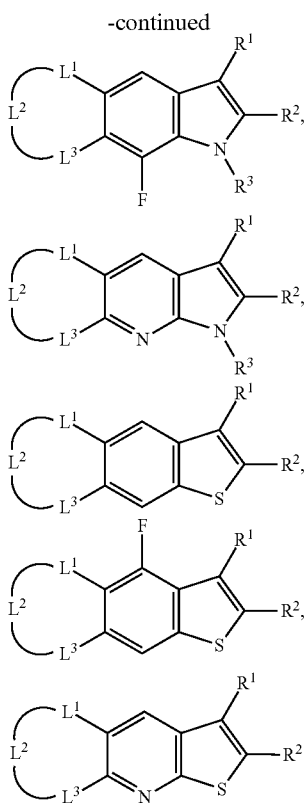

wherein,
L¹, L² and L³ together with the attached carbons of the aromatic ring form a 5-12 member ring, containing 0-4 heteroatoms of N, O, S, P and/or Si;
L¹, L², or L³ is independently selected from the group of divalent substituents consisting of a bond, —O—, —C(R$^{15}$R$^{16}$)—, —NR³—, —S(O)$_n$—, —P(O)—, —Si(R⁴R⁵)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;
n is 0, 1, or 2;
R¹ is selected from hydrogen, halide, —CF₃, —CN, —C(O)H, —C(O)OR⁶—, —C(O)NHR⁷, —C(O)N(OH)R⁷, —C(=NR⁷)OMe, —C(=NOR')NHR⁷, —CH(CF₃)NHR⁸, —CH(CN)NHR⁹, —S(O)₂NHR¹⁰, —C(=NCN)NHR¹¹,

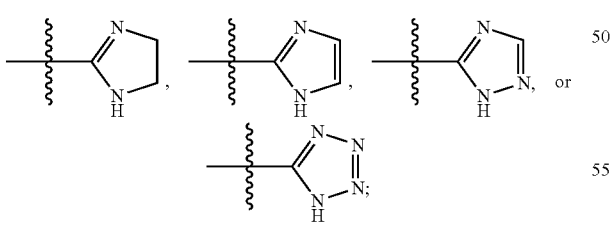

R' is selected from hydrogen, —(CH₂CH₂O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatoms of O, NR$^N$, and/or S;
R² is a substituted or unsubstituted aryl or heteroaryl;
R³ is selected from the group consisting of hydrogen, alkylcarbonyl, cycloalkylcarbonyl, alkoxylcarbonyl, cycloalkoxycarbonyl, alkylsulfonyl and cycloalkylsulfonyl;

R⁴ and R⁵ are each independently methyl, ethyl, or cyclopropyl;
R⁶ is hydrogen, allyl, C$_{1-4}$ alkyl, cyclopropyl, or benzyl;
R⁷ is hydrogen, C$_{1-4}$ alkyl, cyclopropyl, C$_{1-4}$ alkoxy, cyclopropoxy, alkylsulfonyl, or cycloalkylsulfonyl;
R⁸, R⁹, R¹⁰, or R¹¹ is independently hydrogen, C$_{1-4}$ alkyl, cyclopropyl, C$_{1-4}$ alkoxy, or cyclopropoxy; and
R¹⁵, R¹⁶ are each independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R¹⁵ and R¹⁶ together are a carbonyl or C$_{1-4}$ alkenylidene or R¹⁵ and R¹⁶ joined together with the attached carbon form a 3-6 member ring optionally containing 0-3 heteroatoms of O, NR$^N$ and/or S.

In a second embodiment of the first aspect,

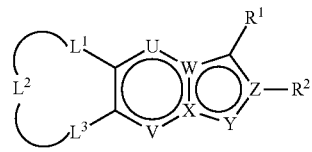

is selected from the group consisting of

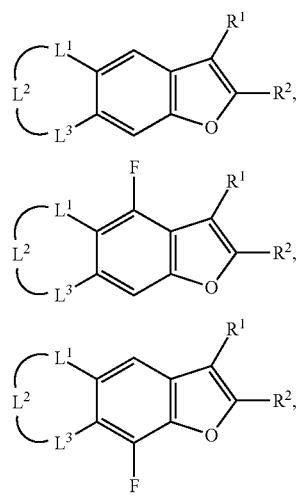

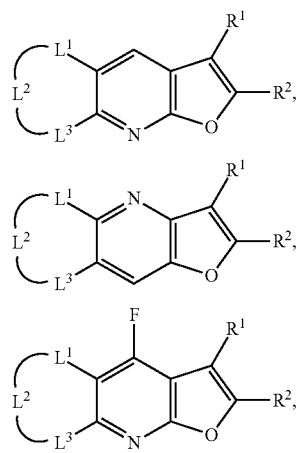

-continued

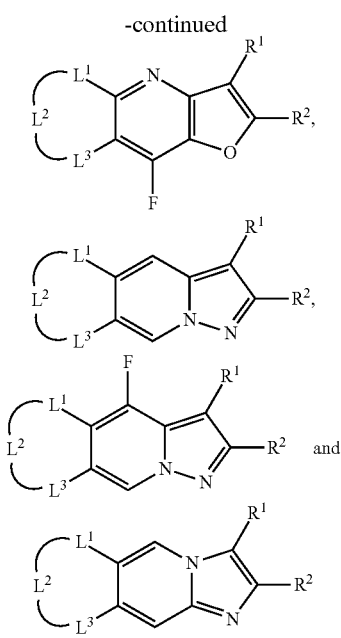

wherein,

L¹, L² and L³ together with the attached carbons of the aromatic ring form a 5-9 member ring, containing 0-4 heteroatoms of N, O, S, P and/or Si;

L¹, L², or L³ is independently selected from the group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^1$ is selected from hydrogen, halide, —$CF_3$, —CN, —C(O)H, —C(O)O$R^6$—, —C(O)NH$R^7$, —C(O)N(OH)$R^7$, —C(=N$R^7$)OMe, —C(=NOR')NH$R^7$, —CH(CF$_3$)NH$R^8$, —CH(CN)NH$R^9$, —S(O)$_2$NH$R^{10}$, —C(=NCN)NH$R^{11}$,

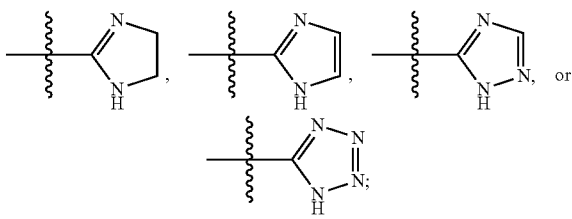

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatoms of O, NR$^N$, and/or S;

$R^2$ is a substituted or unsubstituteed aryl or heteroaryl;

$R^3$ is selected from the group consisting of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^6$ is hydrogen, allyl, C$_{1-4}$ alkyl, cyclopropyl, or benzyl;

$R^7$ is hydrogen, C$_{1-4}$ alkyl, cyclopropyl, C$_{1-4}$ alkoxy, cyclopropoxy, alkylsulfonyl, or cycloalkylsulfonyl;

$R^8$, $R^9$, $R^{10}$, or $R^{11}$ is independently hydrogen, C$_{1-4}$ alkyl, cyclopropyl, C$_{1-4}$ alkoxy, or cyclopropoxy; and $R^{15}$, $R^{16}$ is each independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or $R^{15}$ and $R^{16}$ together are a carbonyl or C$_{1-4}$ alkenylidene or $R^{15}$ and $R^{16}$ joined together with the attached carbon are 3-6 member rings optionally containing 0-3 heteroatoms of O, NR$^N$ and/or S.

In a third embodiment of the first aspect, $R^1$ is hydrogen, halide, —C(O)O$R^6$—, —C(O)NH$R^7$, —C(=N$R^7$)OMe, —C(O)N(OH)$R^7$, —C(=NOR')NH$R^7$, —CH(CF$_3$)NH$R^8$, —CH(CN)NH$R^9$,

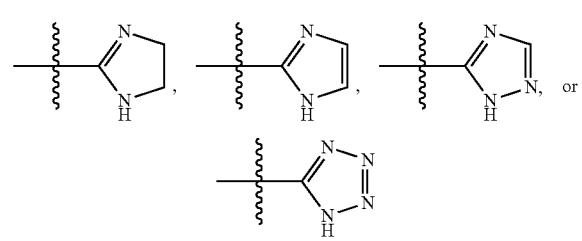

wherein,

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

$R^6$ is hydrogen, allyl, C$_{1-4}$ alkyl, cyclopropyl, or benzyl;

$R^7$ is hydrogen, C$_{1-4}$ alkyl, cyclopropyl, C$_{1-4}$ alkoxy, cyclopropoxy, alkylsulfonyl, or cycloalkylsulfonyl; and $R^8$, $R^9$, $R^{10}$, or $R^{11}$ is independently hydrogen, C$_{1-4}$ alkyls, cyclopropyl, C$_{1-4}$ alkoxys, or cyclopropoxy.

In a fourth embodiment of the first aspect, $R^1$ is hydrogen, Br, I, —COOH, —C(O)OMe, —C(O)OEt, —C(O)O tBu, —C(O)NHMe, —C(O)NHOMe, —C(=NOMe)NHMe, —C(=NOH)NHMe, —C(=NMe)OMe, —C(O)N(OH)Me, —C(O)NHS(O)$_2$Me, —CH(CF$_3$)NHMe, —CH(CN)NHMe, —C(=NCN)NHMe,

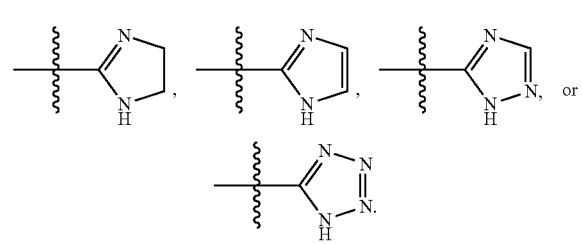

In a fifth embodiment of the first aspect, $R^1$ is —C(O)NHMe or

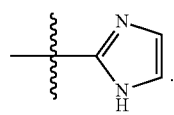

In a sixth embodiment of the first aspect, $R^2$ is selected from the group consisting of

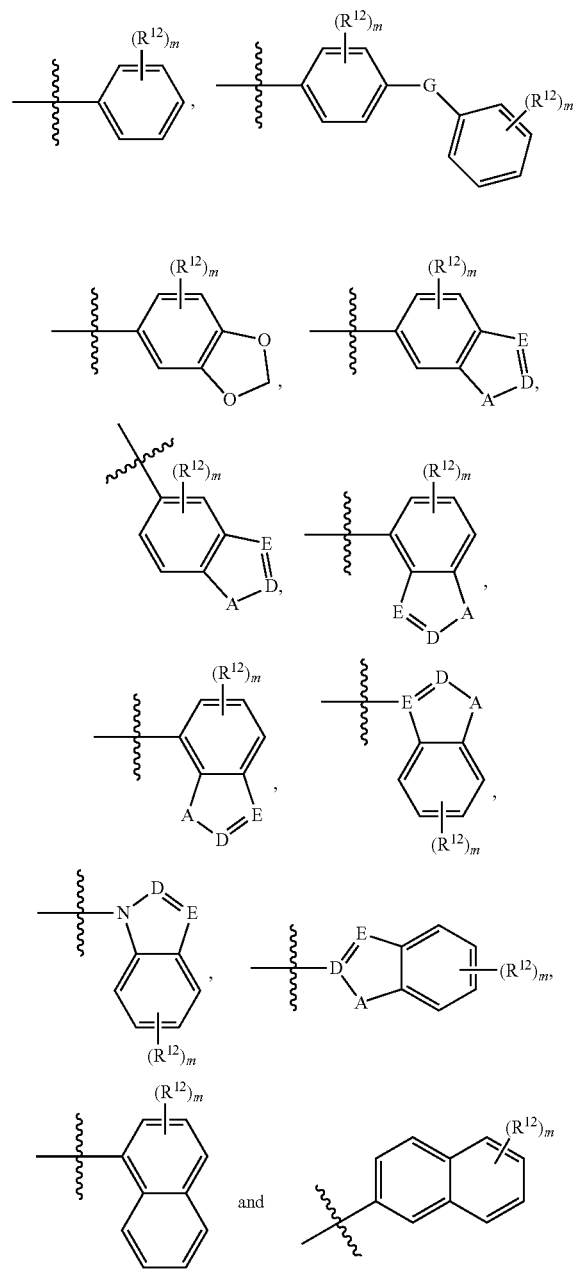

wherein, each phenyl moiety is optionally substituted with 0-2 nitrogen atoms;

$R^{12}$ is selected from the group of hydrogen, halide, —CN, —OCHF$_2$, —OCF$_3$, alkyl, cycloalkyl, alkoxy, cycloalkoxy, arylalkyl, aryloxy, alkenyl, alkynyl, amide, alkylsulfonyl, arylsulfonyl, sulfonamide, carbamate;

m is 0, 1, 2, 3, or 4;

G is O, NR$^N$, S, or CR$^a$R$^b$;

A is N, O, S, or or CR$^a$R$^b$; and

D, E is each independently C or N.

In a seventh embodiment of the first aspect, $R^2$ is selected from the group consisting of

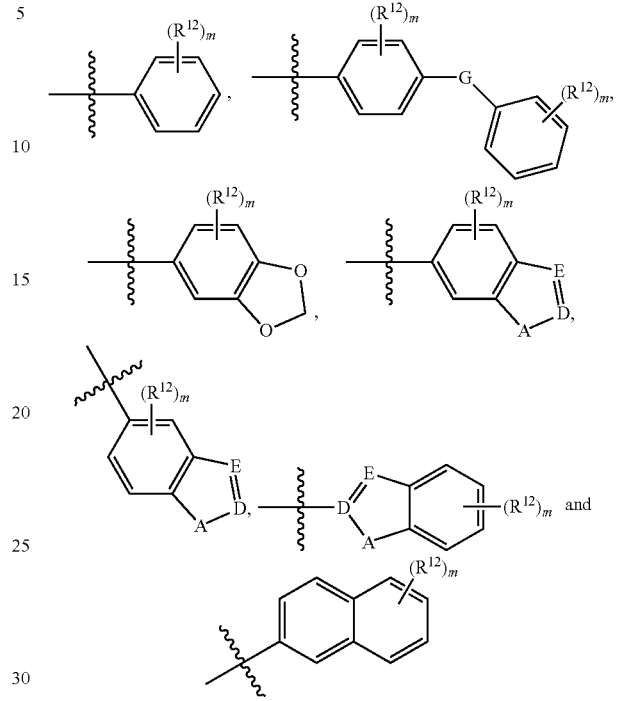

wherein, each phenyl moiety is optionally substituted with 0-2 nitrogen atoms;

$R^{12}$ is selected from the group of hydrogen, halide, —CN, —OCHF$_2$, —OCF$_3$, alkyl, cycloalkyl, alkoxy, cycloalkoxy, arylalkyl, aryloxy, alkenyl, alkynyl, amide, alkylsulfonyl, arylsulfonyl, sulfonamide, carbamate;

m is 0, 1, 2, 3, or 4;

G is O, NR$^N$, S, or CR$^a$R$^b$;

A is N, O, S, or CR$^a$R$^b$; and

D, E is independently C or N.

In an eighth embodiment of the first aspect, $R^2$ is selected from the group consisting of

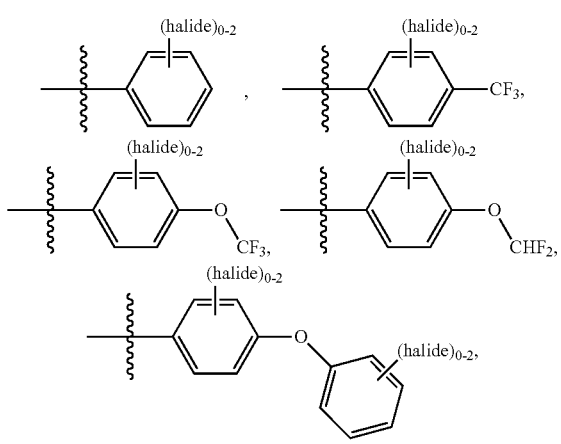

-continued

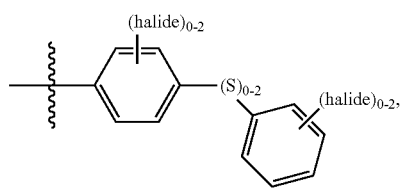

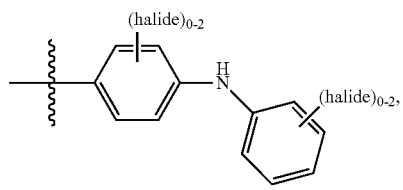

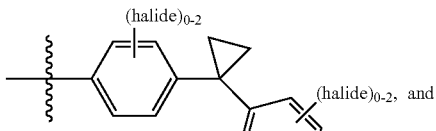

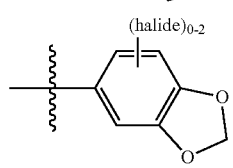

wherein, each phenyl moiety is optionally substituted with 0-2 nitrogen atoms.

In a ninth embodiment of the first aspect, $R^2$ is

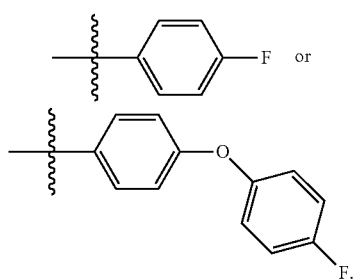

In a tenth embodiment of the first aspect,

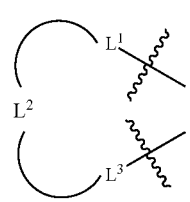

is selected from the group consisting

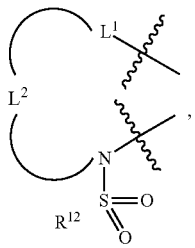 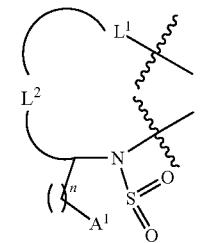

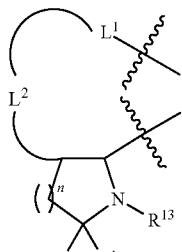 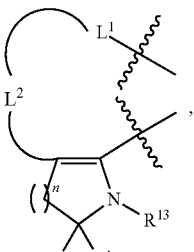

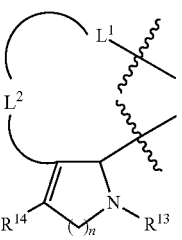 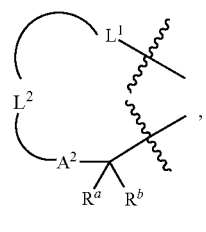

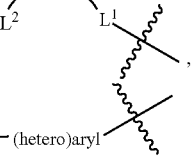 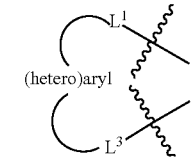

wherein, $L^1$, $L^2$, or $L^3$ is independently selected from the group consisting of a bond, —O—, —C($R^{15}R^{16}$), —$NR^3$—, —S(O)$_n$—, —P(O)$_n$—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^1$ is selected from hydrogen, halide, —CF$_3$, —CN, —C(O)H, —C(O)OR$^6$—, —C(O)NHR$^7$, —C(O)N(OH)R$^7$, —C(=NMe)OMe, —C(=NOR')NHR$^7$, —CH(CF$_3$)NHR$^8$, —CH(CN)NHR$^9$, —S(O)$_2$NHR$^{10}$, —C(=NCN)NHR$^{11}$,

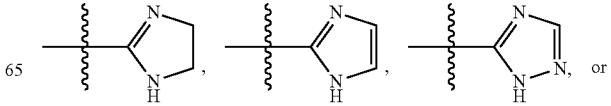

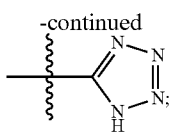

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatoms of O, NR$^N$, and/or S;

R$^2$ is a substituted or unsubstituted aryl or heteroaryl;

R$^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

R$^4$ and R$^5$ are independently methyl, ethyl, or cyclopropyl;

R$^6$ is hydrogen, allyl, C$_{1-4}$ alkyl, cyclopropyl, or benzyl;

R$^7$ is hydrogen, C$_{1-4}$ alkyl, cyclopropyl, C$_{1-4}$ alkoxy, cyclopropoxy, alkylsulfonyl, or cycloalkylsulfonyl;

R$^8$, R$^9$, R$^{10}$, or R$^{11}$ is independently hydrogen, C$_{1-4}$ alkyls, cyclopropyl, C$_{1-4}$ alkoxys, or cyclopropoxy;

R$^{12}$ is independently C$_{1-3}$ alkyl, cyclorpopyl, —OMe, or —NHMe;

R$^{13}$ is independently hydrogen, —Ac, or —S(O)$_2$Me;

R$^{14}$ is independently hydrogen or Me;

R$^{15}$, R$^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R$^{15}$ and R$^{16}$ together are a carbonyl or C$_{1-4}$ alkenylidene or R$^{15}$ and R$^{16}$ joined together with the attached carbon are 3-6 member ring optionally containing 0-3 heteroatoms of O, NR$^N$ and/or S; and A$^1$ or A$^2$ is independently —CR$^a$R$^b$—, —N(R$^N$)—, or —O—.

In an eleventh embodiment of the first aspect,

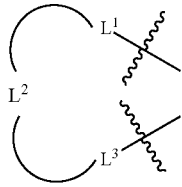

is selected from the group consisting of

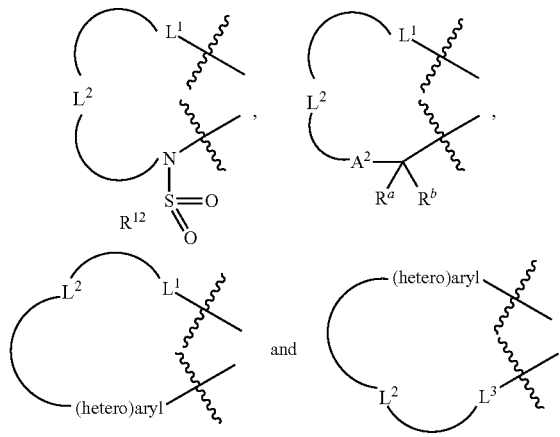

wherein,

L$^1$, L$^2$, or L$^3$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R$^1$ is selected from hydrogen, halide, —CF$_3$, —CN, —C(O)H, —C(O)OR$^6$—, —C(O)NHR$^7$, —C(O)N(OH)R$^7$, —C(=NMe)OMe, —C(=NOR')NHR$^7$, —CH(CF$_3$)NHR$^8$, —CH(CN)NHR$^9$, —S(O)$_2$NHR$^{10}$, —C(=NCN)NHR$^{11}$,

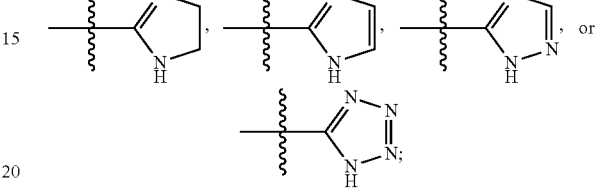

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatoms of O, NR$^N$, and/or S;

R$^2$ is a substituted or unsubstituted aryl or heteroaryl;

R$^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

R$^4$ and R$^5$ are independently methyl, ethyl, or cyclopropyl;

R$^6$ is hydrogen, allyl, C$_{1-4}$ alkyl, cyclopropyl, or benzyl;

R$^7$ is hydrogen, C$_{1-4}$ alkyl, cyclopropyl, C$_{1-4}$ alkoxy, cyclopropoxy, alkylsulfonyl, or cycloalkylsulfonyl;

R$^8$, R$^9$, R$^{10}$, or R$^{11}$ is independently hydrogen, C$_{1-4}$ alkyls, cyclopropyl, C$_{1-4}$ alkoxys, or cyclopropoxy;

R$^{12}$ is independently C$_{1-3}$ alkyl, cyclorpopyl, —OMe, or —NHMe;

R$^{15}$, R$^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R$^{15}$ and R$^{16}$ together are a carbonyl or C$_{1-4}$ alkenylidene or R$^{15}$ and R$^{16}$ joined together with the attached carbon are 3-6 member ring optionally containing 0-3 heteroatoms of O, NR$^N$ and/or S; and A$^2$ is independently —CR$^a$R$^b$—, —N(R$^N$)—, or —O—

In a twelfth embodiment of the first aspect,

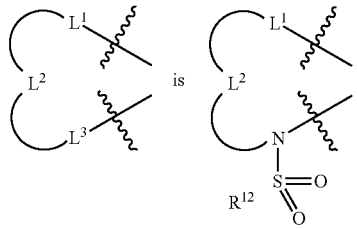

wherein,

L$^1$ or L$^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^1$ is selected from hydrogen, halide, —$CF_3$, —CN, —C(O)H, —C(O)O$R^6$—, —C(O)NH$R^7$, —C(O)N(OH)$R^7$, —C(=NMe)OMe, —C(=NOR')NH$R^7$, —CH(CF$_3$)NH$R^8$, —CH(CN)NH$R^9$, —S(O)$_2$NH$R^{10}$, —C(=NCN)NH$R^{11}$,

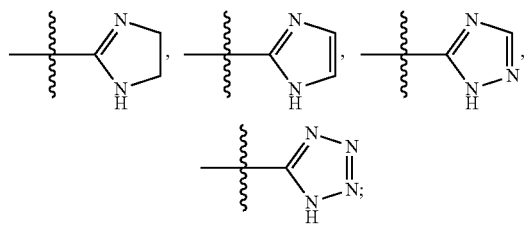

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

$R^2$ is a substituted or unsubstituted aryl or heteroaryl;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl; and $R^{15}$, $R^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or $R^{15}$ and $R^{16}$ together are a carbonyl or C$_{1-4}$ alkenylidene or $R^{15}$ and $R^{16}$ joined together with the attached carbon are 3-6 member ring optionally containing 0-3 heteroatoms of O, NR$^N$ and/or S.

In a second aspect of the invention is a compound that has the structure:

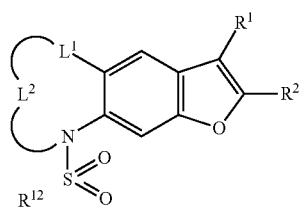

wherein, $L^1$, $L^2$ and —N(SO$_2$R$^{12}$)— together with the attached carbons of the aromatic ring to form a 5-12 member ring, containing 1-4 heteroatoms of N, O, S, P and/or Si;

$L^1$ or $L^2$ is independently selected from the group consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2; and $R^1$ is selected from hydrogen, halide, —$CF_3$, —CN, —C(O)H, —C(O)O$R^6$—, —C(O)NH$R^7$, —C(O)N(OH)$R^7$, —C(=NOR')NH$R^7$, —C(CF$_3$)NH$R^8$, —C(CN)NH$R^9$, —S(O)$_2$NH$R^{10}$, —C(=NCN)NH$R^{11}$,

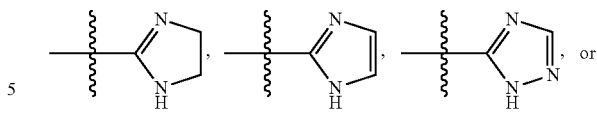

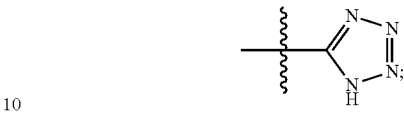

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

$R^2$ is an aryl or heteroaryl having one or more $R^{17}$ substituents;

$R^3$ is selected from the group of hydrogen, alkylcarbonyl, cycloalkylcarbonyl, alkoxylcarbonyl, cycloalkoxycarbonyl, alkyl sulfonyl and cycloalkylsulfonyl;

$R^4$ and $R^5$ are independently methyl, ethyl, or cyclopropyl;

$R^{12}$ is independently C$_{1-3}$ alkyl, cyclopropyl, —OMe, or —NHMe;

$R^{15}$, $R^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or $R^{15}$ and $R^{16}$ together are a carbonyl or C$_{1-4}$ alkenylidene or $R^{15}$ and $R^{16}$ joined together with the attached carbon are 3-6 member ring optionally containing 0-3 heteroatoms of O, NR$^N$ and/or S; and $R^{17}$ is F, Cl or CN.

The compound of this embodiment may have an inhibitory activity with respect to HCV, as measured by the concentration of the compound effective to produce a half-maximal inhibition of HCV 1b replication (EC$_{50}$) in a 1b_Huh-Luc/Neo-ET cell line in culture, of 100 nM or less.

The compound of this embodiment may have the structure in which

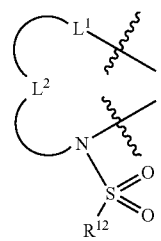

is one of

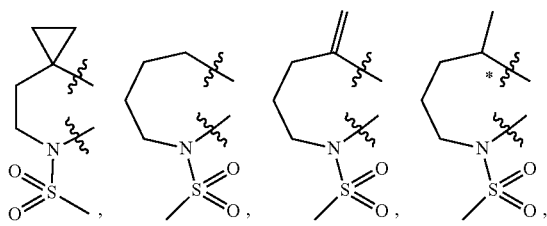

-continued

-continued
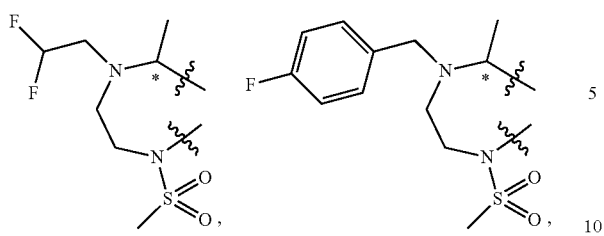
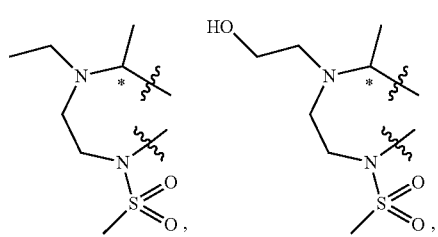
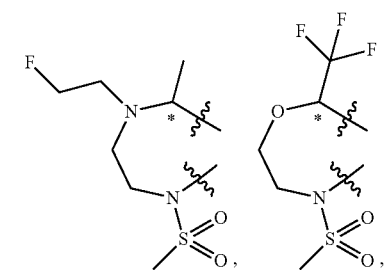
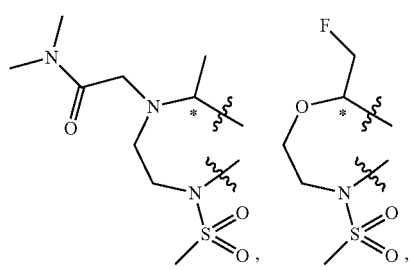
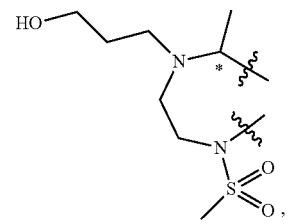
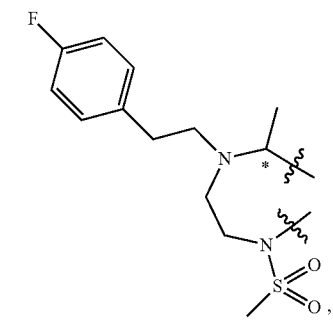
-continued
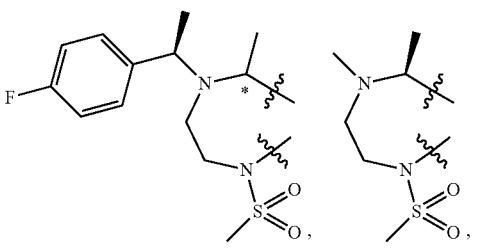
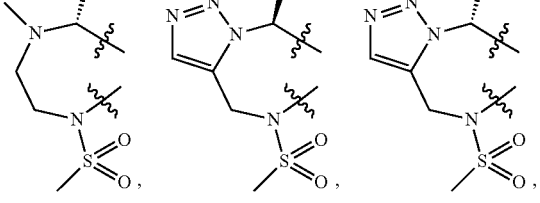
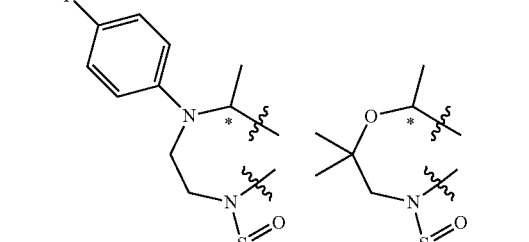
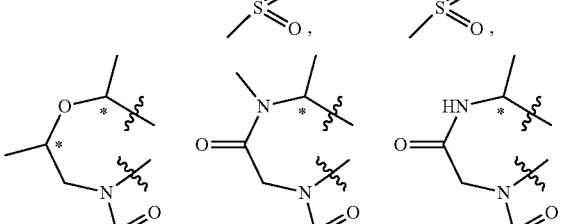
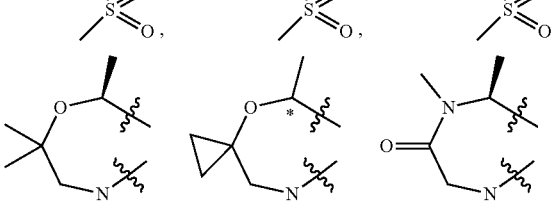
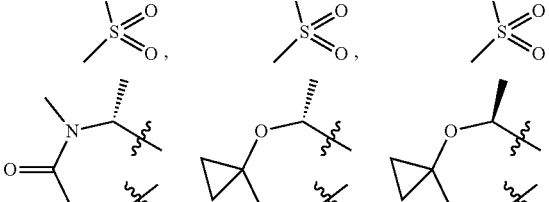
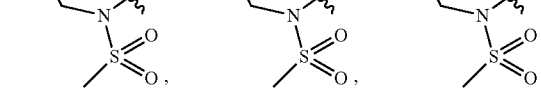

21
-continued
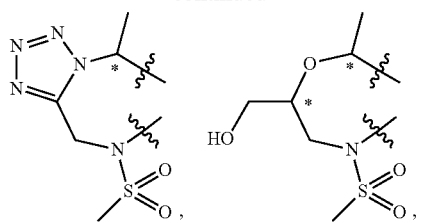
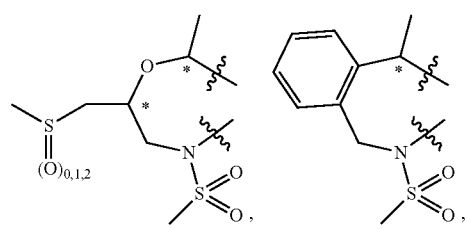
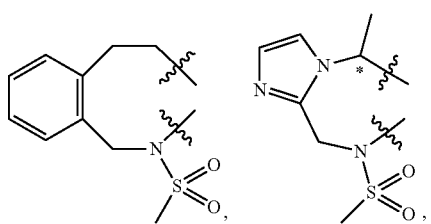
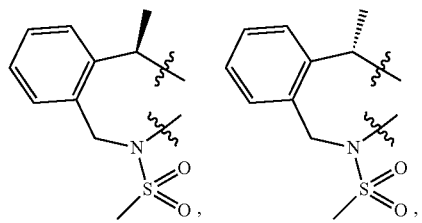
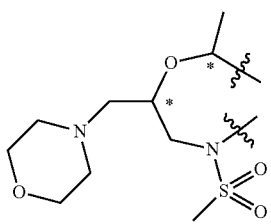
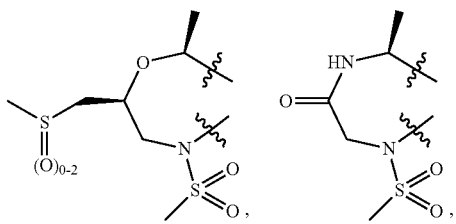
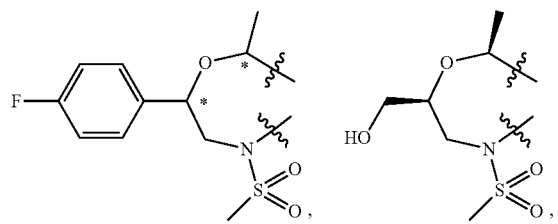
22
-continued
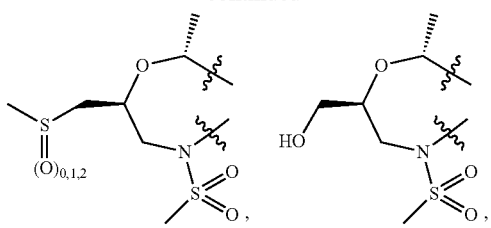
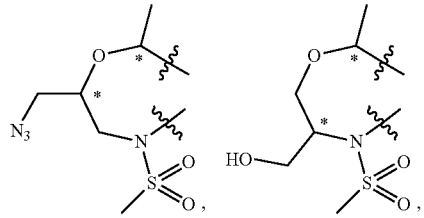
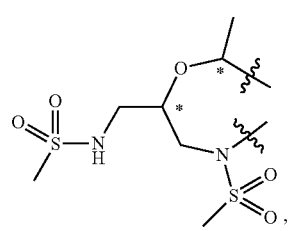
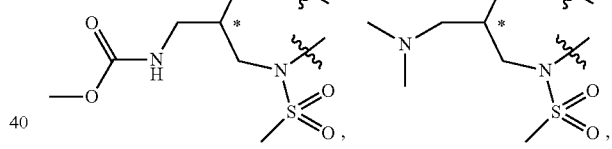
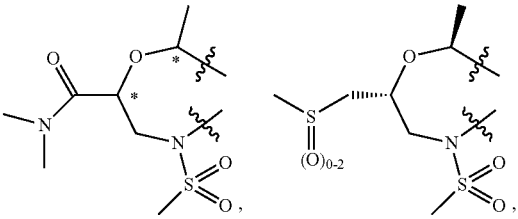
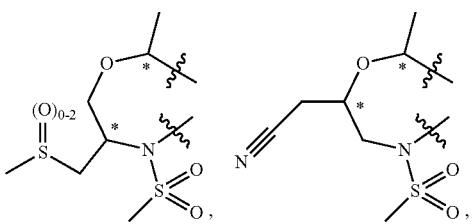
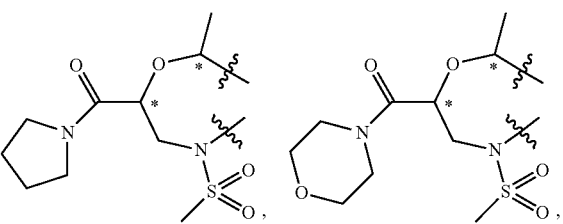

-continued
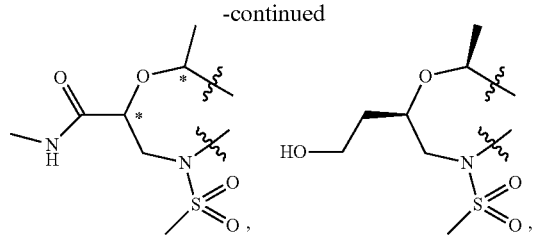
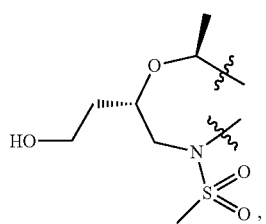
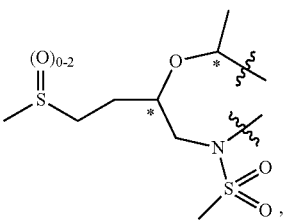
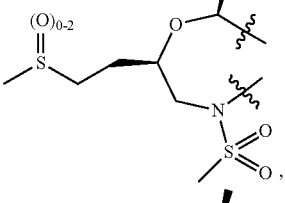
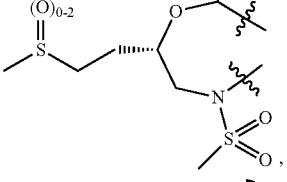
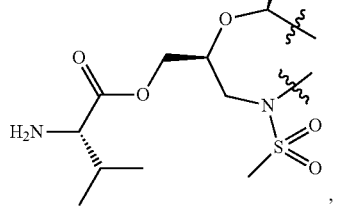
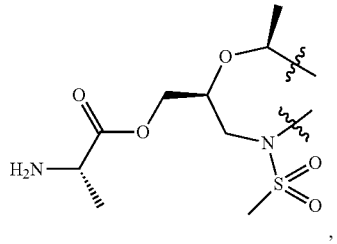
-continued
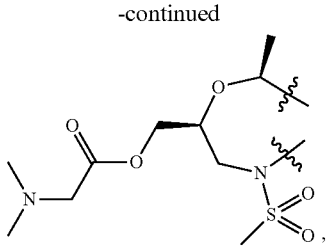
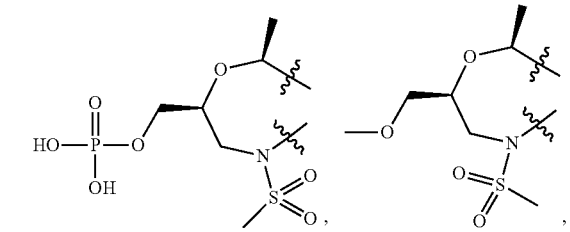
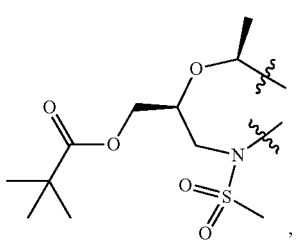
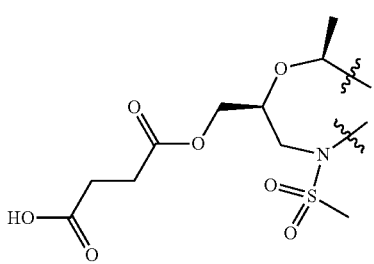
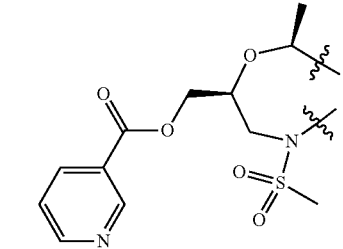
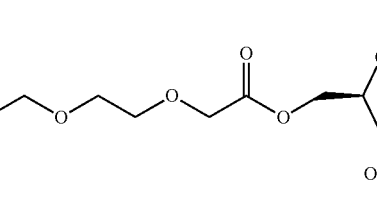
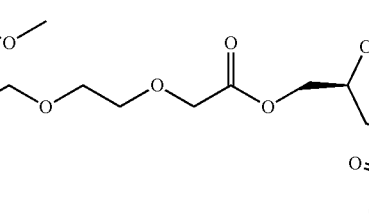

25
-continued
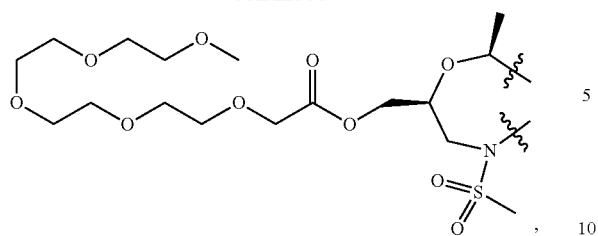
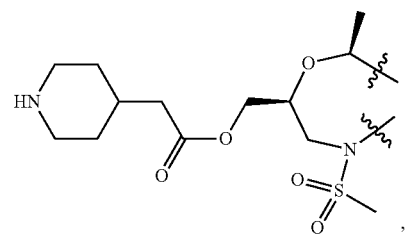
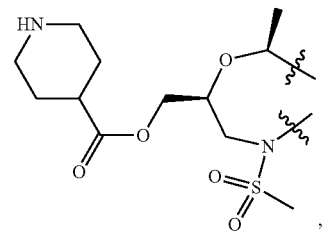
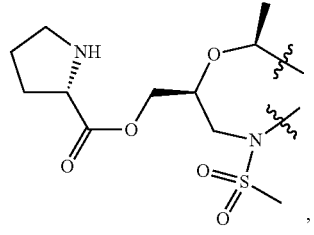
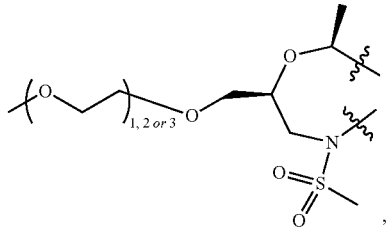
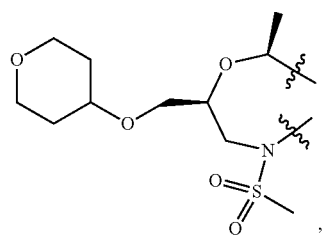
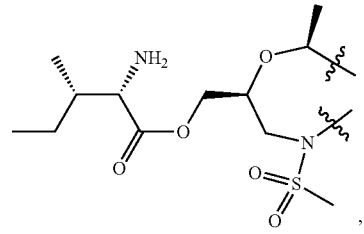
26
-continued
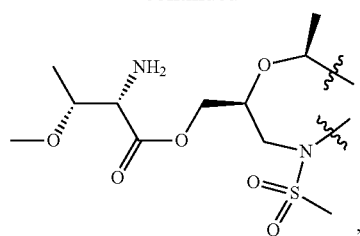
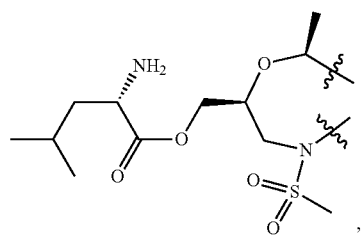
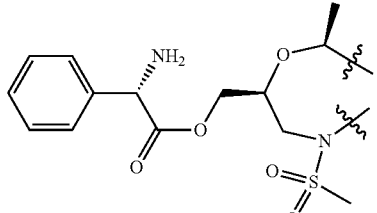
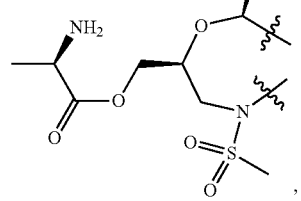
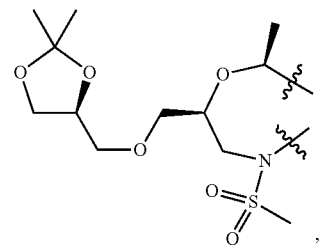
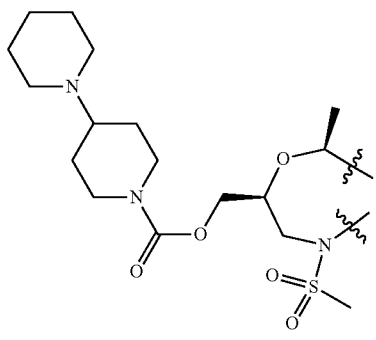

-continued

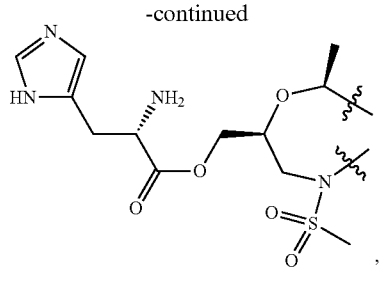

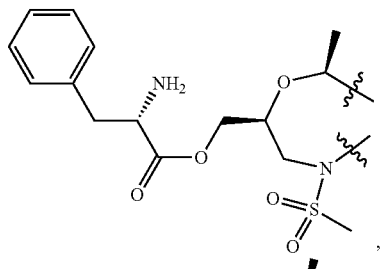

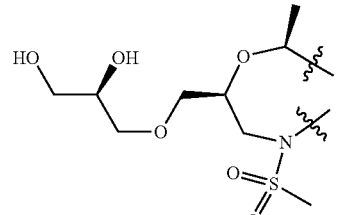

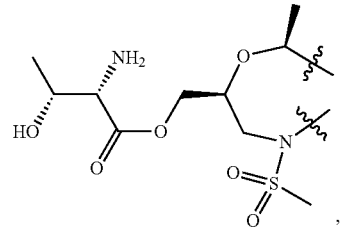

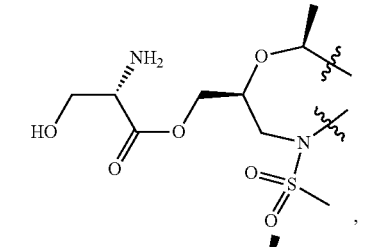

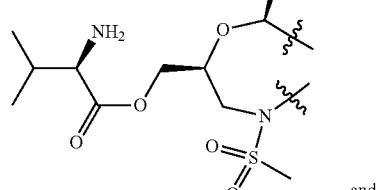

, and

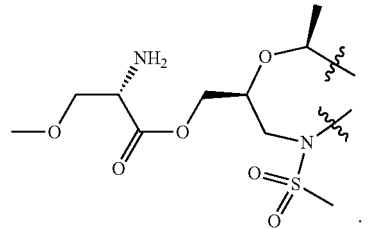

.

$R^1$ is selected from the group consisting of

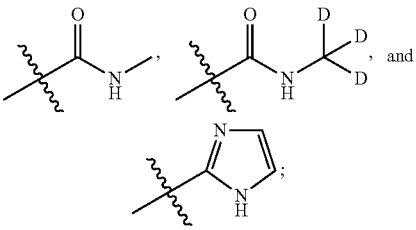

and $R^2$ is selected from the group consisting of

[structures: 4-F-phenyl; 2-methoxy-4-F-phenyl; 3-F-phenyl; 2-F-phenyl; 2,4-diF-phenyl; 3,4-diF-phenyl; 4-Br-phenyl; 4-(4-F-phenoxy)phenyl; 4-(3-F-phenoxy)phenyl, and 4-(3,4-diF-phenoxy)phenyl].

The compound in this embodiment may be selected from the group consisting of compounds identified by ID NOS: B5, B15, B20, B33, B35, B45, B67, B85, B92, B94, B107, B118, B120, B121, B127, B128, B130, B131, B132, B138, B139, B145, B148, B158, B163, B168, B169, B171, B187, B190, B191, B192, B196, B197, B198, B201, B207, B208, B212, B214, B218, B221, B226, B232, B233, B236, B237, B238, B239, B240, B243, B244, B245, B246, B247, B248, B249, B252, B253, B254, B255, B256, B257, B258, B259, B260, B261, B263, B265, B266, B267, B268, B269, B270, B271, B272, B273, B275, B276, B277, B278, B280, B281, B282, B285, B286, B2, B3, B4, B6, B7, B9, B16, B18, B19, B22, B29, B31, B32, B34, B36, B47, B48, B54, B55, B57, B60, B63, B71, B84, B93, B100, B101, B106, B108, B109, B111, B112, B113, B115, B116, B119, B123, B124, B134, B136, B137, B142, B144, B146, B147, B150, B151, B153, B154, B155, B156, B157, B159, B160, B161, B162, B164, B165, B166, B167, B170, B172, B173, B174, B175, B176, B178, B179, B180, B181, B183, B184, B186, B188, B189, B193, B195, B199, B200, B202, B203, B204, B205, B210, B215, B216, B217, B219, B220, B222, B223, B224, B225, B227, B228, B229, B230, B231, B234, B235, B241, B262, B264, B279, and B287.
In some preferred embodiments,
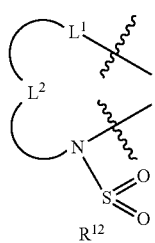
is selected from the group consisting of
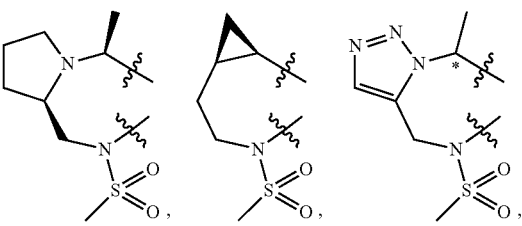
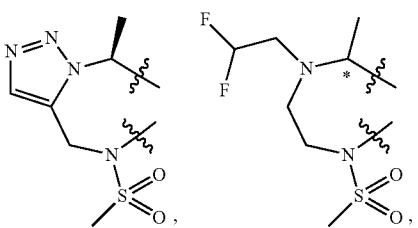
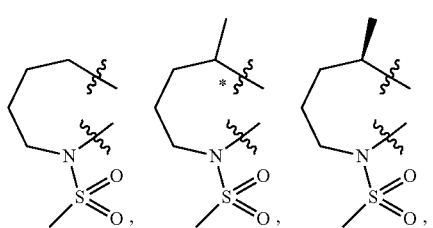
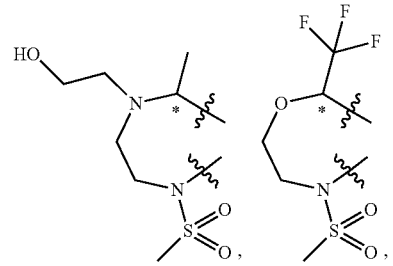
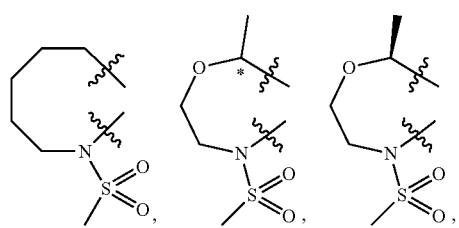
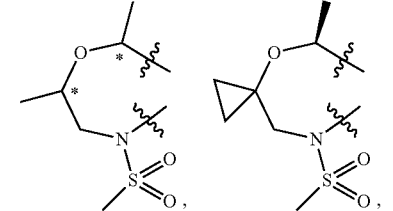
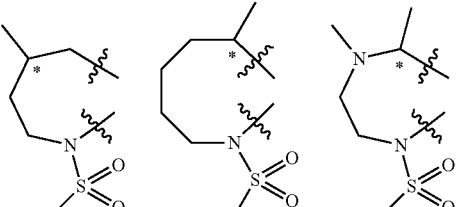
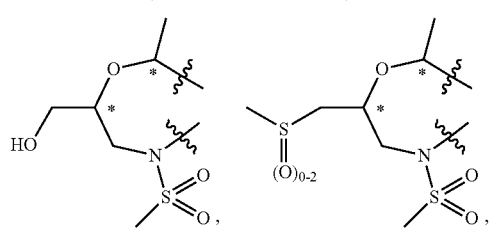
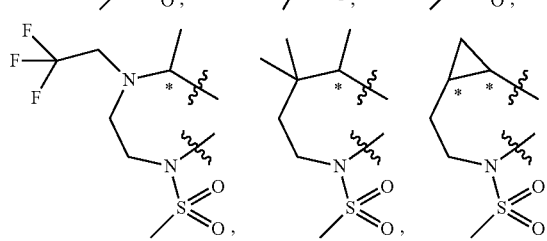
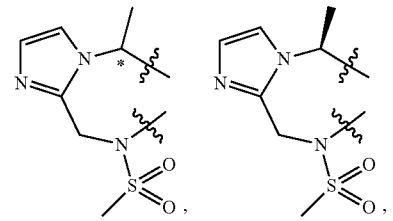
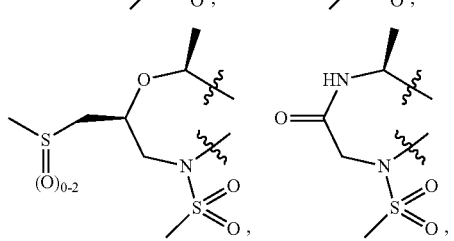

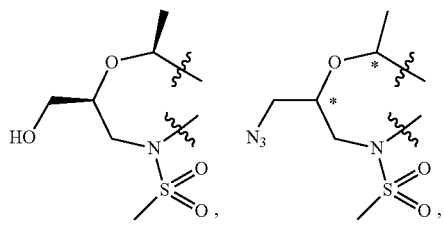
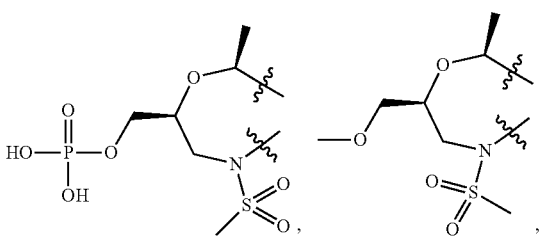
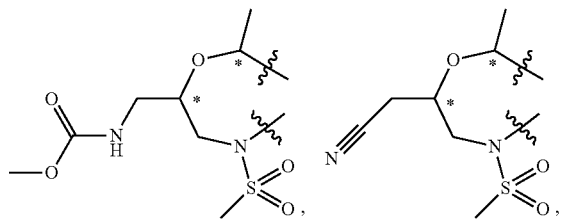
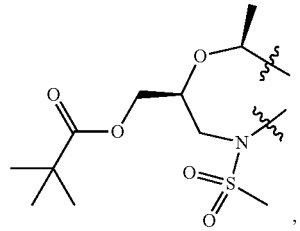
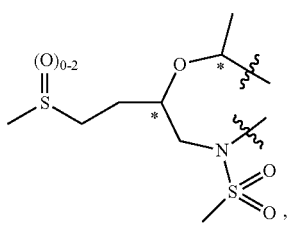
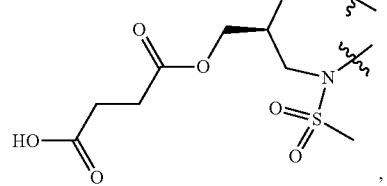
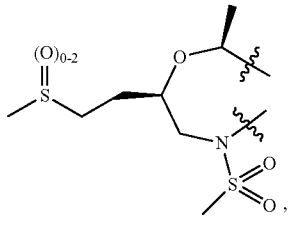
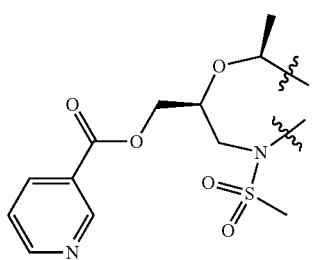
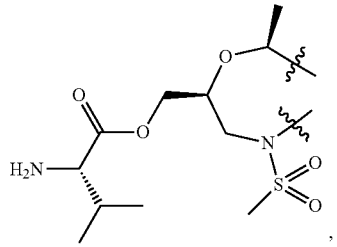
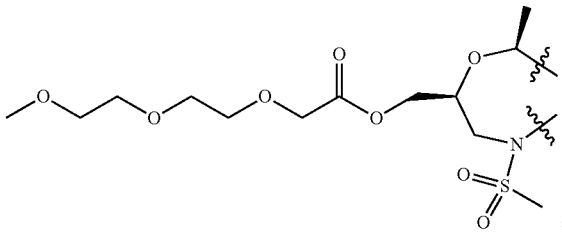
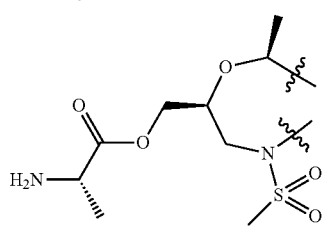
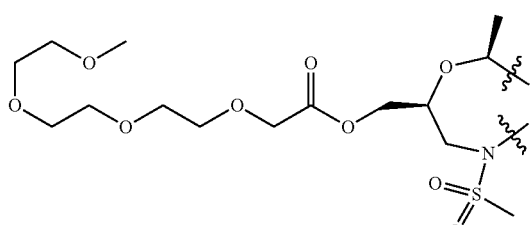
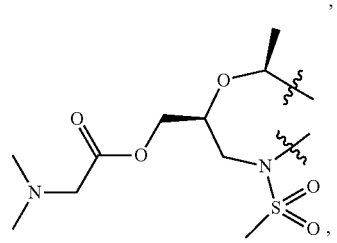

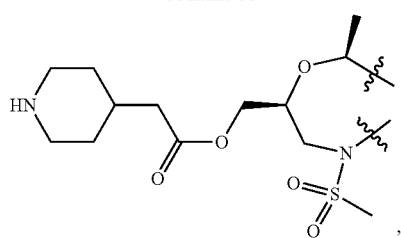
,
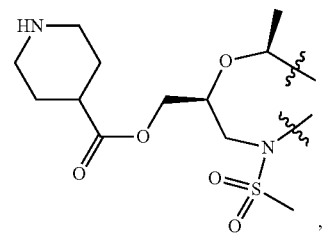
,
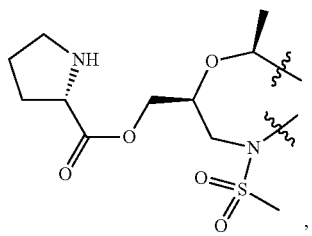
,
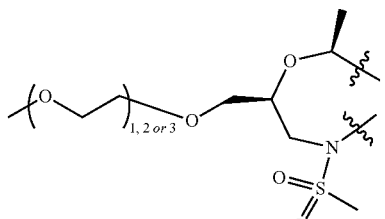
,
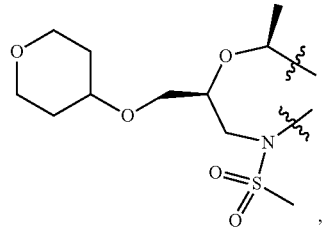
,
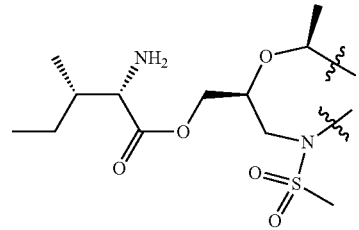
,
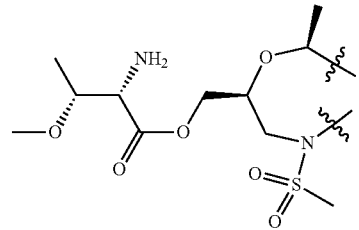
,
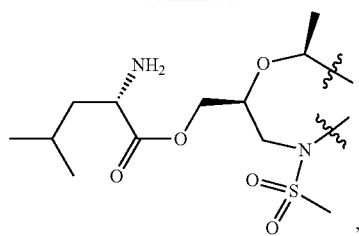
,
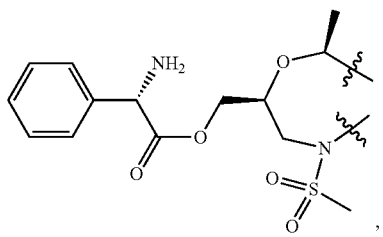
,
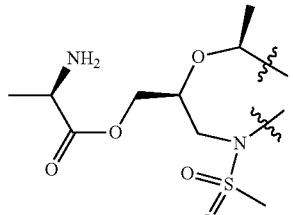
,
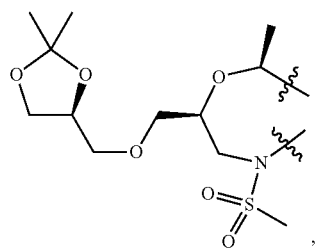
,
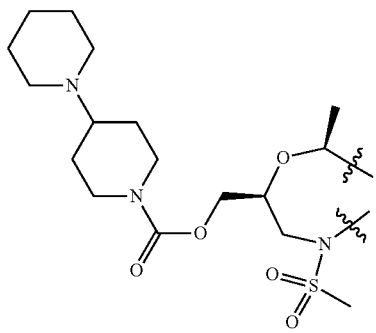
,
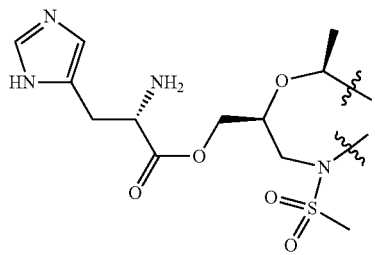
,

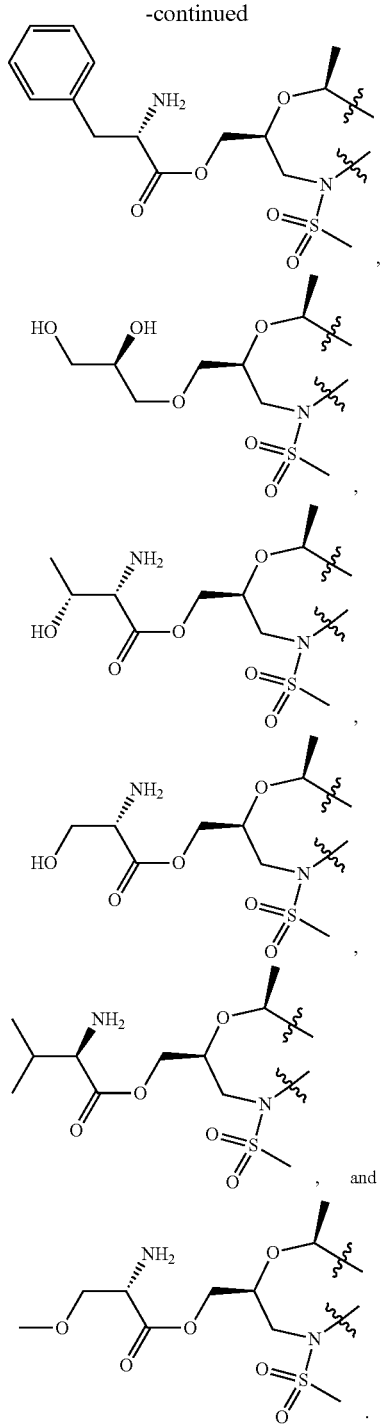

, , , , and

.

The above compounds include compounds identified by ID NOS: B5, B15, B20, B33, B35, B45, B67, B85, B92, B94, B107, B118, B120, B121, B127, B128, B130, B131, B132, B138, B139, B145, B148, B158, B163, B168, B169, B171, B187, B190, B191, B192, B196, B197, B198, B201, B207, B208, B212, B214, B218, B221, B226, B232, B233, B236, B237, B238, B239, B240, B243, B244, B245, B246, B247, B248, B249, B252, B253, B254, B255, B256, B257, B258, B259, B260, B261, B263, B265, B266, B267, B268, B269, B270, B271, B272, B273, B275, B276, B277, B278, B280, B281, B282, B285, and B286.

As can be appreciated, the compounds in this embodiment may be subdivided into subsets wherein

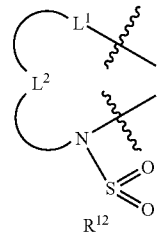

is:

(i) a 7 or 8 member aliphatic ring, as exemplified by compounds B5, B15, B35, B67, B85, B92, B120, B130, B198, B94, and B130;

(ii) a 7 or 8 member ring having an internal oxygen atom, as exemplified by compounds B45, B118, B148, B197, B168, B187, B190; B192, B196, B207, B214, B191, B212, B218, B221, B222, B226, B232, B233, B236, B237, B238, B239, B240, B243, B244, B245, B246, B247, B248, B249, B252, B253, B254, B255, B256, B257, B258, B259, B260, B261, B263, B265, B266, B267, B268, B269, B270, B271, B272, B273, B275, B276, B277, B278, B279, B280, B281, B282, B285, B286, and B287;

(iii) a 7 or 8 member ring having a second internal nitrogen atom, as exemplified by compounds B107, B139, B145, B171, and B208; and (iv) a fused 7 or 8 member ring, as exemplified by compounds B127, B128, B131, B132, B138, B158, B163, B169, B189, and B201.

$R^1$ in this embodiment may be

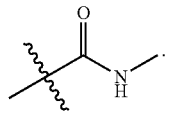

The structure

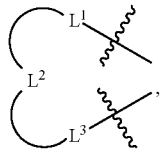

together with the attached carbons of the aromatic ring in this embodiment may be a seven- or eight-member ring.

$R^2$ in this embodiment may be a phenyl substituted with one or more $R^{17}$ substituents.

$R^2$ in this embodiment may be a 4-phenoxyphenyl and the phenoxy group is substituted with one or more $R^{17}$ substituents.

$R^2$ in this embodiment may be selected from

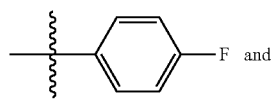

and

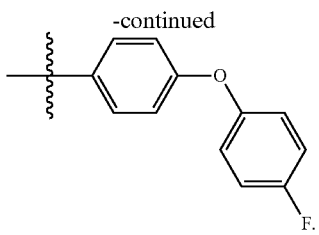

In a third aspect of the invention is a compound of formula II,

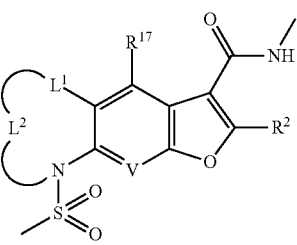

wherein,

L$^1$, L$^2$ and —N(SO$_2$Me)— together with the attached carbons of the aromatic ring form a 5-12 member ring, containing 1-4 heteroatoms of N, O, S, P and/or Si;

L$^1$ or L$^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R$^2$ is an aryl or heteroaryl and may be substituted with one or more R$^{17}$ substituents, R$^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

R$^4$ and R$^5$ are independently methyl, ethyl, or cyclopropyl;

R$^{15}$, R$^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R$^{15}$ and R$^{16}$ together are a carbonyl or C$_{1-4}$ alkenylidene or R$^{15}$ and R$^{16}$ joined together with the attached carbon are 3-6 member ring optionally containing 0-3 heteroatoms of O, NR$^N$ and/or S;

R$^{17}$ is H, F, Cl or CN; and

V is CH, N, CF, CCl, or CCN.

In a fourth aspect of the invention is a compound that the structure:

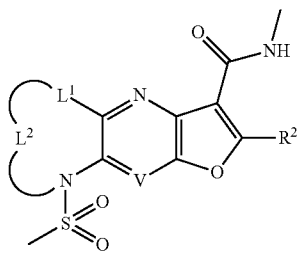

wherein,

L$^1$, L$^2$ and —N(SO$_2$Me)— together with the attached carbons of the aromatic ring form a 5-12 member ring, containing 1-4 heteroatoms of N, O, S, P and/or Si;

L$^1$ or L$^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R$^2$ is an aryl or heteroaryl and may be substituted with one or more R$^{17}$ substituents, R$^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

R$^4$ and R$^5$ are independently methyl, ethyl, or cyclopropyl;

R$^{15}$, R$^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R$^{15}$ and R$^{16}$ together are a carbonyl or C$_{1-4}$ alkenylidene or R$^{15}$ and R$^{16}$ joined together with the attached carbon are 3-6 member ring optionally containing 0-3 heteroatoms of O, NR$^N$ and/or S;

R$^{17}$ is H, F, Cl or CN; and

V is CH, N, CF, CCl, or CCN.

In a fifth aspect of the invention is a compound that has the structure:

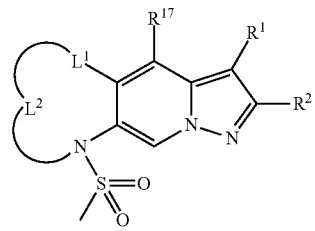

wherein,

L$^1$, L$^2$ and —N(SO$_2$Me)— together with the attached carbons of the aromatic ring form a 5-12 member ring, containing 1-4 heteroatoms of N, O, S, P and/or Si;

L$^1$ or L$^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R$^1$ is selected from hydrogen, halide, —CF$_3$, —CN, —C(O)H, —C(O)OR$^6$—, —C(O)NHR$^7$, —C(O)N(OH)R$^7$, —C(=NR$^7$)OMe, —C(=NOR')NHR$^7$, —CH(CF$_3$)NHR$^8$, —CH(CN)NHR$^9$, —S(O)$_2$NHR$^{10}$, —C(=NCN)NHR$^{11}$,

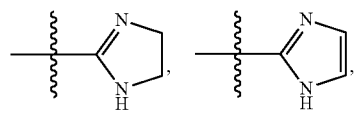

-continued

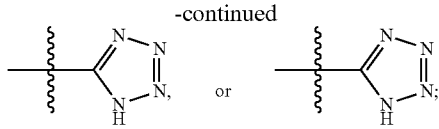

R' is selected from hydrogen, —$(CH_2CH_2O)_{0-8}$-Me, $C_{2-24}$ alkyl optionally containing 0-6 heteroatoms of O, $NR^N$ and/or S, and $C_{3-8}$ cycloalkyl optionally containing 0-2 heteroatom of O, $NR^N$, and/or S;

$R^2$ is an aryl or heteroaryl and may be substituted with one or more $R^{17}$ substituents;

$R^3$ is selected from the group of hydrogen, alkylcarbonyl, cycloalkylcarbonyl, alkoxycarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

For the compounds in this embodiment,

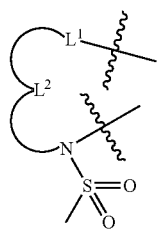

may be selected from the group consisting of

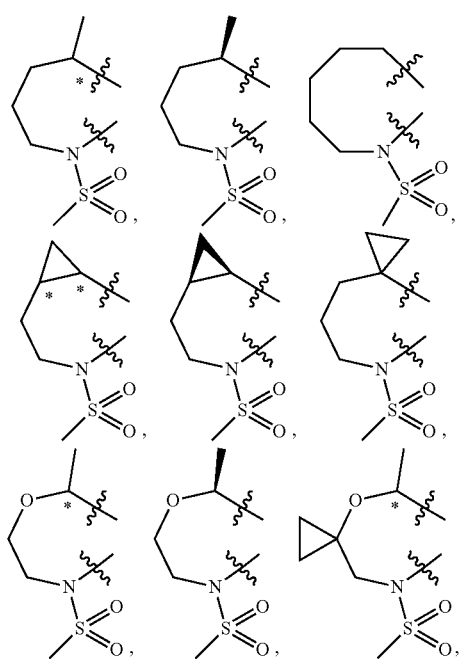

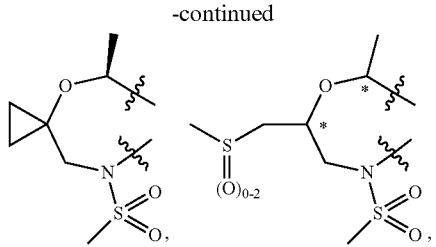

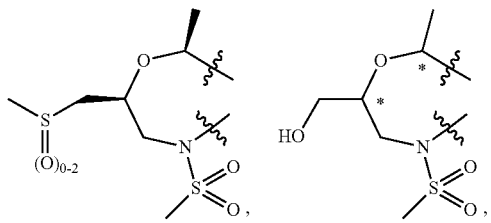

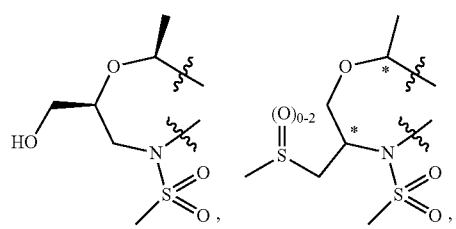

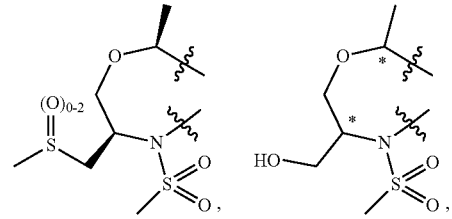

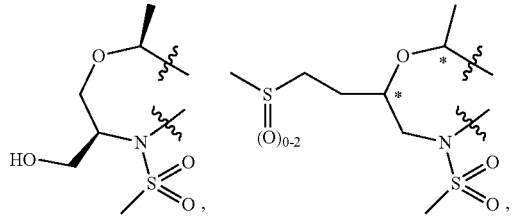

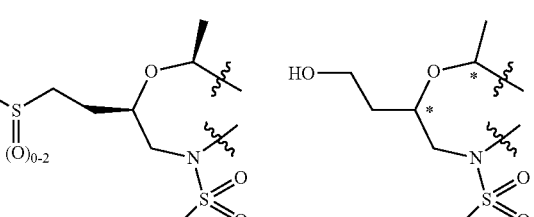

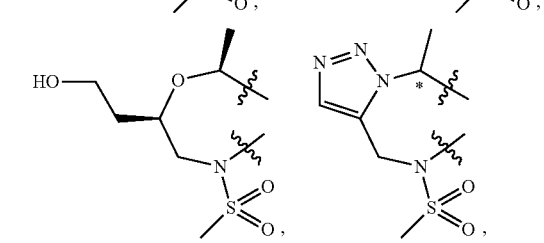

-continued

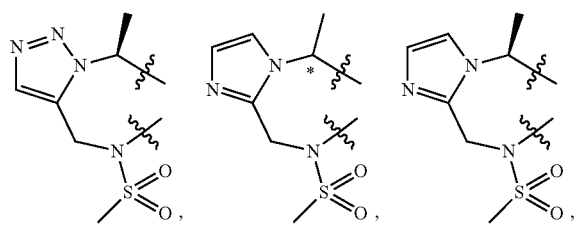

$R^1$ is selected from the group consisting of

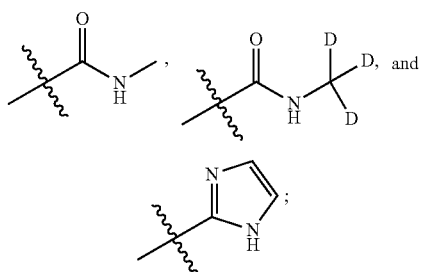

and $R^2$ is selected from the group consisting of

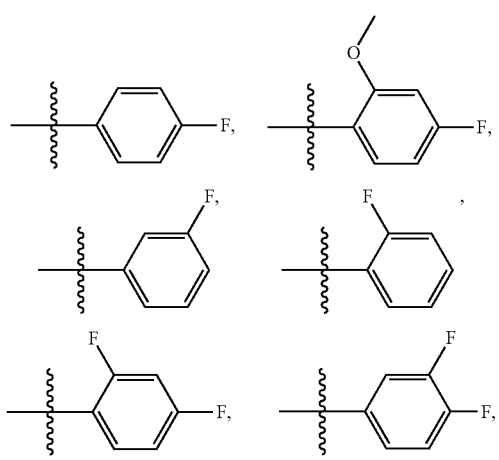

Exemplary compounds in this embodiment include those identified by ID NOS: B89, B96, B97, B125, B126, B129, B247, B250, and B251.

$R^1$ in this embodiment may be

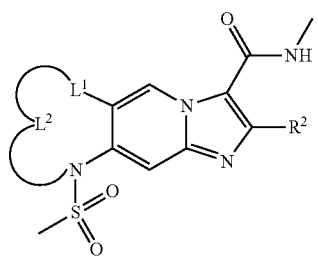

$R^2$ in this embodiment may be a phenyl substituted with one or more $R^{17}$ substituents.

$R^2$ in this embodiment may be a 4-phenoxyphenyl and the phenoxy group is substituted with one or more $R^{17}$ substituents.

$R^2$ in this embodiment may be selected from

In a sixth aspect of the invention is a compound of formula IV:

wherein,
- $L^1$, $L^2$ and —N(SO$_2$Me)— together with the attached carbons of the aromatic ring form a 5-12 member ring, containing 1-4 heteroatoms of N, O, S, P and/or Si;
- $L^1$ or $L^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;
- n is 0, 1, or 2;
- $R^2$ is an aryl or heteroaryl and may be substituted with one or more $R^{17}$ substituents;
- $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;
- $R^4$ and $R^5$ are independently methyl, ethyl, or cyclopropyl; and
- $R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, NR$^N$ and/or S; and
- $R^{17}$ is H, F, Cl or CN.

In a seventh aspect of the invention is a compound of formula V:

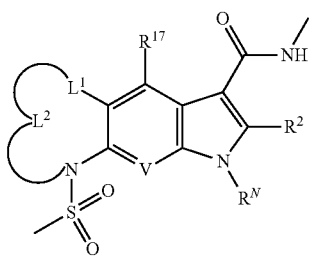

V wherein,
- $L^1$, $L^2$ and —N(SO$_2$Me)— together with the attached carbons of the aromatic ring form a 5-12 member ring, containing 1-4 heteroatoms of N, O, S, P and/or Si;
- $L^1$ or $L^2$ is independently selected from the group consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;
- n is 0, 1, or 2;
- $R^N$ is hydrogen, $C_{1-4}$ alkyl, $C_{3-6}$ cycloalkyl, $C_{4-5}$ heterocycle, aryl, heteroaryl, amide, sulfonamide, or carbamate;
- $R^2$ is an aryl or heteroaryl and may be substituted with one or more $R^{17}$ substituents;
- $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;
- $R^4$ and $R^5$ are independently methyl, ethyl, or cyclopropyl;
- $R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, NR$^N$ and/or S;
- $R^{17}$ is H, F, Cl or CN; and
- V is CH, N, CF, CCl, or CCN.

In an eighth aspect of the invention is a compound of formula VI:

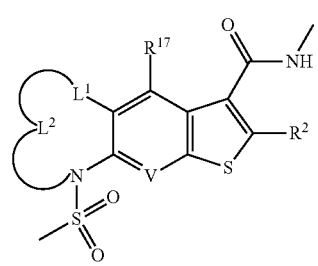

VI wherein,
- $L^1$, $L^2$ and —N(SO$_2$Me)— together with the attached carbons of the aromatic ring form a 5-12 member ring, containing 1-4 heteroatoms of N, O, S, P and/or Si;
- $L^1$ or $L^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;
- n is 0, 1, or 2;
- $R^2$ is an aryl or heteroaryl and may be substituted with one or more $R^{17}$ substituents;
- $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;
- $R^4$ and $R^5$ are independently methyl, ethyl, or cyclopropyl;
- $R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, NR$^N$ and/or S;
- $R^{17}$ is H, F, Cl or CN; and
- V is CH, N, CF, CCl, or CCN.

In a ninth aspect of the invention is a compound of formula VII:

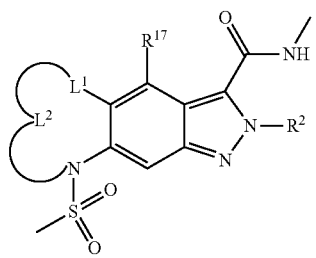

VII wherein,
- $L^1$, $L^2$ and —N(SO$_2$Me)— together with the attached carbons of the aromatic ring form a 5-12 member ring, containing 1-4 heteroatoms of N, O, S, P and/or Si;
- $L^1$ or $L^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a tenth aspect of the invention is a compound of formula VIII:

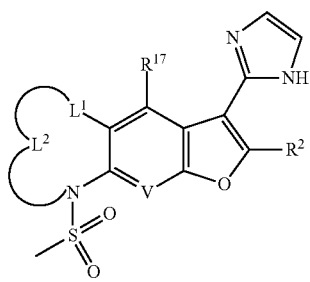

wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents, $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN.

In an eleventh aspect of the invention is a compound that has the structure:

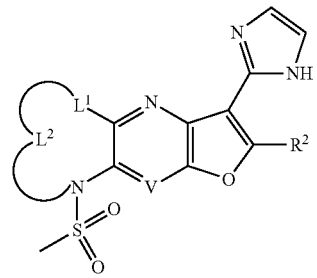

wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents, $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN

In a twelfth aspect of the invention is a compound of formula X,

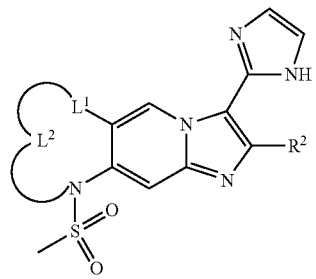

wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl; and $R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a thirteen aspect of the invention is a compound of formula XI,

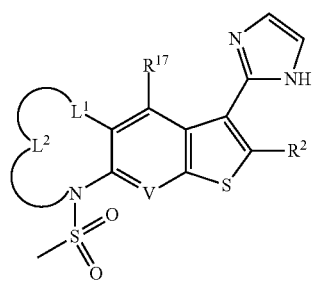

XI wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN.

In a fourteenth aspect of the invention is a compound of formula XII,

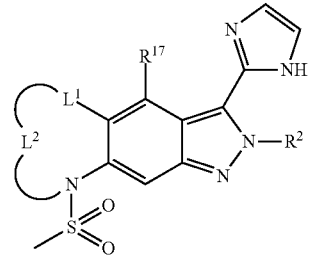

XII wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a fifteenth aspect, provided herein is a compound of formula XIV:

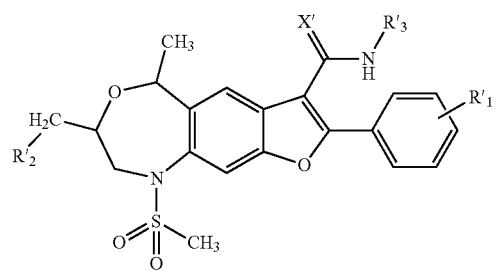

Formula XIV wherein:

$R'_1$ is selected from

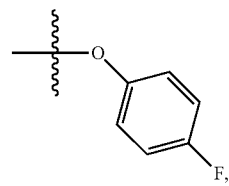 [SMILES: *Oc1ccc(F)cc1]

H, —F, —Cl, —Br, and —I;

R'$_2$ is selected from —OH, —OCH$_3$,

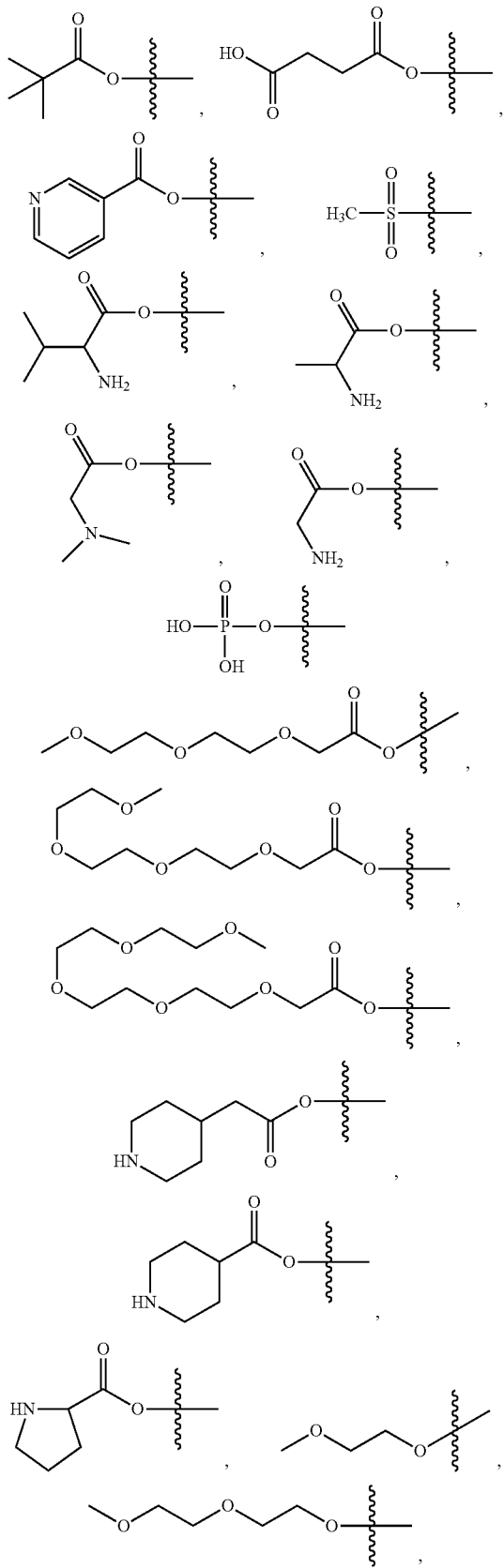

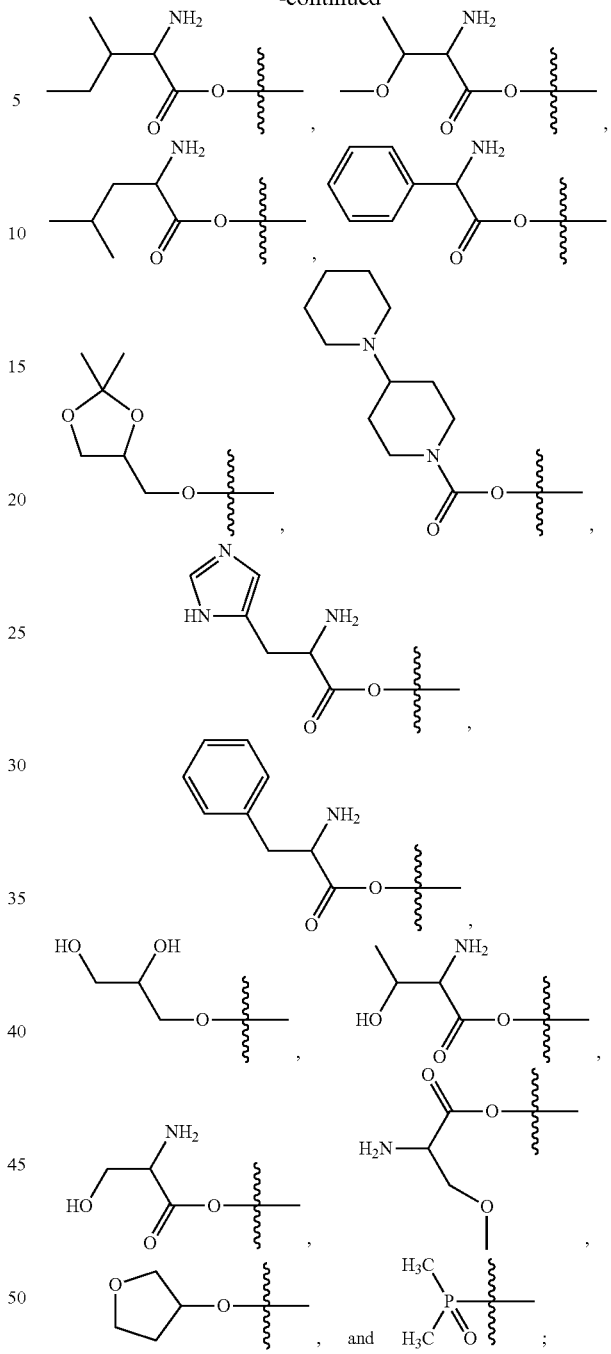

X' is selected from =O, =N—OH, =N—O(CH$_2$CH$_2$O)$_{0-8}$ CH$_3$, and =N—O(CH$_2$)$_{1-23}$CH$_3$, and R'$_3$ is selected from —CH$_3$ and —OCH$_3$. Examples of =N—O(CH$_2$CH$_2$O)$_{0-8}$CH$_3$ include =N—O—CH$_3$, =N—O(CH$_2$CH$_2$O)CH$_3$, =N—O(CH$_2$CH$_2$O)$_2$CH$_3$, =N—O(CH$_2$CH$_2$O)$_3$CH$_3$, =N—O(CH$_2$CH$_2$O)$_4$CH$_3$, =N—O(CH$_2$CH$_2$O)$_5$CH$_3$, =N—O(CH$_2$CH$_2$O)$_6$CH$_3$, =N—O(CH$_2$CH$_2$O)$_7$CH$_3$, and =N—O(CH$_2$CH$_2$O)$_8$CH$_3$. Examples of =N—O(CH$_2$)$_{1-23}$CH$_3$ include =N—O(CH$_2$)CH$_3$, =N—O(CH$_2$)$_2$CH$_3$, =N—O(CH$_2$)$_3$CH$_3$, =N—O(CH$_2$)$_4$CH$_3$, =N—O(CH$_2$)$_5$CH$_3$, =N—O(CH$_2$)$_6$CH$_3$, =N—O(CH$_2$)$_7$CH$_3$, =N—O(CH$_2$)$_8$CH$_3$, =N—O(CH$_2$)$_9$CH$_3$, =N—O(CH$_2$)$_{10}$CH$_3$, =N—O(CH$_2$)$_{11}$CH$_3$, =N—O(CH$_2$)$_{12}$CH$_3$, =N—O(CH$_2$)$_{13}$CH$_3$, =N—O(CH$_2$)$_{14}$CH$_3$,  =N—O(CH$_2$)$_{15}$CH$_3$,  =N—O(CH$_2$)$_{16}$CH$_3$, =N—O(CH$_2$)$_{17}$CH$_3$, =N—O(CH$_2$)$_{18}$CH$_3$, =N—O(CH$_2$)$_{19}$CH$_3$, =N—O(CH$_2$)$_{20}$CH$_3$, =N—O(CH$_2$)$_{21}$CH$_3$, =N—O(CH$_2$)$_{22}$CH$_3$, and =N—O(CH$_2$)$_{23}$CH$_3$.
In a first embodiment related to the fifteenth aspect, provided is a compound of formula XIV having the following features:
R'$_1$ is
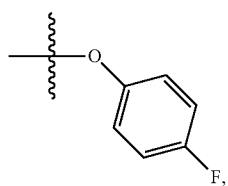 [SMILES: *Oc1ccc(F)cc1]
R'$_2$ is selected from —OH, —OCH$_3$,
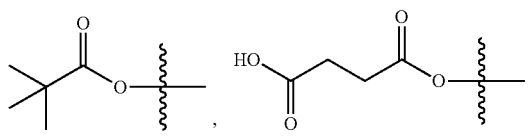
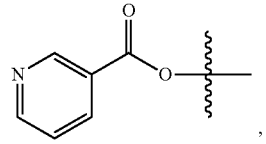
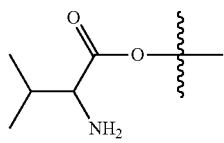
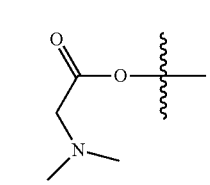
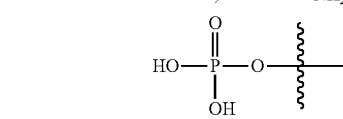
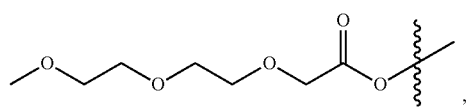
-continued
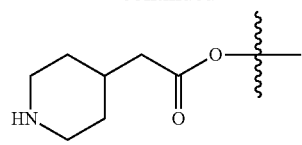
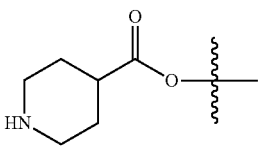
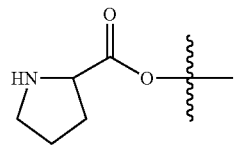
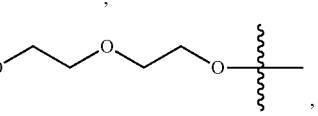
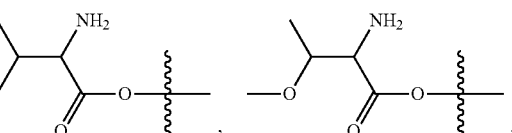
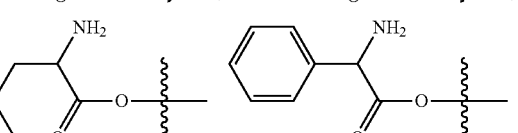
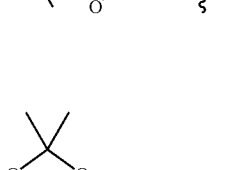 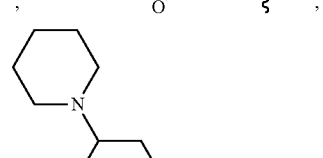
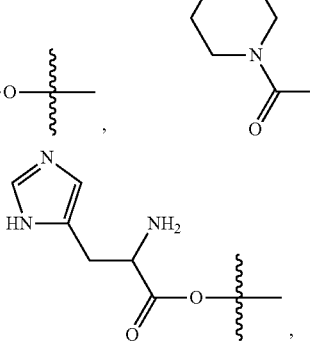
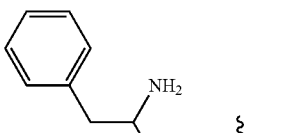
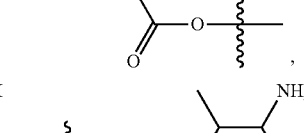
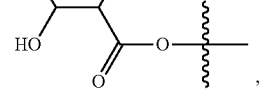

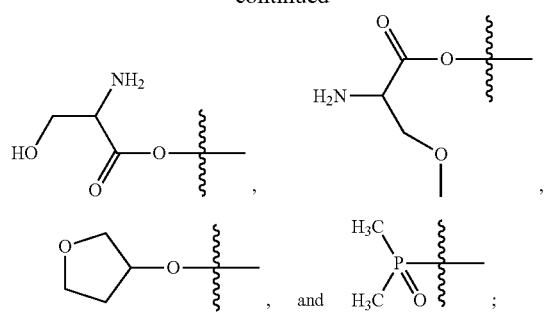
X' is =O, and
R'$_3$ is —CH$_3$.
In a second embodiment related to the fifteenth aspect, provided is a compound of formula XIV, wherein:
R'$_1$ is
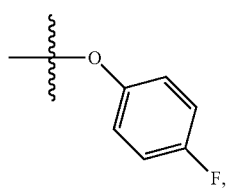 [SMILES: *Oc1ccc(F)cc1]
R'$_2$ is selected from —OH, —OCH$_3$,
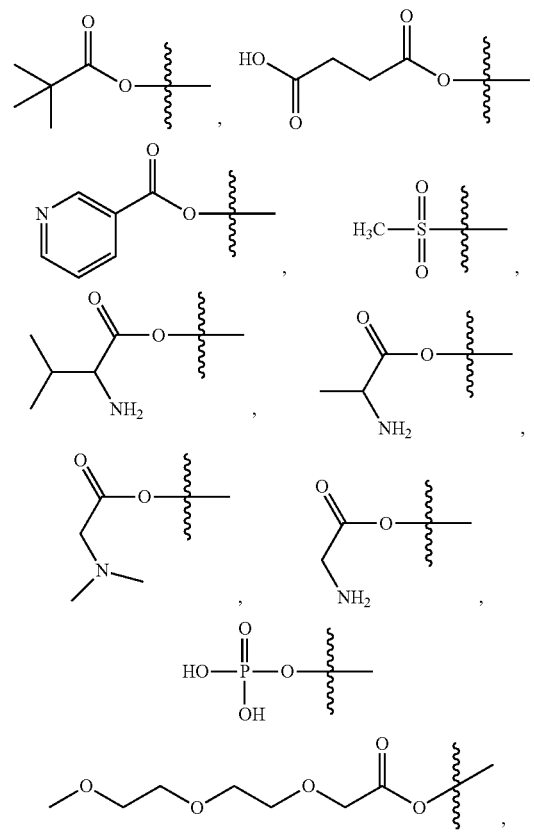
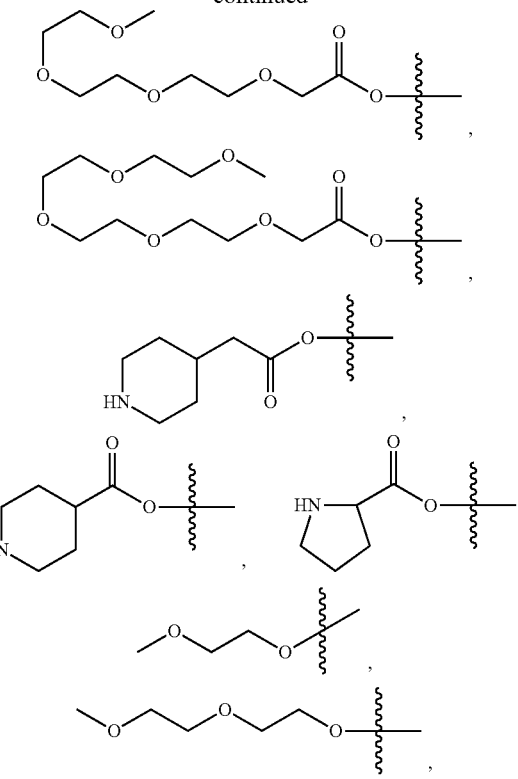
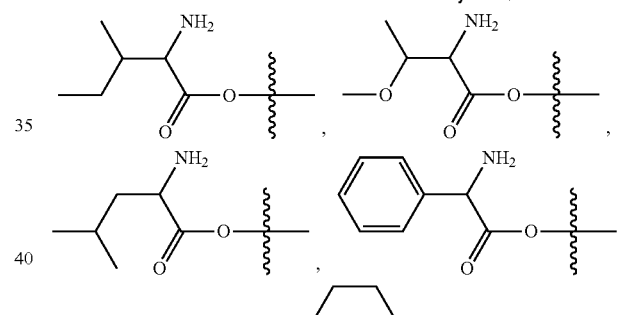
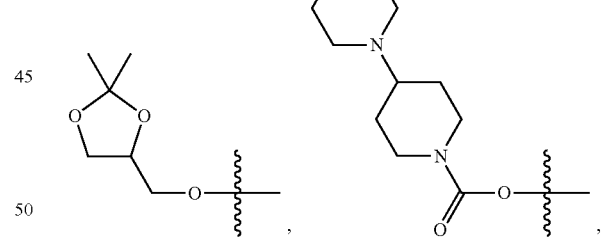
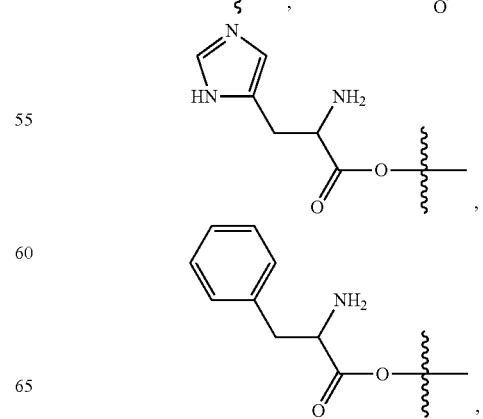

-continued

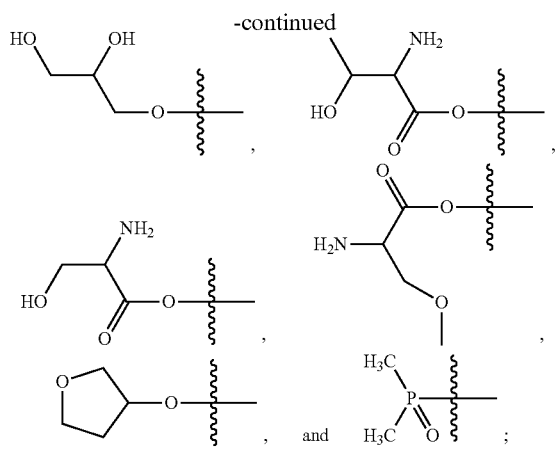

X' is =O, and
R'₃ is —OCH₃.

In a third embodiment related to the fifteenth aspect, provided is a compound of formula XIV, wherein:
R'₁ is

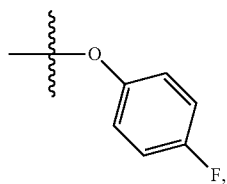 [SMILES: *Oc1ccc(F)cc1]

R'₂ is selected from —OH, —OCH₃,

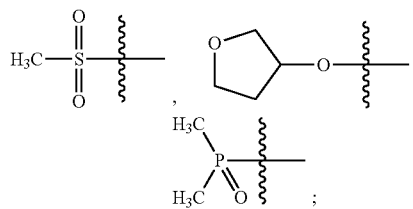

X' is selected from =N—OH, =N—OCH₃, =N—OCH₂CH₂OCH₃, =N—O(CH₂CH₂O)₂CH₃, and =N—O(CH₂CH₂O)₃CH₃, and
R'₃ is —CH₃.

In a fourth embodiment related to the fifteenth aspect, provided is a compound of formula XIV, wherein
R'₁ is —F,
R'₂ is selected from —OH, —OCH₃,

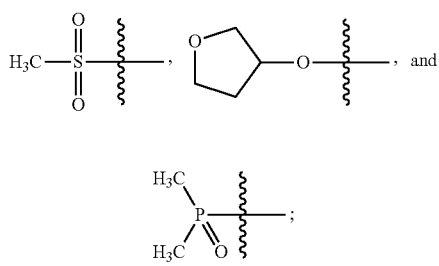

X' is selected from =N—OH, =N—OCH₃, =N—OCH₂CH₂OCH₃=N—O(CH₂CH₂O)₂CH₃ and =N—O(CH₂CH₂O)₃CH₃, and
R'₃ is —CH₃.

In a fifth embodiment related to the fifteenth aspect, provided is a compound of formula XIV, wherein:
R'₁ is —F,
R'₂ is selected from —OH, —OCH₃,

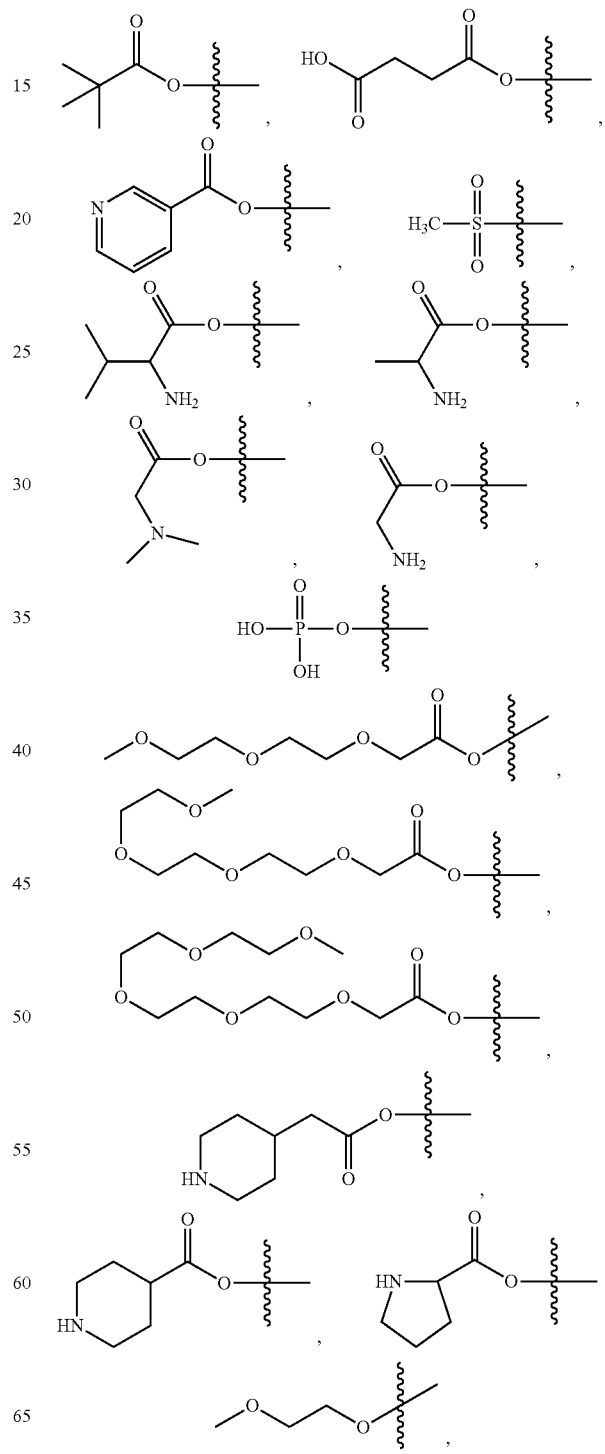

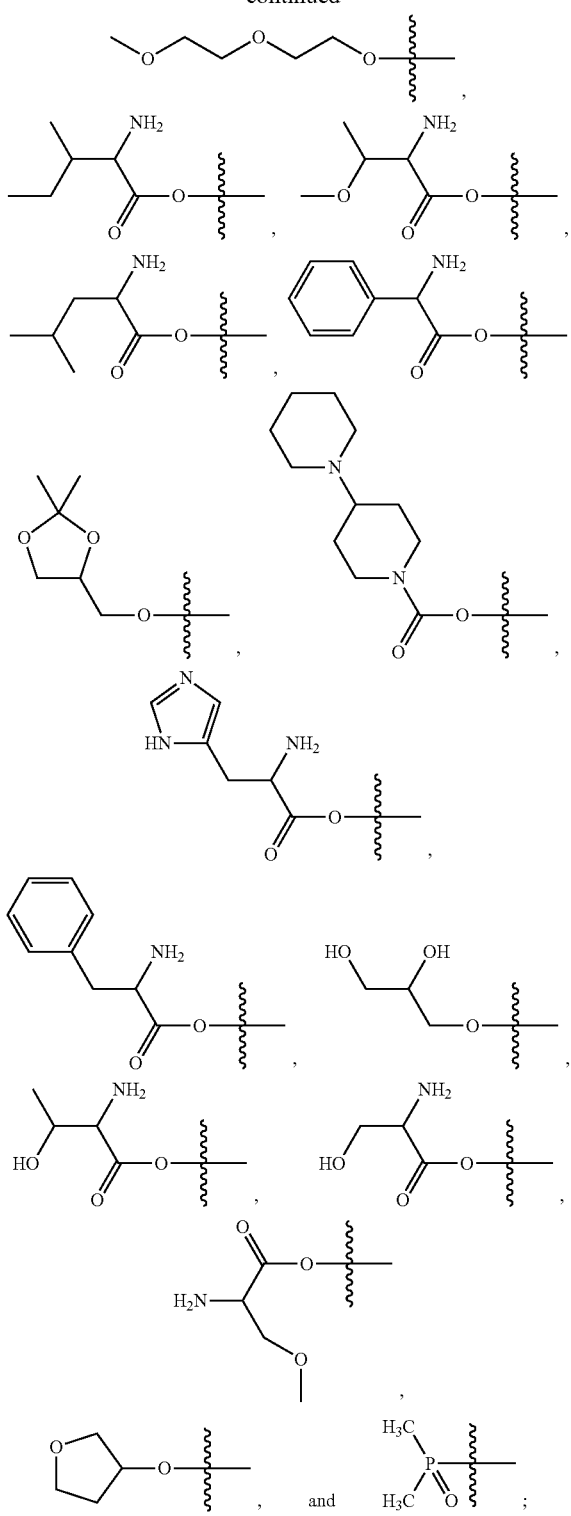
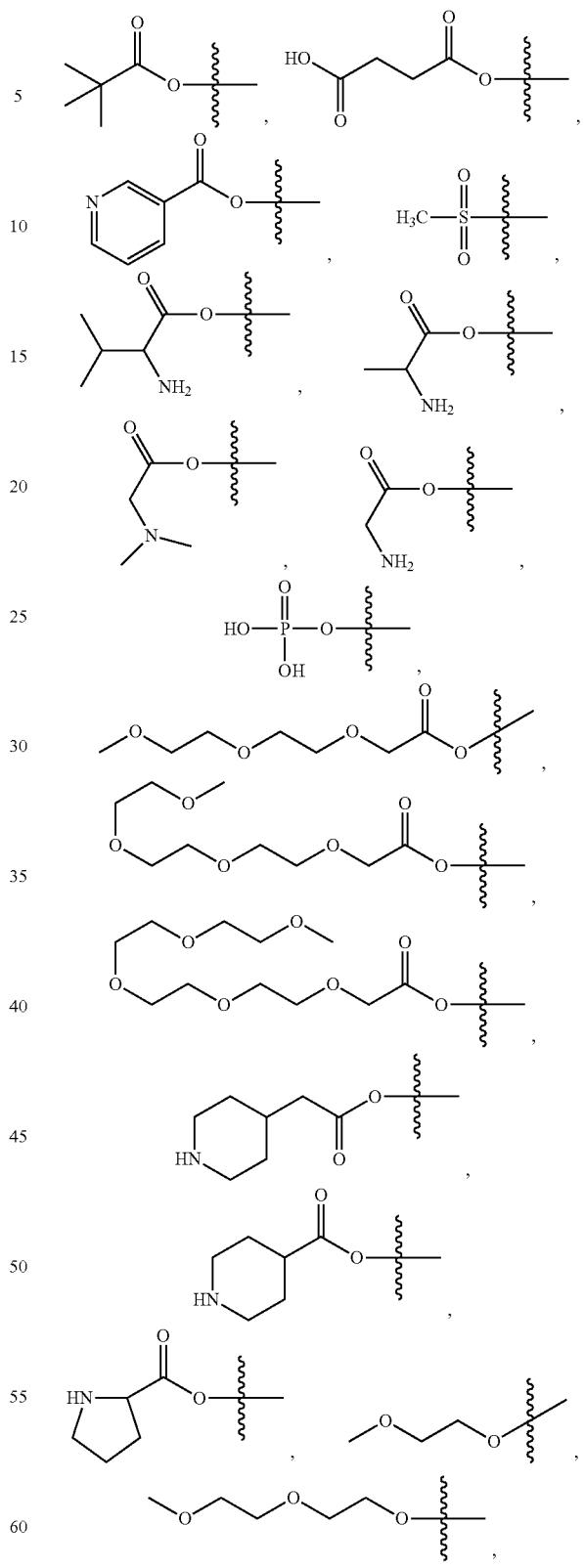
X' is =O, and
R'$_3$ is —CH$_3$.
In a sixth embodiment related to the fifteenth aspect, provided is a compound of formula XIV, wherein:
R'$_1$ is —F,
R'$_2$ is selected from —OH, —OCH$_3$,

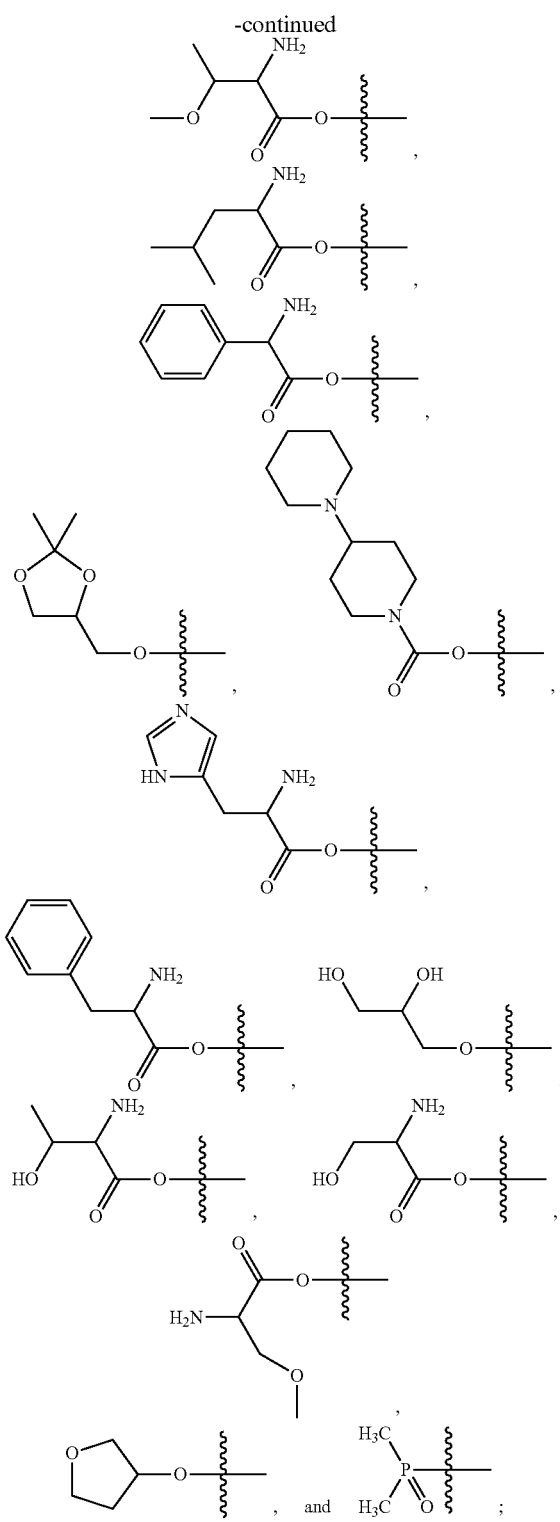

X' is =O, and
R'₃ is —OCH₃.

In a seventh embodiment related to the fifteenth aspect, and any one or more of the fourth, fifth or sixth embodiments, R'₁ is para-F.

In an eighth embodiment related to the fifteenth aspect, and the second and third embodiments thereof, R'₁ is para-

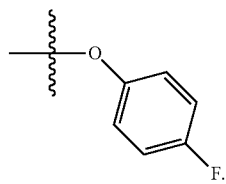 [SMILES: *Oc1ccc(F)cc1]

In a sixteenth aspect, provided herein is a compound according to structural Formula XIV-a:

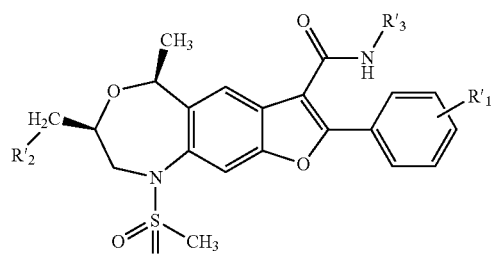

wherein:
R'₁ is selected from

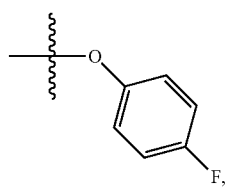

—H, —F, —Cl, —Br, and —I;
R'₂ is selected from —OH, —OCH₃,

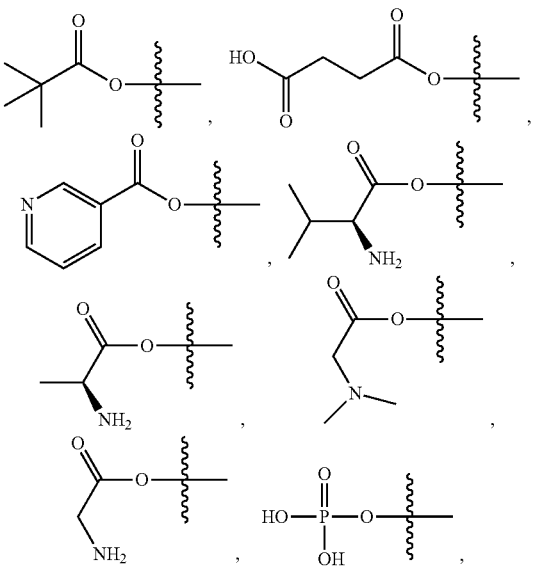

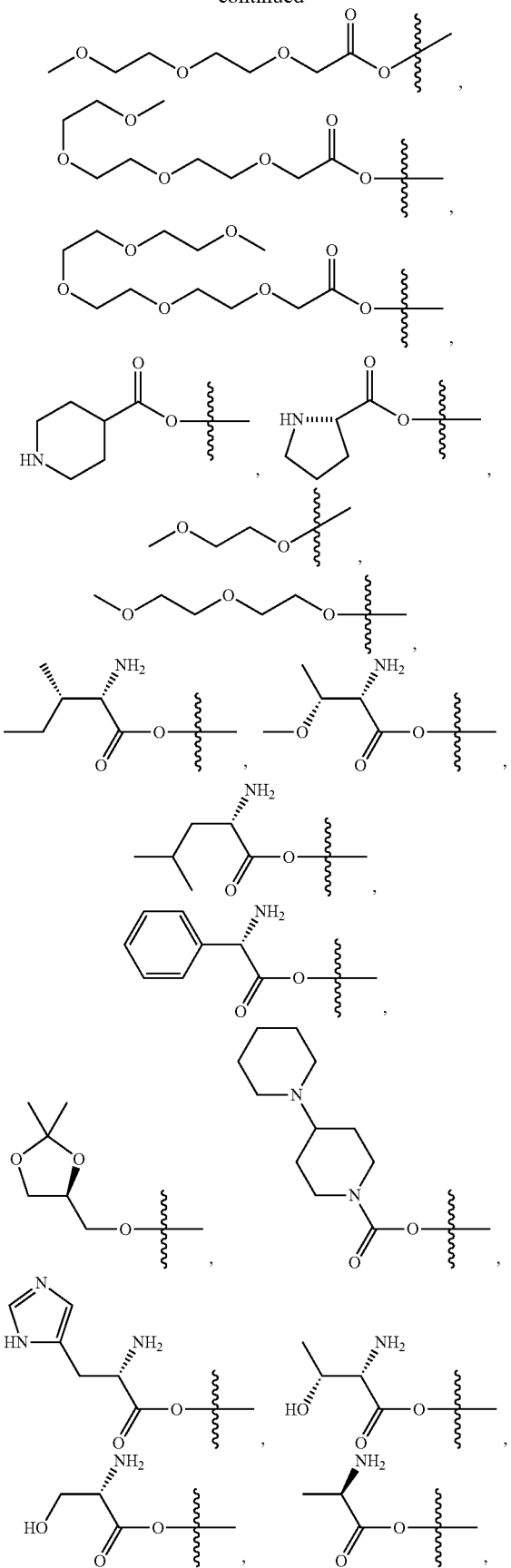
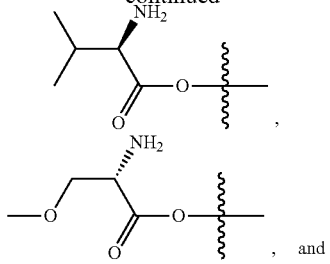
R'$_3$ is selected from —CH$_3$ and —OCH$_3$.
In a first embodiment related to the sixteenth aspect, in reference to Formula XIV-a:
R'$_1$ is
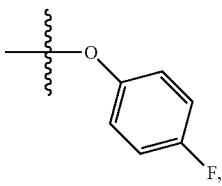
R'$_2$ is selected from —OH, —OCH$_3$,
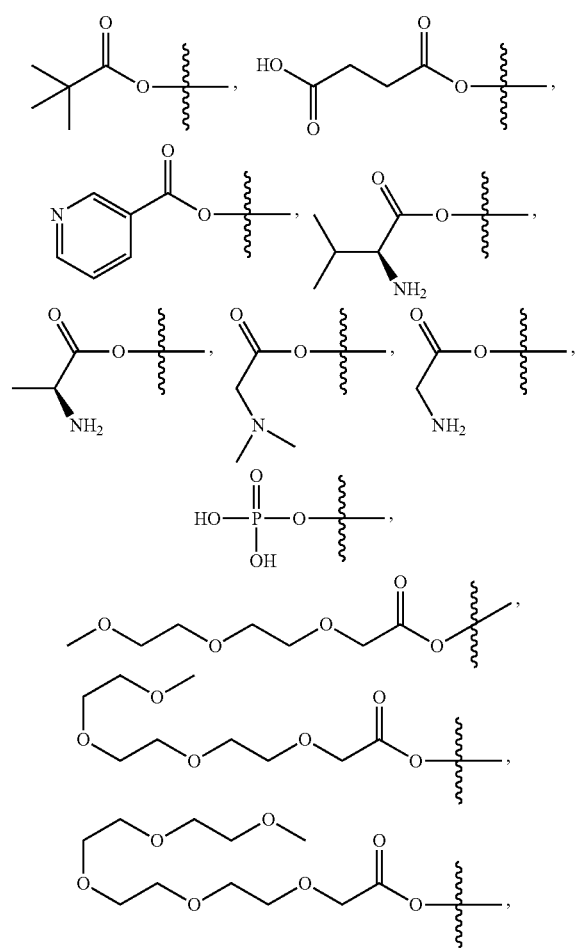

-continued
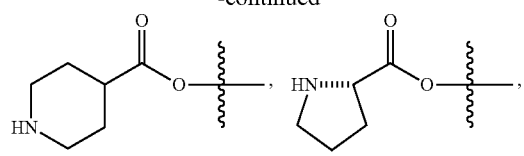
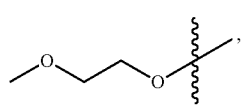
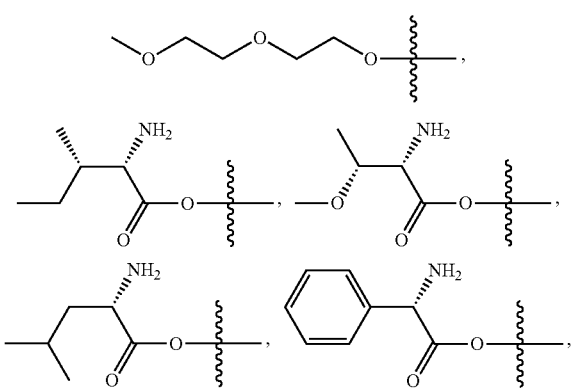
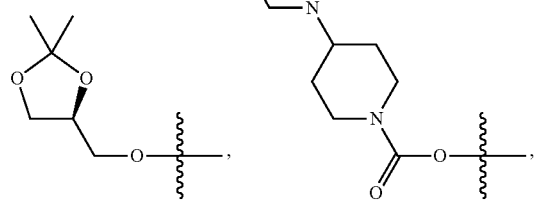
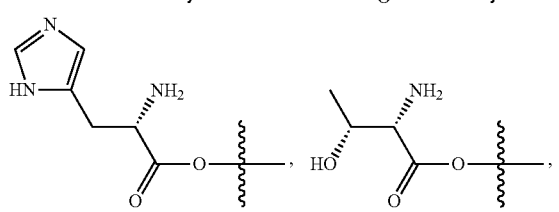
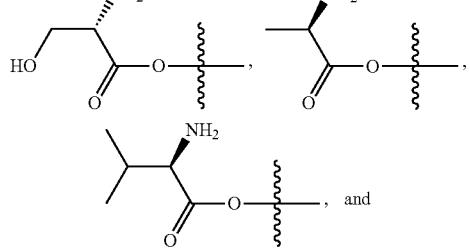
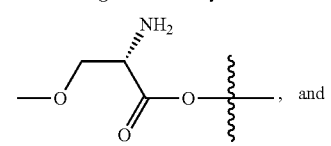
$R'_3$ is —$CH_3$.
In a second embodiment related to the sixteenth aspect, in reference to Formula XIV-a:
$R'_1$ is
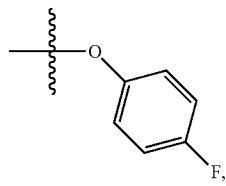
$R'_2$ is selected from —OH, —$OCH_3$,
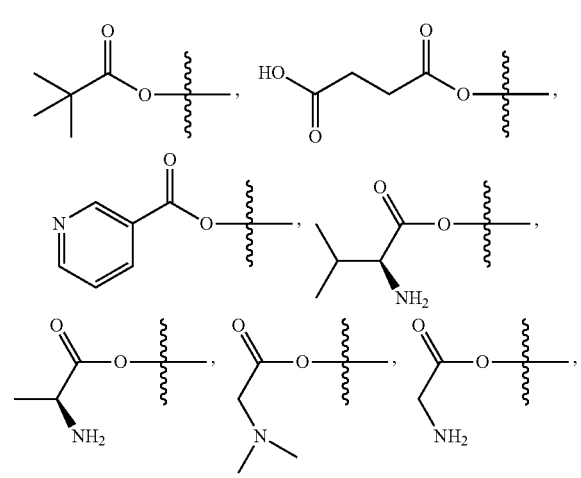
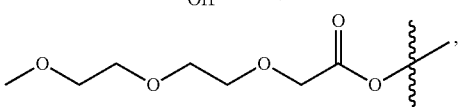
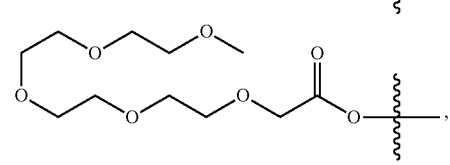
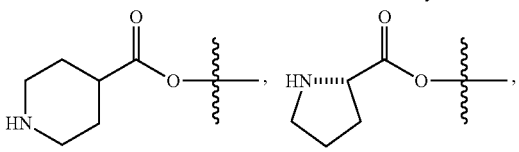
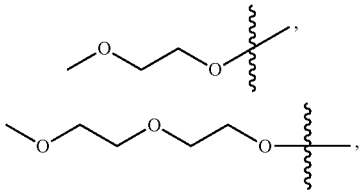

-continued
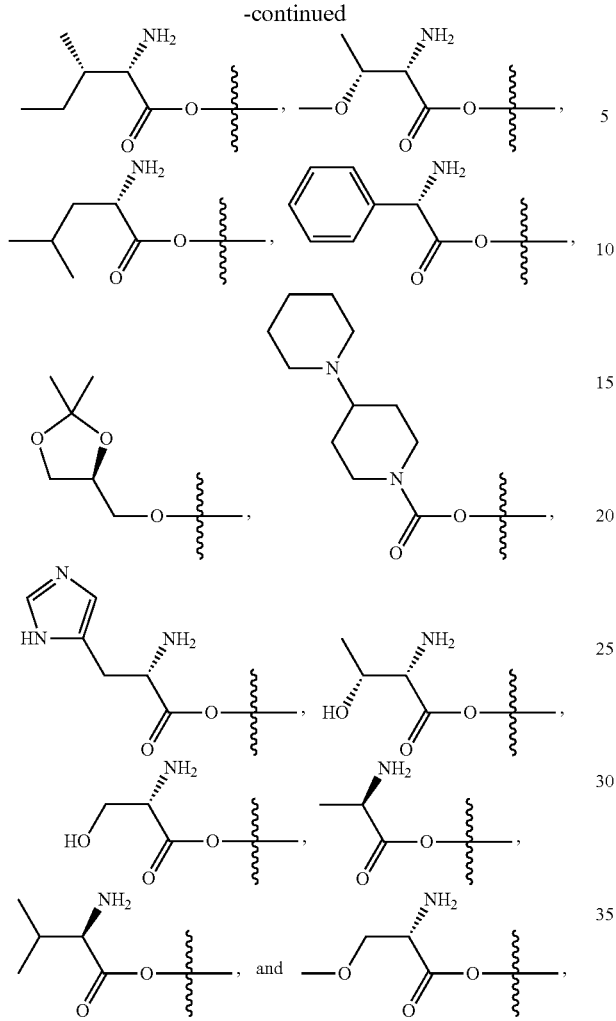
and
R'$_3$ is —OCH$_3$.
In a third embodiment related to the sixteenth aspect of the invention, in reference to Formula XIV-a:
R'$_1$ is —F,
R'$_2$ is selected from —OH, —OCH$_3$,
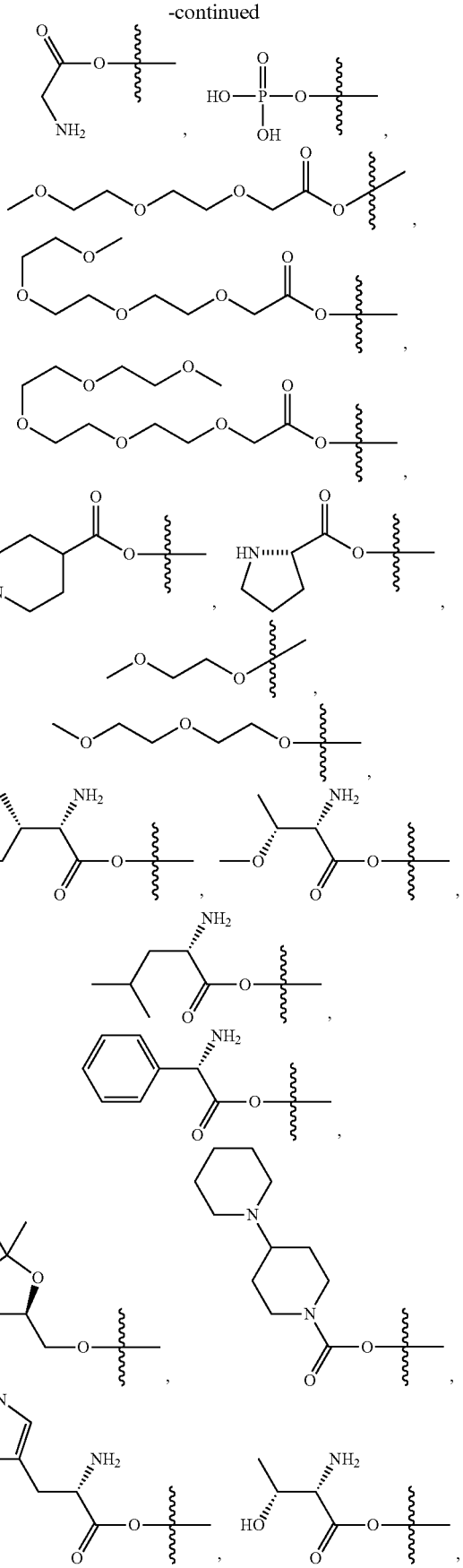

and
R'₃ is —CH₃.

In yet a fourth embodiment related to the sixteenth aspect of the invention, in reference to Formula XIV-a:
R'₁ is —F,
R'₂ is selected from —OH, —OCH₃, and
R'₃ is —OCH₃.

In yet a fifth embodiment related to the sixteenth aspect of the invention, in reference to formula XIV-a and in particular the third and fourth embodiments thereof, R'₁ is para-F.

In yet a sixth embodiment related to the sixteenth aspect of the invention, in reference to formula XIV-a and in particular the first and second embodiments thereof, R'₁ is para- In a seventeenth aspect of the invention, provided herein is a compound according to structural formula XIV-a,
Formula XIV-a
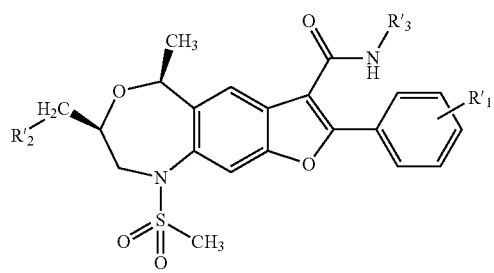
wherein:
R'₁ is selected from para-
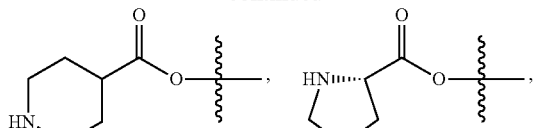
and para-F,
R'₂ is selected from
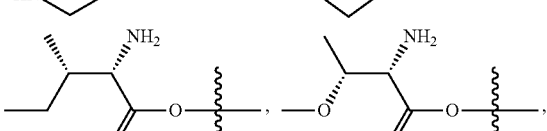
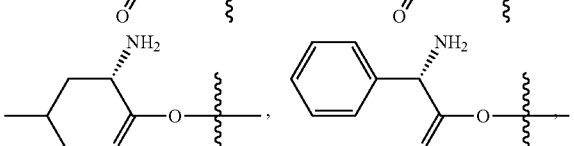
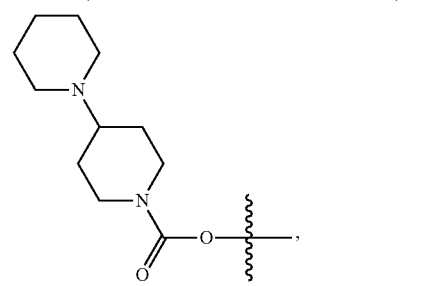
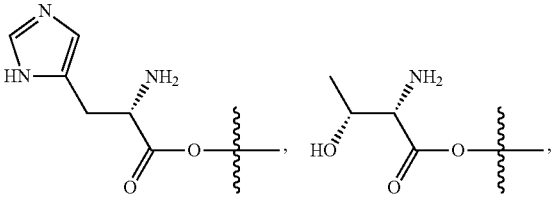
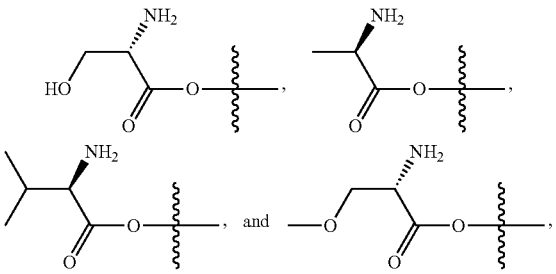
and
R'₃ is selected from —CH₃ and —OCH₃.
In a seventeenth aspect of the invention, provided herein is a compound having the structure:
XIV-b
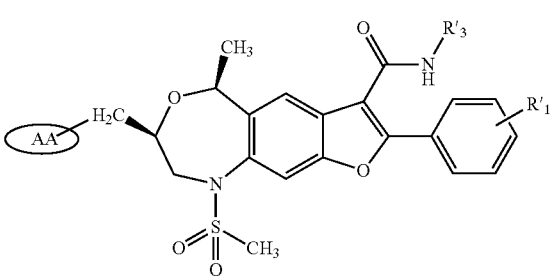

where R'₁ is either para-

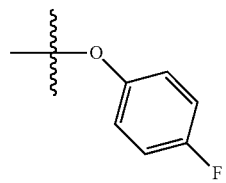 [SMILES: *Oc1ccc(F)cc1]

or para-F,

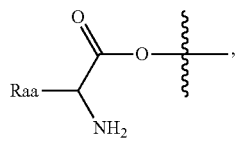

is a residue of an amino acid according to the structure:

$$\text{Raa} - \overset{\text{O}}{\underset{\text{NH}_2}{\text{C}}} - \text{O} - \xi,$$

where $R_{aa}$ is the side-chain of the amino acid, and $R'_3$ is selected from —CH₃ and —OCH₃.

In a first embodiment related to the seventeenth aspect of the invention, in reference to formula XIV-b,

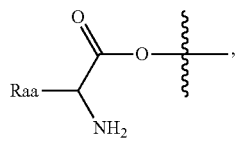

is a residue of an amino acid selected from the group consisting of D/L-, D- or L-alanine, isoleucine, leucine, valine, phenylalanine, tryptophan, tyrosine, asparagine, cysteine, glutamine, methionine, serine, threonine, aspartic acid, glutamic acid, arginine, histidine, lysine, glyine, and proline.

In an eighteenth aspect of the invention, provided herein is a compound selected from the group consisting of B243, B244, B245, B246, B247, B248, B249, B250, B251, B252, B253, B254, B255, B256, B257, B258, B259, B260, B261, B262, B263, B264, B265, B266, B267, B268, B269, B270, B271, B272, B273, B274, B275, B276, B277, B278, B279, B280, B281, B282, B283, B284, B285, B286, B287, B288, B289, D8, D9, D10, D11, D12, D13, D14, D26, D27, D37, D38, D42, D43, D44, D45, D46, D47, D48, D49, D50, D51, D52, D53, D54, D55, D56, D57, D71, D72, D75, D76, D77, D78, D79. D80, D81, D82, D83, D84, D85, D86, D87, D88, D89, and D90.

In an embodiment related to the eighteenth aspect of the invention, the compound is selected from B243, B244, B245, B246, B248, B249, B252, B253, B254, B255, B256, B257, B258, B259, B260, B261, B263, B264, B265, B266, B267, B268, B269, B270, B271, B272, B273, B275, B276, B277, B278, B280, B281, B282, B283, B284, B285, B286, and B289.

In a nineteenth aspect of the invention, provided is a compound selected from:

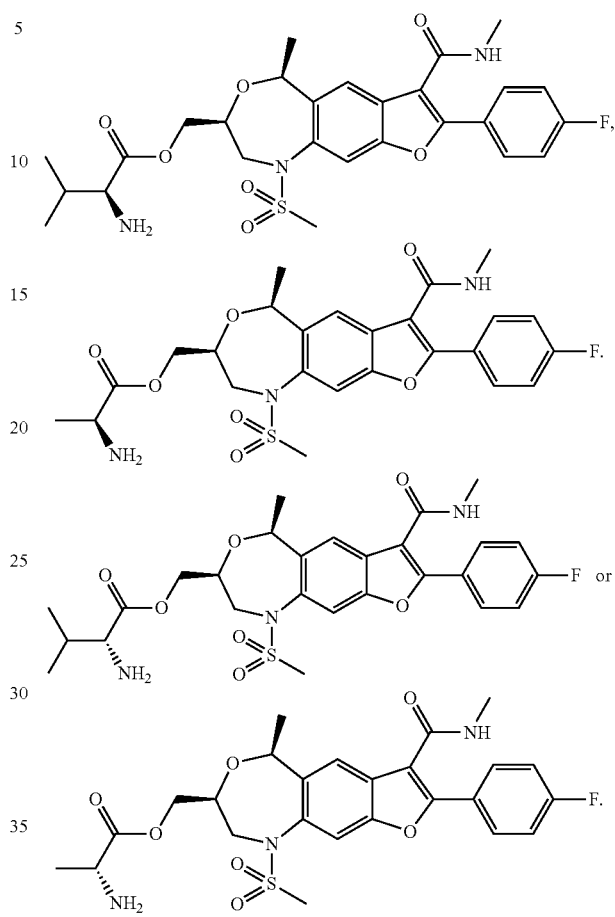

A twentieth aspect of the invention provides a pharmaceutical composition comprising the compounds of the invention, including the exemplary compounds identified by the above ID NOS. The composition may be formulated for oral delivery, and may include a second and/or third anti-HCV agents.

Also disclosed is a method of treating HCV infection in a subject by the steps of administering to the subject, a pharmaceutically acceptable dose of a compound as provided herein, and continuing the administering until a selected reduction of in the subject's HCV titer is achieved. Preferred compounds are those indicated above.

The compound administered may be one or more of the exemplary compounds identified by the ID NOS provided herein. Particular preferred compounds are identified above. The method may include administering to the subject, either in a single or separate administrations, a second anti-HCV agent selected from the group consisting of interferon-alpha, ribavirin, or both. The administering may be by oral route.

Also provided is a compound as provided herein, for use in the treatment of HCV infection in an infected subject. The compound may be one of those identified by ID NOS above.

Further disclosed is the use of a compound as set forth herein, such as one of the compounds identified by ID NOS, in the preparation of a medicament for the treatment of HCV in an HCV-infected subject.

Some of the compounds of the invention possess chiral carbons. The invention included all stereoisomeric forms, including enantiomers and diastereomers as well as mixtures of stereoisomers such as racemates. The stereoisomers or their precursors can be either asymmetrically synthesized or obtained by separations of the racemates according to methods commonly known in the art.

The invention is intended to include all isotopically labeled analogs of the compounds of the invention. Isotopes include those atoms having the same atomic number but different mass. For example, isotopes of hydrogen include $^2$H(D) and $^3$H(T) and isotopes of carbon include $^{13}$C and $^{14}$C. Isotopically labeled compounds of the invention can be prepared according to methods commonly known in the art. Such compounds may have various potential uses as, but not limited to, standards and reagents in determining biological/pharmacological activities. For those stable isotopically labeled compounds of the invention, they may have the potential to favorably modulate biological, pharmacological, or pharmacokinetic properties.

Additional embodiments of the compounds, compositions, methods, uses and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description, particularly when considered in conjunction with the accompanying examples.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "alkanoyl" as used herein contemplates a carbonyl group with a lower alkyl group as a substituent.

The term "alkenyl" as used herein contemplates substituted or unsubstituted, straight and branched chain alkene radicals, including both the E- and Z-forms, containing from two to eight carbon atoms. The alkenyl group may be optionally substituted with one or more substituents selected from the group consisting of halogen, —CN, —NO$_2$, CO$_2$R, C(O) R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, S(O)R, SO$_2$R, —SO$_3$R, —S(O)$_2$N(R$^N$)$_2$, phosphate, phosphonate, cycloalkyl, cycloalkenyl, aryl and heteroaryl.

The term "alkoxy" as used herein contemplates an oxygen with a lower alkyl group as a substituent and includes methoxy, ethoxy, butoxy, trifluoromethoxy and the like. It also includes divalent substituents linked to two separated oxygen atoms such as, without limitation, —O—CF$_2$—O—, —O—(CH$_2$)$_{1-4}$—O—(CH$_2$CH$_2$—O)$_{1-4}$— and —(O—CH$_2$CH$_2$—O)$_{1-4}$—.

The term "alkoxycarbonyl" as used herein contemplates a carbonyl group with an alkoxy group as a substituent.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "alkylene," "alkenylene" and "alkynylene" as used herein refers to the groups "alkyl," "alkenyl" and "alkynyl" respectively, when they are divalent, i.e., attached to two atoms.

The term "alkylsulfonyl" as used herein contemplates a sulfonyl group which has a lower alkyl group as a substituent.

The term "alkynyl" as used herein contemplates substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "amino" as used herein contemplates a group of the structure —NR$^N$$_2$.

The term "amino acid" as used herein contemplates a group of the structure

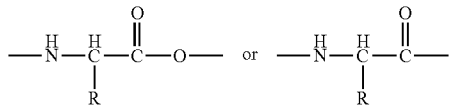

in either the D or the L configuration and includes but is not limited to the twenty "standard" amino acids: isoleucine, leucine, lysine, methionine, phenylalanine, threonine, tryptophan, valine, alanine, asparagine, aspartate, cysteine, glutamate, glutamine, glycine, proline, serine, tyrosine, arginine and histidine. The present invention also includes, without limitation, D-configuration amino acids, beta-amino acids, amino acids having side chains as well as all non-natural amino acids known to one skilled in the art.

The term "aralkyl" as used herein contemplates a lower alkyl group which has as a substituent an aromatic group, which aromatic group may be substituted or unsubstituted. The aralkyl group may be optionally substituted with one or more substituents selected from halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "arylsulfonyl" as used herein contemplates a sulfonyl group which has as a substituent an aryl group. The term is meant to include, without limitation, monovalent as well as multiply valent aryls (eg, divalent aryls).

The term "carbamoyl" as used herein contemplates a group of the structure

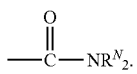

The term "carbonyl" as used herein contemplates a group of the structure

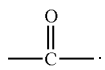

The term "carboxyl" as used herein contemplates a group of the structure

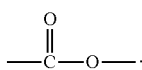

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "cycloalkenyl" as used herein contemplates substituted or unsubstituted cyclic alkenyl radicals containing from four to twelve carbon atoms in which there is at least one double bond between two of the ring carbons and includes cyclopentenyl, cyclohexenyl and the like. The term "cycloalkenyl" also includes polycyclic systems having two rings in which two or more atoms are common to two adjoining rings (the rings are "fused"). The cycloalkenyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "halo" or "halogen" as used herein includes fluorine, chlorine, bromine and iodine.

The term "heteroalkyl" as used herein contemplates an alkyl with one or more heteroatoms.

The term "heteroatom", particularly within a ring system, refers to N, O and S.

The term "heterocyclic group," "heterocycle" or "heterocyclic ring" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "oxo" as used herein contemplates an oxygen attached with a double bond.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained. "Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

The terms "phosphate" and "phosphonate" as used herein refer to the moieties having the following structures, respectively:

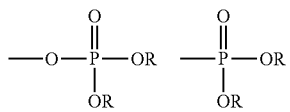

The terms "salts" and "hydrates" refers to the hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity, flowability and manufacturability of the resulting bulk drug.

The term sulfonamide as used herein contemplates a group having the structure

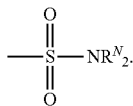

The term "sulfonate" as used herein contemplates a group having the structure

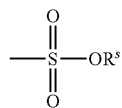

wherein $R^s$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

The term "sulfonyl" as used herein contemplates a group having the structure

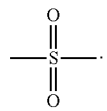

"Substituted sulfonyl" as used herein contemplates a group having the structure

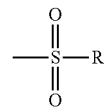

including, but not limited to alkylsulfonyl and arylsulfonyl.

The term "thiocarbonyl," as used herein, means a carbonyl wherein an oxygen atom has been replaced with a sulfur.

Each R is independently selected from hydrogen, —OH, —CN, —NO$_2$, halogen, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino, and oxo.

Each $R^N$ is independently selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide. Two $R^N$ may be taken together with C, O, N or S to which they are attached to form a five to seven membered ring which may optionally contain a further heteroatom.

The compounds of the present invention may be used to inhibit or reduce the activity of HCV, particularly HCV's NS5B protein. In these contexts, inhibition and reduction of activity of the NS5B protein refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

In a first aspect of the invention, compounds of formula I are provided:

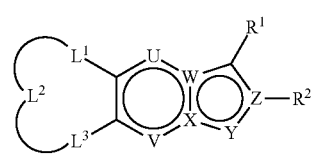

wherein, $L^1$, $L^2$ and $L^3$ together with the attached carbons of the aromatic ring to form a 5-12 member ring, containing 0-4 heteroatoms of N, O, S, P and/or Si;

$L^1$, $L^2$, or $L^3$ is independently selected from a group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

U or V is independently CH, N, CF, CCl, or CCN;

W, X, or Z is independently C or N;

Y is NR$^N$, N, O, S, Se, or —CR$^a$R$^b$;

$R^N$ is hydrogen, $C_{1-4}$ alkyl, $C_{3-6}$ cycloalkyl, $C_{4-5}$ heterocycle, aryl, heteroaryl, amide, sulfonamide, or carbamate;

$R^a$, $R^b$ is independently hydrogen, methyl, or together form a $C_{3-6}$ cycloalkyl bearing 0-1 heteroatom of O or $NR^3$;

$R^1$ is selected from hydrogen, halide, —$CF_3$, —CN, —C(O)H, —C(O)$OR^6$—, —C(O)$NHR^7$, —C(O)N(OH)$R^7$, —C(=$NR^7$)OMe, —C(=NOR')$NHR^7$, —CH($CF_3$)$NHR^8$, —CH(CN)$NHR^9$, —S(O)$_2NHR^{10}$, —C(=NCN)$NHR^{11}$,

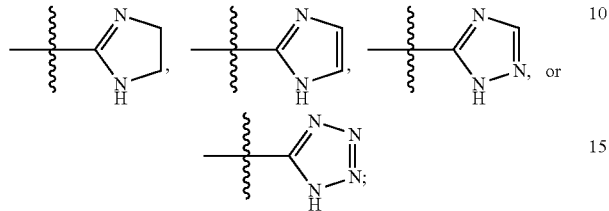

R' is selected from hydrogen, —(CH$_2$CH$_2$O)$_{0-8}$-Me, $C_{2-24}$ alkyl optionally containing 0-6 heteroatoms of O, $NR^N$ and/or S, and $C_{3-8}$ cycloalkyl optionally containing 0-2 heteroatom of O, $NR^N$, and/or S;

$R^2$ is a substituted or unsubstituted aryl or heteroaryl;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^6$ is hydrogen, allyl, $C_{1-4}$ alkyl, cyclopropyl, or benzyl;

$R^7$ is hydrogen, $C_{1-4}$ alkyl, cyclopropyl, $C_{1-4}$ alkoxy, cyclopropoxy, alkylsulfonyl, or cycloalkylsulfonyl;

$R^8$, $R^9$, $R^{10}$, or $R^{11}$ is independently hydrogen, $C_{1-4}$ alkyls, cyclopropyl, $C_{1-4}$ alkoxys, or cyclopropoxy; and $R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and In a first embodiment of the first aspect,

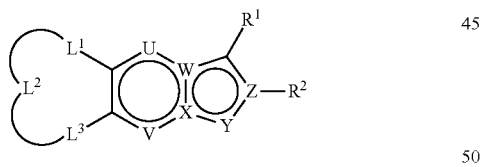

is selected from the group consisting of

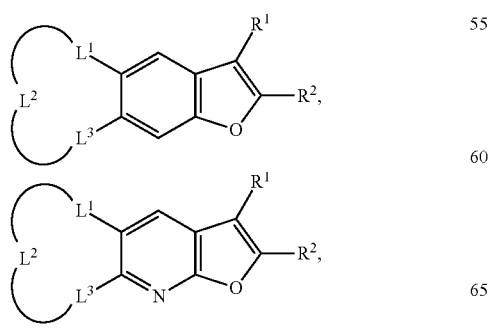

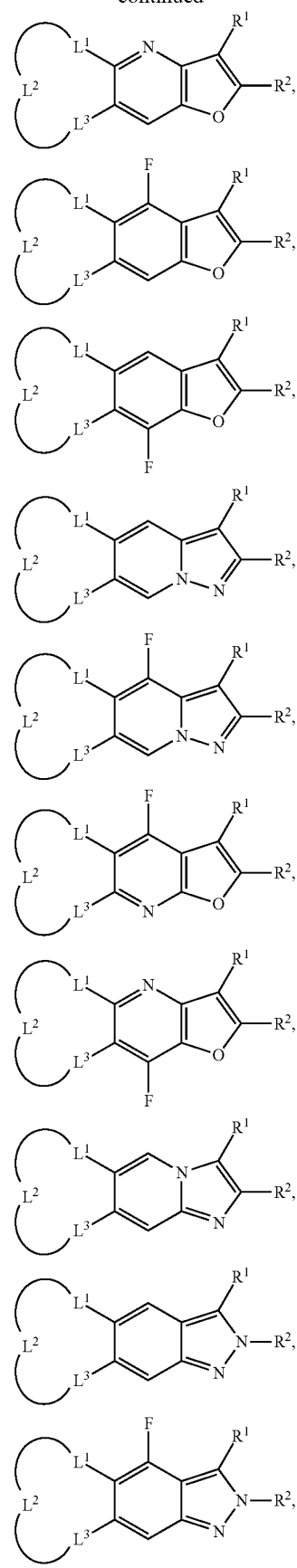

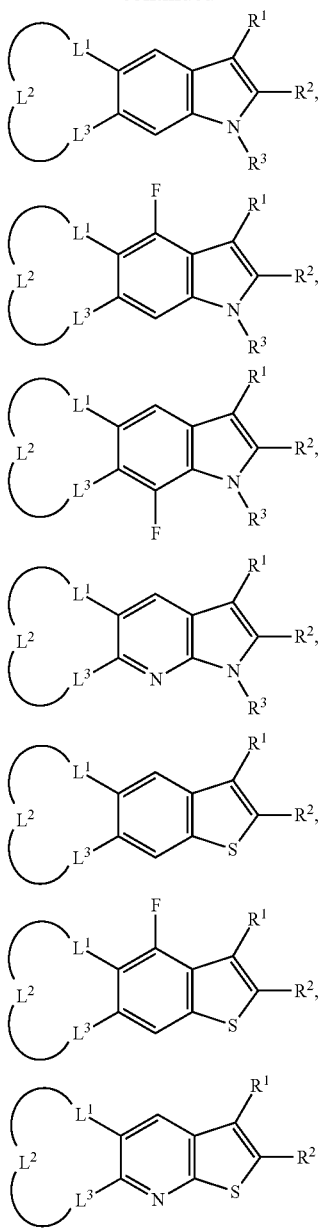

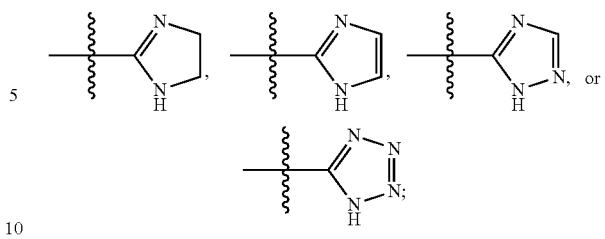

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

R$^2$ is a substituted or unsubstituted aryl or heteroaryl;

R$^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

R$^4$ and R$^5$ are independently methyl, ethyl, or cyclopropyl;

R$^6$ is hydrogen, allyl, C$_{1-4}$ alkyl, cyclopropyl, or benzyl;

R$^7$ is hydrogen, C$_{1-4}$ alkyl, cyclopropyl, C$_{1-4}$ alkoxy, cyclopropoxy, alkylsulfonyl, or cycloalkylsulfonyl;

R$^8$, R$^9$, R$^{10}$, or R$^{11}$ is independently hydrogen, C$_{1-4}$ alkyls, cyclopropyl, C$_{1-4}$ alkoxys, or cyclopropoxy;

R$^{15}$, R$^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R$^{15}$ and R$^{16}$ together are a carbonyl or C$_{1-4}$ alkenylidene or R$^{15}$ and R$^{16}$ joined together with the attached carbon are 3-6 member ring optionally containing 0-3 heteroatoms of O, NR$^N$ and/or S; and In a second embodiment of the first aspect,

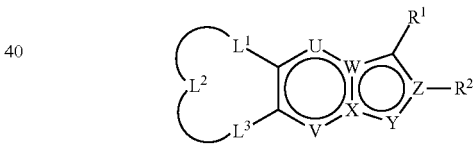

is selected from the group consisting of wherein,

L$^1$, L$^2$ and L$^3$ together with the attached carbons of the aromatic ring form a 5-12 member ring, containing 0-4 heteroatoms of N, O, S, P and/or Si;

L$^1$, L$^2$, or L$^3$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R$^1$ is selected from hydrogen, halide, —CF$_3$, —CN, —C(O)H, —C(O)OR$^6$—, —C(O)NHR$^7$, —C(O)N(OH)R$^7$, —C(=NR$^7$)OMe, —C(=NOR')NHR$^7$, —CH(CF$_3$)NHR$^8$, —CH(CN)NHR$^9$, —S(O)$_2$NHR$^{10}$, —C(=NCN)NHR$^{11}$,

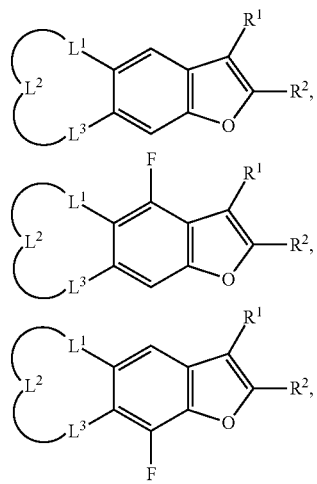

-continued

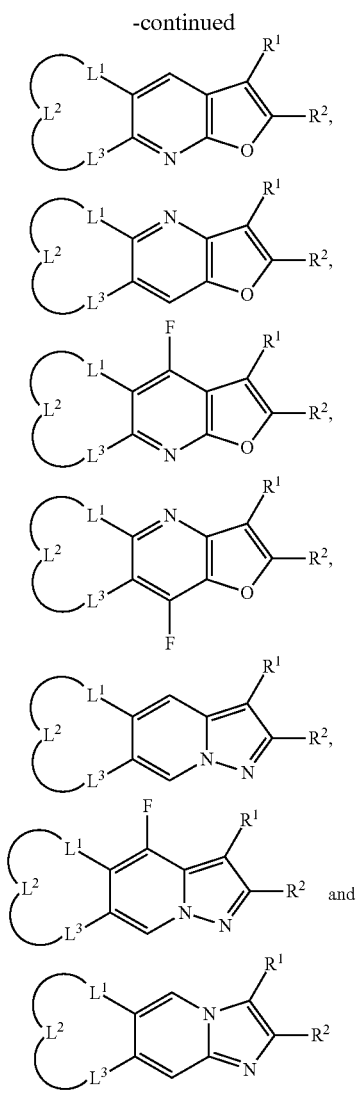

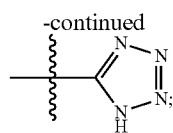

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

R$^2$ is a substituted or unsubstituteed aryl or heteroaryl;

R$^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

R$^4$ and R$^5$ are independently methyl, ethyl, or cyclopropyl;

R$^6$ is hydrogen, allyl, C$_{1-4}$ alkyl, cyclopropyl, or benzyl;

R$^7$ is hydrogen, C$_{1-4}$ alkyl, cyclopropyl, C$_{1-4}$ alkoxy, cyclopropoxy, alkylsulfonyl, or cycloalkylsulfonyl;

R$^8$, R$^9$, R$^{10}$, or R$^{11}$ is independently hydrogen, C$_{1-4}$ alkyls, cyclopropyl, C$_{1-4}$ alkoxys, or cyclopropoxy; and R$^{15}$, R$^{16}$ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R$^{15}$ and R$^{16}$ together are a carbonyl or C$_{1-4}$ alkenylidene or R$^{15}$ and R$^{16}$ joined together with the attached carbon are 3-6 member ring optionally containing 0-3 heteroatoms of O, NR$^N$ and/or S; and In a third embodiment of the first aspect, R$^1$ is hydrogen, halide, —C(O)OR$^6$—, —C(O)NHR$^7$, —C(═NR$^7$)OMe, —C(O)N(OH)R$^7$, —C(═NOR')NHR$^7$, —CH(CF$_3$)NHR$^8$, —CH(CN)NHR$^9$,

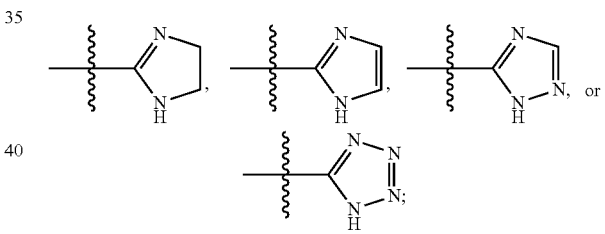

wherein,

L$^1$, L$^2$ and L$^3$ together with the attached carbons of the aromatic ring form a 5-9 member ring, containing 0-4 heteroatoms of N, O, S, P and/or Si;

L$^1$, L$^2$, or L$^3$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R$^1$ is selected from hydrogen, halide, —CF$_3$, —CN, —C(O)H, —C(O)OR$^6$—, —C(O)NHR$^7$, —C(O)N(OH)R$^7$, —C(═NR$^7$)OMe, —C(═NOR')NHR$^7$, —CH(CF$_3$)NHR$^8$, —CH(CN)NHR$^9$, —S(O)$_2$NHR$^{10}$, —C(═NCN)NHR$^{11}$,

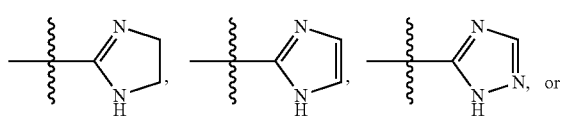

wherein,

R' is selected from hydrogen, —(CH$_2$CH$_2$O)$_{0-8}$-Me (e.g., Me, —(CH$_2$CH$_2$O)Me, —(CH$_2$CH$_2$O)$_2$-Me, —(CH$_2$CH$_2$O)$_3$-Me, —(CH$_2$CH$_2$O)$_4$-Me, —(CH$_2$CH$_2$O)$_5$- Me, —(CH$_2$CH$_2$O)$_6$-Me, —(CH$_2$CH$_2$O)$_7$-Me, —(CH$_2$CH$_2$O)$_8$-Me,) C$_{2-24}$ alkyl (e.g., C$_1$, C$_2$, C$_3$ C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$ alkyl) optionally containing 0-6 heteroatoms of O, NR$^N$ and/or S, and C$_{3-8}$ cycloalkyl optionally containing 0-2 heteroatom of O, NR$^N$, and/or S;

R$^6$ is hydrogen, allyl, C$_{1-4}$ alkyl, cyclopropyl, or benzyl;

R$^7$ is hydrogen, C$_{1-4}$ alkyl, cyclopropyl, C$_{1-4}$ alkoxy, cyclopropoxy, alkylsulfonyl, or cycloalkylsulfonyl; and R$^8$, R$^9$, R$^{10}$, or R$^{11}$ is independently hydrogen, C$_{1-4}$ alkyls, cyclopropyl, C$_{1-4}$ alkoxys, or cyclopropoxy.

In a fourth embodiment of the first aspect, R$^1$ is hydrogen, Br, I, —COOH, —C(O)OMe, —C(O) OEt, —C(O)O tBu, —C(O)NHMe, —C(O)NHOMe, —C(═NOMe)NHMe, —C(═NOH)NHMe, —C(═NMe)OMe, —C(O)N(OH)Me, —C(O)NHS(O)$_2$Me, —CH(CF$_3$)NHMe, —CH(CN)NHMe, —C(═NCN)NHMe,

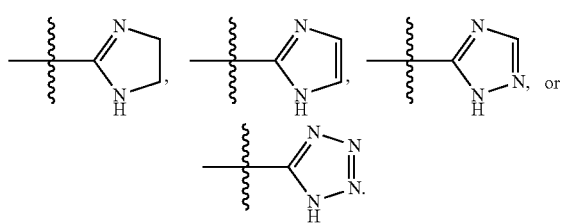

In a fifth embodiment of the first aspect, $R^1$ is —C(O)NHMe or

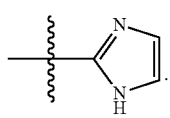

In a sixth embodiment of the first aspect, $R^2$ is selected from the group consisting of

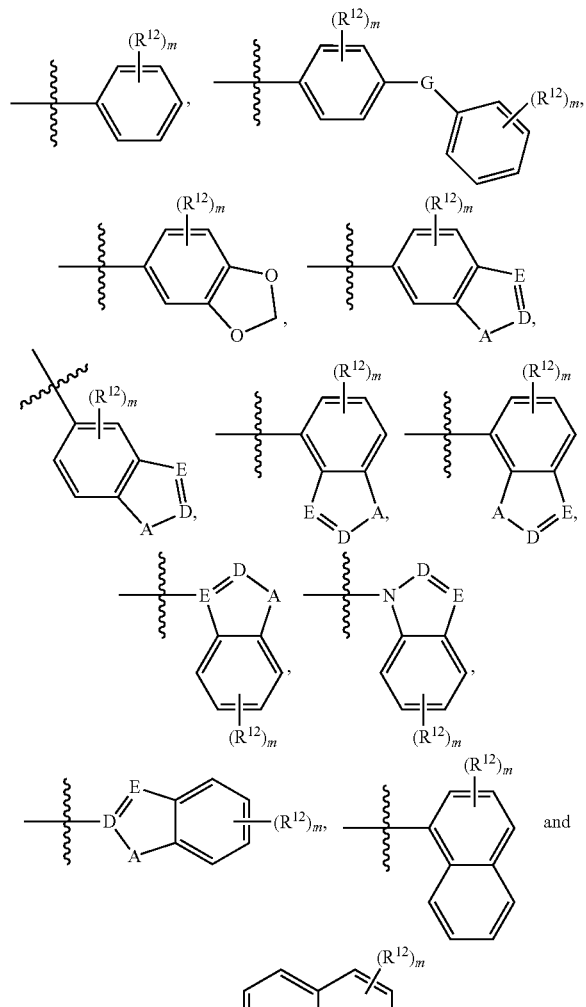

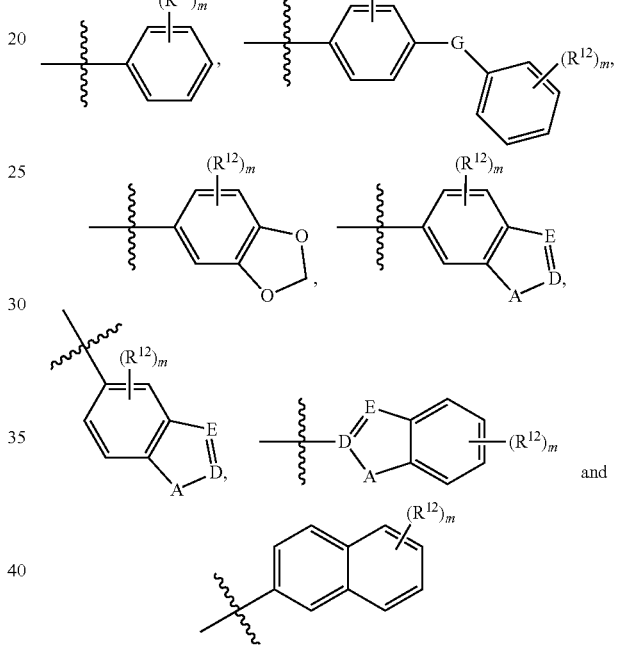

wherein,

Each phenyl moiety is optionally substituted with 0-2 nitrogen atoms;

$R^{12}$ is selected from the group of hydrogen, halide, —CN, —OCHF$_2$, —OCF$_3$, alkyl, cycloalkyl, alkoxy, cycloalkoxy, arylalkyl, aryloxy, alkenyl, alkynyl, amide, alkylsulfonyl, arylsulfonyl, sulfonamide, carbamate;

m is 0, 1, 2, 3, or 4;

G is O, NR$^N$, S, or CR$^a$R$^b$;

A is N, O, S, or or CR$^a$R$^b$; and

D, E is independently C or N.

In a seventh embodiment of the first aspect, $R^2$ is selected from the group consisting of

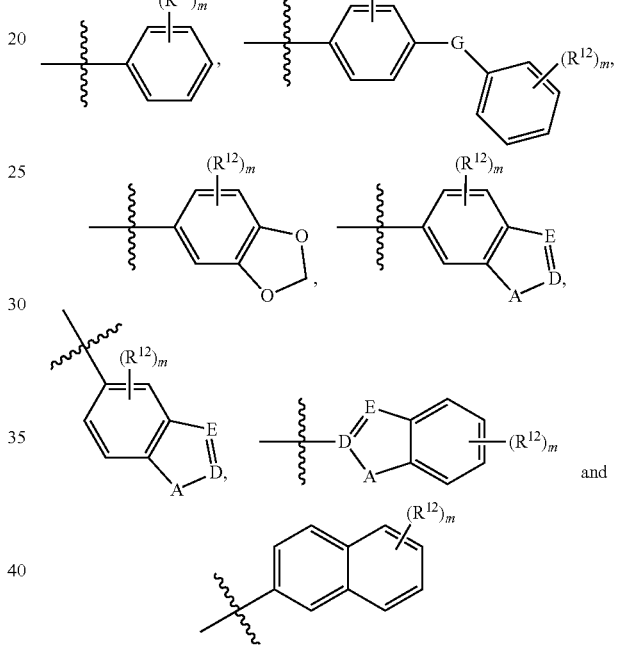

wherein,

Each phenyl moiety is optionally substituted with 0-2 nitrogen atoms;

$R^{12}$ is selected from the group of hydrogen, halide, —CN, —OCHF$_2$, —OCF$_3$, alkyl, cycloalkyl, alkoxy, cycloalkoxy, arylalkyl, aryloxy, alkenyl, alkynyl, amide, alkylsulfonyl, arylsulfonyl, sulfonamide, carbamate;

m is 0, 1, 2, 3, or 4;

G is O, NR$^N$, S, or CR$^a$R$^b$;

A is N, O, S, or CR$^a$R$^b$; and

D, E is independently C or N.

In an eighth embodiment of the first aspect, $R^2$ is selected from the group consisting of

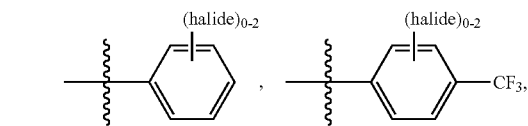

-continued

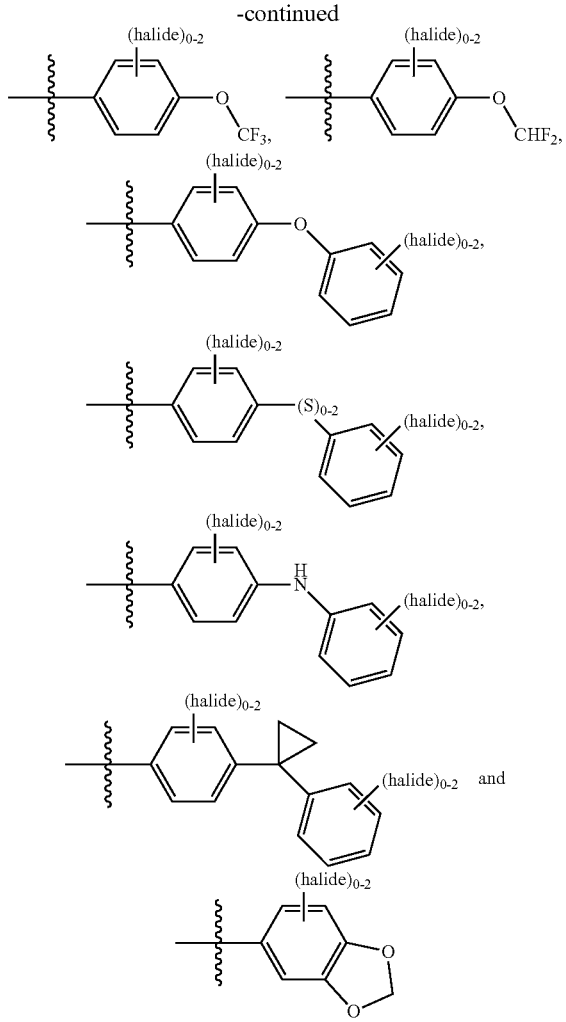

wherein, each phenyl moiety is optionally substituted with 0-2 nitrogen atoms.

In a ninth embodiment of the first aspect, $R^2$ is

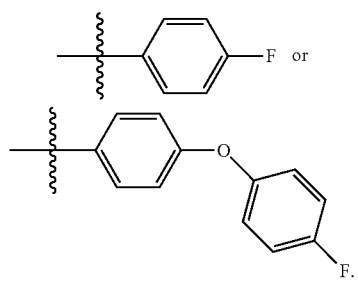

In a tenth embodiment of the first aspect,

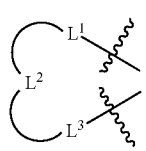

is selected from the group consisting of

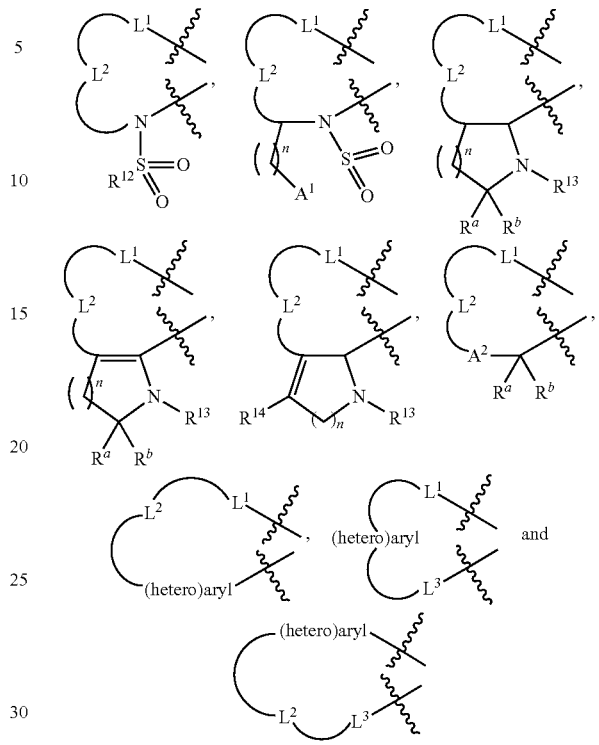

wherein, $L^1$, $L^2$, or $L^3$ is independently selected from the group consisting of a bond, —O—, —C($R^{15}R^{16}$), —$NR^3$—, —S(O)$_n$—, —P(O)$_n$—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^1$ is selected from hydrogen, halide, —$CF_3$, —CN, —C(O)H, —C(O)O$R^6$—, —C(O)NH$R^7$, —C(O)N(OH)$R^7$, —C(=NMe)OMe, —C(=NOR')NH$R^7$, —CH(CF$_3$)NH$R^8$, —CH(CN)NH$R^9$, —S(O)$_2$NH$R^{10}$, —C(=NCN)NH$R^{11}$,

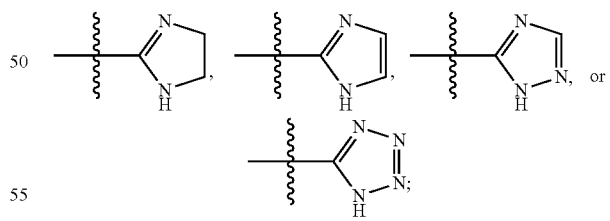

R' is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

$R^2$ is a substituted or unsubstituted aryl or heteroaryl;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^6$ is hydrogen, allyl, C$_{1-4}$ alkyl, cyclopropyl, or benzyl;

$R^7$ is hydrogen, $C_{1-4}$ alkyl, cyclopropyl, $C_{1-4}$ alkoxy, cyclopropoxy, alkylsulfonyl, or cycloalkylsulfonyl;

$R^8$, $R^9$, $R^{10}$, or $R^{11}$ is independently hydrogen, $C_{1-4}$ alkyls, cyclopropyl, $C_{1-4}$ alkoxys, or cyclopropoxy;

$R^{12}$ is independently $C_{1-3}$ alkyl, cyclorpopyl, —OMe, or —NHMe;

$R^{13}$ is independently hydrogen, —Ac, or —S(O)$_2$Me;

$R^{14}$ is independently hydrogen or Me;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, NR$^N$ and/or S; and $A^1$ or $A^2$ is independently —CR$^a$R$^b$—, —N(R$^N$)—, or —O—.

In an eleventh embodiment of the first aspect,

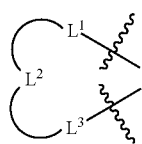

is selected from the group consisting of

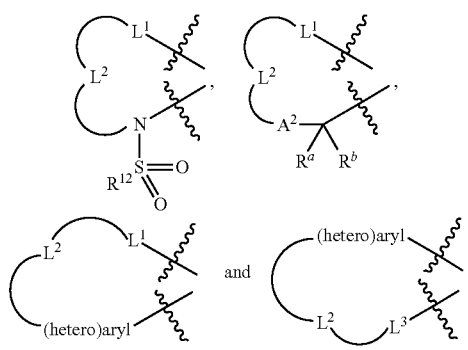

and

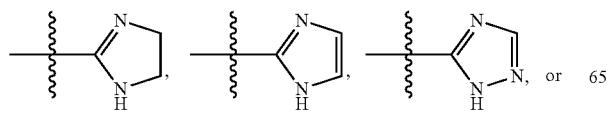

wherein, $L^1$, $L^2$, or $L^3$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^1$ is selected from hydrogen, halide, —CF$_3$, —CN, —C(O)H, —C(O)OR$^6$—, —C(O)NHR$^7$, —C(O)N(OH)R$^7$, —C(=NMe)OMe, —C(=NOR')NHR$^7$, —CH(CF$_3$)NHR$^8$, —CH(CN)NHR$^9$, —S(O)$_2$NHR$^{10}$, —C(=NCN)NHR$^{11}$,

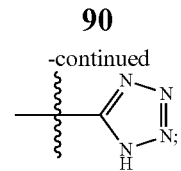

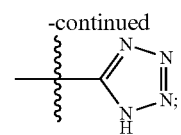

R' is selected from hydrogen, —(CH$_2$CH$_2$O)$_{0-8}$-Me, $C_{2-24}$ alkyl optionally containing 0-6 heteroatoms of O, NR$^N$ and/or S, and $C_{3-8}$ cycloalkyl optionally containing 0-2 heteroatom of O, NR$^N$, and/or S;

$R^2$ is a substituted or unsubstituted aryl or heteroaryl;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^6$ is hydrogen, allyl, $C_{1-4}$ alkyl, cyclopropyl, or benzyl;

$R^7$ is hydrogen, $C_{1-4}$ alkyl, cyclopropyl, $C_{1-4}$ alkoxy, cyclopropoxy, alkylsulfonyl, or cycloalkylsulfonyl;

$R^8$, $R^9$, $R^{10}$, or $R^{11}$ is independently hydrogen, $C_{1-4}$ alkyls, cyclopropyl, $C_{1-4}$ alkoxys, or cyclopropoxy;

$R^{12}$ is independently $C_{1-3}$ alkyl, cyclorpopyl, —OMe, or —NHMe;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, NR$^N$ and/or S; and $A^2$ is independently —CR$^a$R$^b$—, —N(R$^N$)—, or —O—.

In a twelfth embodiment of the first aspect,

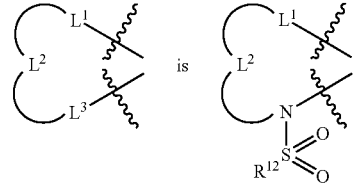

wherein, $L^1$ or $L^2$ is independently selected from the group of divalent substituents consisting of a bond, —O—, —C(R$^{15}$R$^{16}$)—, —NR$^3$—, —S(O)$_n$—, —P(O)—, —Si(R$^4$R$^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^1$ is selected from hydrogen, halide, —CF$_3$, —CN, —C(O)H, —C(O)OR$^6$—, —C(O)NHR$^7$, —C(O)N(OH)R$^7$, —C(=NMe)OMe, —C(=NOR')NHR$^7$, —CH(CF$_3$)NHR$^8$, —CH(CN)NHR$^9$, —S(O)$_2$NHR$^{10}$, —C(=NCN)NHR$^{11}$,

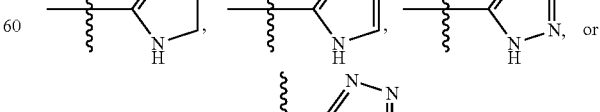

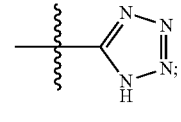

R¹ is selected from hydrogen, —(CH$_2$CH$_2$O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

R² is a substituted or unsubstituted aryl or heteroaryl;

R³ is selected from the group of hydrogen, alkylcarbonyl, cycloalkylcarbonyl, alkoxylcarbonyl, cycloalkoxycarbonyl, alkylsulfonyl and cycloalkylsulfonyl;

R⁴ and R⁵ are independently methyl, ethyl, or cyclopropyl; and

R¹⁵ and R¹⁶ are independently hydrogen, hydroxyl, azide, C$_{2-4}$ alkyenes, C$_{2-4}$ alkynes, C$_{1-4}$ alkyls, cyclopropyl, C$_{1-4}$ alkoxys, or cyclopropoxy or R¹⁵ and R¹⁶ together are a carbonyl or C$_{1-4}$ alkenyls.

In a second aspect of the invention is a compound has the structure:

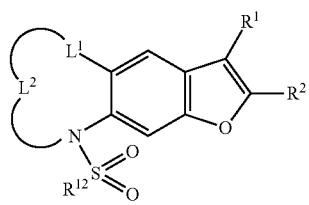

wherein,

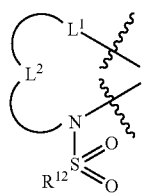

is selected from the group consisting of

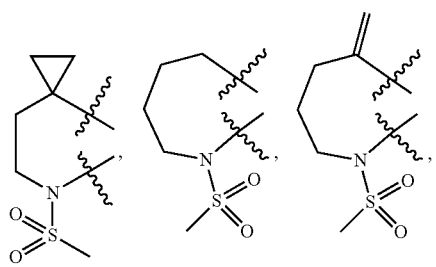

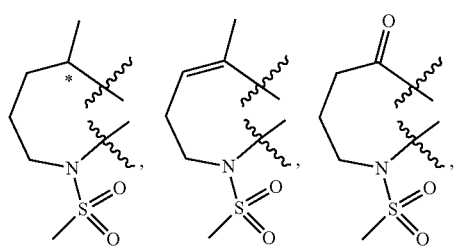

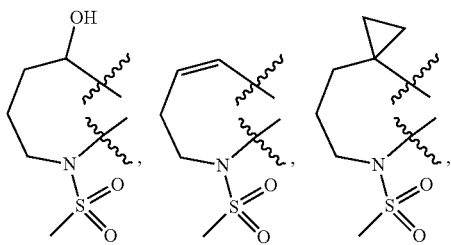

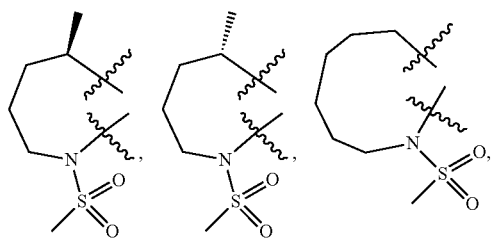

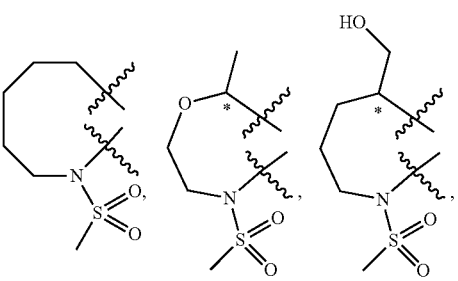

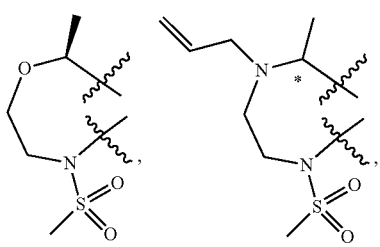

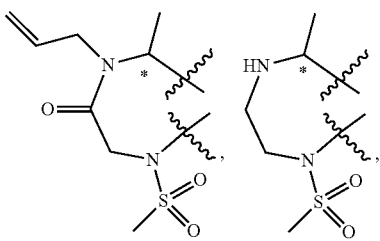

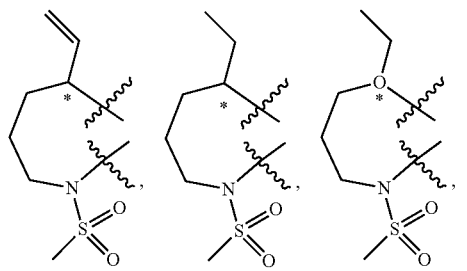

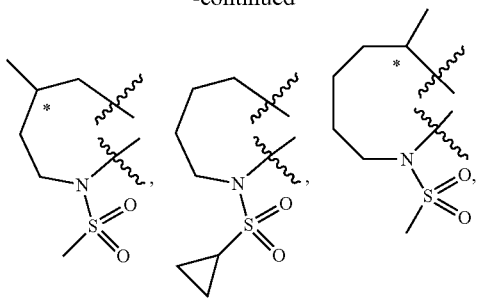
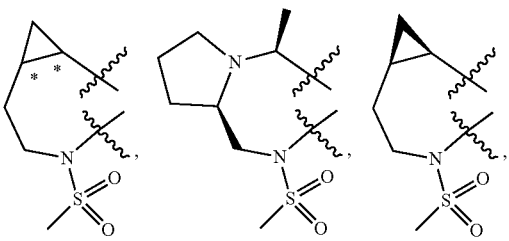
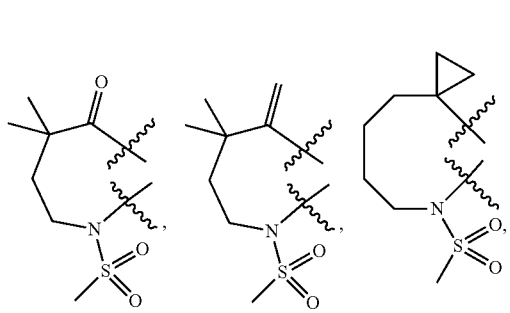
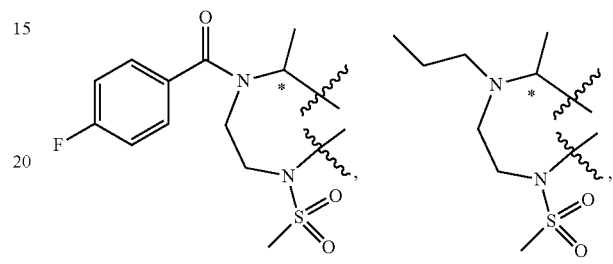
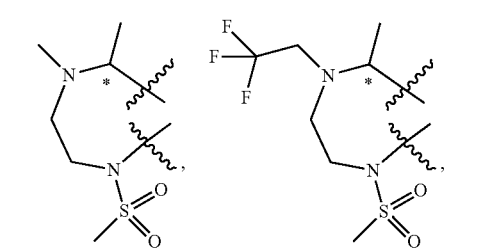
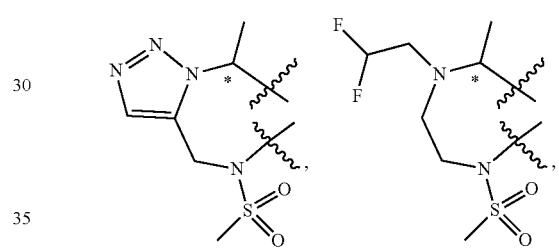
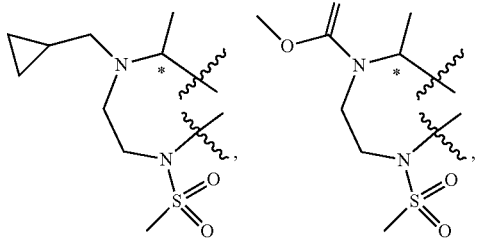
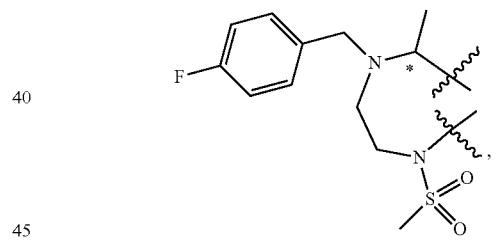
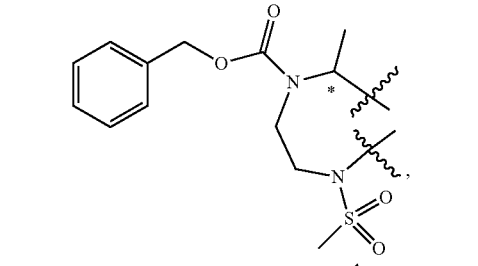
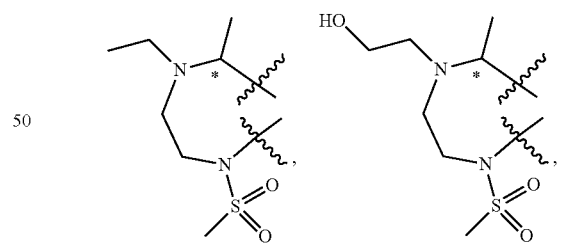
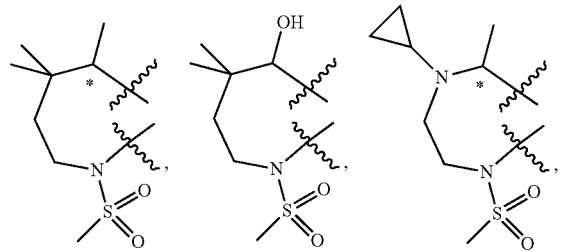
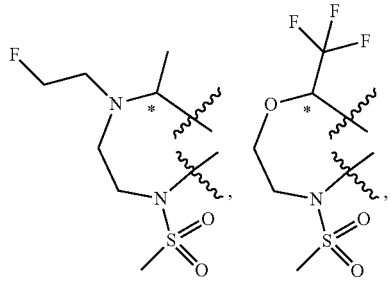

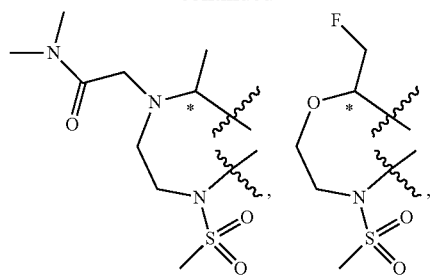
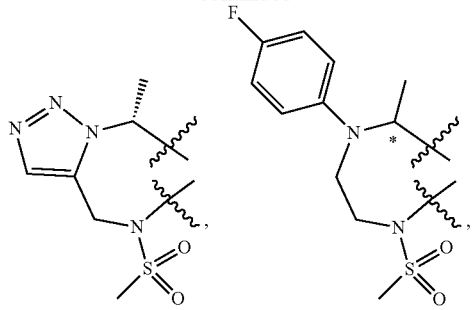
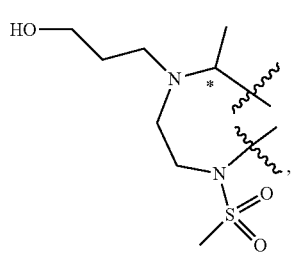
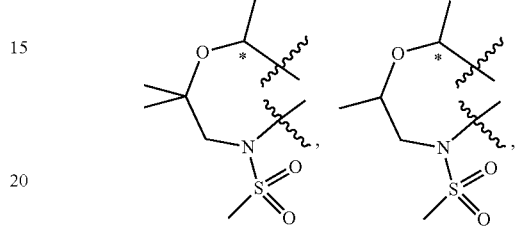
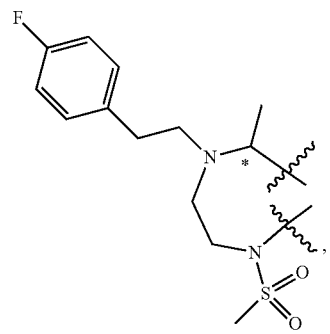
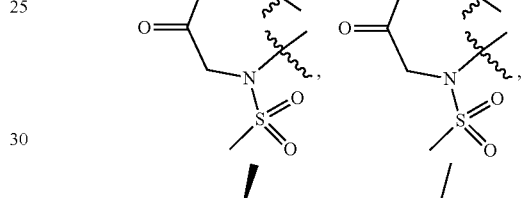
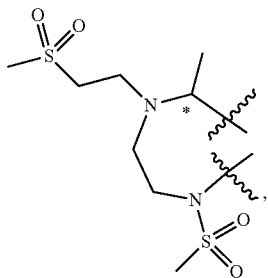
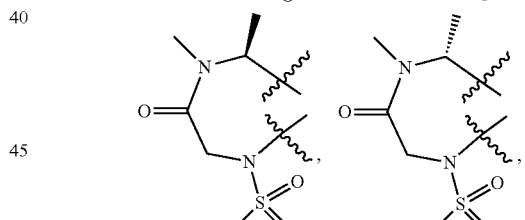
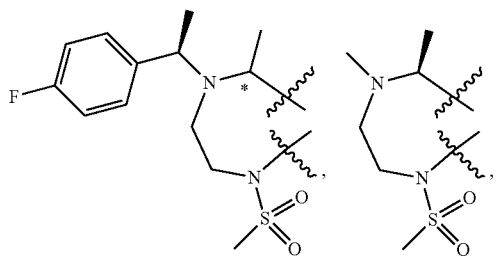
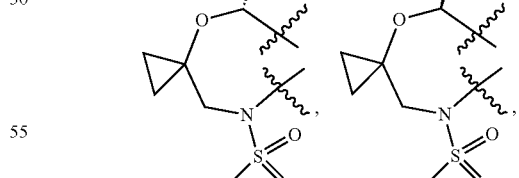
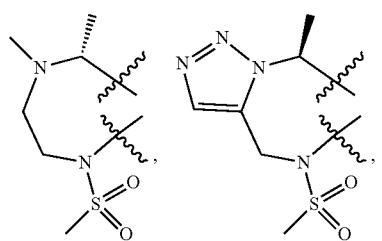

-continued
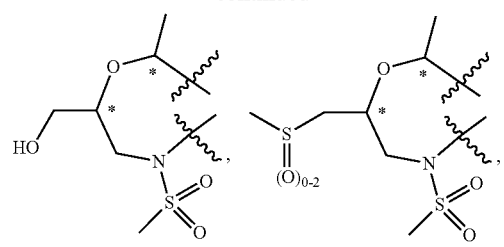
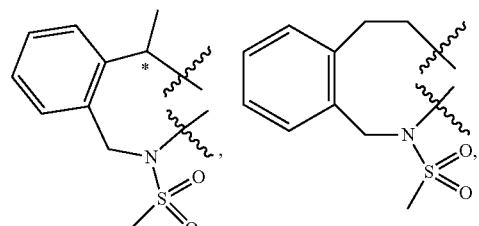
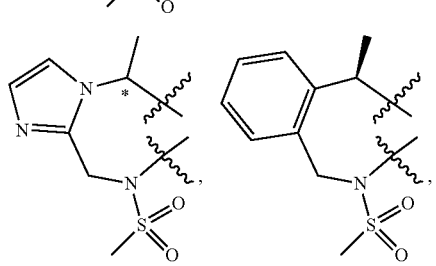
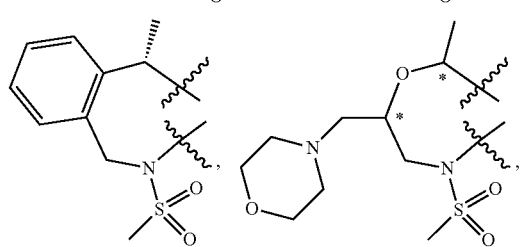
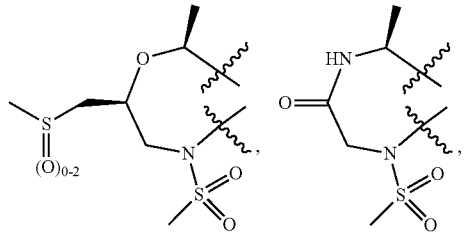
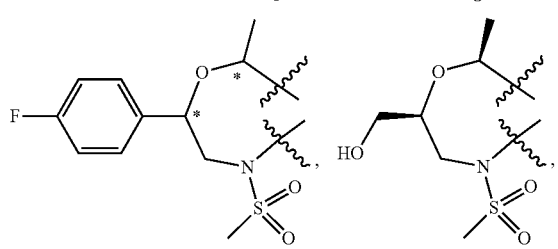
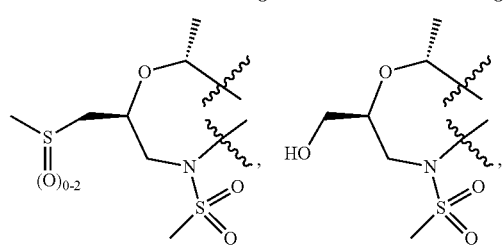
-continued
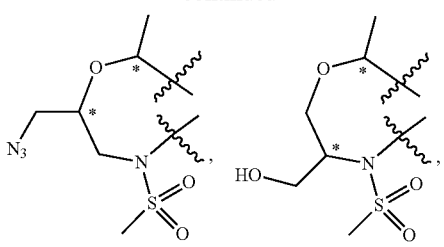
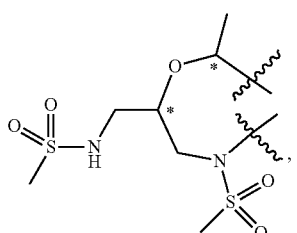
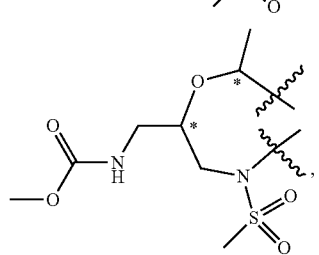
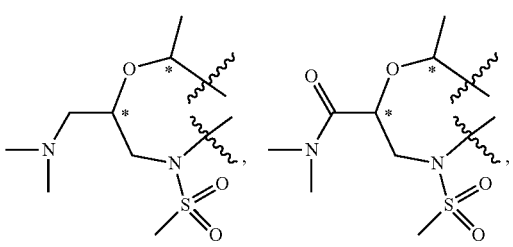
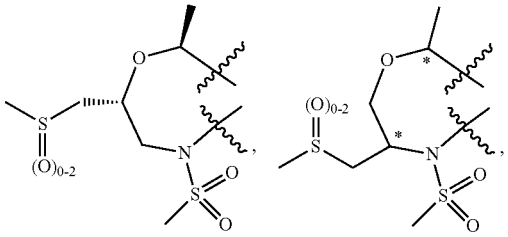
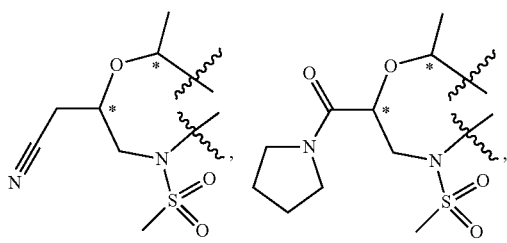

99
-continued
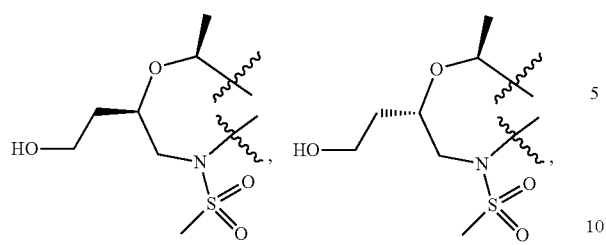
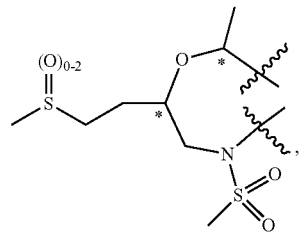
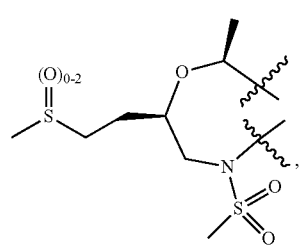
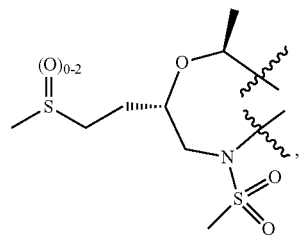
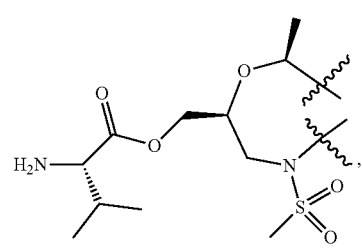
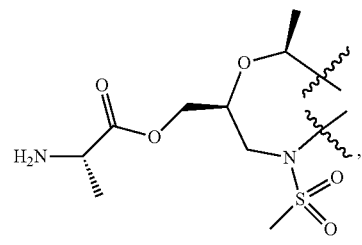
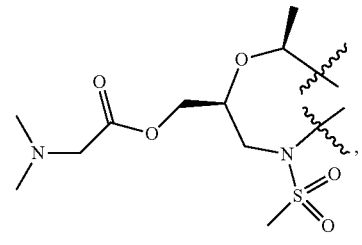
100
-continued
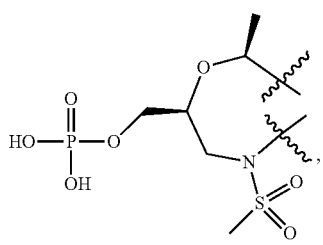
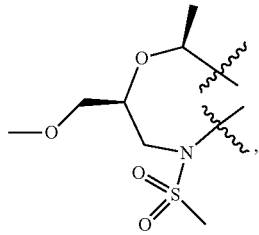
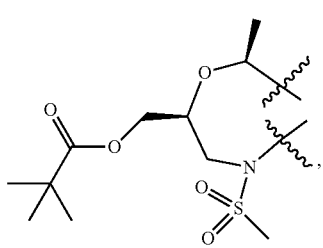
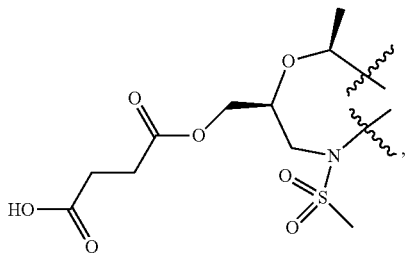
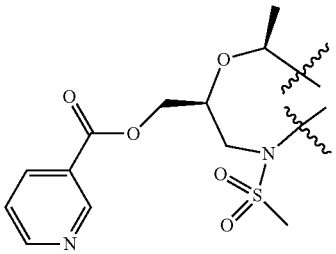
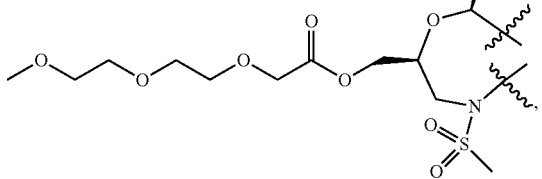
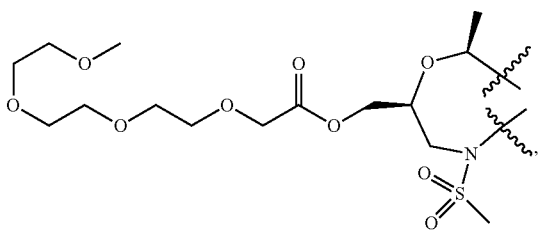

101
-continued
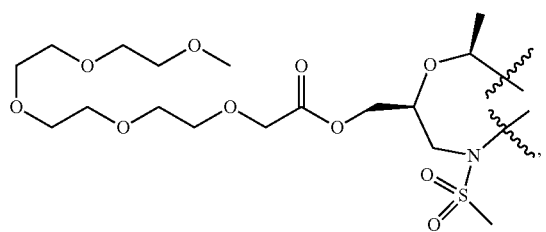
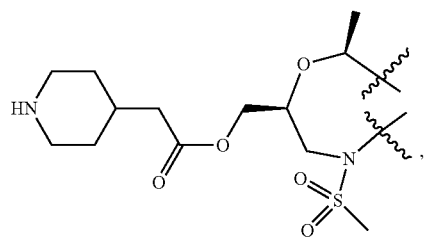
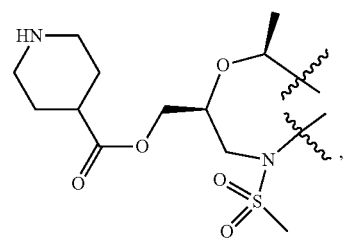
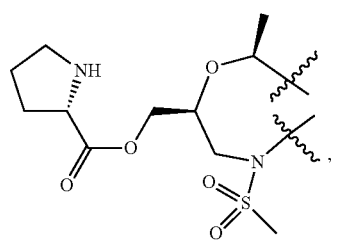
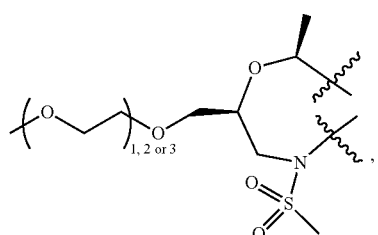
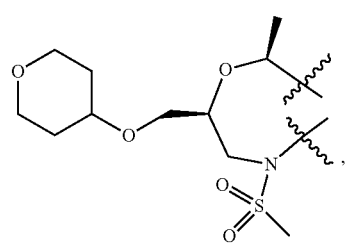
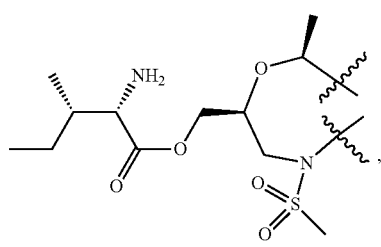
102
-continued
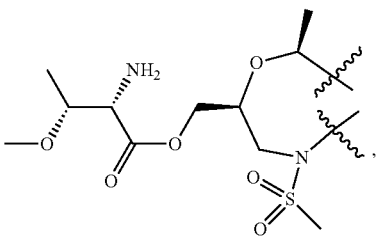
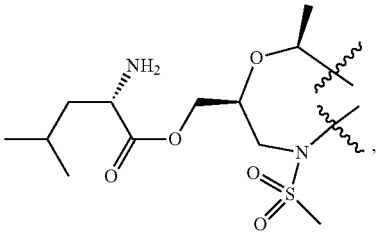
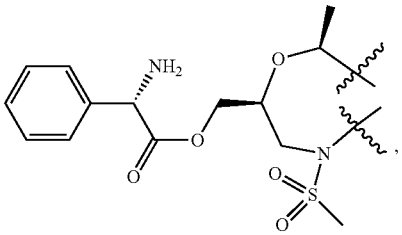
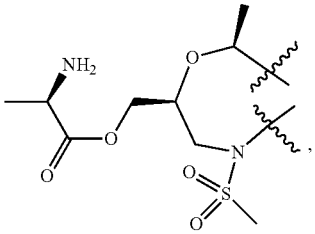
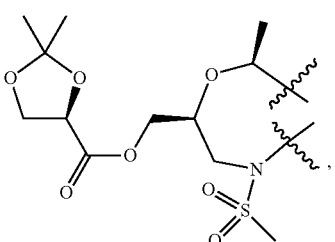
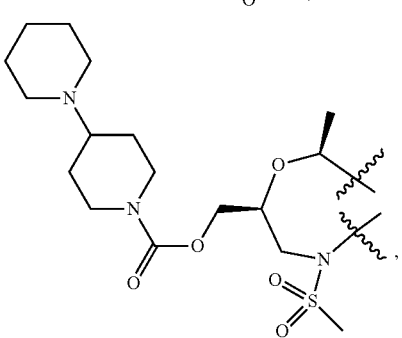

-continued
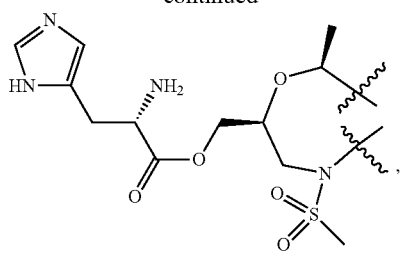
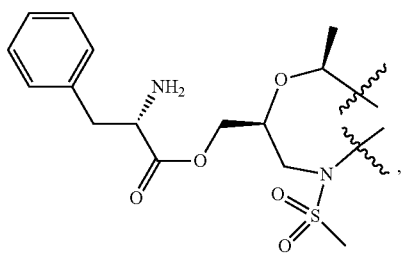
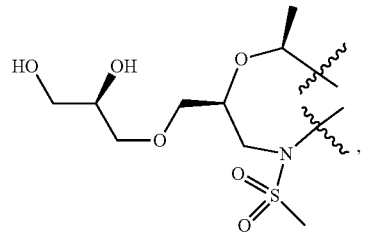
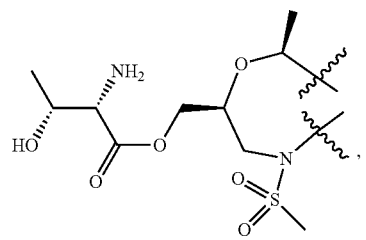
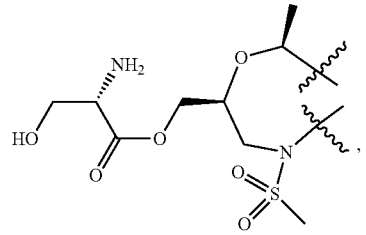
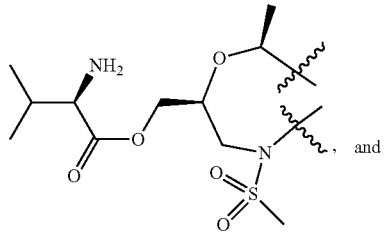
-continued
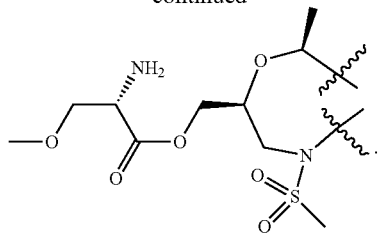
R¹ is selected from the group consisting of
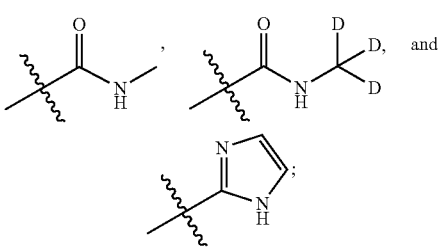
and R² is selected from the group consisting of
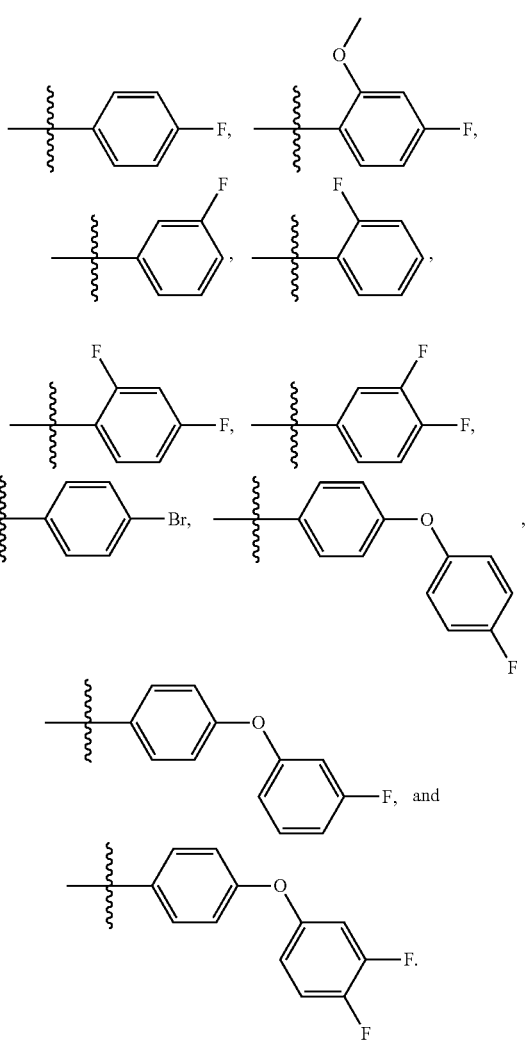

R¹ may be

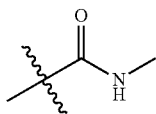

and R² may be

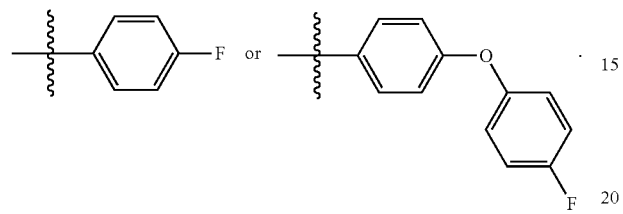

One group of exemplary high-activity compounds are identified by ID NOS: B5, B15, B20, B33, B35, B45, B67, B85, B92, B94, B107, B118, B120, B121, B127, B128, B130, B131, B132, B138, B139, B145, B148, B158, B163, B168, B169, B171, B187, B190, B191, B192, B196, B197, B198, B201, B207, B208, B212, B214, B218, B221, B226, B232, B233, B236, B237, B238, B239, B240, B243, B244, B245, B246, B247, B248, B249, B252, B253, B254, B255, B256, B257, B258, B259, B260, B261, B263, B265, B266, B267, B268, B269, B270, B271, B272, B273, B275, B276, B277, B278, B280, B281, B282, B285, and B286 in Appendix A, and a second group of high-activity compounds are identified by ID NOS: B2, B3, B4, B6, B7, B9, B16, B18, B19, B22, B29, B31, B32, B34, B36, B47, B48, B54, B55, B57, B60, B63, B71, B84, B93, B100, B101, B106, B108, B109, B111, B112, B113, B115, B116, B119, B123, B124, B134, B136, B137, B142, B144, B146, B147, B150, B151, B153, B154, B155, B156, B157, B159, B160, B161, B162, B164, B165, B166, B167, B170, B172, B173, B174, B175, B176, B178, B179, B180, B181, B183, B184, B186, B188, B189, B193, B195, B199, B200, B202, B203, B204, B205, B210, B215, B216, B217, B219, B220, B222, B223, B224, B225, B227, B228, B229, B230, B231, B234, B235, B241, B262, B264, B279, and B287.

As can be appreciated, the compounds in this embodiment may be subdivided into subsets wherein

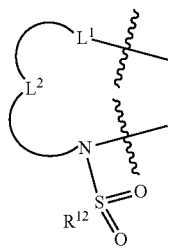

is:

(i) a 7 or 8 member aliphatic ring, as exemplified by compounds B5, B15, B35, B67, B85, B92, B120, B130, B198, B94, and B130;

(ii) a 7 or 8 member ring having an internal oxygen atom, as exemplified by compounds B45, B118, B148, B197, B168, B187, B190; B192, B196, B207, B214, B191, B212, B218, B221, B222, B226, B232, B233, B236, B237, B238, B239, B240, B243, B244, B245, B246, B247, B248, B249, B252, B253, B254, B255, B256, B257, B258, B259, B260, B261, B263, B265, B266, B267, B268, B269, B270, B271, B272, B273, B275, B276, B277, B278, B279, B280, B281, B282, B285, B286, and B287;

(iii) a 7 or 8 member ring having a second internal nitrogen atom, as exemplified by compounds B107, B139, B145, B171, and B208; and (iv) a fused 7 or 8 member ring, as exemplified by compounds B127, B128, B131, B132, B138, B158, B163, B169, B189, and B201.

In a third aspect of the invention is a compound of formula II:

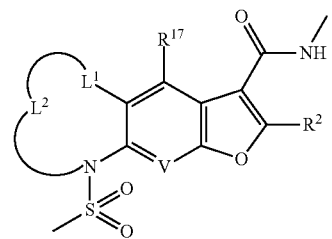

wherein,

L¹, L² and —N(SO₂Me)— together with the attached carbons of the aromatic ring form a 5-12 member ring, containing 1-4 heteroatoms of N, O, S, P and/or Si;

L¹ or L² is independently selected from the group of divalent substituents consisting of a bond, —O—, —C(R¹⁵R¹⁶)—, —NR³—, —S(O)$_n$—, —P(O)—, —Si(R⁴R⁵)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R² is an aryl or heteroaryl and may be substituted with one or more R¹⁷ substituents, R³ is selected from the group of hydrogen, alkylcarbonyl, cycloalkylcarbonyl, alkoxylcarbonyl, cycloalkoxycarbonyl, alkylsulfonyl and cycloalkylsulfonyl;

R⁴ and R⁵ are independently methyl, ethyl, or cyclopropyl;

R¹⁵, R¹⁶ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R¹⁵ and R¹⁶ together are a carbonyl or C$_{1-4}$ alkenylidene or R¹⁵ and R¹⁶ joined together with the attached carbon are 3-6 member ring optionally containing 0-3 heteroatoms of O, NR$^N$ and/or S; and;

R¹⁷ is H, F, Cl or CN; and

V is CH, N, CF, CCl, or CCN.

In a fourth aspect of the invention is a compound that the structure:

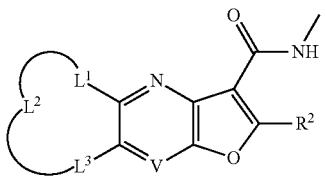

wherein,

L¹, L² and —N(SO₂Me)— together with the attached carbons of the aromatic ring form a 5-12 member ring, containing 1-4 heteroatoms of N, O, S, P and/or Si;

L¹ or L² is independently selected from the group of divalent substituents consisting of a bond, —O—, —C(R¹⁵R¹⁶)—, —NR³—, —S(O)$_n$—, —P(O)—, —Si(R⁴R⁵)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R² is an aryl or heteroaryl and may be substituted with one or more R¹⁷ substituents, R³ is selected from the group of hydrogen, alkylcarbonyl, cycloalkylcarbonyl, alkoxylcarbonyl, cycloalkoxycarbonyl, alkylsulfonyl and cycloalkylsulfonyl;

R⁴ and R⁵ are independently methyl, ethyl, or cyclopropyl;

R¹⁵, R¹⁶ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R¹⁵ and R¹⁶ together are a carbonyl or C$_{1-4}$ alkenylidene or R¹⁵ and R¹⁶ joined together with the attached carbon are 3-6 member ring optionally containing 0-3 heteroatoms of O, NR$^N$ and/or S;

R¹⁷ is H, F, Cl or CN; and

V is CH, N, CF, CCl, or CCN.

In a fifth aspect of the invention is a compound that has the structure:

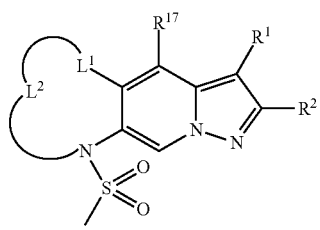

wherein,

L¹, L² and —N(SO₂Me)— together with the attached carbons of the aromatic ring form a 5-12 member ring, containing 1-4 heteroatoms of N, O, S, P and/or Si;

L¹ or L² is independently selected from the group of divalent substituents consisting of a bond, —O—, —C(R¹⁵R¹⁶)—, —NR³—, —S(O)$_n$—, —P(O)—, —Si(R⁴R⁵)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R¹ is selected from hydrogen, halide, —CF₃, —CN, —C(O)H, —C(O)OR⁶, —C(O)NHR⁷, —C(O)N(OH)R⁷, —C(=NMe)OMe, —C(=NOR')NHR⁷, —CH(CF₃)NHR⁸, —CH(CN)NHR⁹, —S(O)₂NHR¹⁰, —C(=NCN)NHR¹¹,

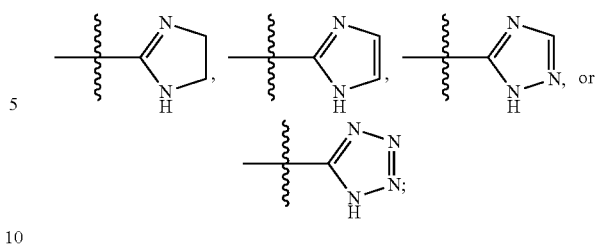

R' is selected from hydrogen, —(CH₂CH₂O)$_{0-8}$-Me, C$_{2-24}$ alkyl optionally containing 0-6 heteroatoms of O, NR$^N$ and/or S, and C$_{3-8}$ cycloalkyl optionally containing 0-2 heteroatom of O, NR$^N$, and/or S;

R² is an aryl or heteroaryl and may be substituted with one or more R¹⁷ substituents;

R³ is selected from the group of hydrogen, alkylcarbonyl, cycloalkylcarbonyl, alkoxylcarbonyl, cycloalkoxycarbonyl, alkylsulfonyl and cycloalkylsulfonyl;

R⁴ and R⁵ are independently methyl, ethyl, or cyclopropyl;

R¹⁵ and R¹⁶ are independently hydrogen, hydroxyl, azide, C$_{2-4}$ alkyenes, C$_{2-4}$ alkynes, C$_{1-4}$ alkyls, cyclopropyl, C$_{1-4}$ alkoxys, or cyclopropoxy or R¹⁵ and R¹⁶ together are a carbonyl or C$_{1-4}$ alkenyls; and R¹⁷ is H, F, Cl, or CN.

In a sixth aspect of the invention is a compound of formula IV:

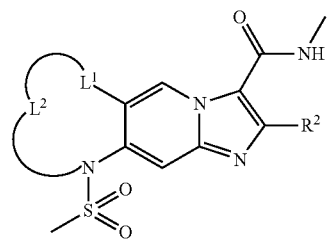

wherein,

L¹, L² and —N(SO₂Me)— together with the attached carbons of the aromatic ring form a 5-12 member ring, containing 1-4 heteroatoms of N, O, S, P and/or Si;

L¹ or L² is independently selected from the group of divalent substituents consisting of a bond, —O—, —C(R¹⁵R¹⁶)—, —NR³—, —S(O)$_n$—, —P(O)—, —Si(R⁴R⁵)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

R² is an aryl or heteroaryl and may be substituted with one or more R¹⁷ substituents;

R³ is selected from the group of hydrogen, alkylcarbonyl, cycloalkylcarbonyl, alkoxylcarbonyl, cycloalkoxycarbonyl, alkylsulfonyl and cycloalkylsulfonyl;

R⁴ and R⁵ are independently methyl, ethyl, or cyclopropyl; and

R¹⁵, R¹⁶ is independently hydrogen, hydroxyl, azide, C$_{2-4}$ alkenyl, C$_{2-4}$ alkynyl, C$_{1-4}$ alkyl, cyclopropyl, C$_{1-4}$ alkoxy, or cyclopropoxy or R¹⁵ and R¹⁶ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a seventh aspect of the invention is a compound of formula V:

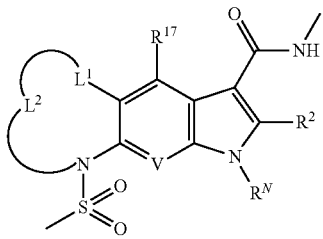

wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^N$ is hydrogen, $C_{1-4}$ alkyl, $C_{3-6}$ cycloalkyl, $C_{4-5}$ heterocycle, aryl, heteroaryl, amide, sulfonamide, or carbamate;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN.

In an eighth aspect of the invention is a compound of formula VI:

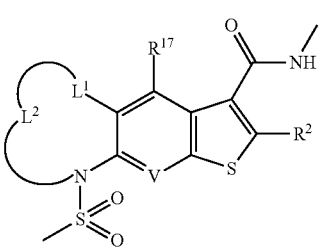

wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN.

In a ninth aspect of the invention is a compound of formula VII:

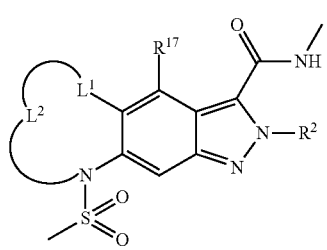

wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a tenth aspect of the invention is a compound of formula VIII:

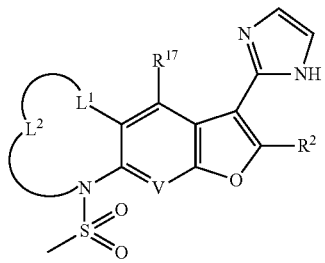

VIII wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents, $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN.

In an eleventh aspect of the invention is a compound that has the structure:

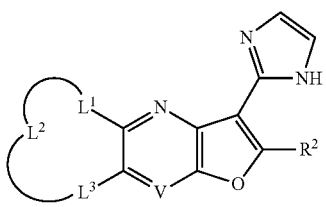

XIII wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents, $R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN

In a twelfth aspect of the invention is a compound of formula X:

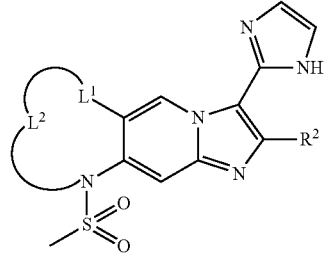

X wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —$NR^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl; and $R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a thirteenth aspect of the invention is a compound of formula XI:

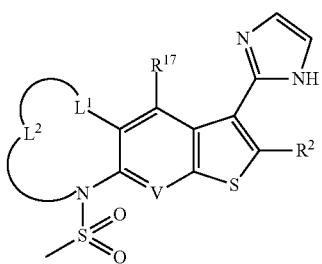

XI wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S;

$R^{17}$ is H, F, Cl or CN; and

V is CH, N, CF, CCl, or CCN.

In a fourteenth aspect of the invention is a compound of formula XII:

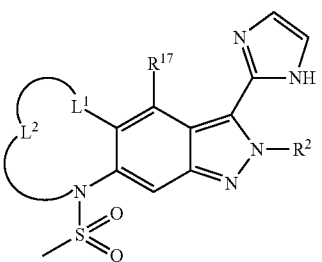

XII wherein, $L^1$, $L^2$ and —N(SO$_2$Me)— together with the attached carbons of the aromatic ring form a 5-12 member ring, containing 1-4 heteroatoms of N, O, S, P and/or Si;

$L^1$ or $L^2$ is independently selected from the group of divalent substituents consisting of a bond, —O—, —C($R^{15}R^{16}$)—, —NR$^3$—, —S(O)$_n$—, —P(O)—, —Si($R^4R^5$)—, —C(O)—, —C(O)O—, and substituted alkyl, alkenyl, alkoxy, cycloalkyl, cycloalkoxy, heterocycle, aryl, heteroaryl, amide, carbamate, urea, and sulfonamide;

n is 0, 1, or 2;

$R^2$ is an aryl or heteroaryl and may be substituted with one or more $R^{17}$ substituents;

$R^3$ is selected from the group of hydrogen, alkylcarbonyl, cycloalkylcarbonyl, alkoxylcarbonyl, cycloalkoxycarbonyl, alkylsulfonyl and cycloalkylsulfonyl;

$R^4$ and $R^5$ are independently methyl, ethyl, or cyclopropyl;

$R^{15}$, $R^{16}$ is independently hydrogen, hydroxyl, azide, $C_{2-4}$ alkenyl, $C_{2-4}$ alkynyl, $C_{1-4}$ alkyl, cyclopropyl, $C_{1-4}$ alkoxy, or cyclopropoxy or $R^{15}$ and $R^{16}$ together are a carbonyl or $C_{1-4}$ alkenylidene or $R^{15}$ and $R^{16}$ joined together with the attached carbon are 3-6 member ring optionally containing 0-3 heteroatoms of O, $NR^N$ and/or S; and $R^{17}$ is H, F, Cl or CN.

In a fifteenth aspect, provided herein is a compound of formula XIV:

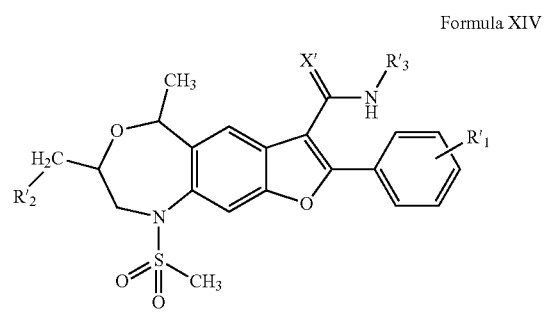

Formula XIV wherein:

R'$_1$ is selected from

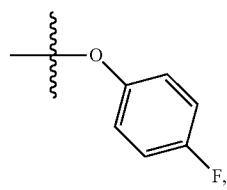 [SMILES: *Oc1ccc(F)cc1]

H, —F, —Cl, —Br, and —I;

R'$_2$ is selected from —OH, —OCH$_3$,

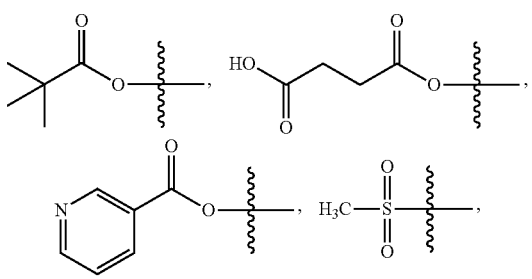

115

-continued

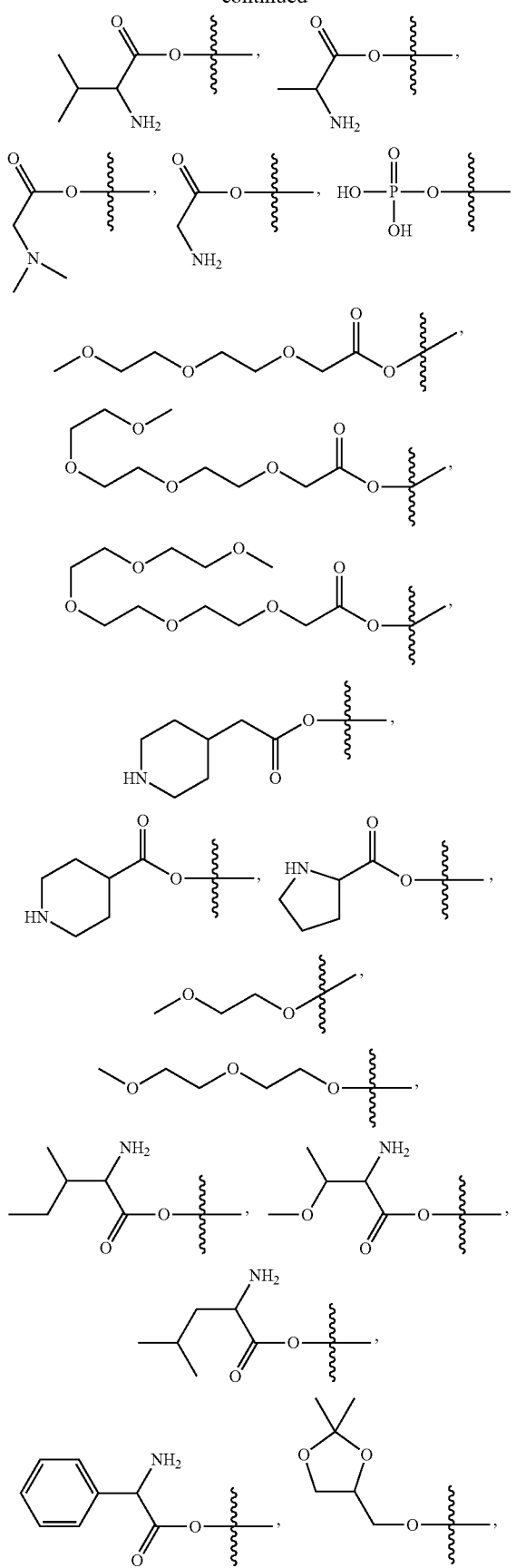

116

-continued

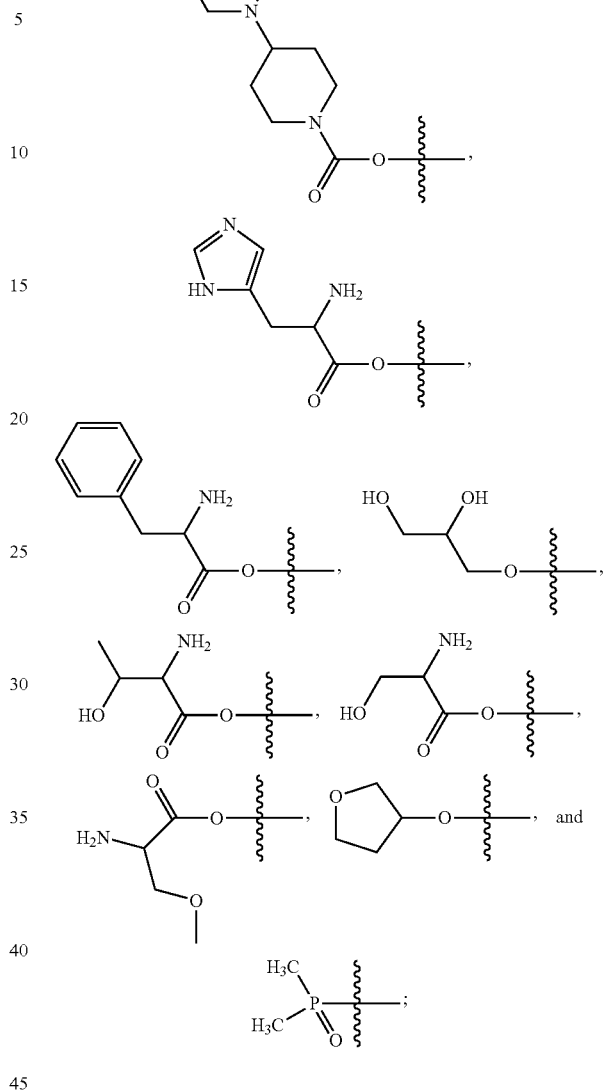

X' is selected from $=O$, $=N-OH$, $=N-O(CH_2CH_2O)_{0-8}CH_3$, and $=N-O(CH_2)_{1-23}CH_3$, and $R'_3$ is selected from $-CH_3$ and $-OCH_3$. Examples of $=N-O(CH_2CH_2O)_{0-8}CH_3$ include $=N-O-CH_3$, $=N-O(CH_2CH_2O)CH_3$, $=N-O(CH_2CH_2O)_2CH_3$, $=N-O(CH_2CH_2O)_3CH_3$, $=N-O(CH_2CH_2O)_4CH_3$, $=N-O(CH_2CH_2O)_5CH_3$, $=N-O(CH_2CH_2O)_6CH_3$, $=N-O(CH_2CH_2O)_7CH_3$, and $=N-O(CH_2CH_2O)_8CH_3$. Examples of $=N-O(CH_2)_{1-23}CH_3$ include $=N-O(CH_2)CH_3$, $=N-O(CH_2)_2CH_3$, $=N-O(CH_2)_3CH_3$, $=N-O(CH_2)_4CH_3$, $=N-O(CH_2)_5CH_3$, $=N-O(CH_2)_6CH_3$, $=N-O(CH_2)_7CH_3$, $=N-O(CH_2)_8CH_3$, $=N-O(CH_2)_9CH_3$, $=N-O(CH_2)_{10}CH_3$, $=N-O(CH_2)_{11}CH_3$, $=N-O(CH_2)_{12}CH_3$, $=N-O(CH_2)_{13}CH_3$, $=N-O(CH_2)_{14}CH_3$, $=N-O(CH_2)_{15}CH_3$, $=N-O(CH_2)_{16}CH_3$, $=N-O(CH_2)_{17}CH_3$, $=N-O(CH_2)_{18}CH_3$, $=N-O(CH_2)_{19}CH_3$, $=N-O(CH_2)_{20}CH_3$, $=N-O(CH_2)_{21}CH_3$, $=N-O(CH_2)_{22}CH_3$, and $=N-O(CH_2)_{23}CH_3$.

In a first embodiment related to the fifteenth aspect, provided is a compound of formula XIV having the following features:
R'₁ is
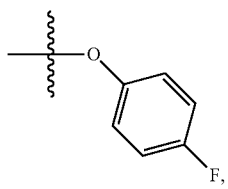 [SMILES: *Oc1ccc(F)cc1]
R'₂ is selected from —OH, —OCH₃,
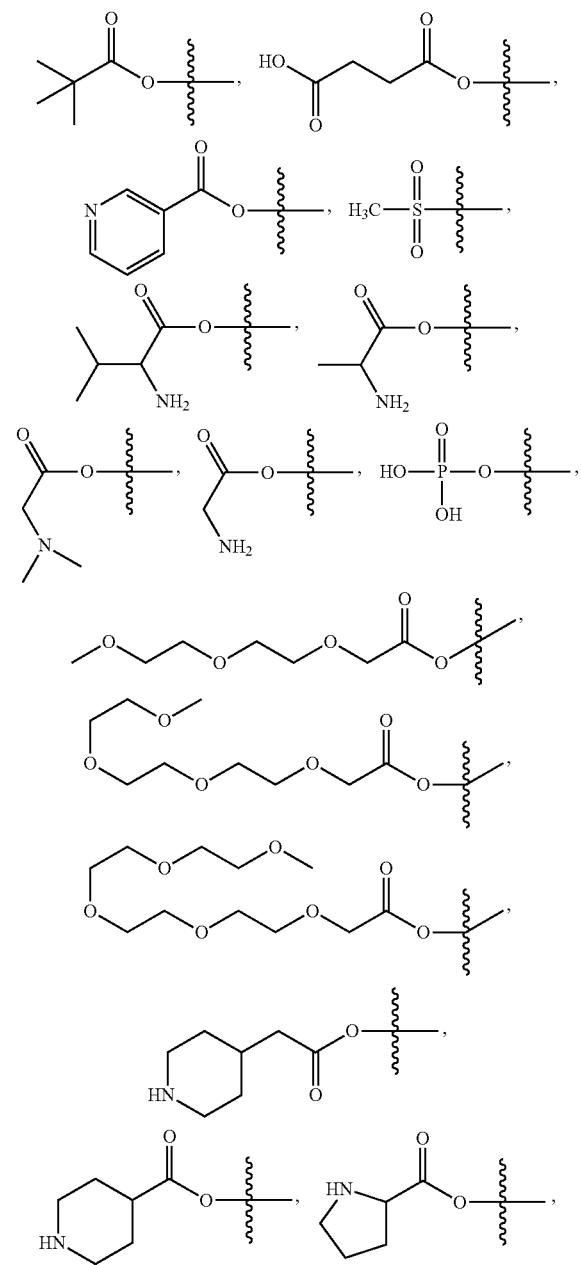
-continued
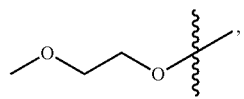
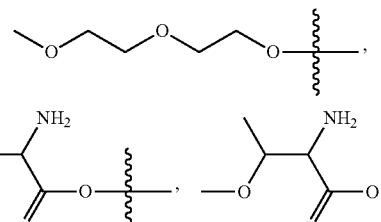
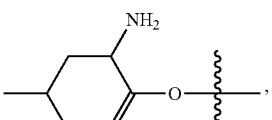
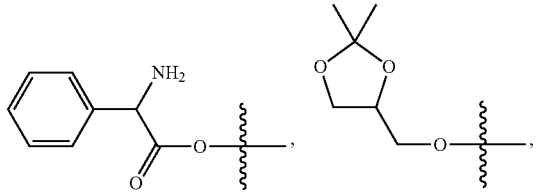
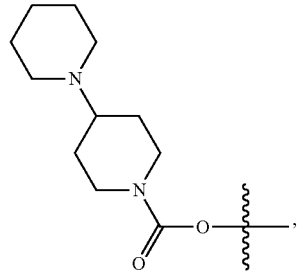
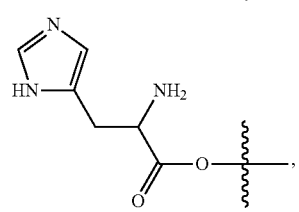
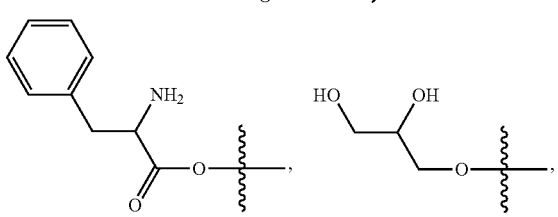
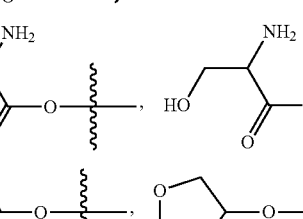
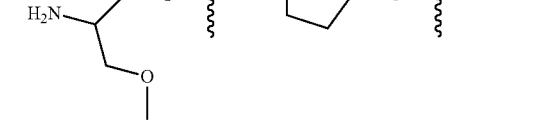
and

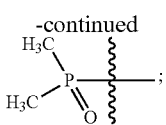
X' is =O, and
R'₃ is —CH₃.
In a second embodiment related to the fifteenth aspect, provided is a compound of formula XIV, wherein:
R'₁ is
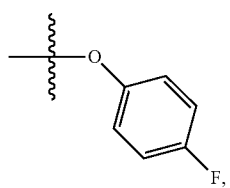
R'₂ is selected from —OH, —OCH₃,
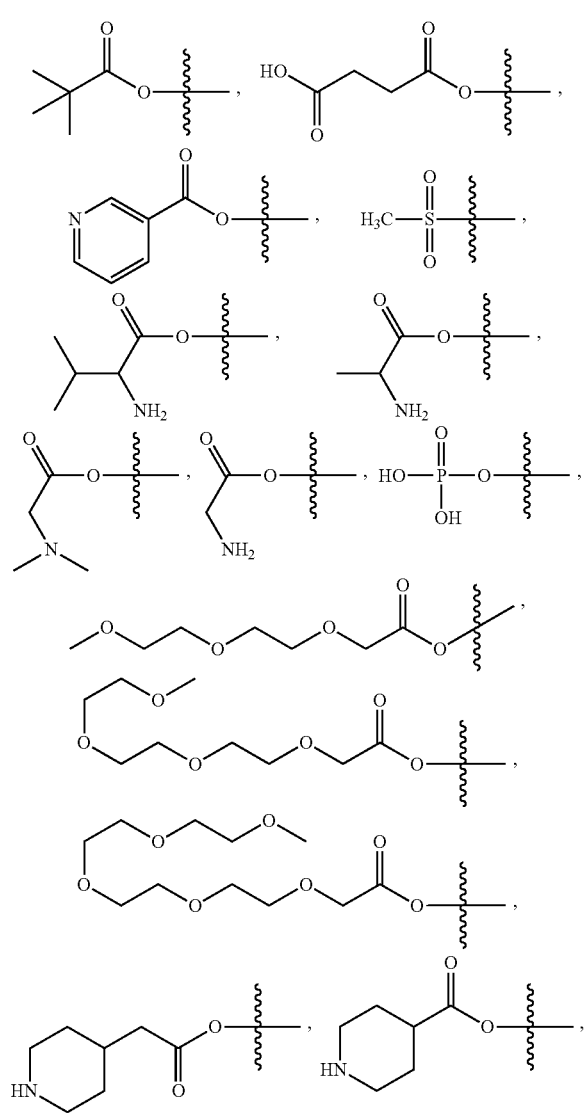
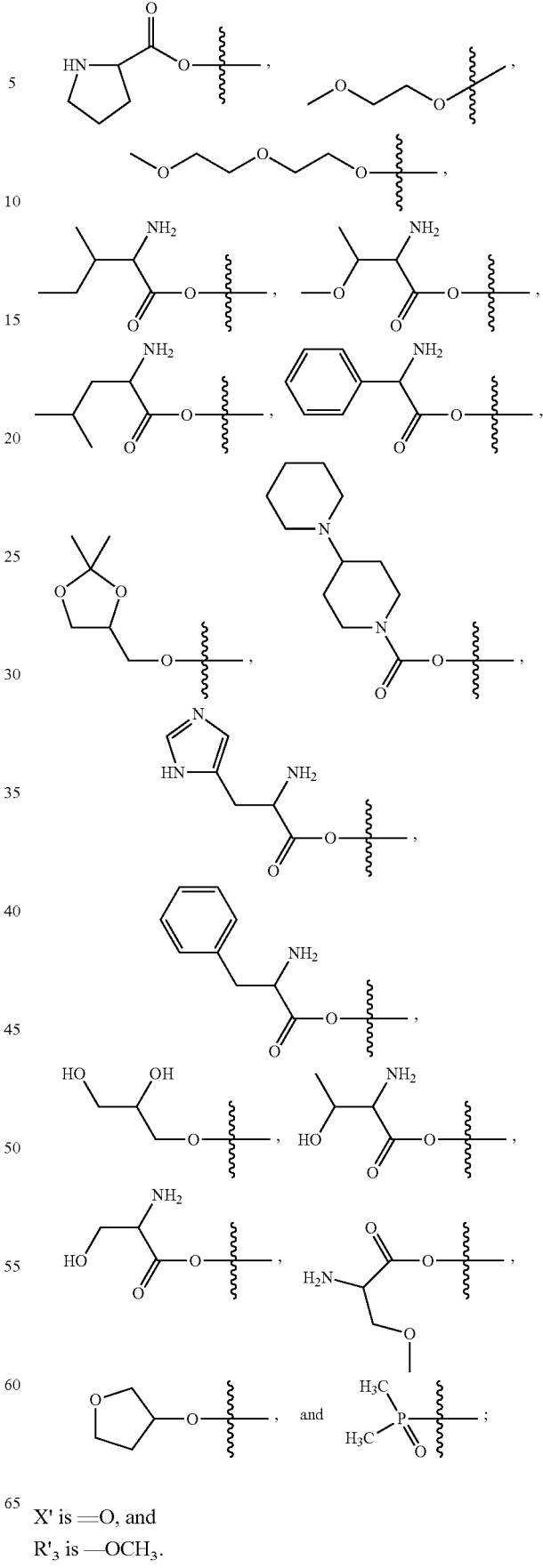
X' is =O, and
R'₃ is —OCH₃.

In a third embodiment related to the fifteenth aspect, provided is a compound of formula XIV, wherein:

R'₁ is

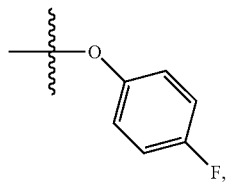

R'₂ is selected from —OH, —OCH₃,

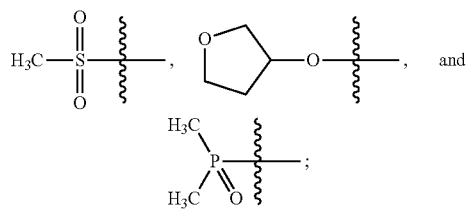
and

X' is selected from =N—OH, =N—OCH₃, =N—OCH₂CH₂OCH₃, =N—O(CH₂CH₂O)₂CH₃, and =N—O(CH₂CH₂O)₃CH₃, and R'₃ is —CH₃.

In a fourth embodiment related to the fifteenth aspect, provided is a compound of formula XIV, wherein
R'₁ is —F,
R'₂ is selected from —OH, —OCH₃,

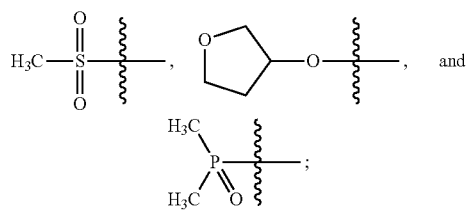
and

X' is selected from =N—OH, =N—OCH₃, =N—OCH₂CH₂OCH₃=N—O(CH₂CH₂O)₂CH₃ and =N—O(CH₂CH₂O)₃CH₃, and R'₃ is —CH₃.

In a fifth embodiment related to the fifteenth aspect, provided is a compound of formula XIV, wherein:
R'₁ is —F,
R'₂ is selected from —OH, —OCH₃,

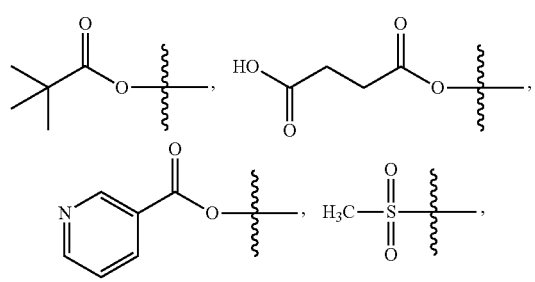

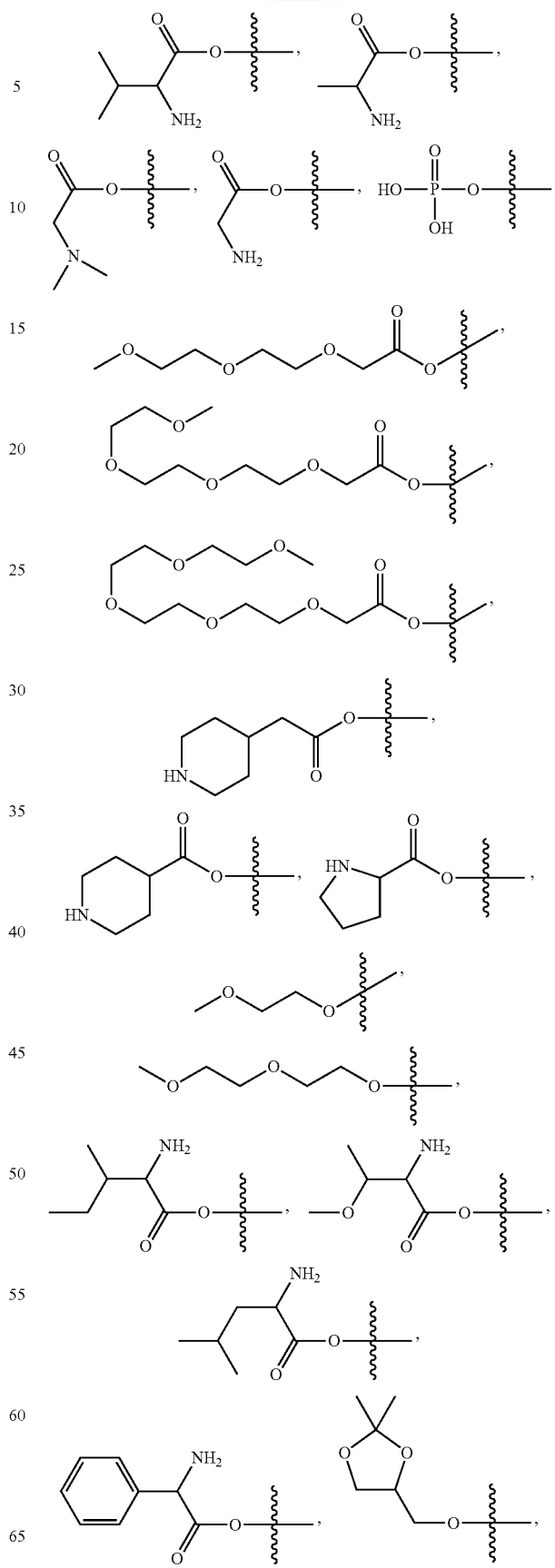

123
-continued
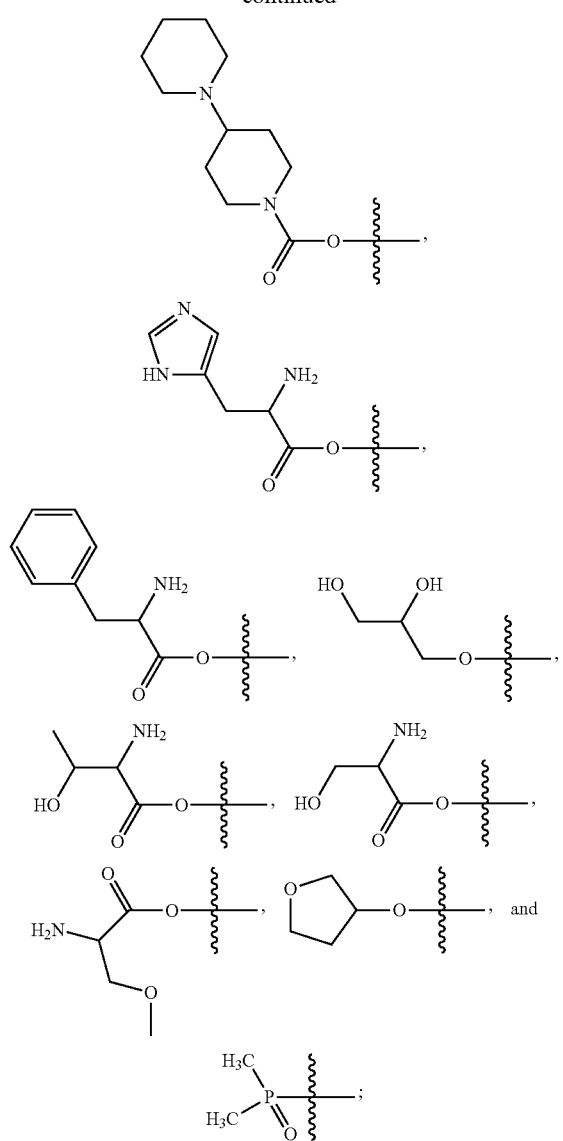
X' is =O, and
R'$_3$ is —CH$_3$.
In a sixth embodiment related to the fifteenth aspect, provided is a compound of formula XIV, wherein:
R'$_1$ is —F,
R'$_2$ is selected from —OH, —OCH$_3$,
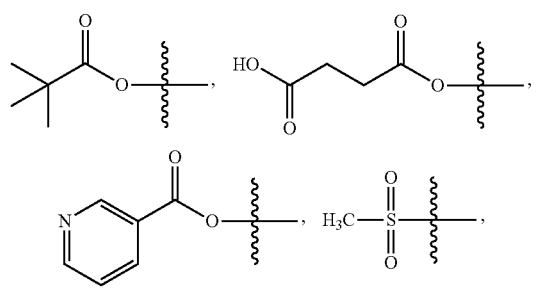
124
-continued
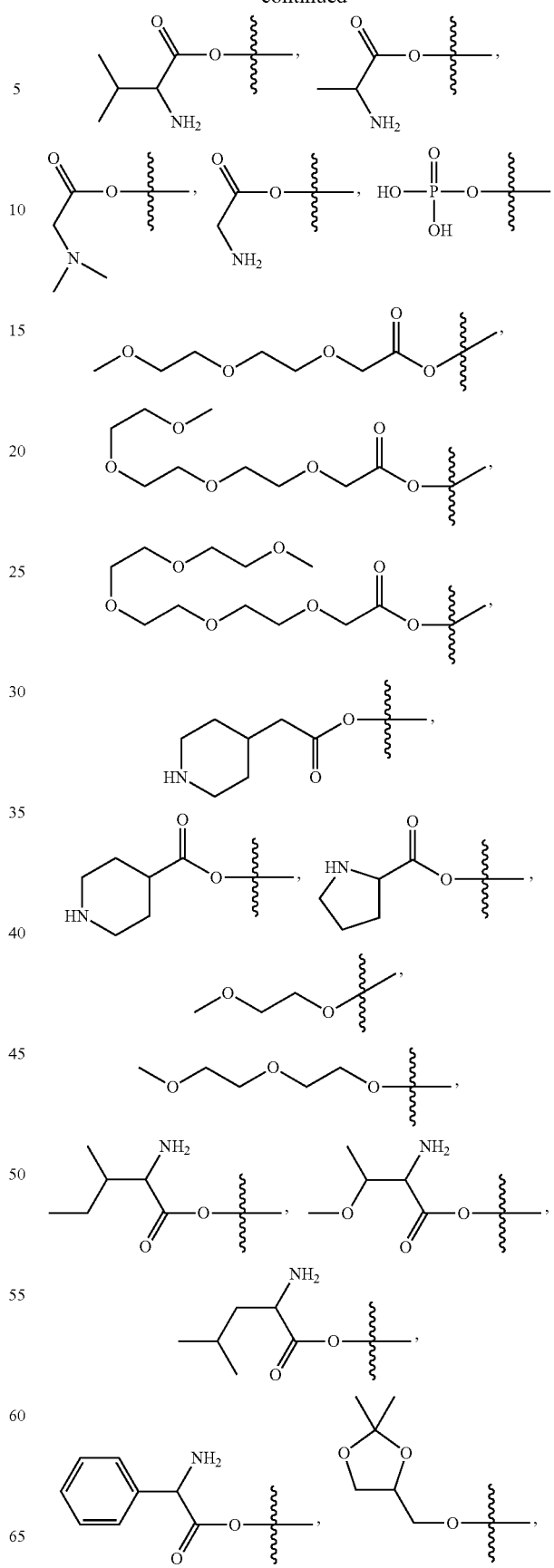

-continued

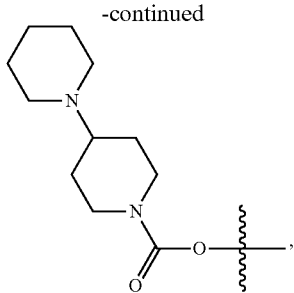

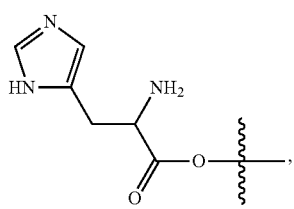

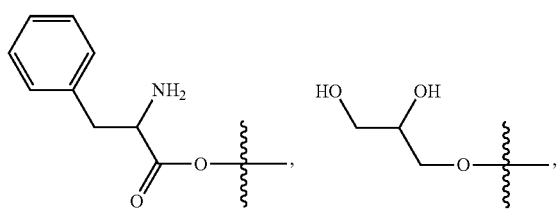

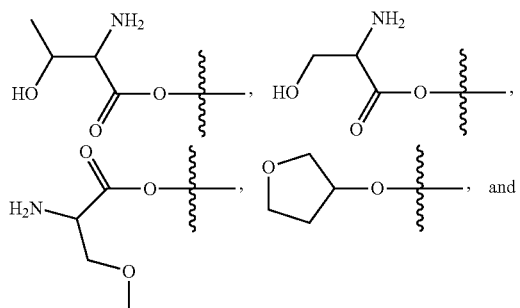

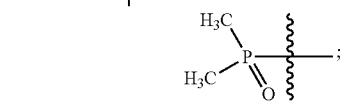

X' is =O, and
R'₃ is —OCH₃.

In a seventh embodiment related to the fifteenth aspect, and any one or more of the fourth, fifth or sixth embodiments, R'₁ is para-F.

In an eighth embodiment related to the fifteenth aspect, and the second and third embodiments thereof, R'₁ is para-

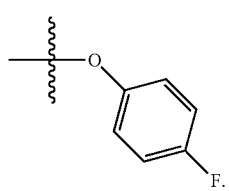

In a sixteenth aspect, provided herein is a compound according to structural Formula XIV-a:

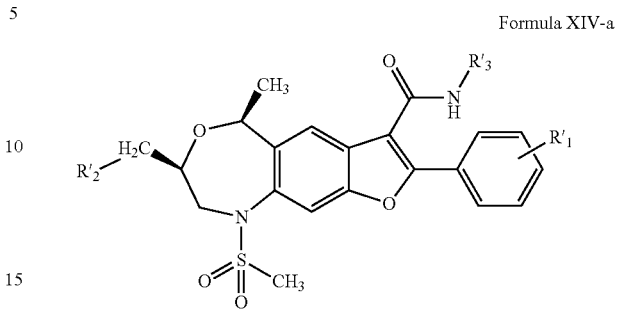

Formula XIV-a wherein:
R'₁ is selected from

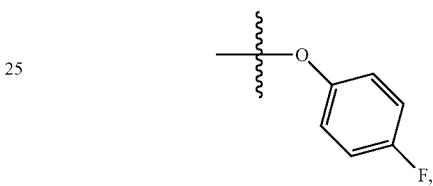

—H, —F, —Cl, —Br, and —I;
R'₂ is selected from —OH, —OCH₃,

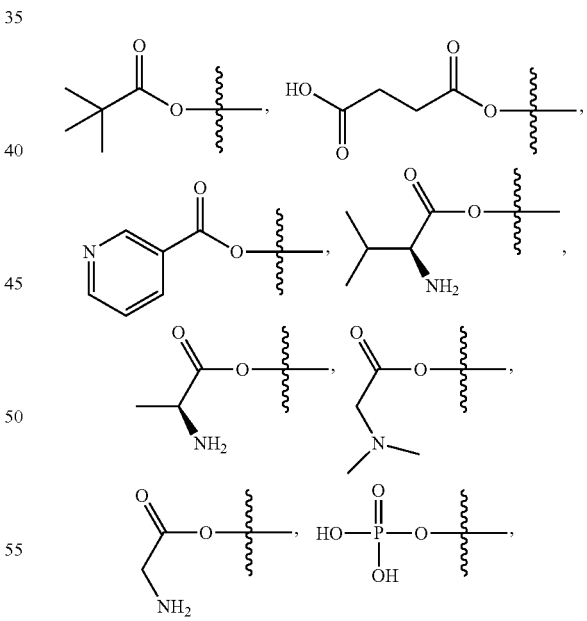

-continued
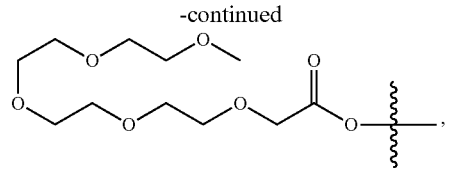
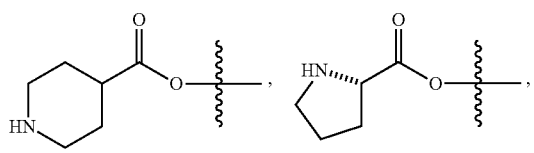
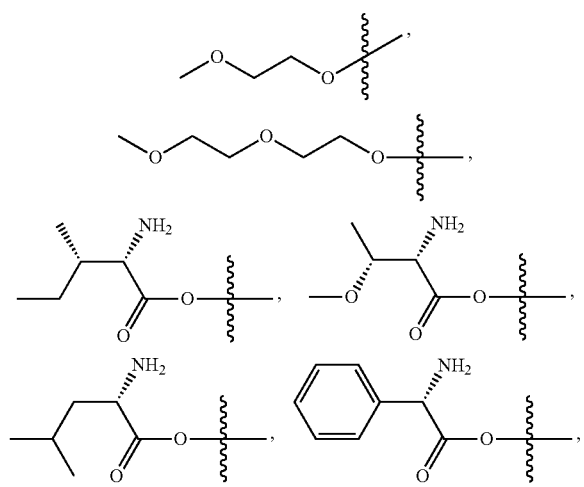
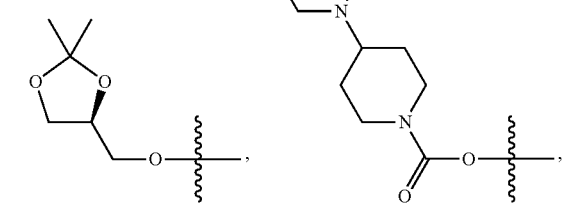
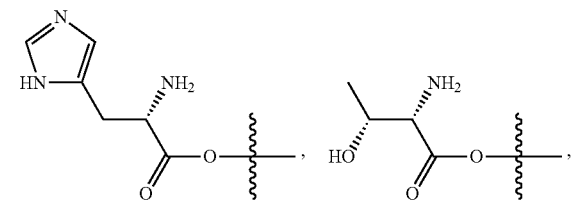
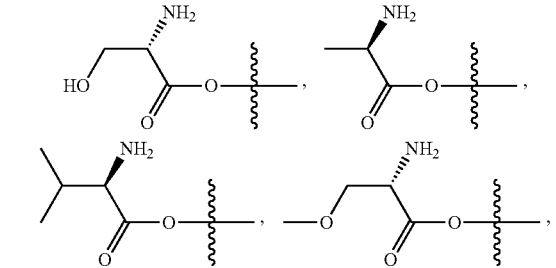
and
R'$_3$ is selected from —CH$_3$ and —OCH$_3$.
In a first embodiment related to the sixteenth aspect, in reference to Formula XIV-a:
R'$_1$ is
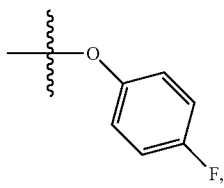
R'$_2$ is selected from —OH, —OCH$_3$,
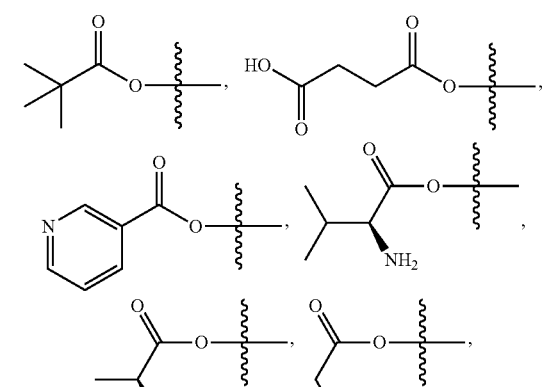
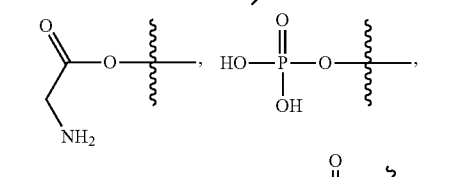
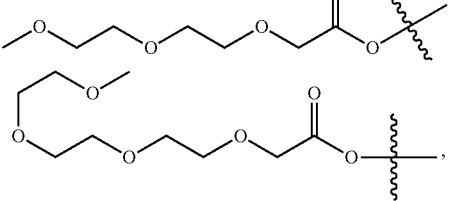
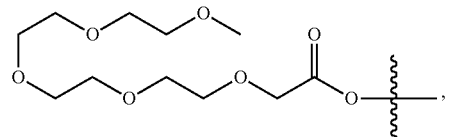
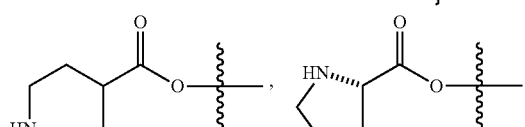
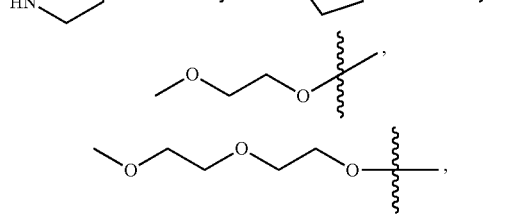

-continued
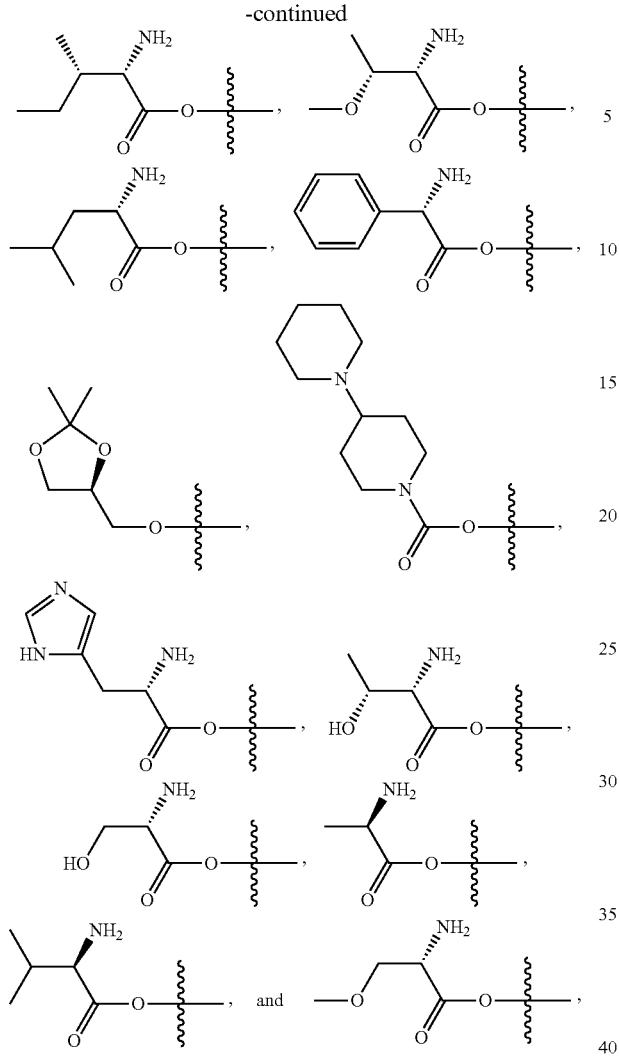
and
R'$_3$ is —CH$_3$.
In a second embodiment related to the sixteenth aspect, in reference to Formula XIV-a:
R'$_1$ is
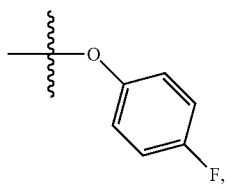
R'$_2$ is selected from —OH, —OCH$_3$,
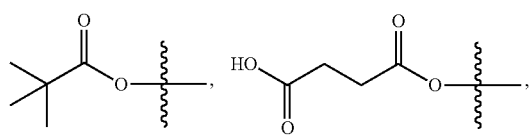
-continued
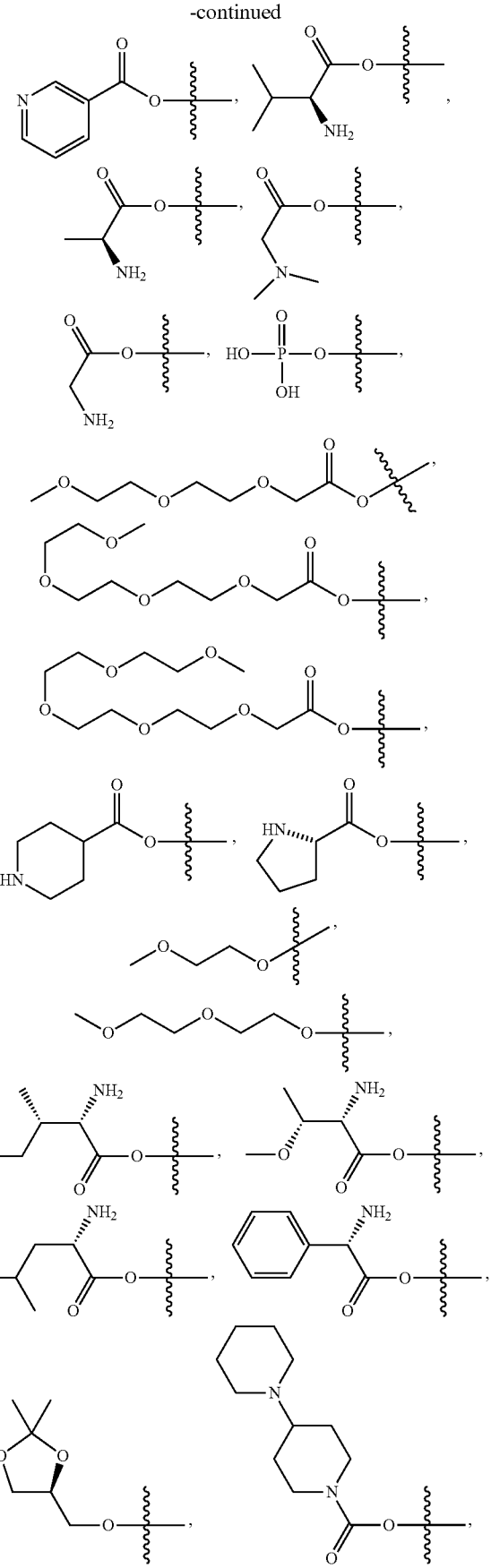

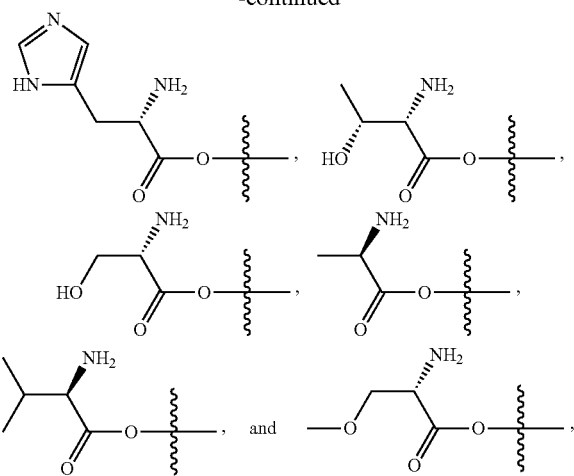
and
R'$_3$ is —OCH$_3$.
In a third embodiment related to the sixteenth aspect of the invention, in reference to Formula XIV-a:
R'$_1$ is —F,
R'$_2$ is selected from —OH, —OCH$_3$,
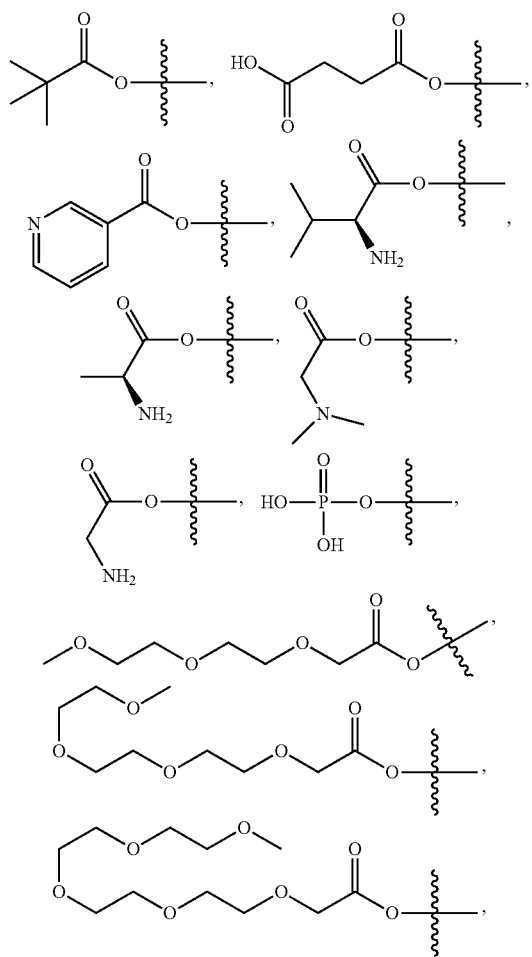
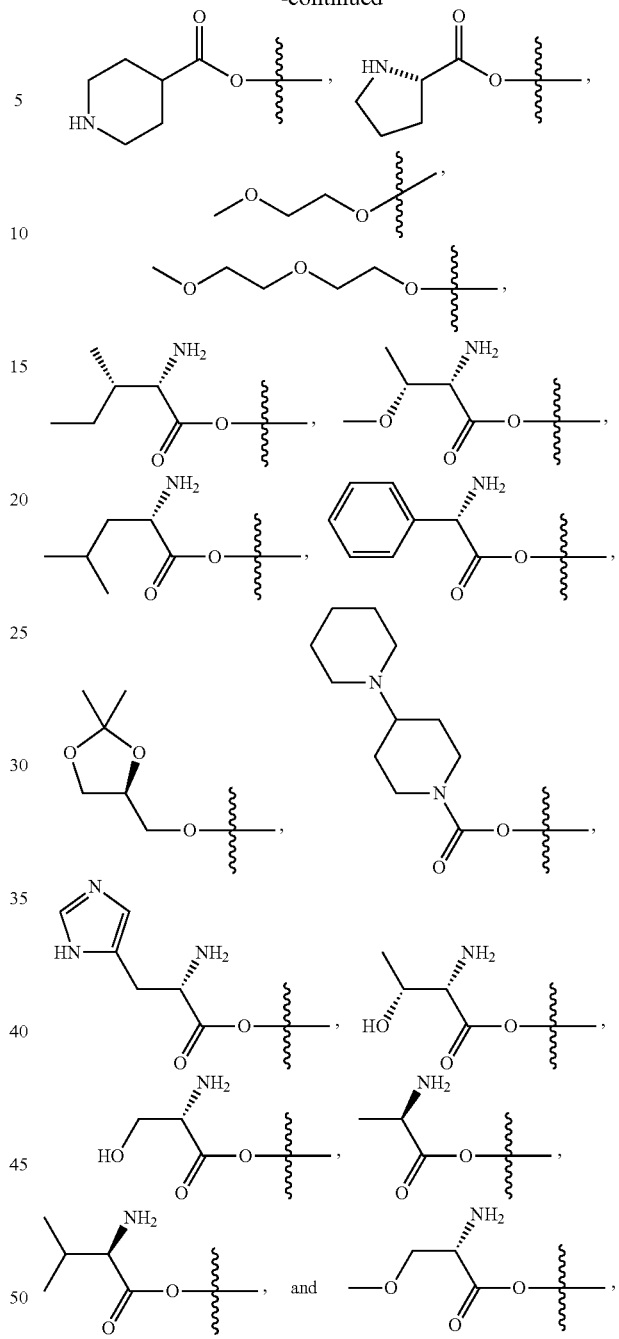
and
R'$_3$ is —CH$_3$.
In yet a fourth embodiment related to the sixteenth aspect of the invention, in reference to Formula XIV-a:
R'$_1$ is —F,
R'$_2$ is selected from —OH, —OCH$_3$,
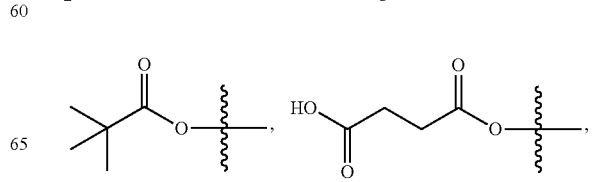

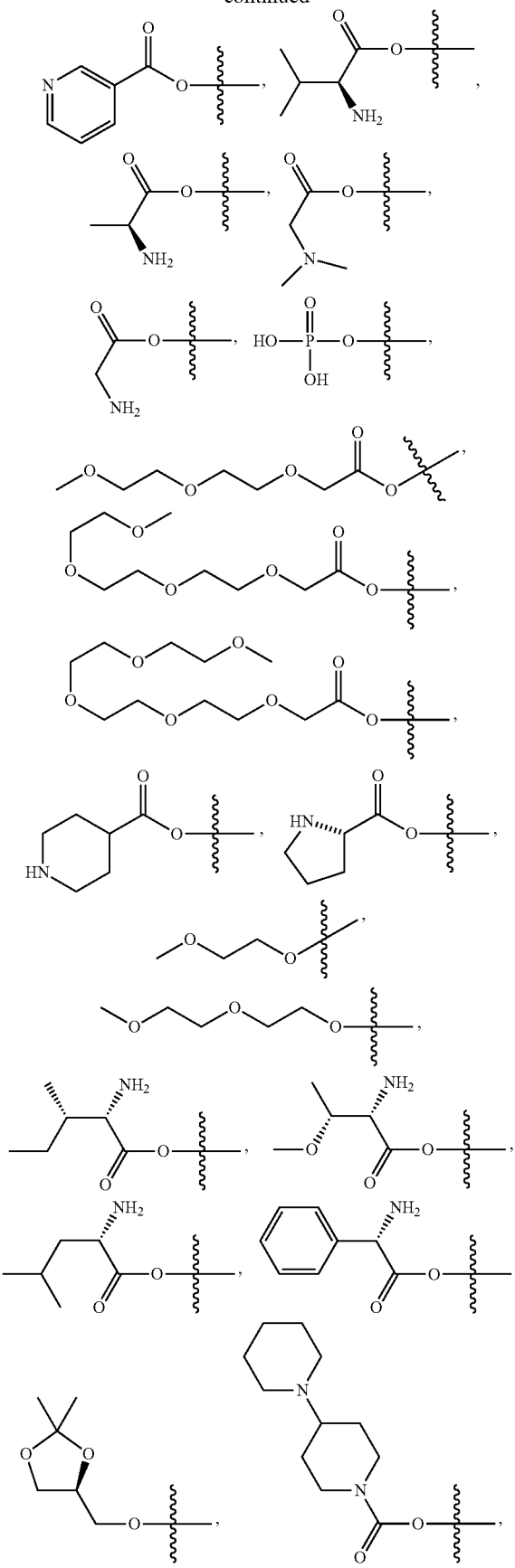

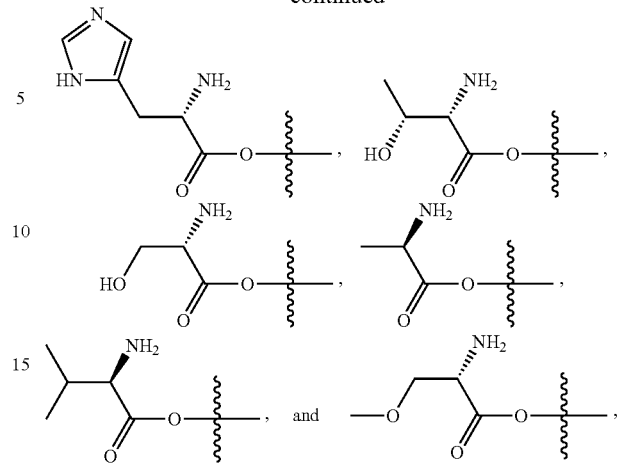

and
R'₃ is —OCH₃.

In yet a fifth embodiment related to the sixteenth aspect of the invention, in reference to formula XIV-a and in particular the third and fourth embodiments thereof, R'₁ is para-F.

In yet a sixth embodiment related to the sixteenth aspect of the invention, in reference to formula XIV-a and in particular the first and second embodiments thereof, R'₁ is para-

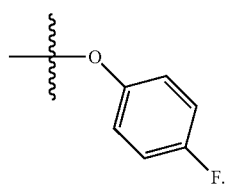 [SMILES: *Oc1ccc(F)cc1]

In a seventeenth aspect of the invention, provided herein is a compound according to structural formula XIV-a, Formula XIV-a

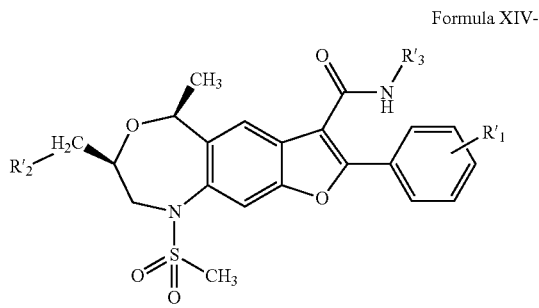

wherein:
R'₁ is selected from para-

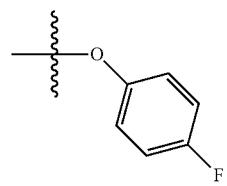 [SMILES: *Oc1ccc(F)cc1]

and para-F,

R'₂ is selected from
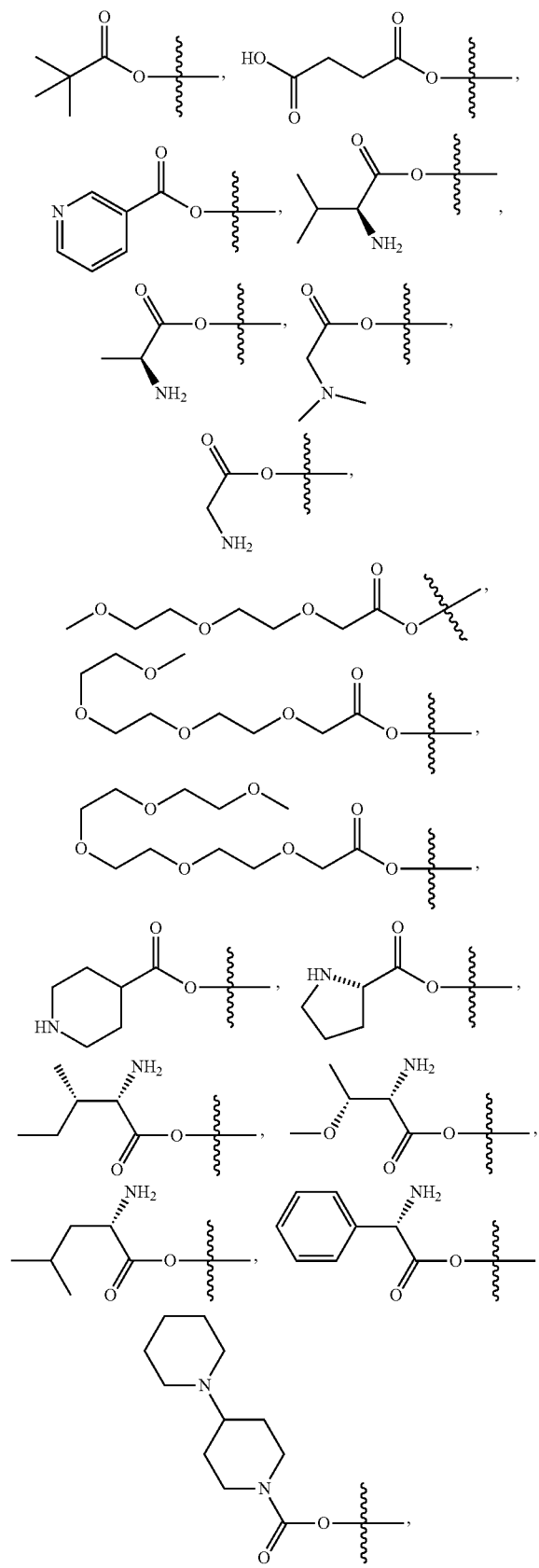
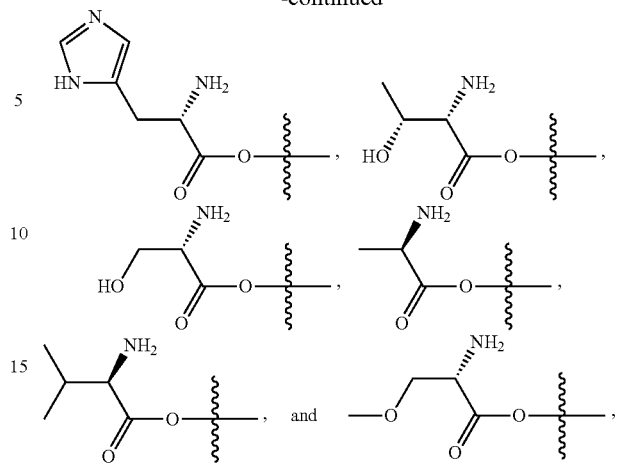
and
R'₃ is selected from —CH₃ and —OCH₃.
In a seventeenth aspect of the invention, provided herein is a compound having the structure:
XIV-b
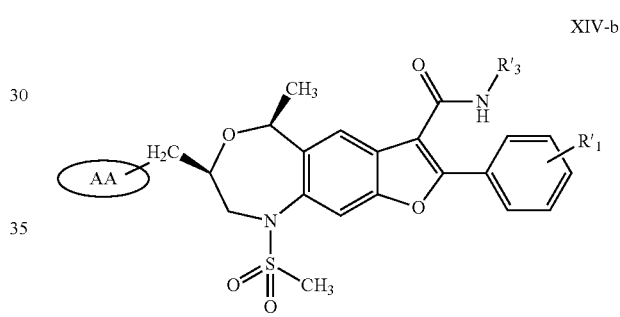
where R'₁ is either para-
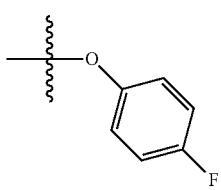 [SMILES: *Oc1ccc(F)cc1]
or para-F,
is a residue of an amino acid according to the structure:
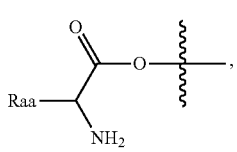

where R$_{aa}$ is the side-chain of the amino acid, and
R'$_3$ is selected from —CH$_3$ and —OCH$_3$. The amino acid may be naturally or non-naturally occurring.

In a first embodiment related to the seventeenth aspect of the invention, in reference to formula XIV-b, (AA)

is a residue of an amino acid selected from the group consisting of D/L-, D- or L-alanine, isoleucine, leucine, valine, phenylalanine, tryptophan, tyrosine, asparagine, cysteine, glutamine, methionine, serine, threonine, aspartic acid, glutamic acid, arginine, histidine, lysine, glyine, and proline.

In an eighteenth aspect of the invention, provided herein is a compound selected from the group consisting of B243, B244, B245, B246, B247, B248, B249, B250, B251, B252, B253, B254, B255, B256, B257, B258, B259, B260, B261, B262, B263, B264, B265, B266, B267, B268, B269, B270, B271, B272, B273, B274, B275, B276, B277, B278, B279, B280, B281, B282, B283, B284, B285, B286, B287, B288, B289, D8, D9, D10, D11, D12, D13, D14, D26, D27, D37, D38, D42, D43, D44, D45, D46, D47, D48, D49, D50, D51, D52, D53, D54, D55, D56, D57, D71, D72, D75, D76, D77, D78, D79. D80, D81, D82, D83, D84, D85, D86, D87, D88, D89, and D90.

In an embodiment related to the eighteenth aspect of the invention, the compound is selected from B243, B244, B245, B246, B248, B249, B252, B253, B254, B255, B256, B257, B258, B259, B260, B261, B263, B264, B265, B266, B267, B268, B269, B270, B271, B272, B273, B275, B276, B277, B278, B280, B281, B282, B283, B284, B285, B286, and B289.

In a nineteenth aspect of the invention, provided is a compound selected from:

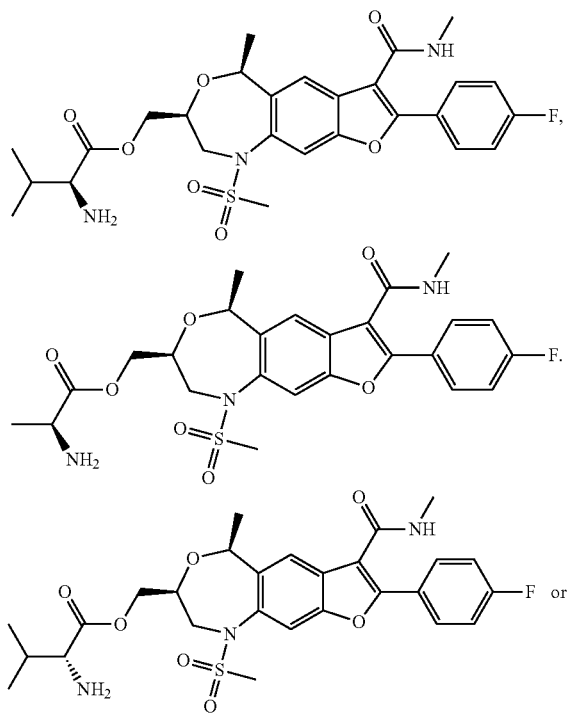

-continued

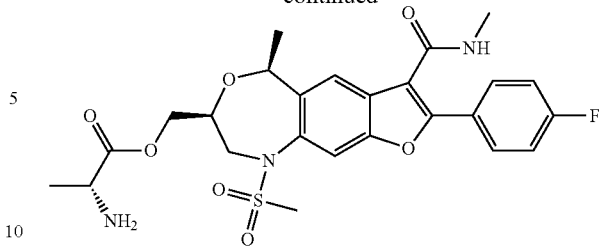

A twentieth aspect of the invention provides a pharmaceutical composition comprising one or more compounds as provided herein and a pharmaceutically acceptable excipient or vehicle. The composition may also comprise additional therapeutic and/or prophylactic ingredients.

A twenty-first aspect of the invention provides use of a compound as provided herein in the manufacture of a medicament, e.g., for treating hepatitis C.

In a first embodiment of the twentifirst aspect, the medicament is for the treatment of hepatitis C.

A twenty-second aspect of the invention provides a method of treating hepatitis C comprising administering to a subject in need thereof a therapeutically effective amount of a compound as provided herein.

General Synthesis

The compounds of the invention may be prepared by a variety of synthetic routes, samples of which are illustrated in the synthetic schemes outlined below. In general, the synthesis starts with constructing the central scaffolds such as benzofuran, benzothiophene, imidazopyridine or pyrazolopyridine by employing various synthetic techniques known to those skilled in the art. (e.g. in *Heterocyclic Chemistry*, J. A. Joule and K. Mills, J Wiley and Sons, 2010.). Once the properly substituted cores are made, further functional group manipulations including but not limited to chain elongation, amidation, esterification, cyclization are performed as necessary to lead to the target molecules. When being allowed chemically and in some cases necessary, the central cores may preferably be introduced toward the end of the synthesis. Often, protection-deprotection and, in some cases, orthogonal protection-deprotection strategies are required to accomplish the desired transformation. More comprehensive descriptions of these synthetic methodologies and techniques can be in found in these and other references: *Comprehensive Organic Transformations*, R. C. Larock Ed., Wiley-RCH, 1999. *Protective Groups in Organic Synthesis*, T. W. Greene and P. G. M. Wuts, 3$^{rd}$ ed. J Willey and Sons, 1999.

The following abbreviations are used throughout this application:

ACN Acetonitrile
AcOH Acetic acid
aq Aqueous
Boc tert-Butoxycarbonyl
Bu Butyl
Cbz Benzoxylcarbonoyl
Concd. Concentrated
CDI 1,1'-carbonyldiimidazole DBU 1,8-Diazabicyclo[5.4.0]undec-7-ene
DCC N,N'-dicyclohexylcarbodiimide
DCM Dichloromethane
DEAD Diethyl azodicarboxylate
DIEA (DIPEA) Diisopropylethylamine
DMA N,N-Dimethylacetamide
DMB 2,4-Dimethoxybenzyl
DMAP N,N-dimethyl-4-aminopyridine
DME 1,2-Dimethoxyethane
DMF N,N-Dimethylformamide
DMSO Dimethylsulfoxide
DPPA Diphenylphosphoryl azide
dppp 1,3-Bis(diphenylphosphino)propane
dppf 1,1'-Bis(diphenylphosphino)ferrocene
DCI 1-Ethyl-3-[3-(dimethylamino) propyl]carbodiimide hydrochloride
$EC_{50}$ Effective concentration to produce 50% of the maximal effect
ESI Electrospray Ionization
$Et_3N$, TEA Triethylamine
EtOAc, EtAc Ethyl acetate
EtOH Ethanol
g Gram(s)
h or hr Hour(s)
HATU 2-(7-Aza-1H-benzotriazole-1-yl)-1,1,3,3-tetramethyluronium hexafluorophosphate
Hex Hexanes
HOBt 1-Hydroxybenzotriazole
HPLC High performance liquid chromatography
$IC_{50}$ The concentration of an inhibitor that causes a 50% reduction in a measured activity
LC-MS Liquid Chromatography-Mass Spectrometry
μM Micromolar(s)
MeI Methyl Iodide
MeOH Methanol
min Minute(s)
mM Millimolar(s)
mmol Millimole(s)
MαNP 2-Methoxy-2-(1-naphthyl)propionic acid
Ms Mesyl, Methylsulfonyl, Methanesulfonyl
MSH O-(mesitylsulfonyl)hydroxyamine
mw Microwave
NBS N-Bromosuccinimide
NIS N-Iodosuccinimide
nM Nanomolar(s)
NMO N-methylmorpholine-N-oxide
NMP N-methylpyrrolidinone
NMR Nuclear magnetic resonance
PE Petroleum ether
PG Protective Group
PPA Polyphosphoric Acid
$PPh_3$ Triphenylphosphine
PPTs Pyridinium p-toluenesulfonate
Py, Pyr Pyridine
rt Room temperature
SEMCl 2-(Trimethylsilyl)ethoxymethyl chloride
TBAF Tetra-n-butylammonium fluoride
TEA Triethylamine
TfOH Trifluoromethanesulfonic acid
TFA Trifluoroacetic acid
THF Tetrahydrofuran
TLC Thin Layer Chromatography
TMSOTf Trimethylsilyl trifluoromethanesulfonate
$t_R$ Retention time
Ts Tosyl, Methylphenylsulfonyl
TsOH Tosylic acid, p-Methylphenylsulfonic acid
w/w Weight/weight
v/v Volume/volume Reagents and solvents used below can be obtained from commercial sources such as Aldrich Chemical Co. (Milwaukee, Wis., USA). $^1H$ NMR spectra were recorded on a Bruker 400 MHz or 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electrospray spray ionization (ESI) mass spectrometry analysis was conducted on a Hewlett-Packard 1100 MSD electrospray mass spectrometer using the HP1 100 HPLC for sample delivery. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Normally the analyte was dissolved in methanol at 0.1 mg/mL and 5 microliter was infused with the delivery solvent into the mass spectrometer, which scanned from 100 to 1500 daltons. All compounds could be analyzed in the positive ESI mode, using an acetonitrile/water gradient (10%-90%) acetonitrile in water with 0.1% formic acid as delivery solvent. The compounds provided below could also be analyzed in the negative ESI mode, using 2 mM $NH_4OAc$ in acetonitrile/water as delivery solvent. Enantiomeric purity was determined using a Hewlett-Packard Series 1050 system equipped with a chiral HLPC column (ChiralPak AD, 4.6 mm×150 mm) and isocratic elution using 5:95 isopropanol-hexane as mobile phase.

The compounds were named using the ChemDraw program from Cambridge Soft Inc.

Scheme A describes a general approach to building fused rings with different sizes that are attached to benzazole moieties along with some chemical transformations on these fused rings. Reduction of $NO_2$ substituted benzazole A-1, followed by sulfonylation gives A-3, upon which is installed a substituted terminal alkyne to afford A-5. A [Pd]-mediated ring cyclization (Heck reaction) forms A-6. Alternatively, A-6 can be prepared using A-7 as a starting material for the Heck reaction. Hydrogenation of A-6 generates A-8, which can also be obtained from A-10 by hydrogenation. A-10 can be converted from A-6 through an isomerization. Cleavage of the double bond of A-6 using conditions such as onzonolysis gives A-9, which can be readily converted into A-11 to A-21 following typical reduction, α-alkylation, O-alkylation, elimination, and/or hydrogenation conditions.

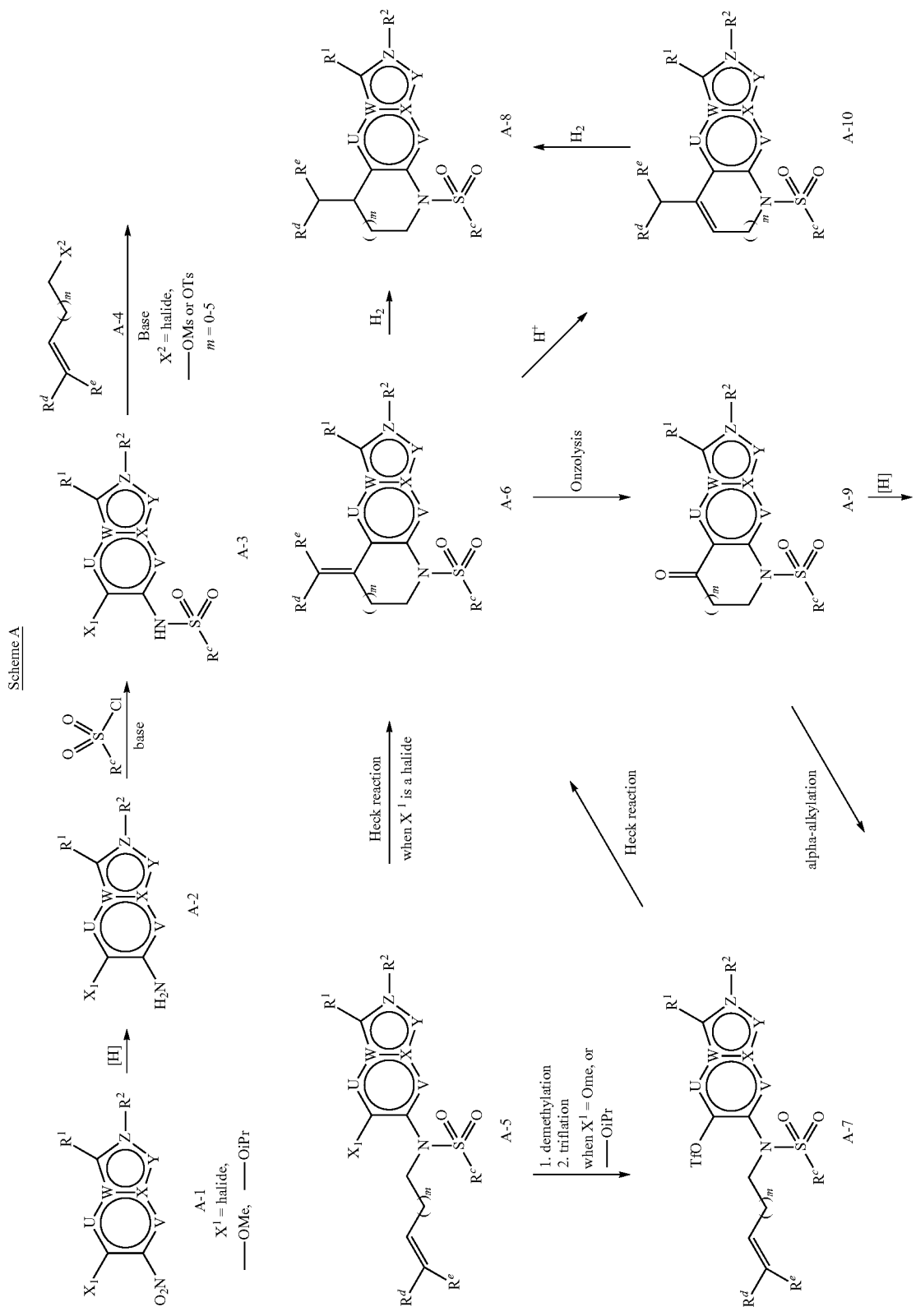
Scheme A

-continued
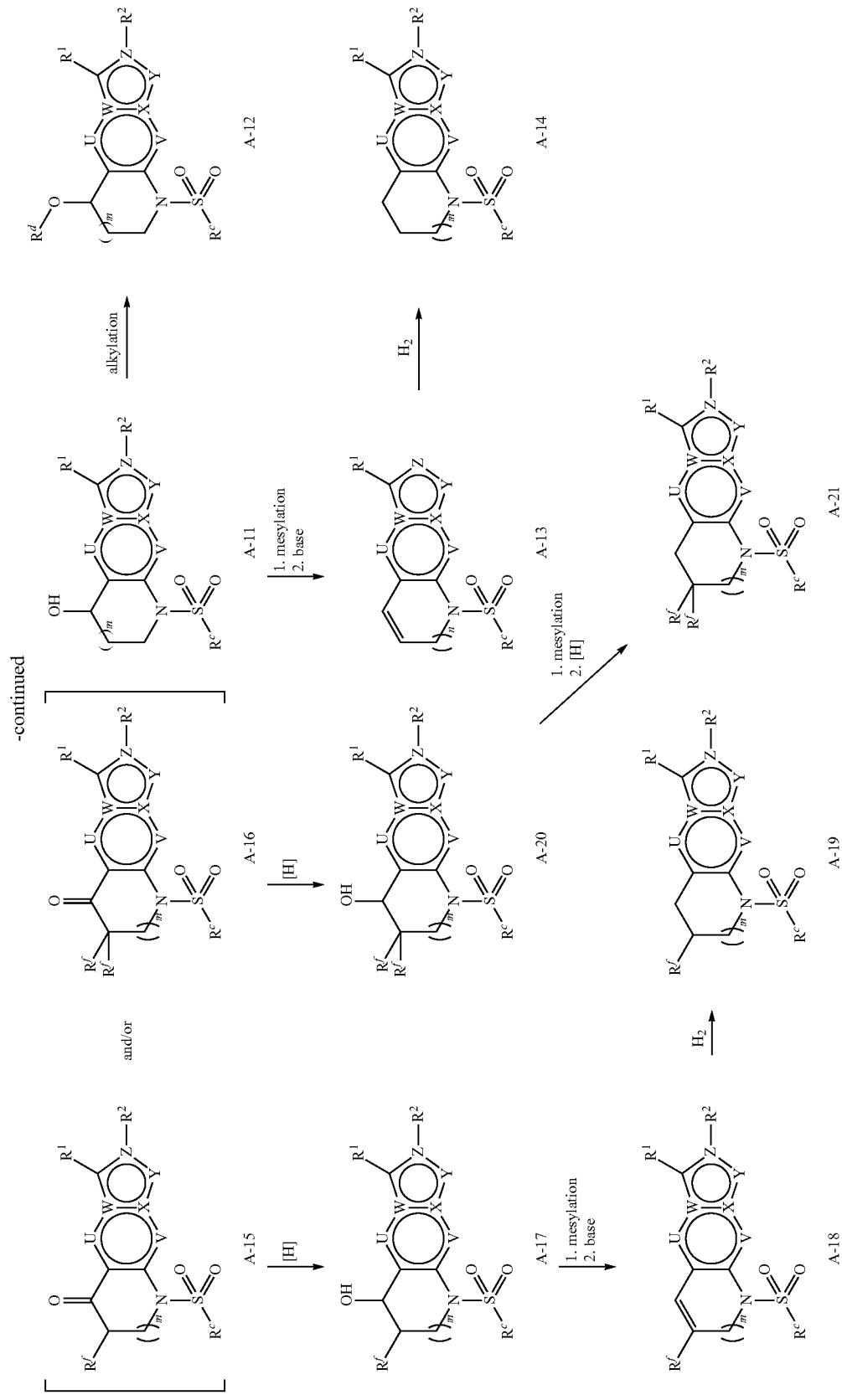

Scheme B
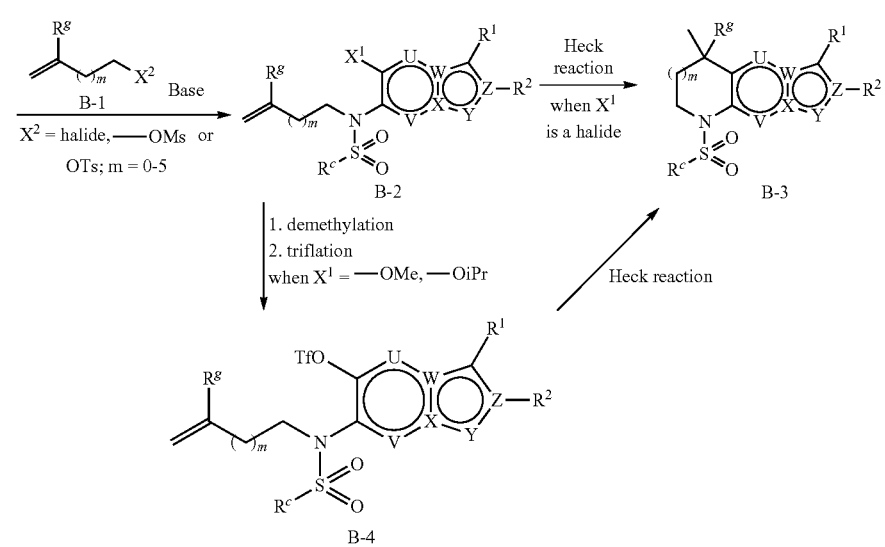
Scheme B describes a general approach to B-3 bearing two substituents at the benzylic carbon. N-alkylation of A-3 with B-1 gives B-2, which is readily converted to B-3 through an intra-molecular Heck reaction when $X^1$ is a halide. When $X^1$ is —OR(R═H, Me, iPr etc), B-3 can be prepared using B-4 as a precursor.
Scheme C
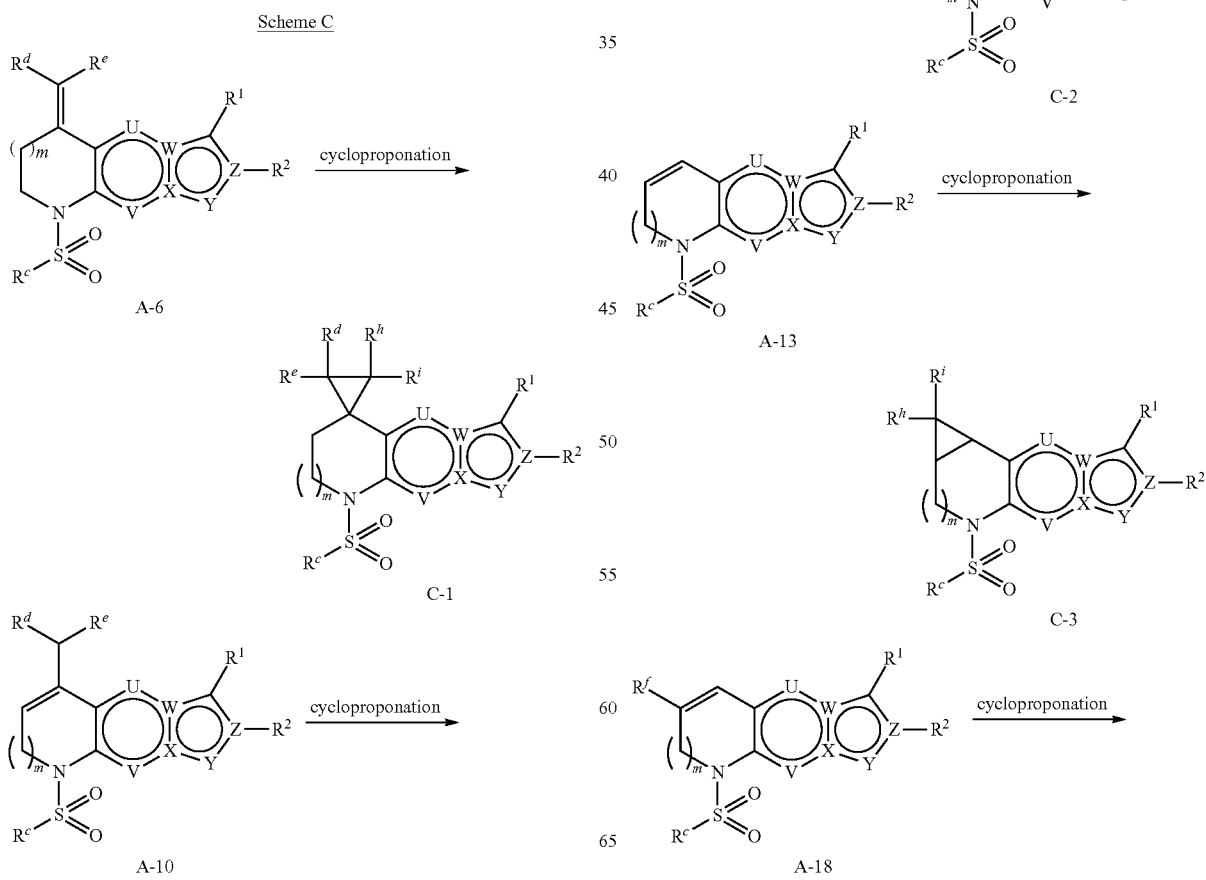
-continued -continued

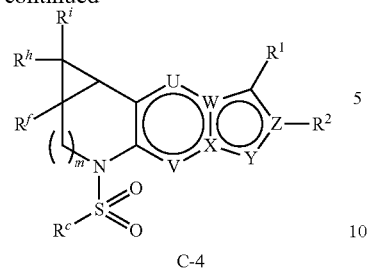

C-4

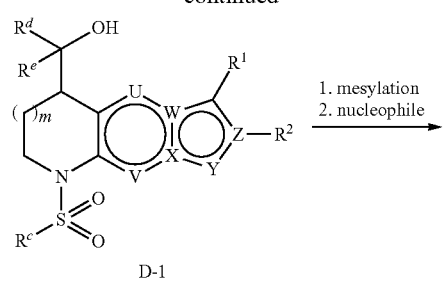

D-1

Scheme C describes a general approach to cyclopropyl-substituted analogs C-1, C-2, C-3 and C-4 from A-6, A-10, A-13 and A-18, respectively.

Scheme D

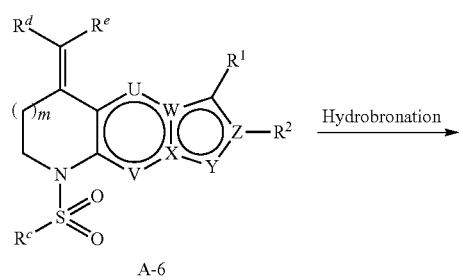

A-6

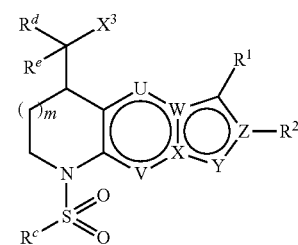

D-2

$X^3$ = F, Cl, CN etc.

Scheme D describes a general approach to analog D-2 from A-6. Hydroboration of A-6 gives D-1, in which the —OH can be readily converted into its mesylate, toyslate, or halide. Subsequent nucleophilic substitution with a nucleophile generates D-2.

Scheme E

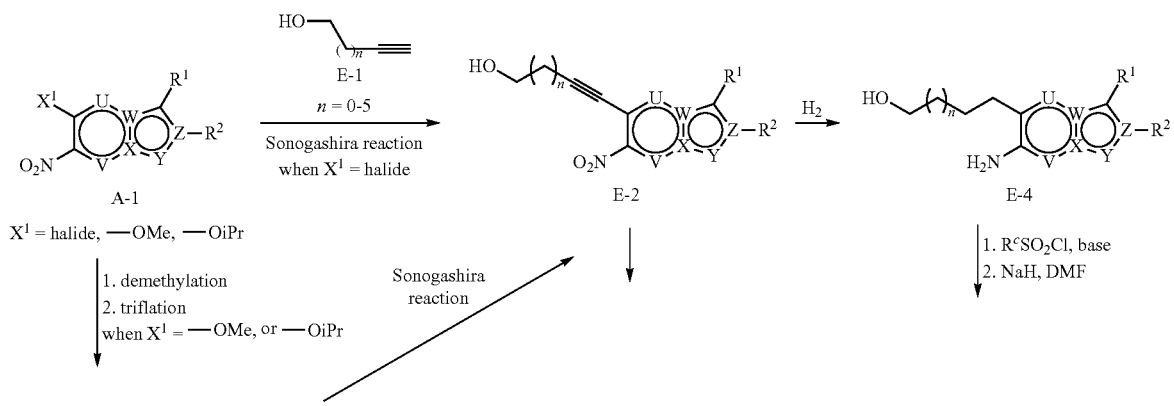

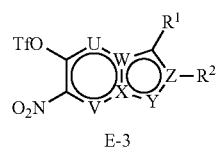

E-3

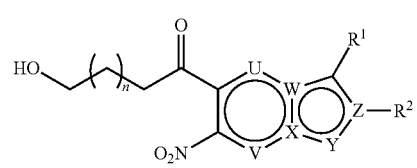

E-5

1. SnCl$_2$
2. R$^c$SO$_2$Cl, nbase
3. NaH, DMF

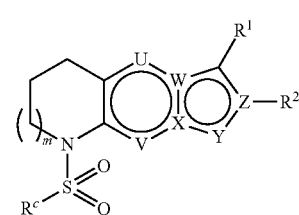

A-14

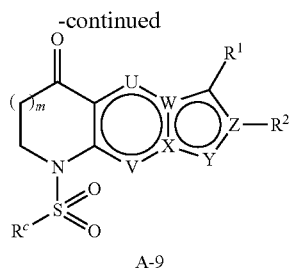

A-9

Scheme E describes an alternative approach to build fused rings with different sizes that are attached to benzazole moieties. Sonogashira reaction of either A-1 or E-3 and E-1 gives E-2, which is hydrogenated to afford E-4. Selective sulfonylation of E-4, followed by ring closure forms A-14. Conversion the triple bond of E-2 into a carbonyl group, followed by reduction of the —NO₂, sulfonylation and ring closure generates A-9.

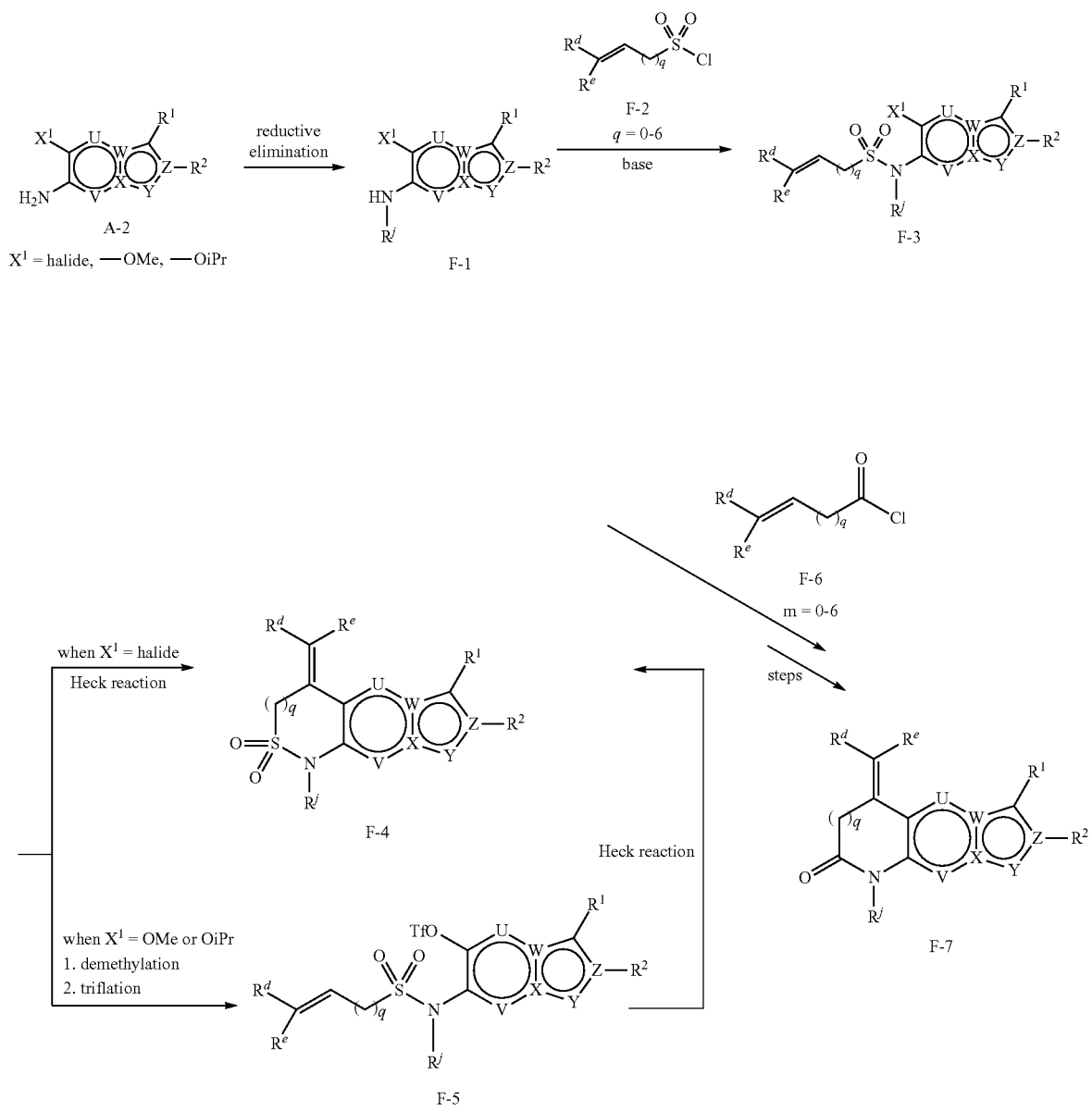

Scheme F describes a general approach to analogs F-4 and F-7 from A-2. Sulfonylation of F-1 with F-2 gives F-3, which undergoes cyclization to afford F-4. Similarly, F-7 can be prepared using F-6 instead of F-2 to react with F-1.
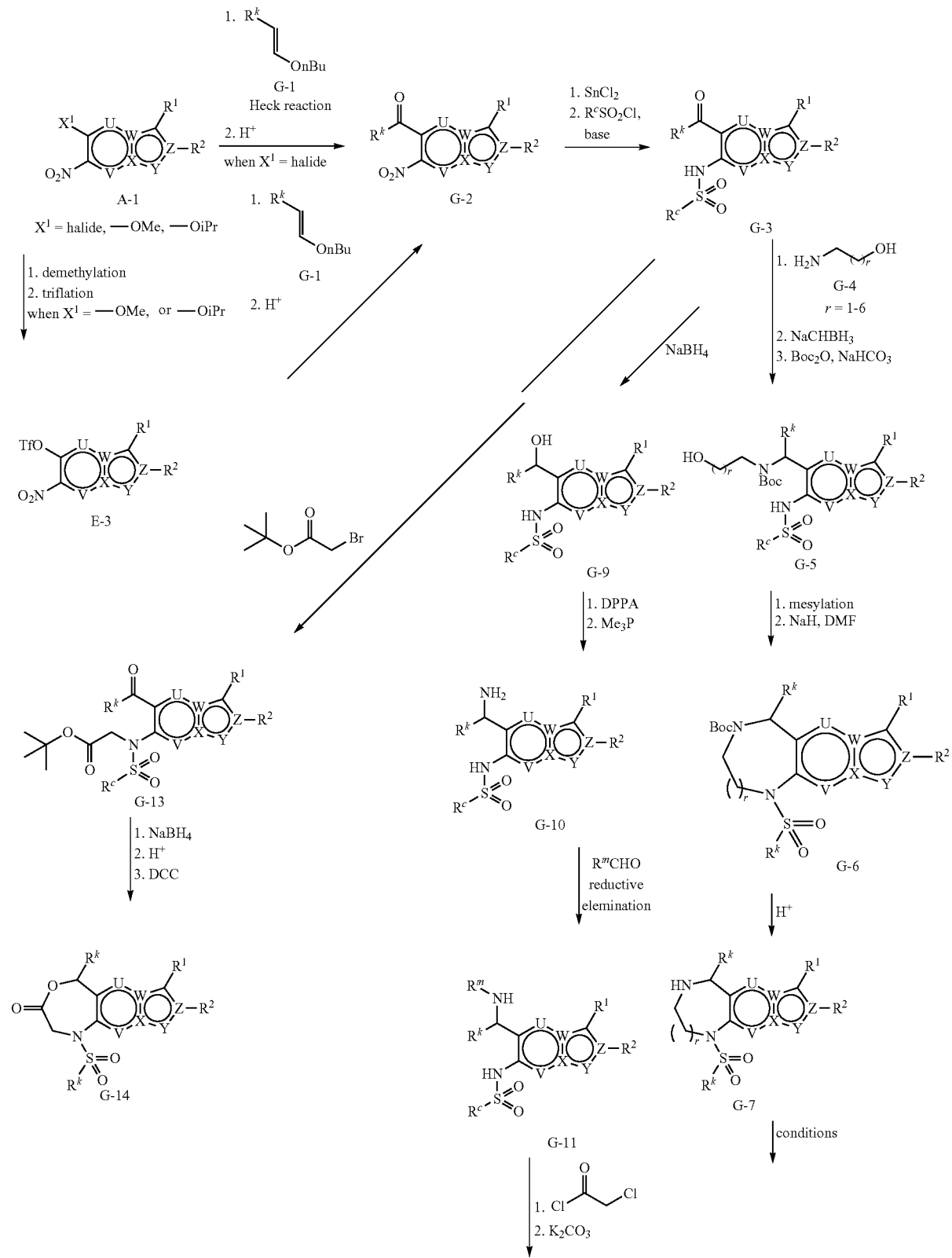
Scheme G

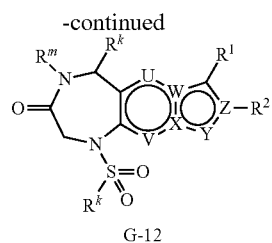 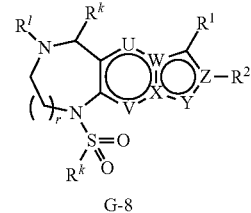
G-12          G-8
Scheme G describes a general approach to fused analogs G-6, G-7, G-8, G-12 and G-14. Heck reaction of A-1 with G-1 gives G-2, which can also be prepared from E-2. Reduction of G-2, followed by sulfonylation affords G-3, which is the key precursor to the following transformations that give various fused analogs G-6, G-7, G-8, G-12 and G-14.
Scheme H
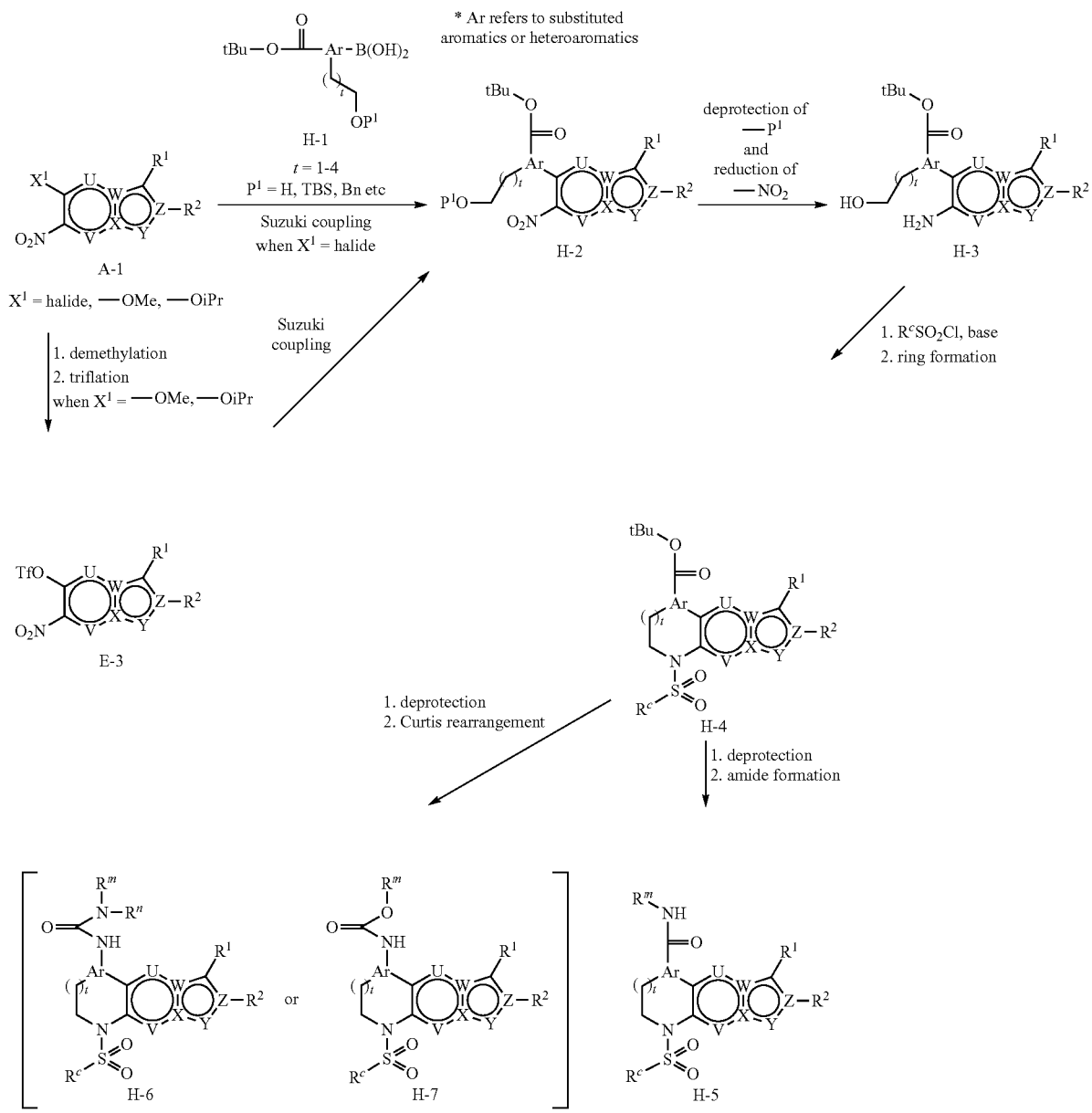

-continued

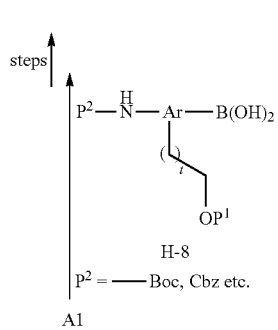

H-8

P² = Boc, Cbz etc.

A1

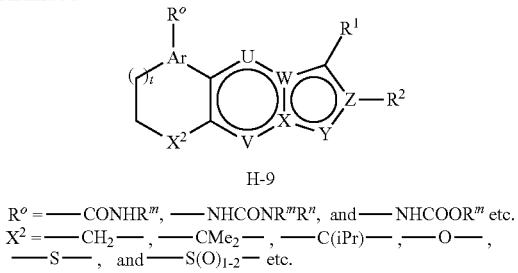

H-9

$R^o =$ —CONHR$^m$, —NHCONR$^m$R$^n$, and —NHCOOR$^m$ etc.
$X^2 =$ —CH$_2$—, —CMe$_2$—, —C(iPr)—, —O—, —S—, and —S(O)$_{1-2}$— etc.

Scheme H describes a general way to prepare H-5, H-6 and H-7. Suzuki coupling of A-1 and H-1 gives H-2, which is converted to H-4 following the same strategy depicted in Scheme E. Further transformations of H-4 may readily afford H-5, H-6 and H-7. Similarly, H-9 can be synthesized by replacing A-1 with suitable starting materials.

Scheme I

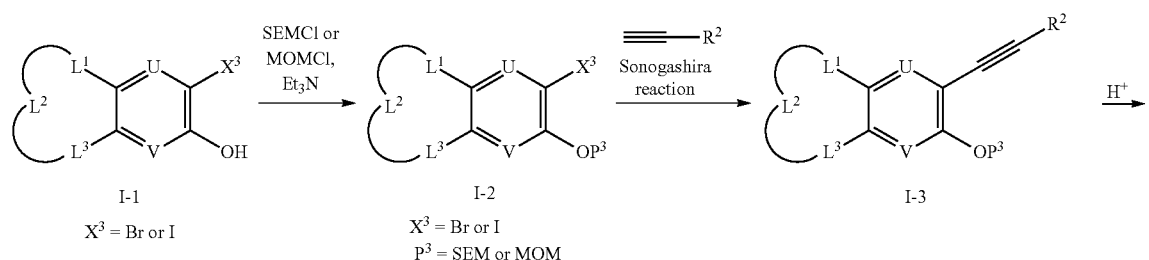

I-1
$X^3 =$ Br or I

I-2
$X^3 =$ Br or I
$P^3 =$ SEM or MOM

I-3

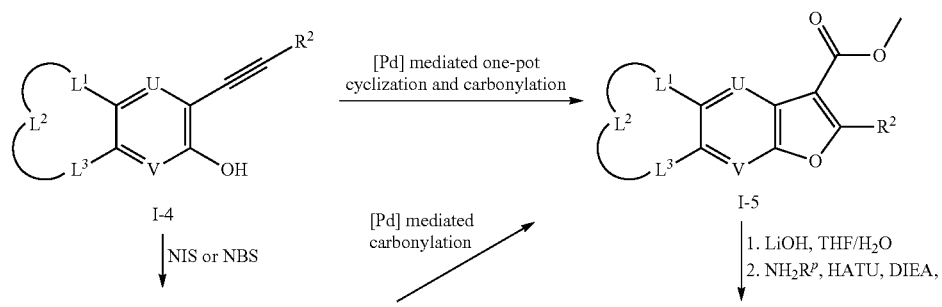

I-4

I-5

1. LiOH, THF/H$_2$O
2. NH$_2$R$^p$, HATU, DIEA,

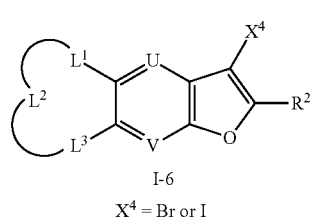

I-6
$X^4 =$ Br or I

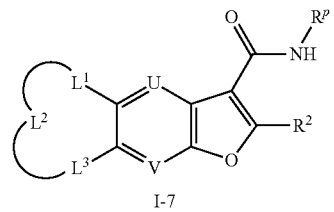

I-7

Scheme I describes general approaches for building a functionalized benzofuran moiety. O-protection of I-1, followed by Sonogashira reaction with a substituted alkyne gives I-3, which is de-protected in the presence of an acid to afford I-4. This compound undergoes a [Pd]-mediated ring cyclization to form I-5, which can be readily converted to I-7 by following a two-step sequence of saponification and amide formation. Alternatively, I-4 can be converted to I-5 through a two-step transformation of NIS or NBS-promoted cyclization and [Pd] mediated carbonylation.

Scheme J

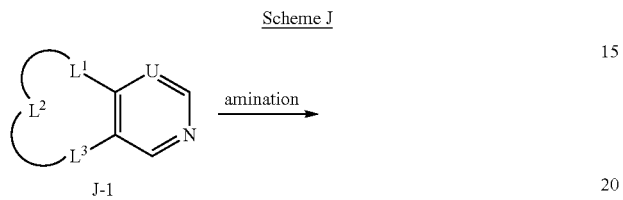

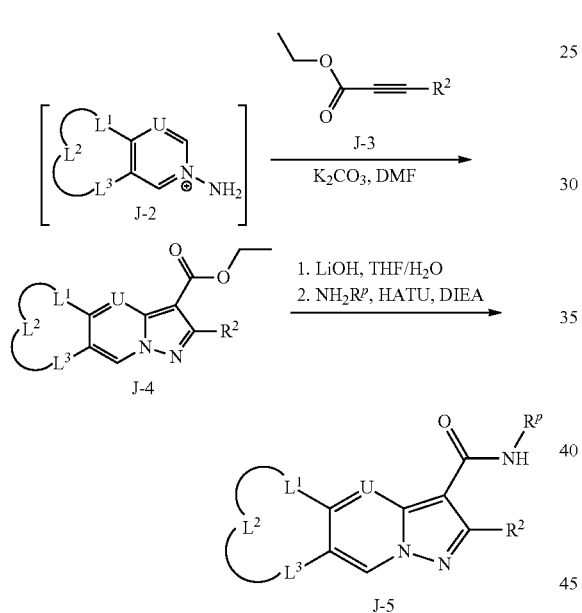

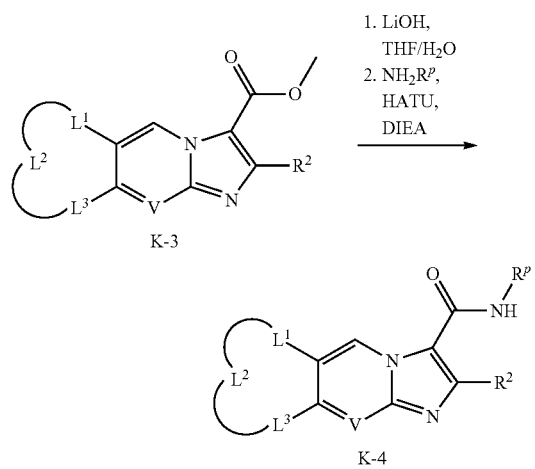

Scheme K describes a general way to build a functionalized imidazole-pyridine moiety. Cyclization of substituted aminopyridine K-1 with bromo-ketoester K-2 gives the cyclized product K-3, which can be readily converted to K-4 by following a two-step sequence of saponification and amide coupling.

Scheme L

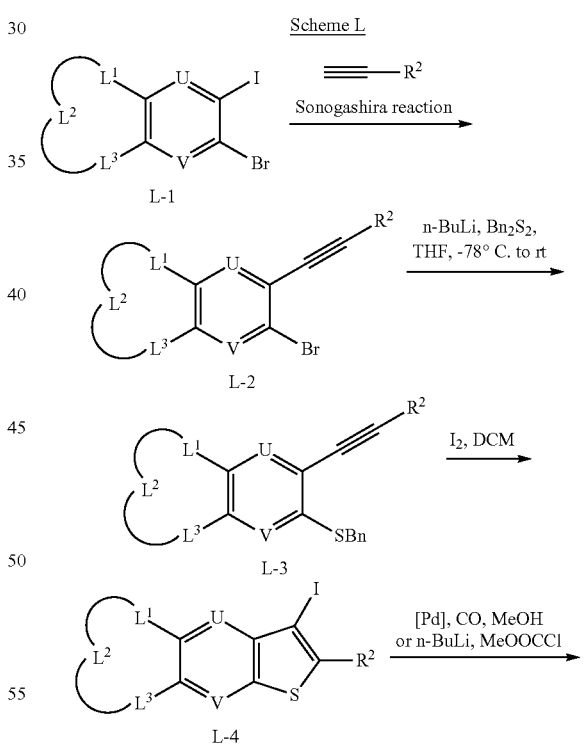

Scheme J describes a general approach for building a functionalized pyrazole-pyridine moiety. N-amination of J-1 gives pyridium salt J-2, which undergoes a ring cyclization with alkynecarboxylate J-3 to form substituted pyrazole-pyridine J-4. Saponification of J-4, followed by amide formation affords J-5.

Scheme K

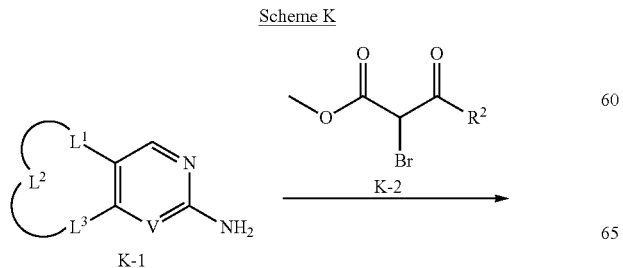

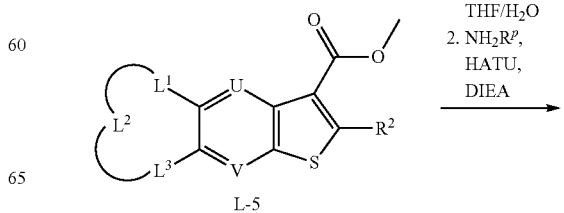

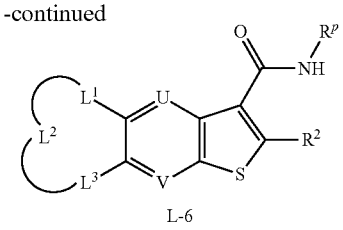

L-6

Scheme L describes a general way to build a functionalized benzothiophene moiety. Sonogashira reaction of L-1 with a substituted alkyne gives L-2, which is converted to thio-ether L-3. An $I_2$-promoted ring cyclization of L-3 affords benzothiophene L-4. The iodo group can be readily transformed into a carboxylate to form functionalized L-5, which undergoes saponification and amide formation to give L-6.

Scheme M

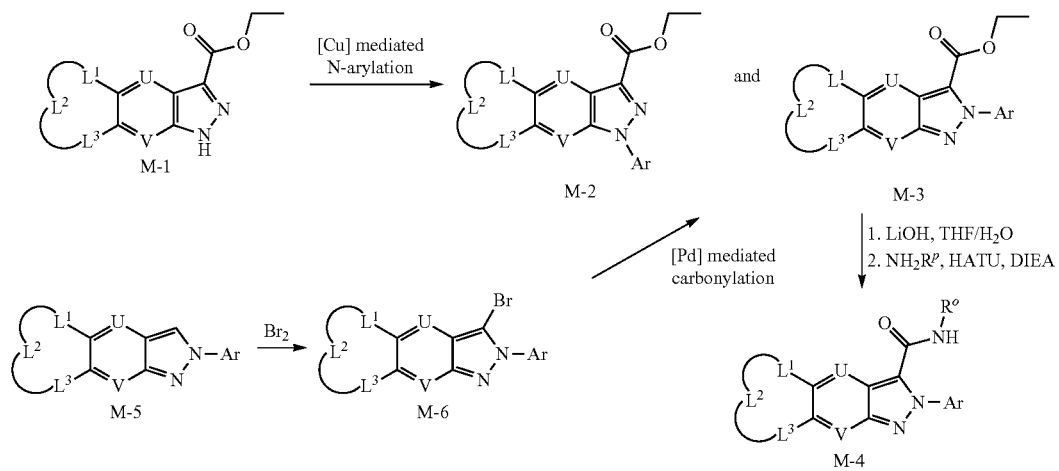

J. Heterocycl. Chem. 2009, 46, 1309
Org. Lett. 2009, 11, 4270
Synlett 2007, 2509
Heterocycl. 2007, 71, 1755
Aust. J. Chem. 1988, 41, 1677

Scheme M describes general ways to build a functionalized 2H-indazole moiety. A Cu-mediated N-arylation gives a mixture of 1H-inzaole M-2 and the desired 2H-indazole M-3. The latter can be readily converted to M-4 following a two-step sequence of saponification and amide formation. Alternatively, 2H-indazole M-5 can be brominated at the C-3 position to give M-6, which undergoes a [Pd]-mediated carbonylation to afford M-3.

Scheme N

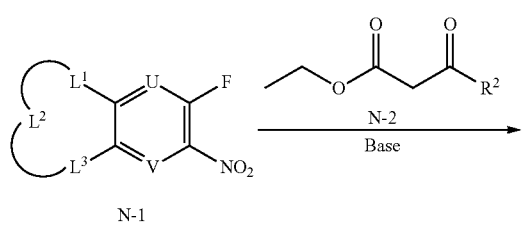

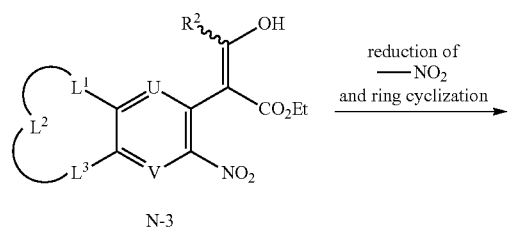

N-3

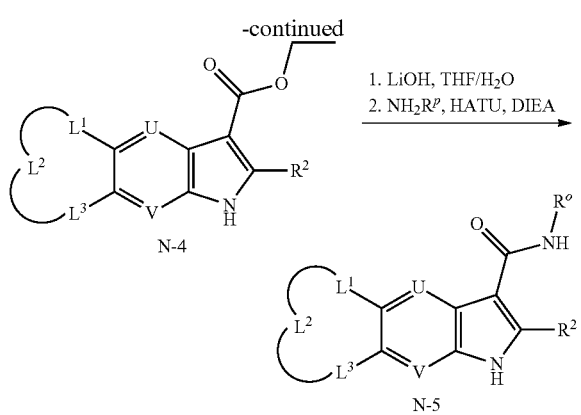

Scheme N describes a general way to build a functionalized indole moiety. A condensation of N-1 and keto-ester N-2 gives N-3. Reduction of N-3, followed by a ring formation affords substituted indole N-4, which can be readily converted to N-5 by following a two-step sequence of saponification and amide formation.

TABLE 1
Substituted benzofuran analogs
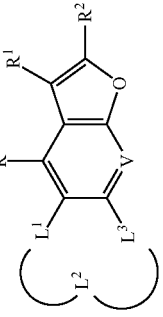

TABLE 1-continued
Substituted benzofuran analogs
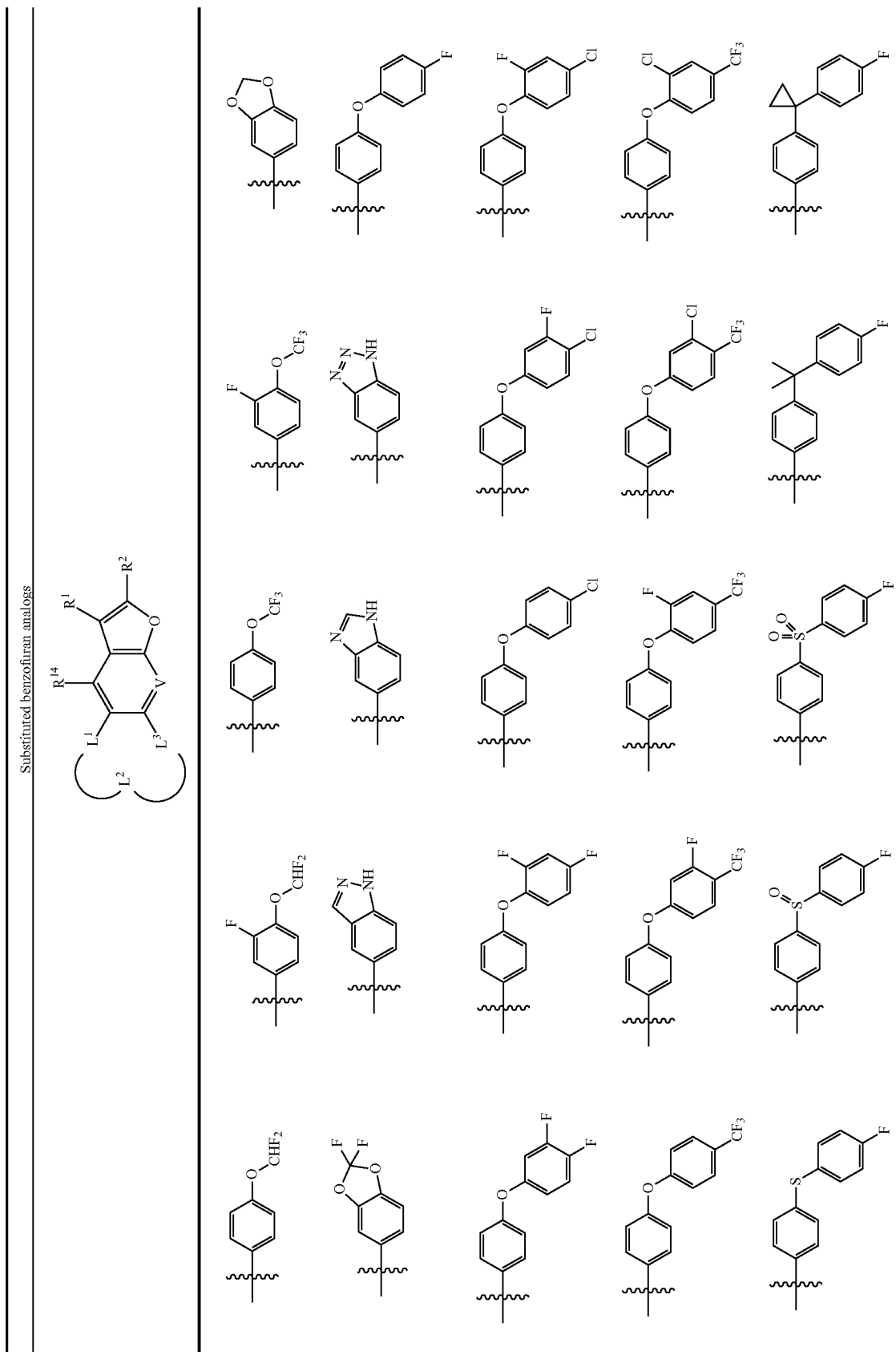

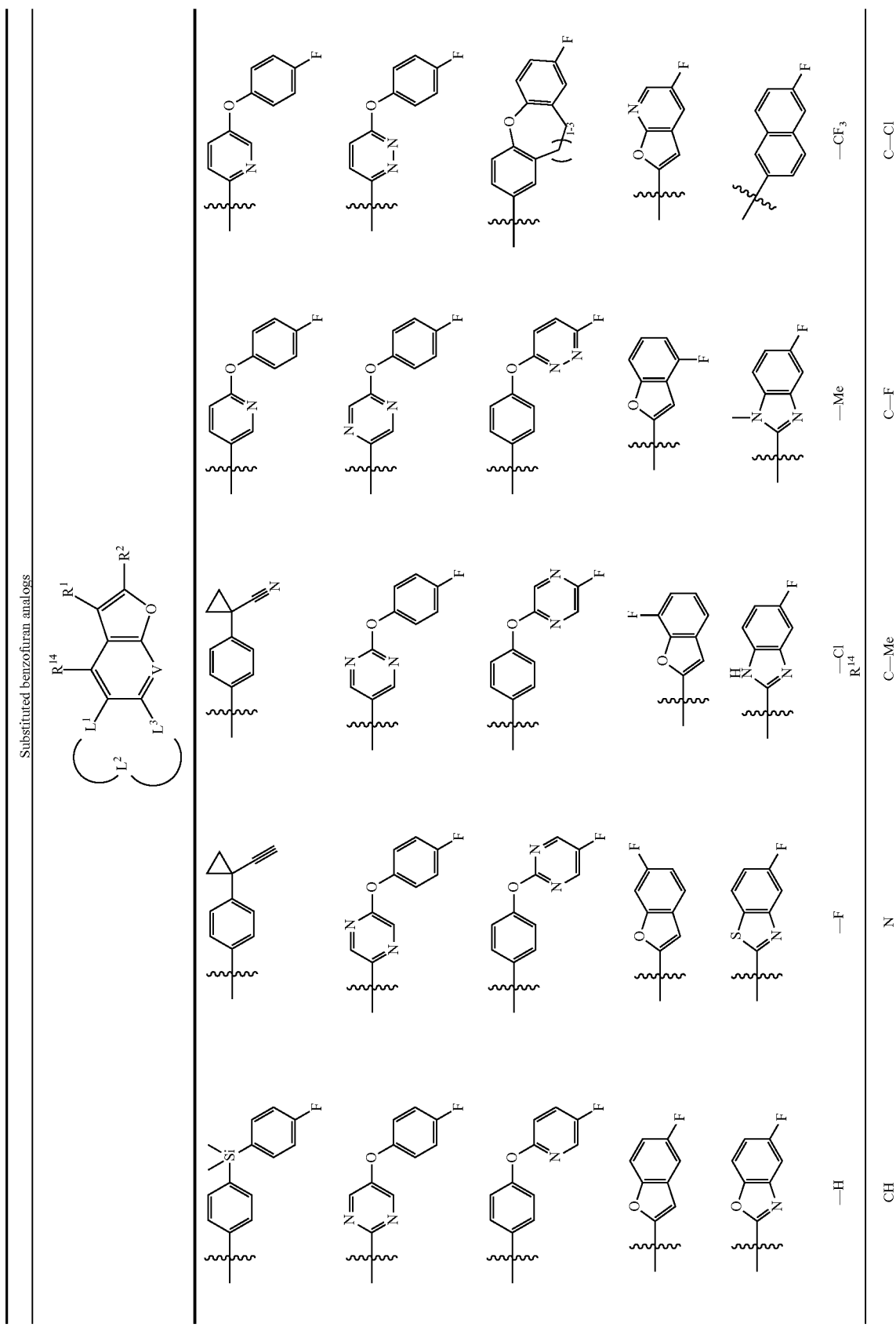

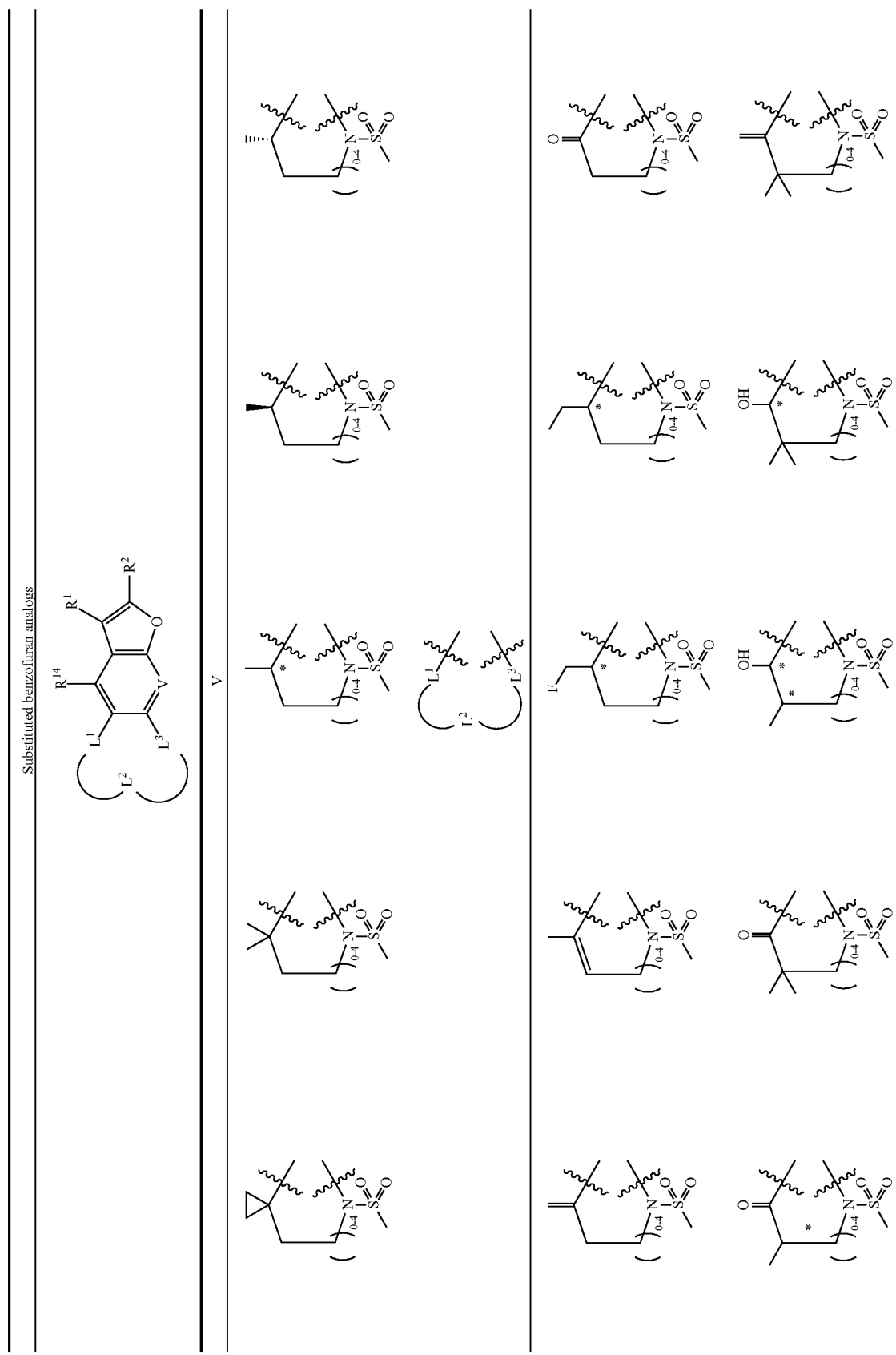

TABLE 1-continued
Substituted benzofuran analogs
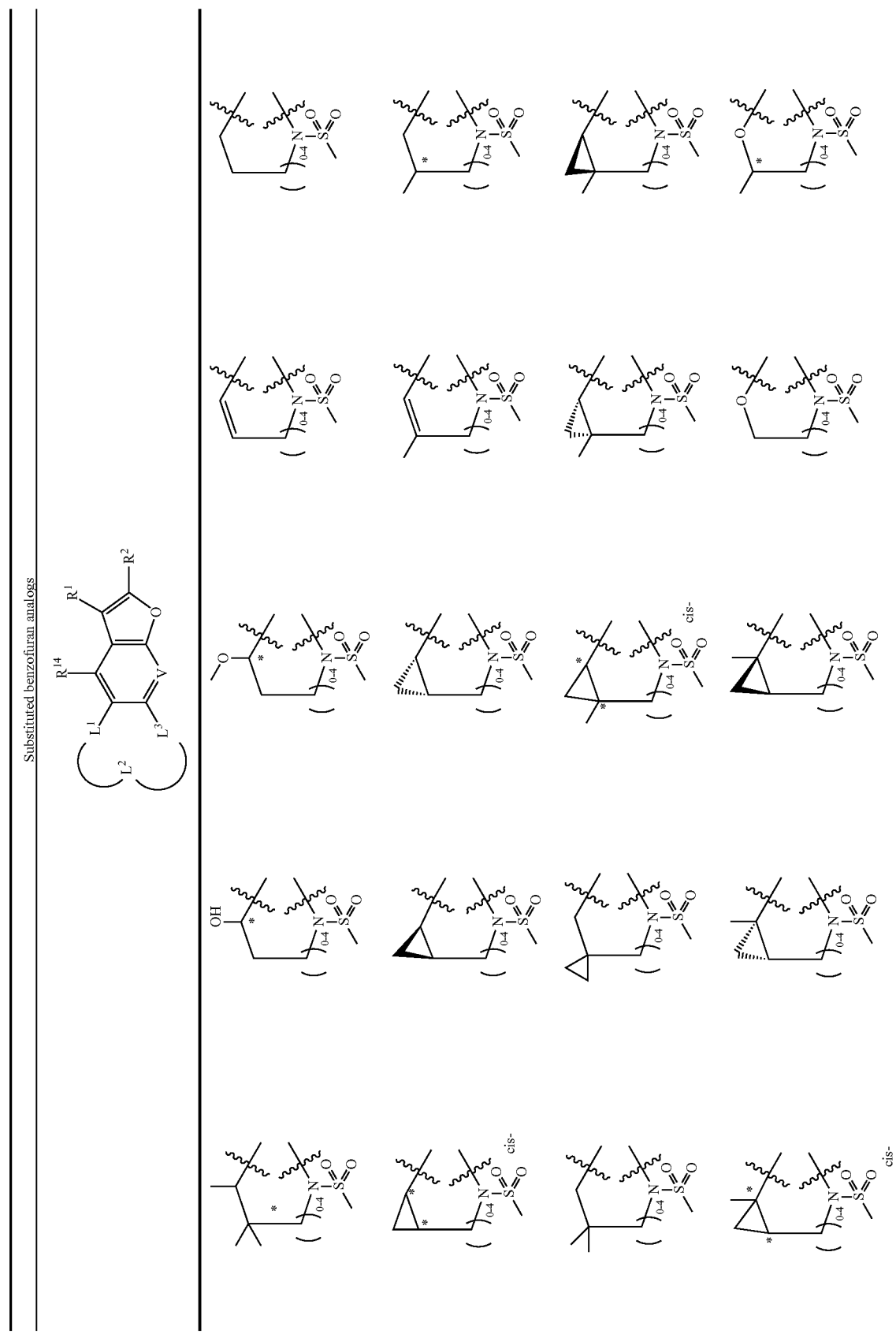

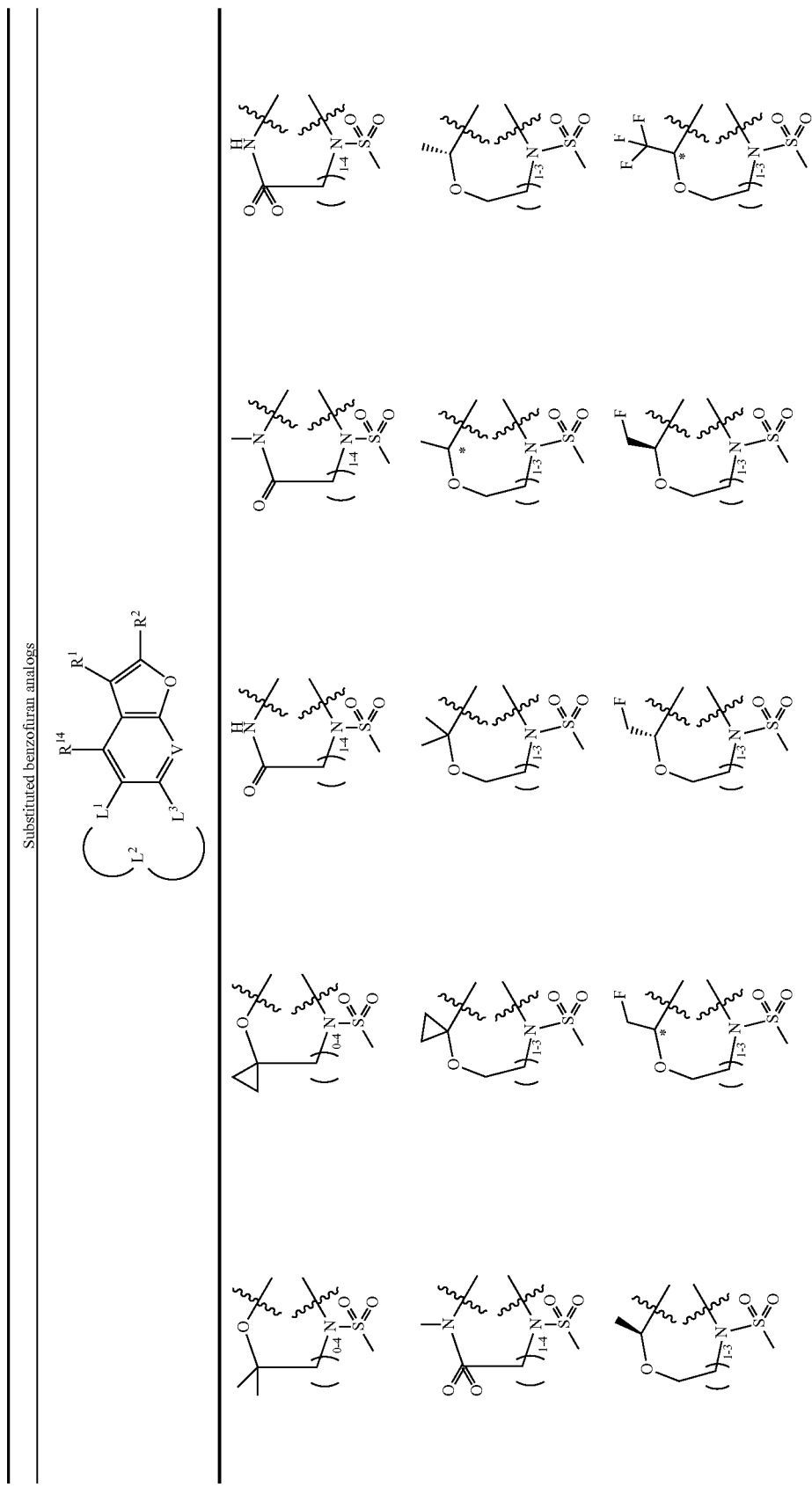

TABLE 1-continued
Substituted benzofuran analogs
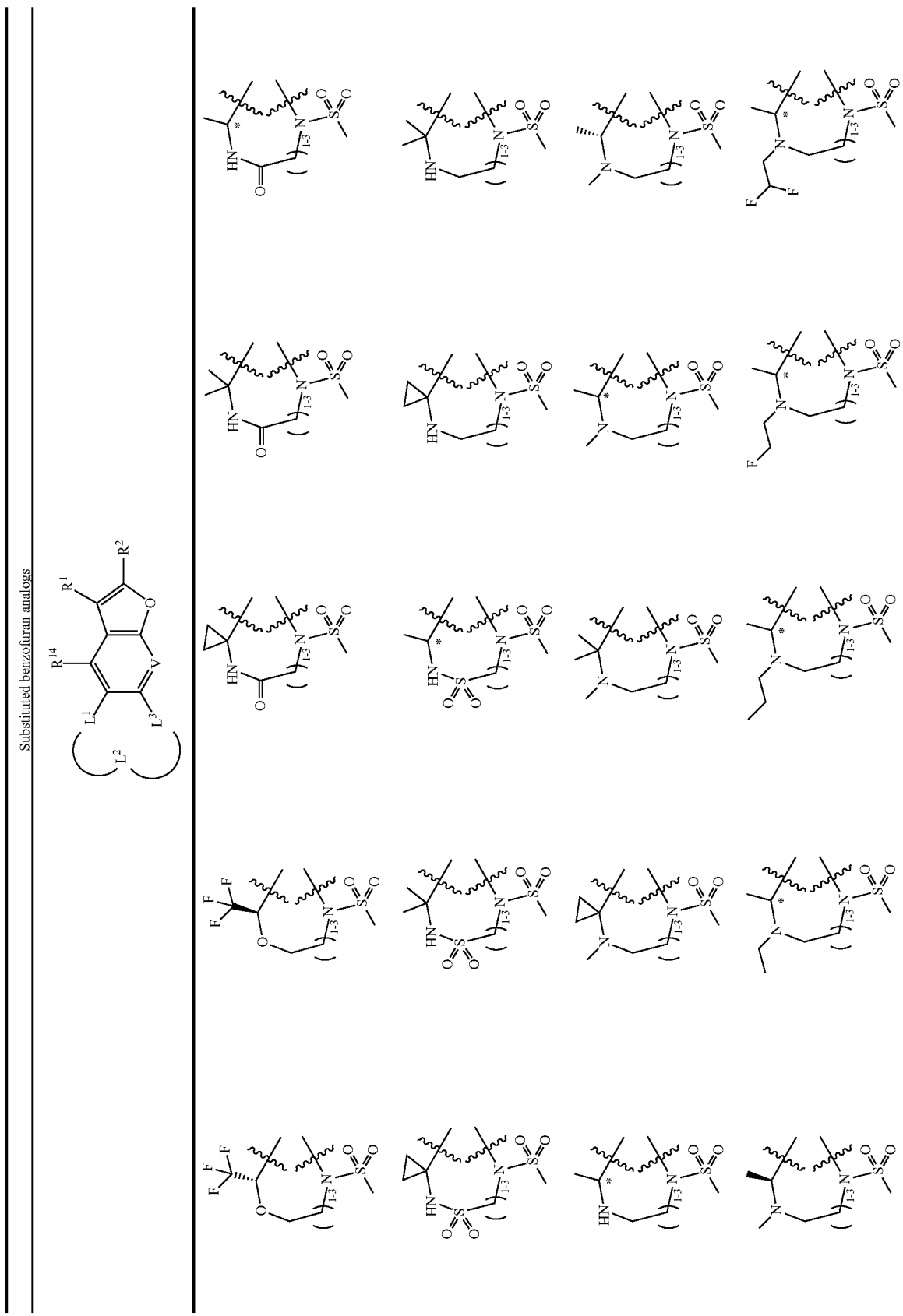

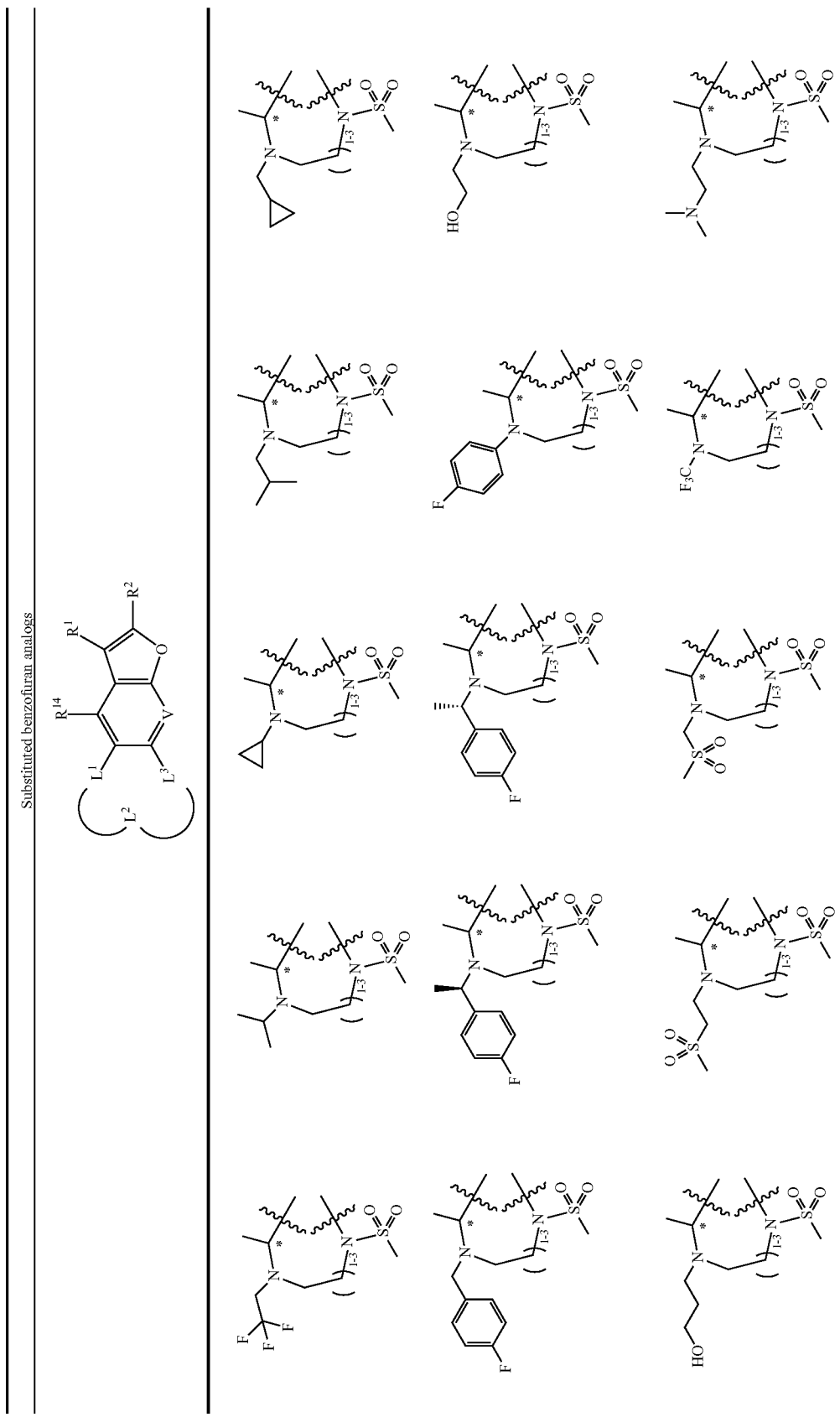

TABLE 1-continued
Substituted benzofuran analogs
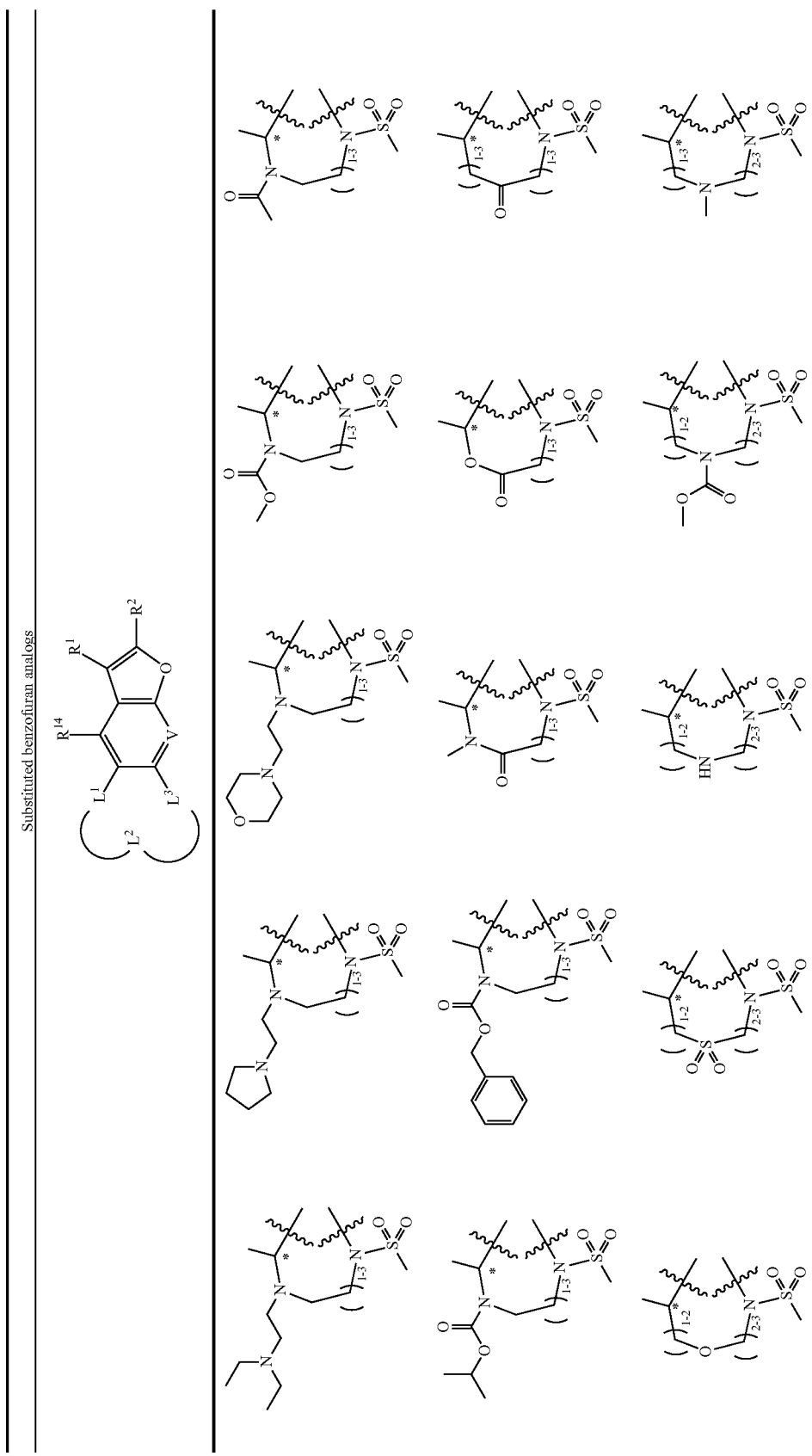

TABLE 1-continued
Substituted benzofuran analogs
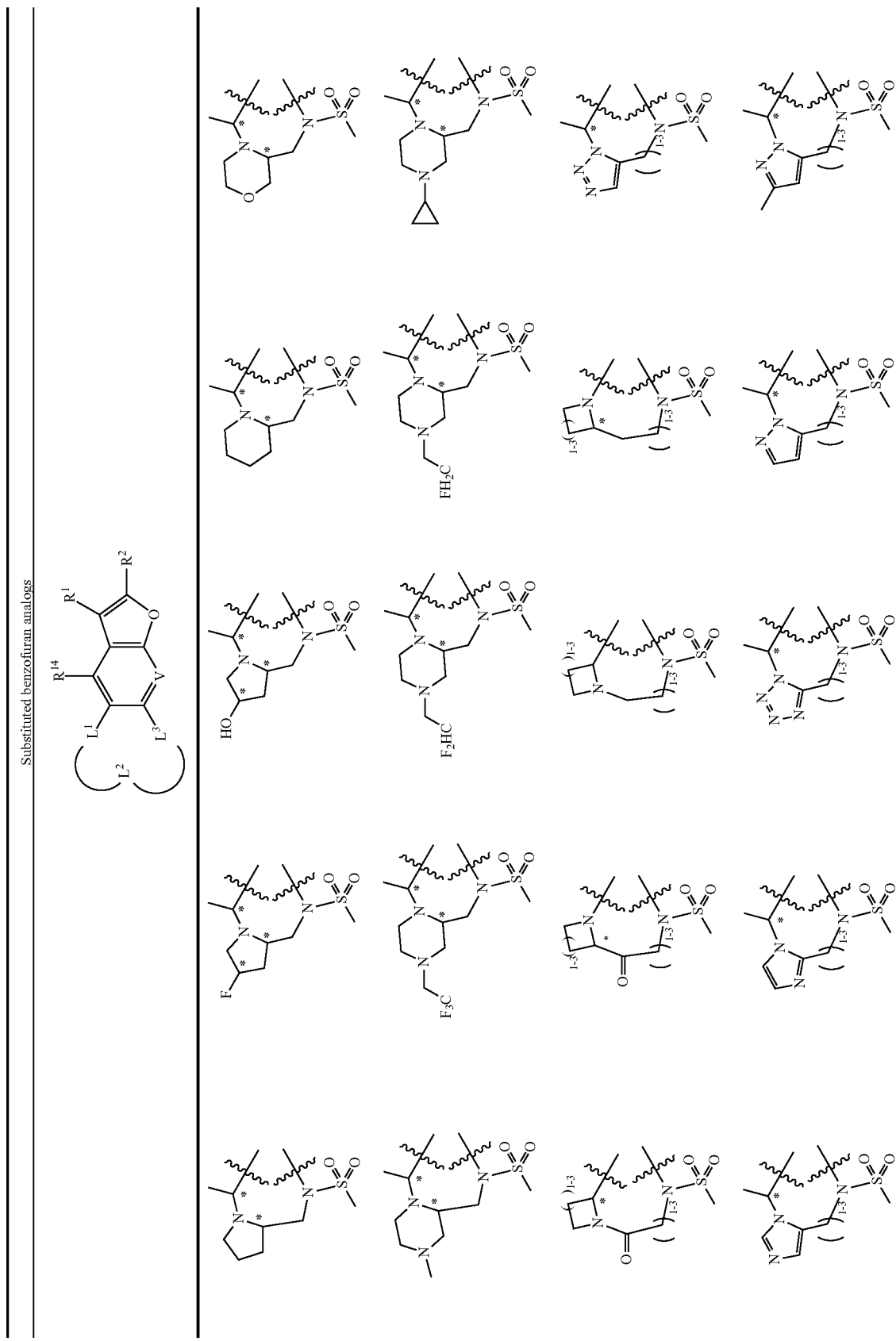

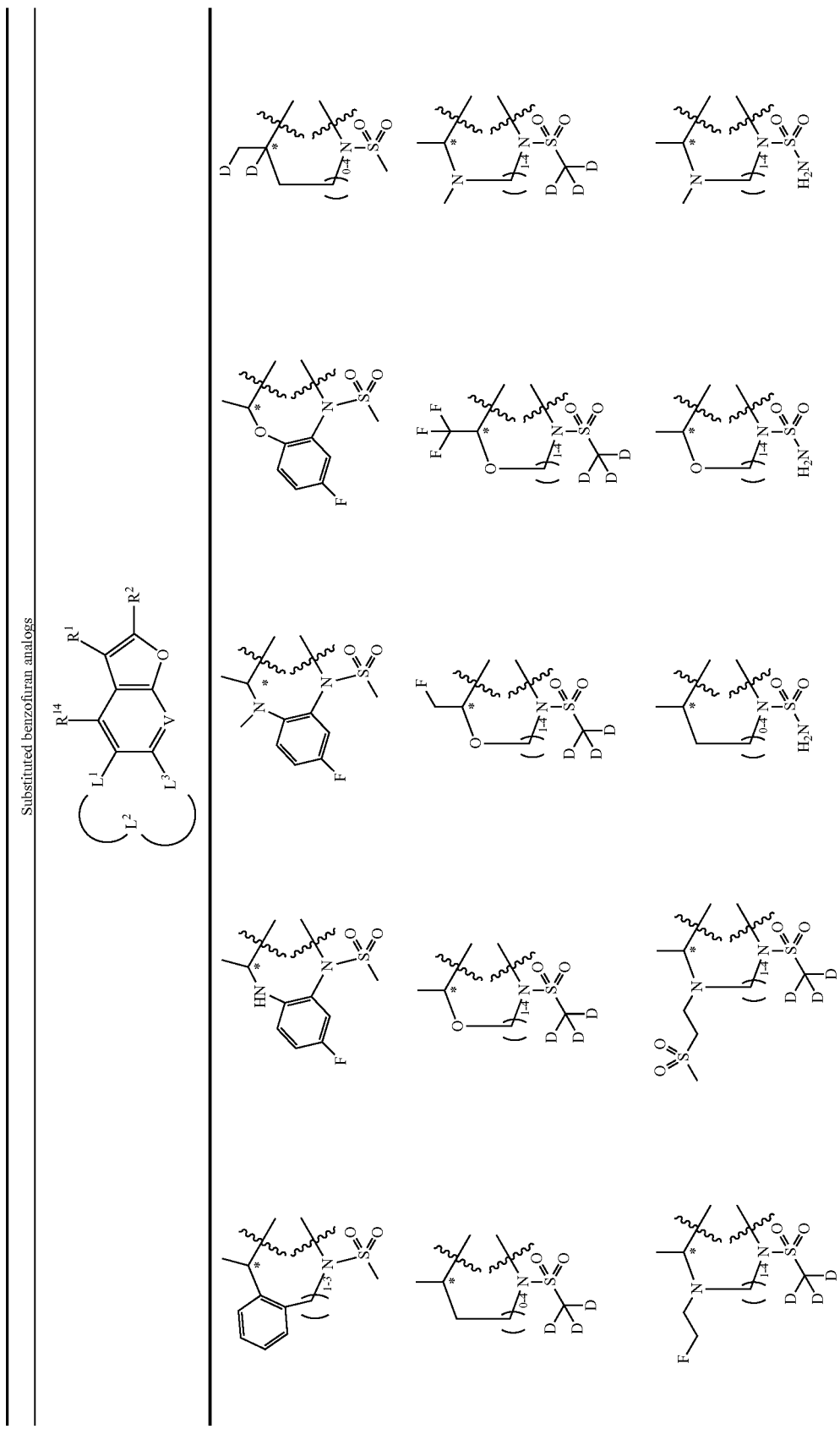

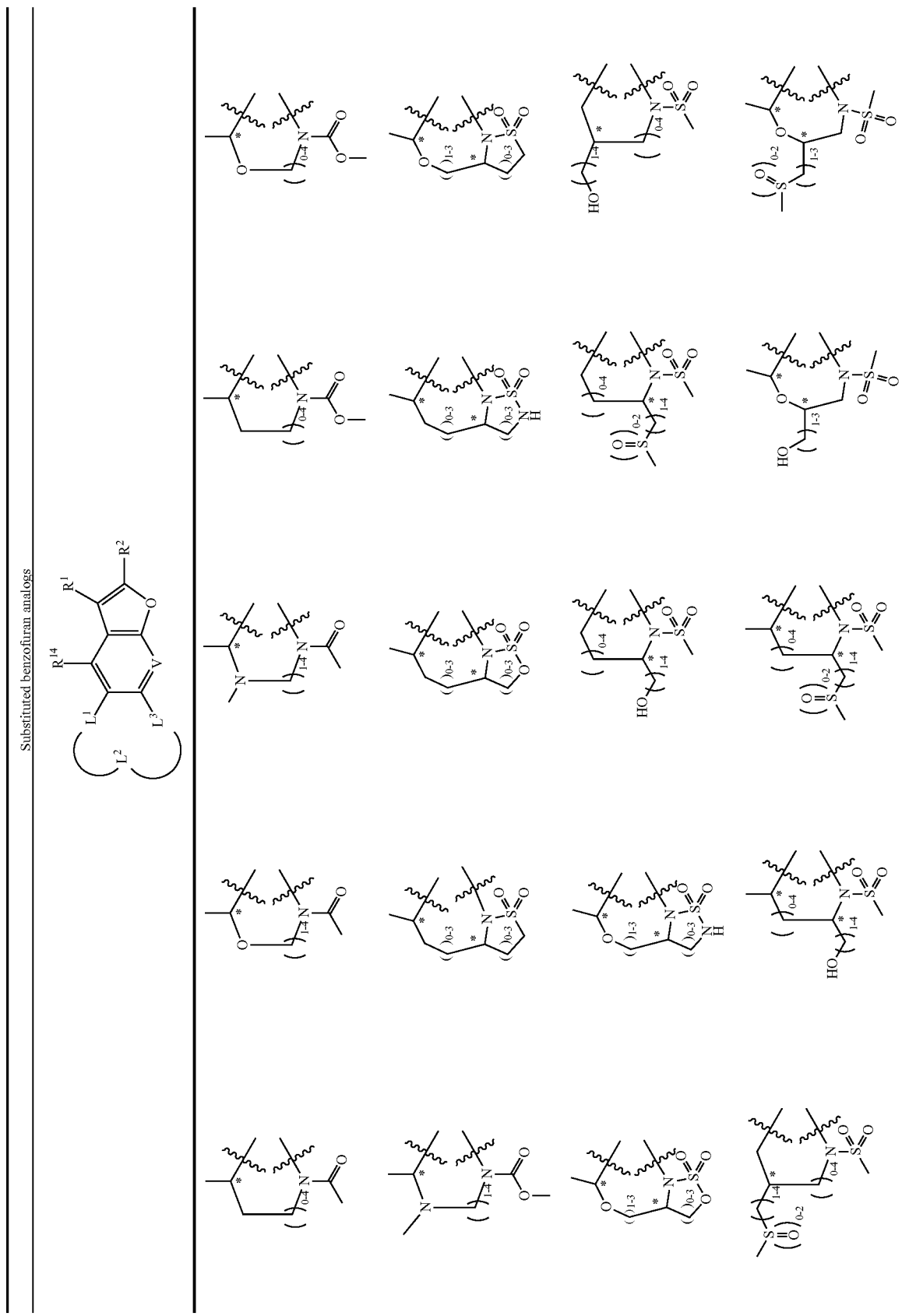

TABLE 1-continued
Substituted benzofuran analogs
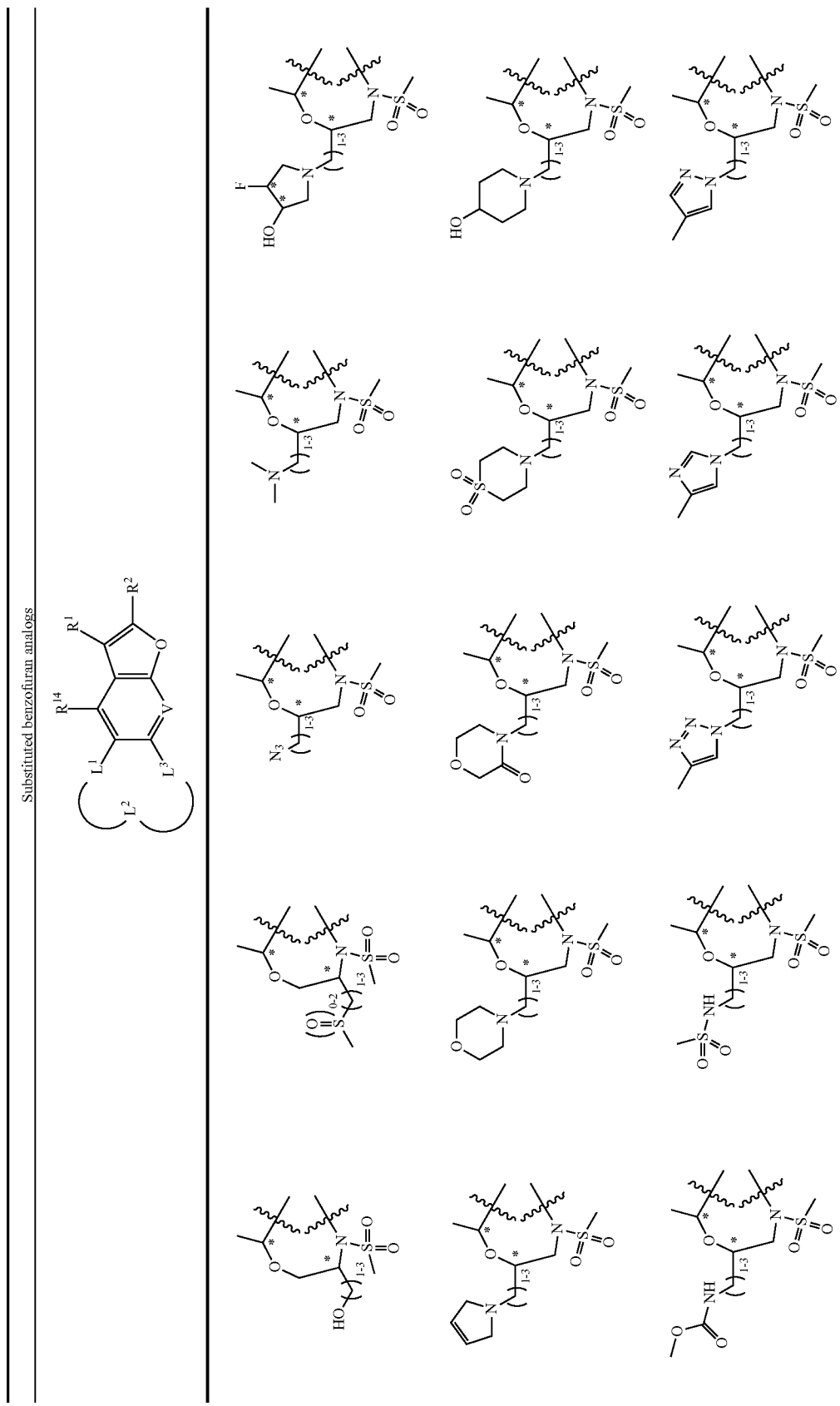

TABLE 1-continued
Substituted benzofuran analogs
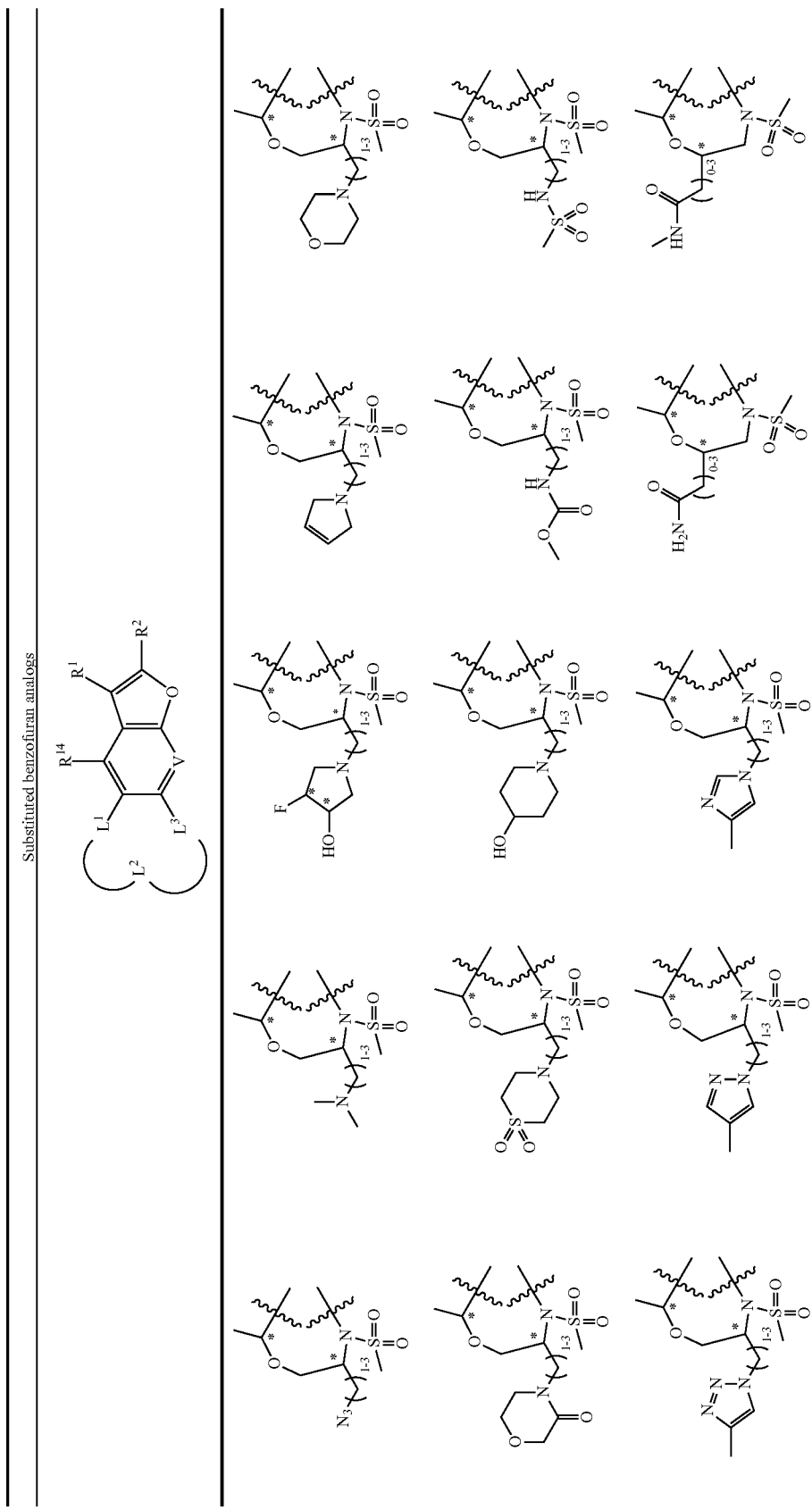

TABLE 1-continued
Substituted benzofuran analogs
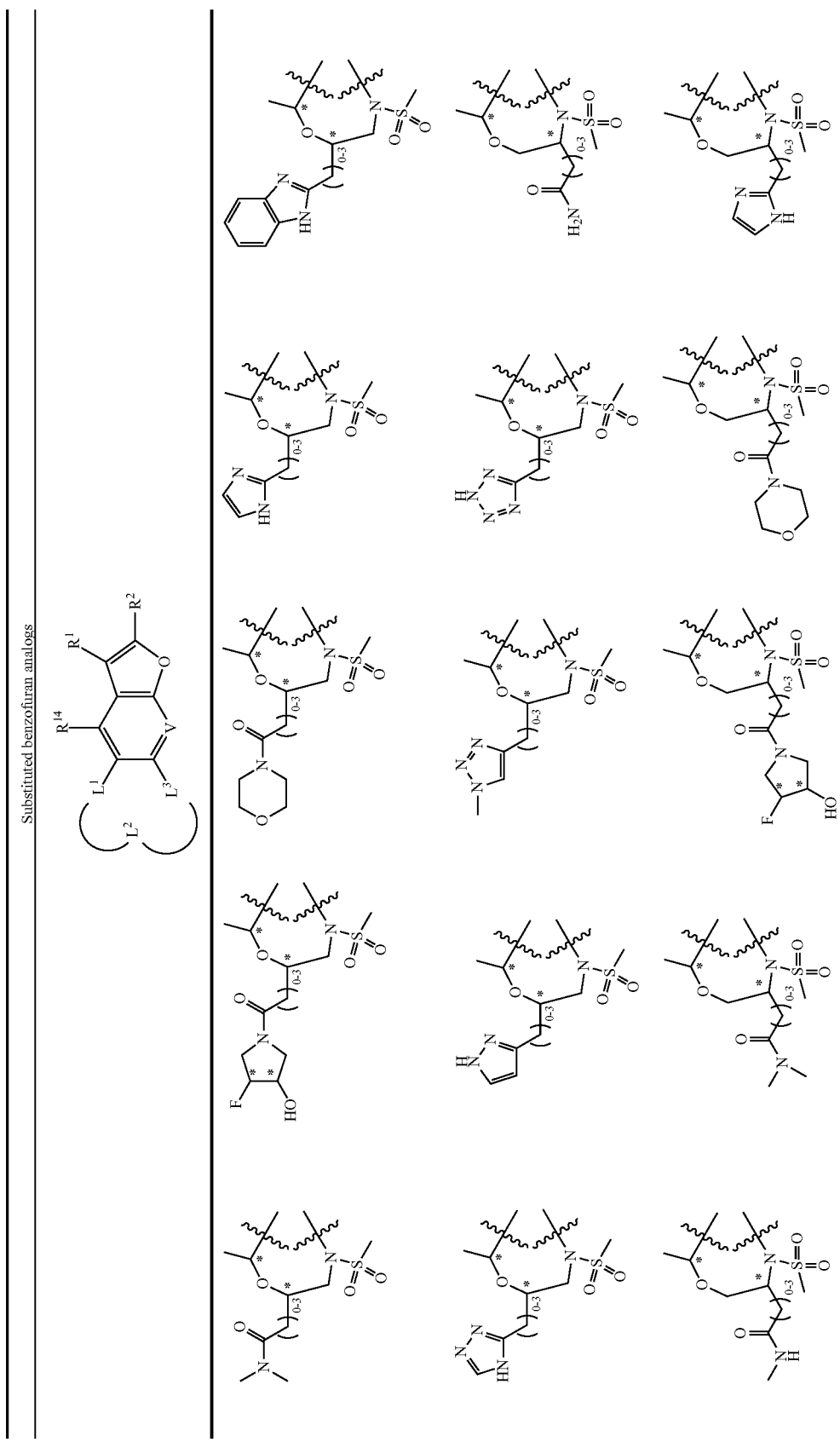

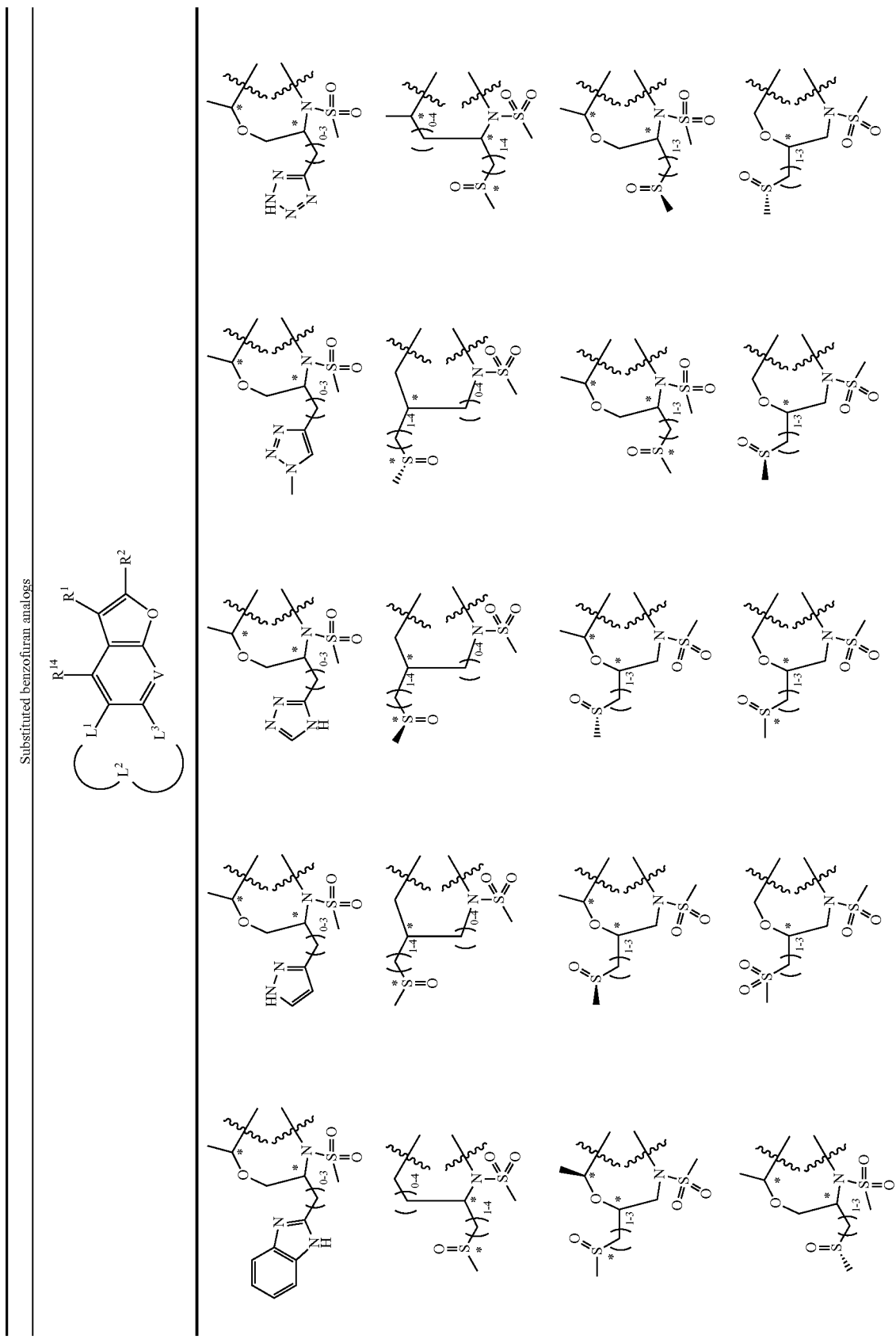

TABLE 1-continued
Substituted benzofuran analogs
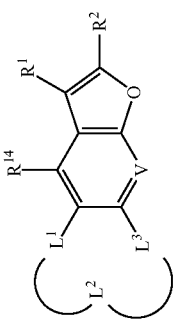
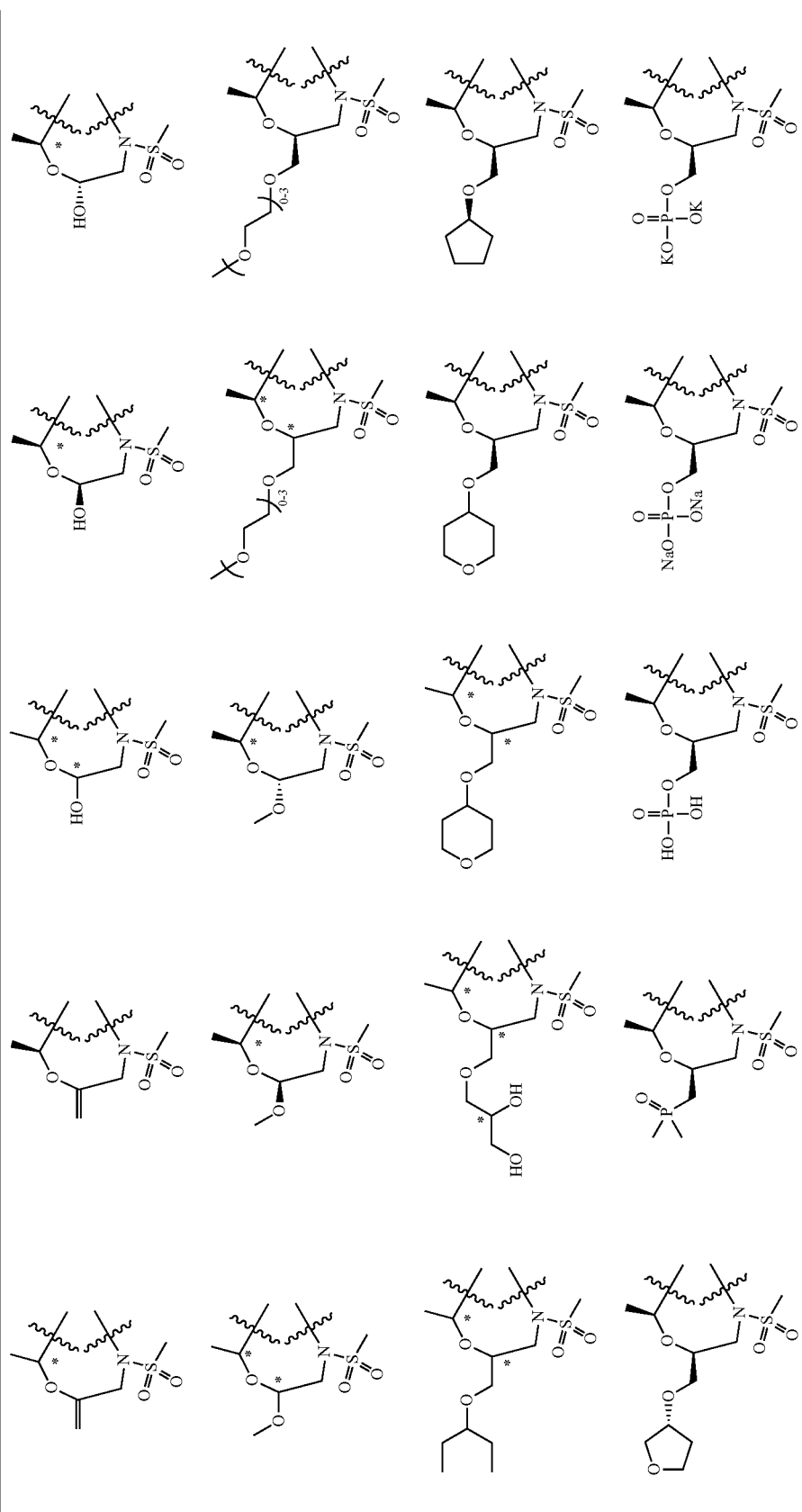

TABLE 1-continued
Substituted benzofuran analogs
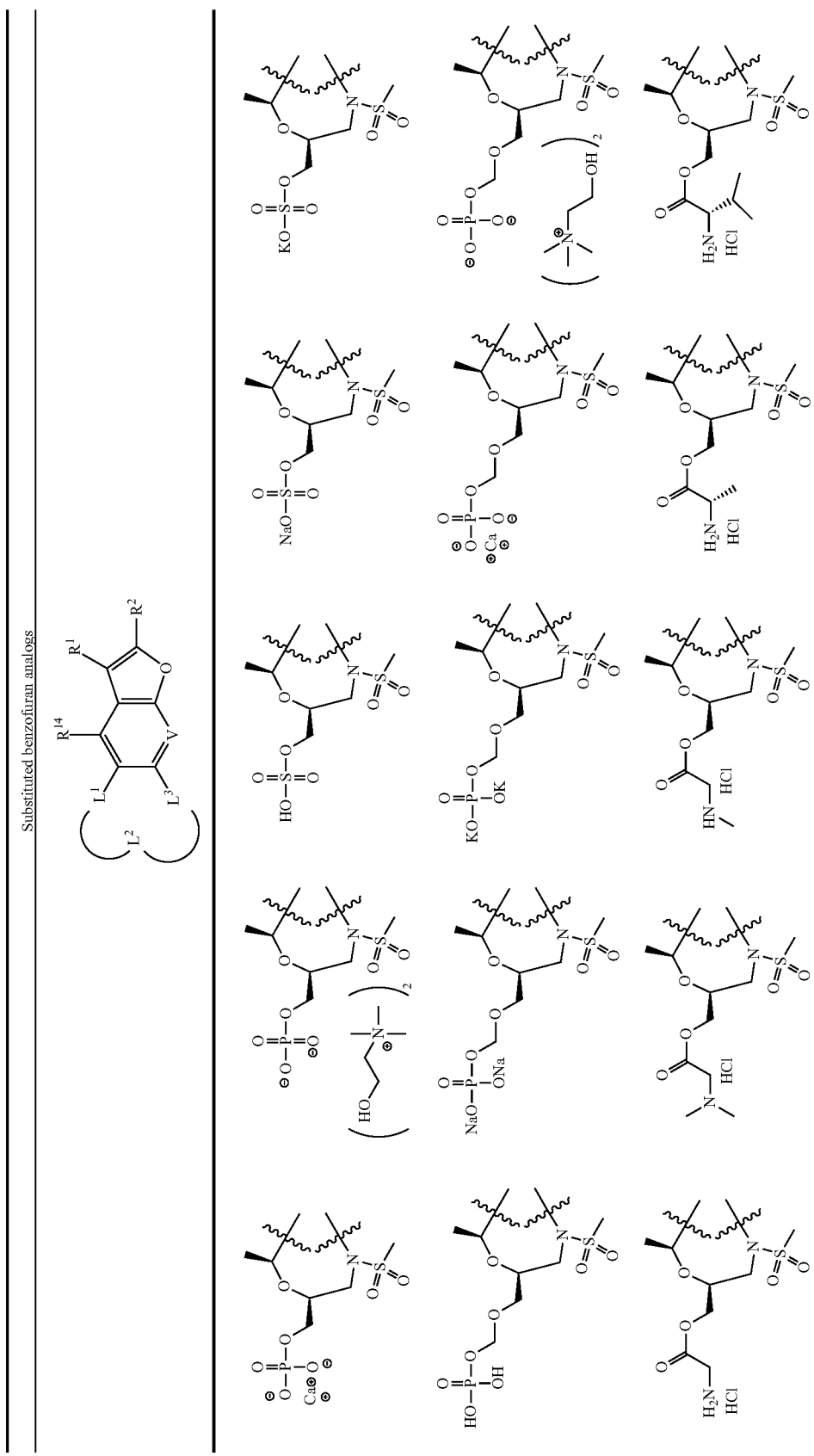

TABLE 1-continued
Substituted benzofuran analogs
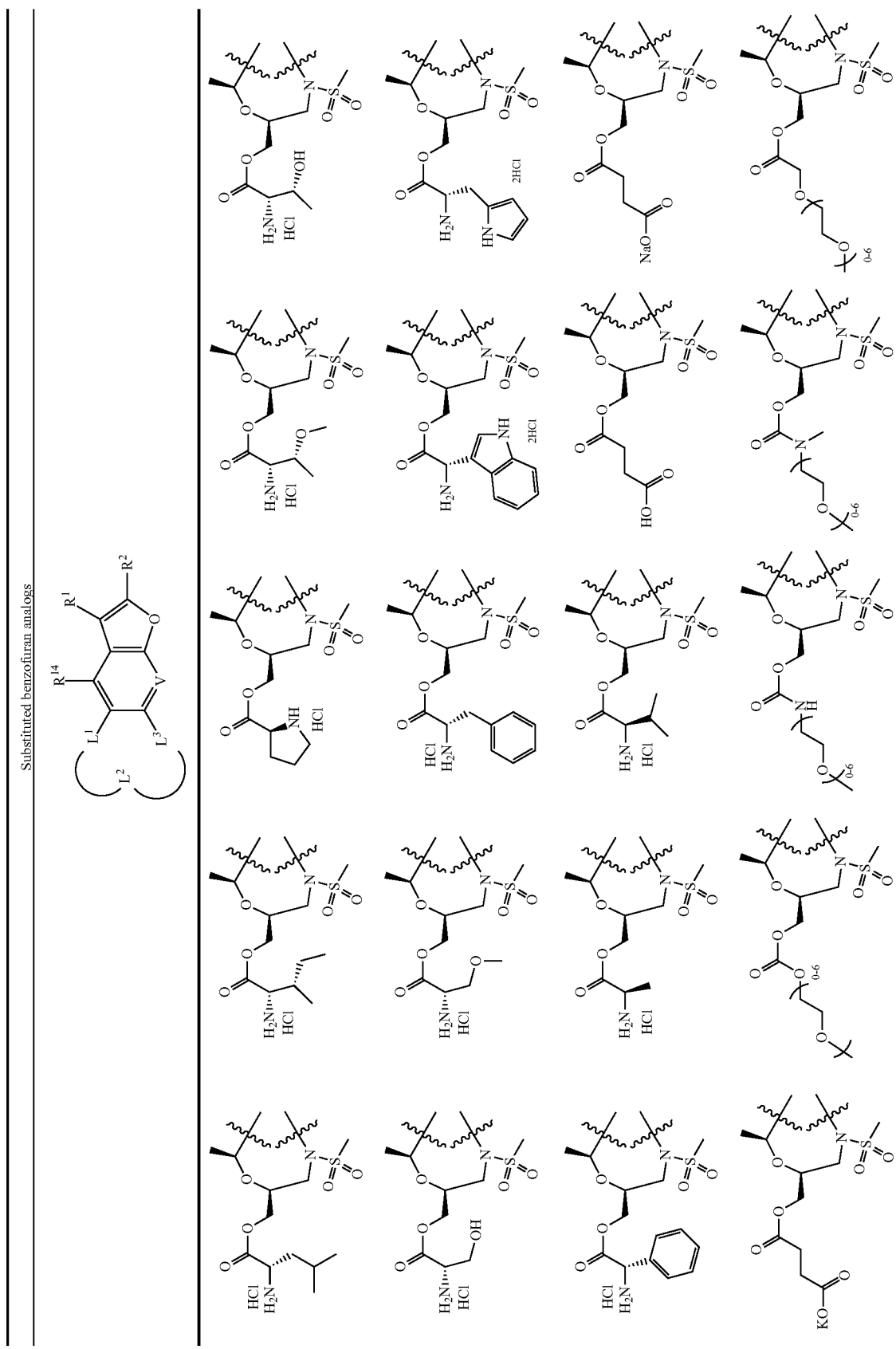

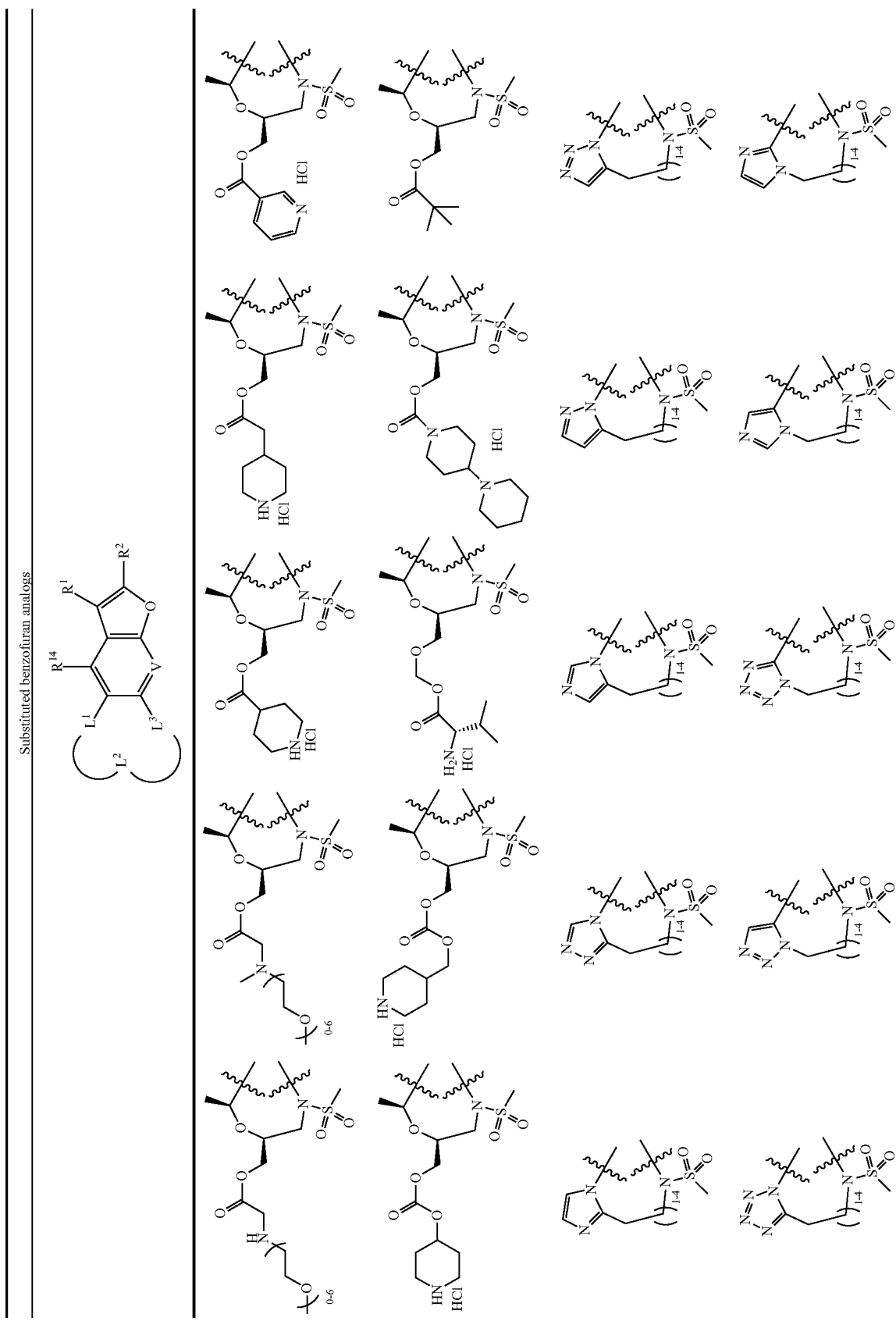

TABLE 1-continued
Substituted benzofuran analogs
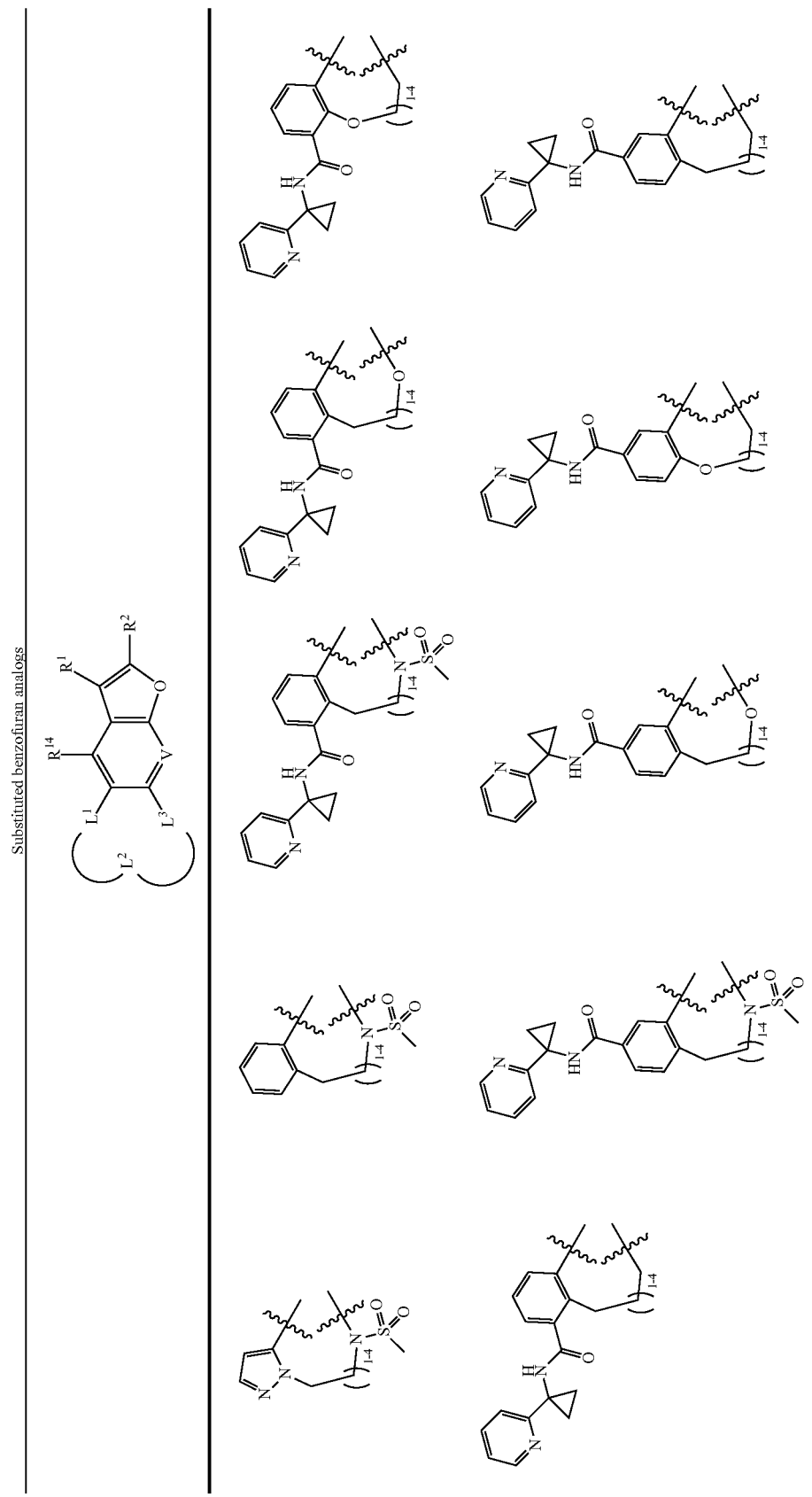

TABLE 2
Substituted 4-azo-benzofuran analogs
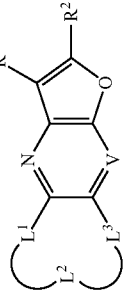

TABLE 2-continued
Substituted 4-azo-benzofuran analogs
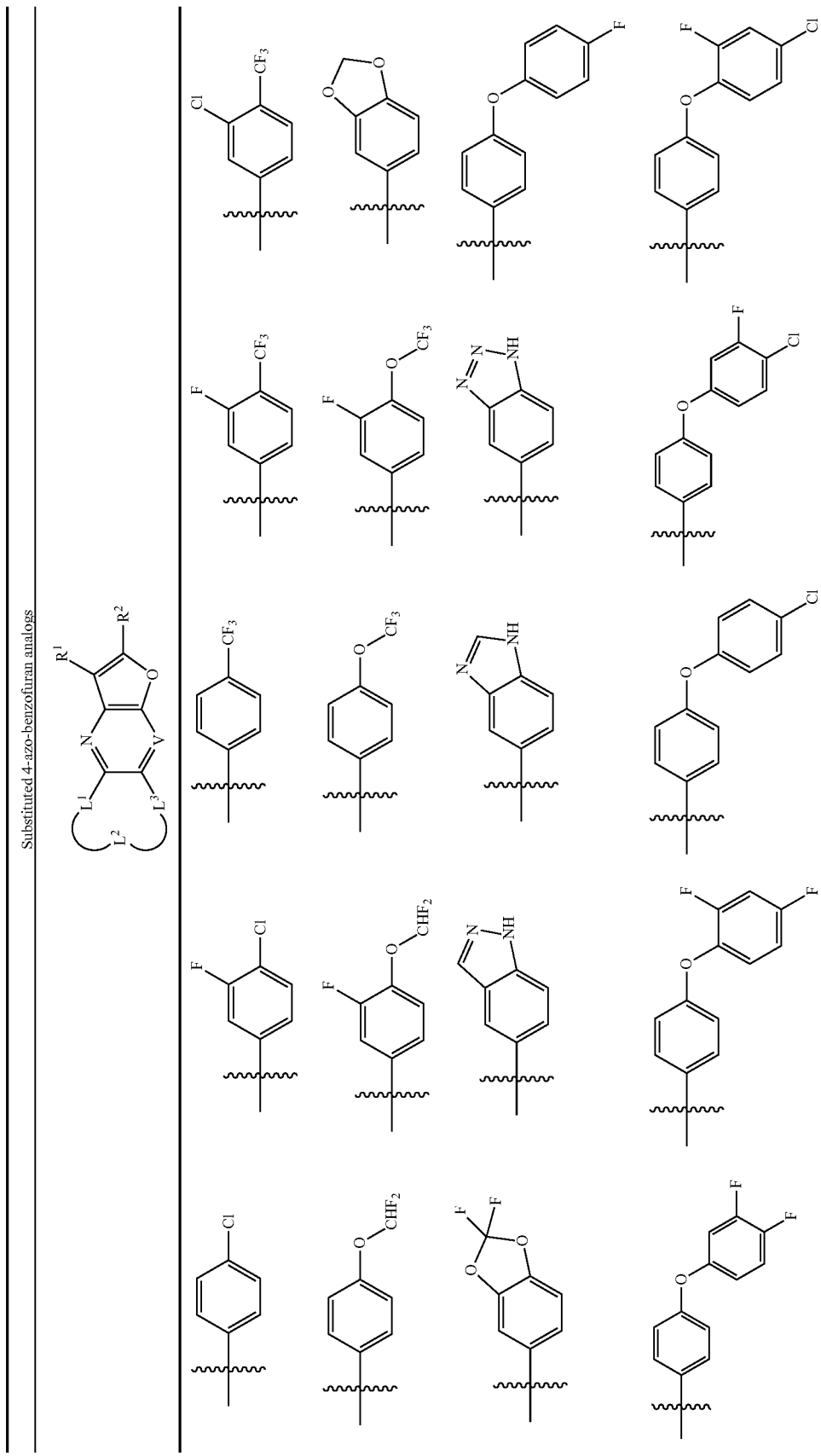

TABLE 2-continued
Substituted 4-azo-benzofuran analogs
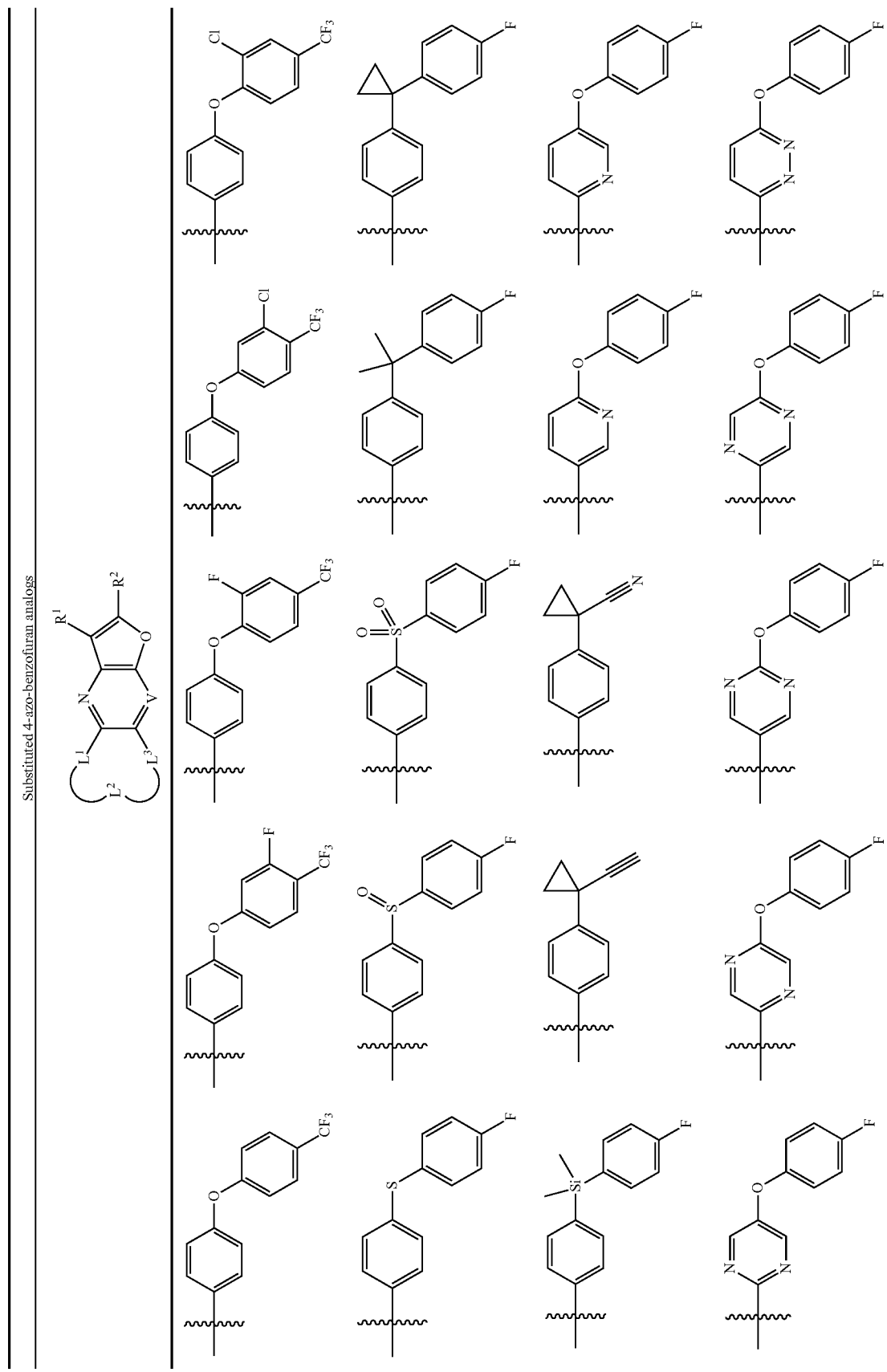

TABLE 2-continued
Substituted 4-azo-benzofuran analogs
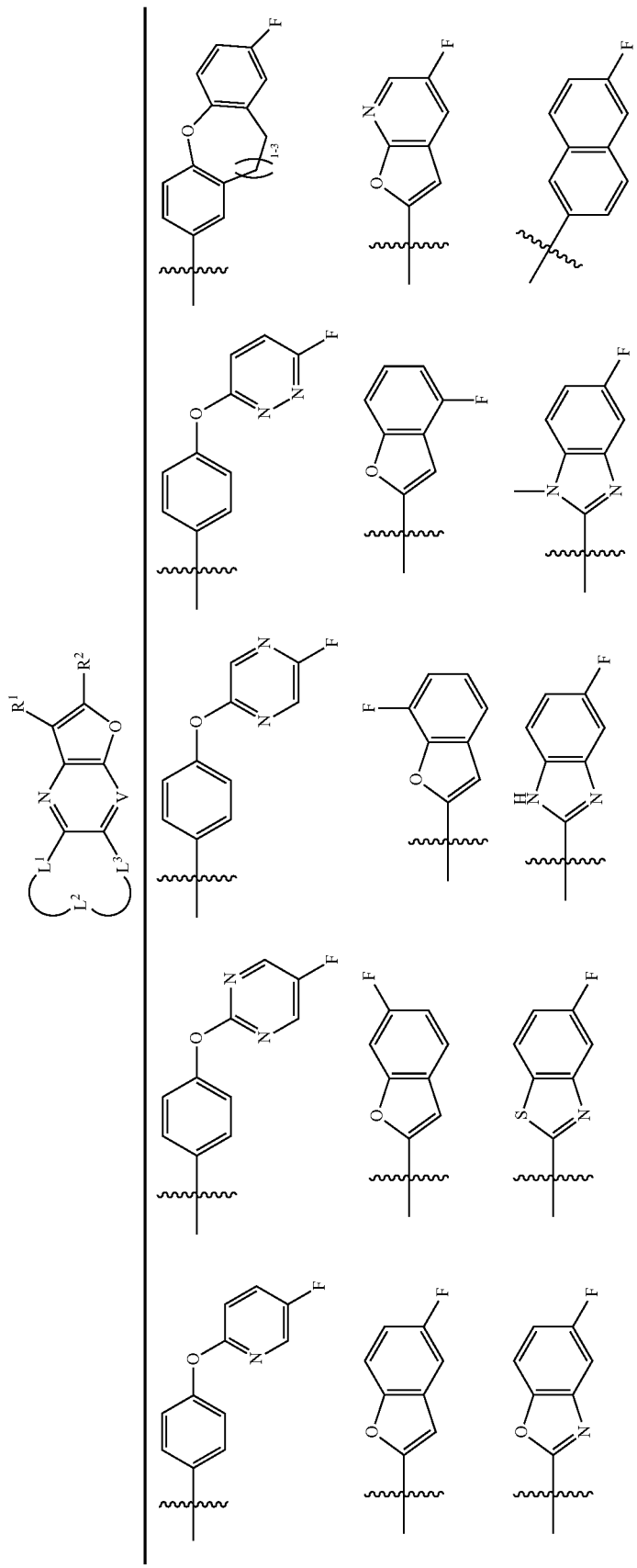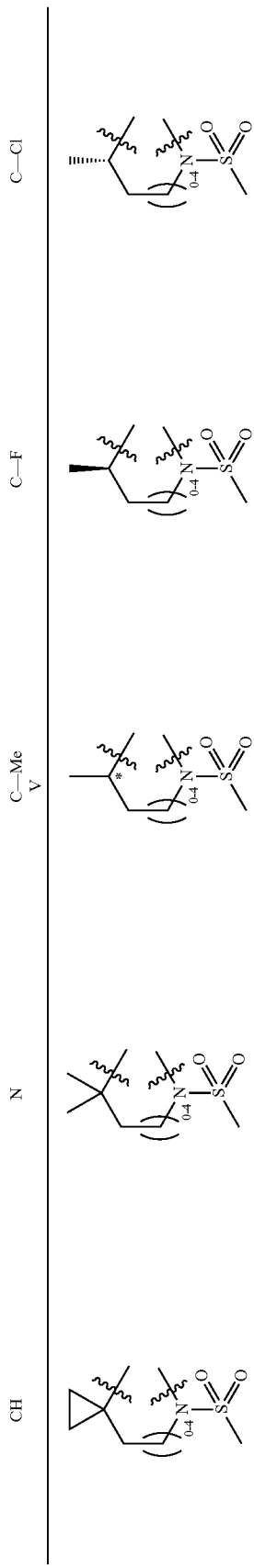

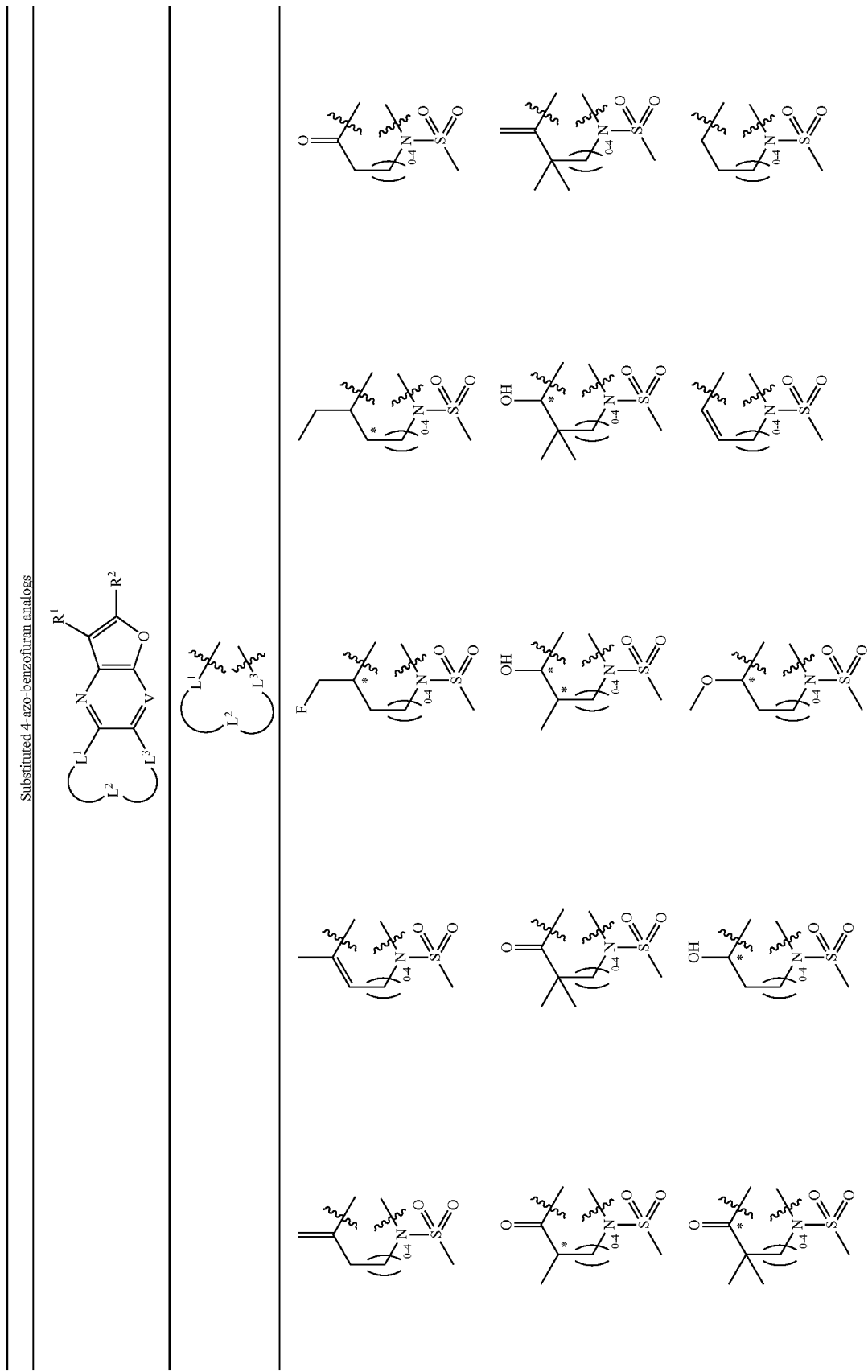

TABLE 2-continued
Substituted 4-azo-benzofuran analogs
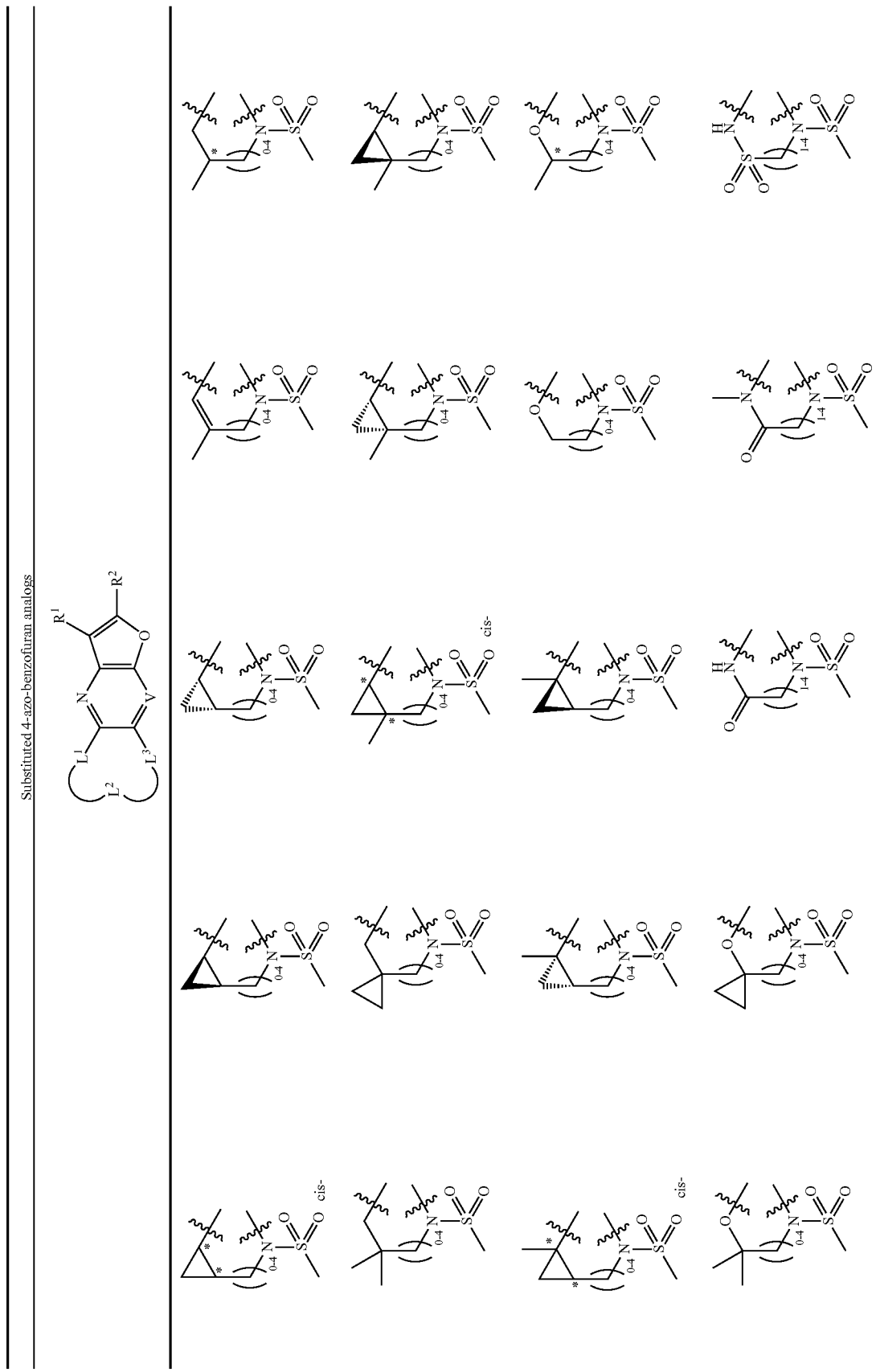

TABLE 2-continued
Substituted 4-azo-benzofuran analogs
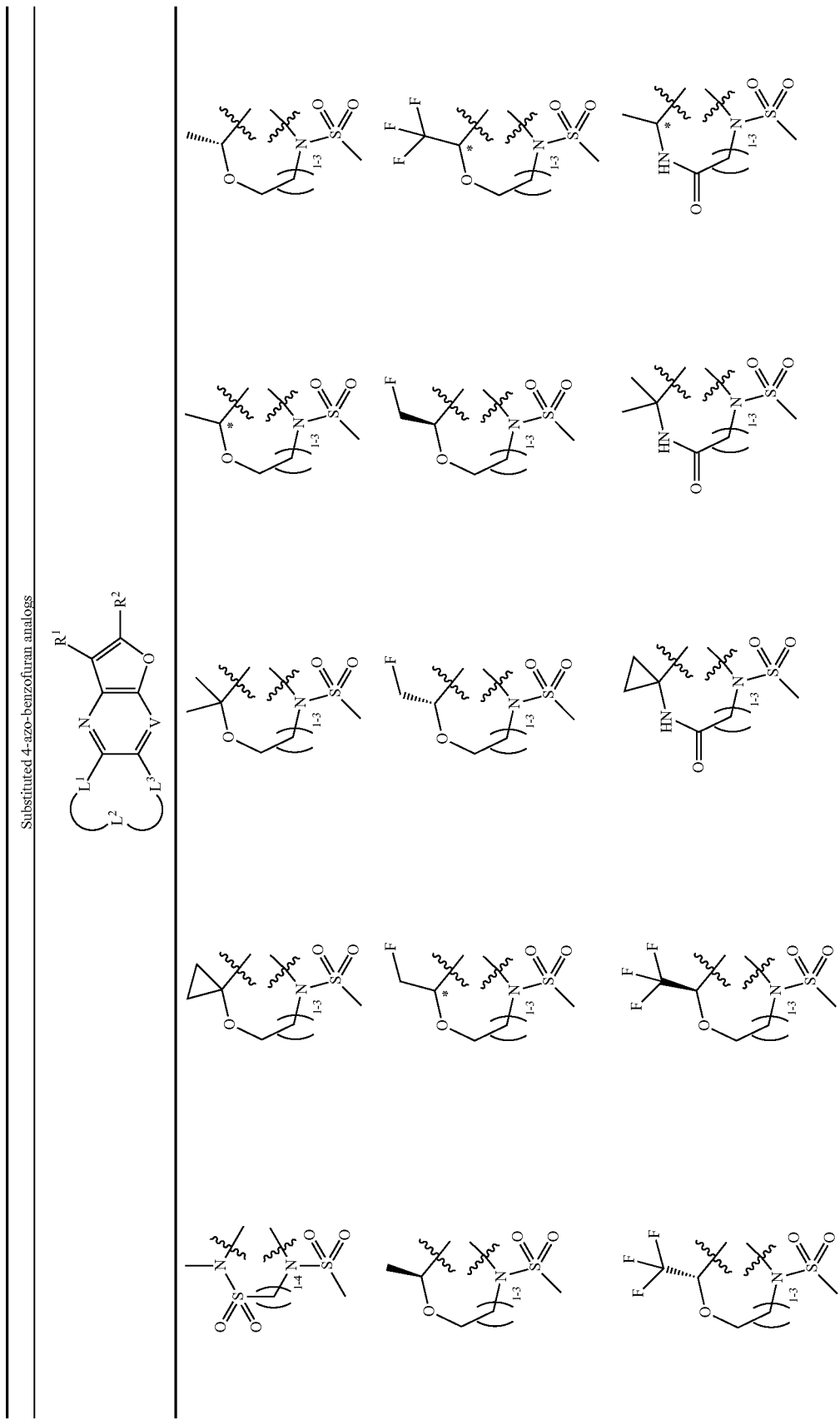

TABLE 2-continued
Substituted 4-azo-benzofuran analogs
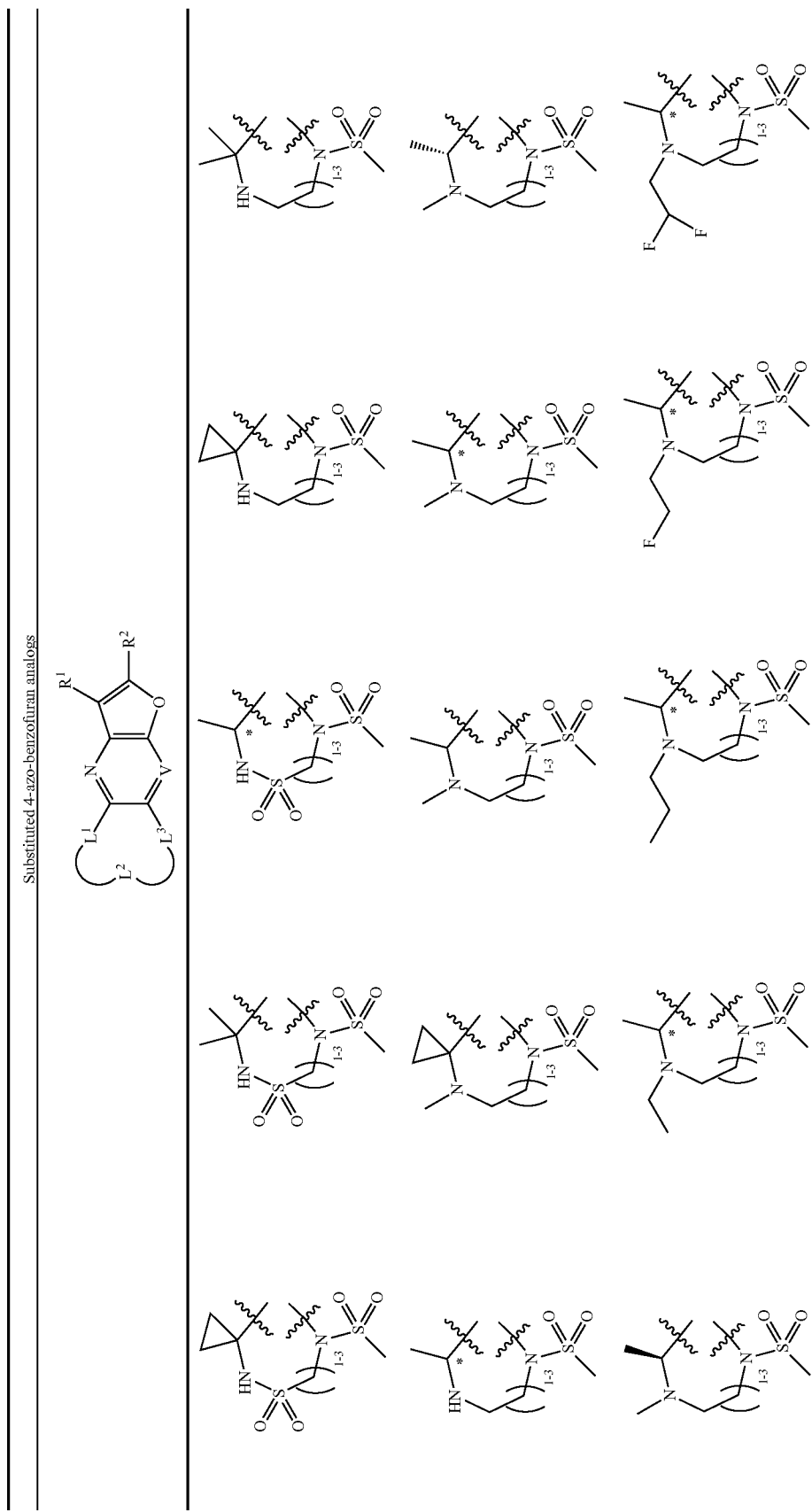

TABLE 2-continued
Substituted 4-azo-benzofuran analogs
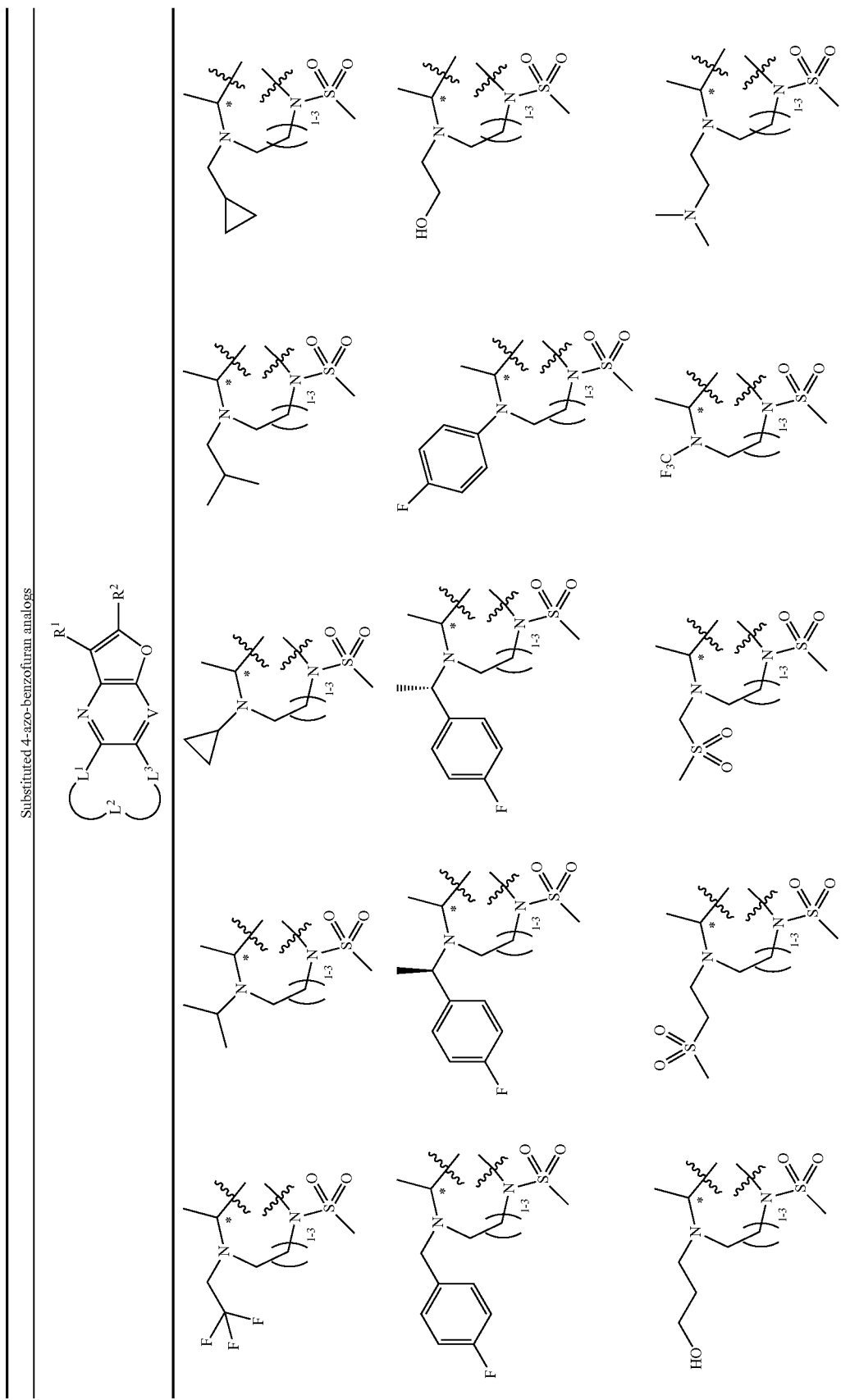

TABLE 2-continued
Substituted 4-azo-benzofuran analogs
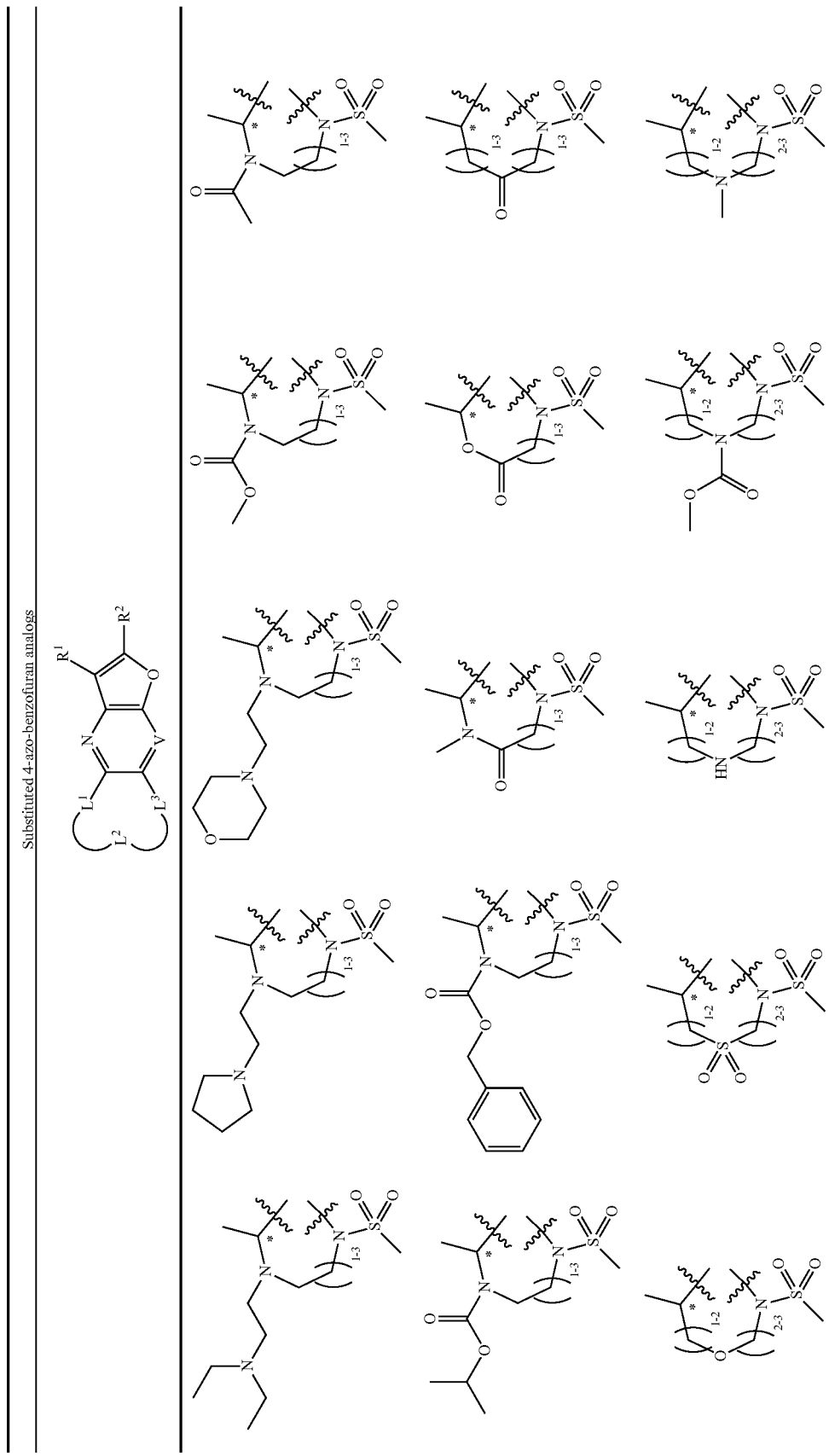

TABLE 2-continued
Substituted 4-azo-benzofuran analogs
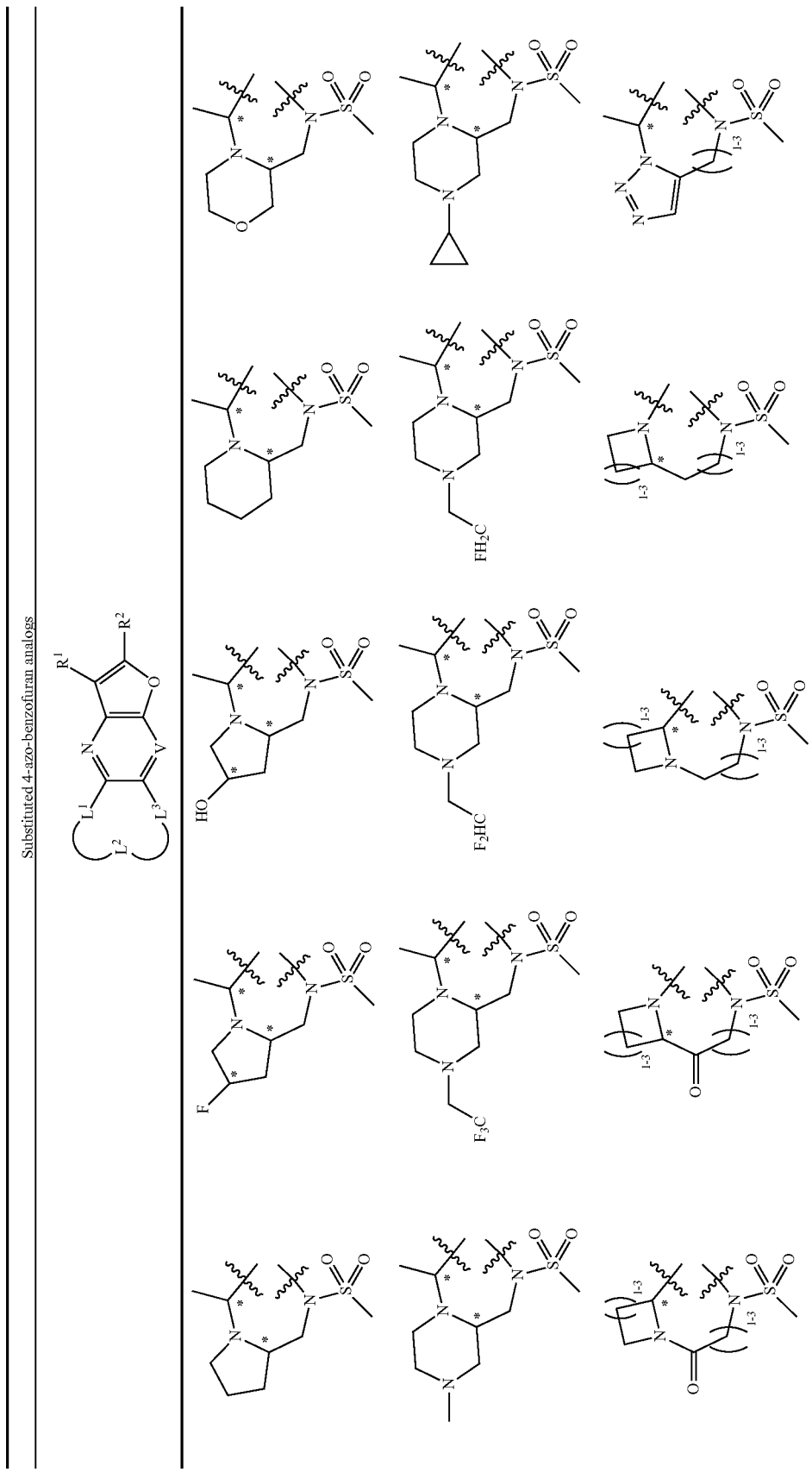

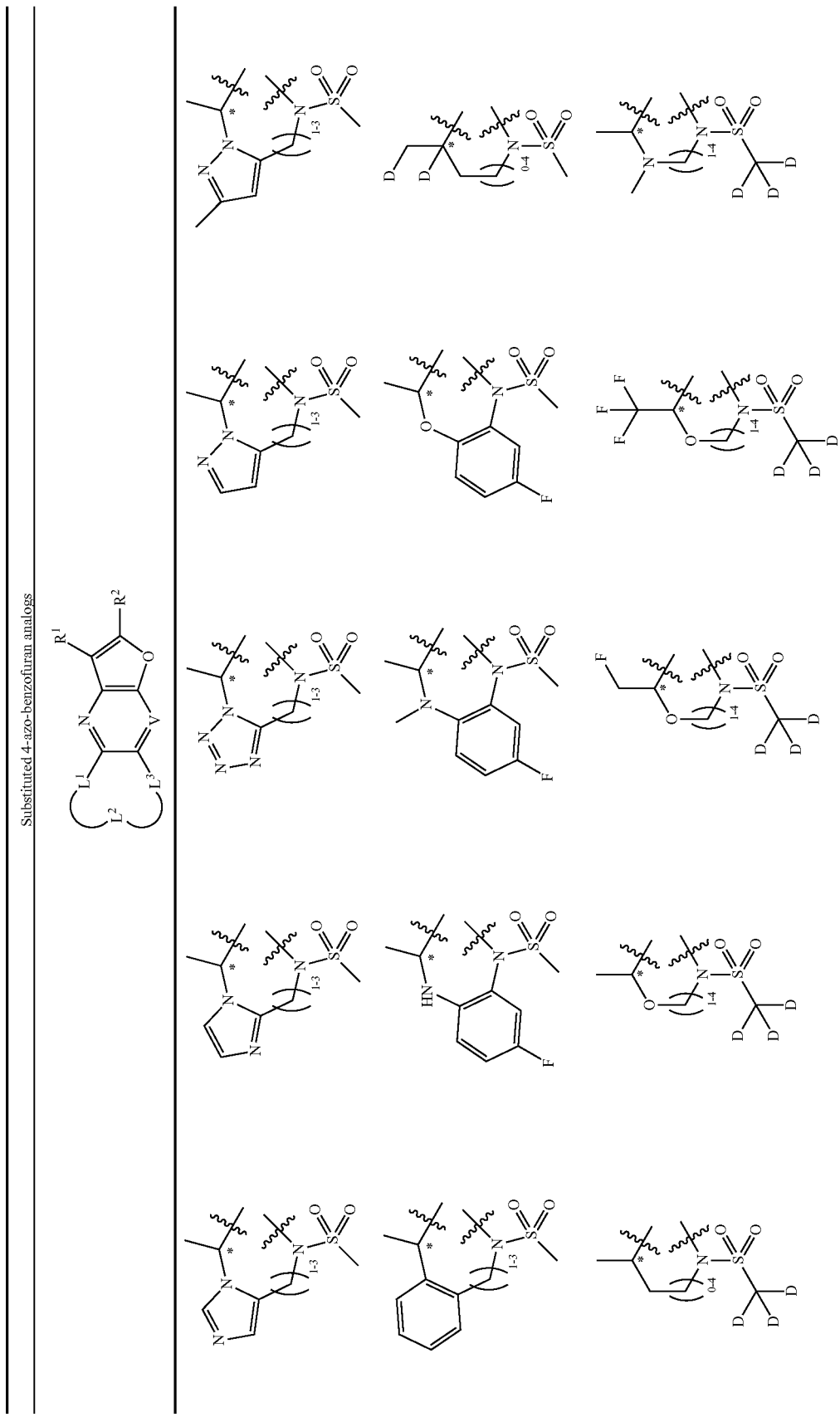

TABLE 2-continued
Substituted 4-azo-benzofuran analogs
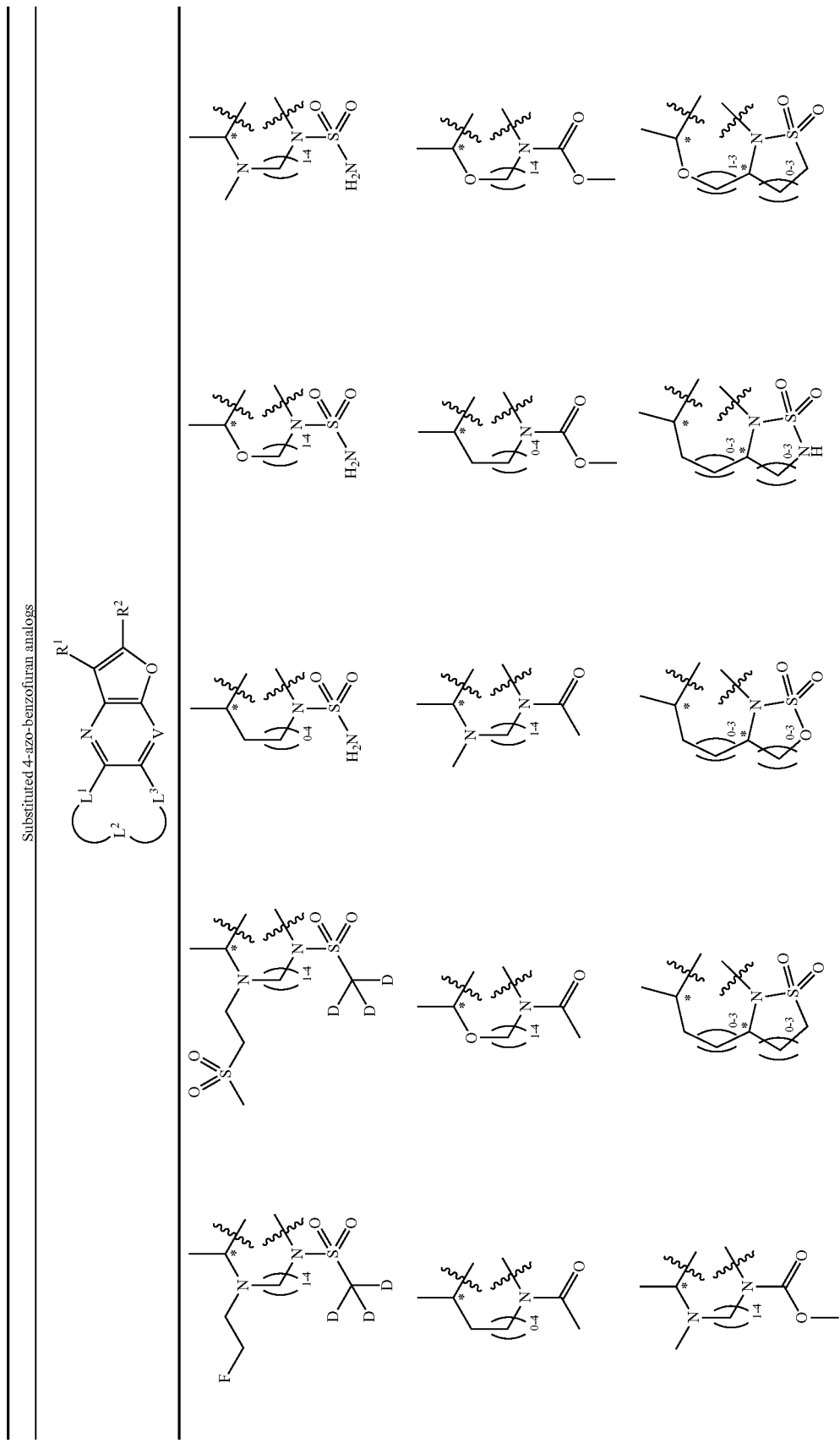

TABLE 2-continued
Substituted 4-azo-benzofuran analogs
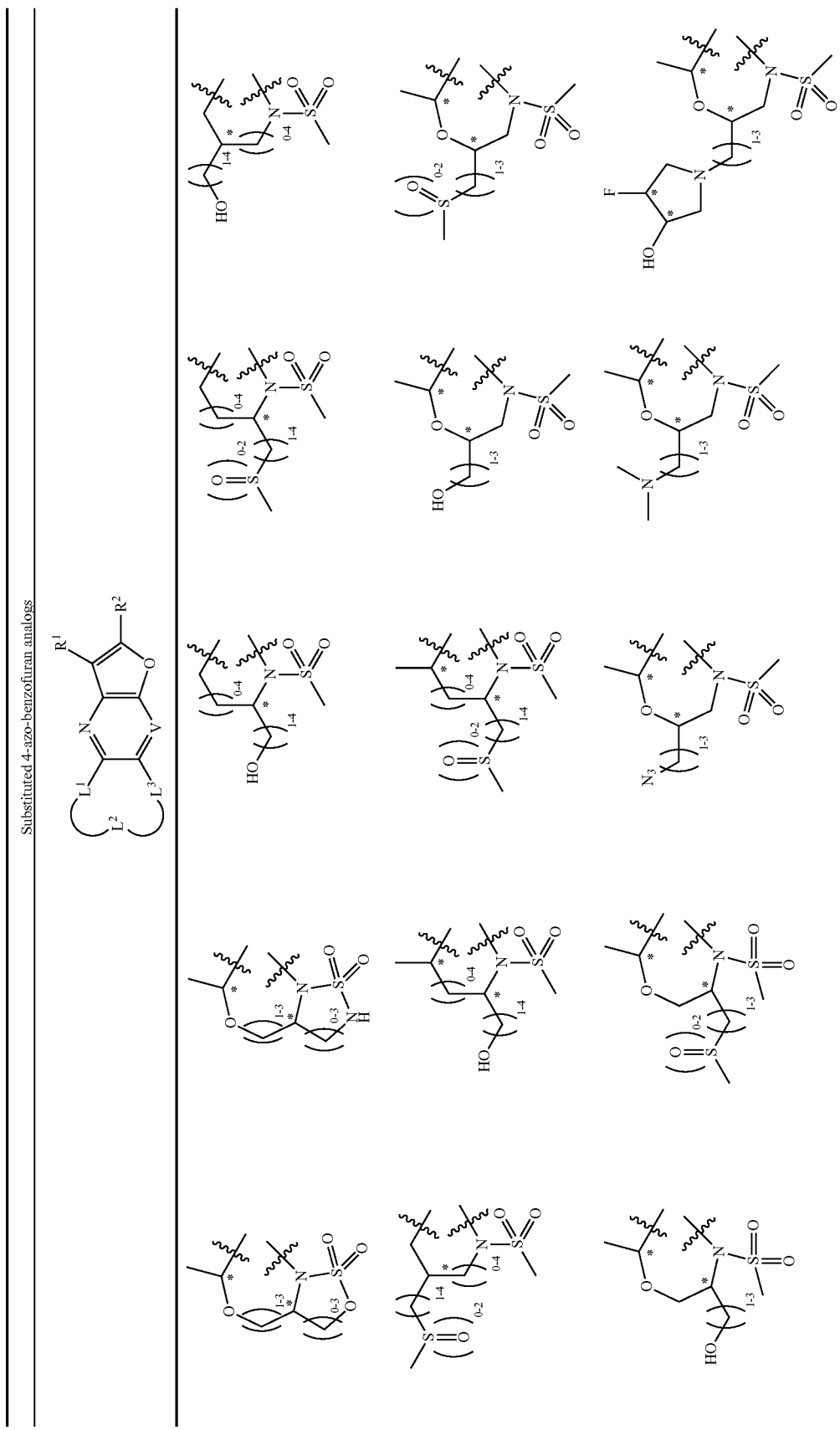

TABLE 2-continued
Substituted 4-azo-benzofuran analogs
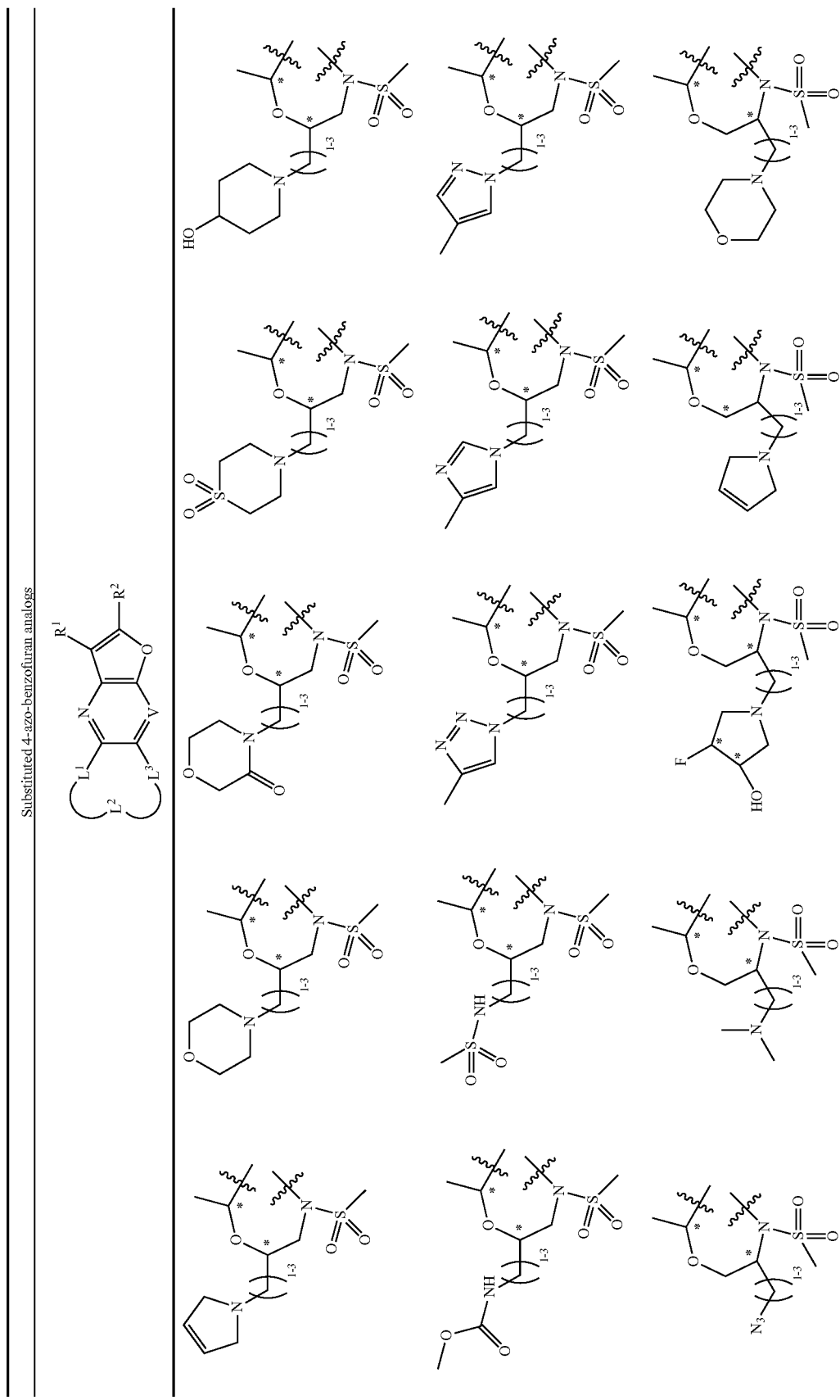

TABLE 2-continued
Substituted 4-azo-benzofuran analogs
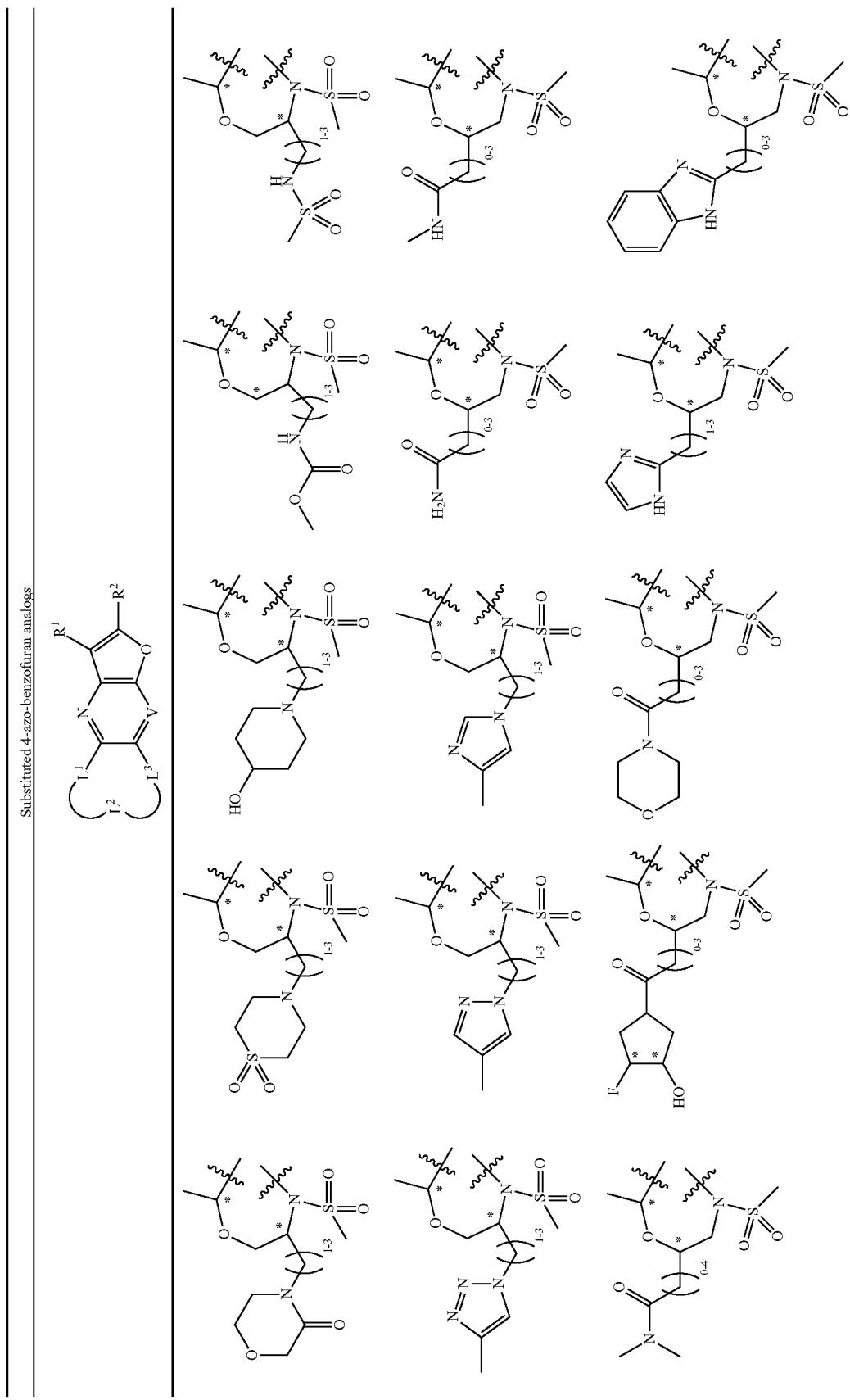

TABLE 2-continued
Substituted 4-azo-benzofuran analogs
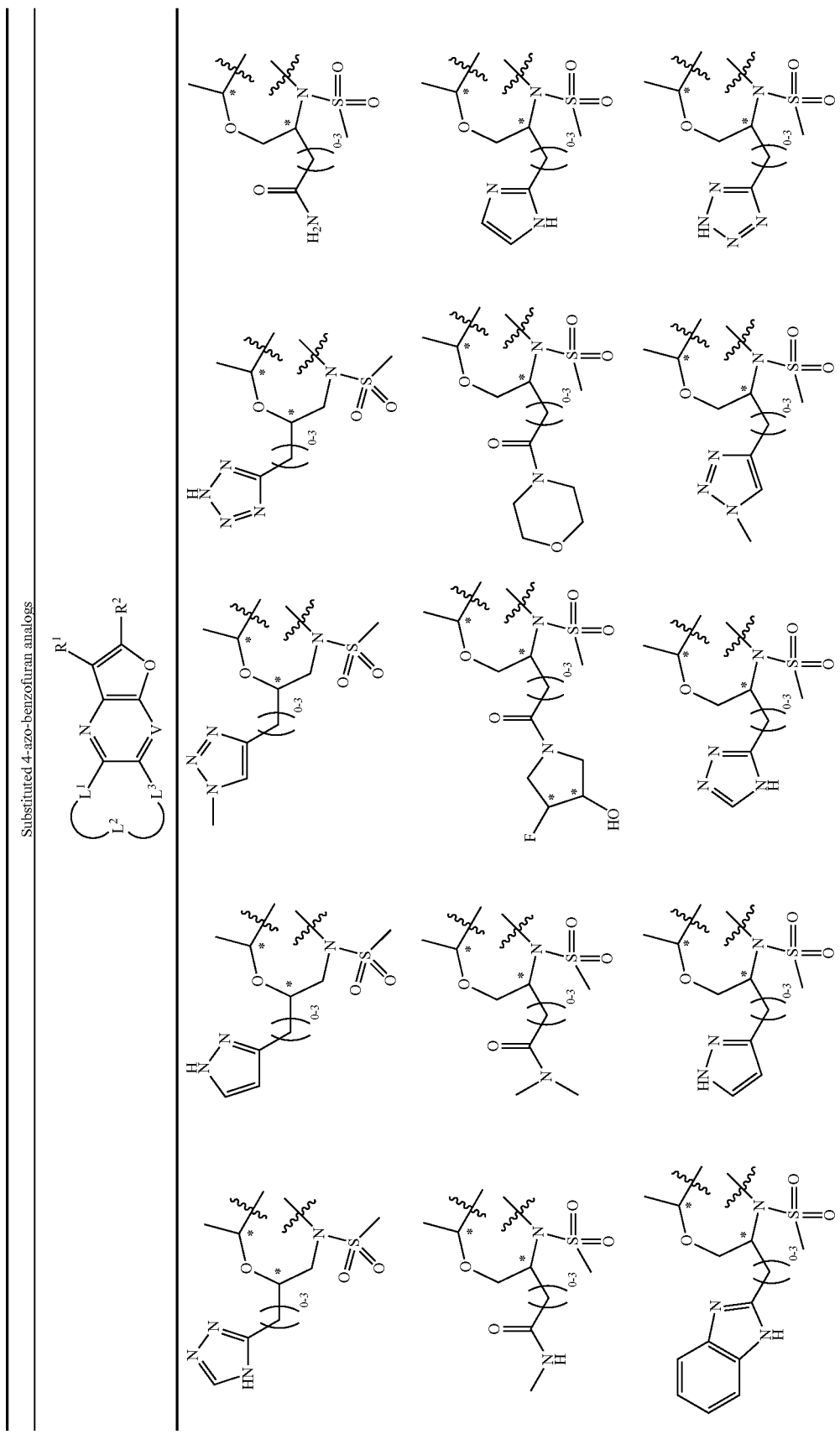

TABLE 2-continued
Substituted 4-azo-benzofuran analogs
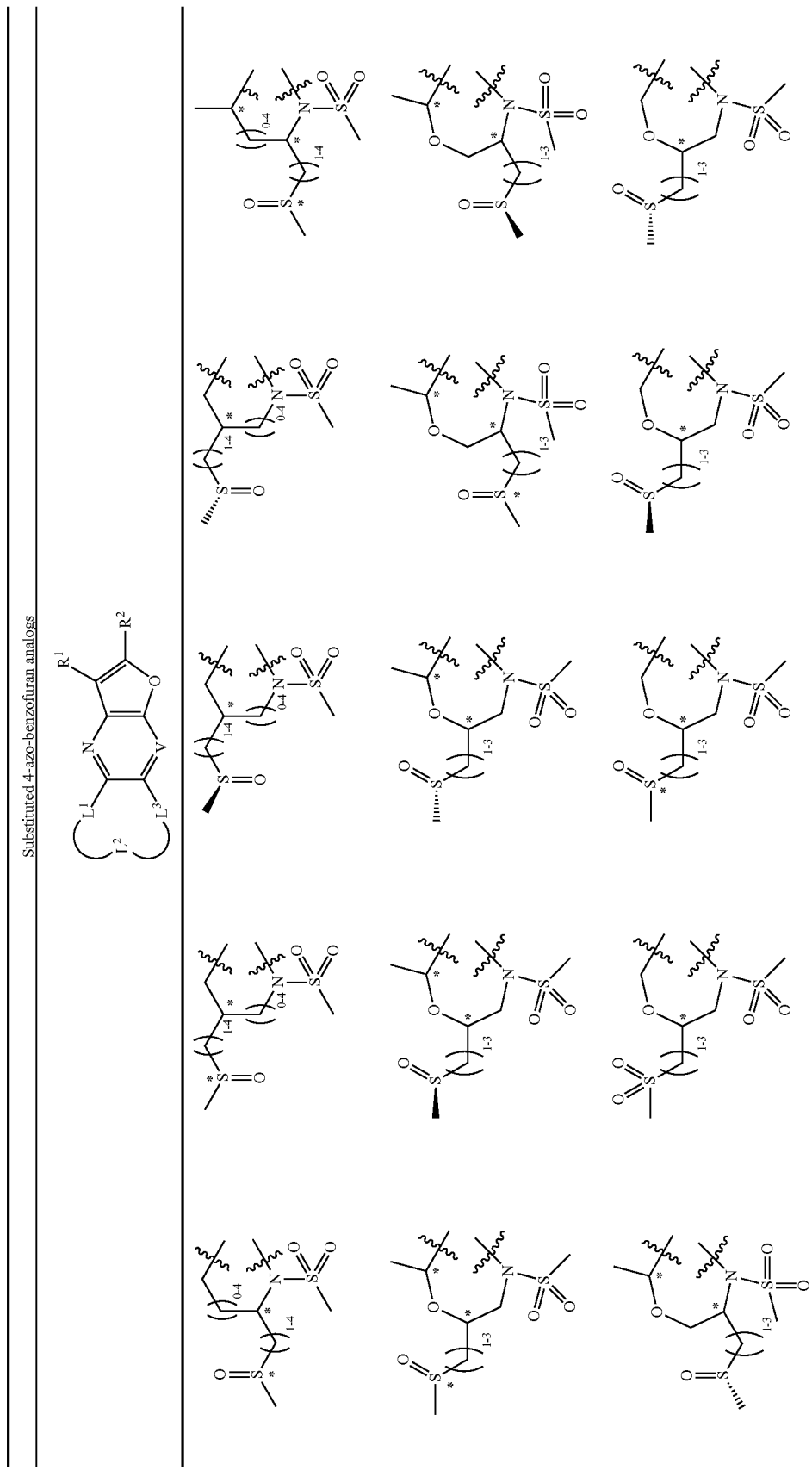

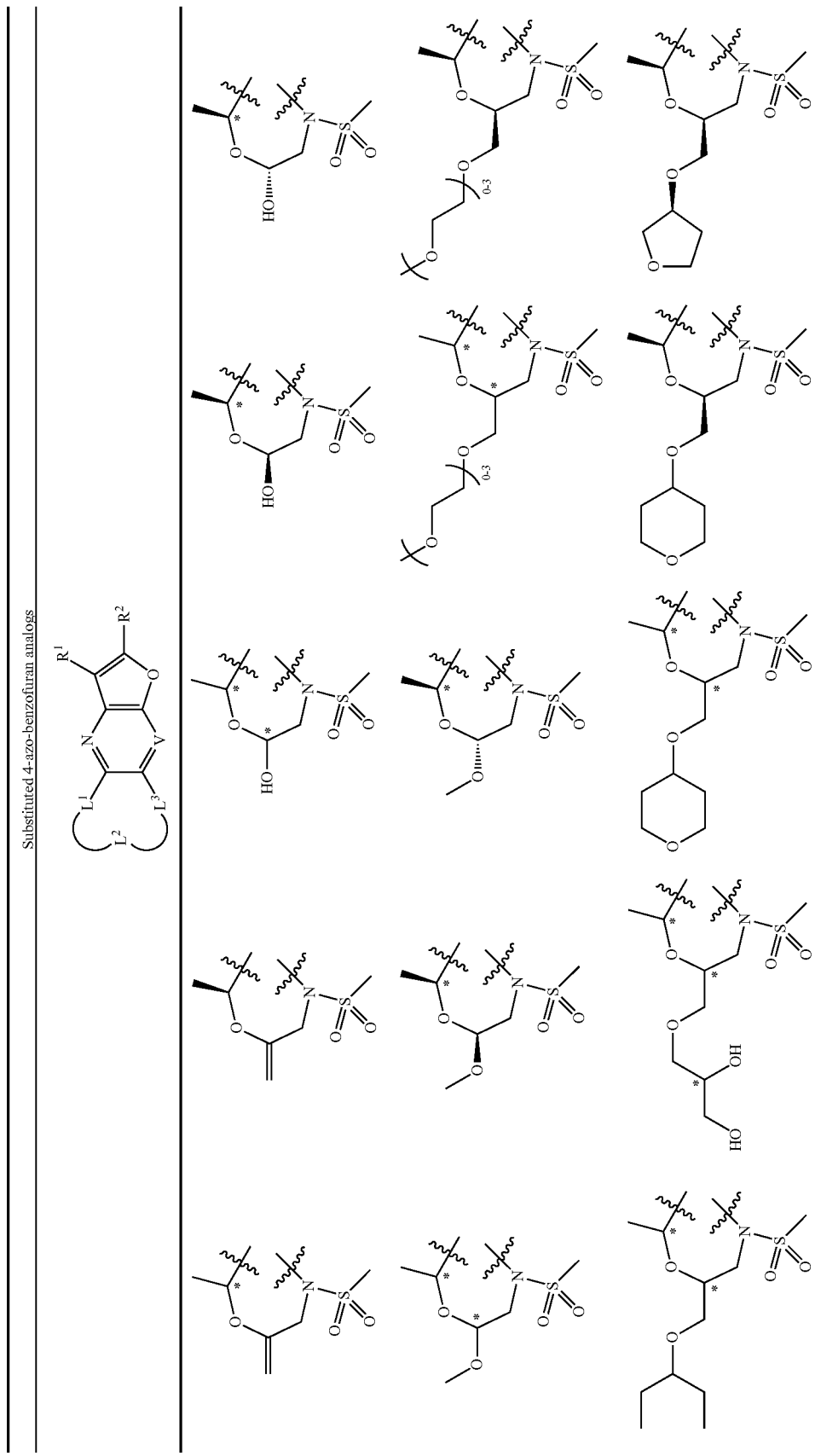

TABLE 2-continued
Substituted 4-azo-benzofuran analogs
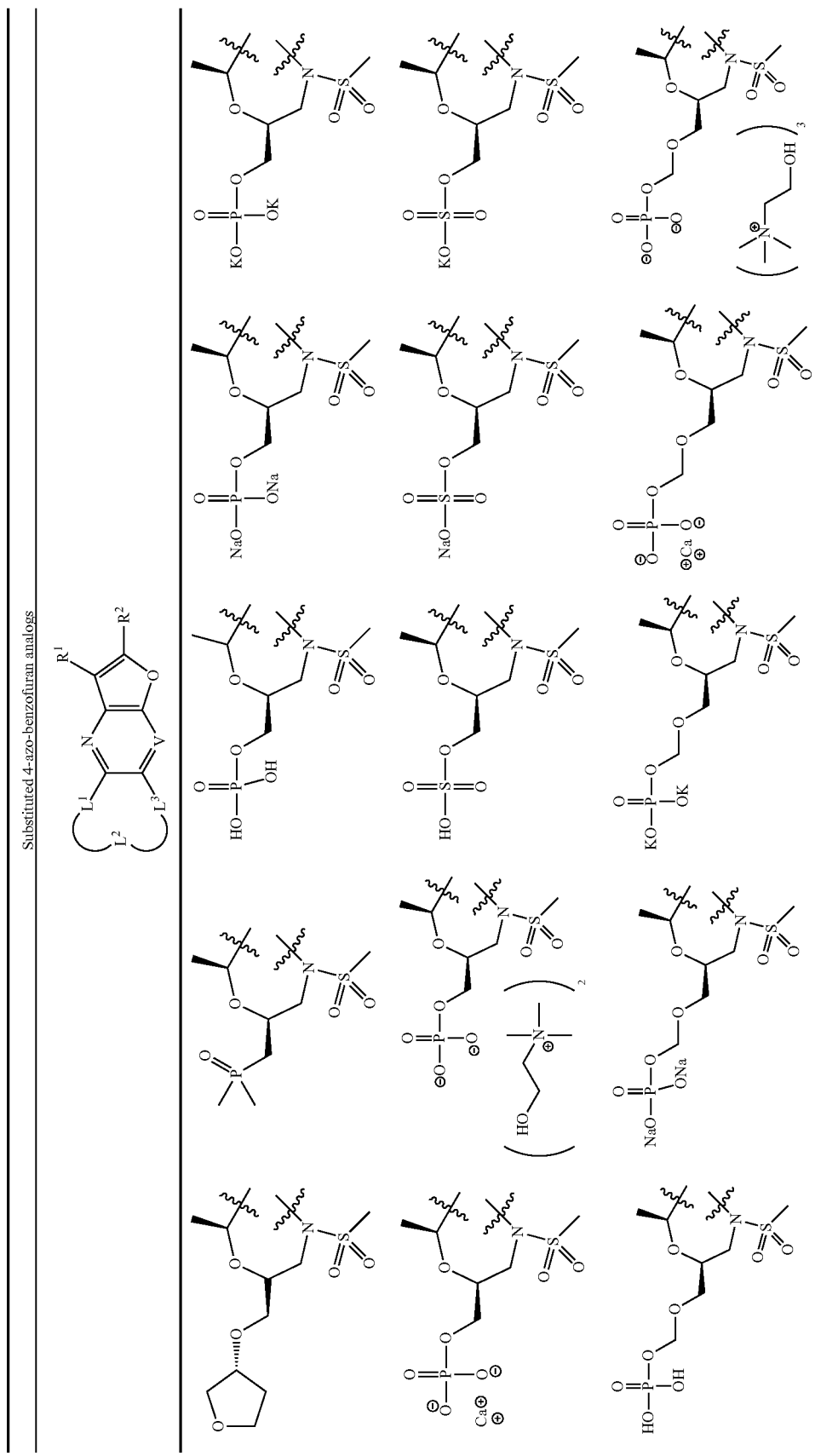

TABLE 2-continued
Substituted 4-azo-benzofuran analogs
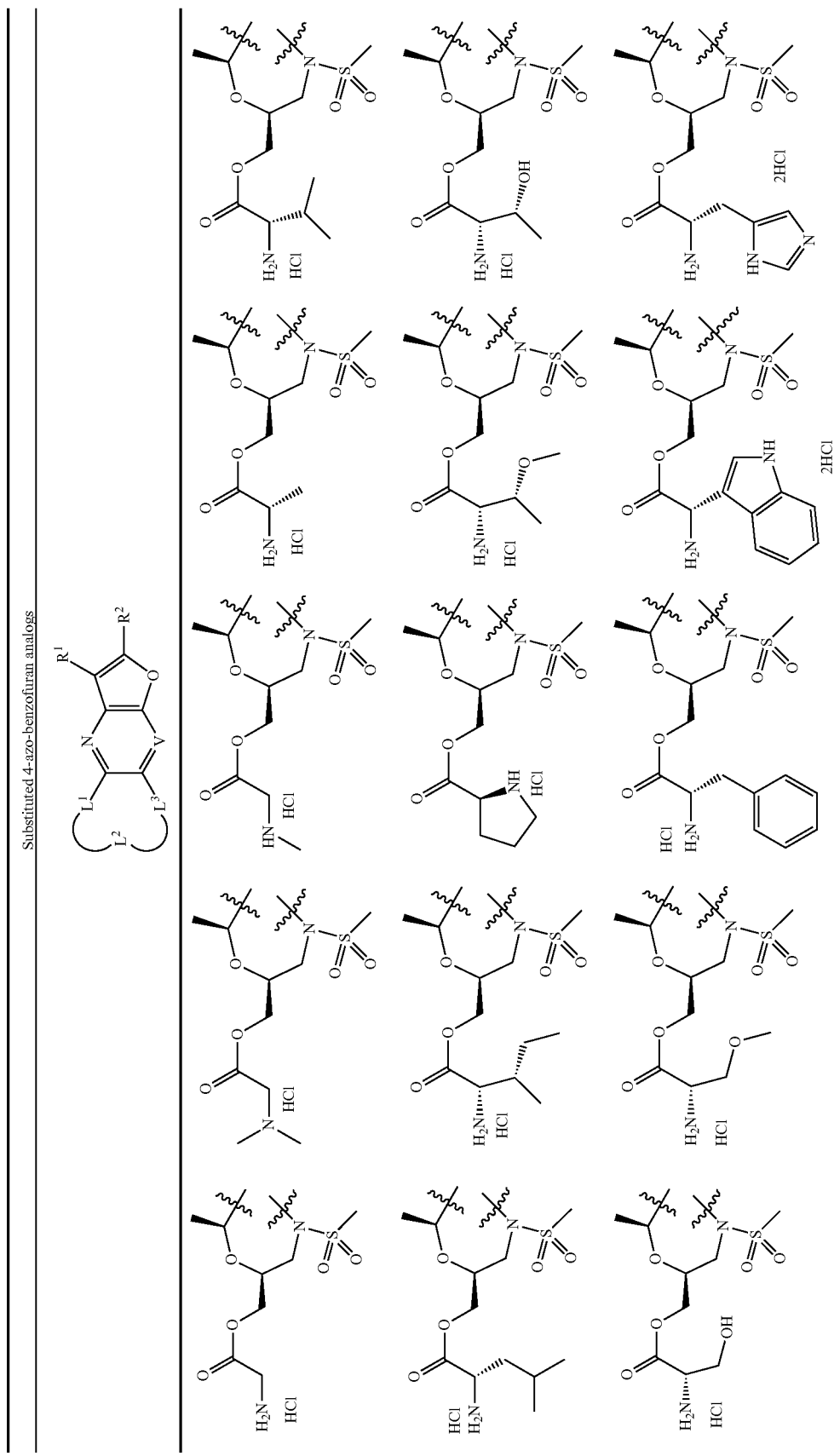

TABLE 2-continued
Substituted 4-azo-benzofuran analogs
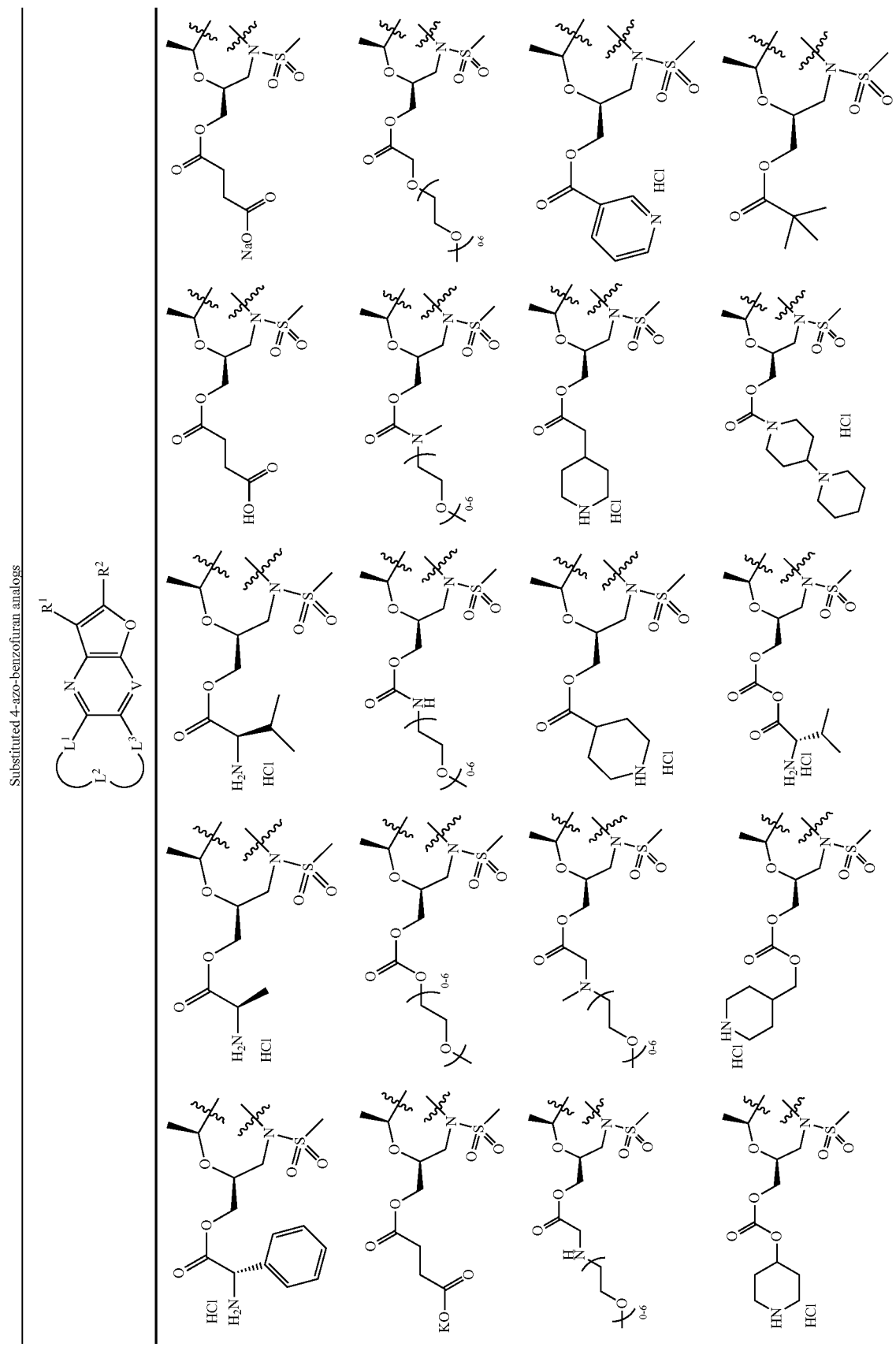

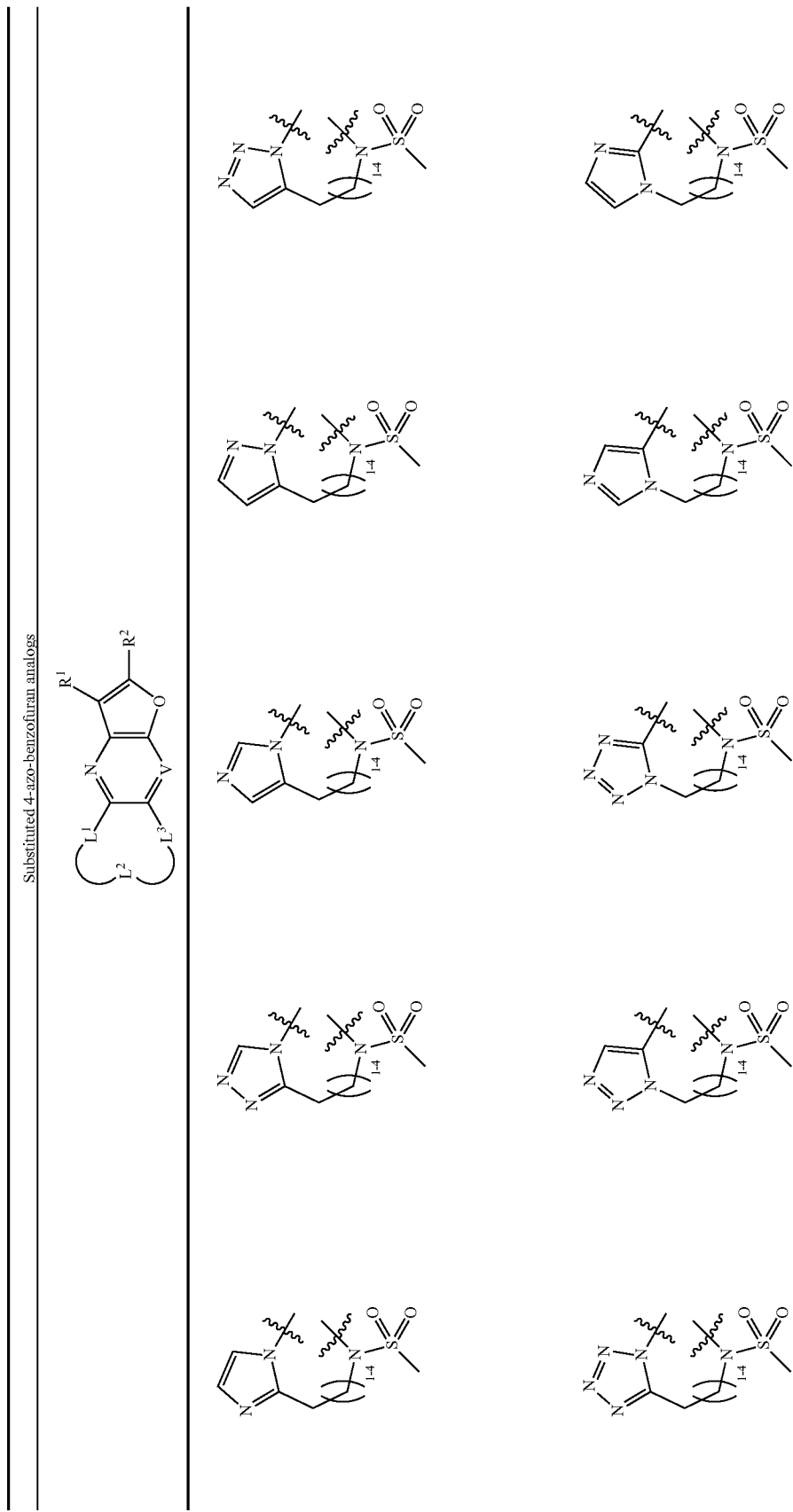

TABLE 2-continued
Substituted 4-azo-benzofuran analogs
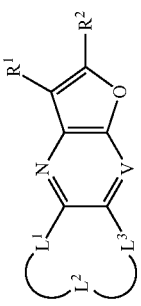
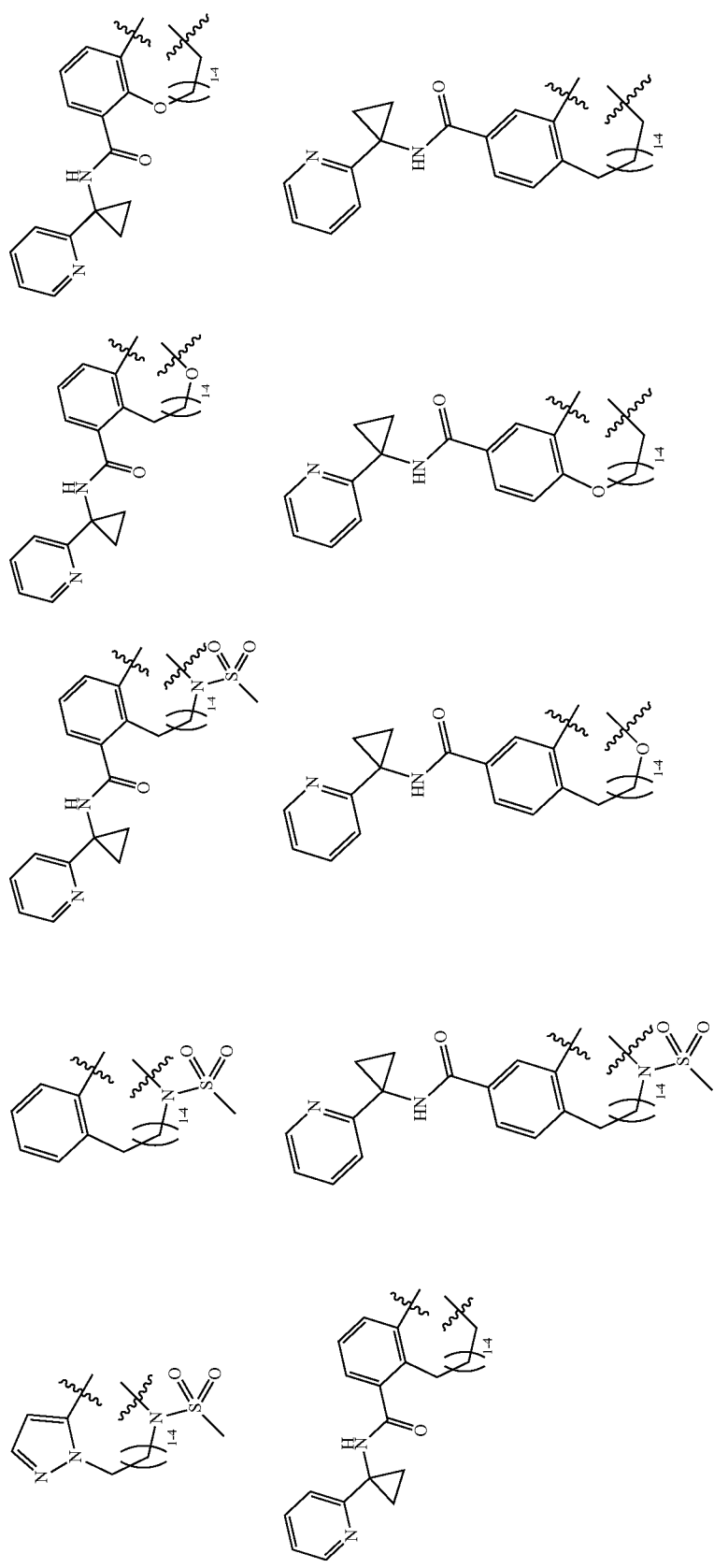

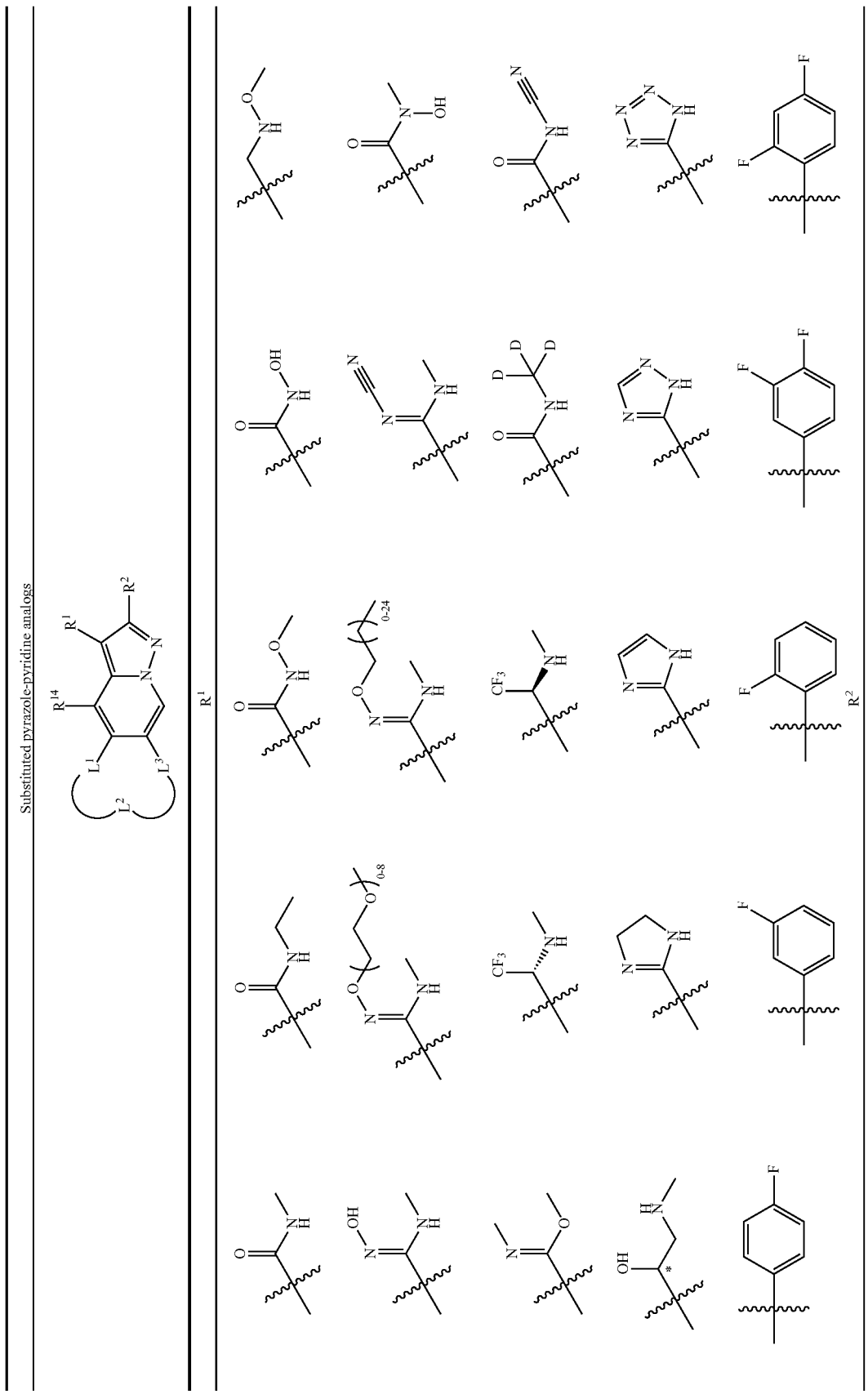

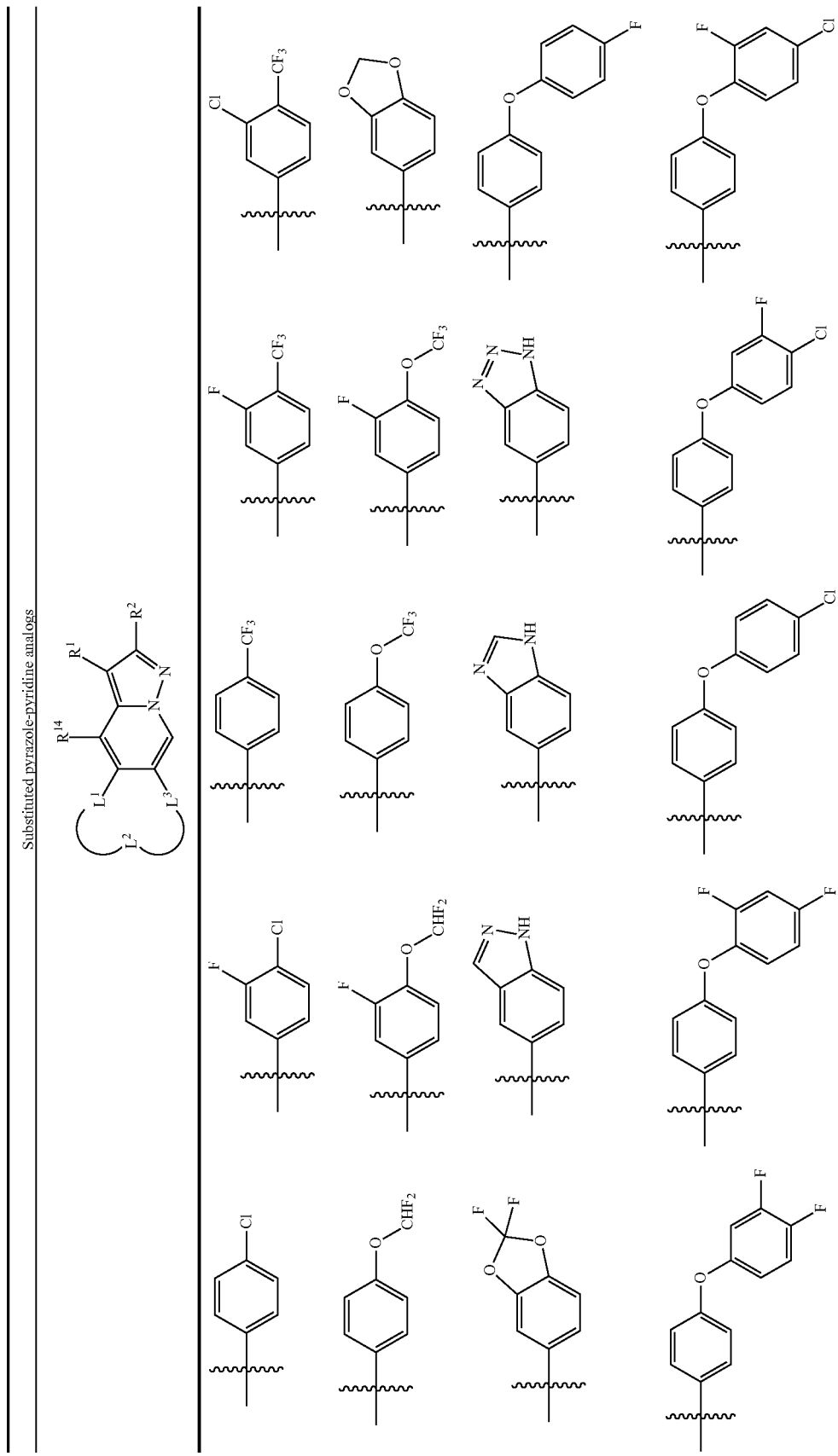

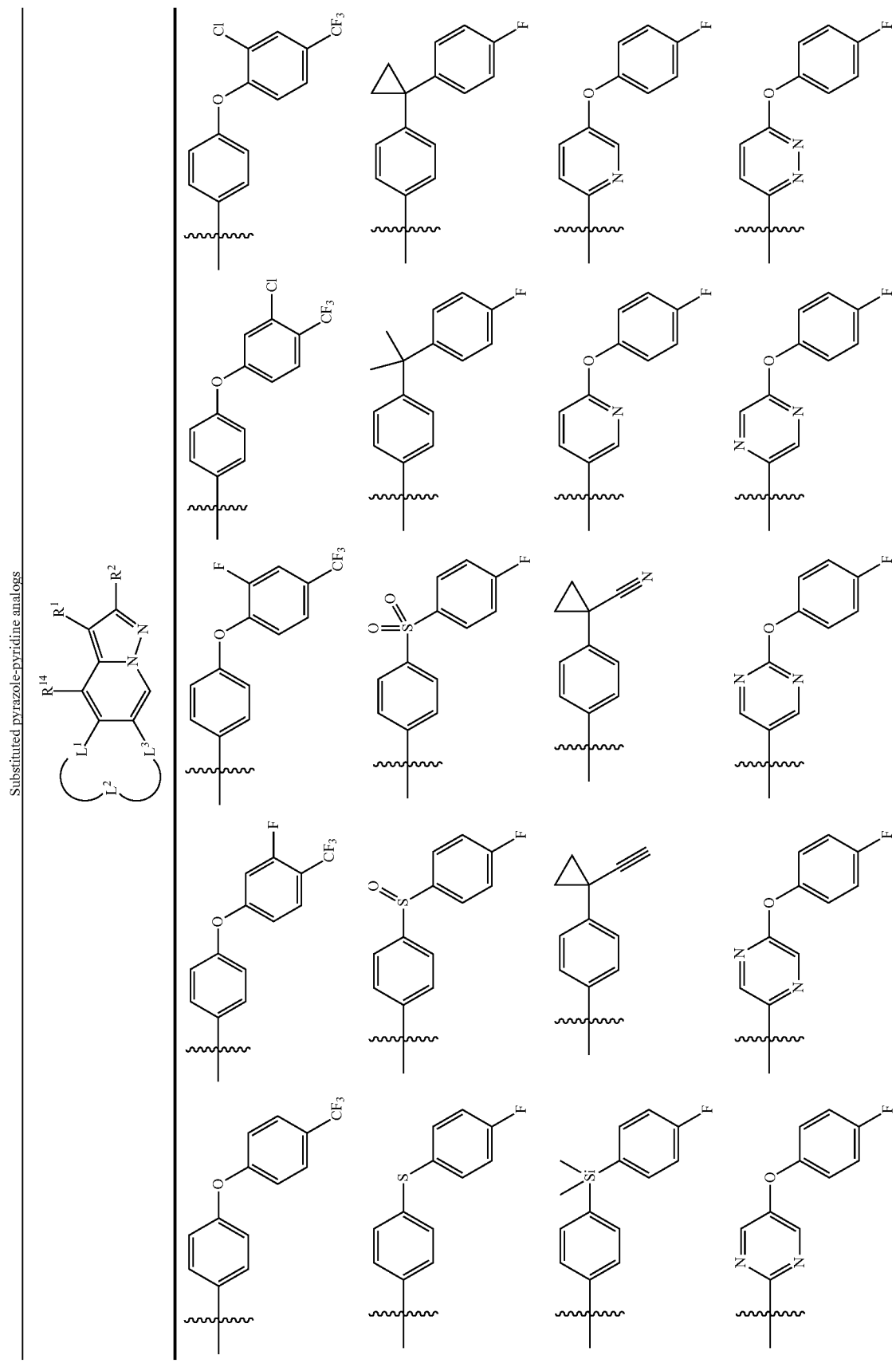

TABLE 3-continued

Substituted pyrazole-pyridine analogs

TABLE 3-continued
Substituted pyrazole-pyridine analogs
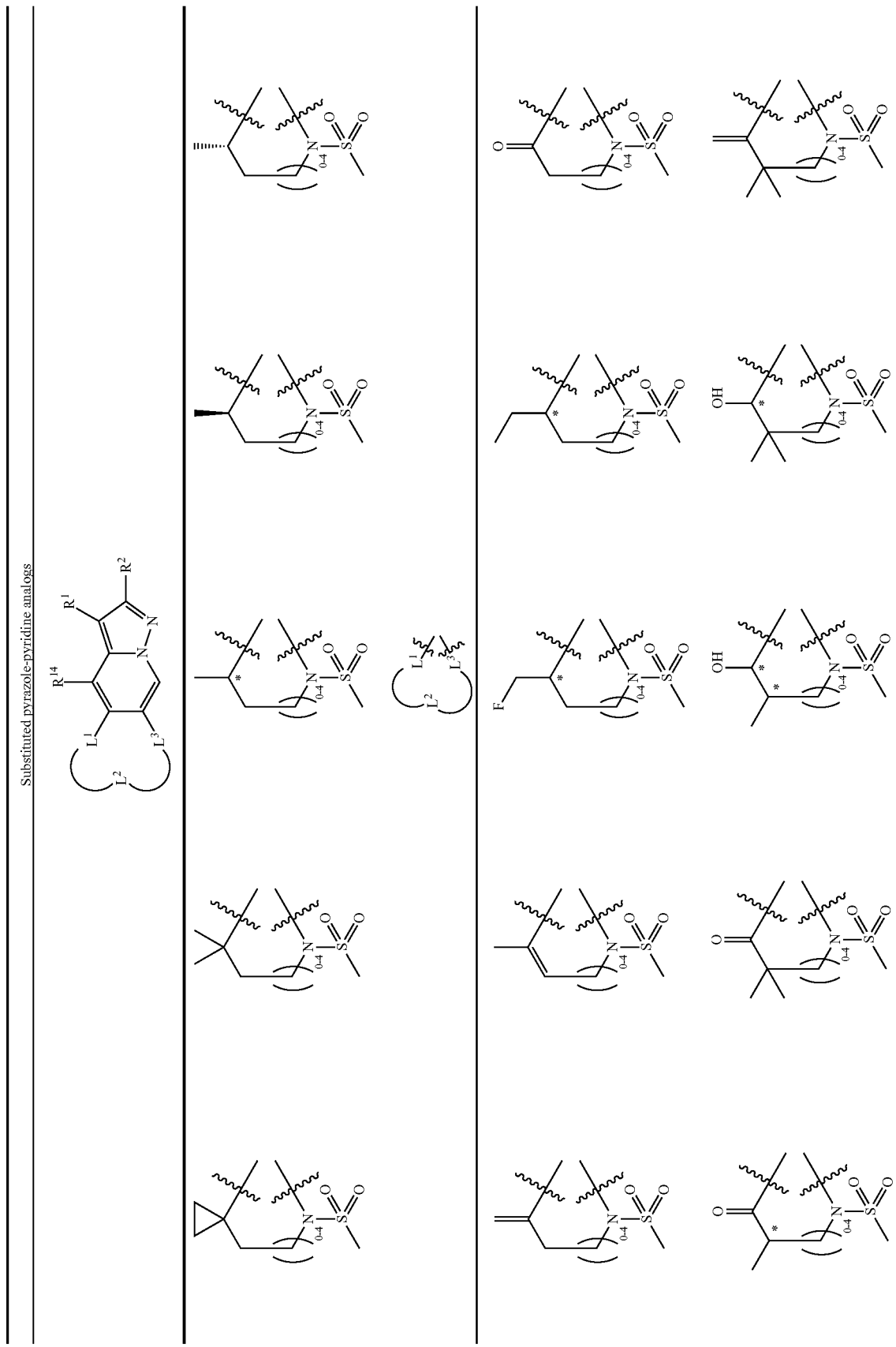

TABLE 3-continued
Substituted pyrazole-pyridine analogs
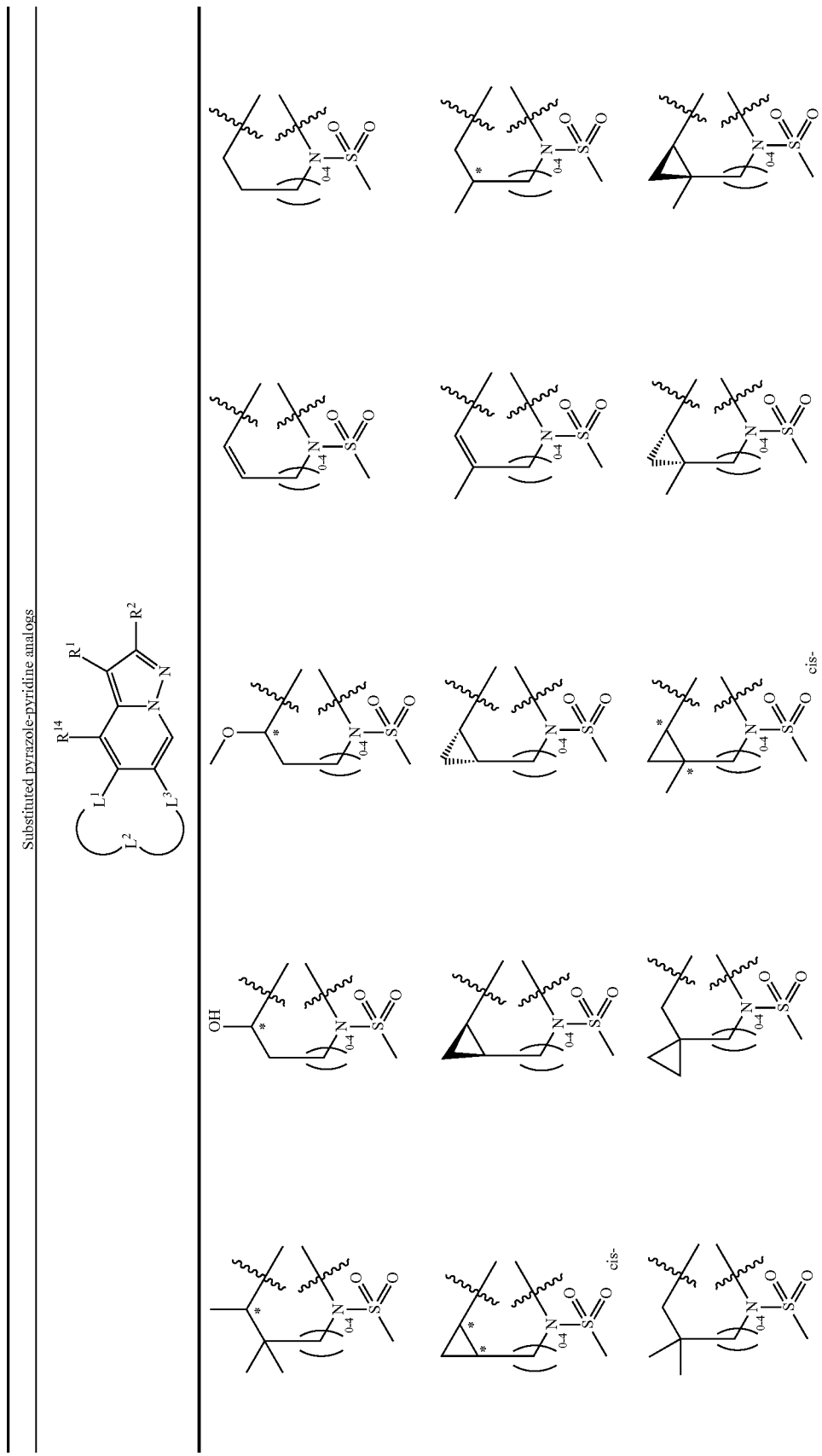

TABLE 3-continued
Substituted pyrazole-pyridine analogs
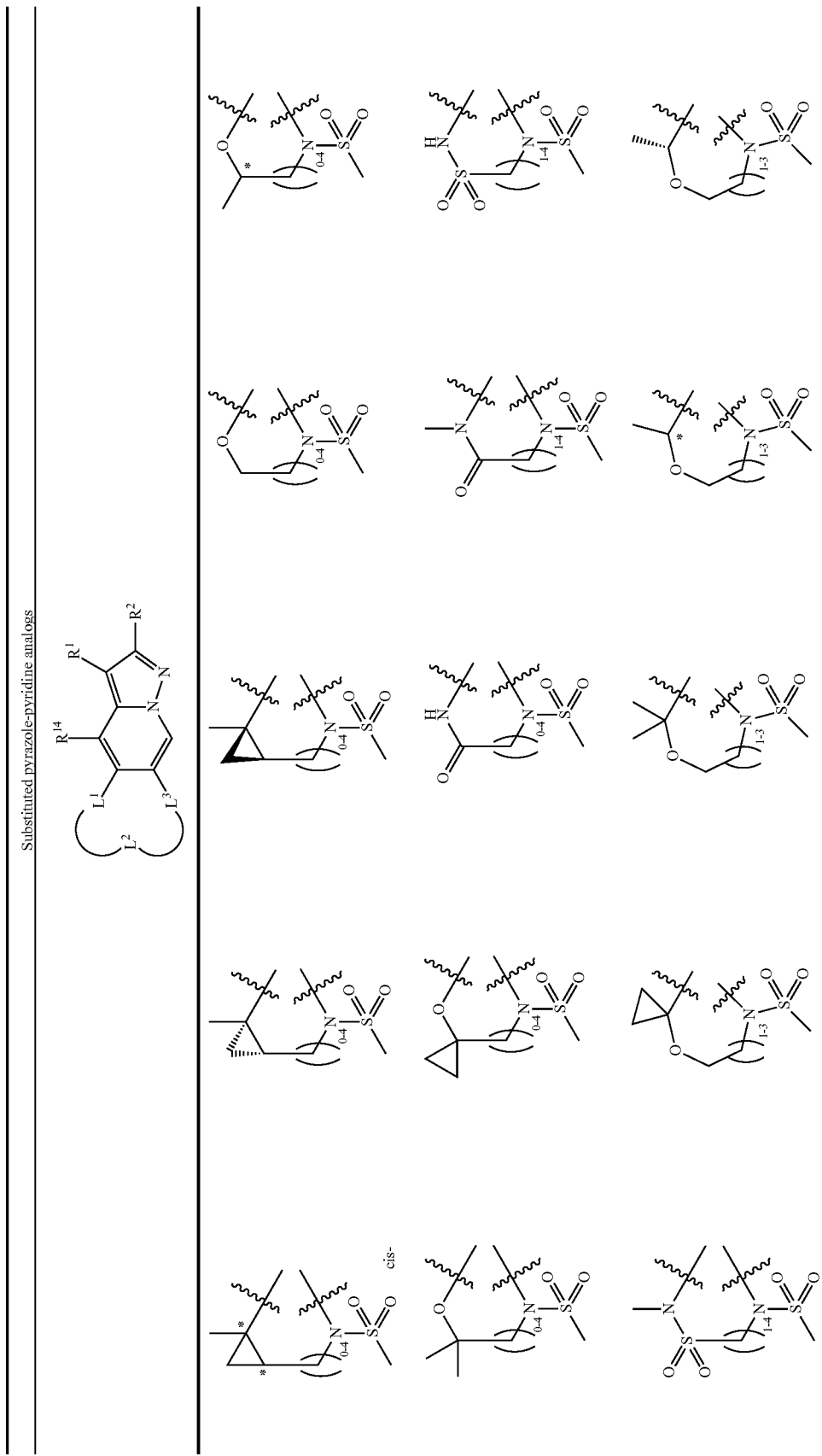

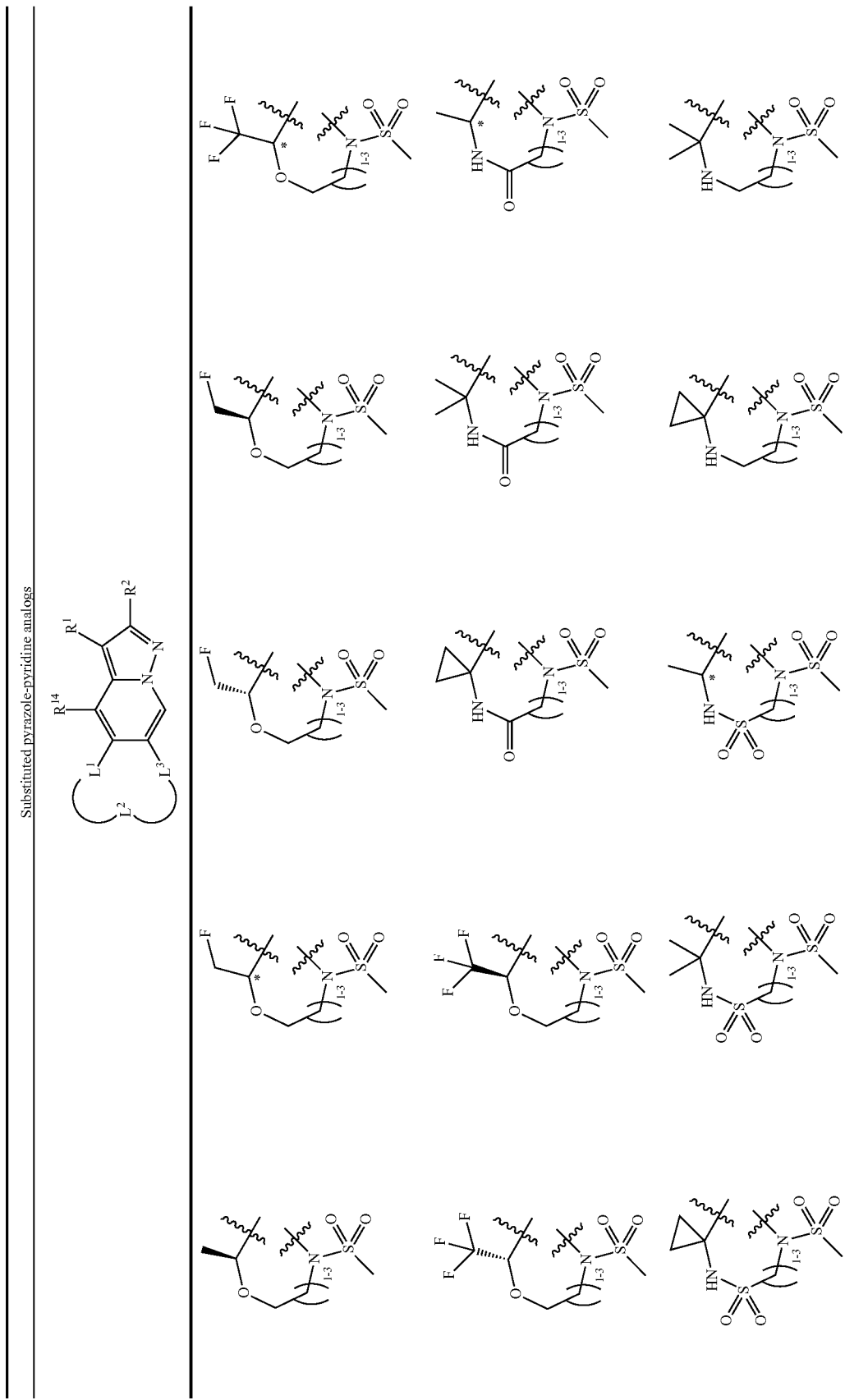

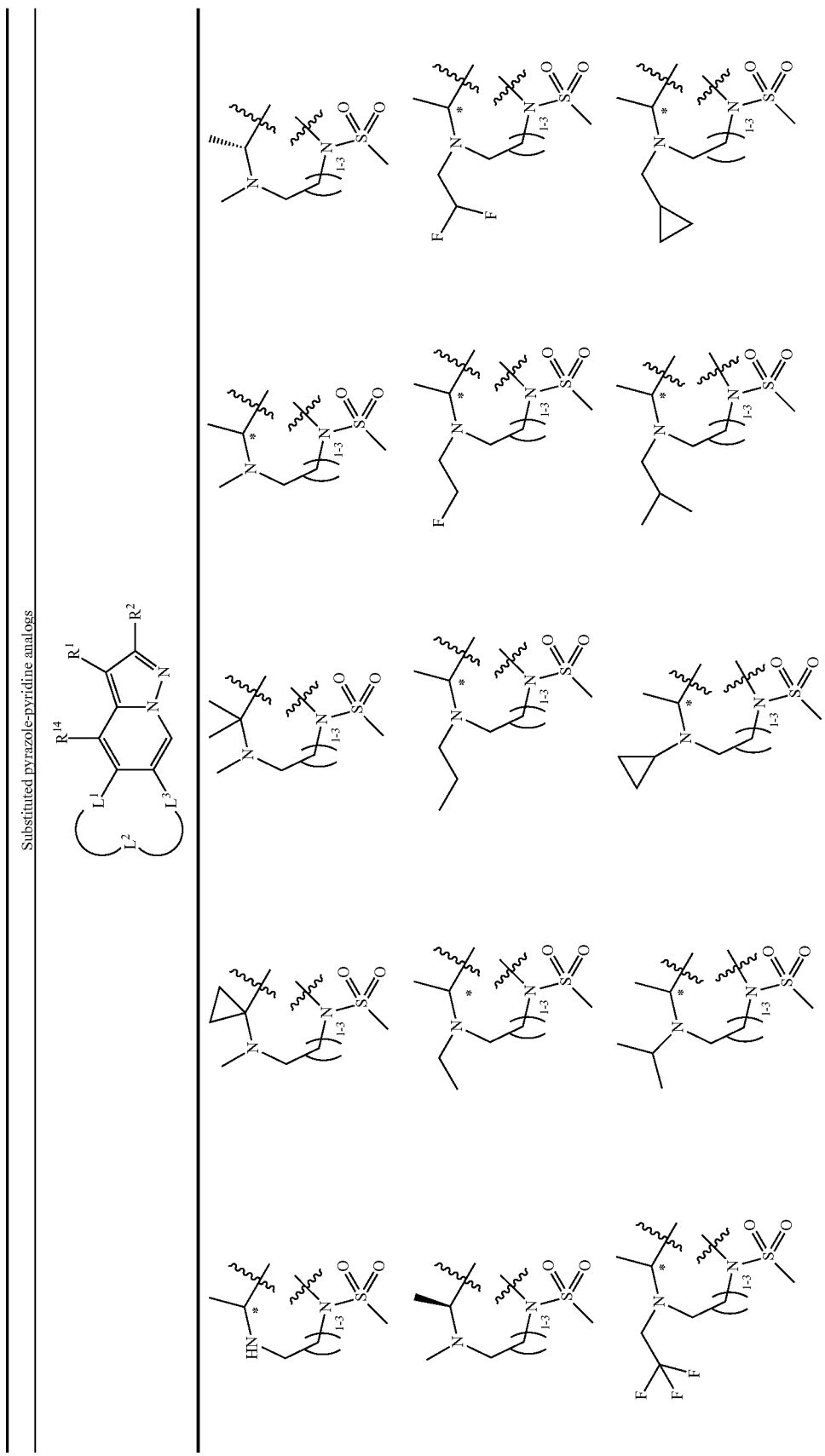

TABLE 3-continued
Substituted pyrazole-pyridine analogs
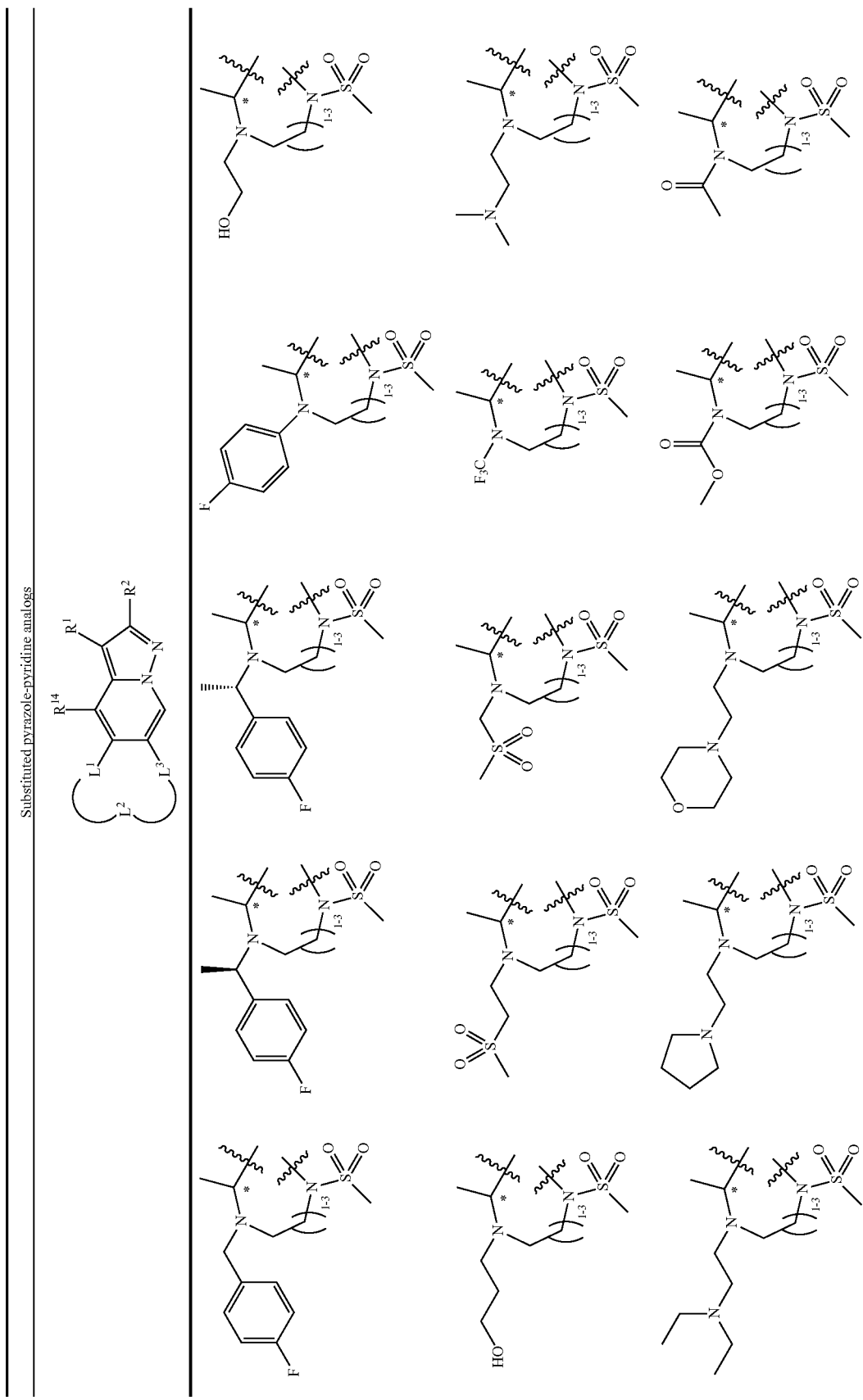

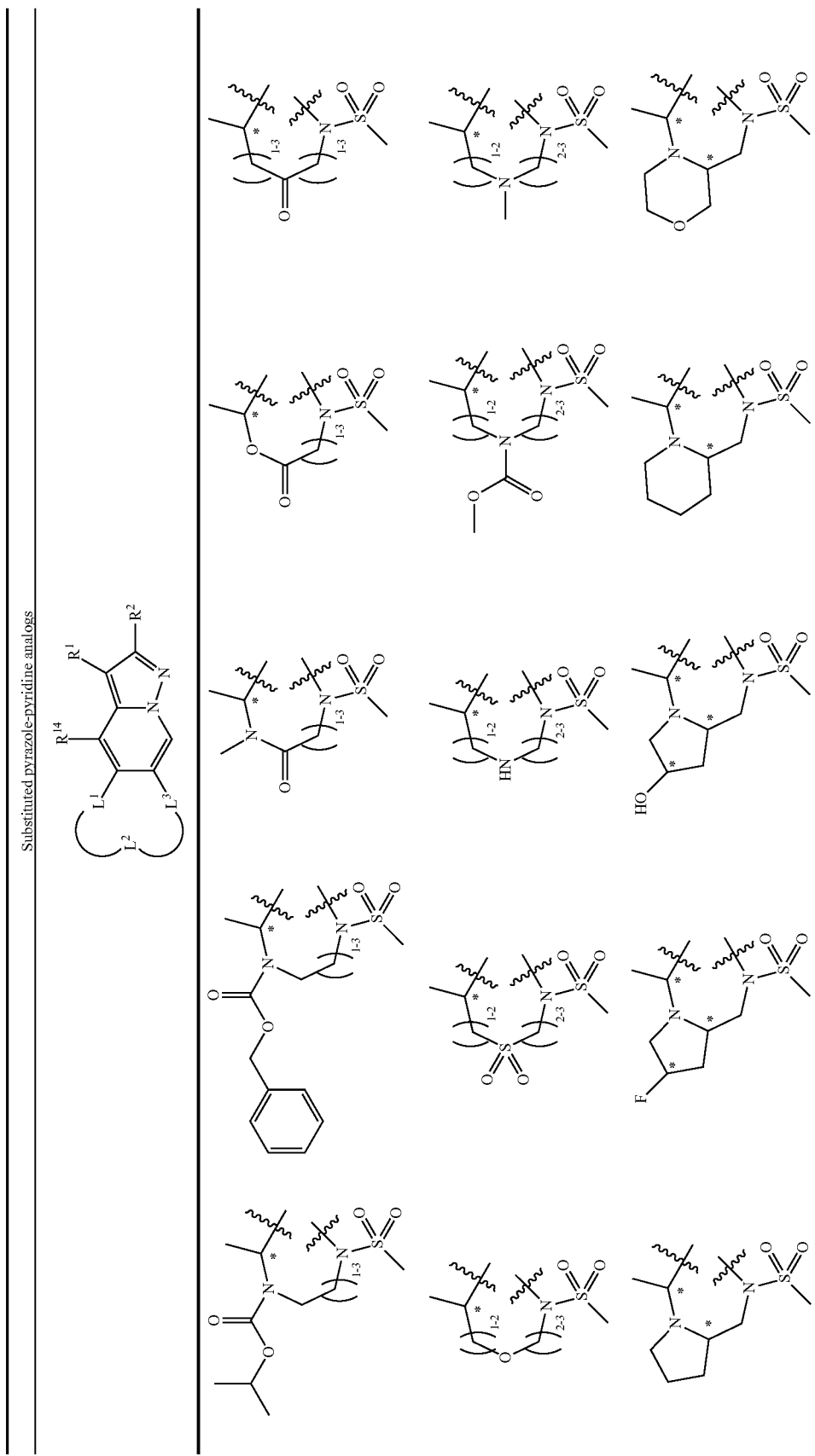

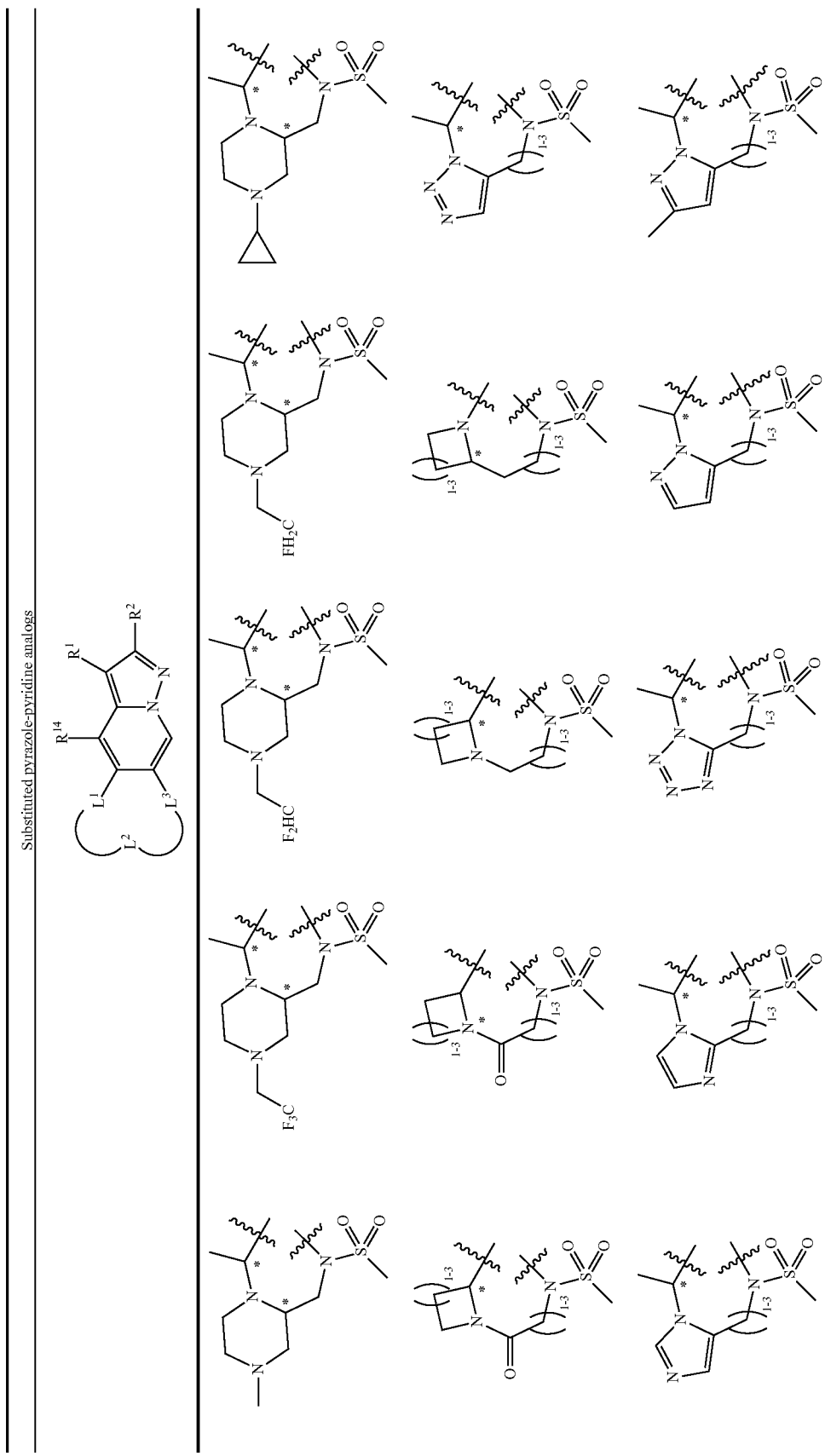

TABLE 3-continued
Substituted pyrazole-pyridine analogs
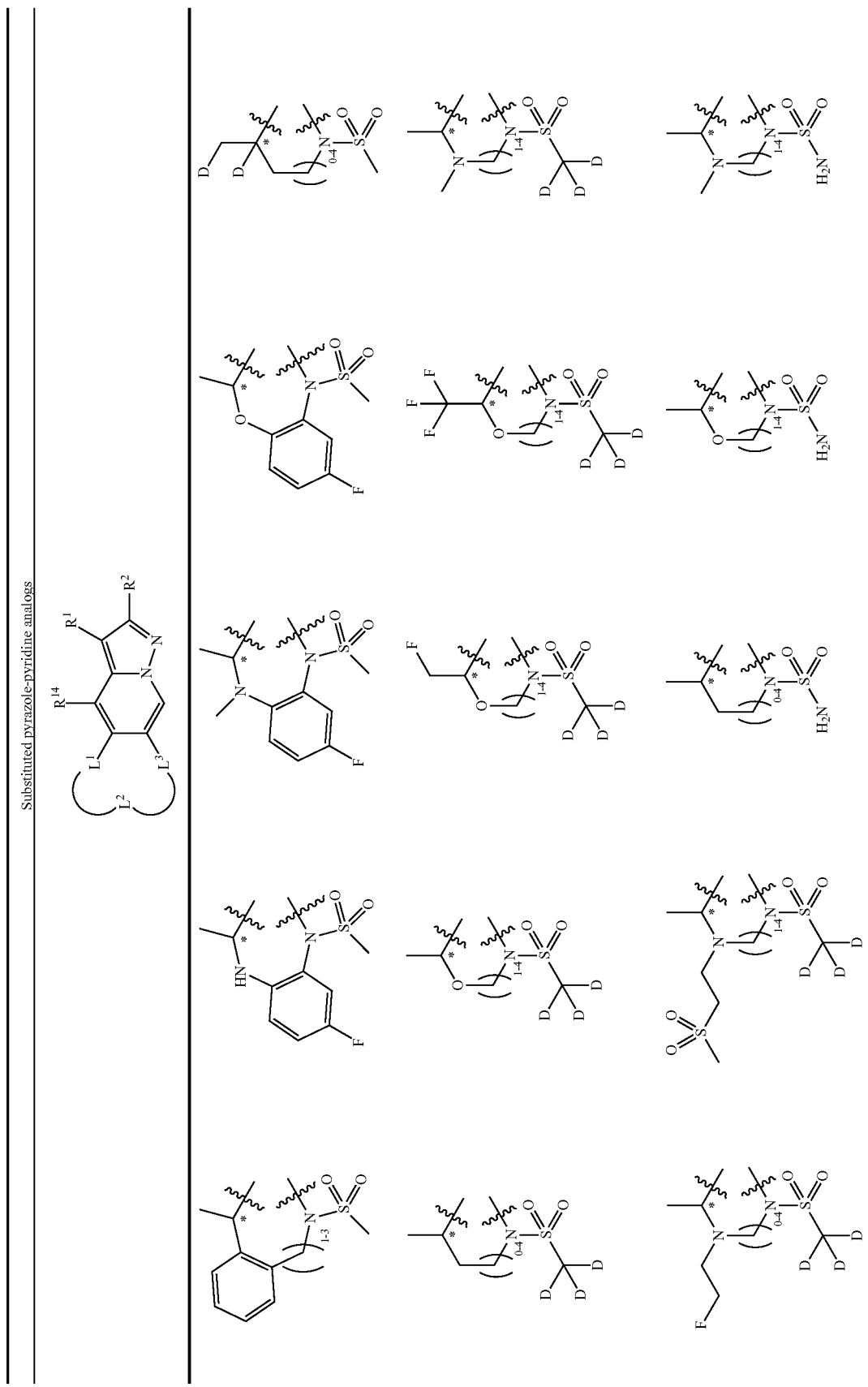

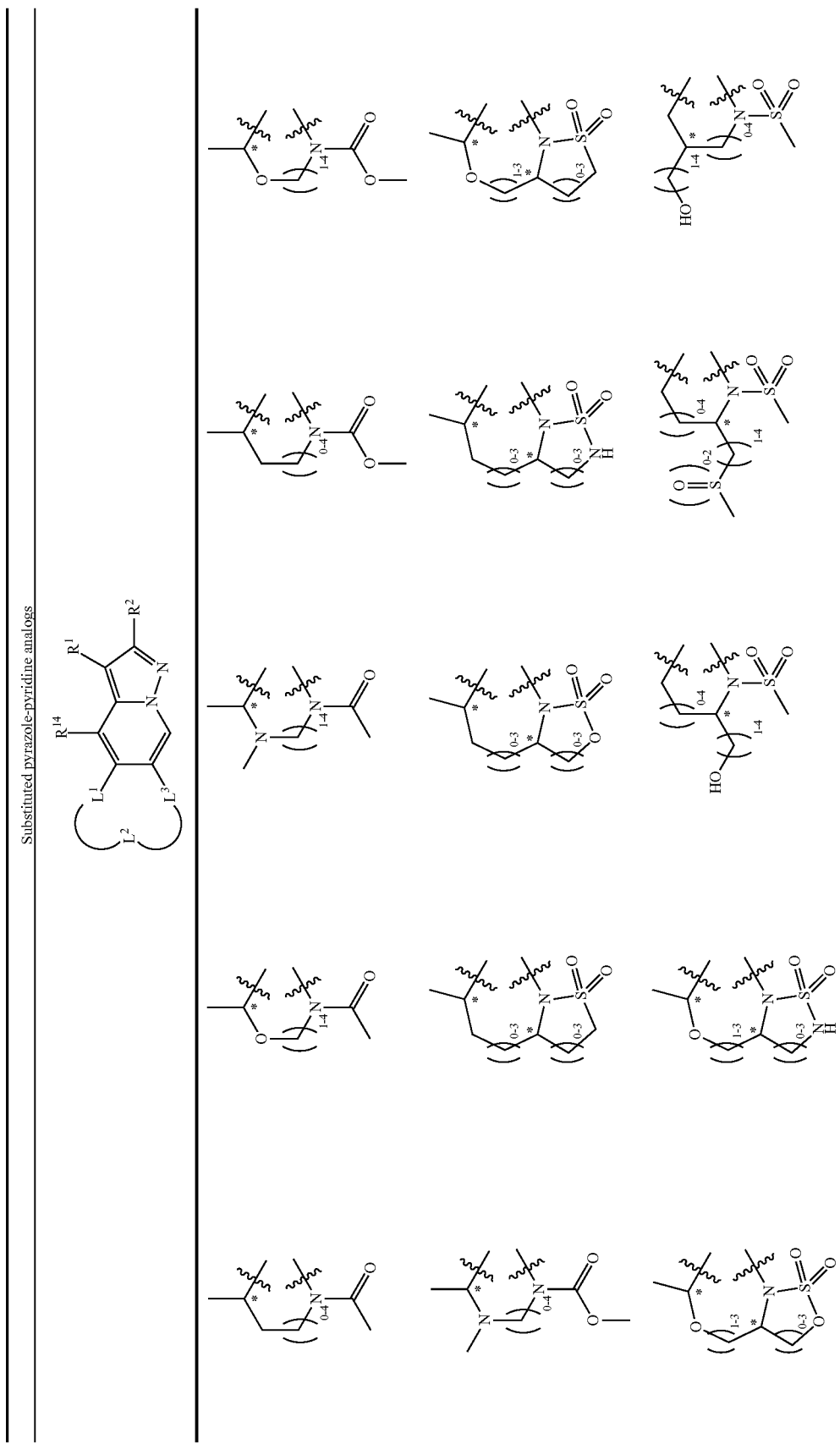

TABLE 3-continued
Substituted pyrazole-pyridine analogs
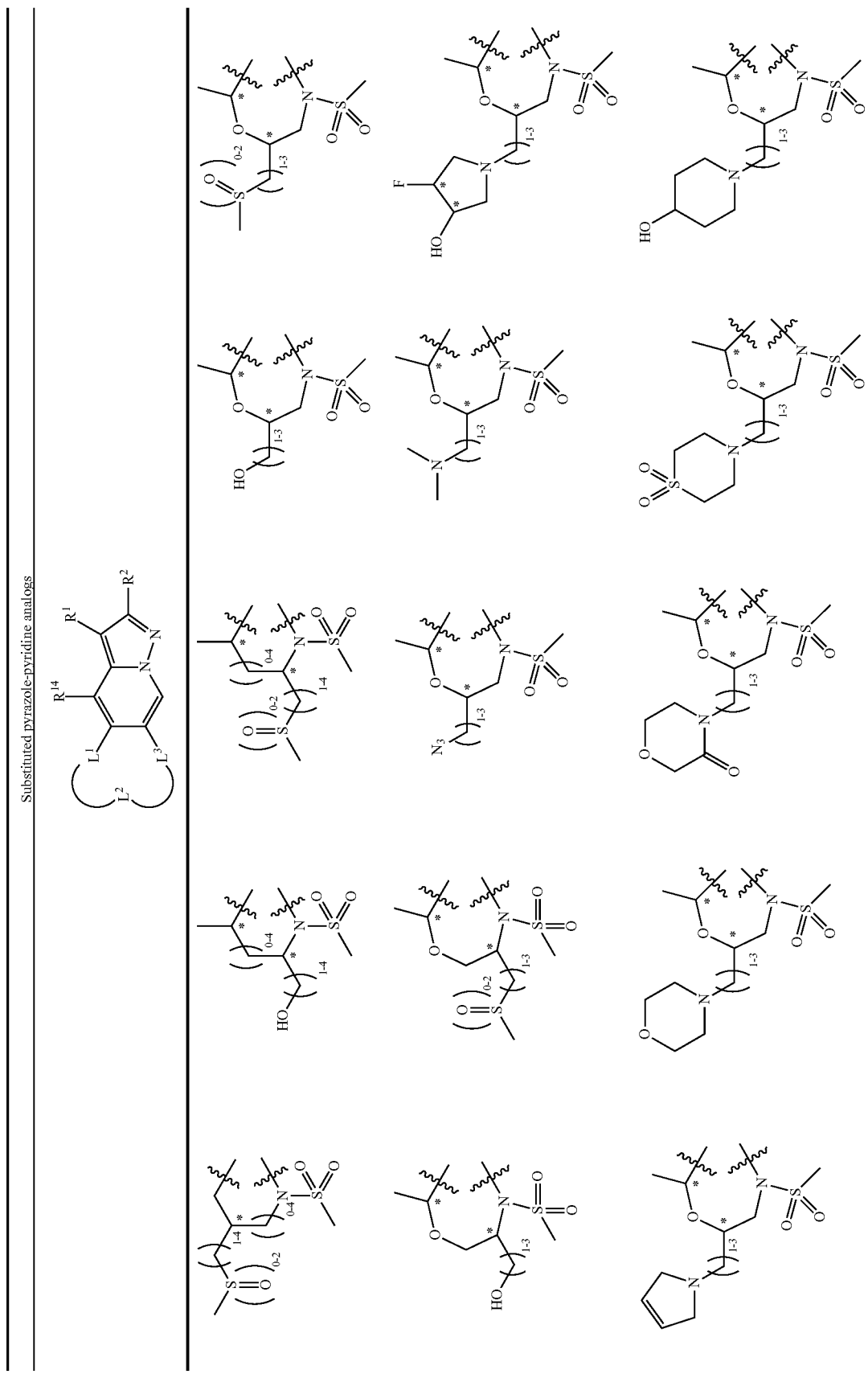

TABLE 3-continued
Substituted pyrazole-pyridine analogs
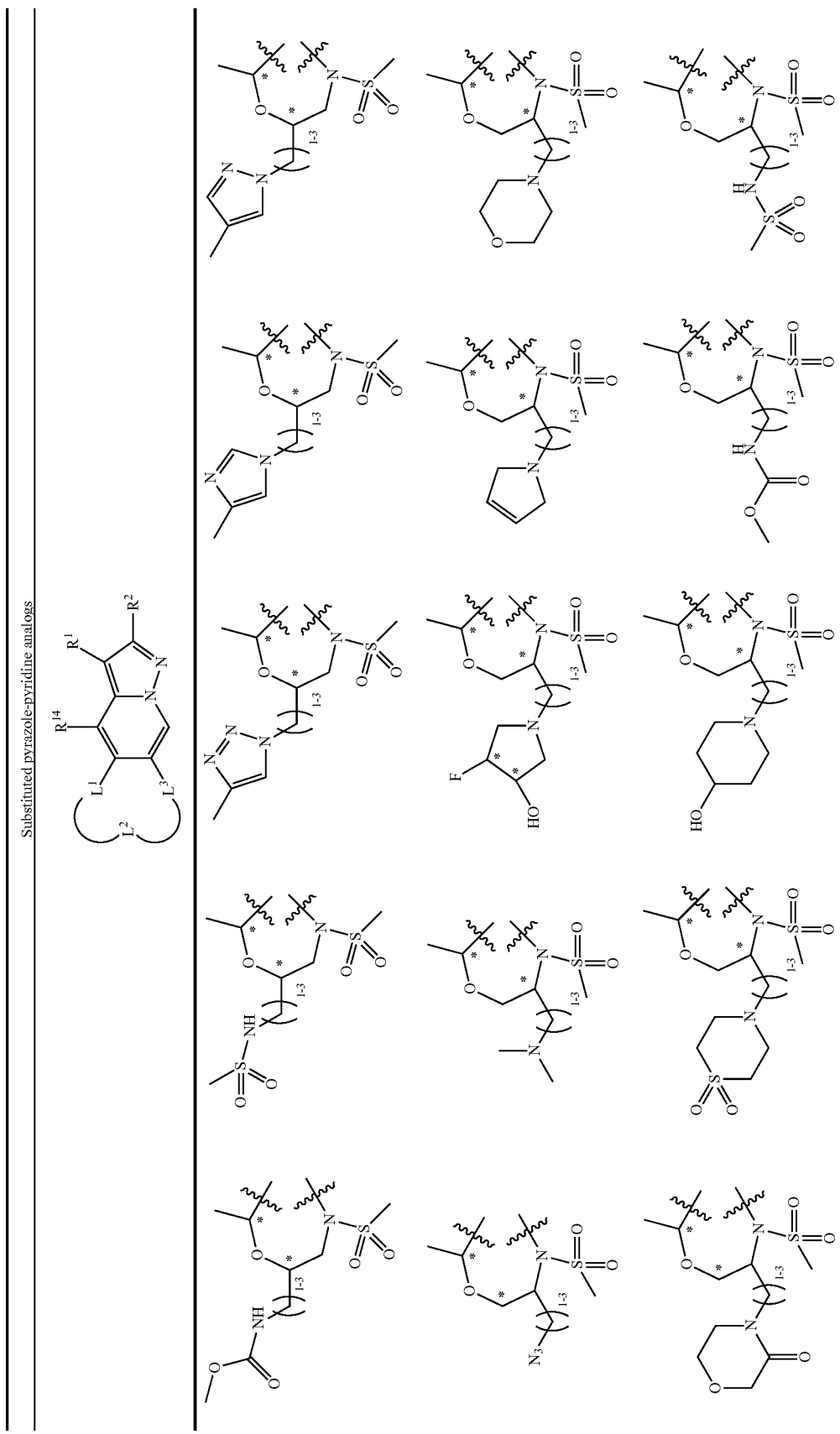

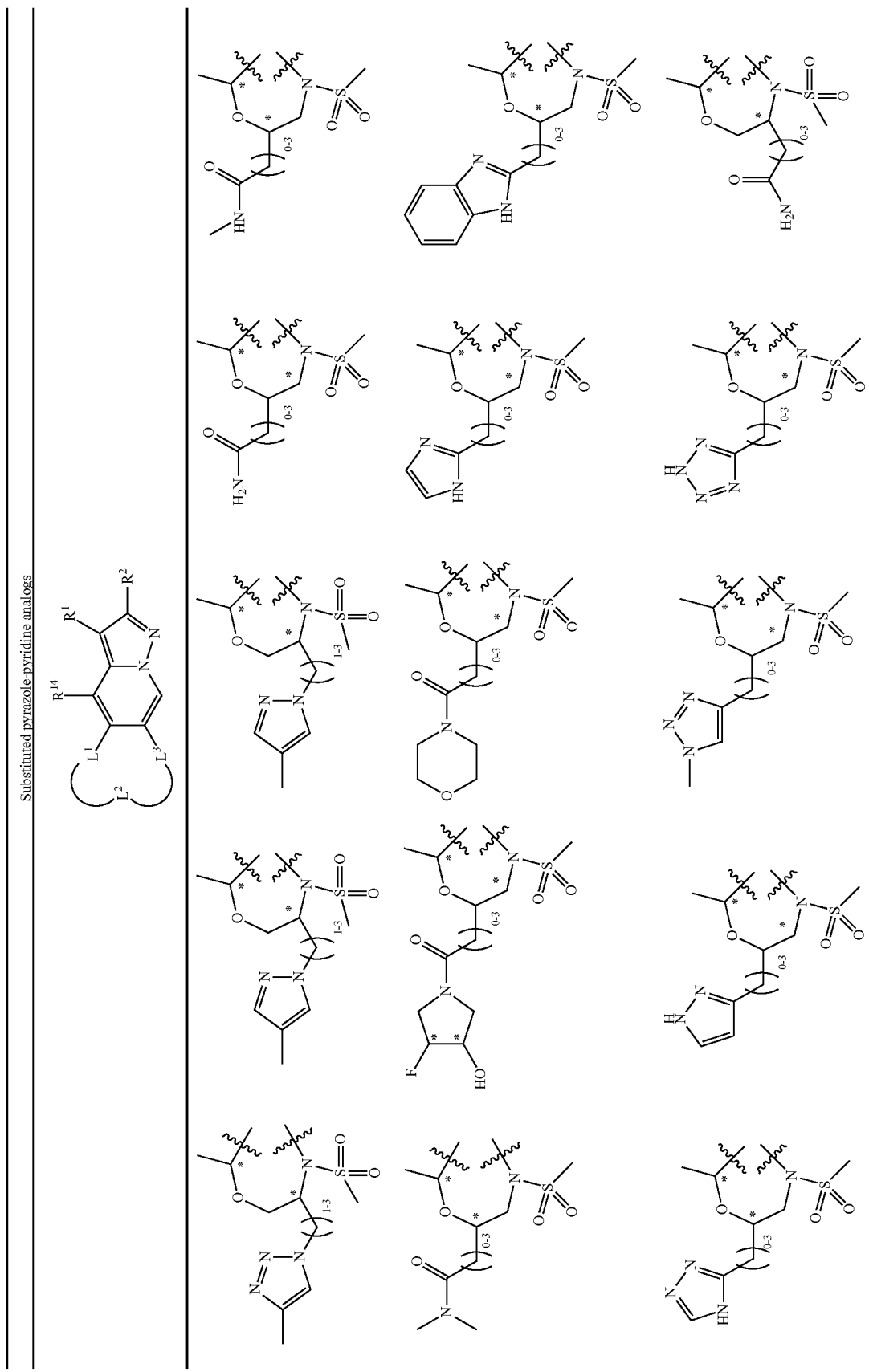

TABLE 3-continued
Substituted pyrazole-pyridine analogs
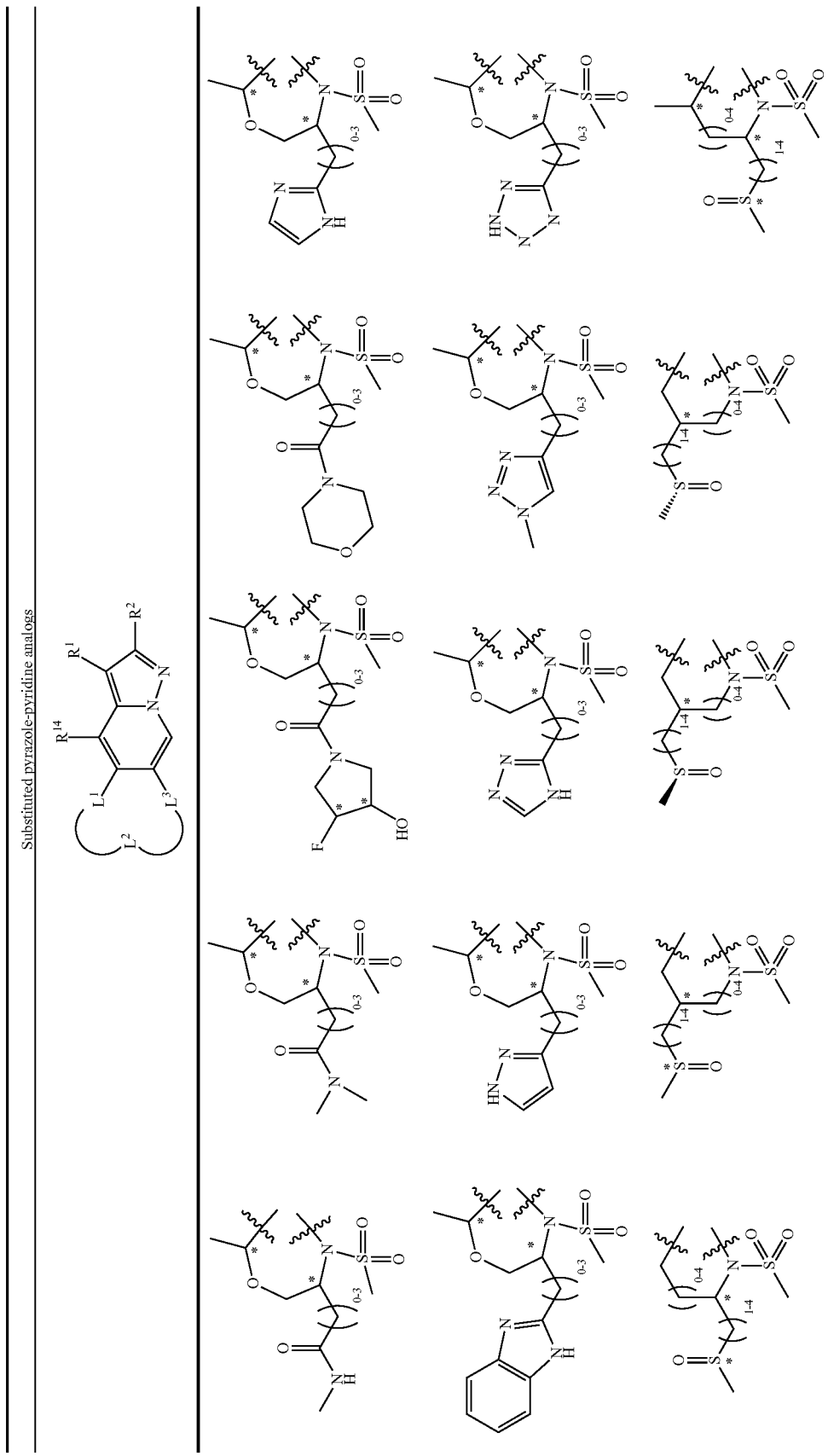

TABLE 3-continued
Substituted pyrazole-pyridine analogs
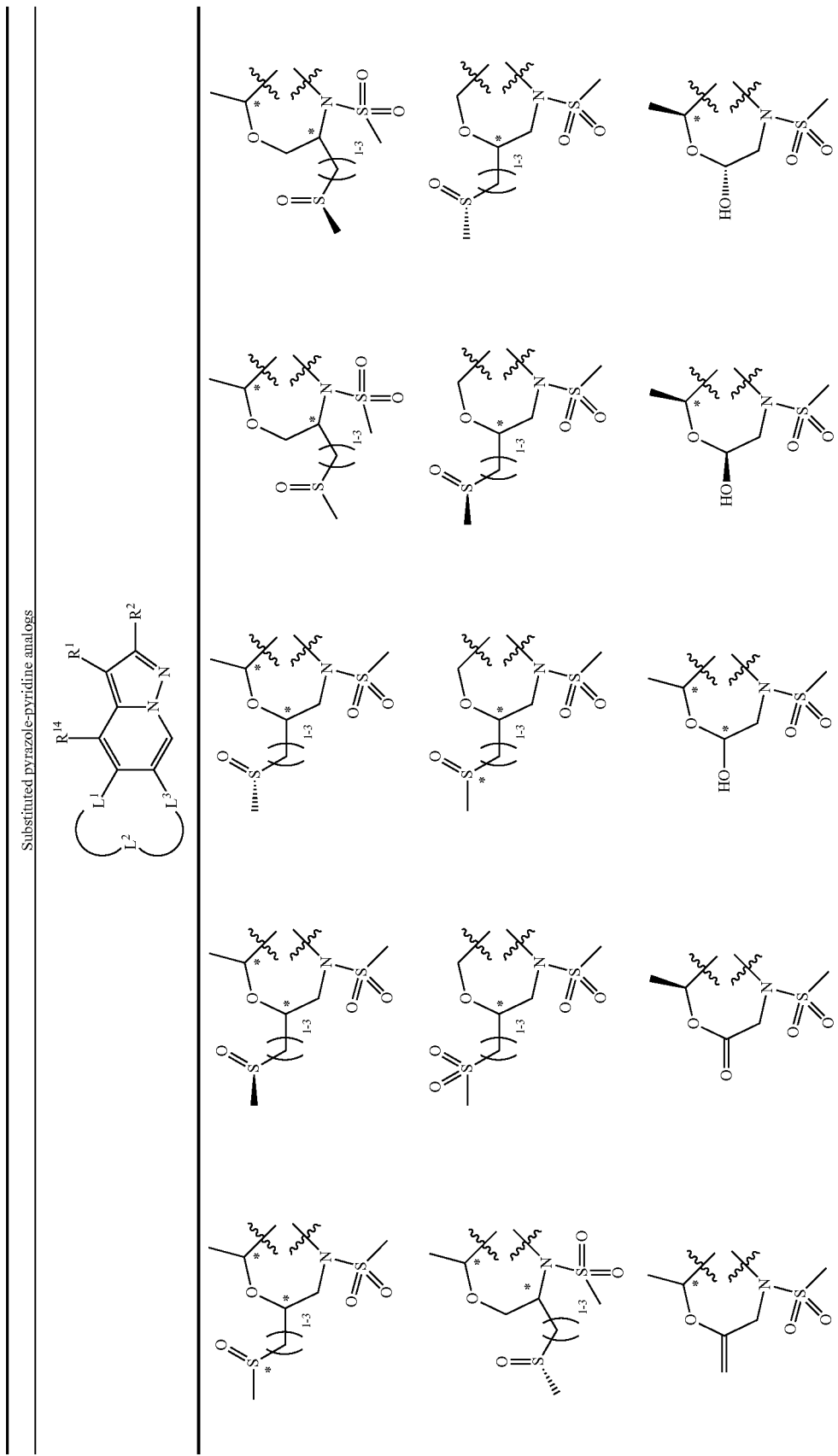

TABLE 3-continued
Substituted pyrazole-pyridine analogs
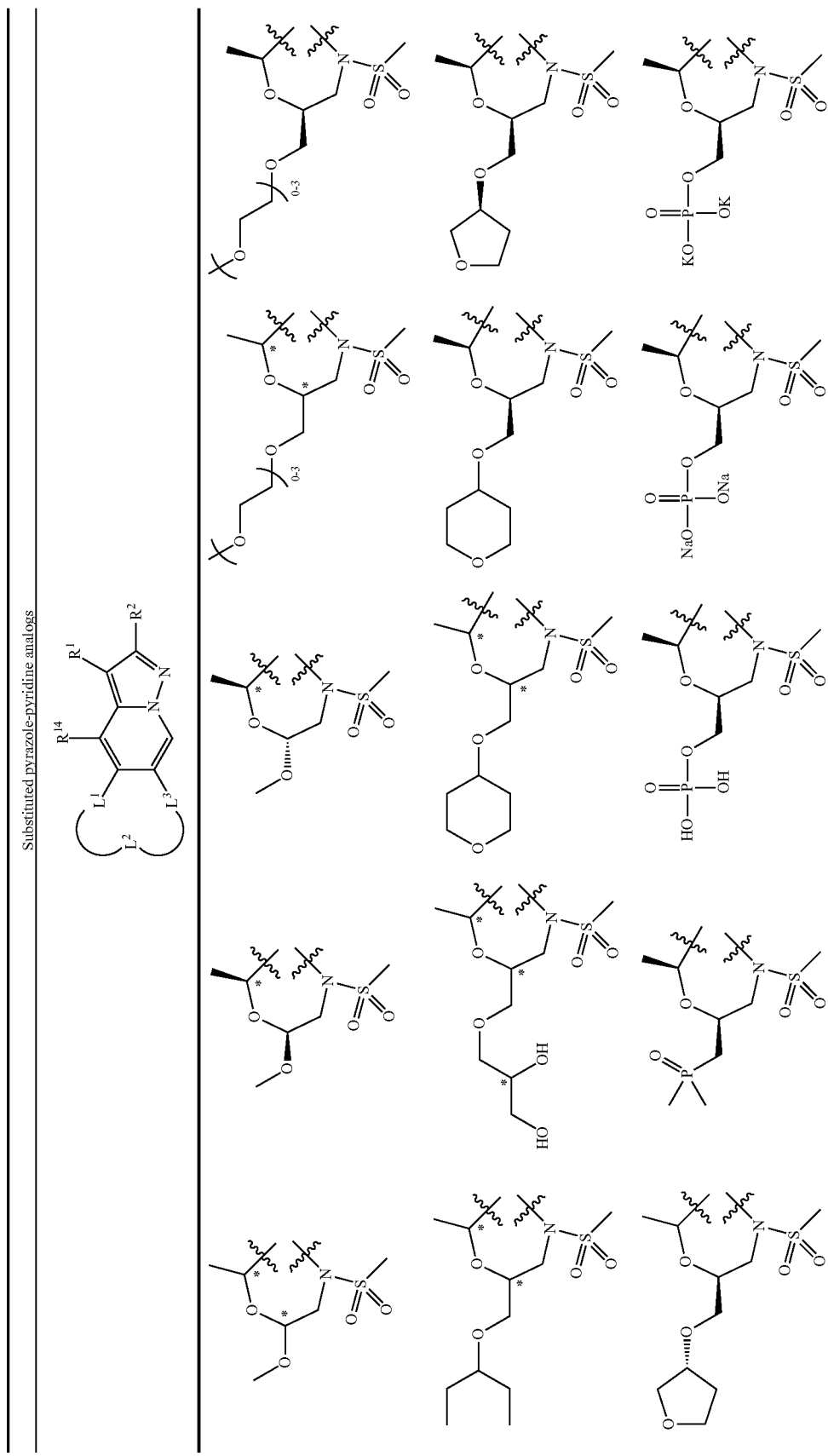

TABLE 3-continued
Substituted pyrazole-pyridine analogs
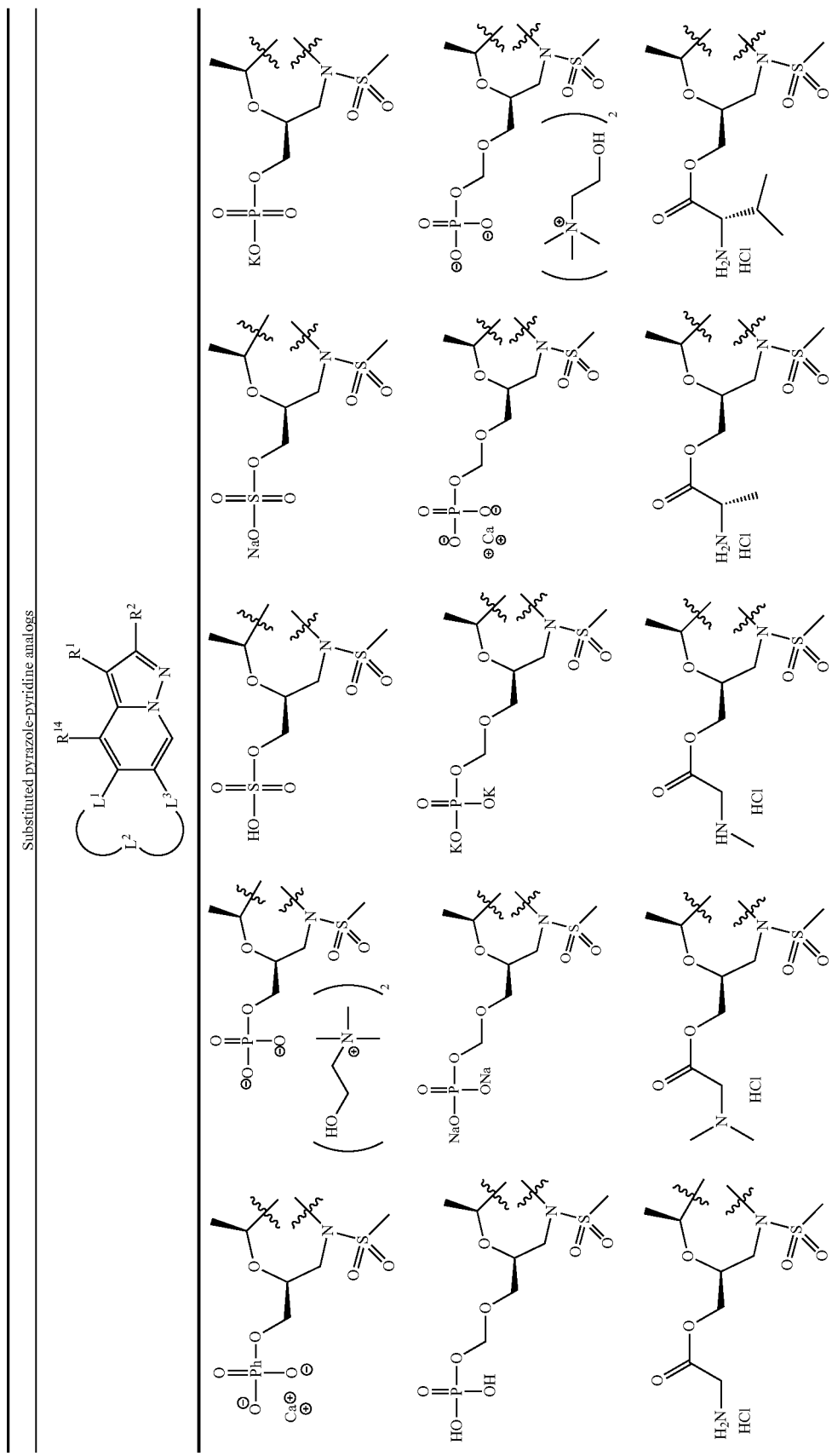

TABLE 3-continued
Substituted pyrazole-pyridine analogs
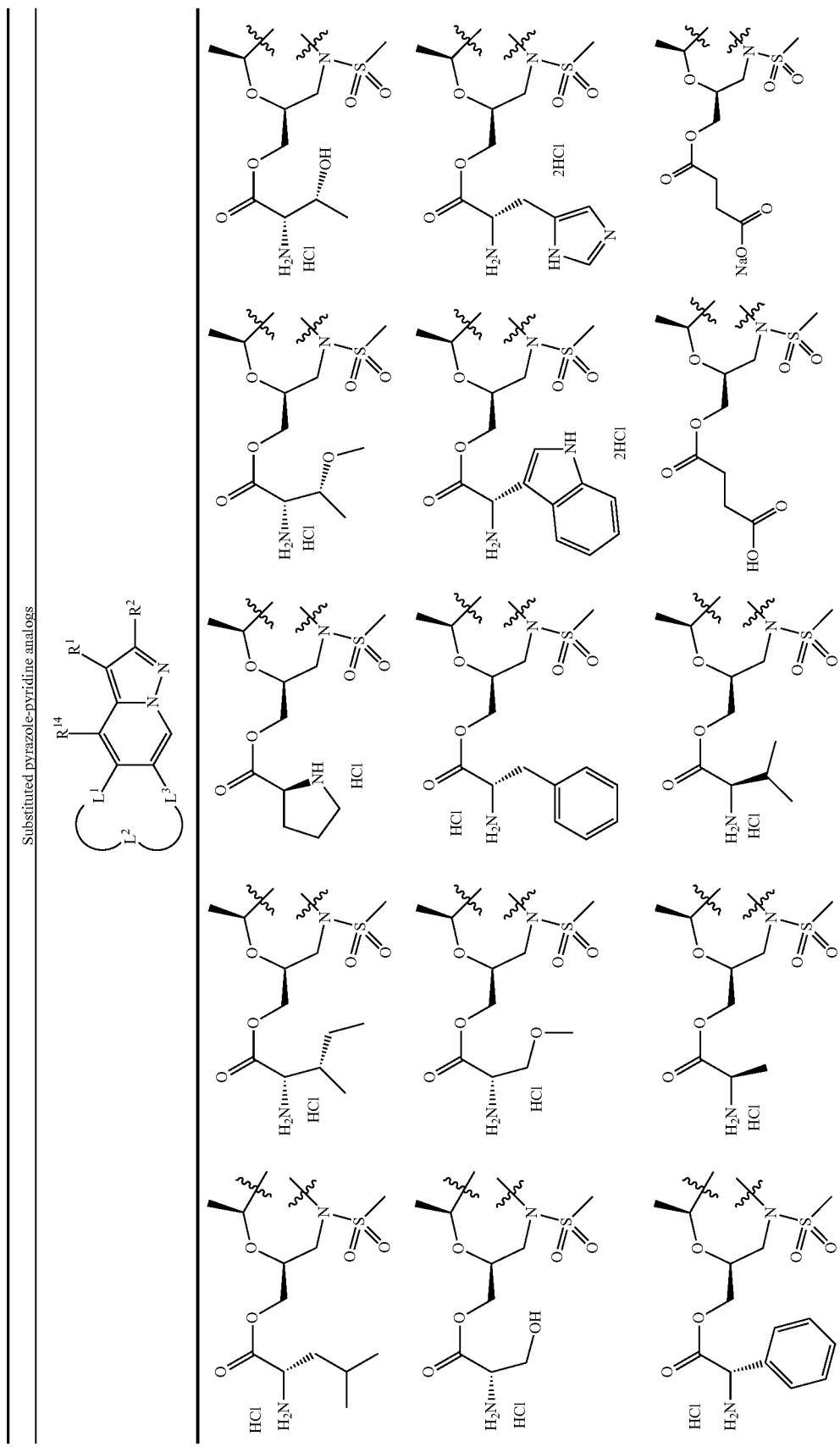

TABLE 3-continued
Substituted pyrazole-pyridine analogs
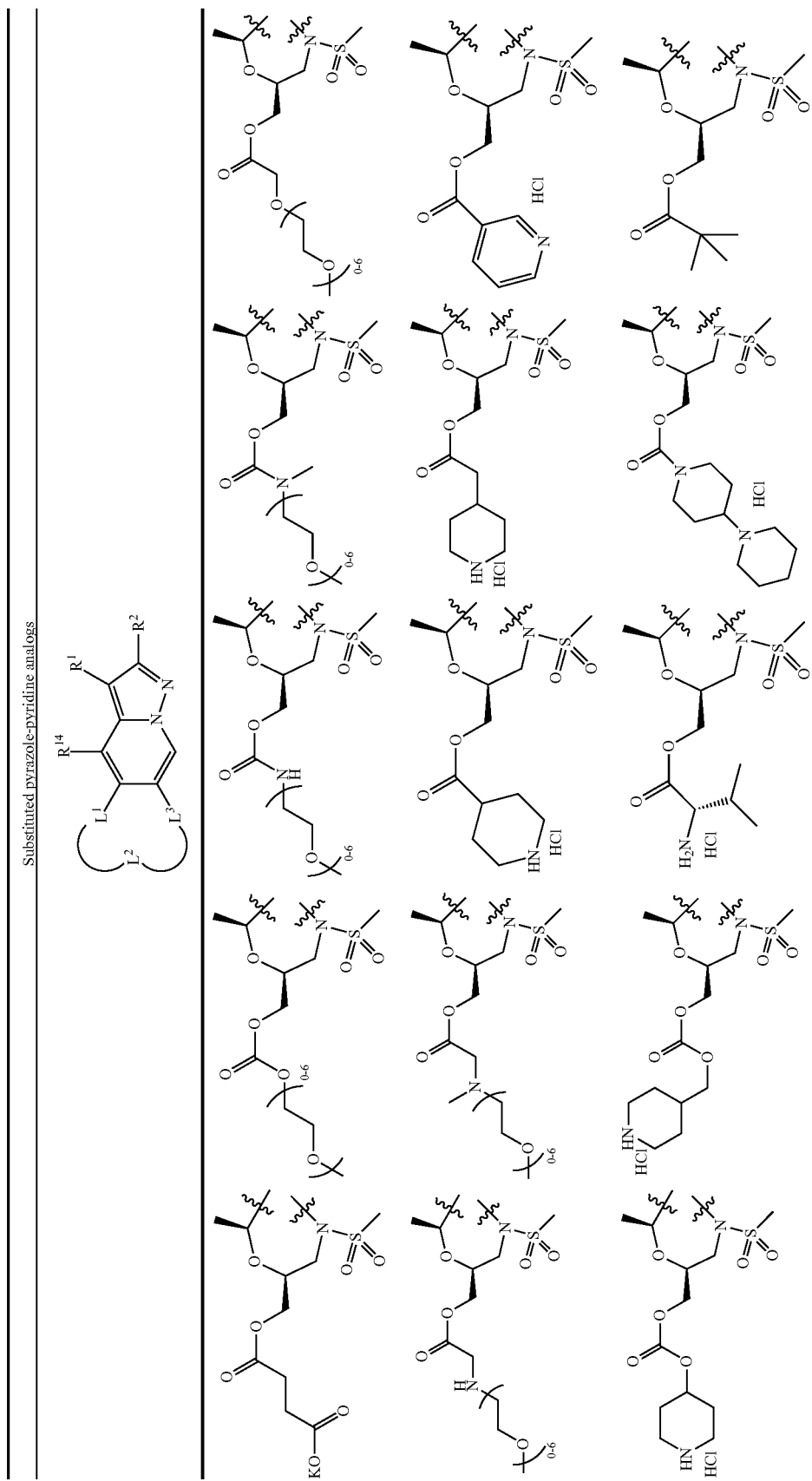

TABLE 3-continued
Substituted pyrazole-pyridine analogs
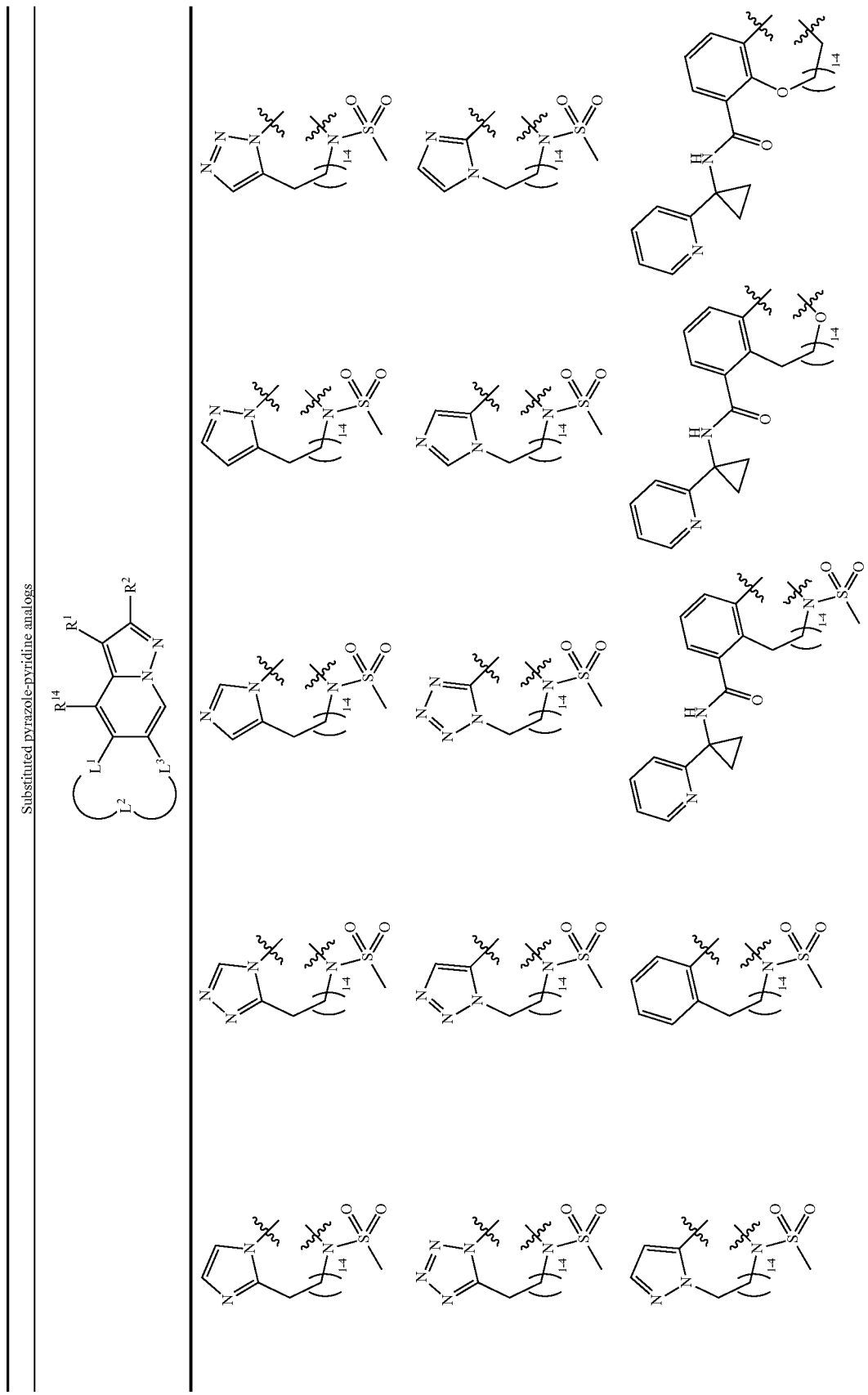

TABLE 3-continued
Substituted pyrazole-pyridine analogs
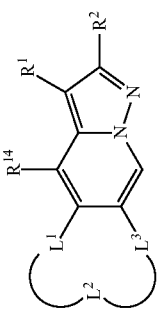
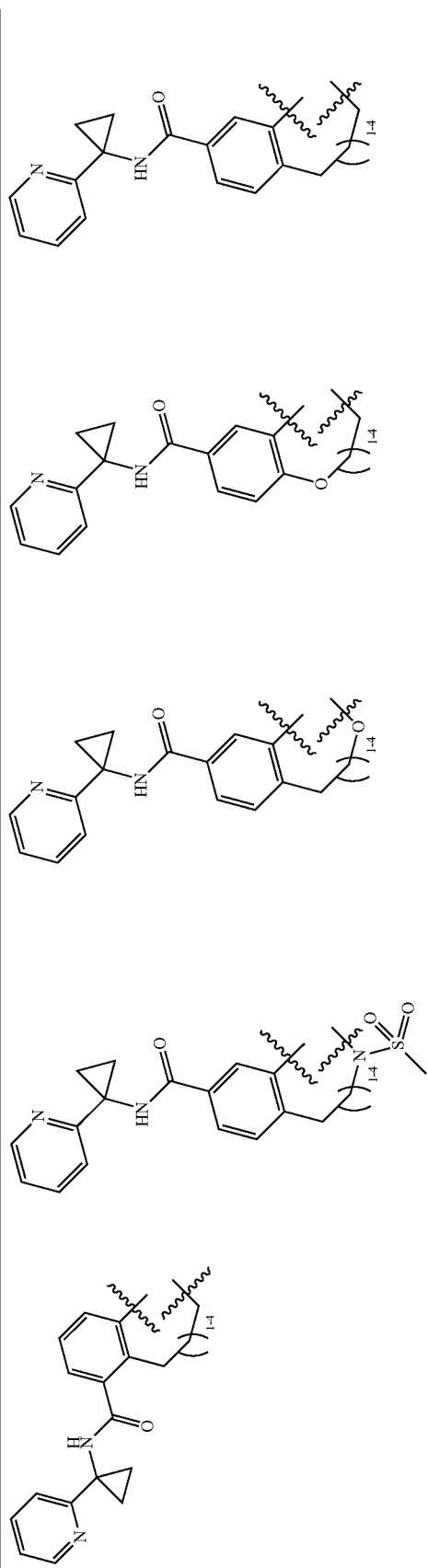

TABLE 4
Substituted imidazole-pyridine analogs
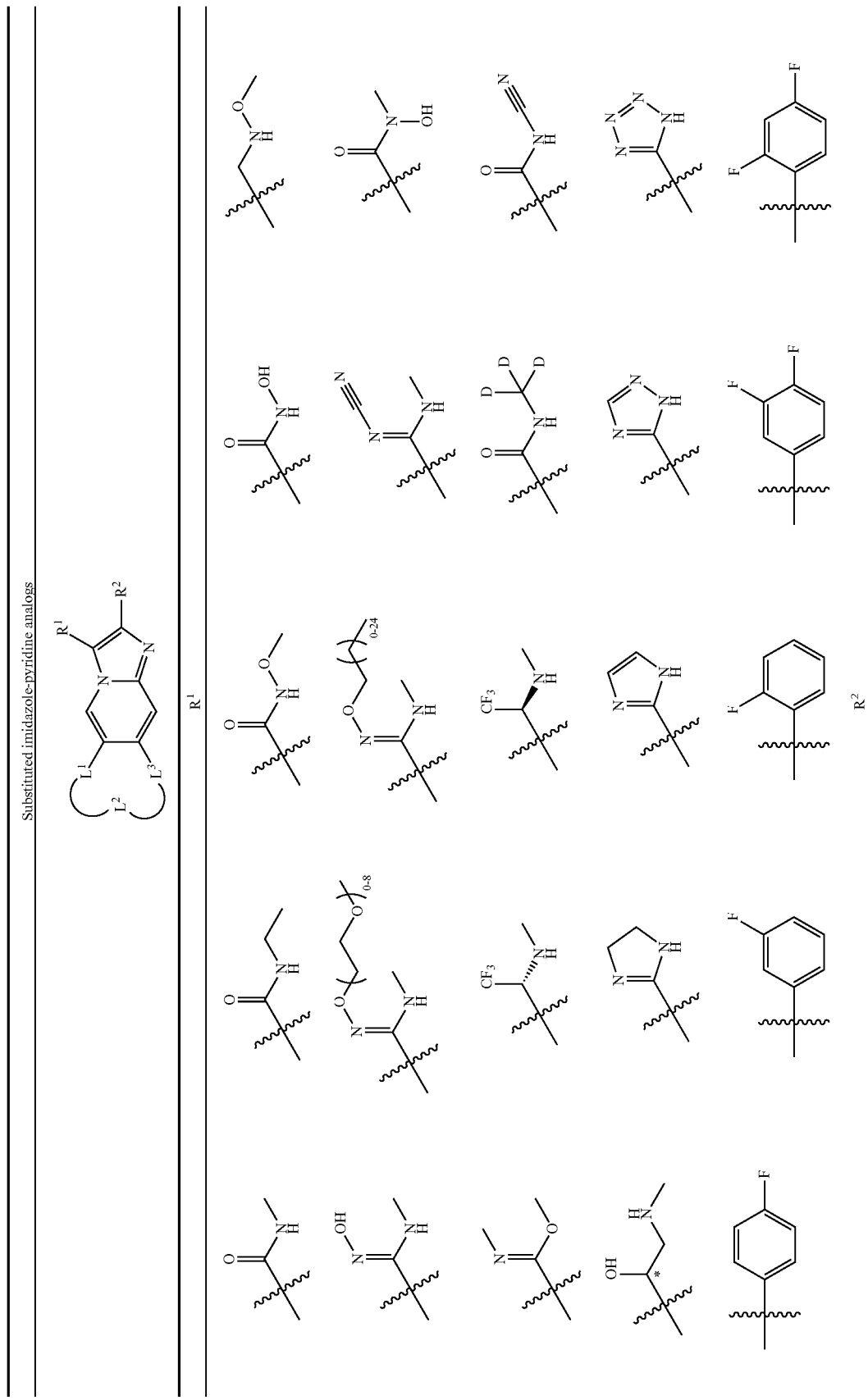

TABLE 4-continued
Substituted imidazole-pyridine analogs
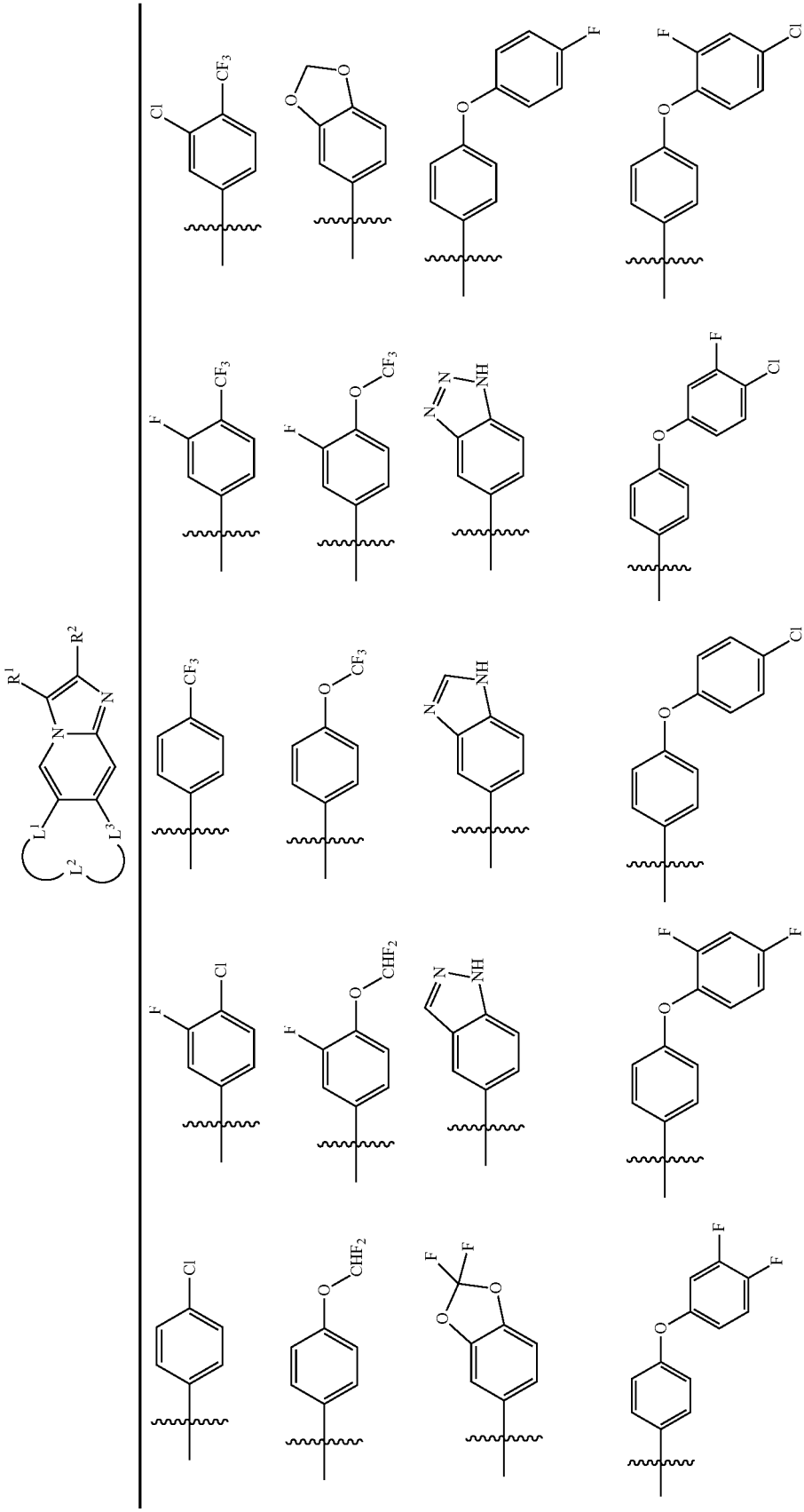

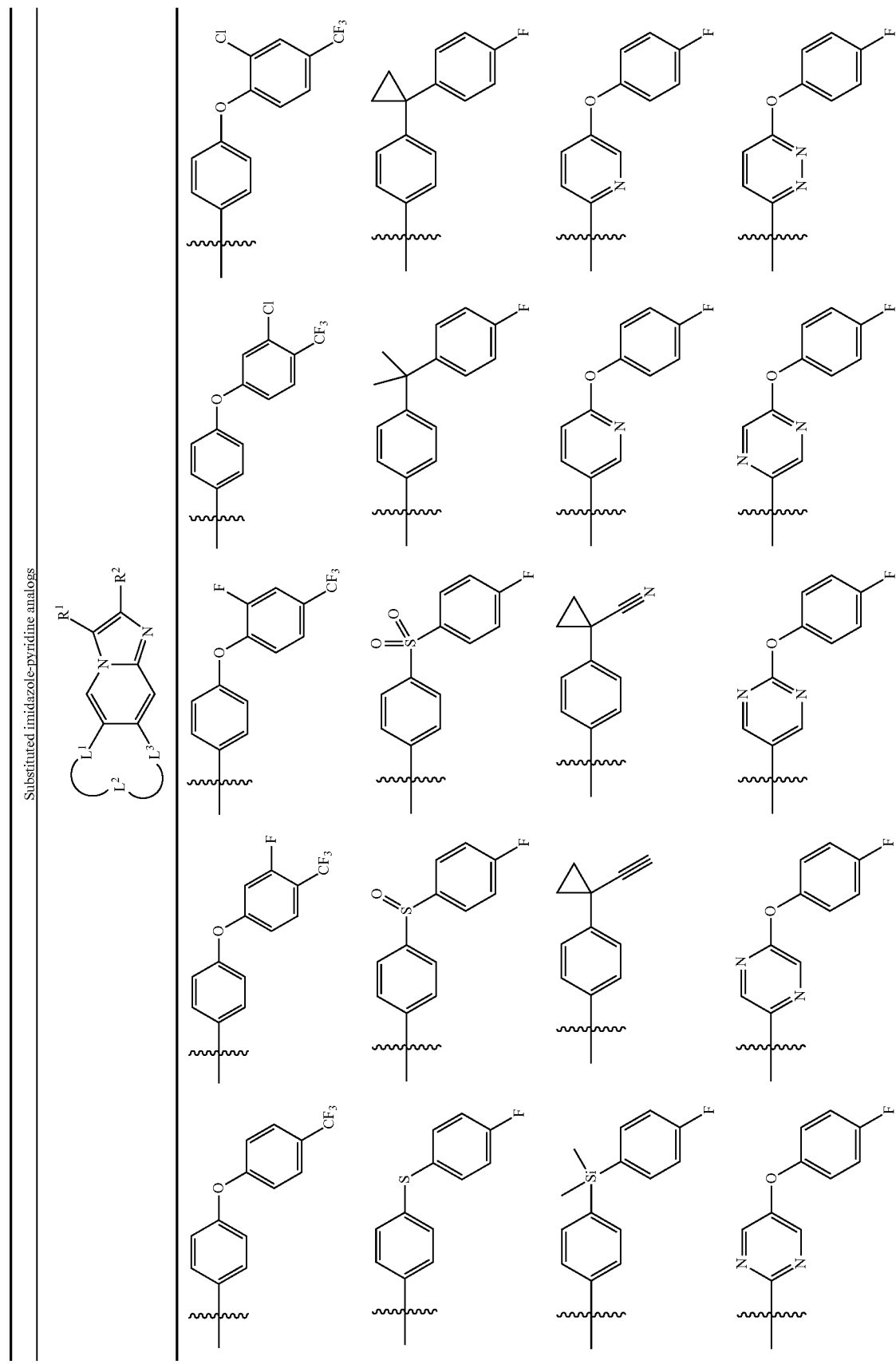

TABLE 4-continued
Substituted imidazole-pyridine analogs
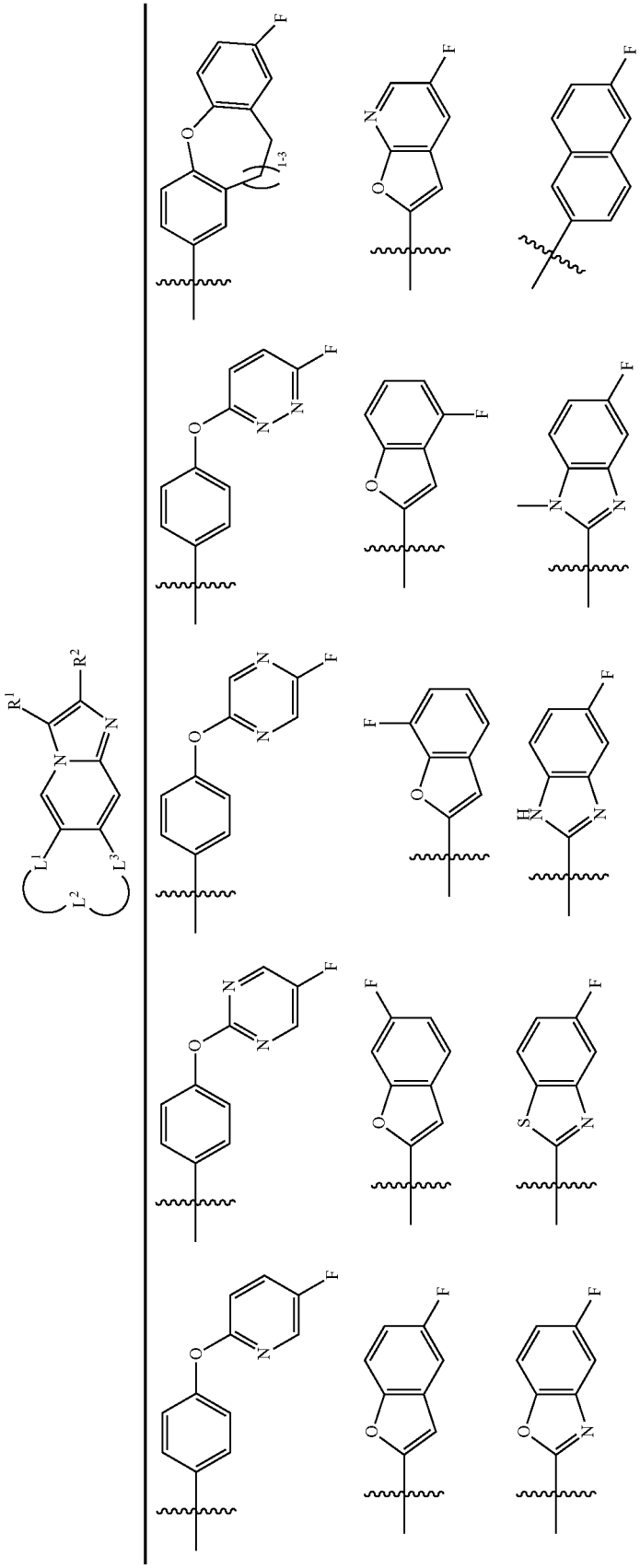
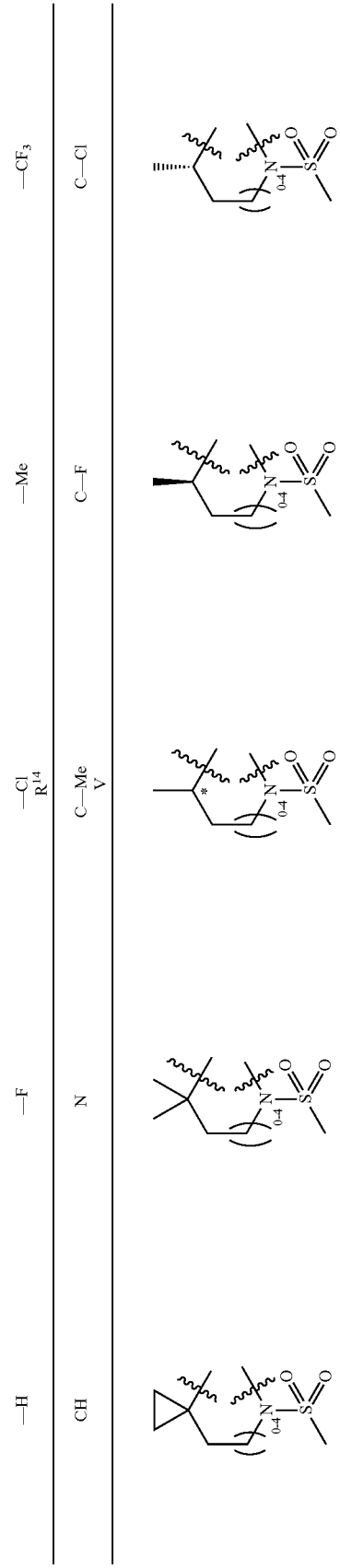

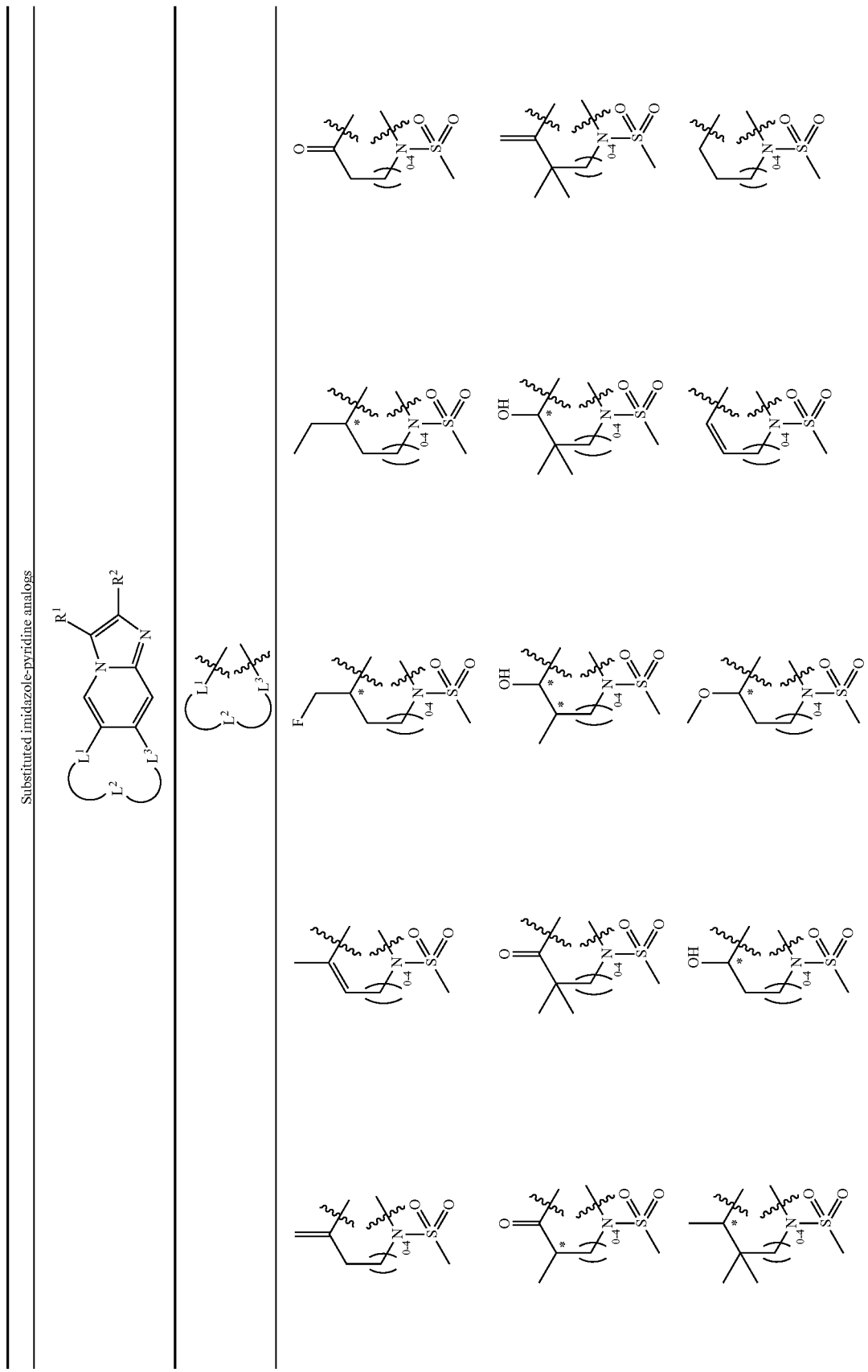

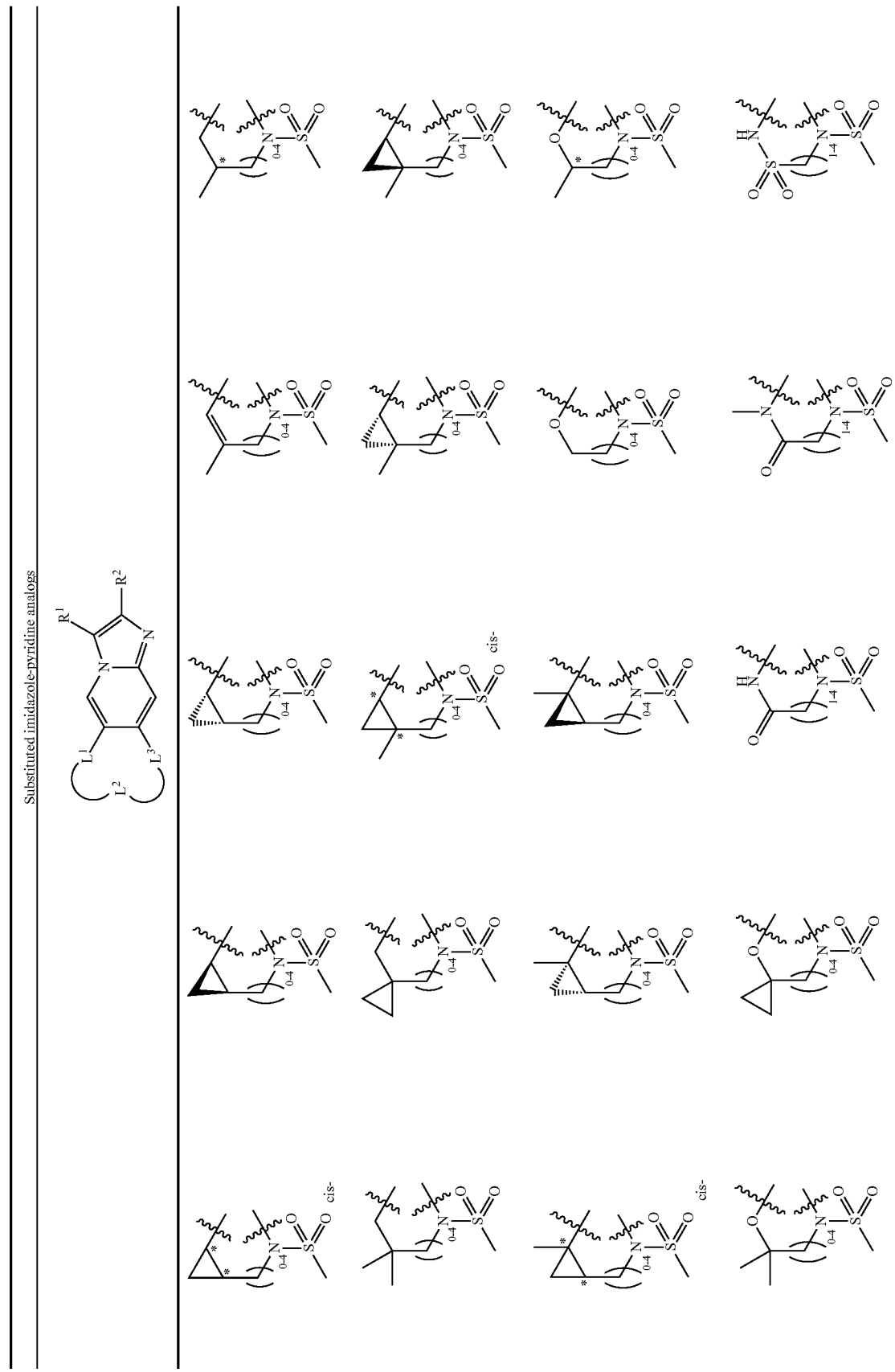

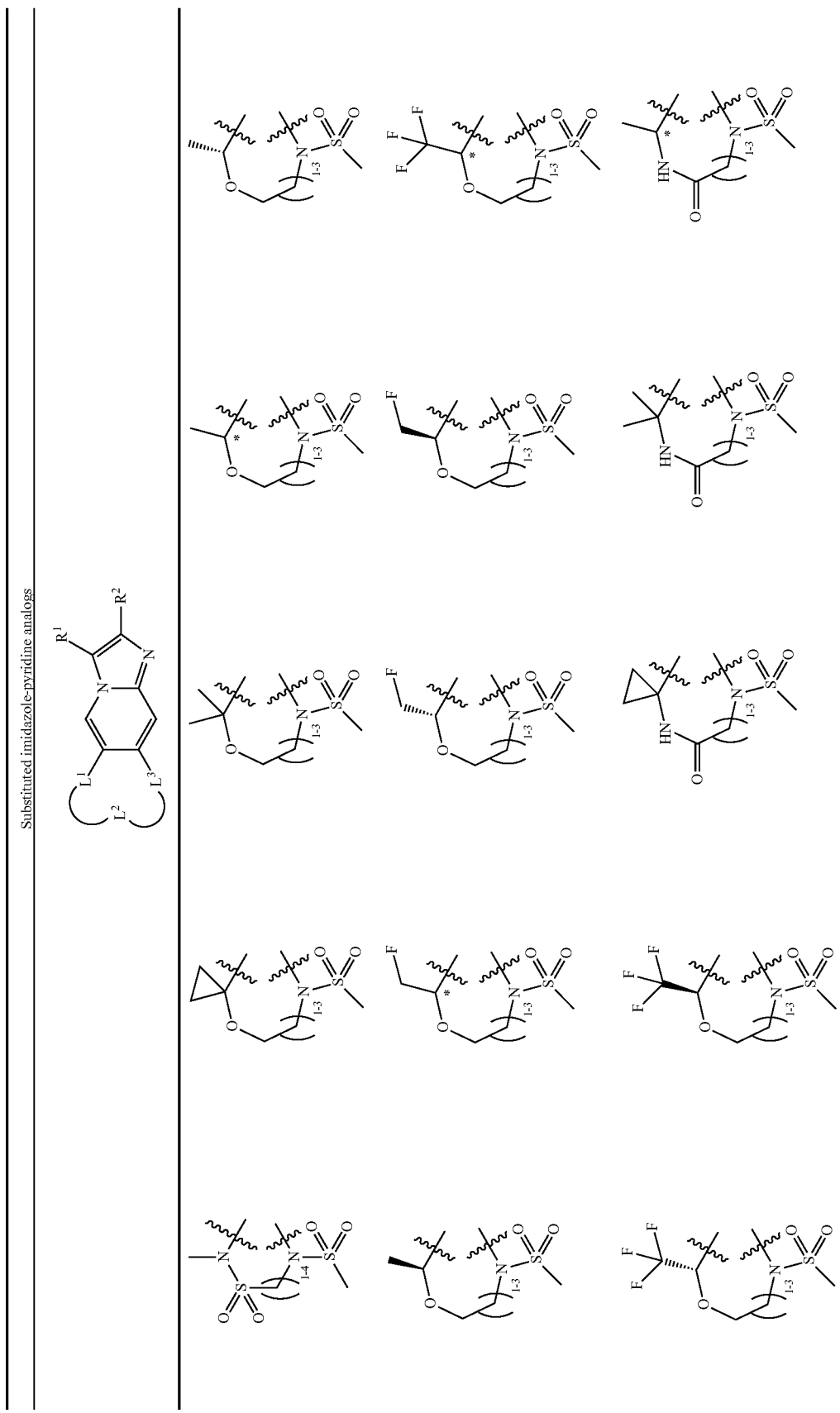

TABLE 4-continued
Substituted imidazole-pyridine analogs
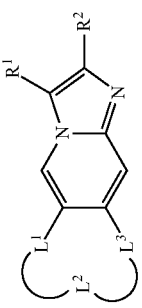
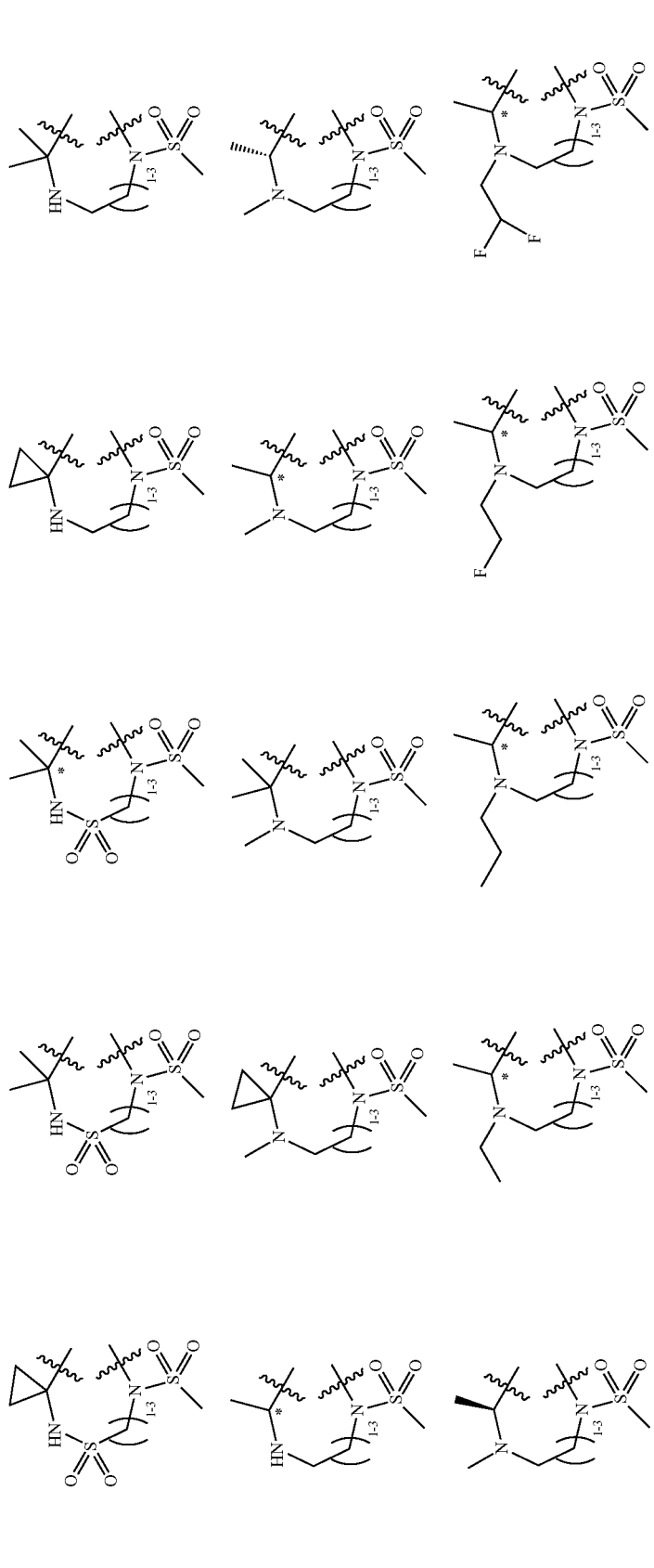

TABLE 4-continued
Substituted imidazole-pyridine analogs
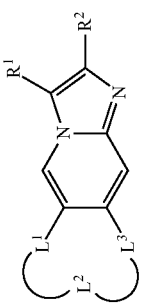
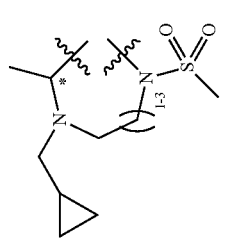 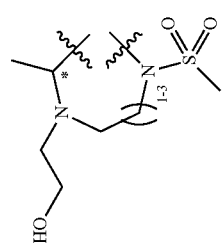 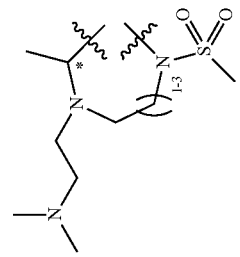
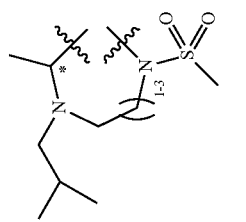 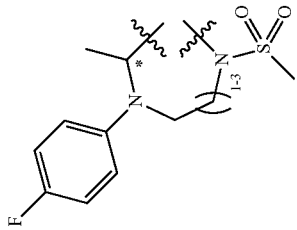 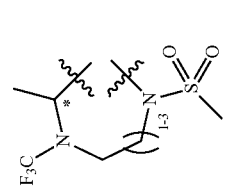
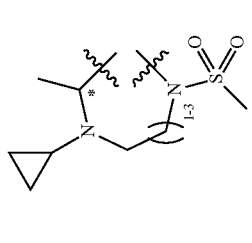 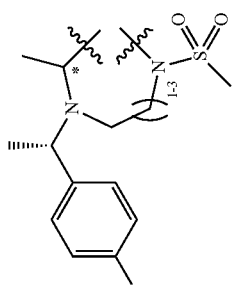 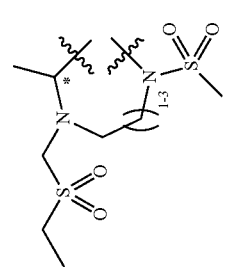
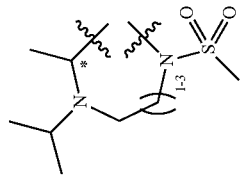 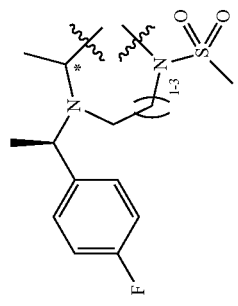 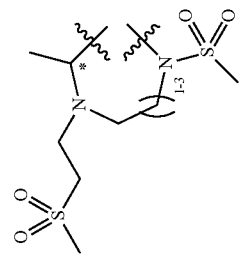
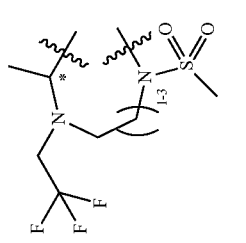 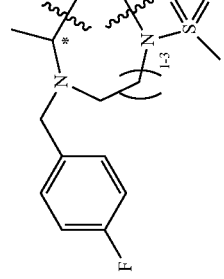 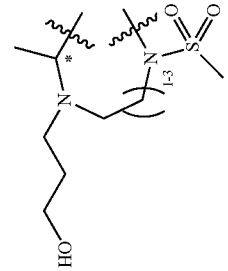

TABLE 4-continued
Substituted imidazole-pyridine analogs
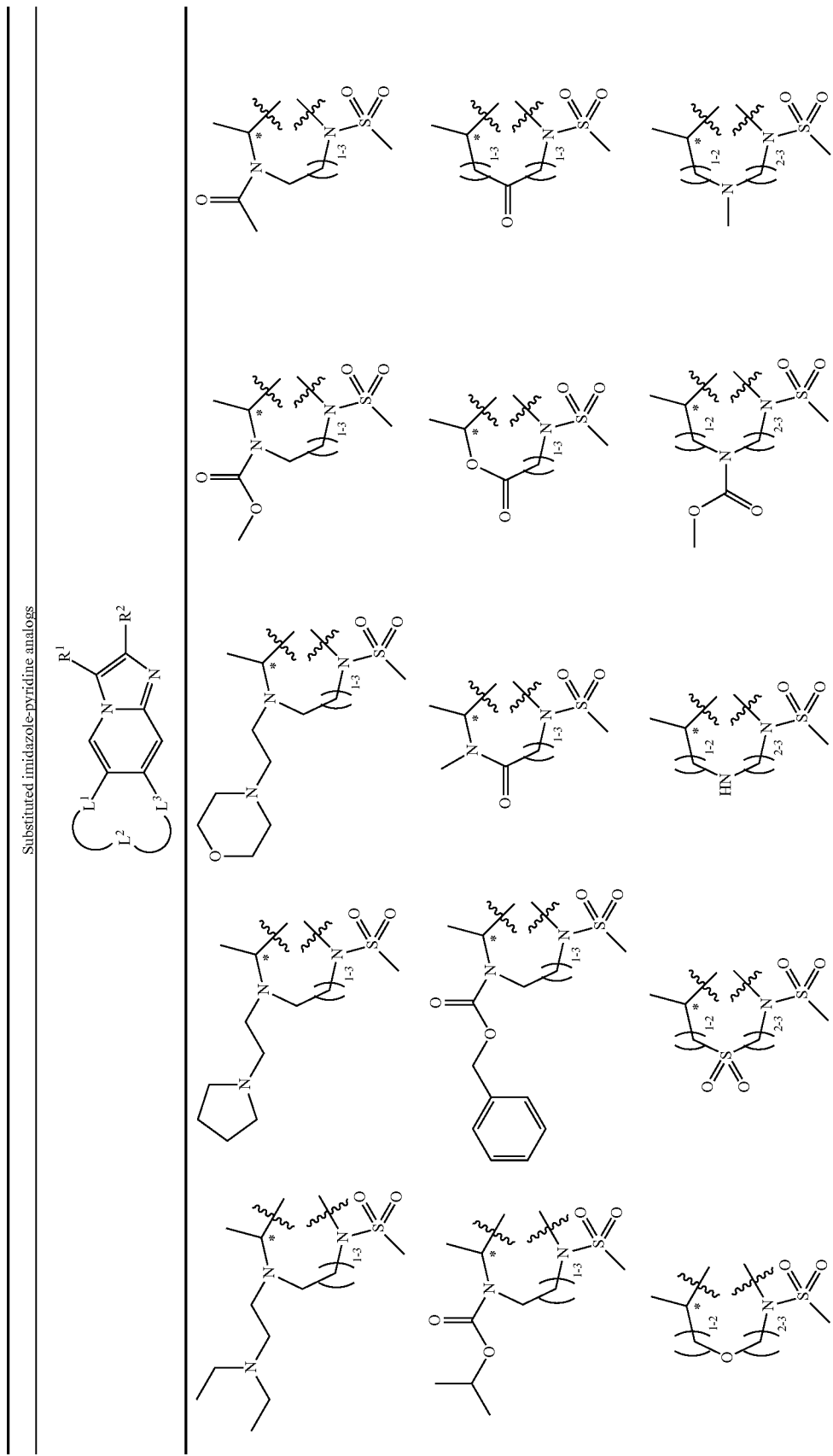

TABLE 4-continued
Substituted imidazole-pyridine analogs
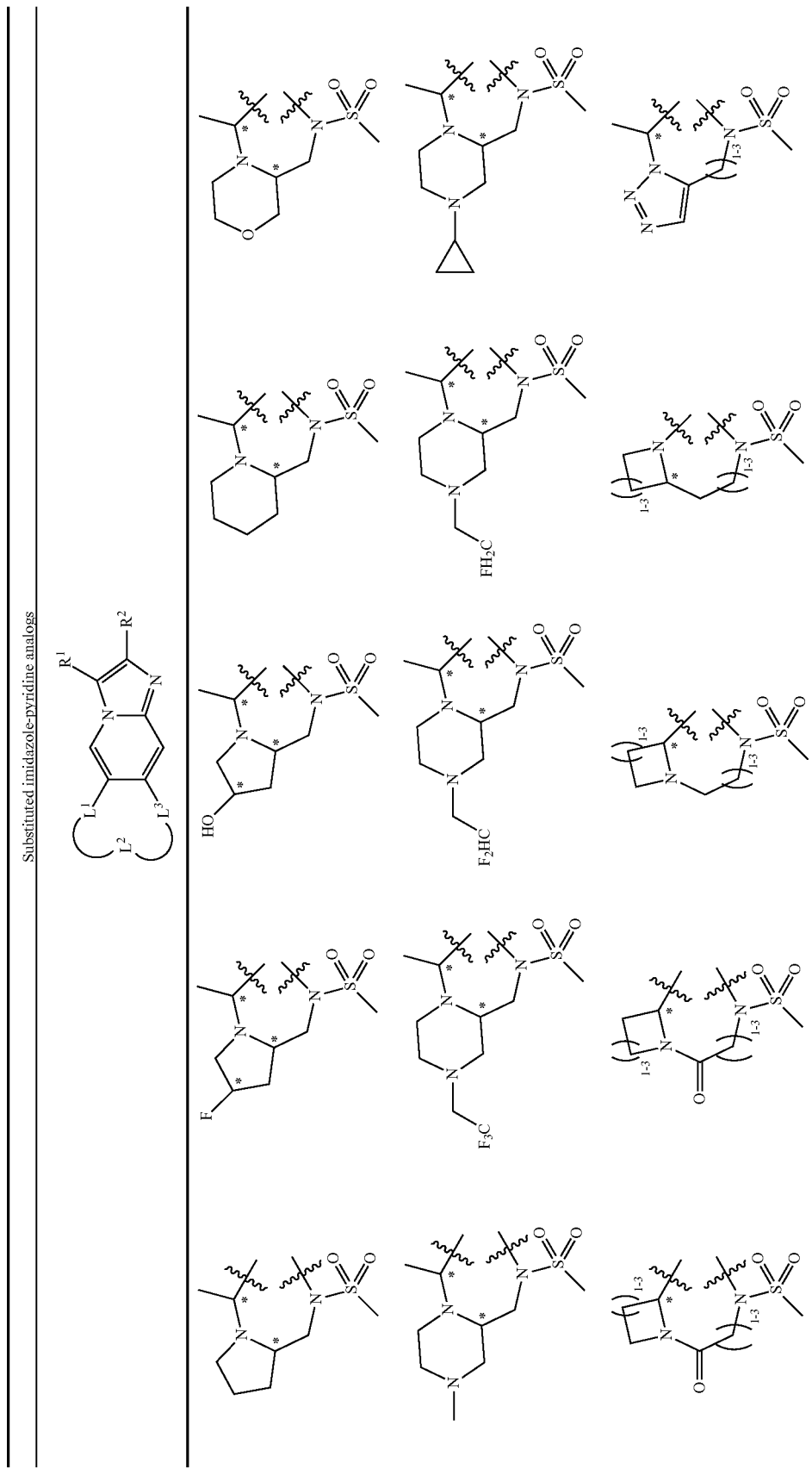

TABLE 4-continued
Substituted imidazole-pyridine analogs
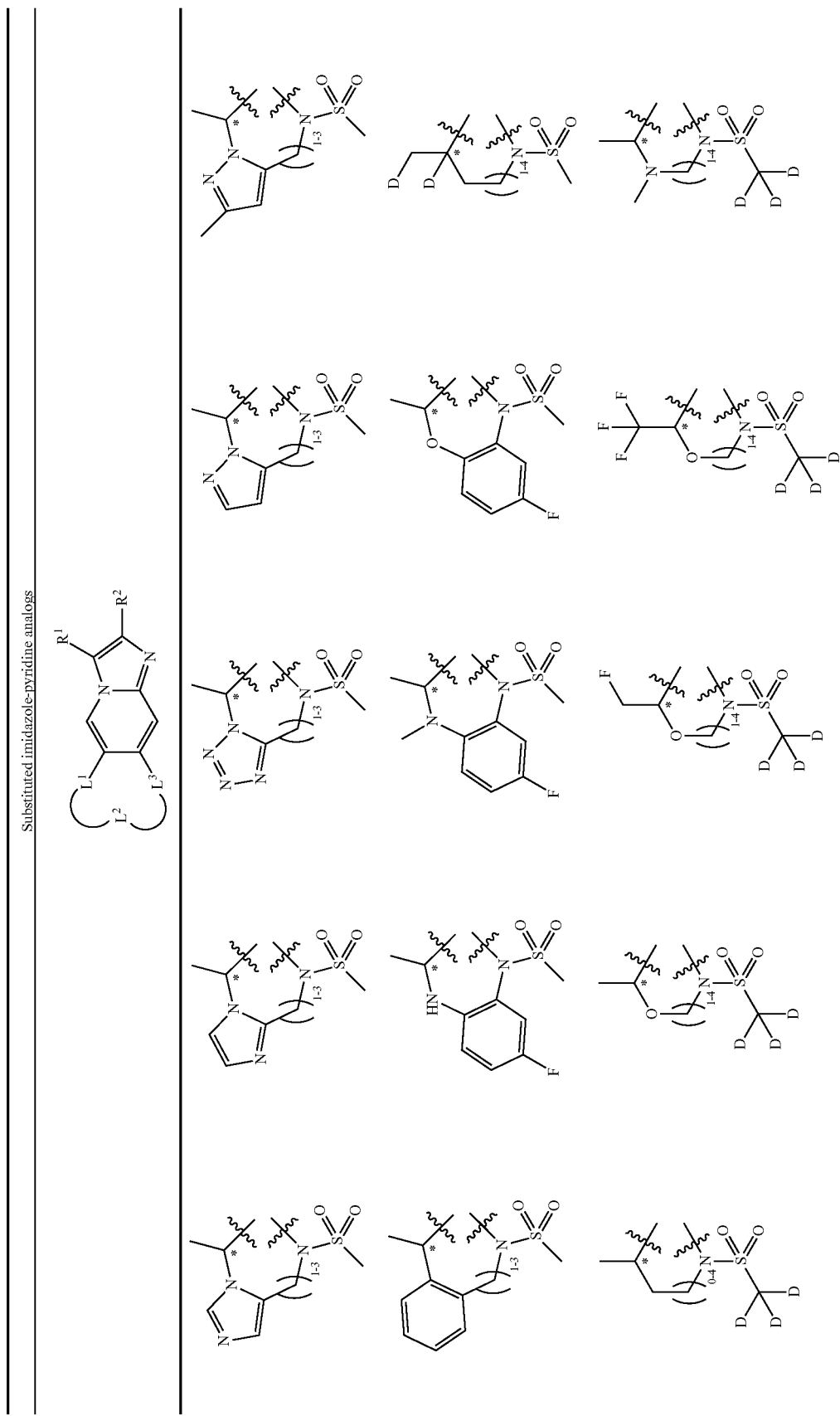

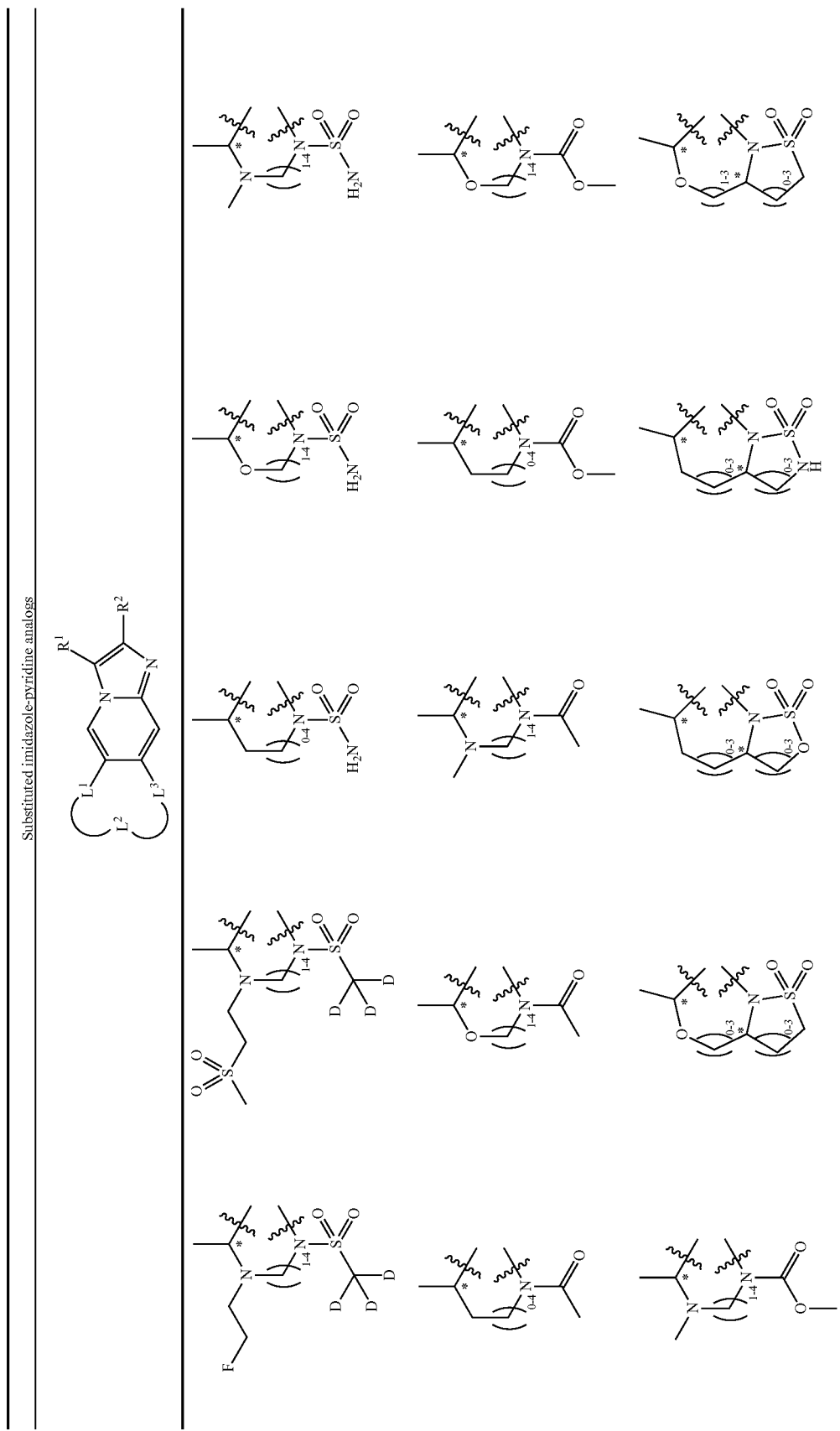

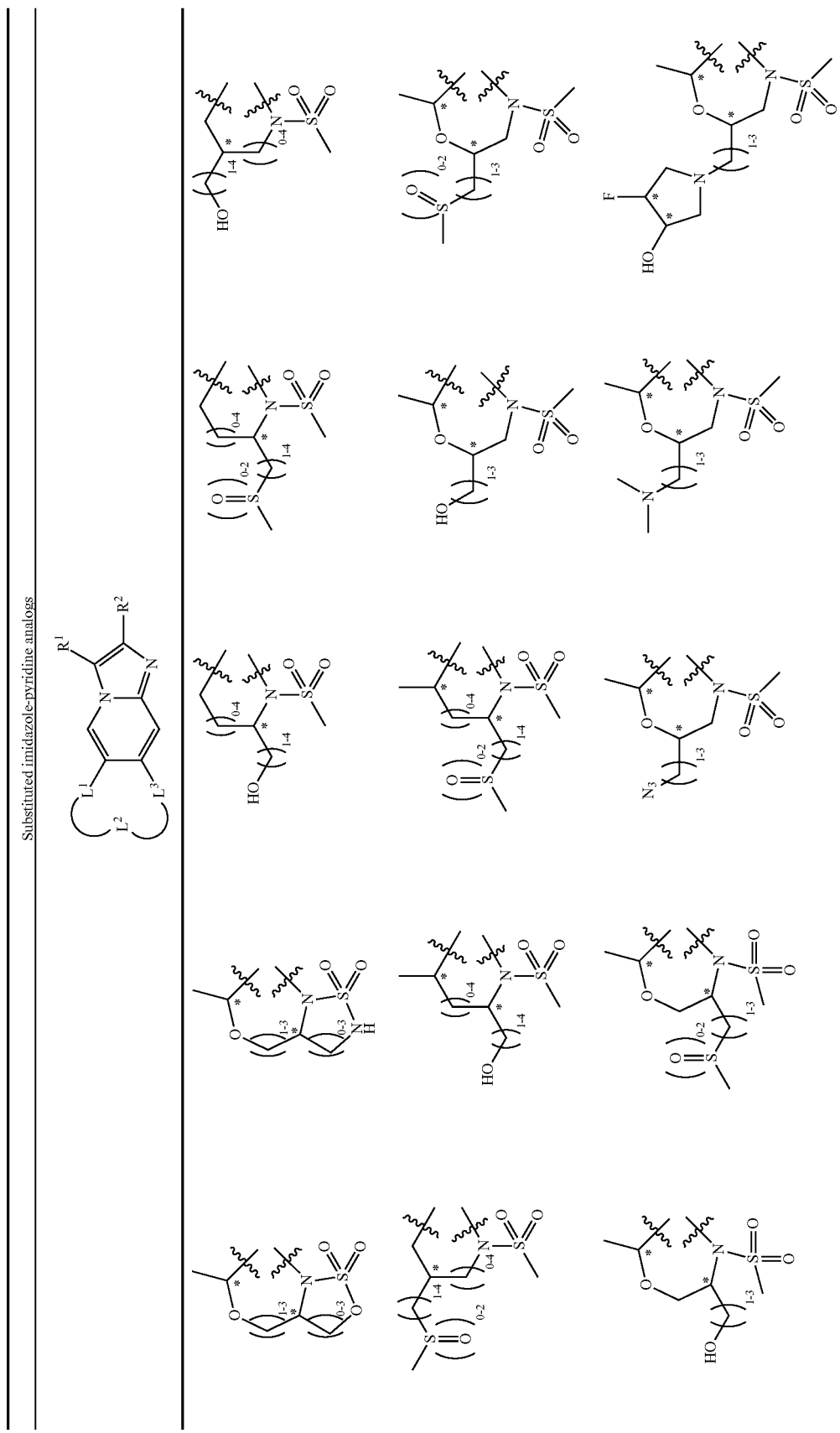

TABLE 4-continued
Substituted imidazole-pyridine analogs
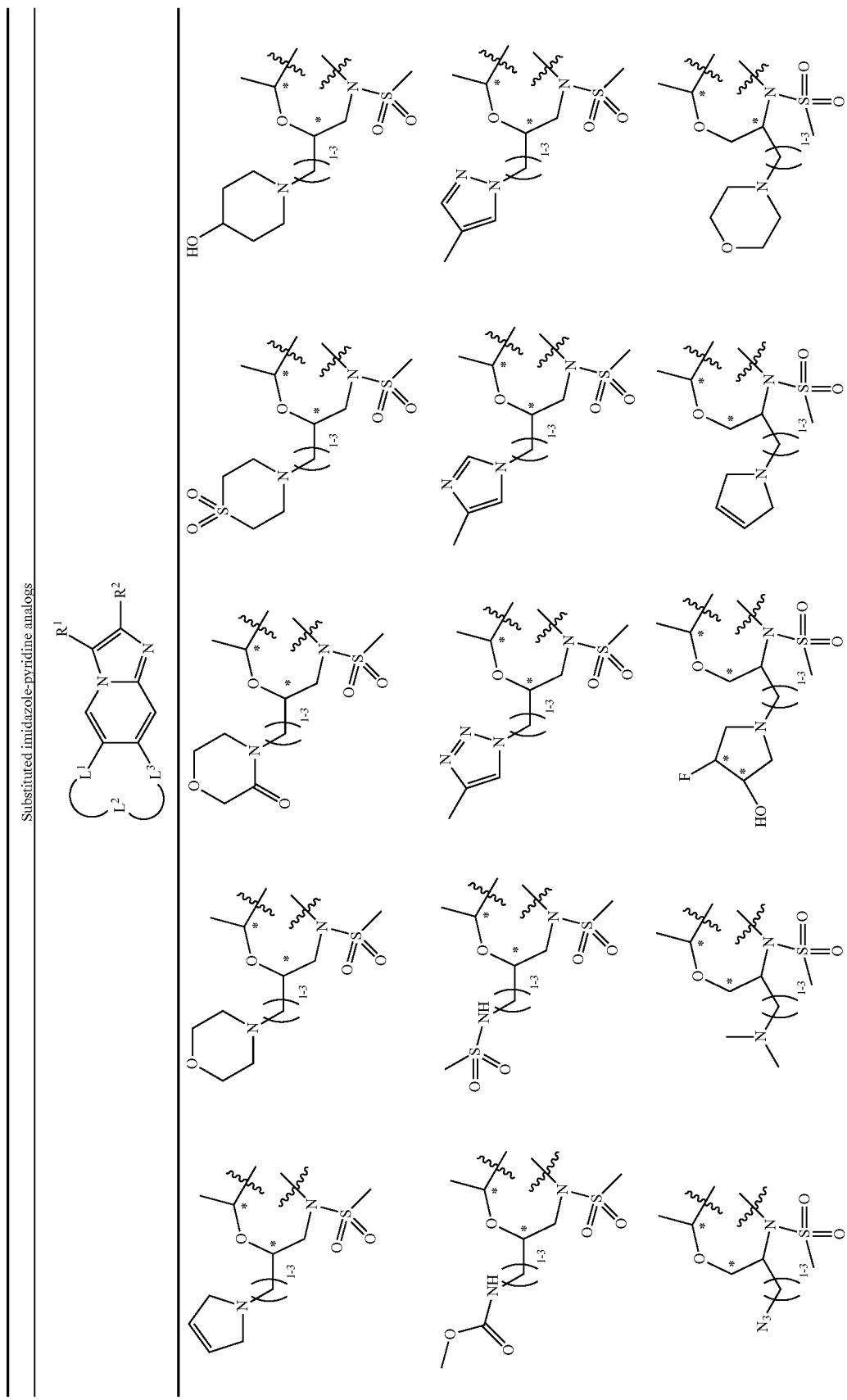

TABLE 4-continued
Substituted imidazole-pyridine analogs
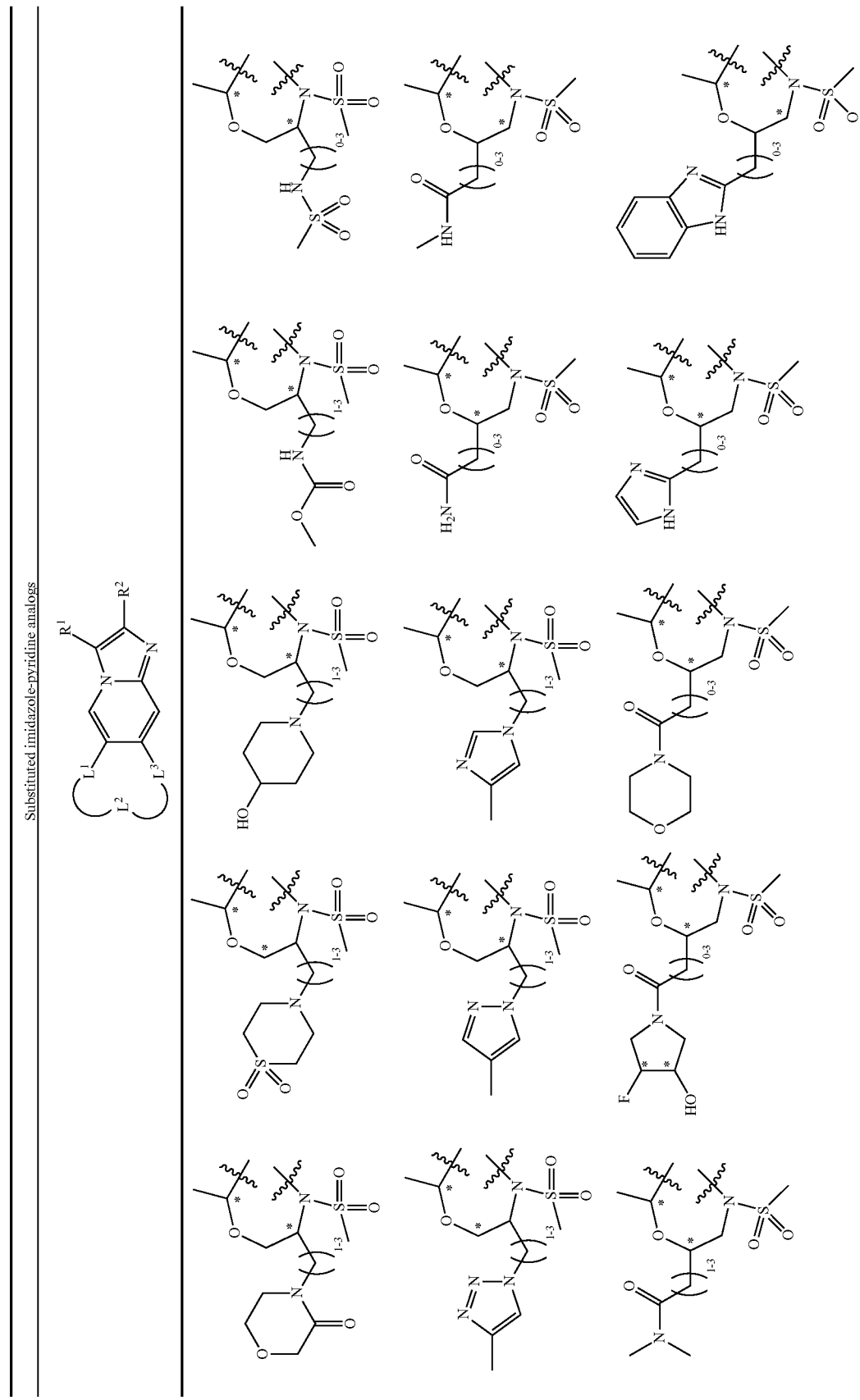

TABLE 4-continued
Substituted imidazole-pyridine analogs
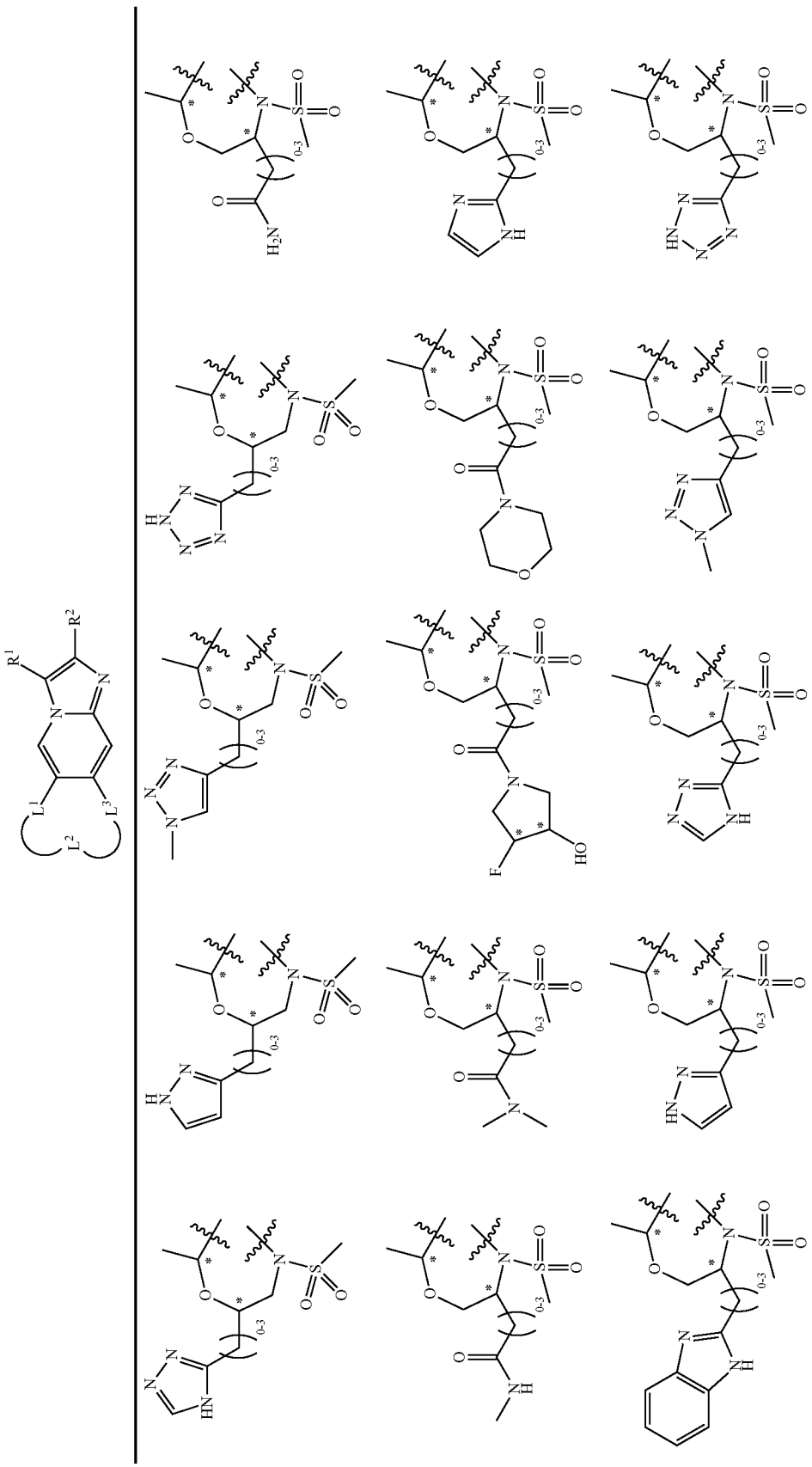

TABLE 4-continued
Substituted imidazole-pyridine analogs
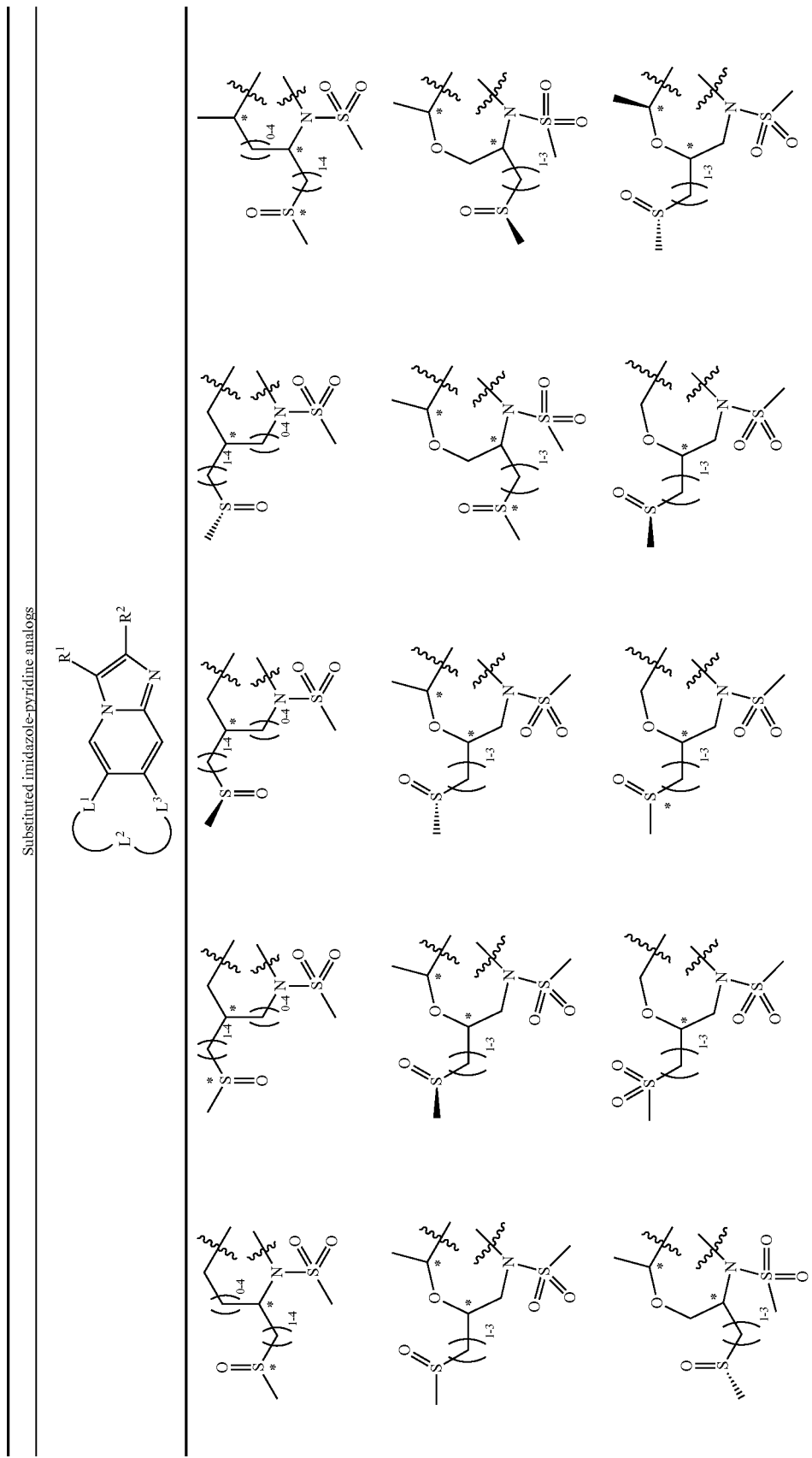

TABLE 4-continued
Substituted imidazole-pyridine analogs
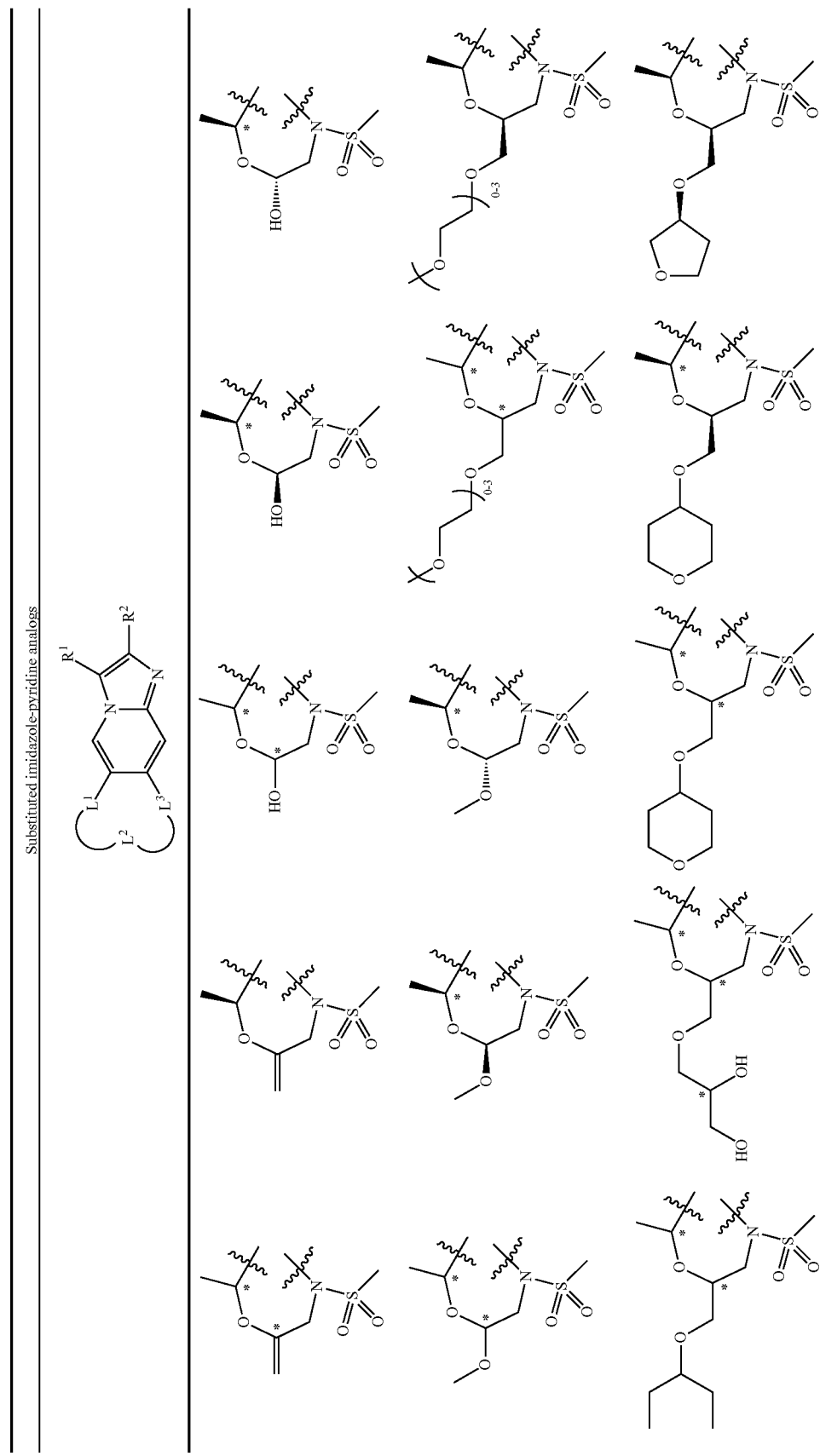

TABLE 4-continued
Substituted imidazole-pyridine analogs
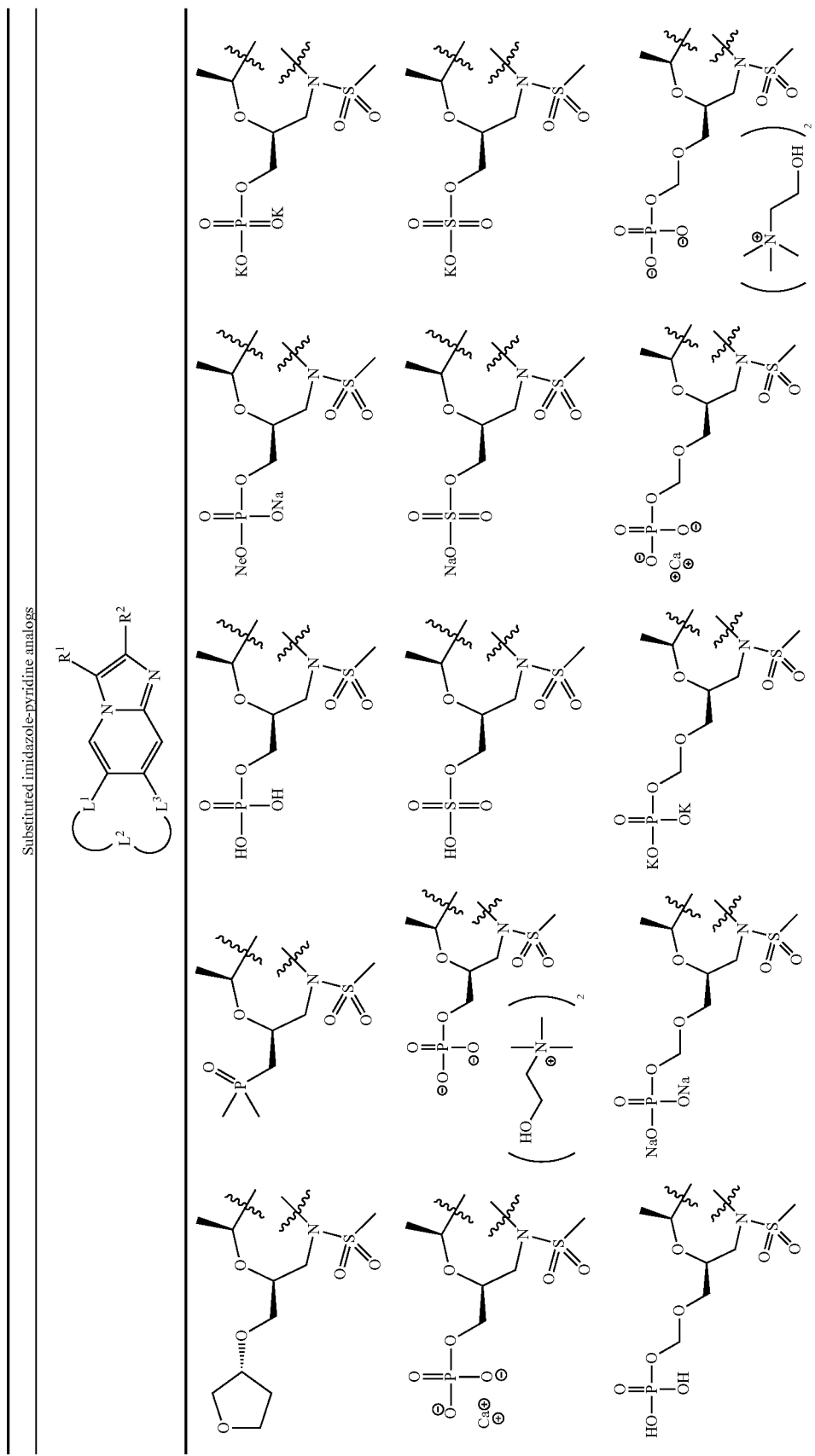

TABLE 4-continued
Substituted imidazole-pyridine analogs
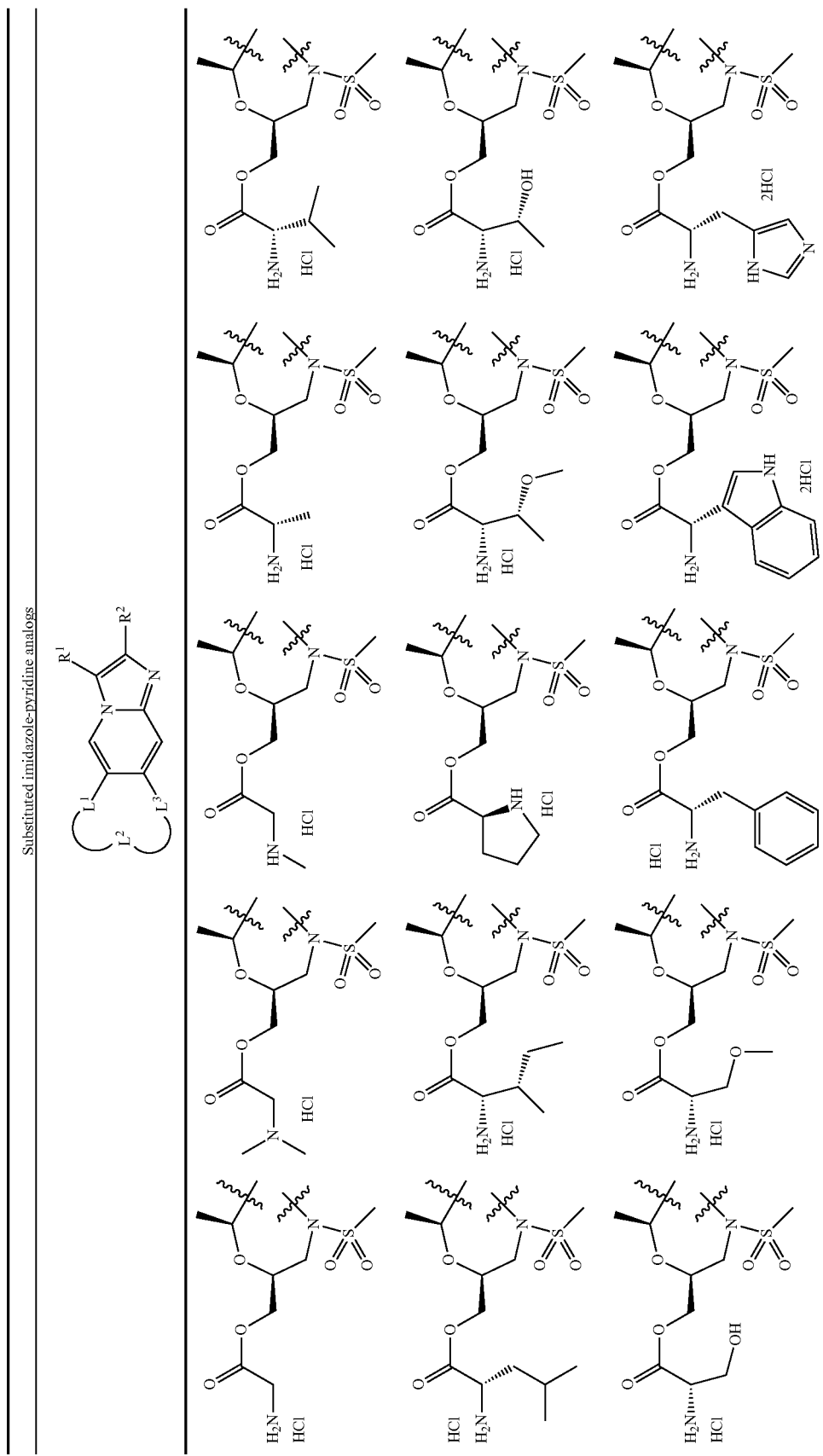

TABLE 4-continued
Substituted imidazole-pyridine analogs
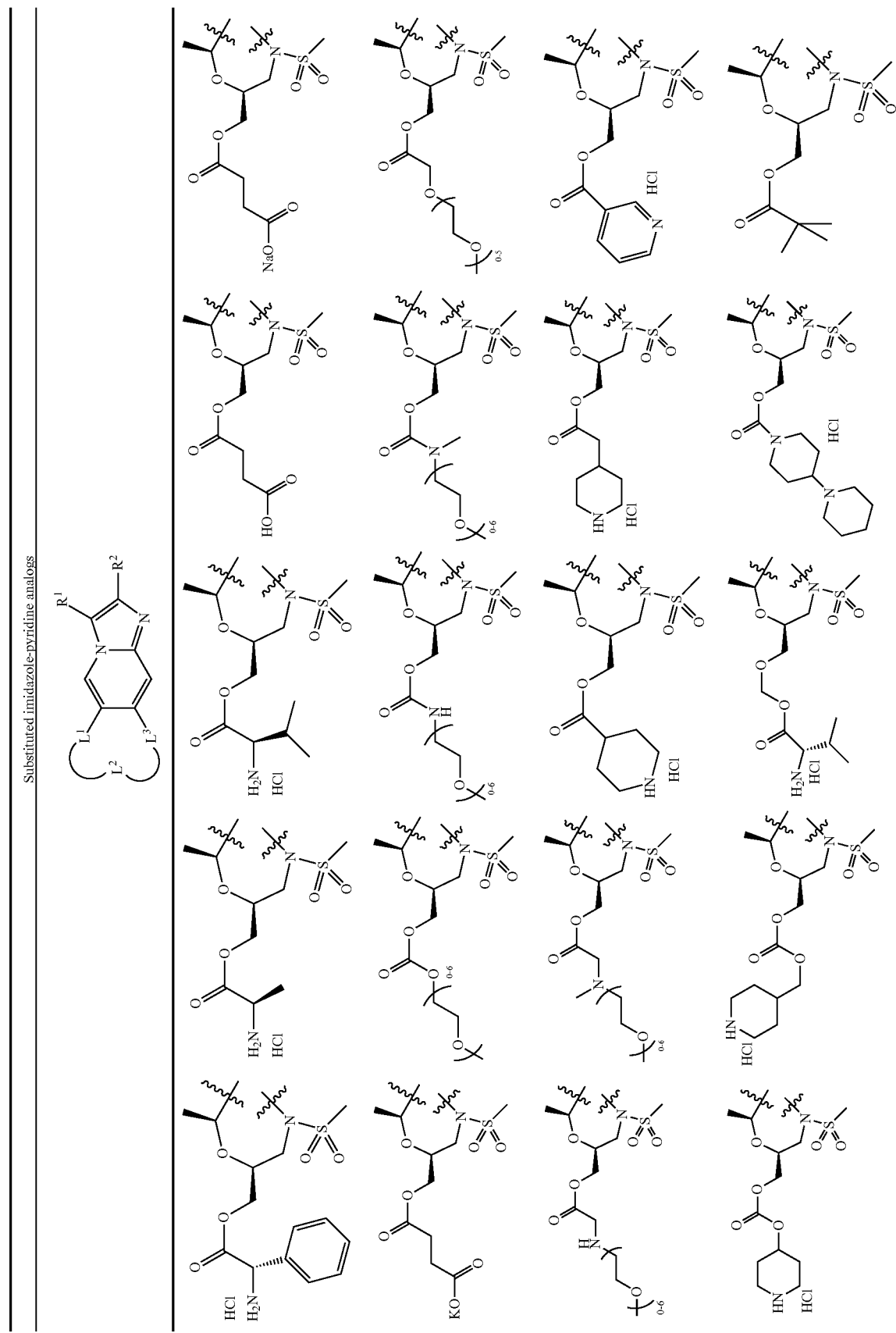

TABLE 4-continued
Substituted imidazole-pyridine analogs
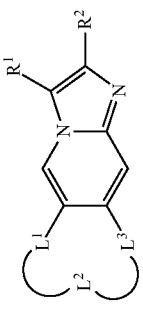
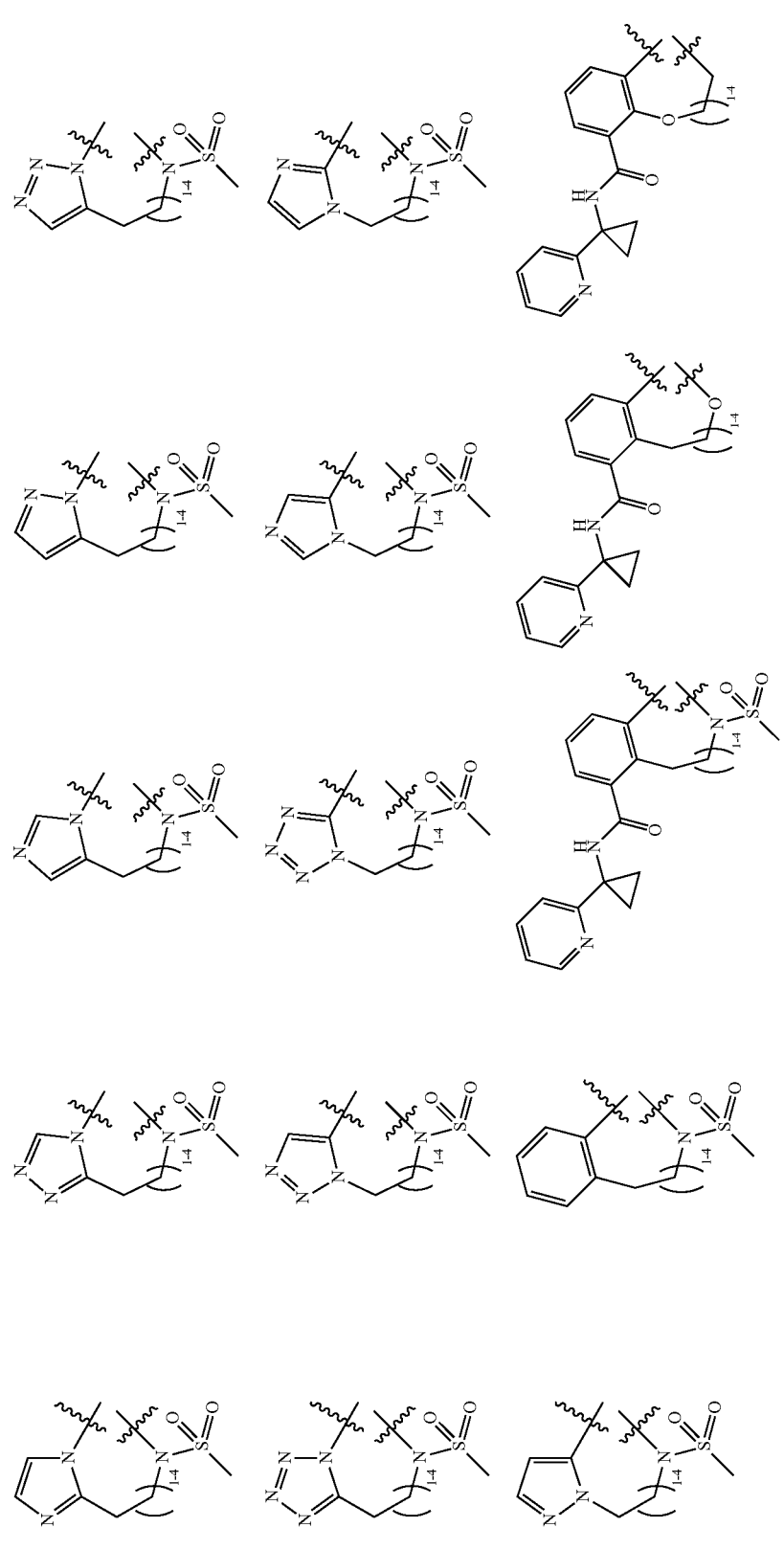

TABLE 4-continued
Substituted imidazole-pyridine analogs
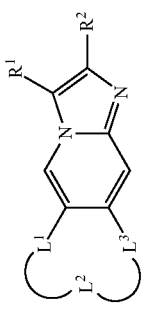
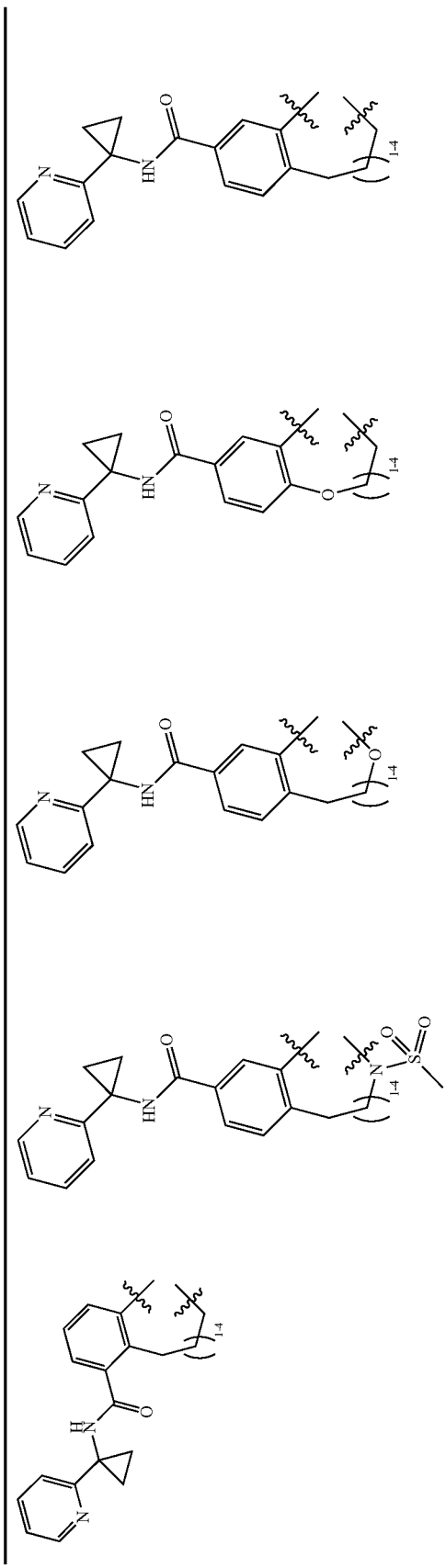

TABLE 5

Substituted indole analogs

TABLE 5-continued
Substituted indole analogs
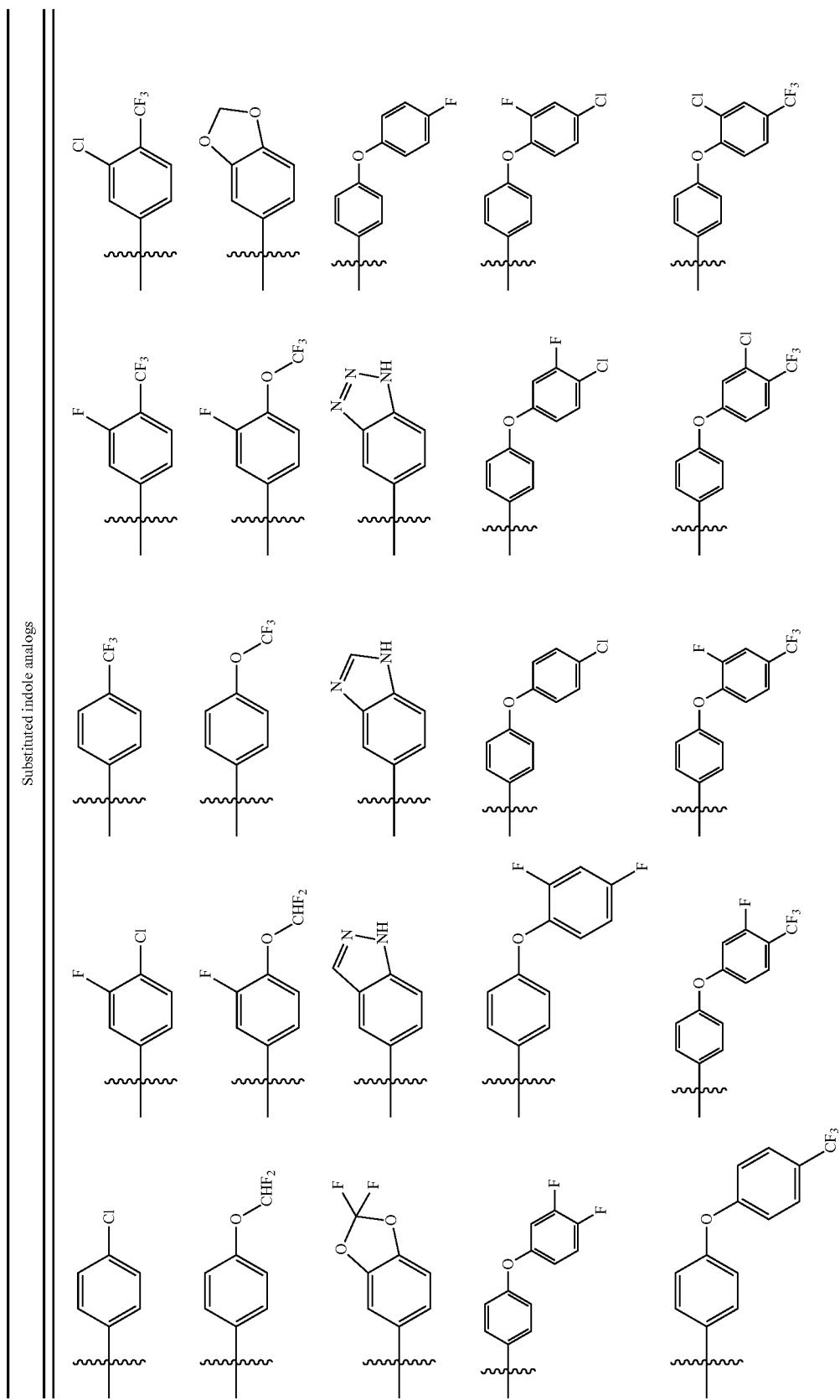

TABLE 5-continued
Substituted indole analogs
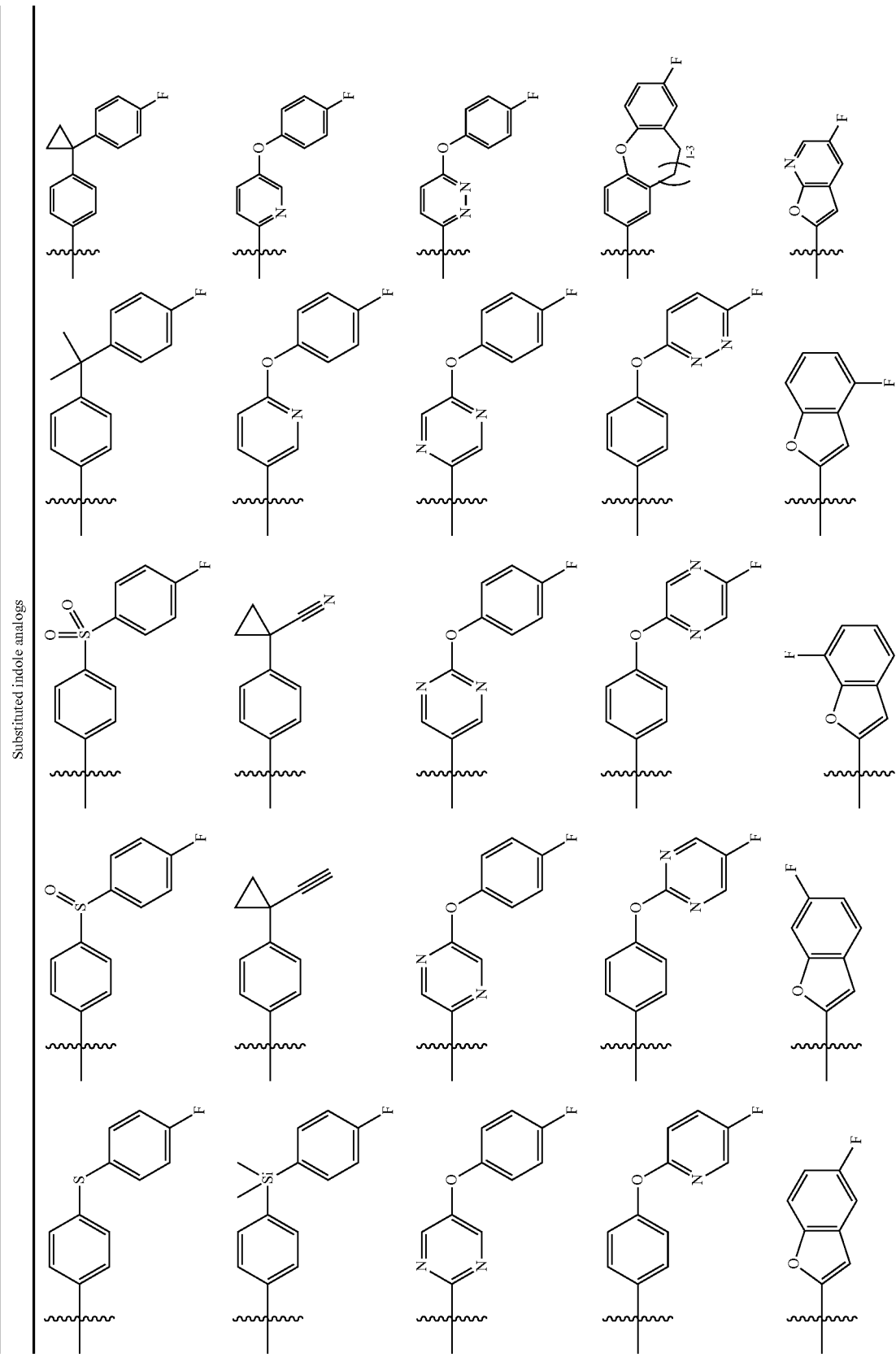

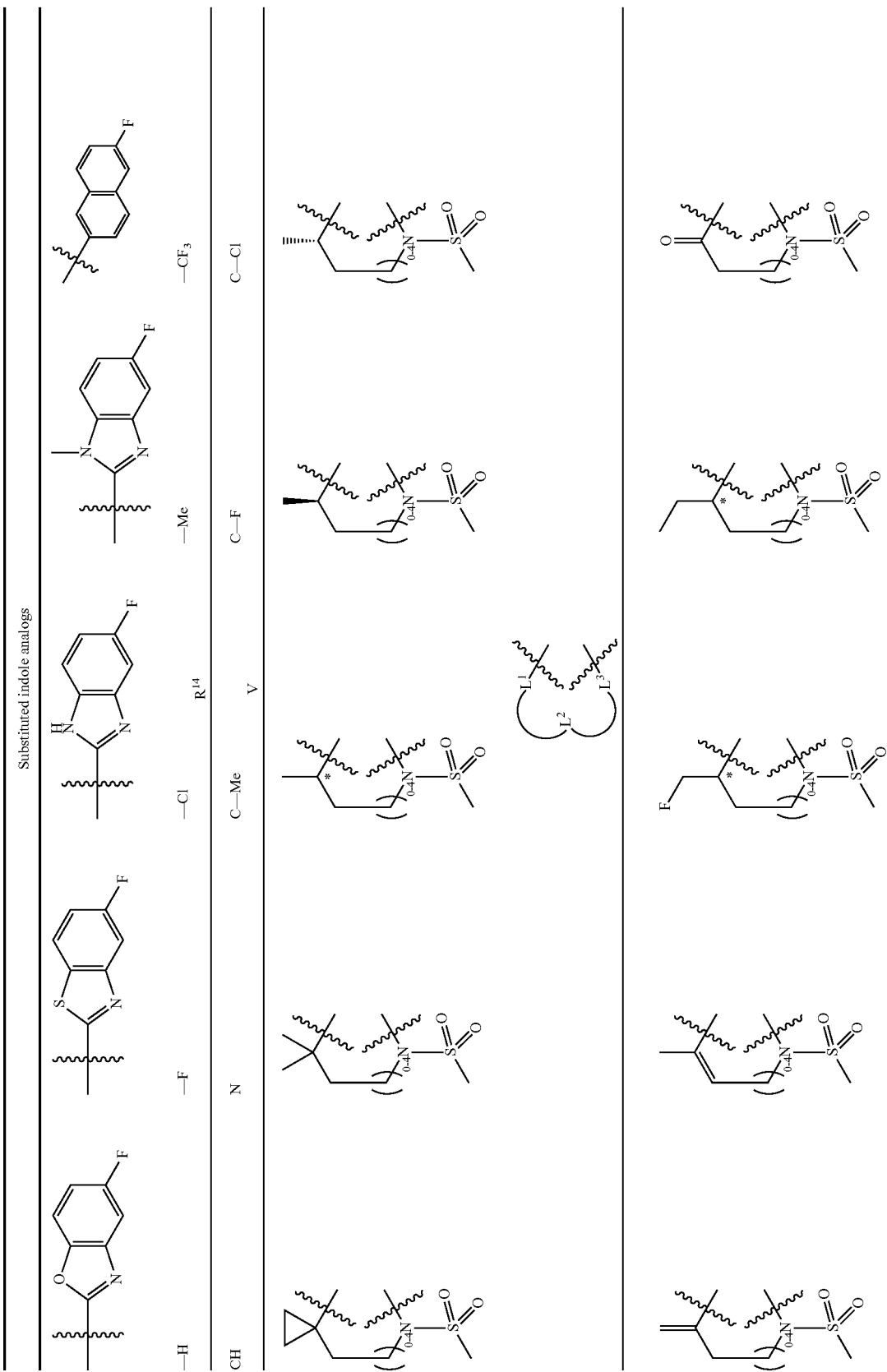

TABLE 5-continued
Substituted indole analogs
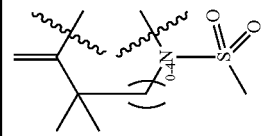 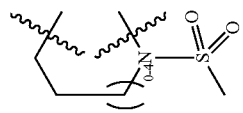 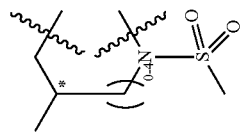 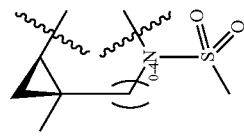
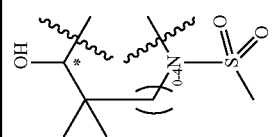 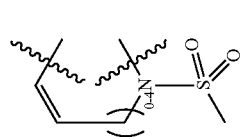 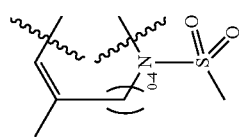 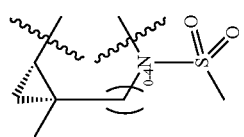
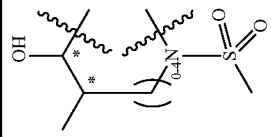 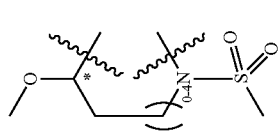 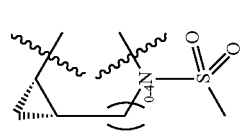 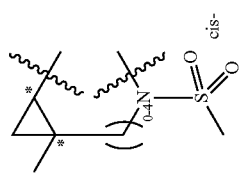
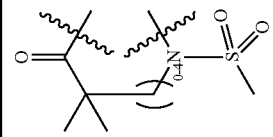 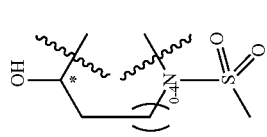 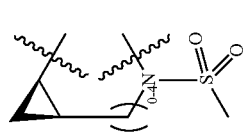 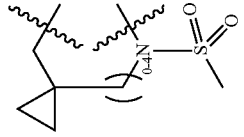
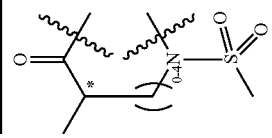 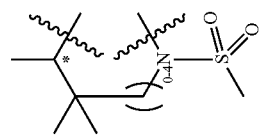 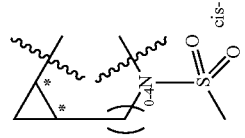 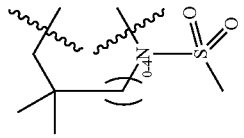

TABLE 5-continued
Substituted indole analogs
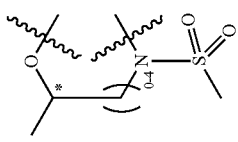 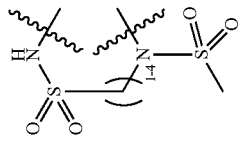 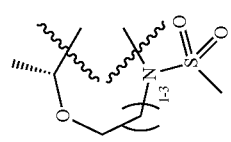
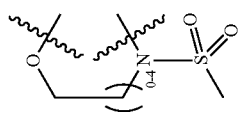 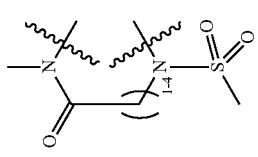 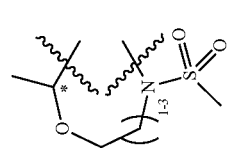
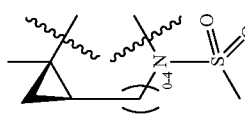 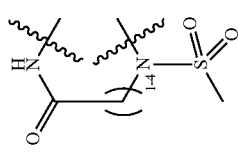 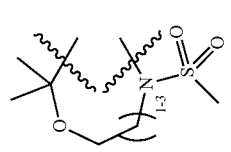
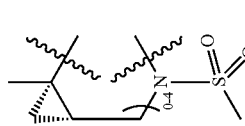 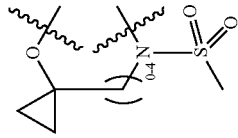 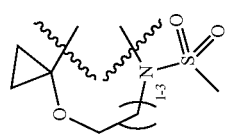
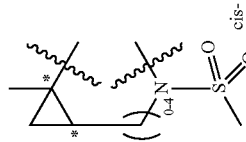 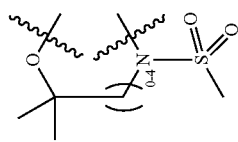 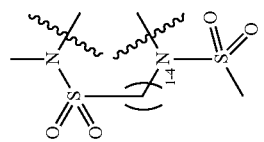

TABLE 5-continued
Substituted indole analogs
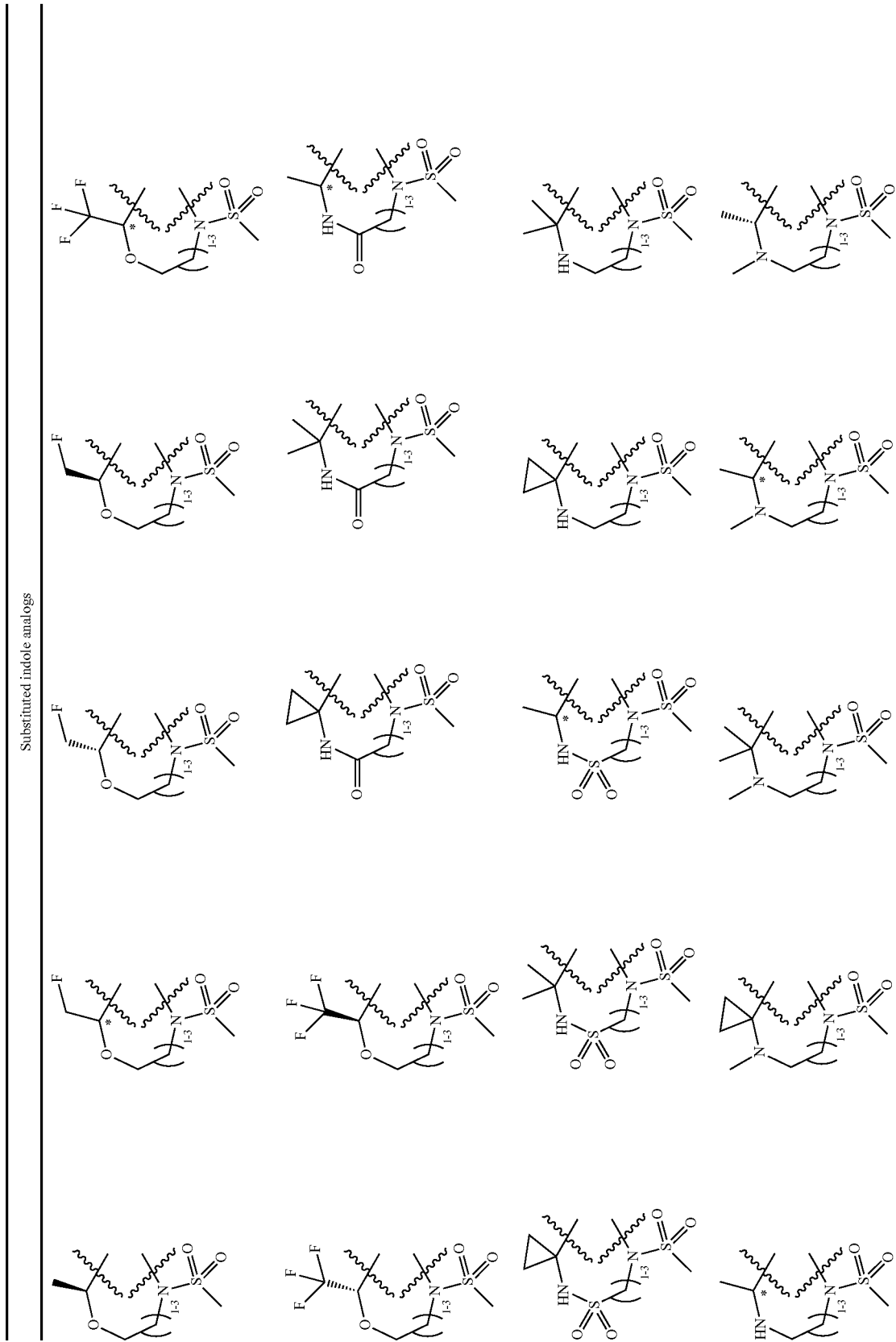

TABLE 5-continued
Substituted indole analogs
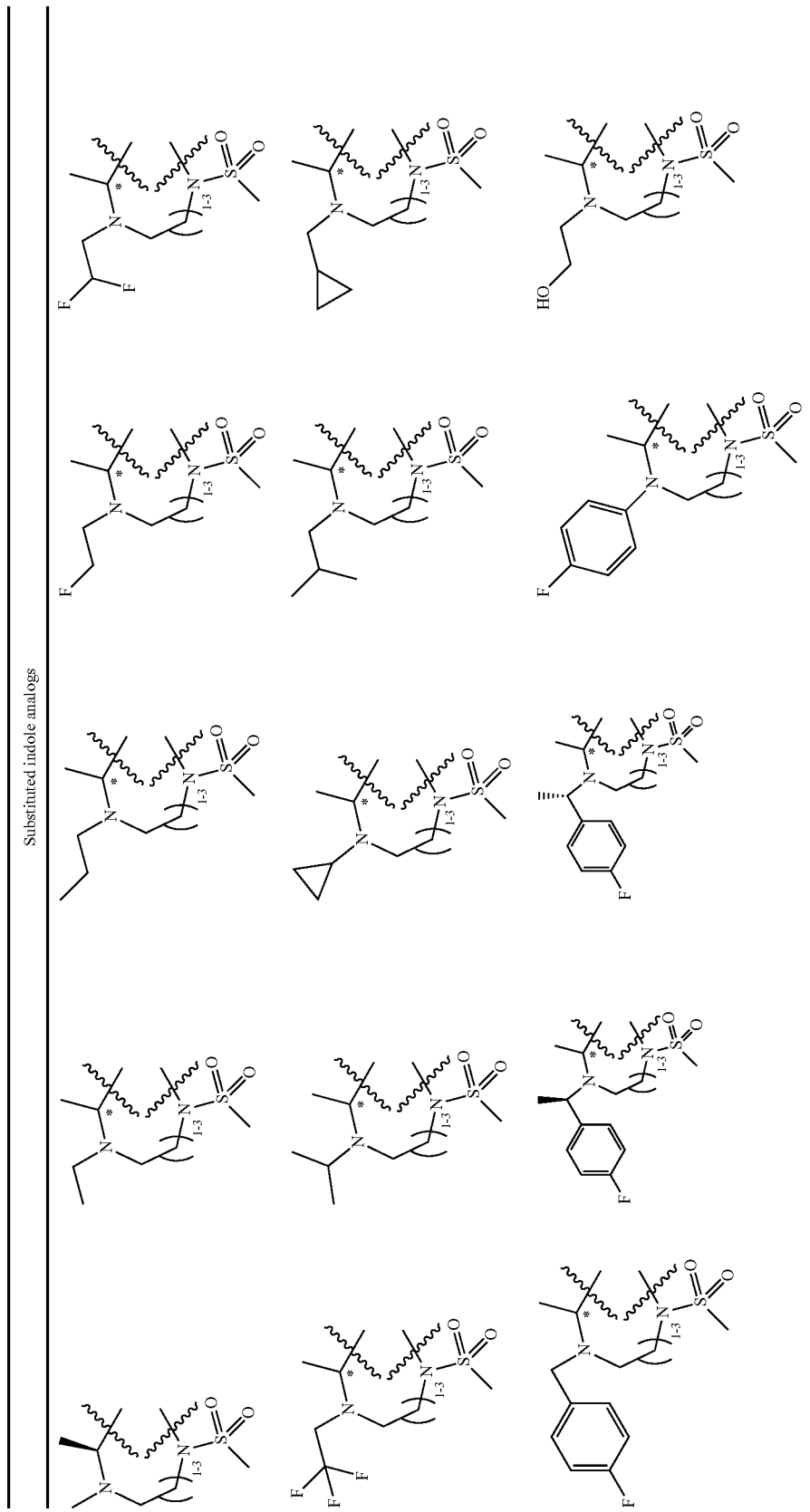

TABLE 5-continued
Substituted indole analogs
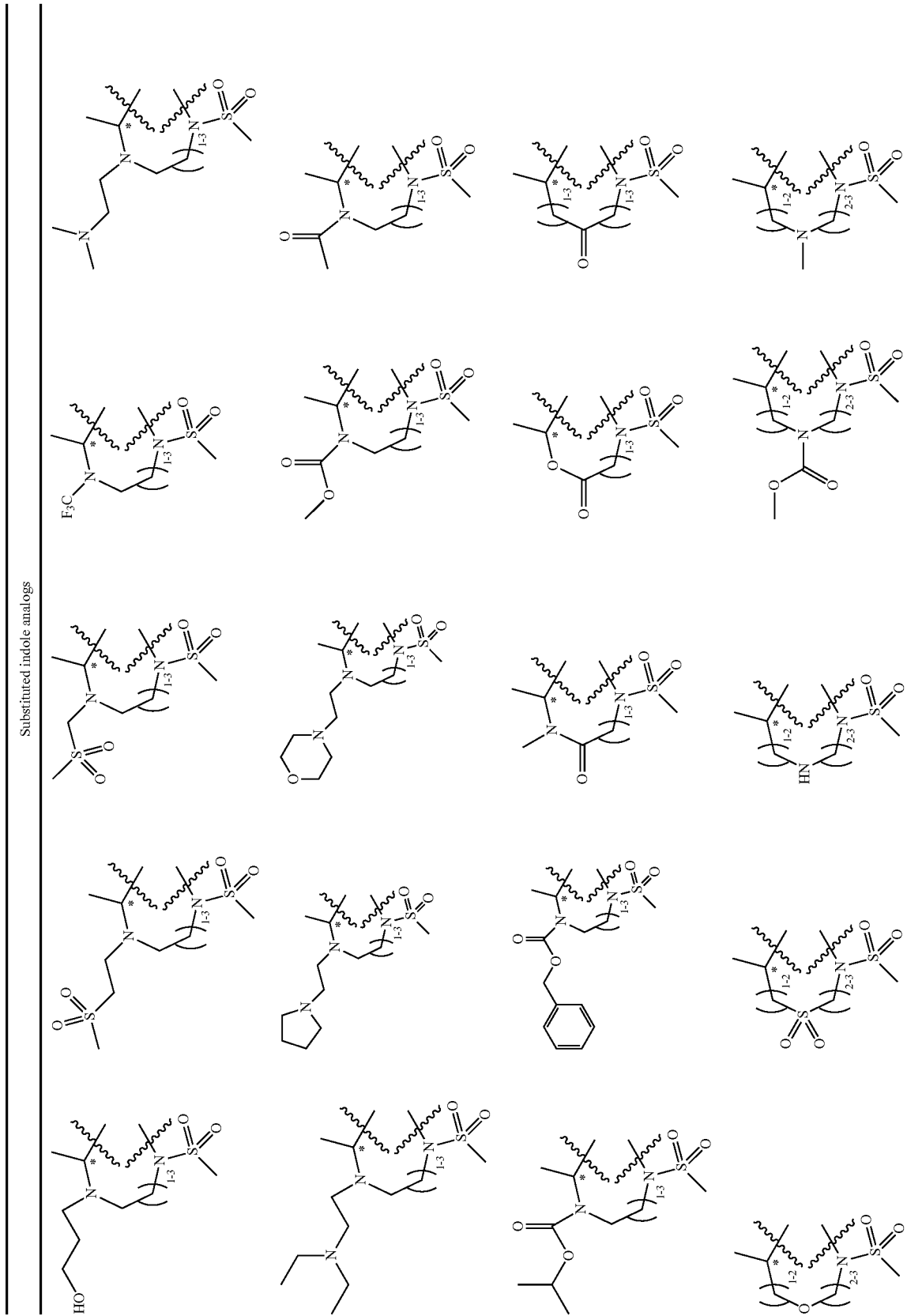

TABLE 5-continued
Substituted indole analogs
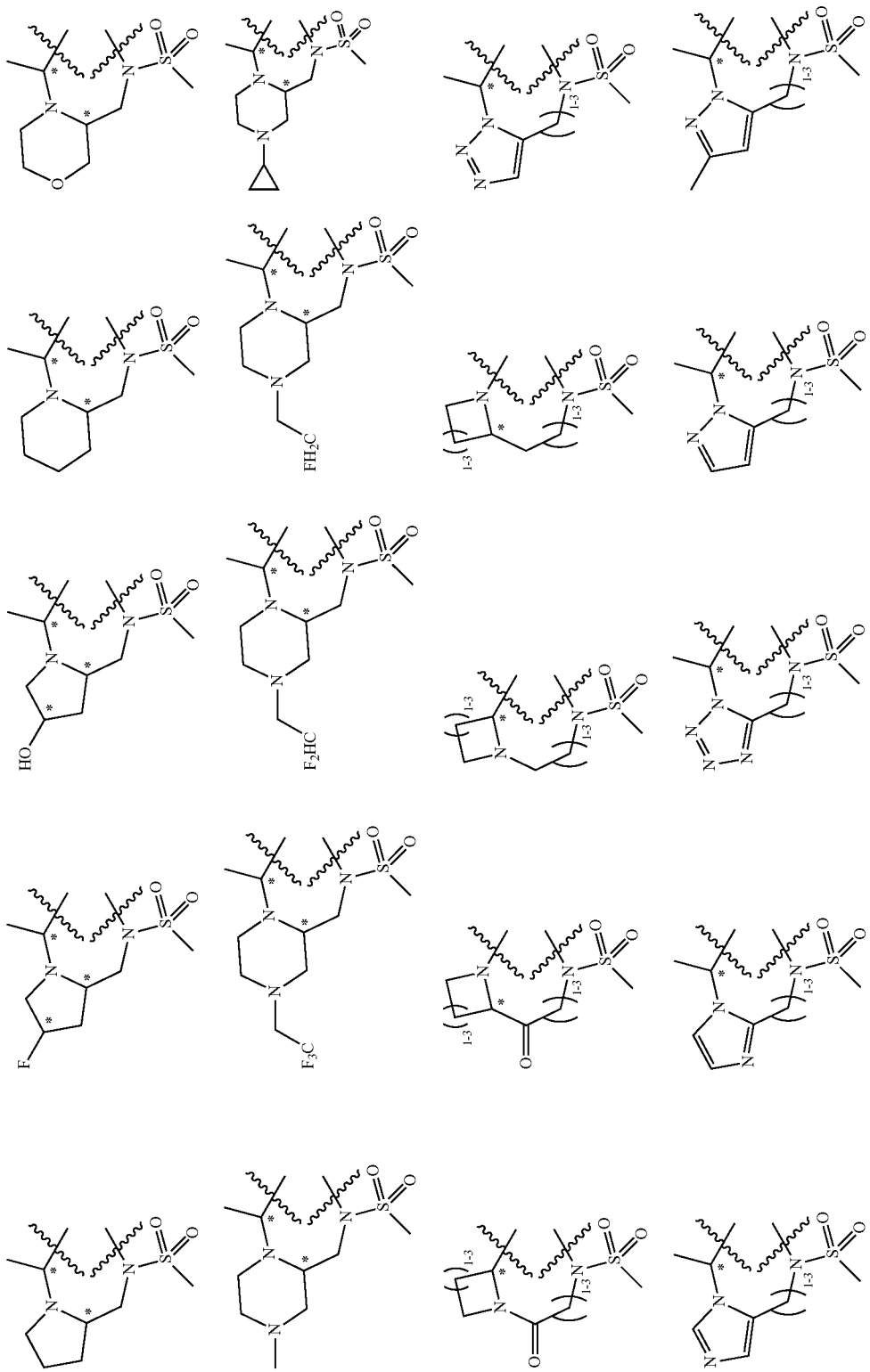

TABLE 5-continued
Substituted indole analogs
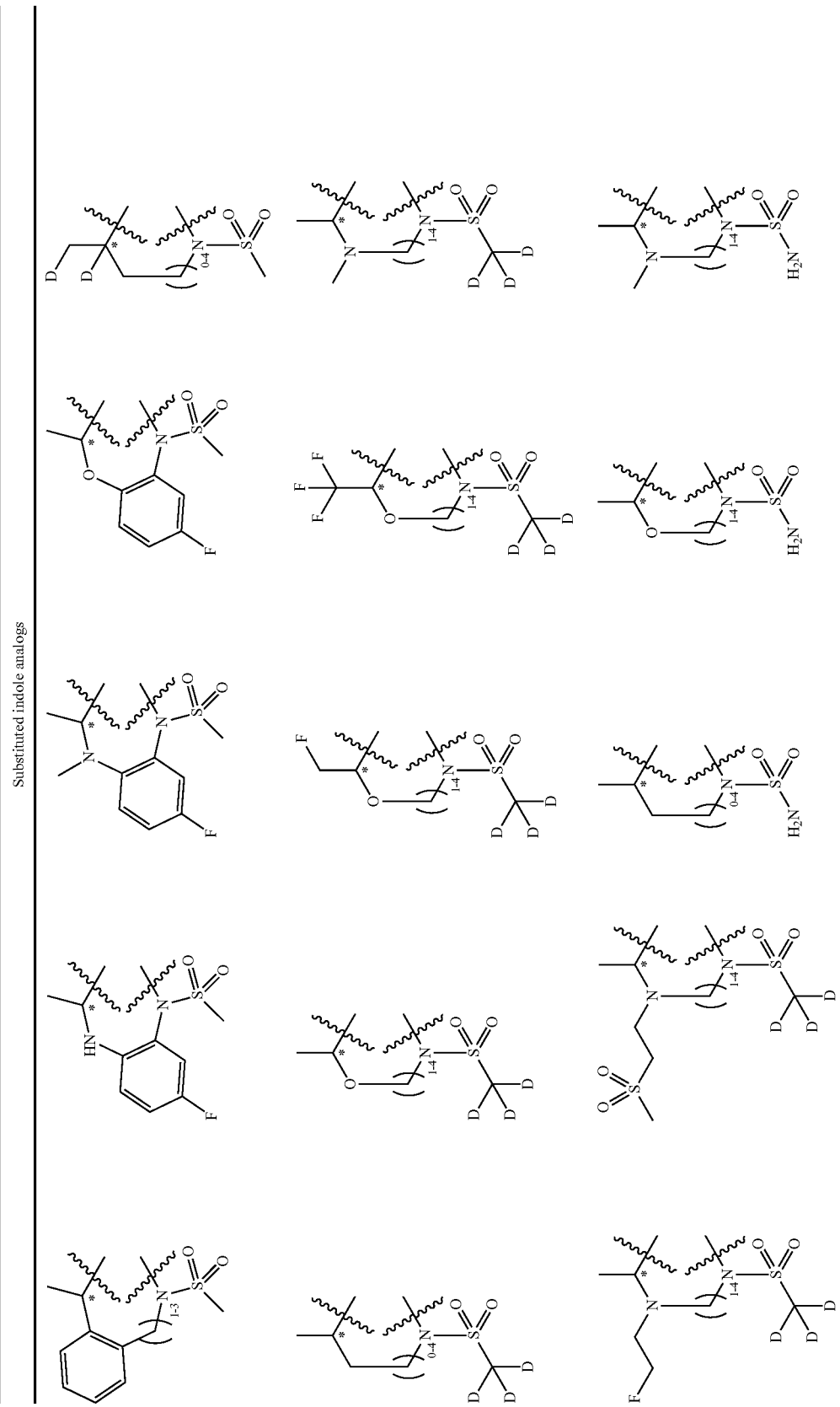

TABLE 5-continued
Substituted indole analogs
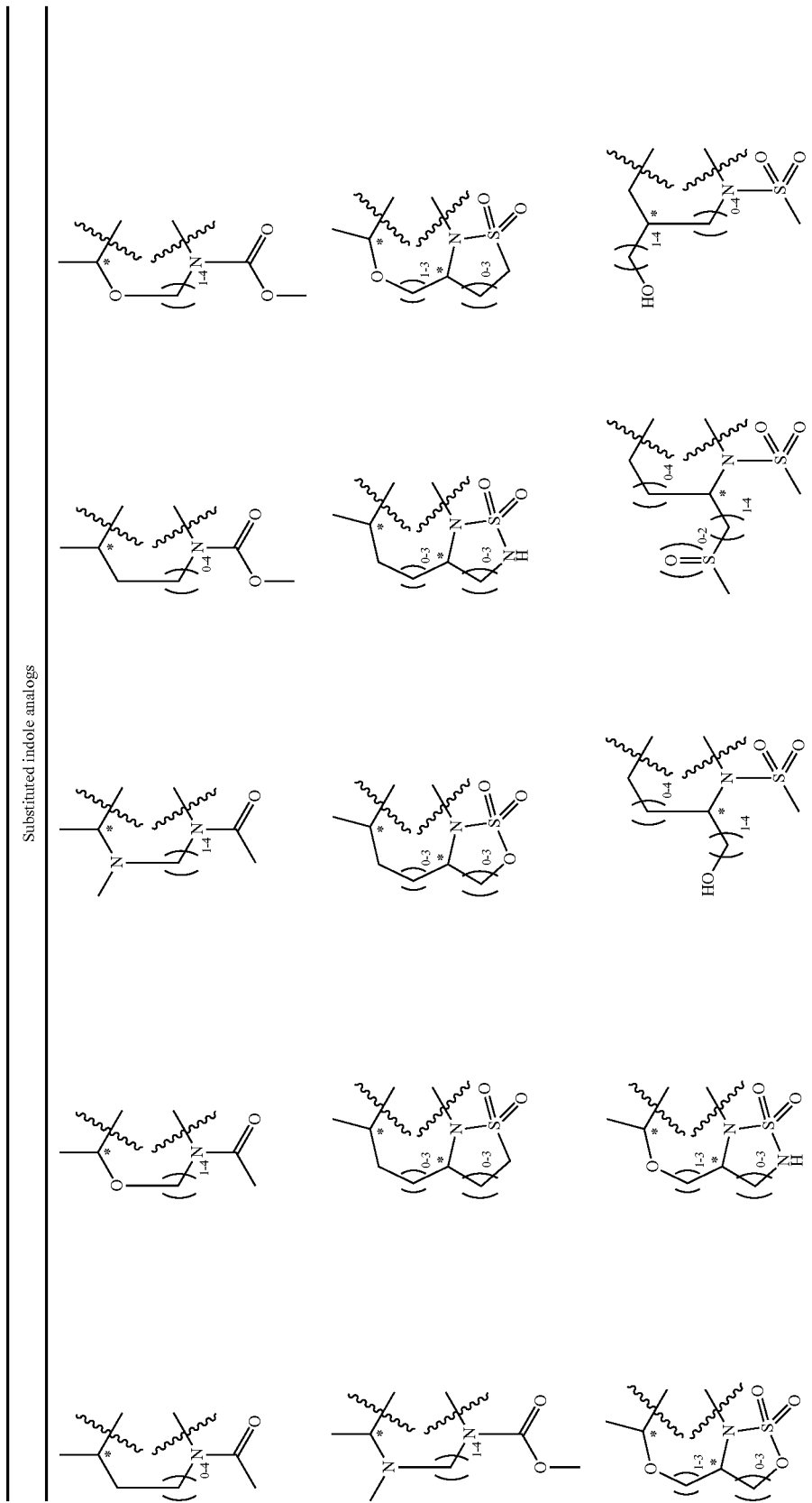

TABLE 5-continued
Substituted indole analogs
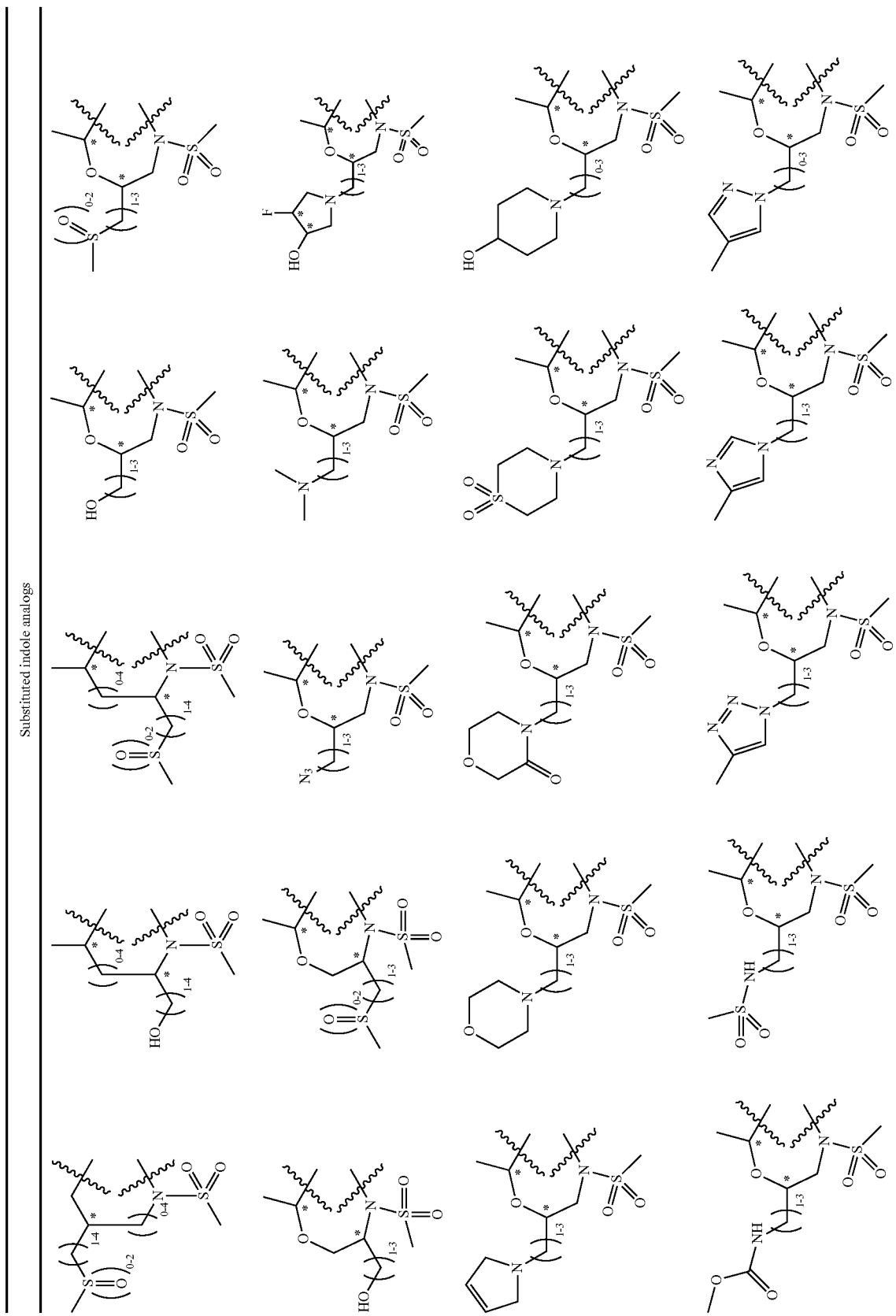

TABLE 5-continued
Substituted indole analogs
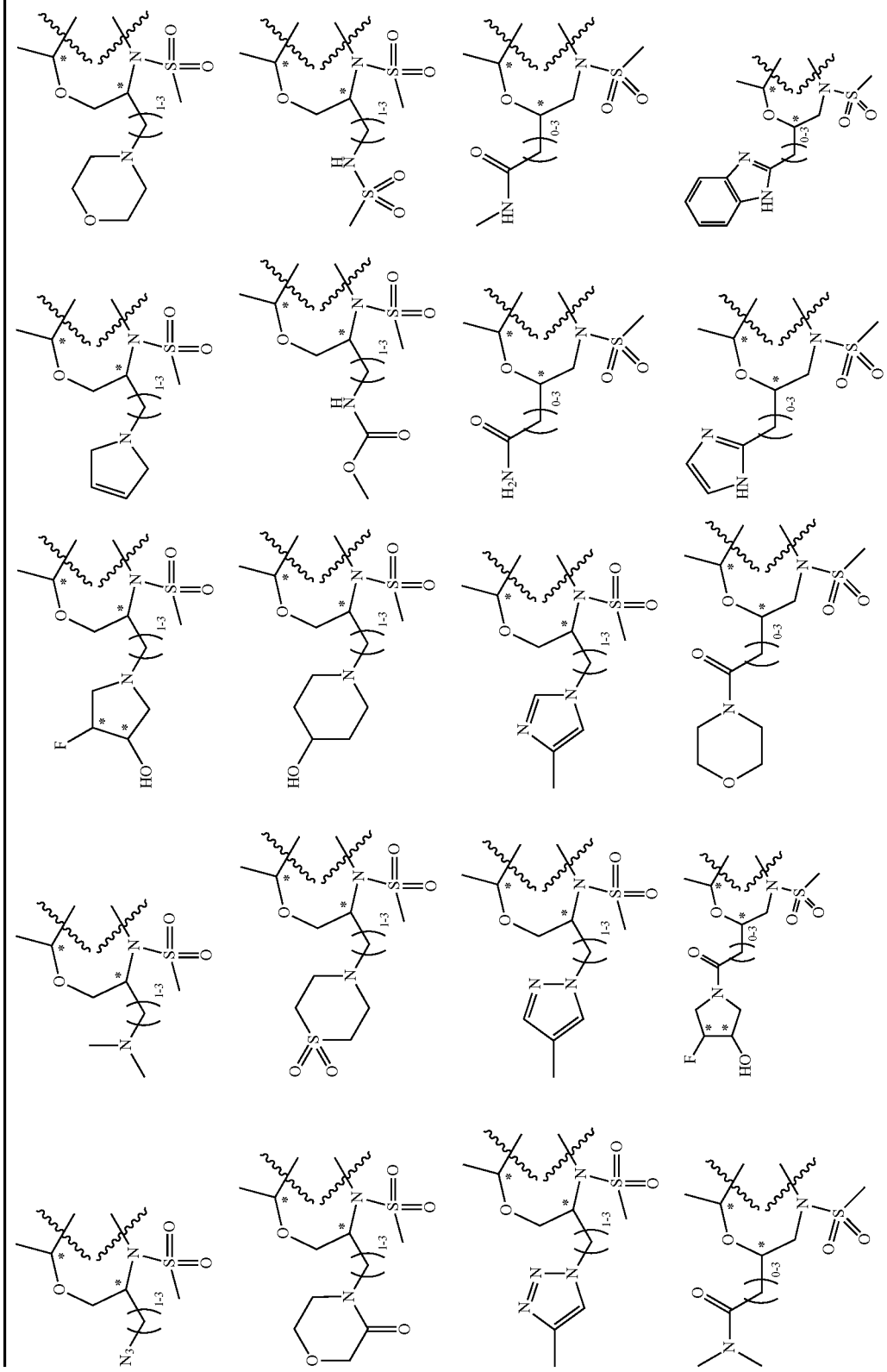

TABLE 5-continued
Substituted indole analogs
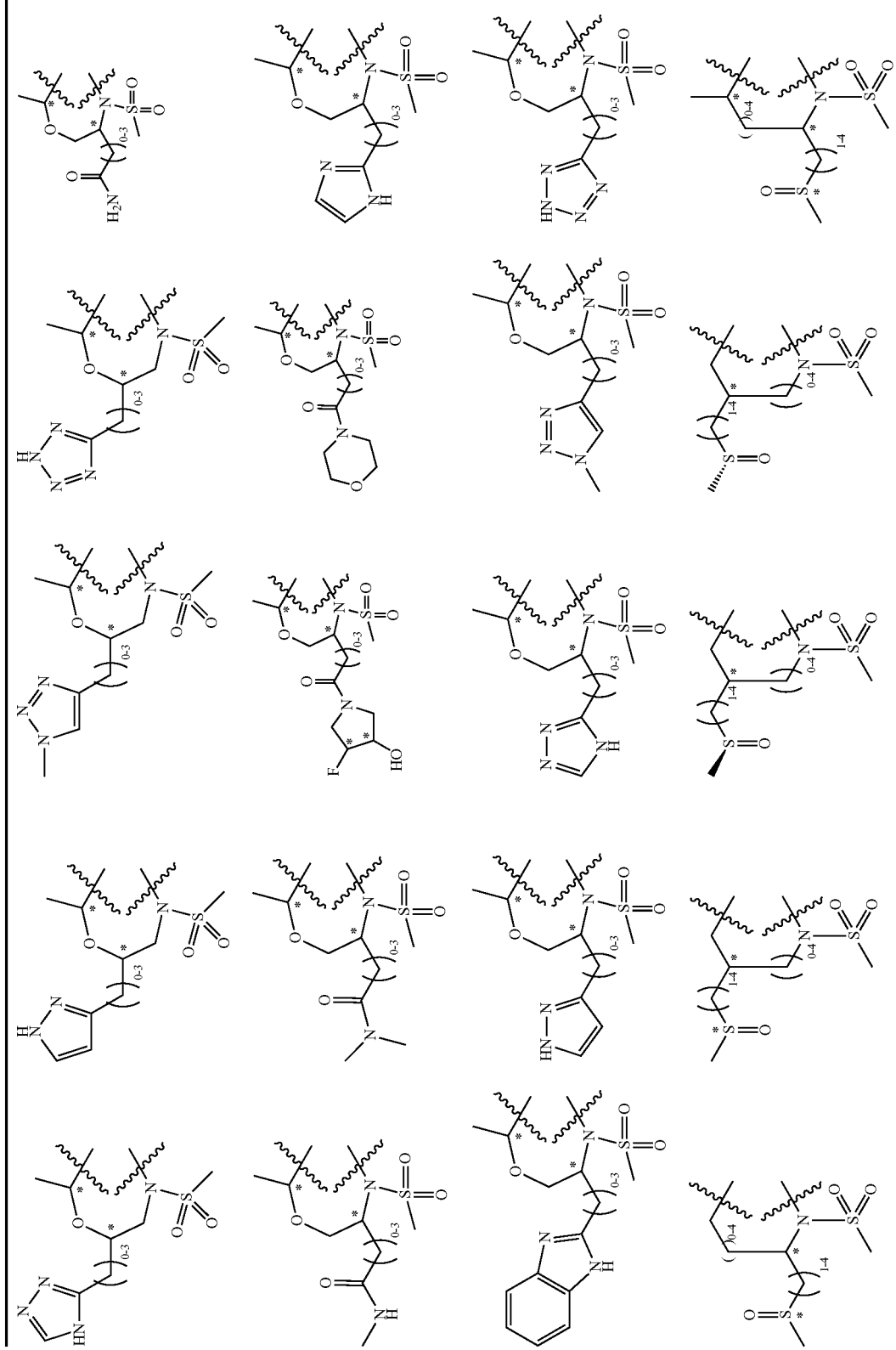

TABLE 5-continued
Substituted indole analogs
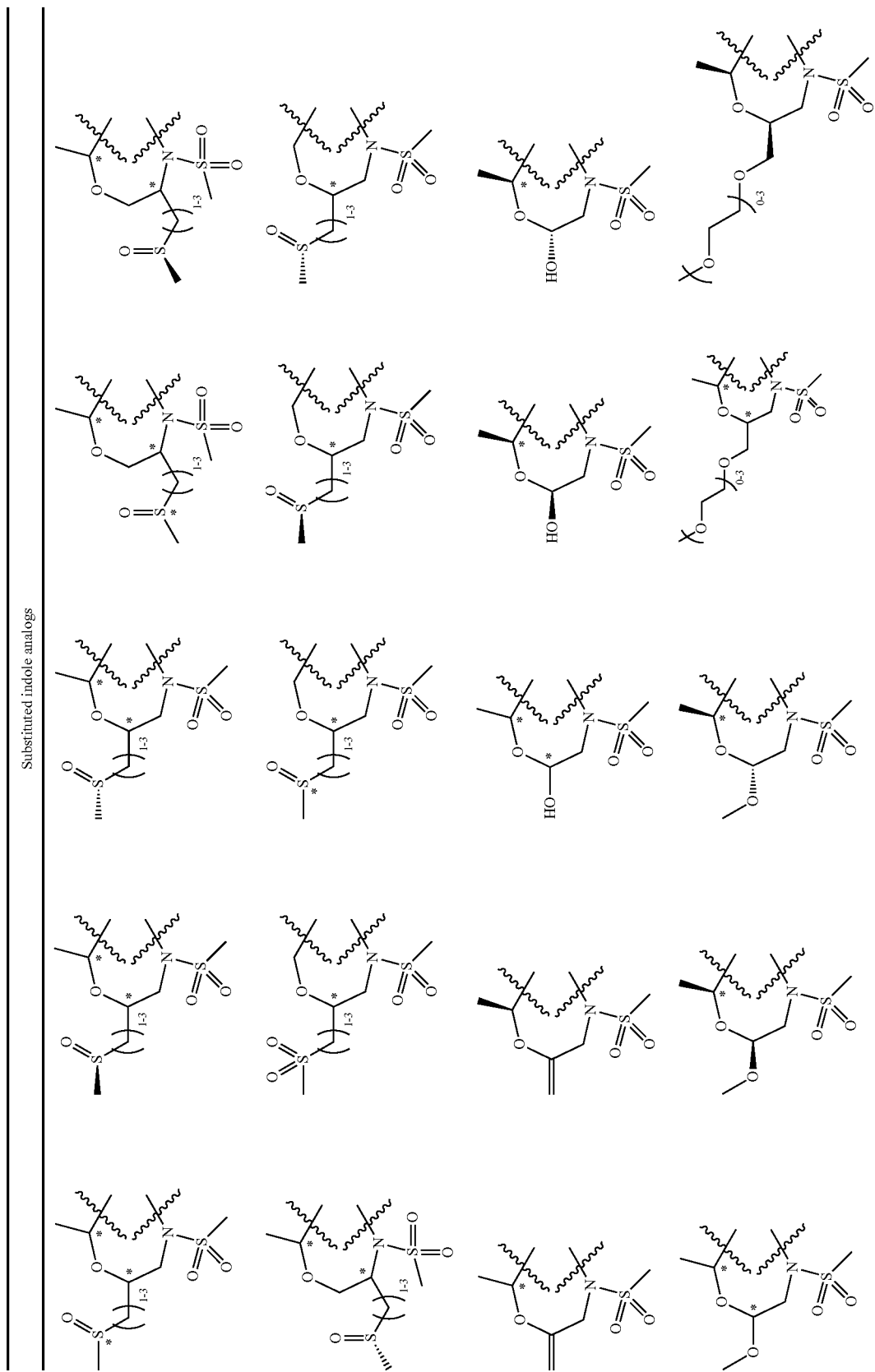

TABLE 5-continued
Substituted indole analogs
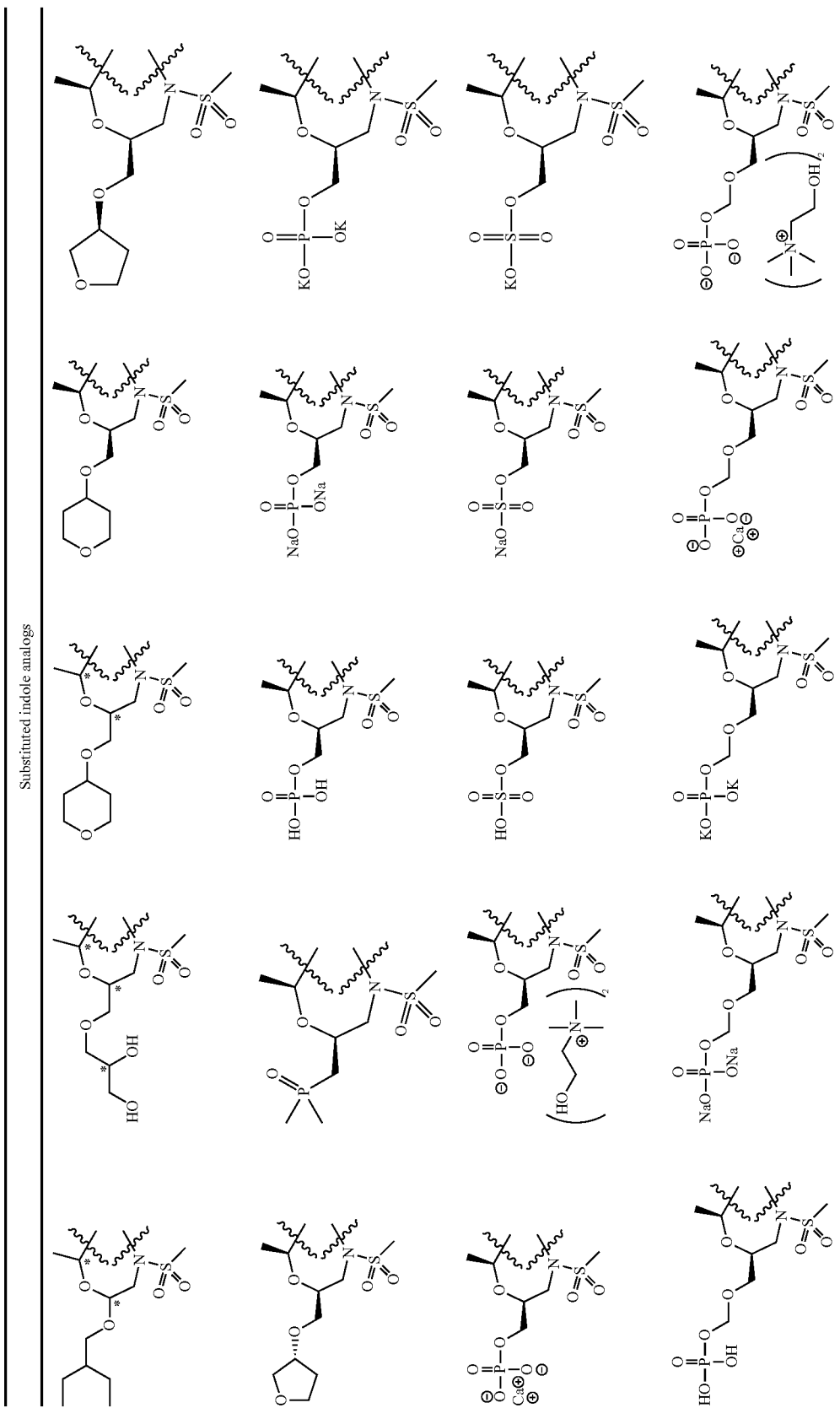

TABLE 5-continued
Substituted indole analogs
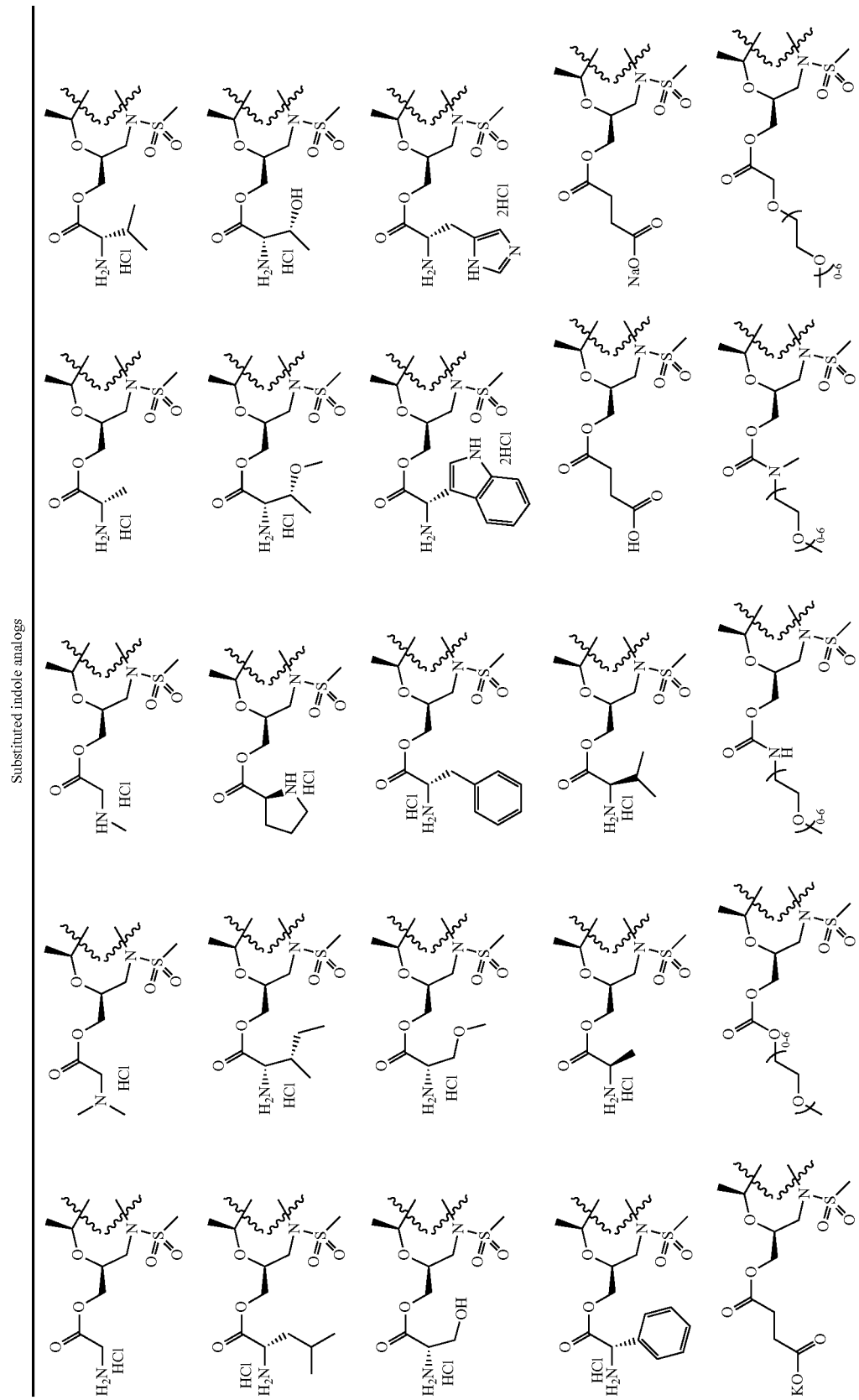

TABLE 5-continued
Substituted indole analogs
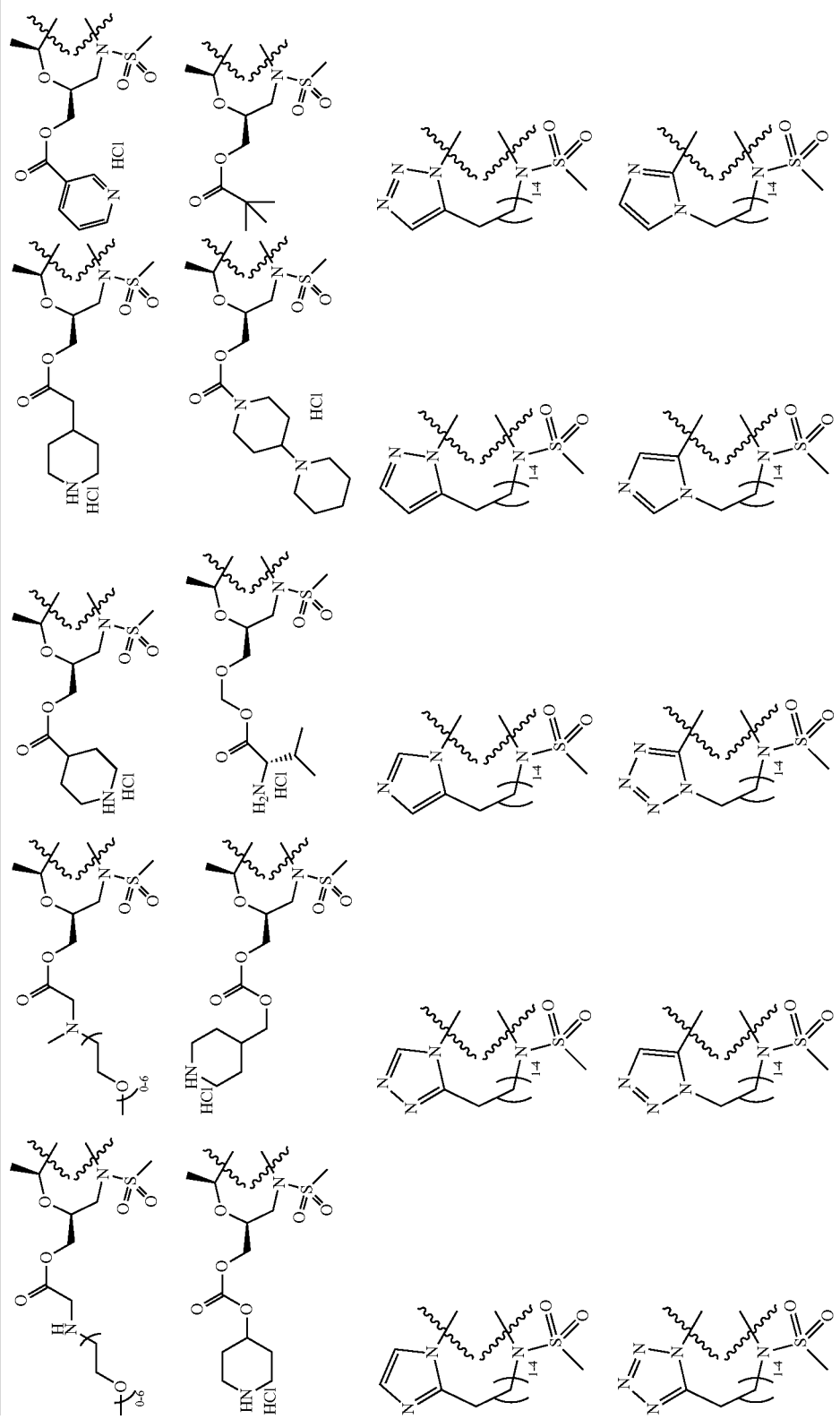

TABLE 5-continued
Substituted indole analogs
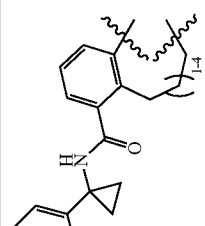 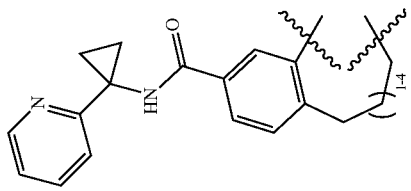
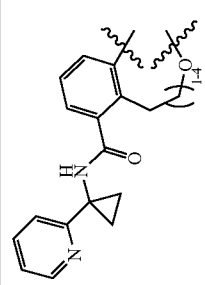 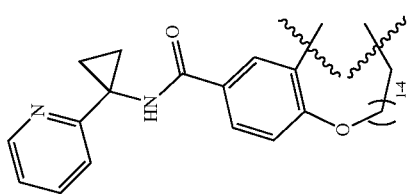
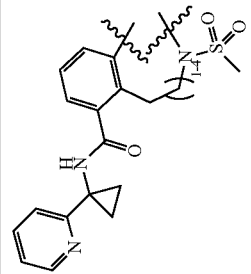 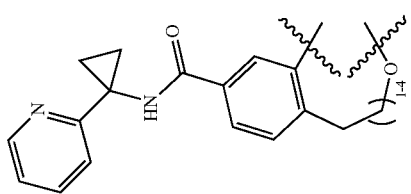
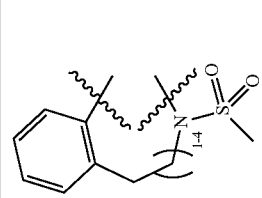 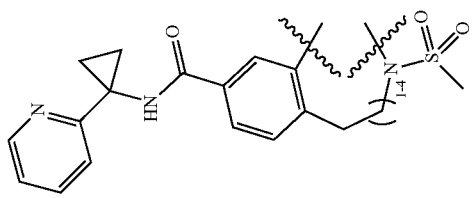
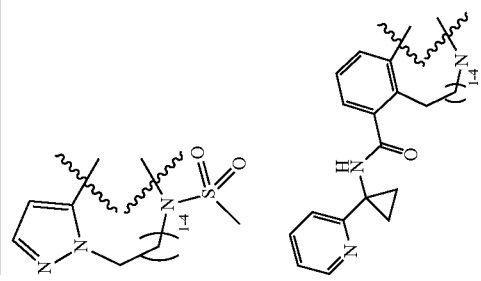

TABLE 6
Substituted benzothiophene analogs
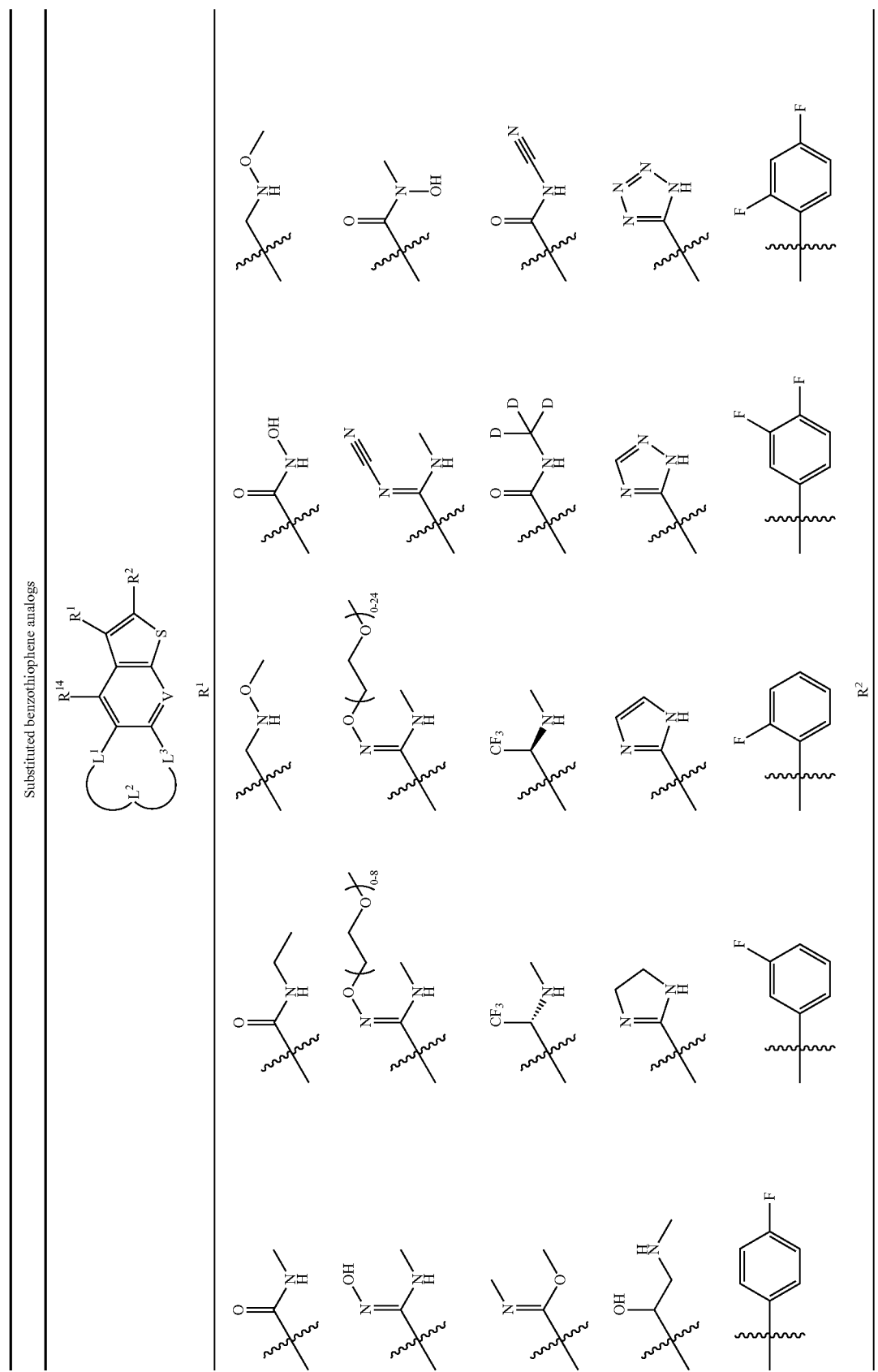

TABLE 6-continued
Substituted benzothiophene analogs
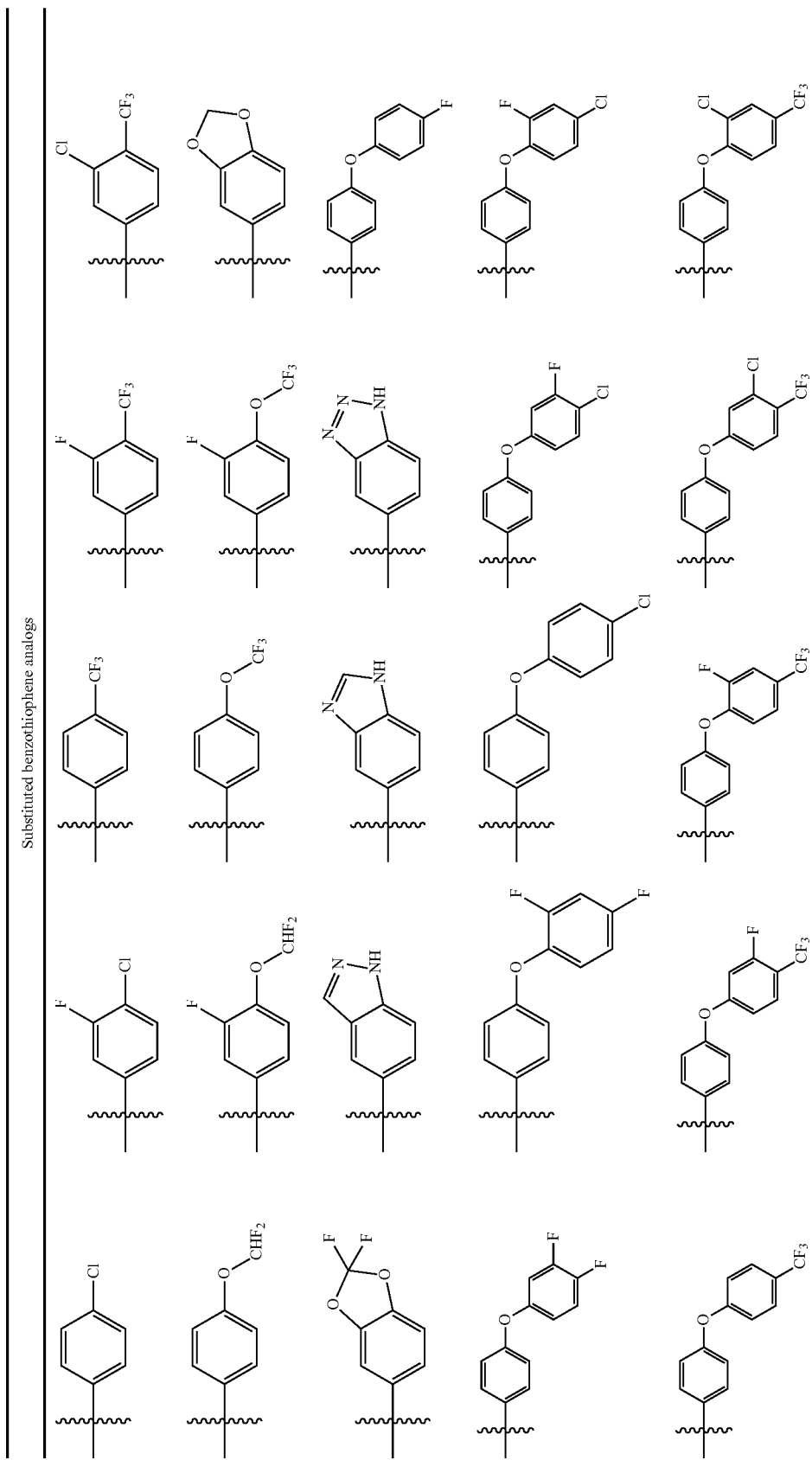

TABLE 6-continued
Substituted benzothiophene analogs
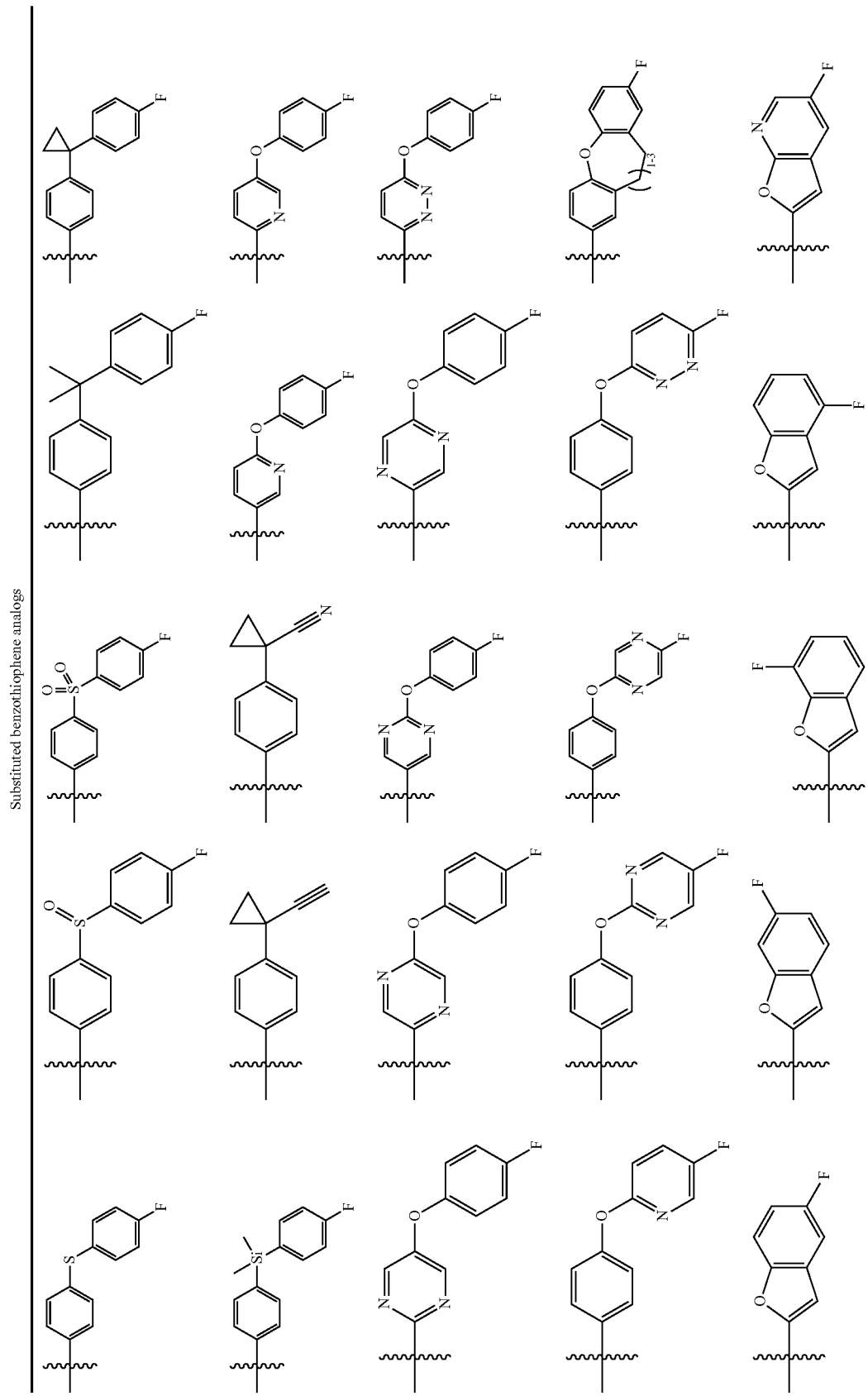

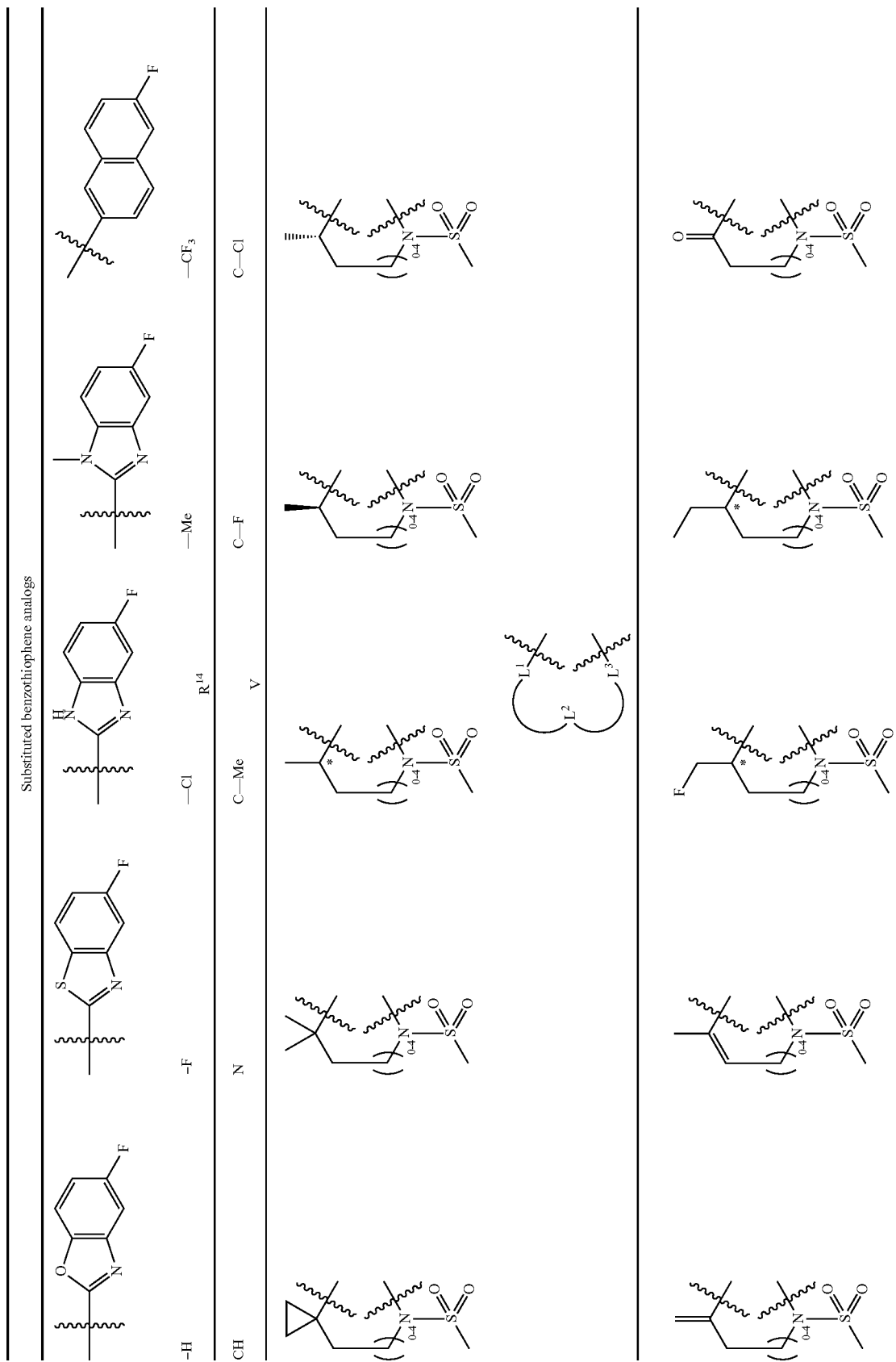

TABLE 6-continued
Substituted benzothiophene analogs
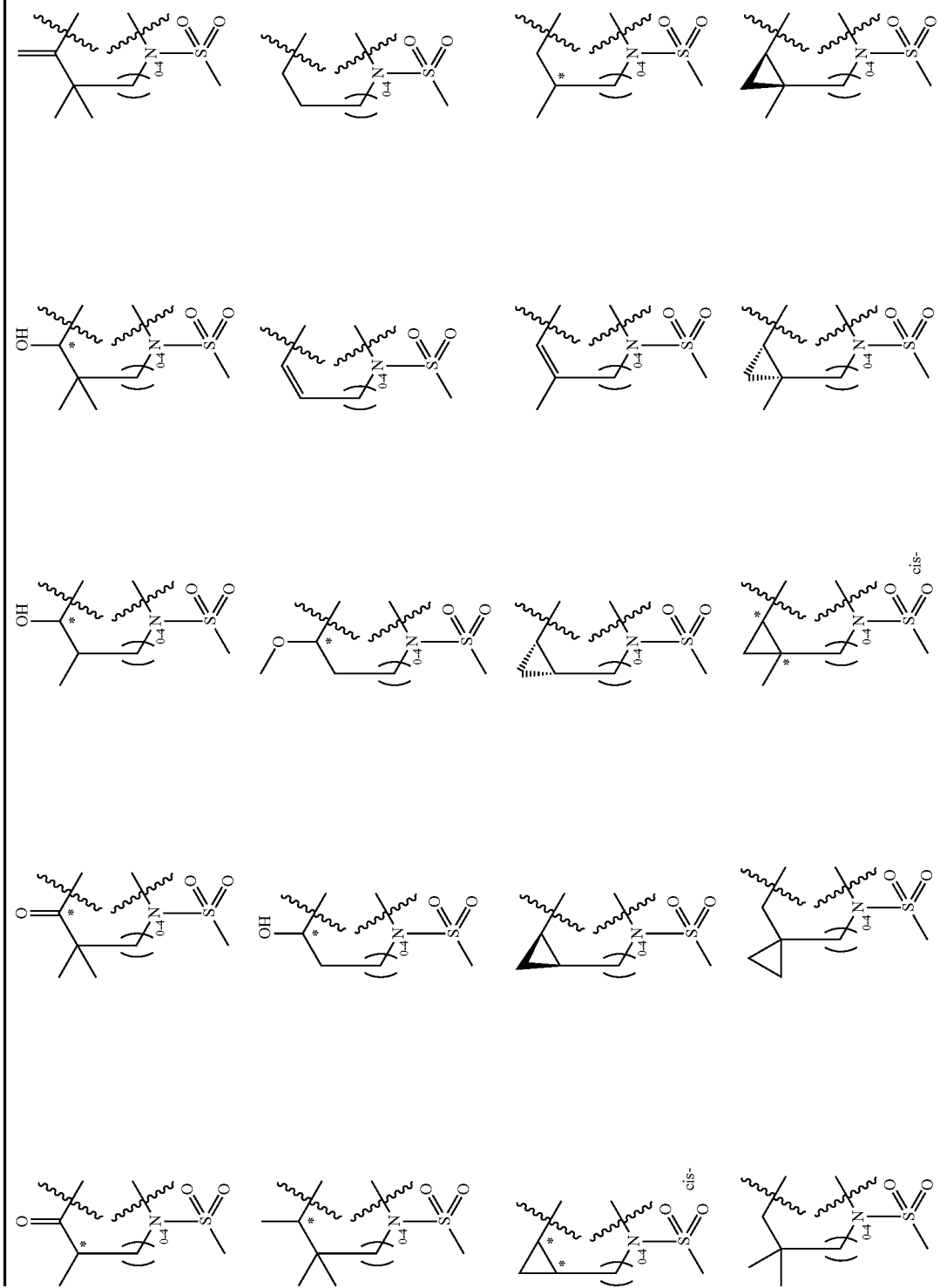

TABLE 6-continued
Substituted benzothiophene analogs
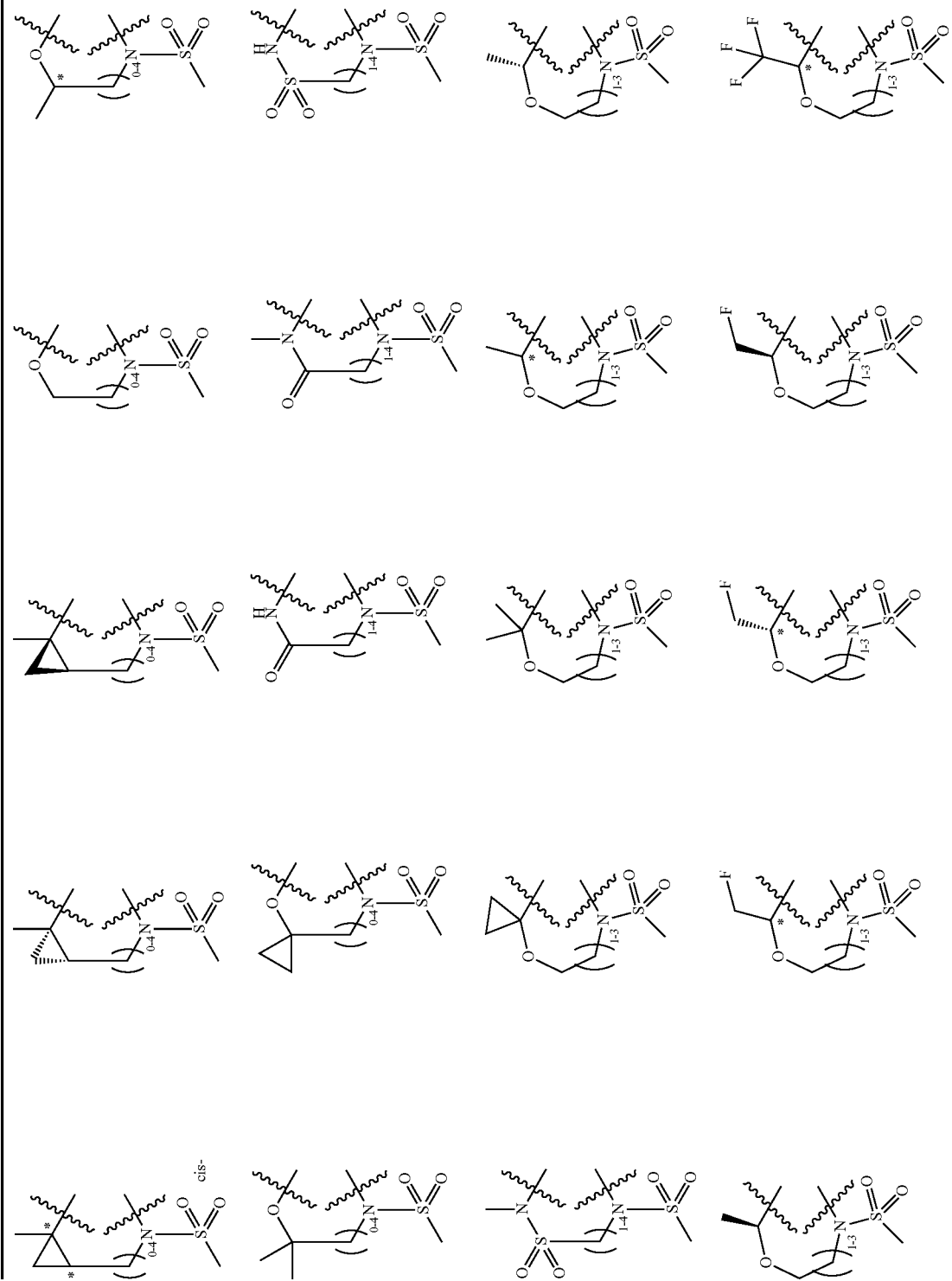

TABLE 6-continued
Substituted benzothiophene analogs
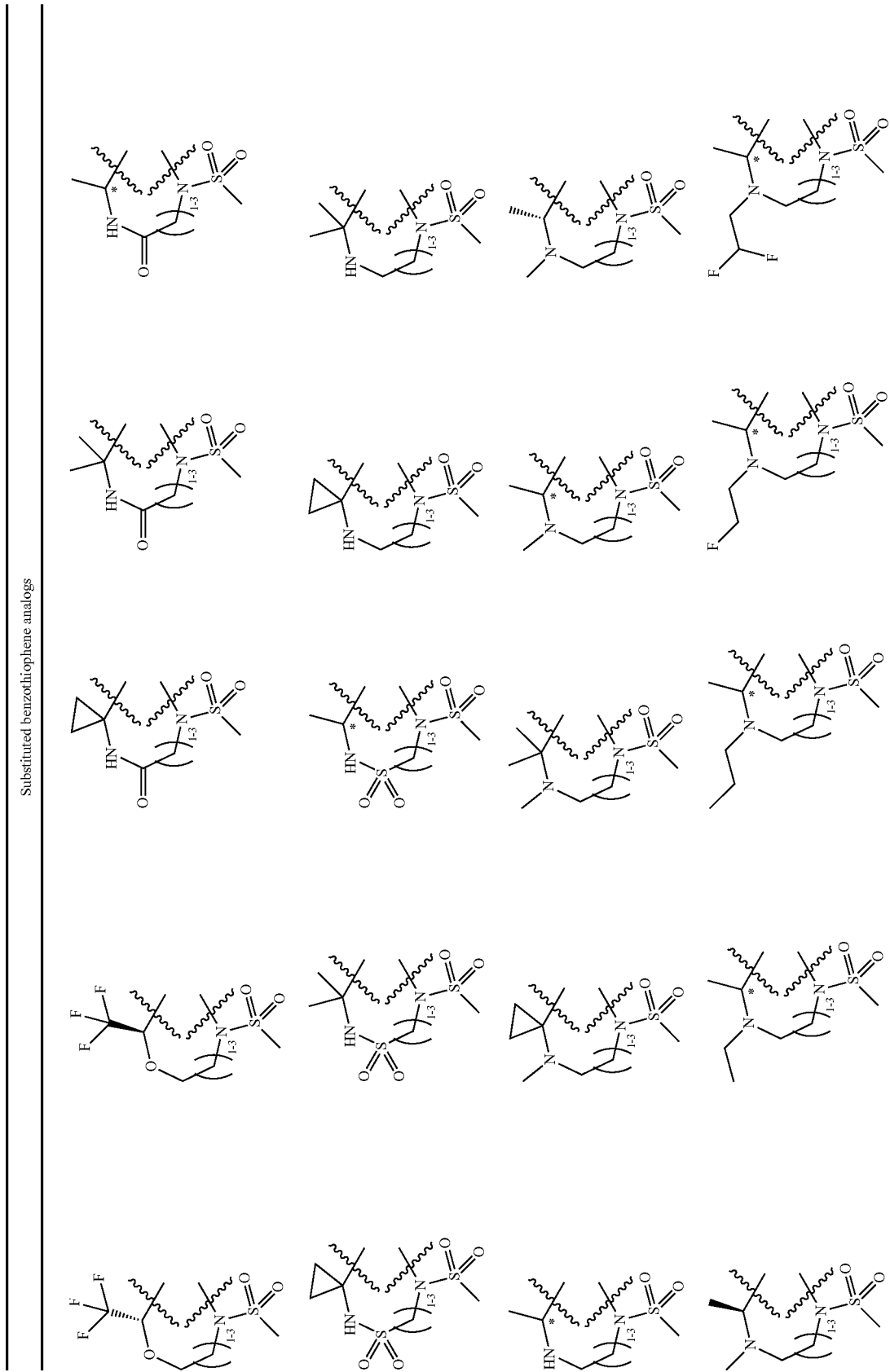

TABLE 6-continued
Substituted benzothiophene analogs
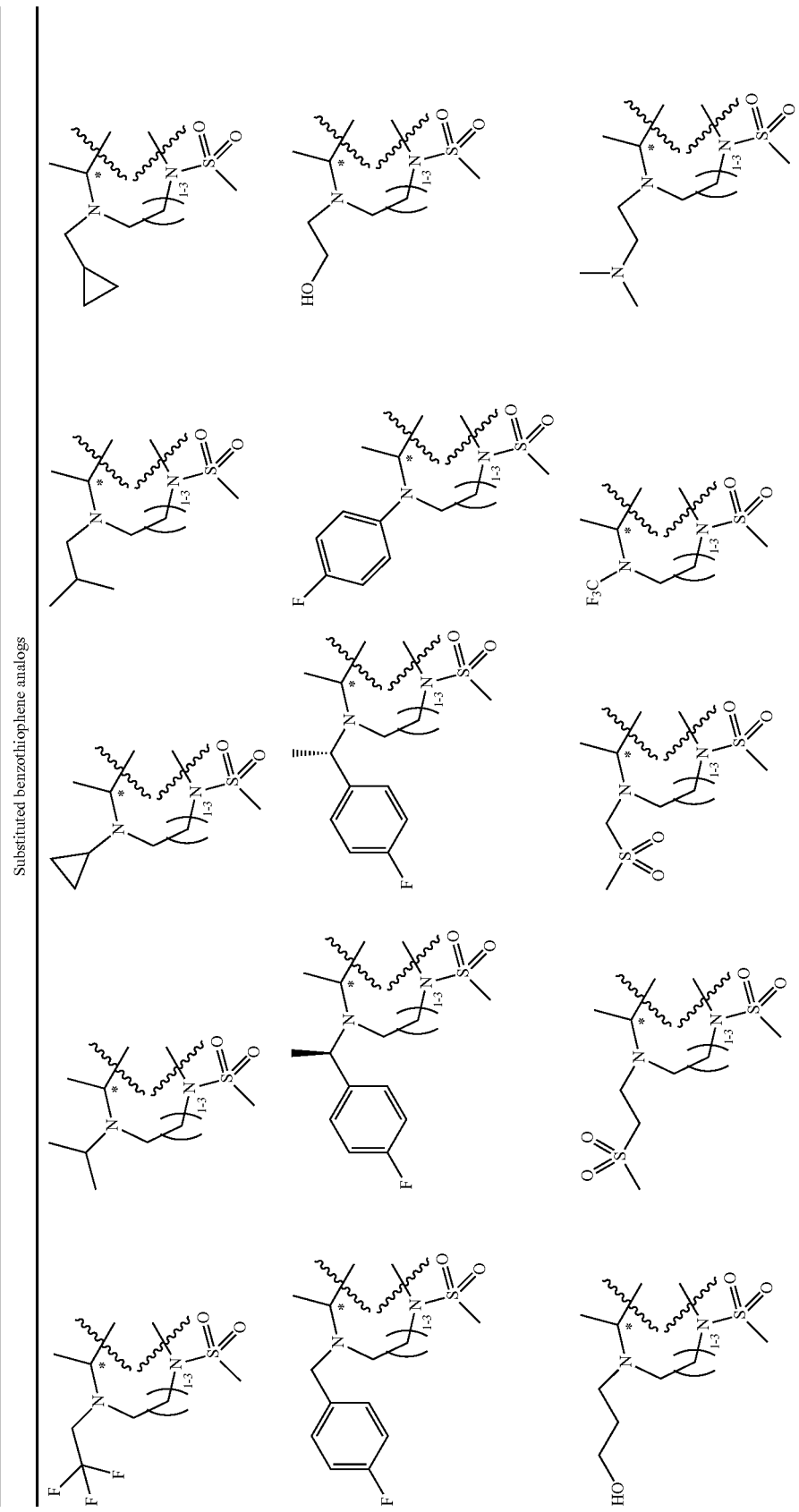

TABLE 6-continued
Substituted benzothiophene analogs
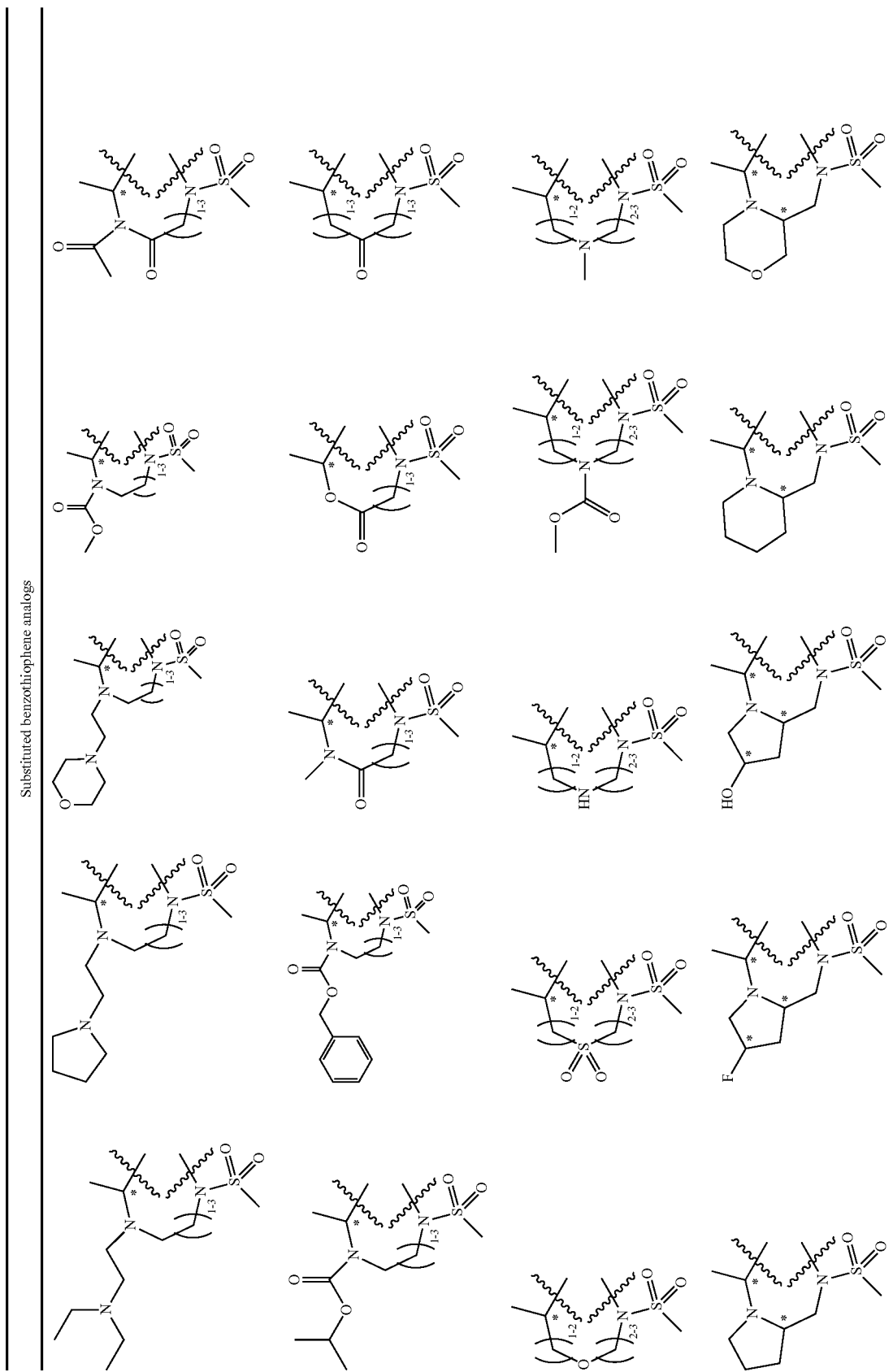

TABLE 6-continued
Substituted benzothiophene analogs
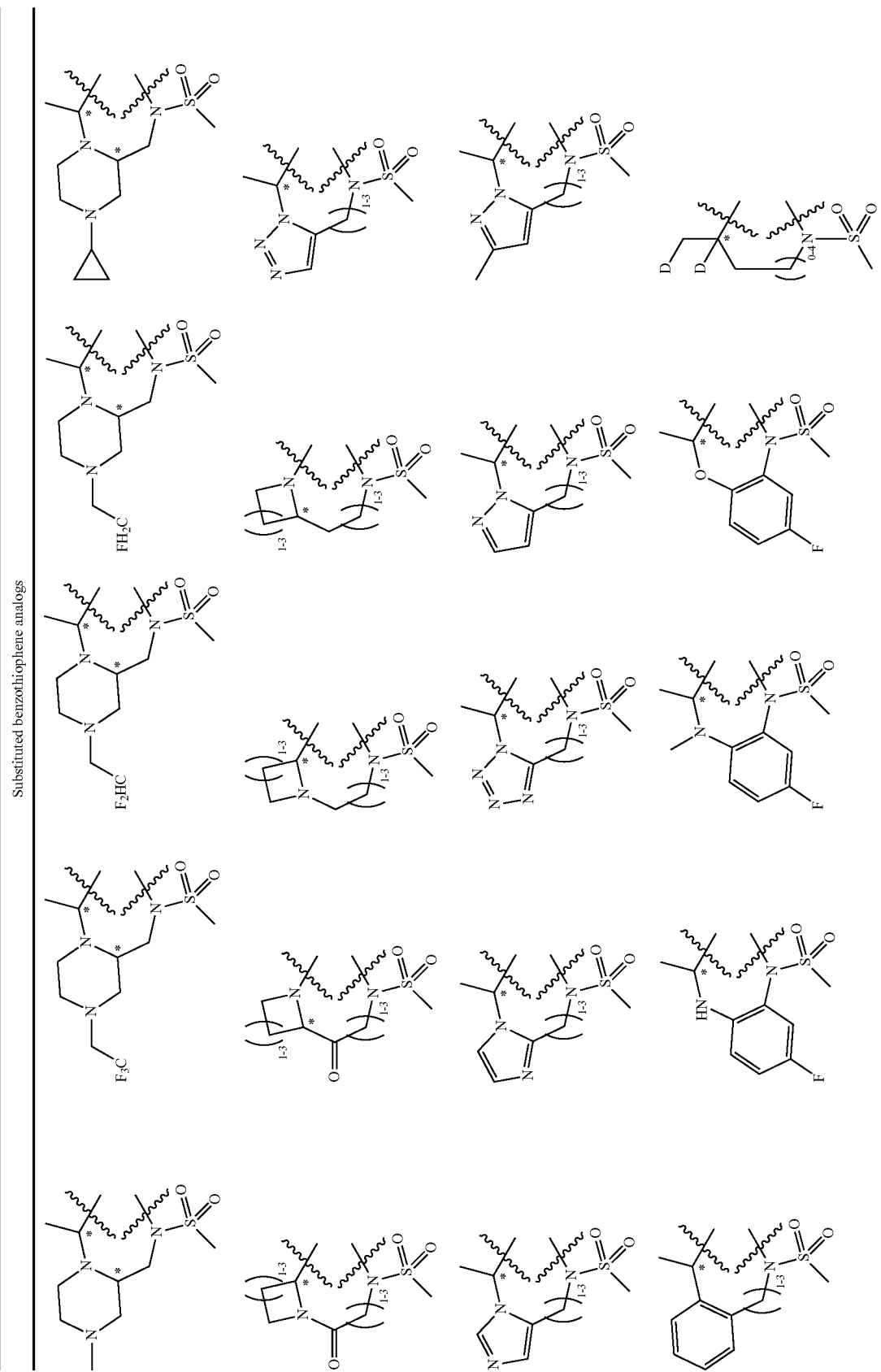

TABLE 6-continued
Substituted benzothiophene analogs
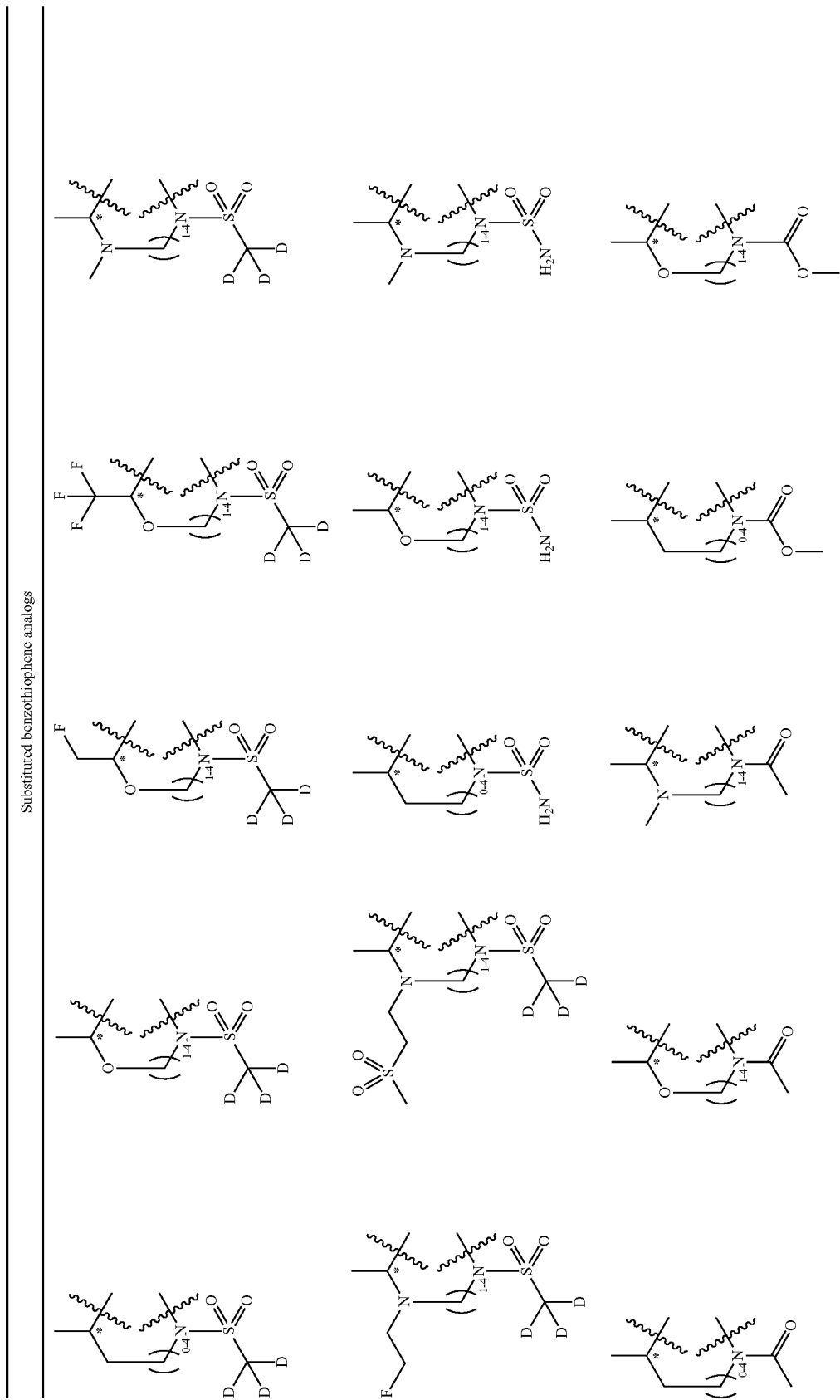

TABLE 6-continued
Substituted benzothiophene analogs
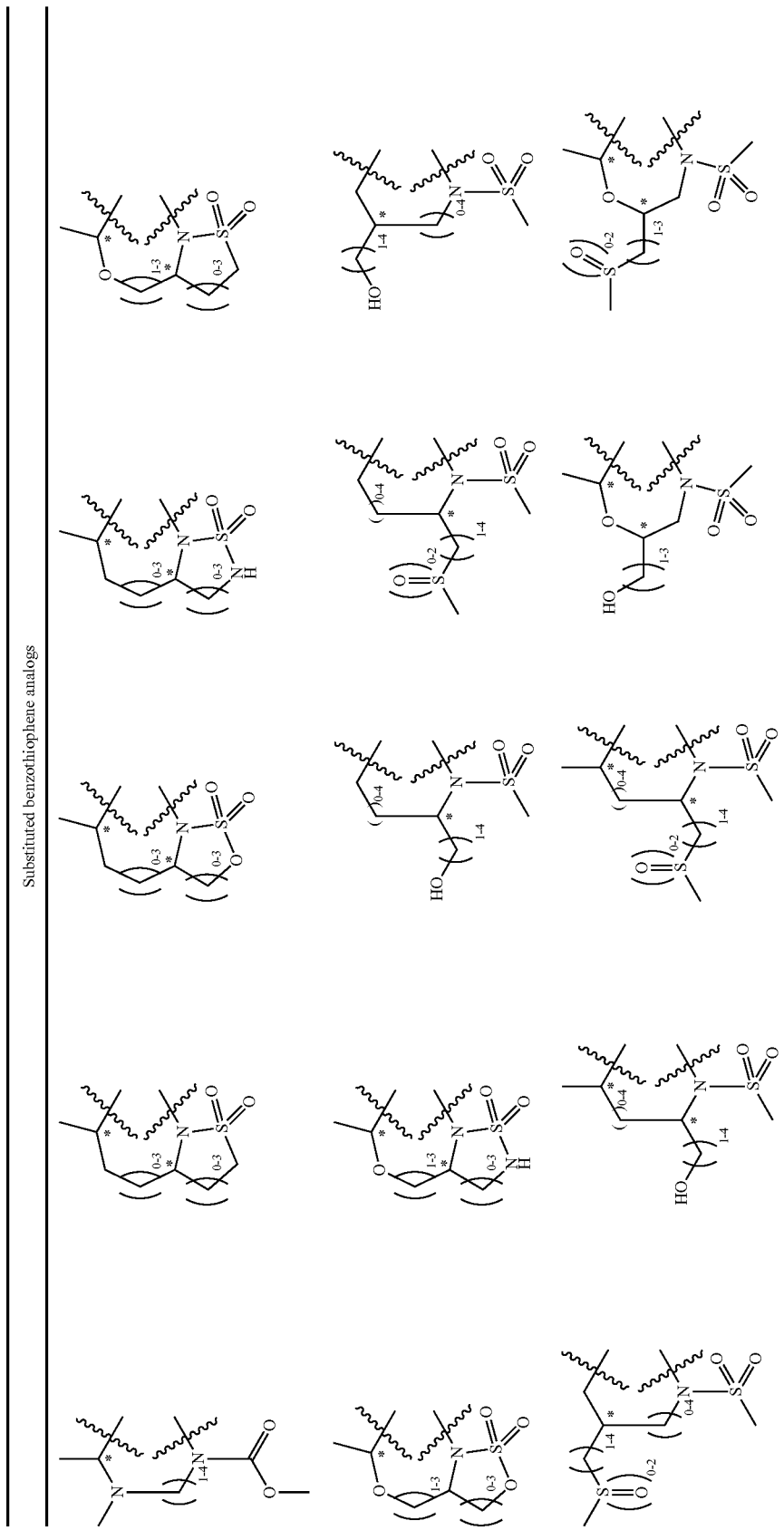

TABLE 6-continued
Substituted benzothiophene analogs
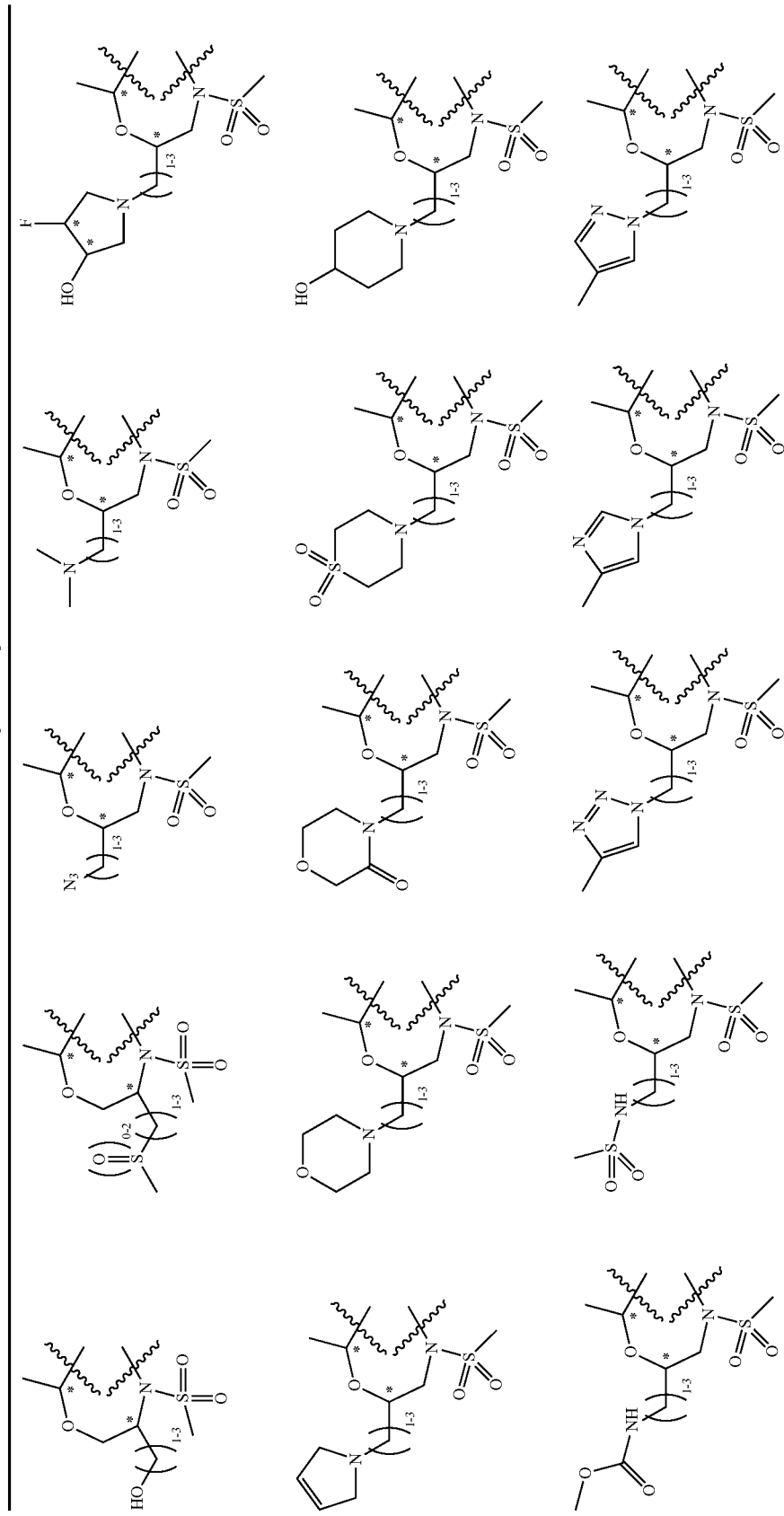

TABLE 6-continued
Substituted benzothiophene analogs
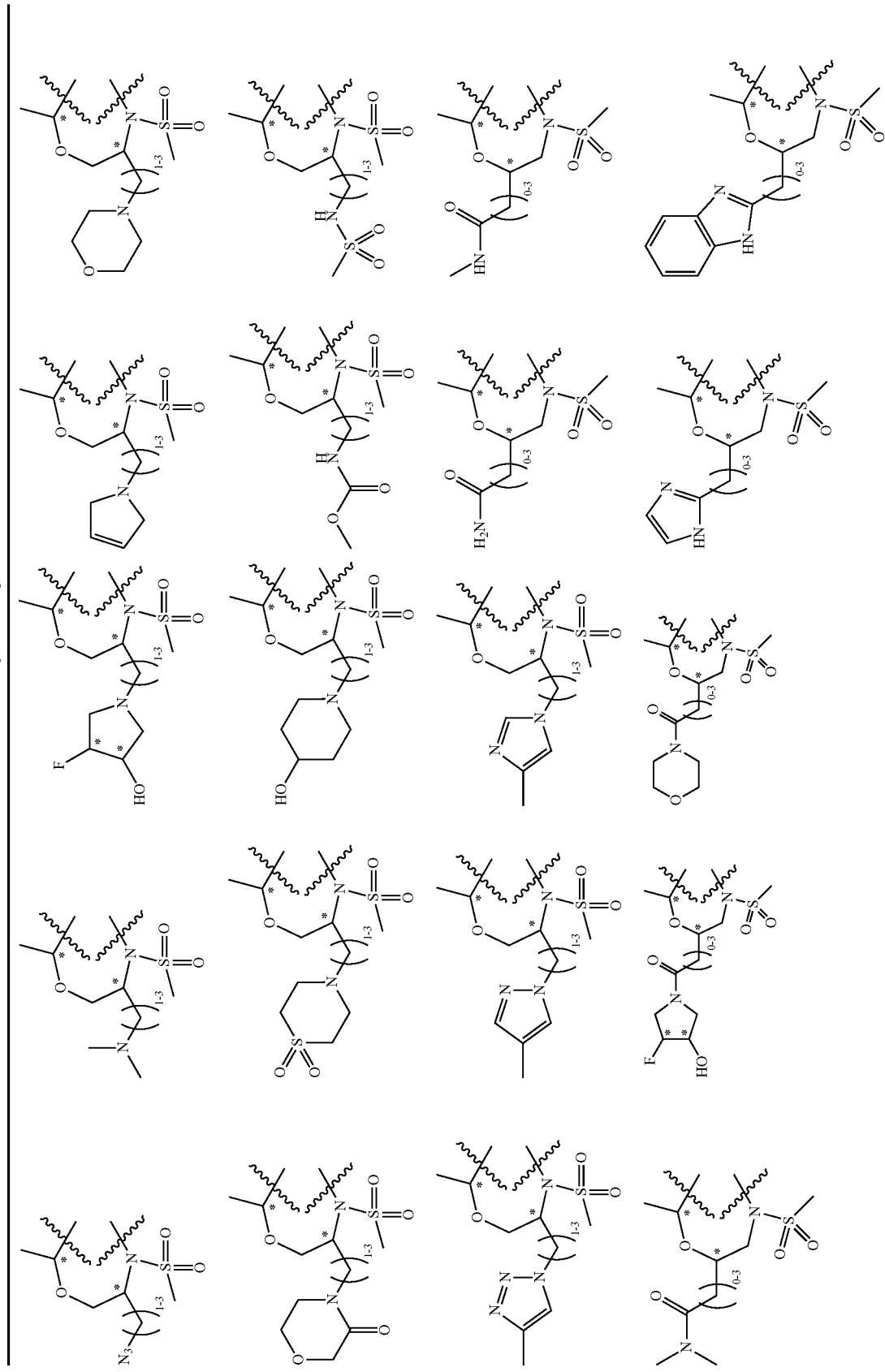

TABLE 6-continued
Substituted benzothiophene analogs
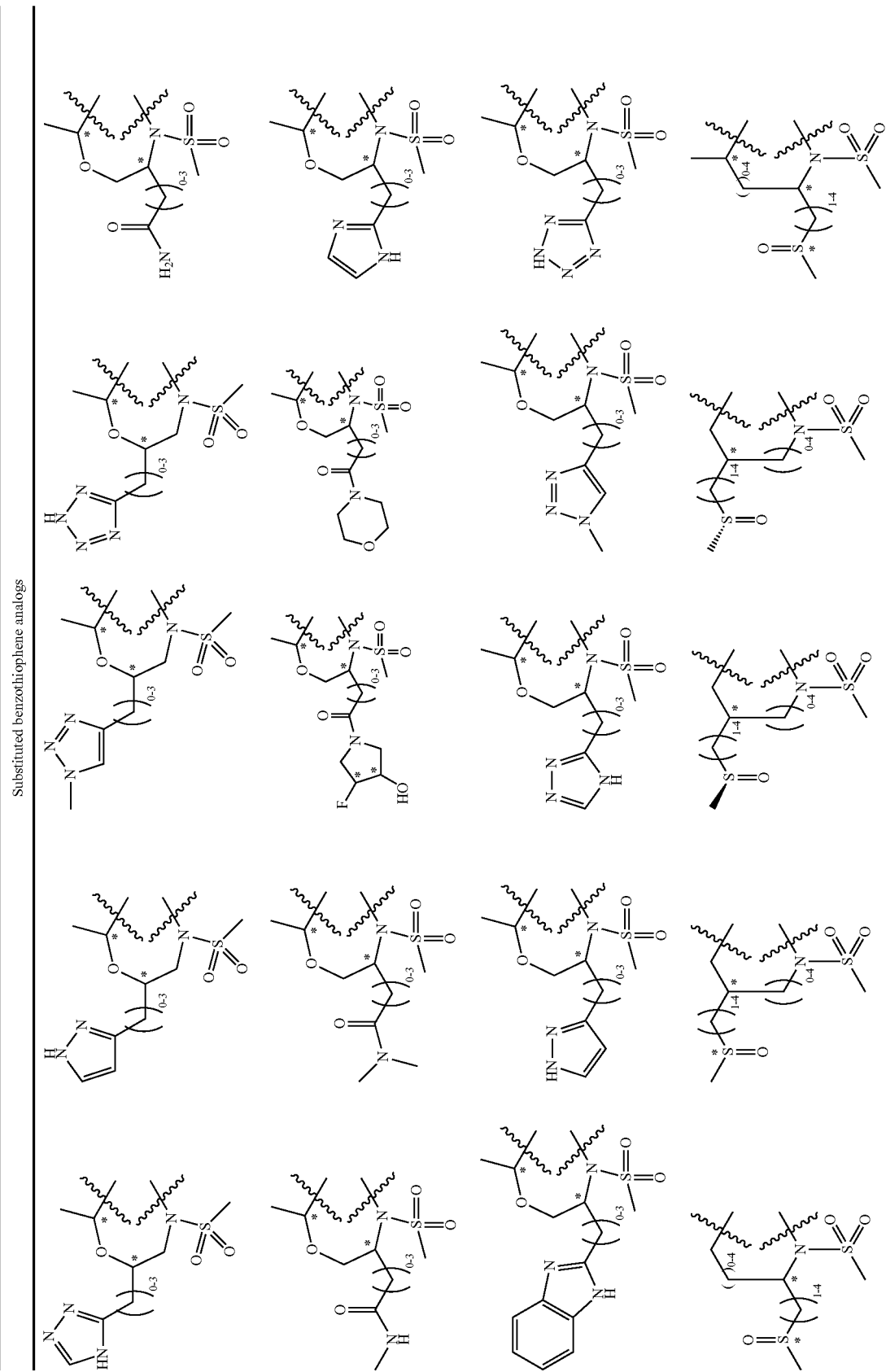

TABLE 6-continued
Substituted benzothiophene analogs
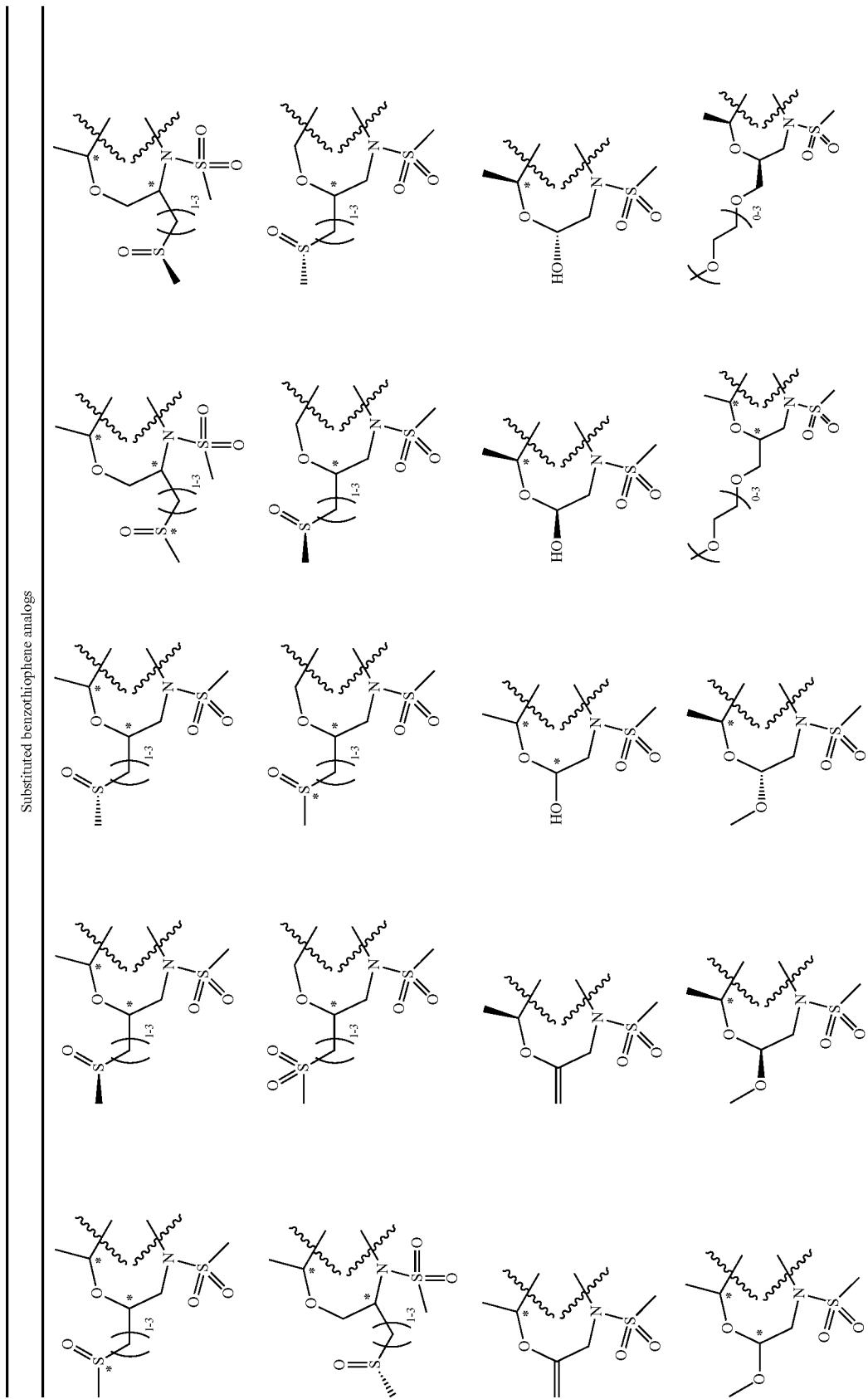

TABLE 6-continued
Substituted benzothiophene analogs
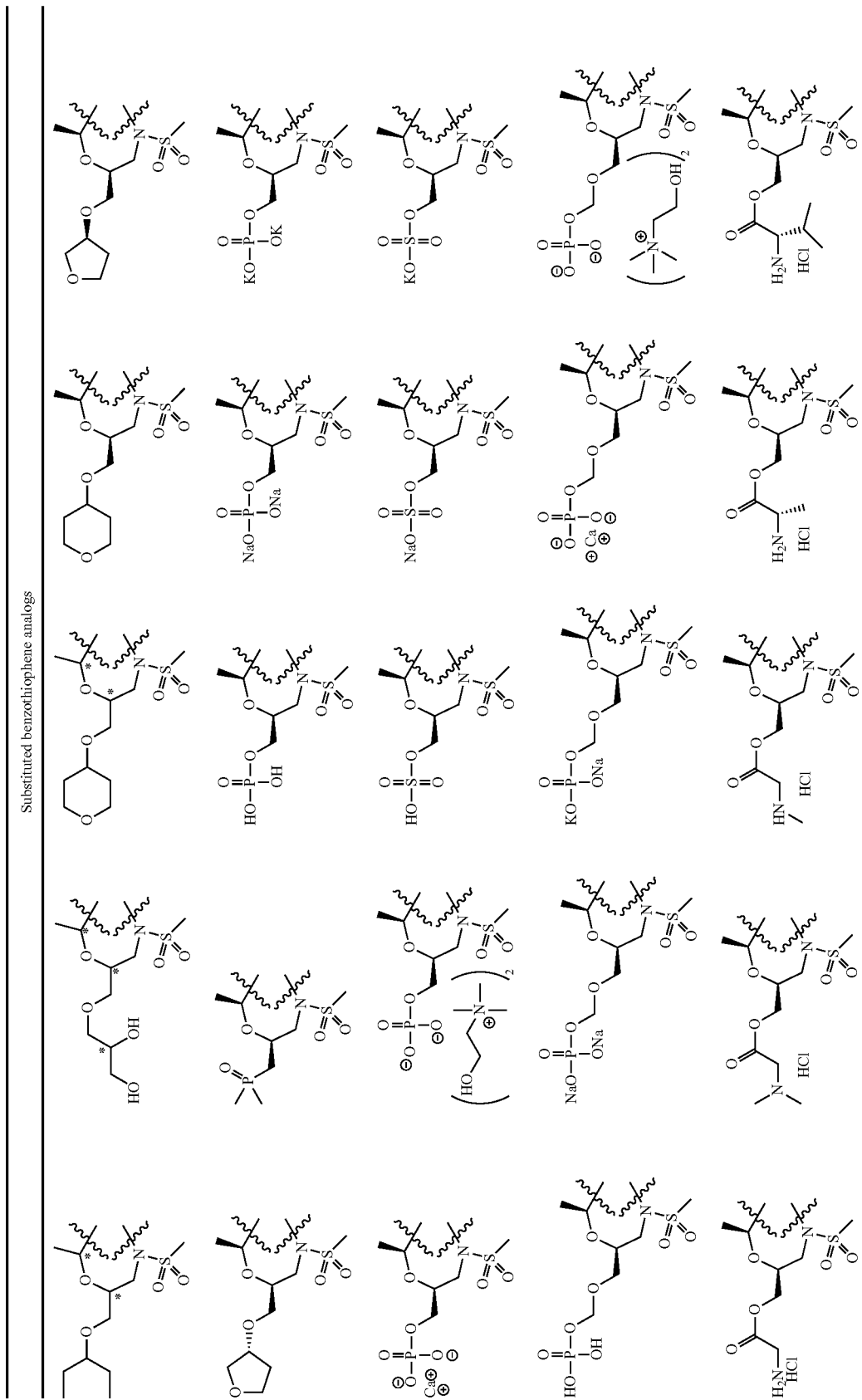

TABLE 6-continued
Substituted benzothiophene analogs
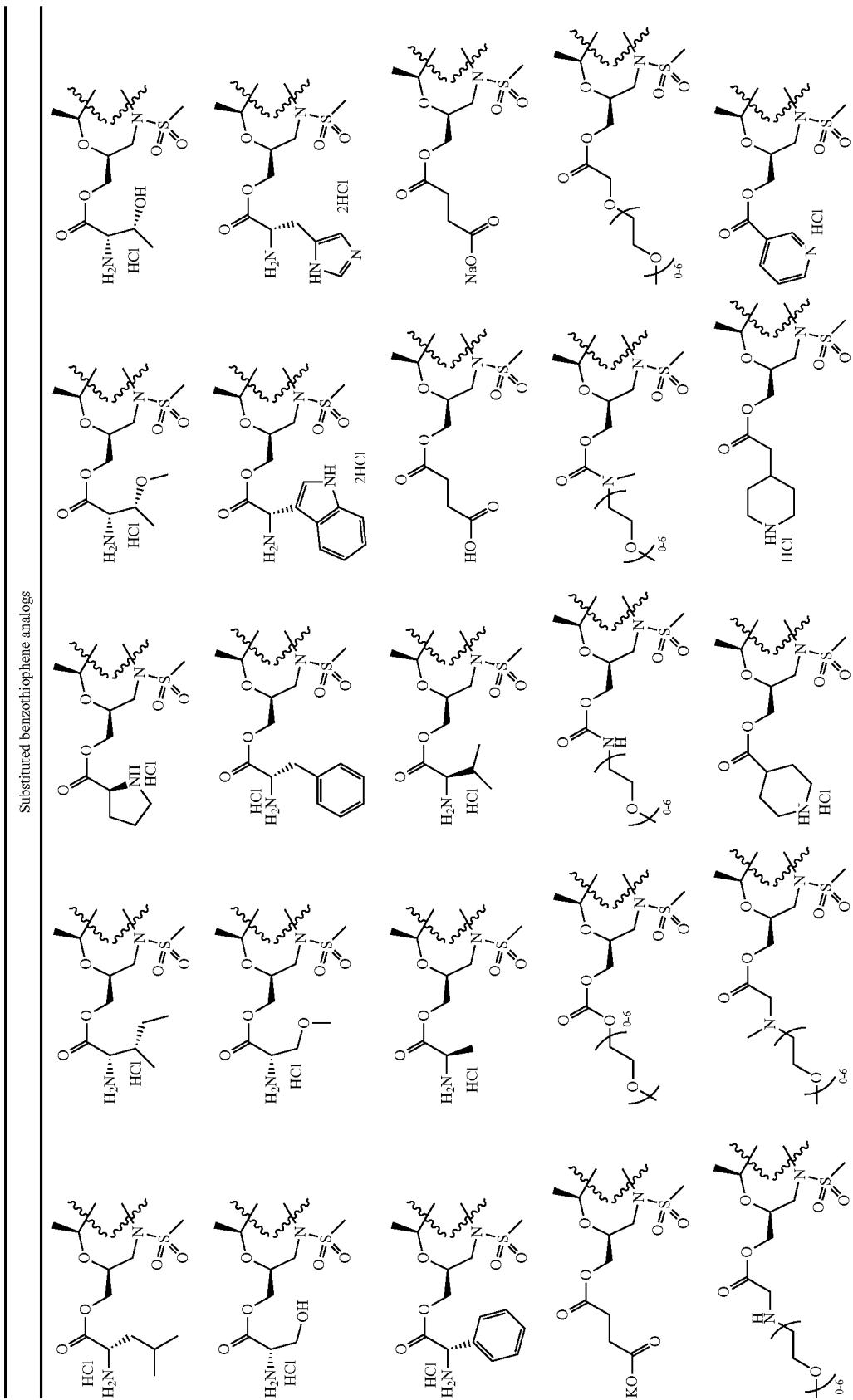

TABLE 6-continued
Substituted benzothiophene analogs
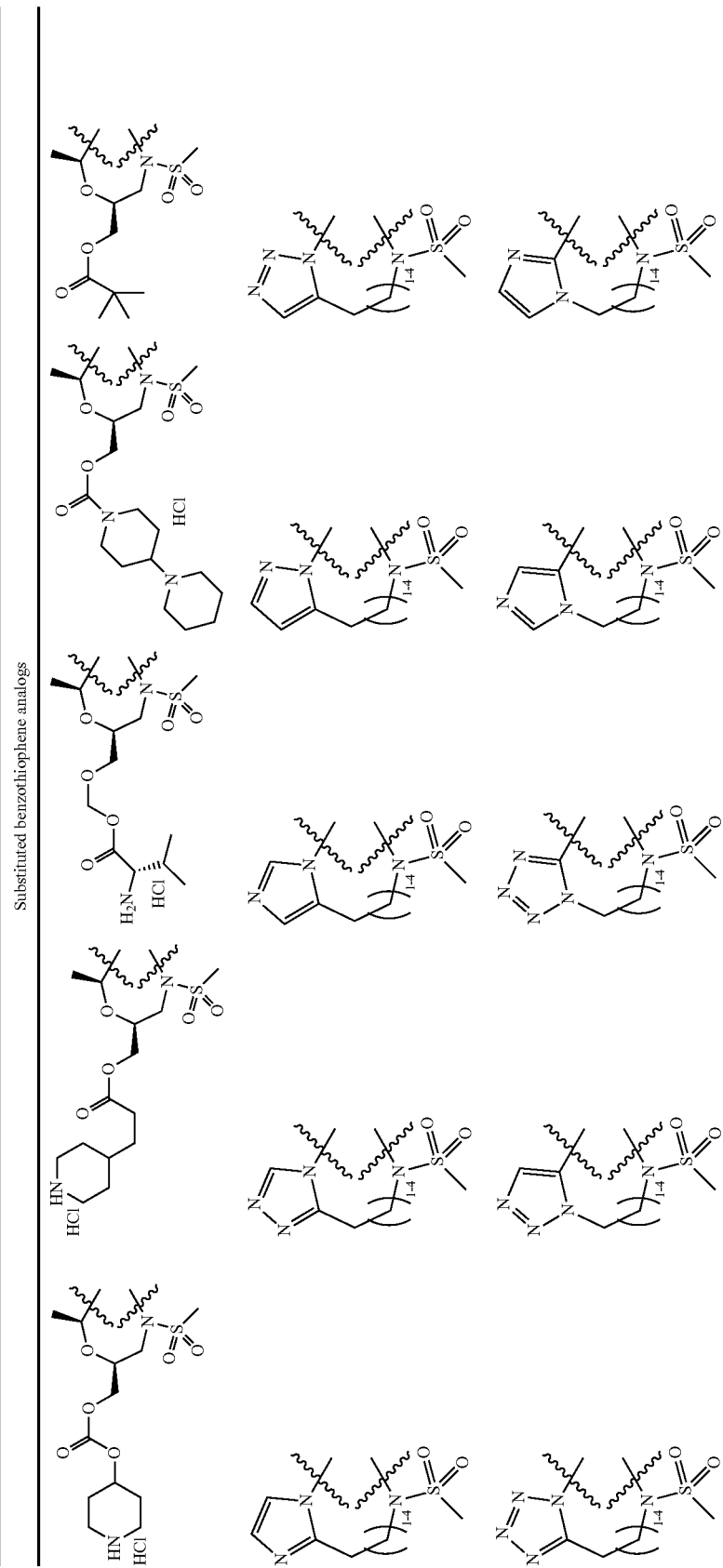

TABLE 6-continued
Substituted benzothiophene analogs
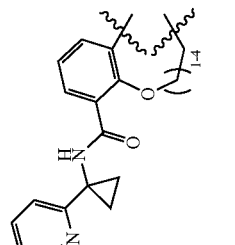 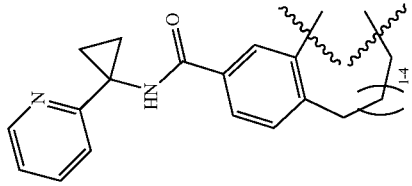
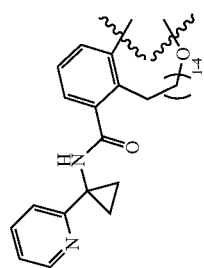 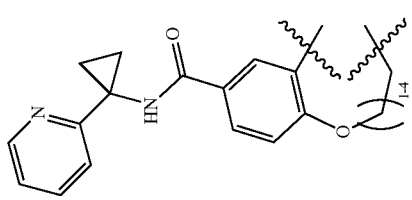
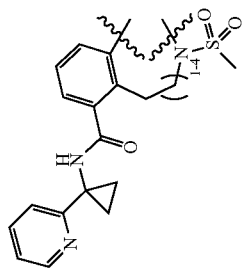 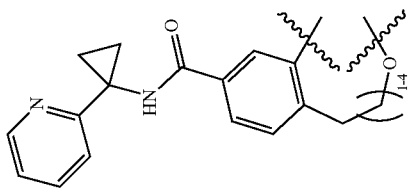
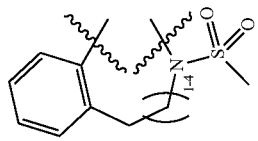 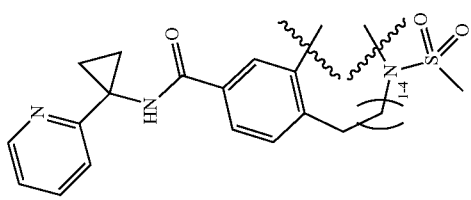
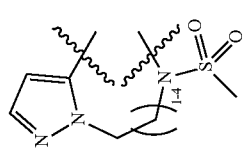 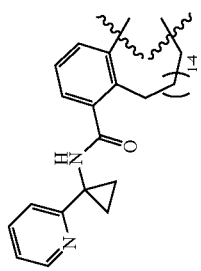

TABLE 7
Substituted indazole analogs
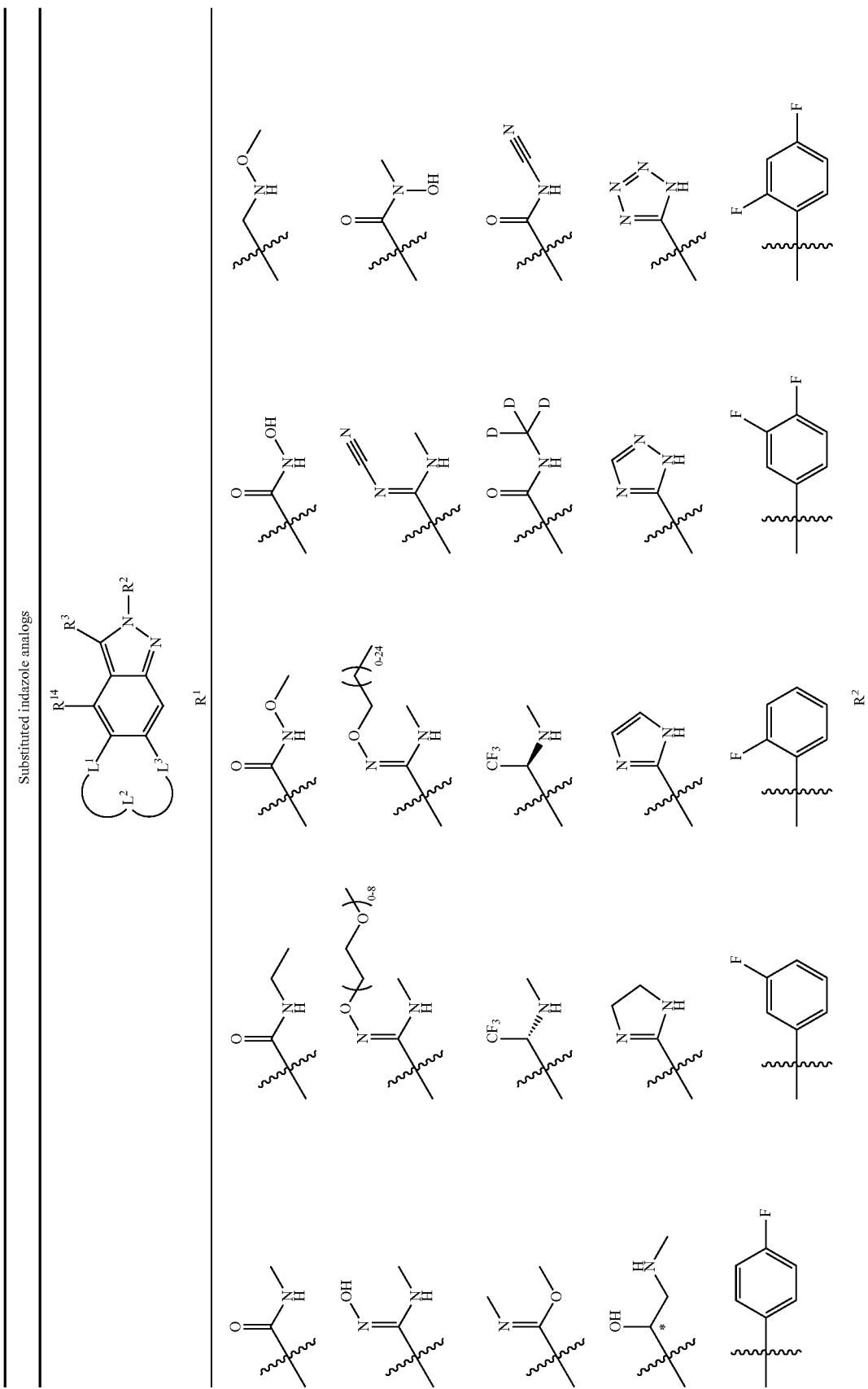

TABLE 7-continued
Substituted indazole analogs
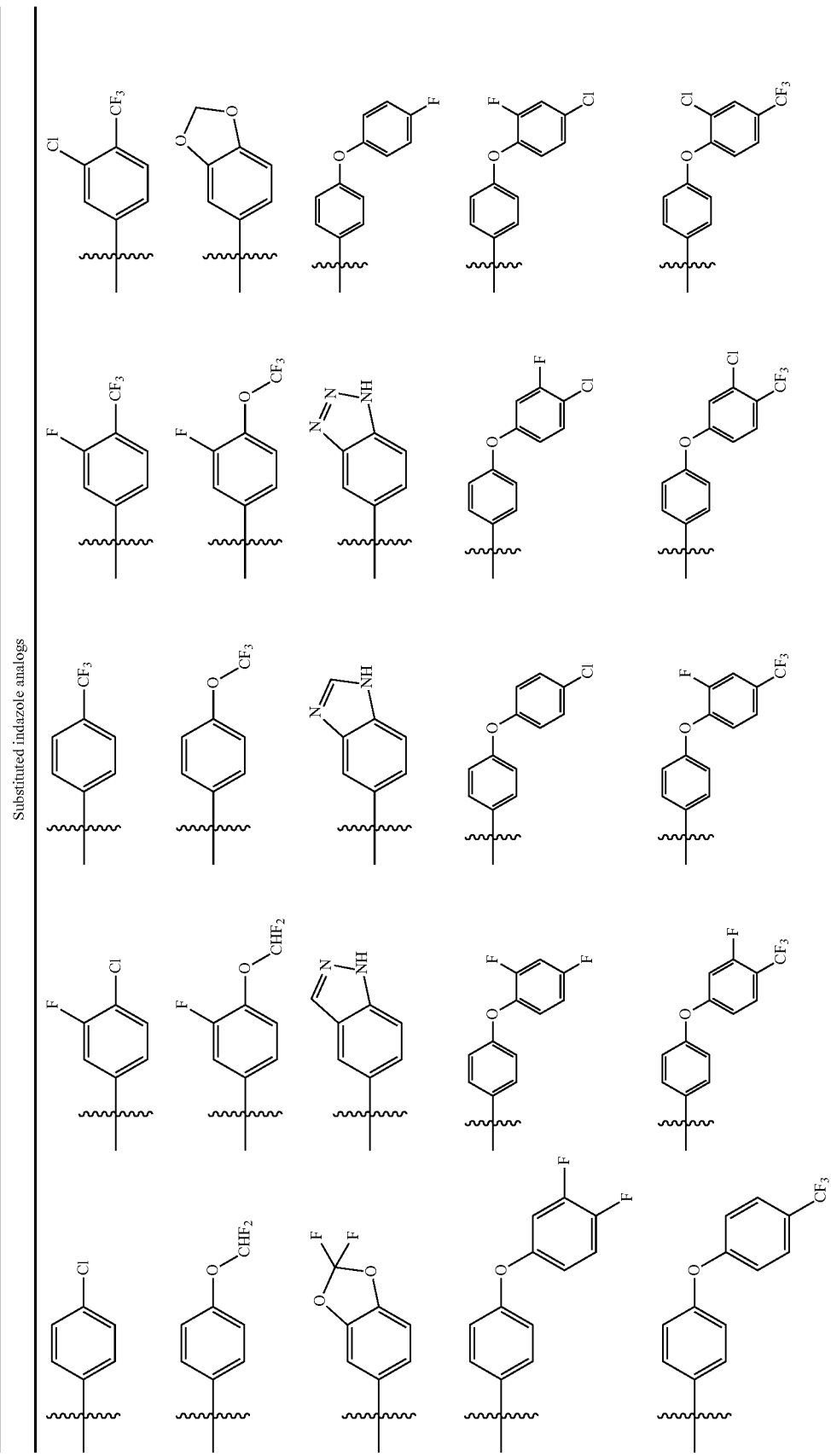

TABLE 7-continued
Substituted indazole analogs
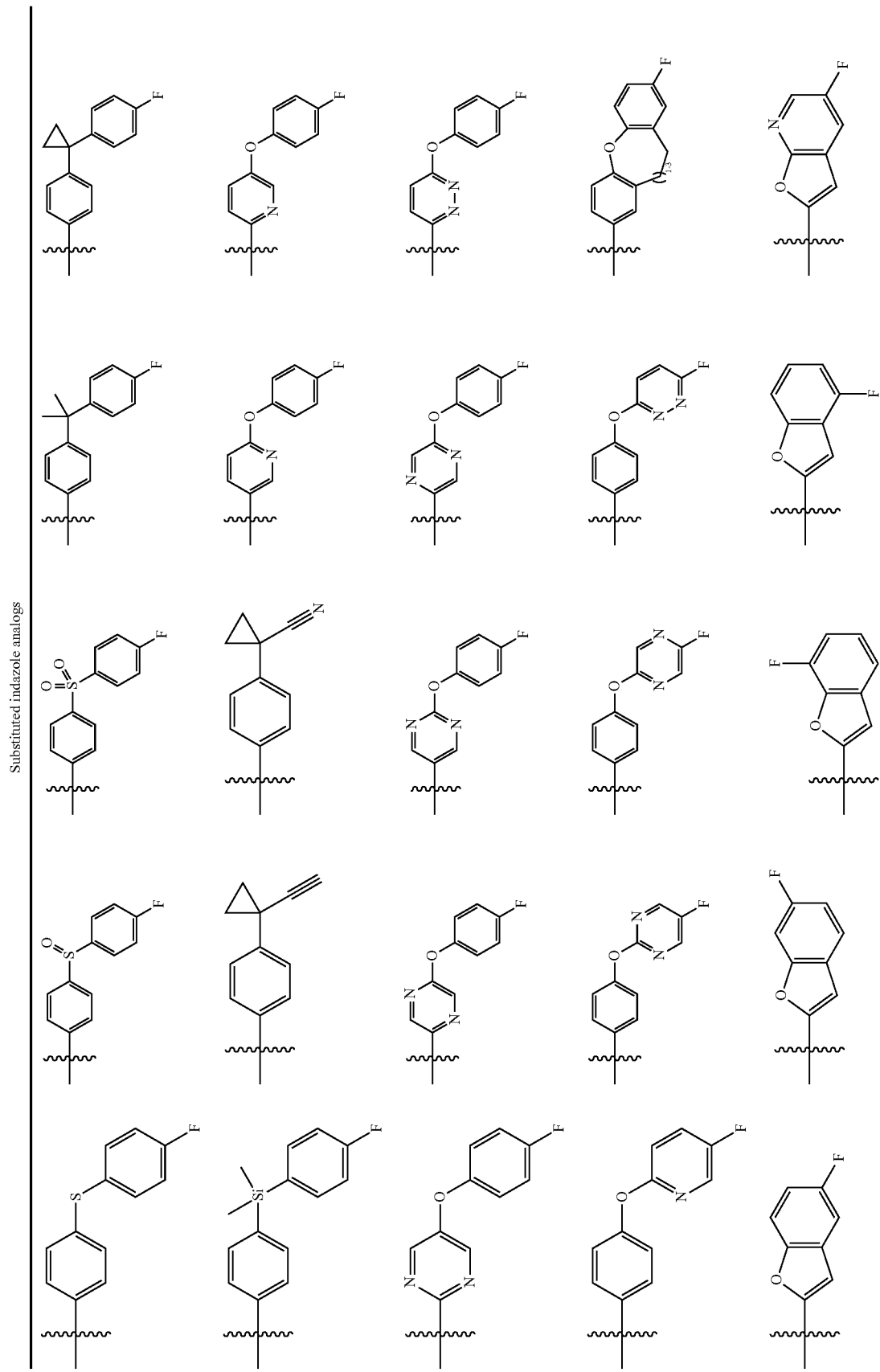

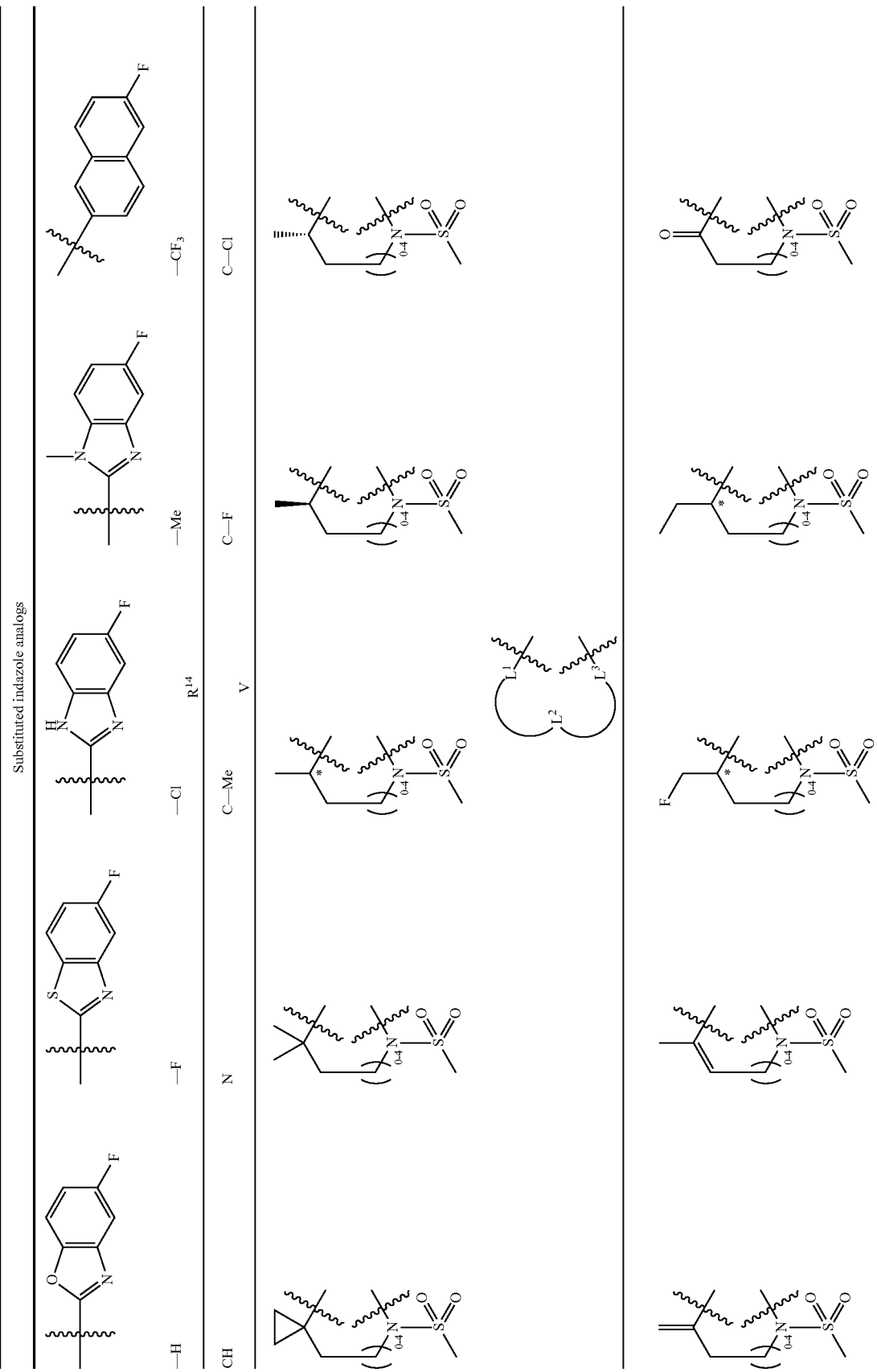

TABLE 7-continued
Substituted indazole analogs
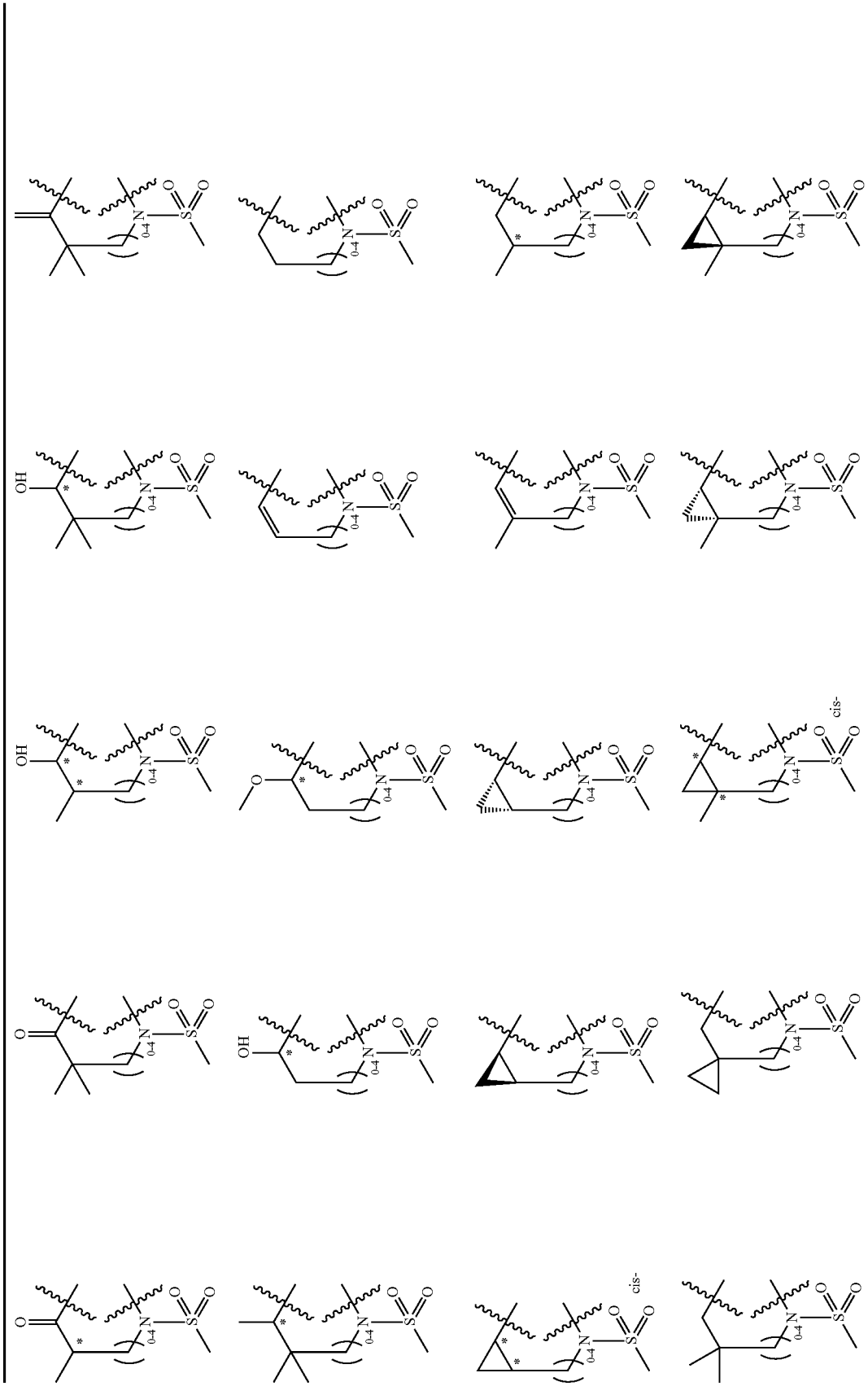

TABLE 7-continued
Substituted indazole analogs
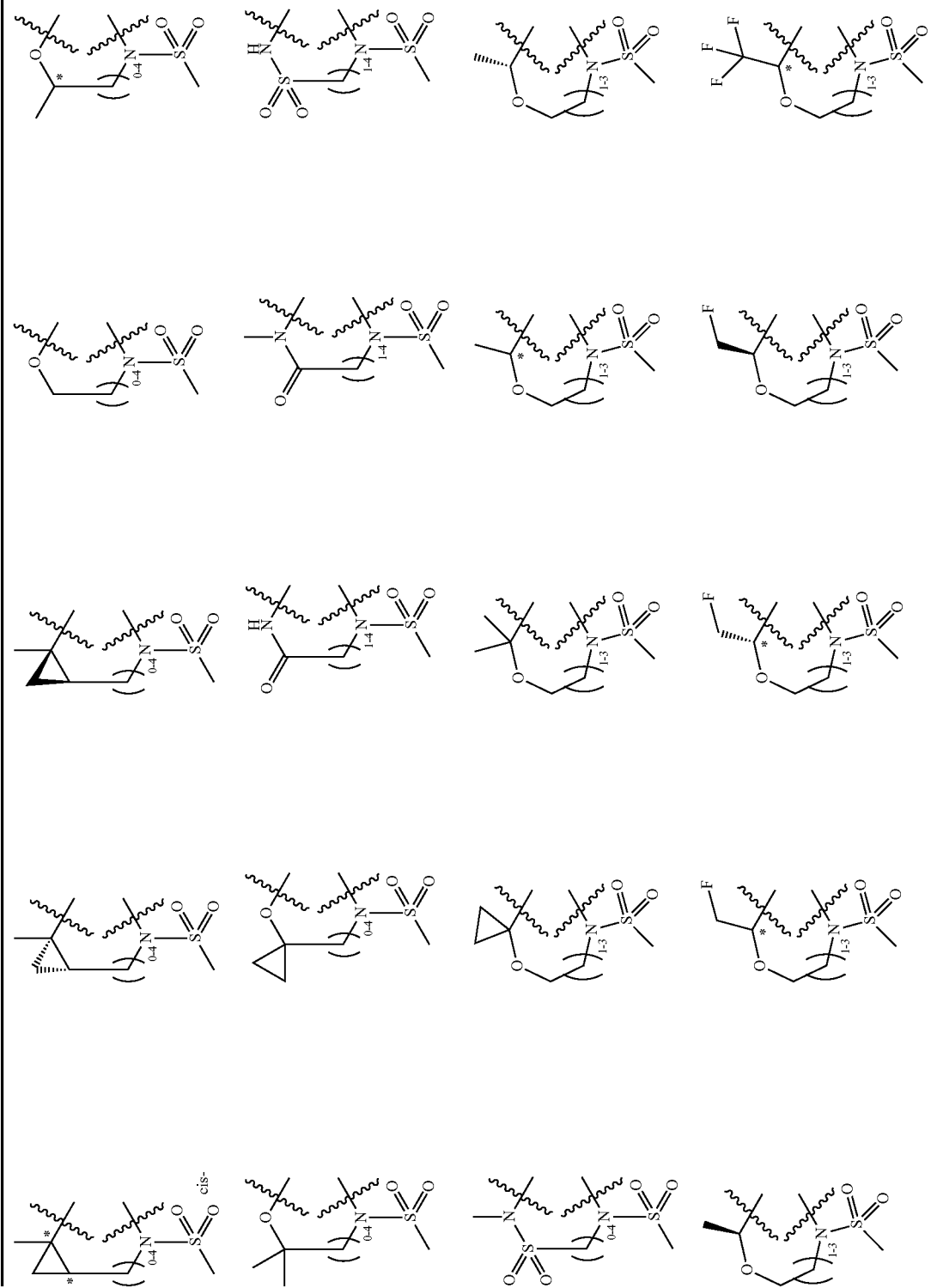

TABLE 7-continued
Substituted indazole analogs
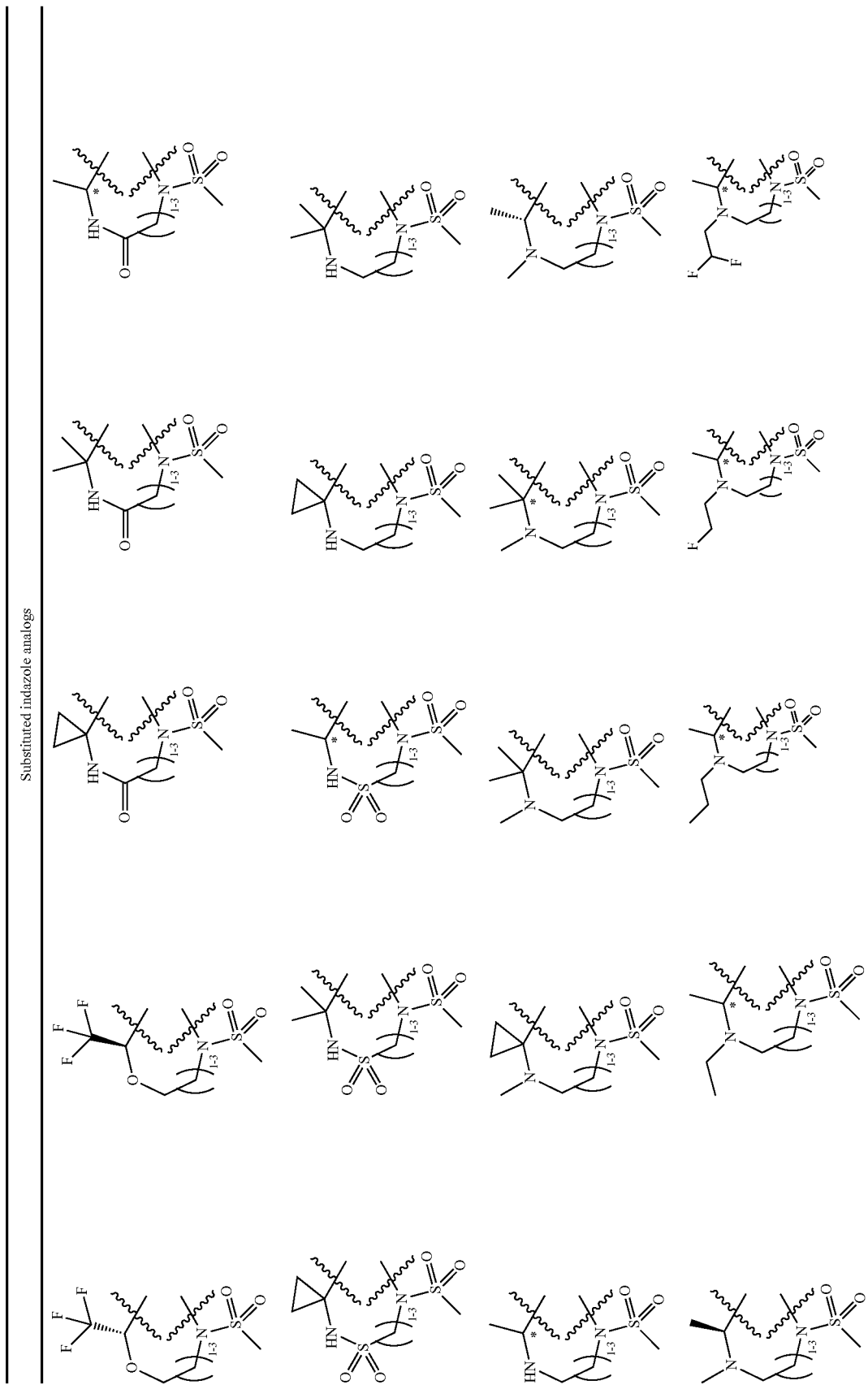

TABLE 7-continued
Substituted indazole analogs
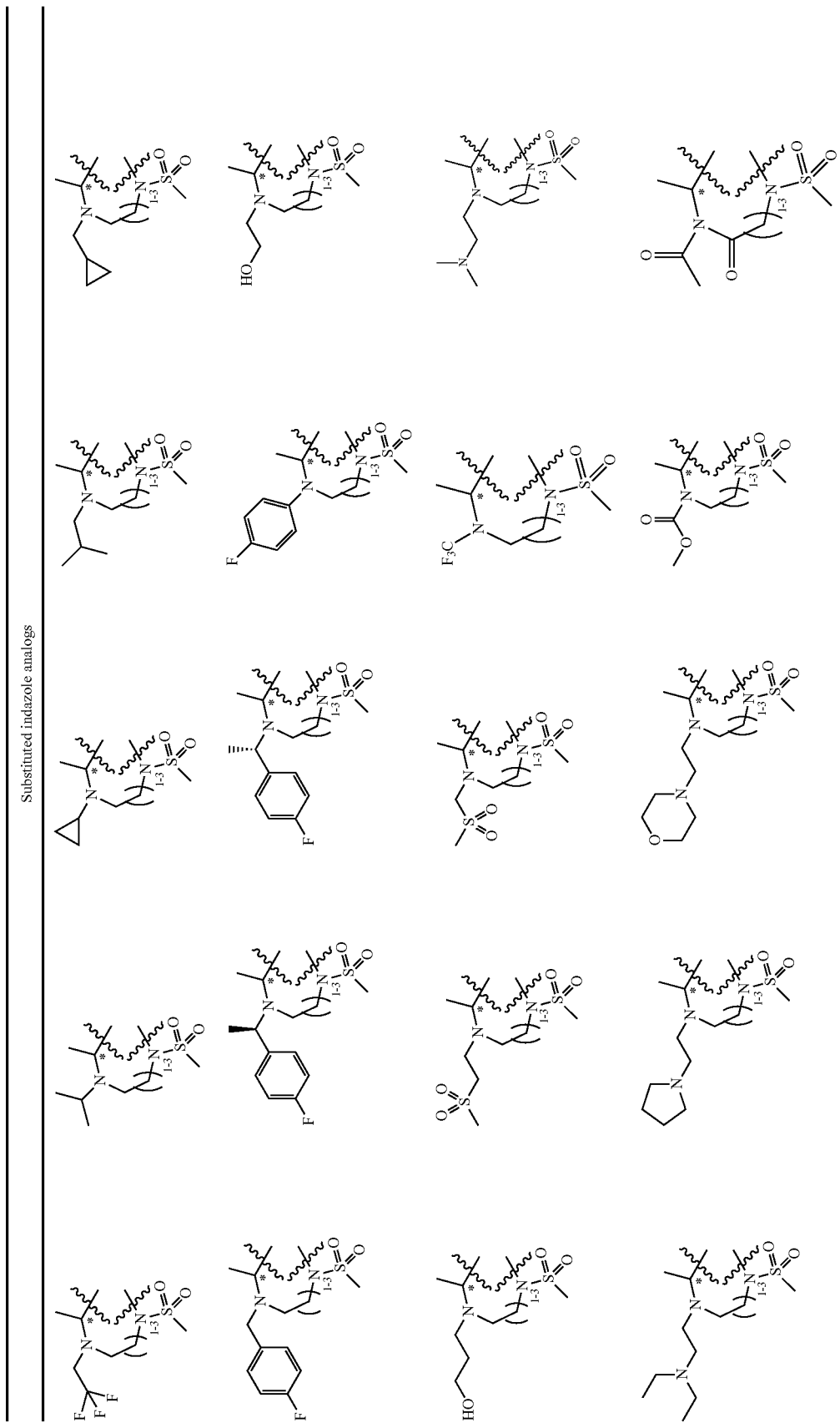

TABLE 7-continued
Substituted indazole analogs
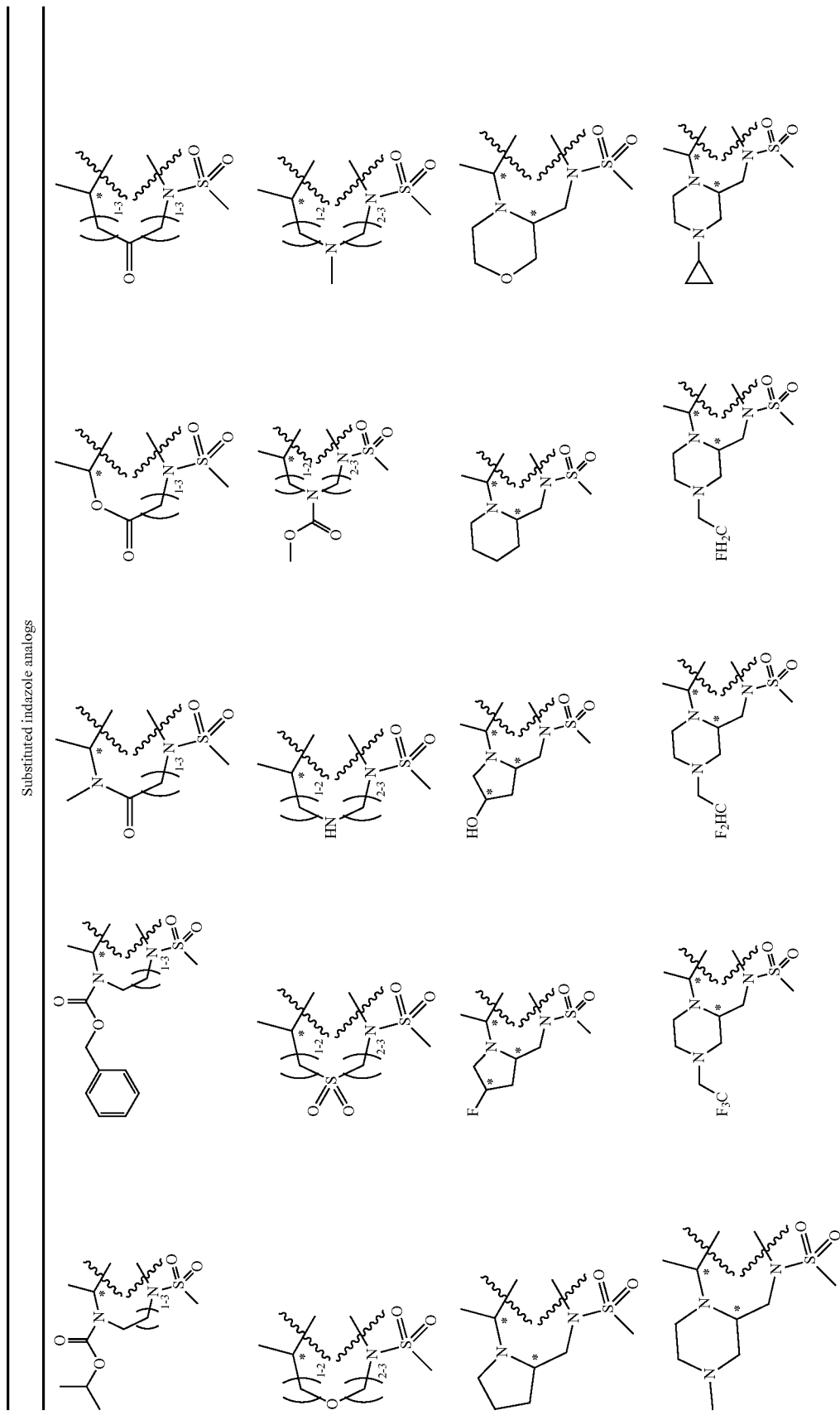

TABLE 7-continued
Substituted indazole analogs
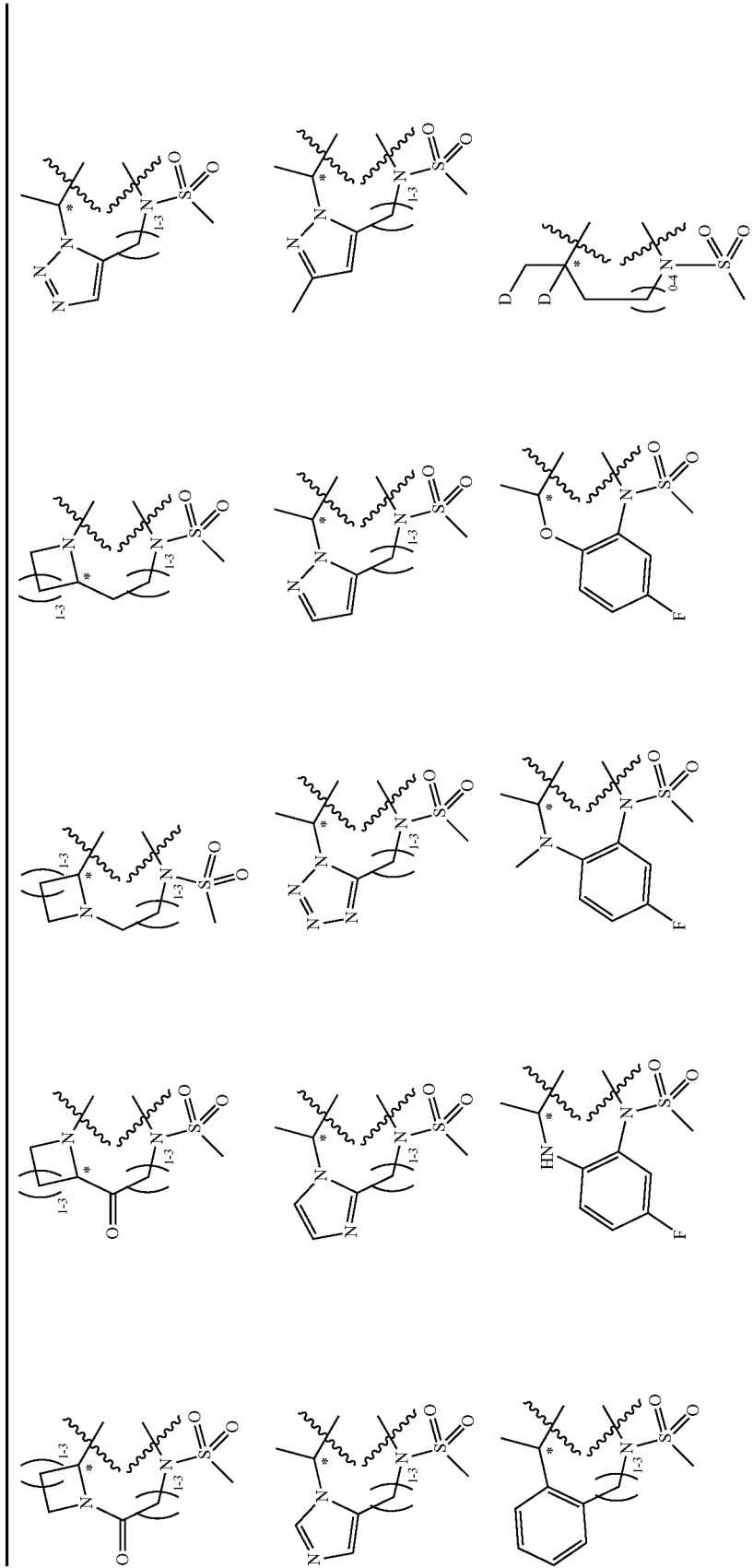

TABLE 7-continued
Substituted indazole analogs
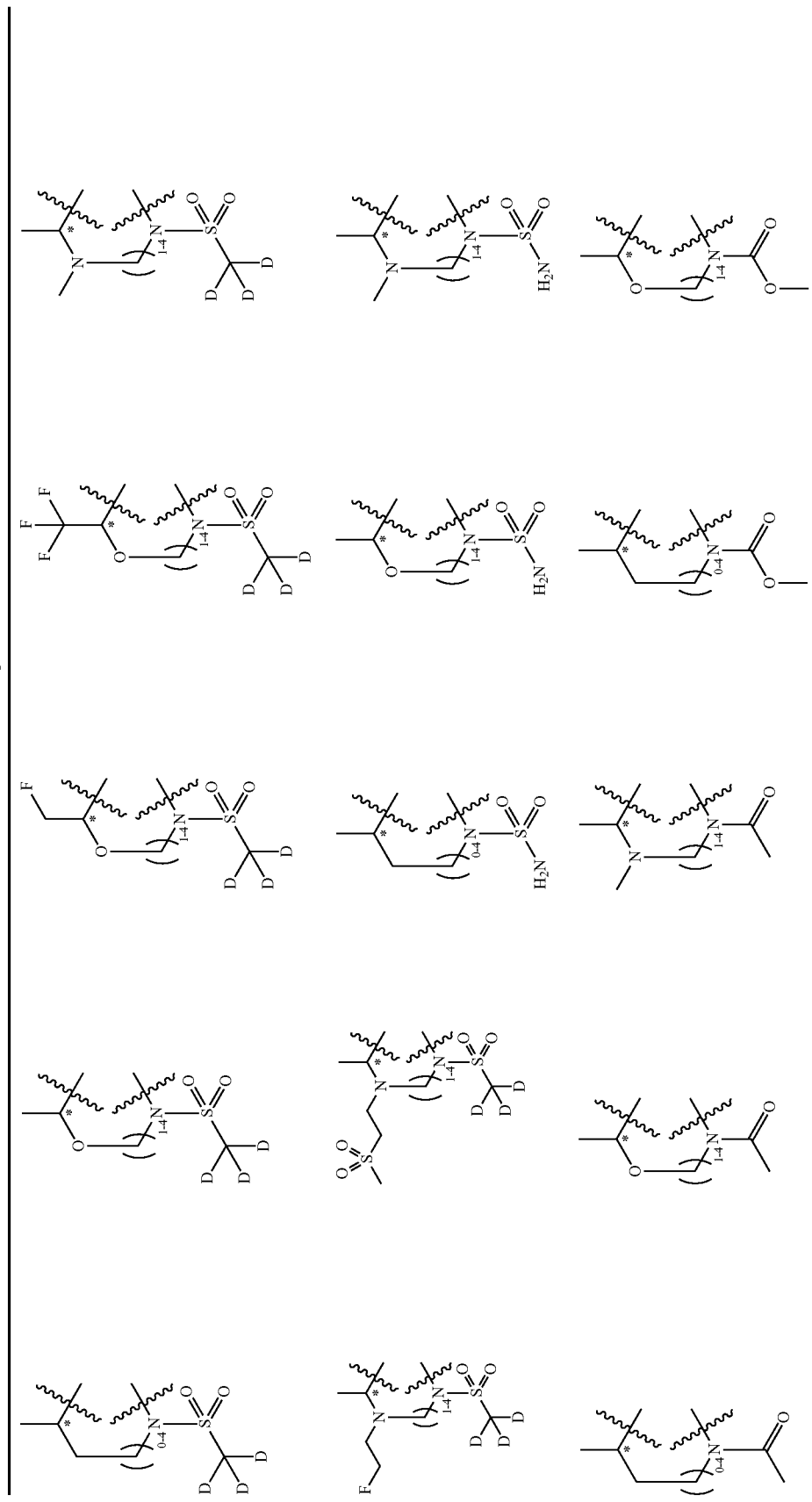

TABLE 7-continued
Substituted indazole analogs
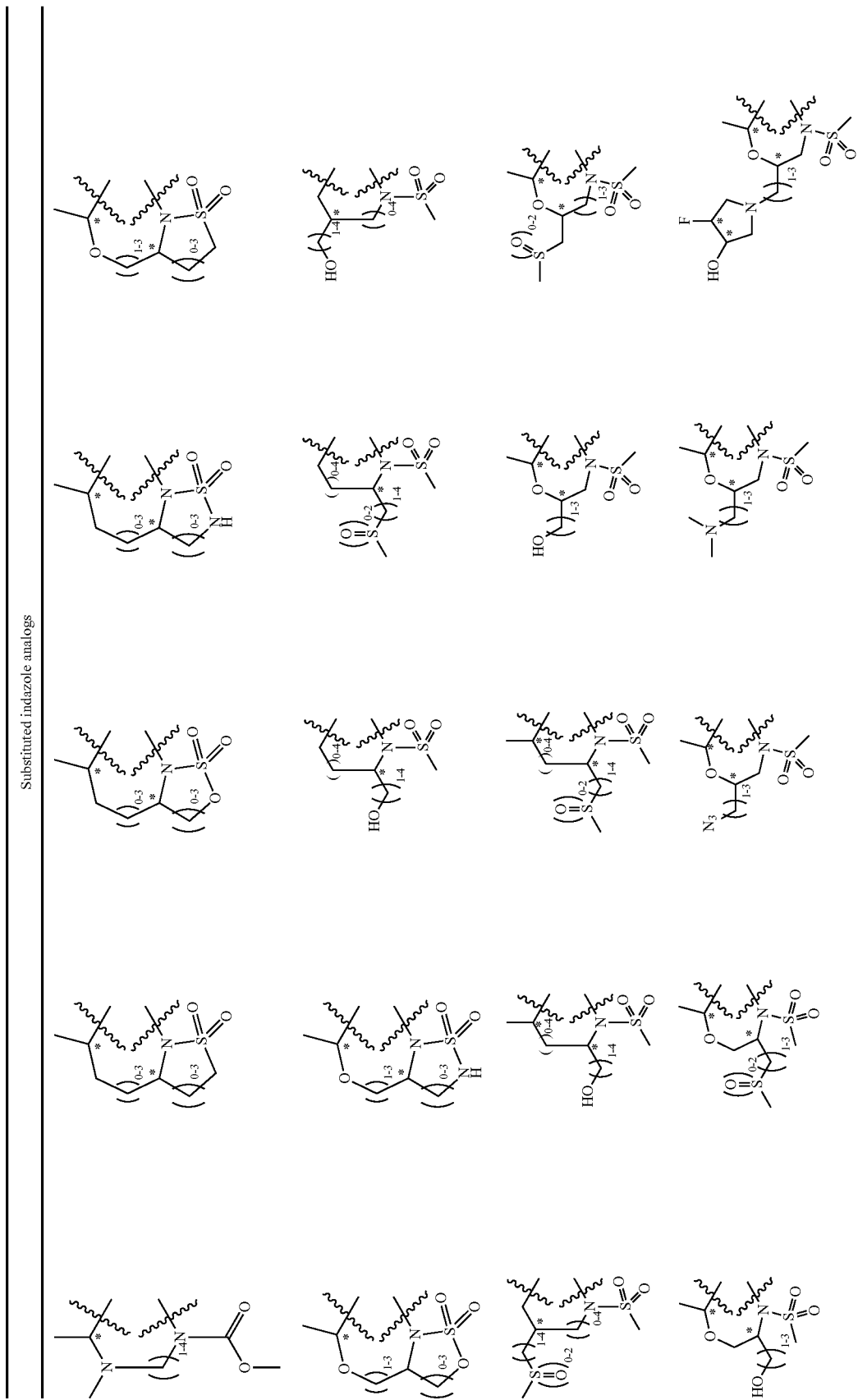

TABLE 7-continued
Substituted indazole analogs
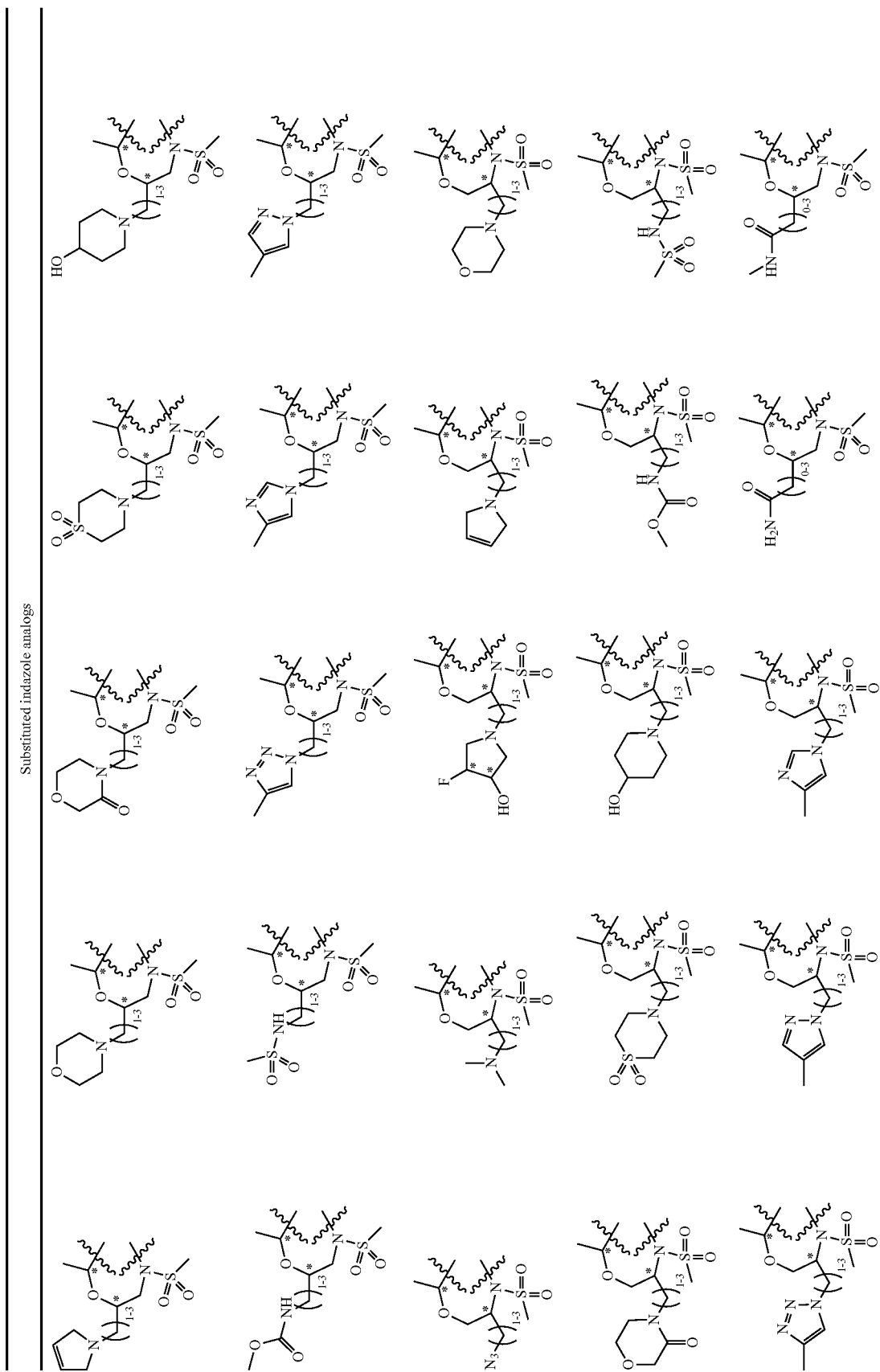

TABLE 7-continued
Substituted indazole analogs
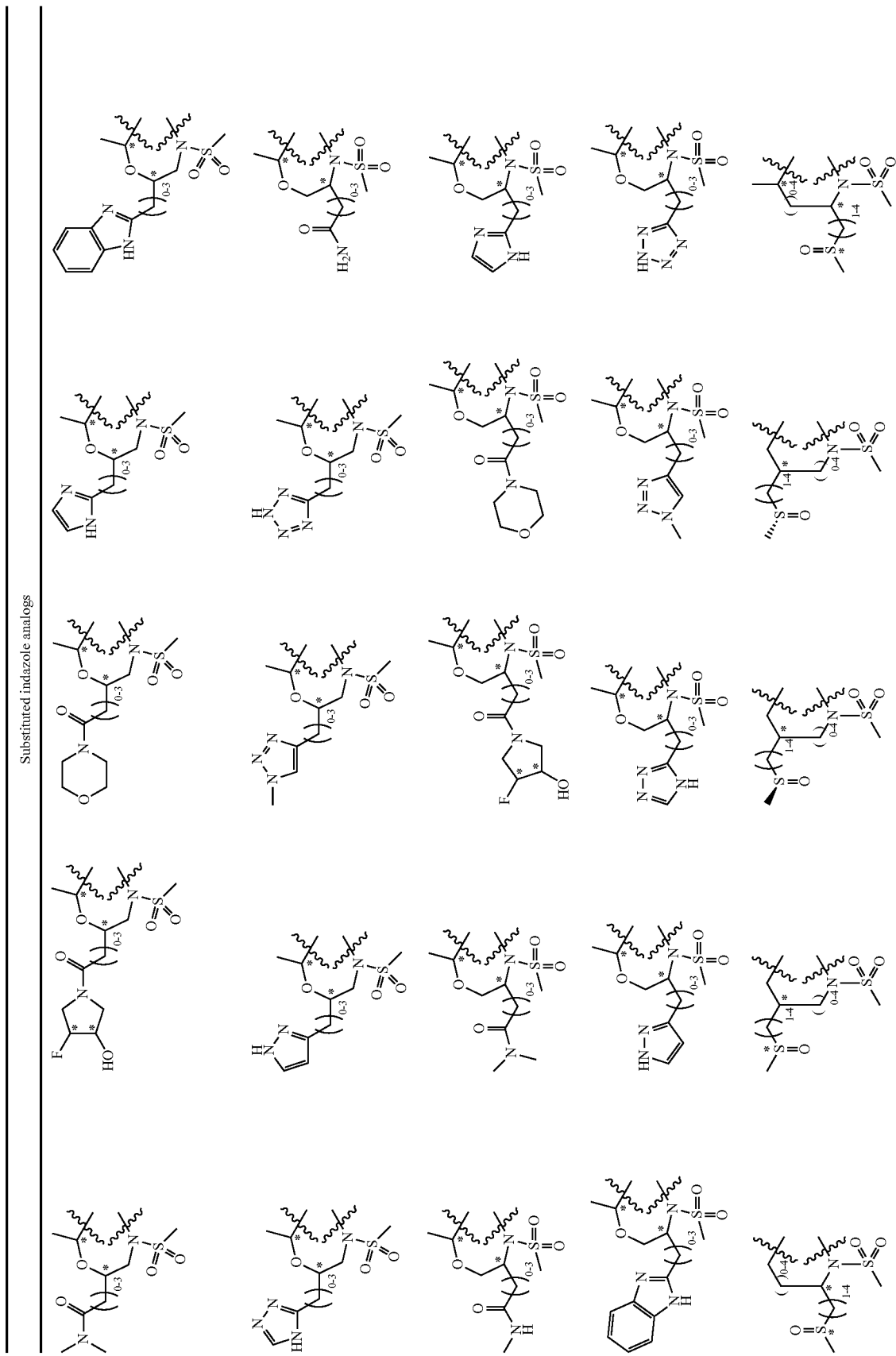

TABLE 7-continued
Substituted indazole analogs
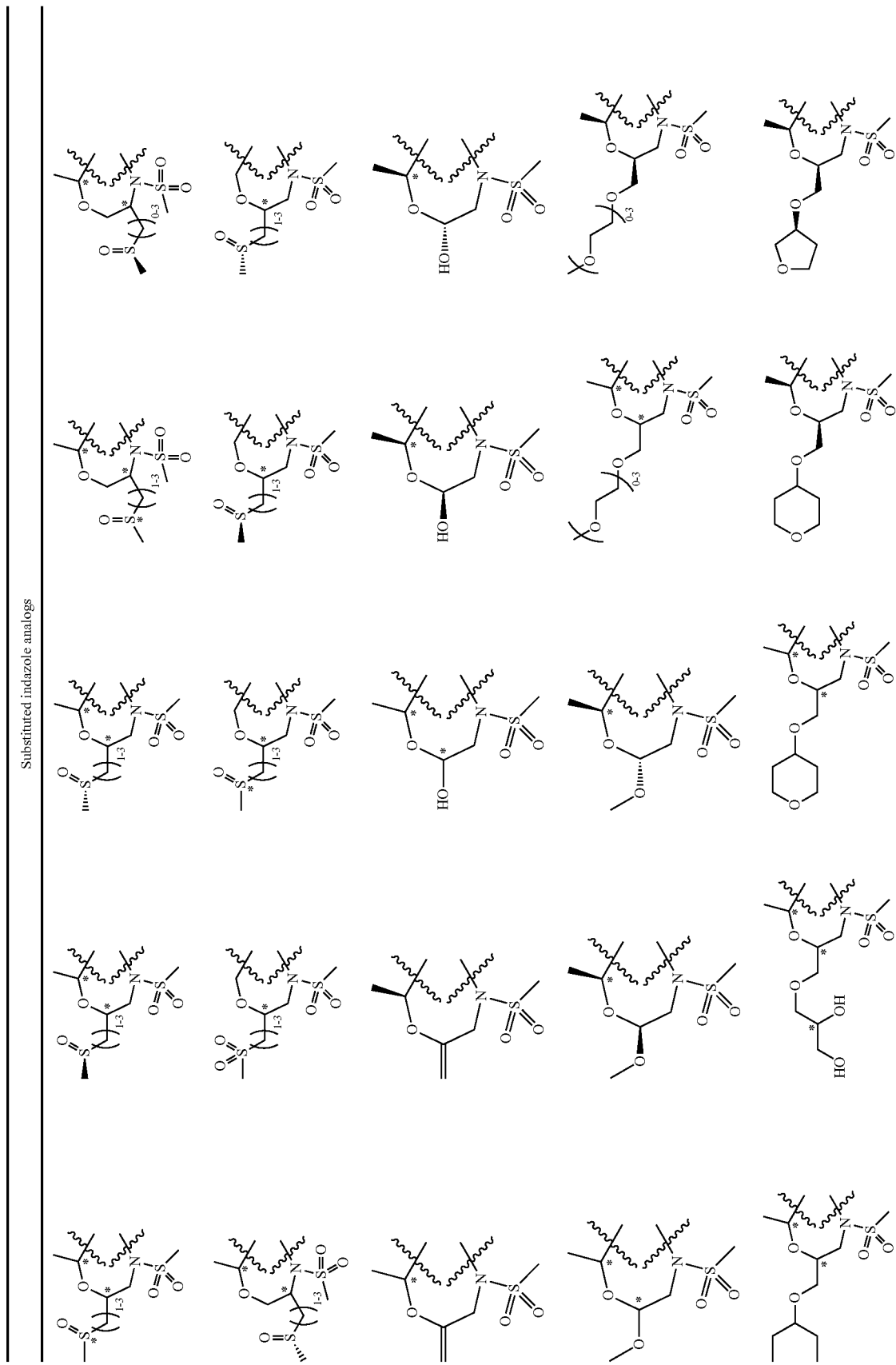

TABLE 7-continued
Substituted indazole analogs
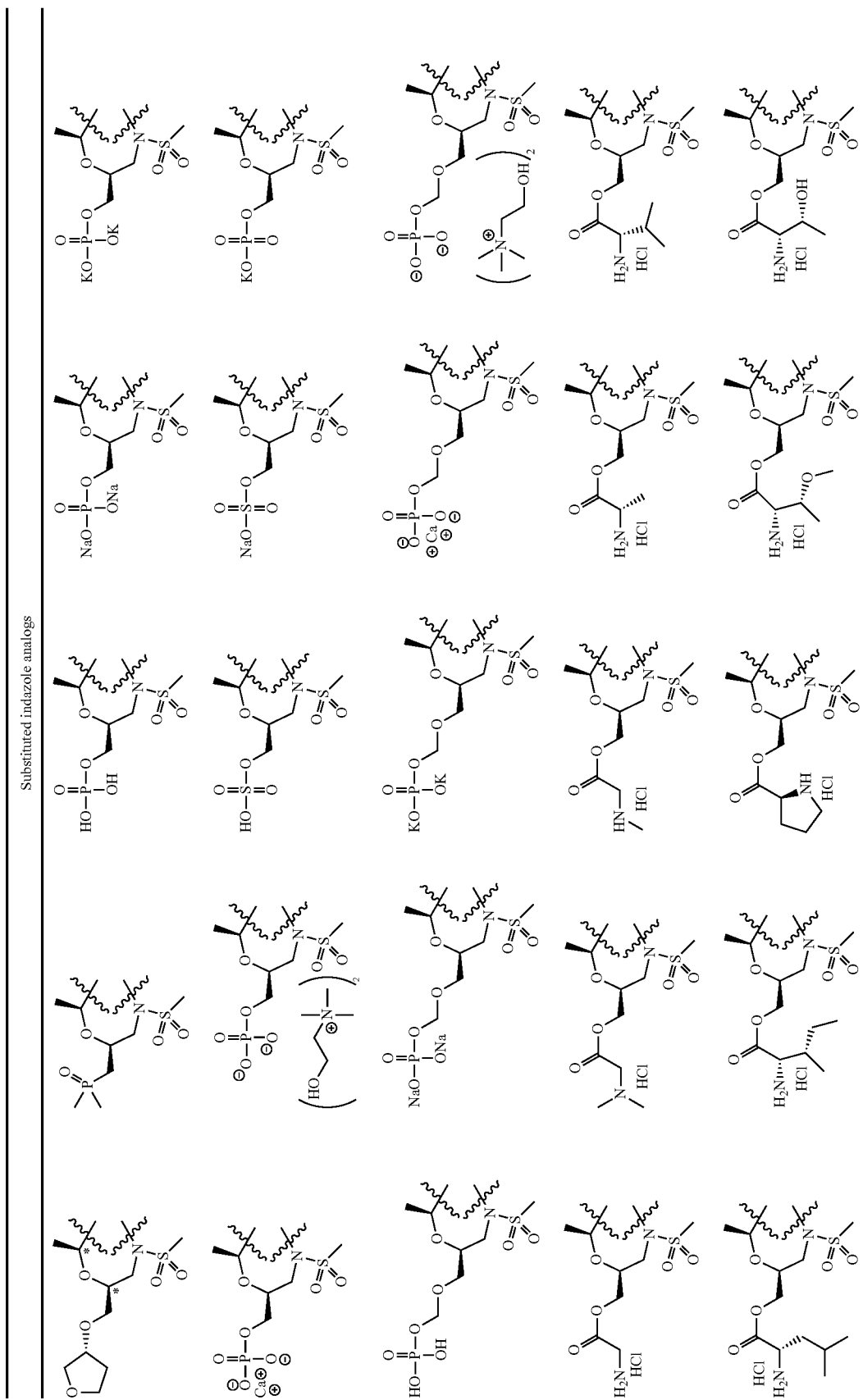

TABLE 7-continued
Substituted indazole analogs
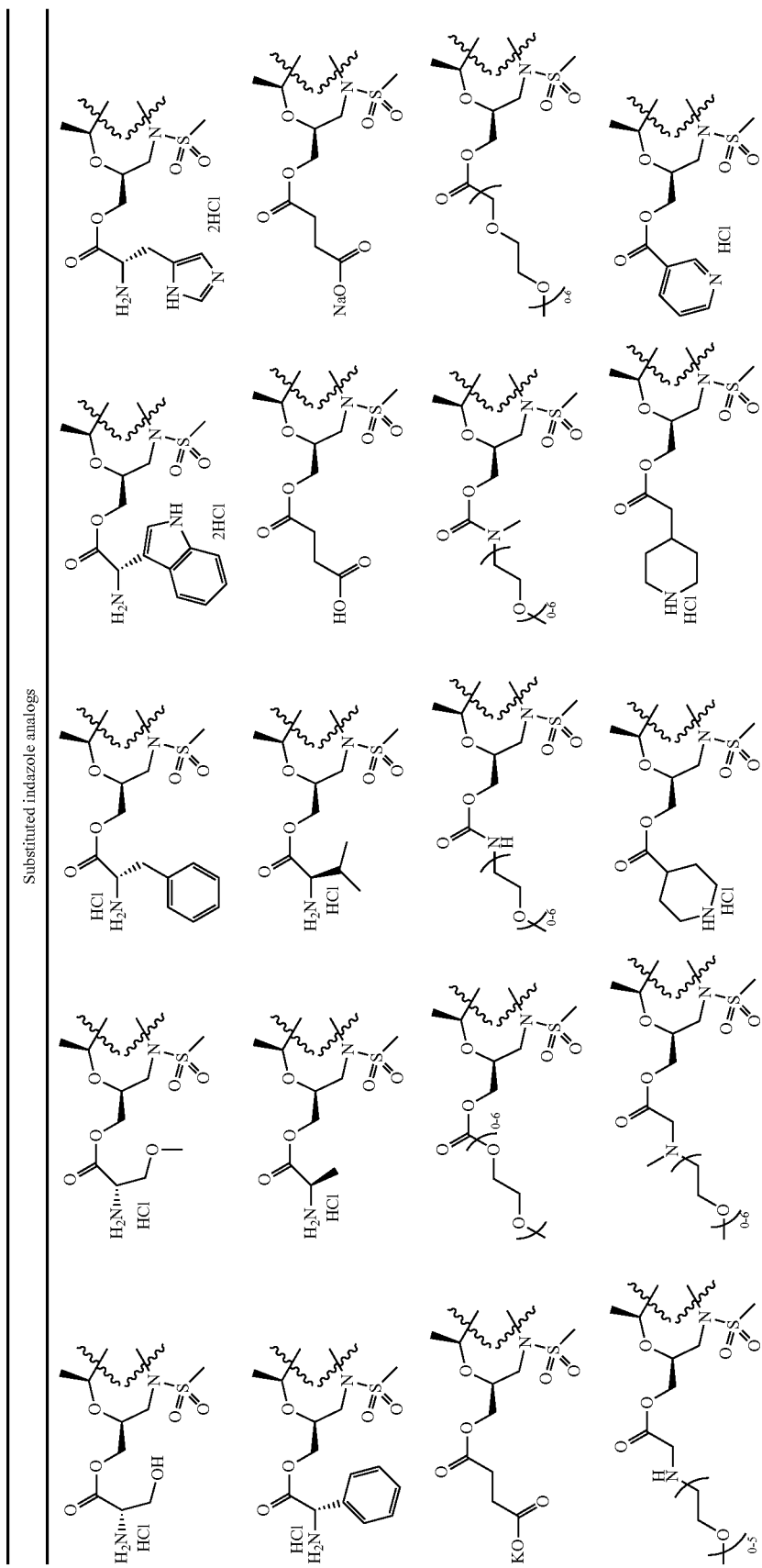

TABLE 7-continued
Substituted indazole analogs
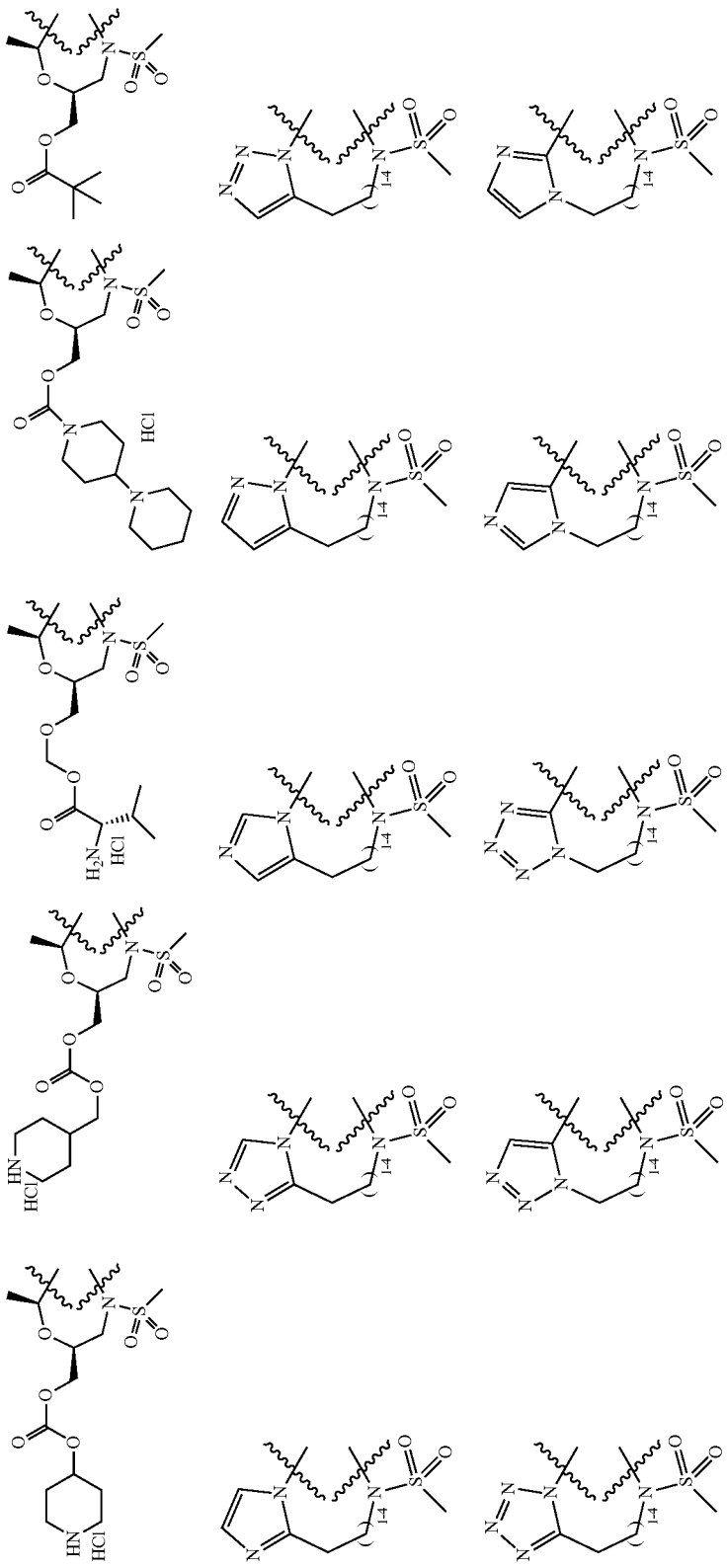

TABLE 7-continued
Substituted indazole analogs
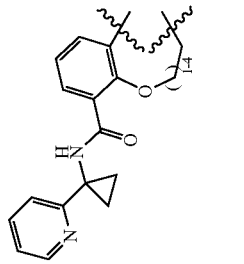 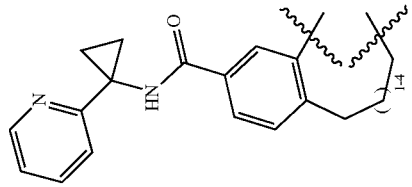
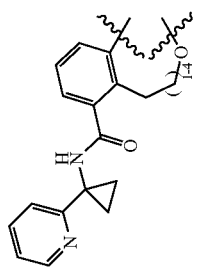 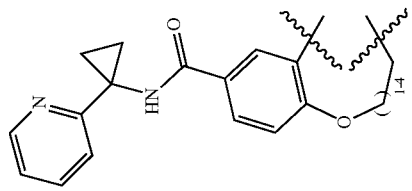
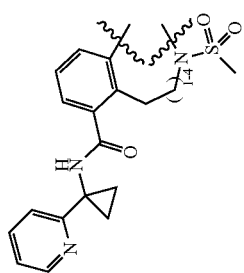 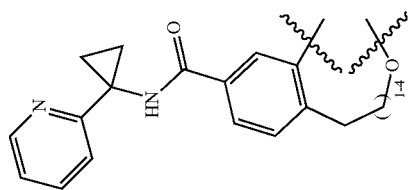
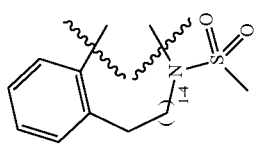 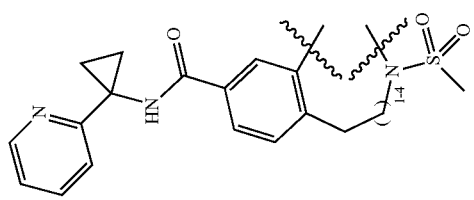
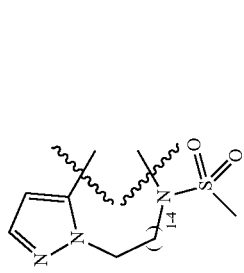 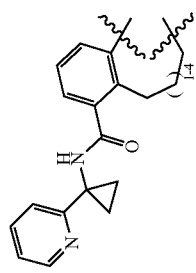

The following examples illustrate the preparation and antiviral evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

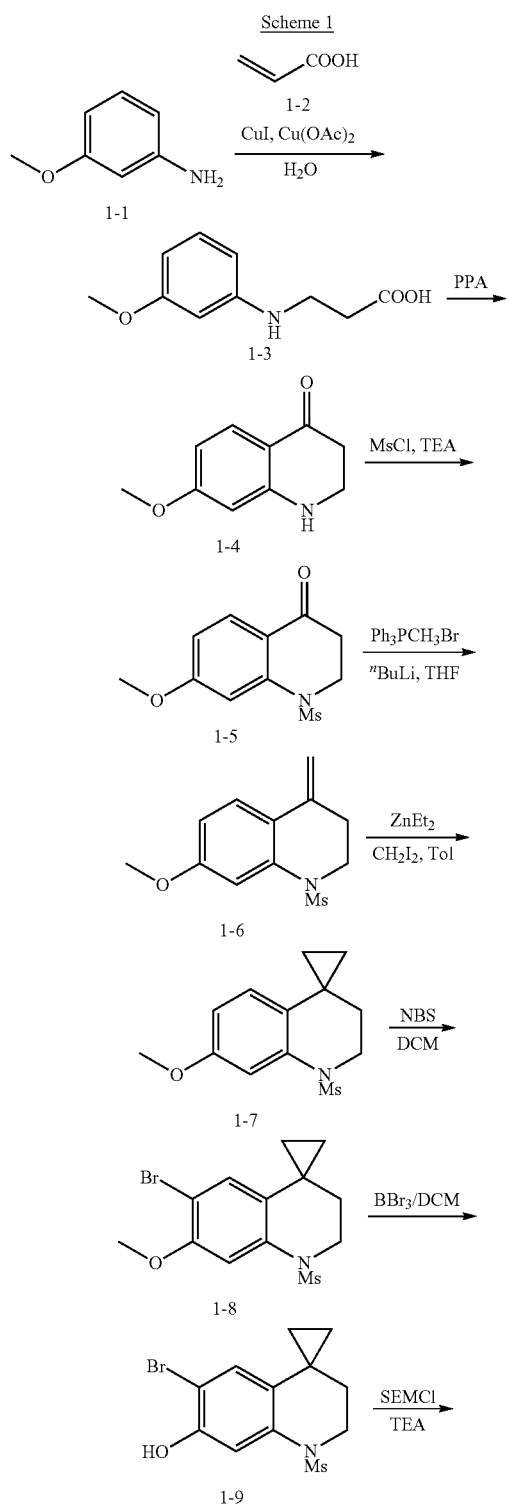

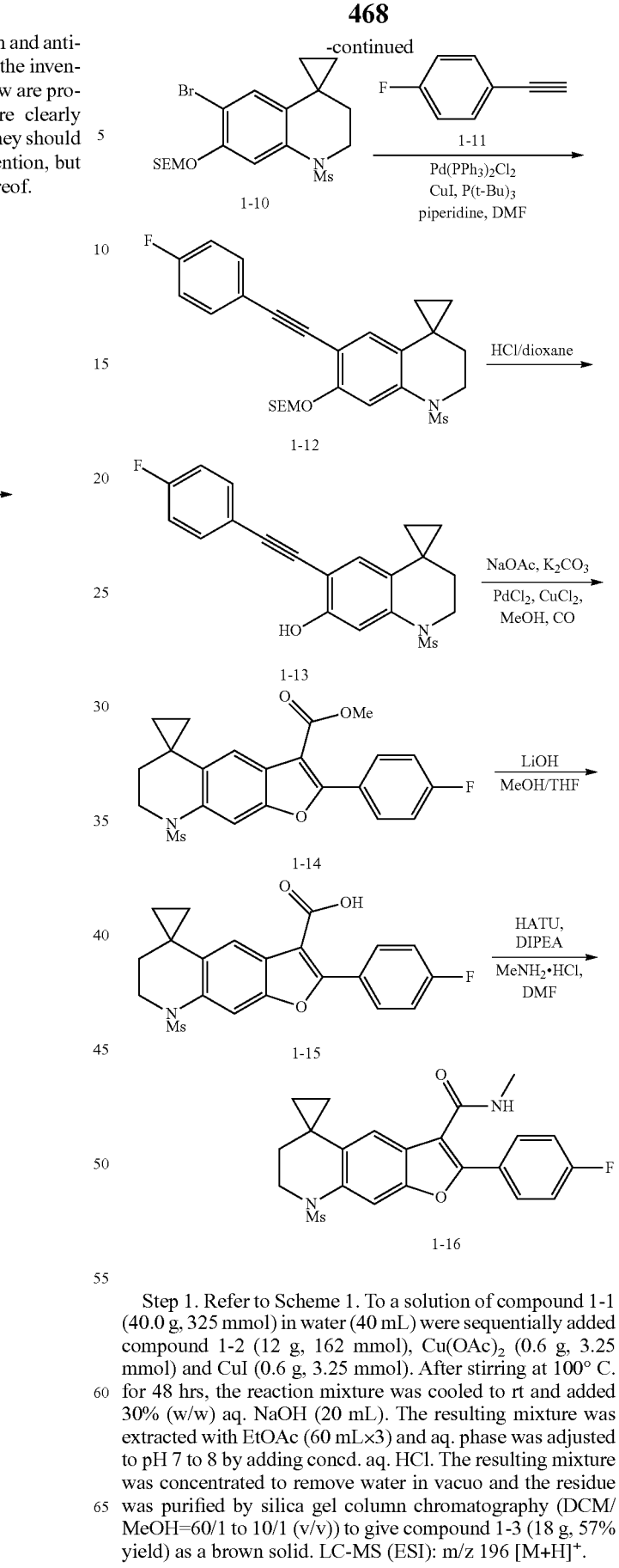

Step 1. Refer to Scheme 1. To a solution of compound 1-1 (40.0 g, 325 mmol) in water (40 mL) were sequentially added compound 1-2 (12 g, 162 mmol), Cu(OAc)$_2$ (0.6 g, 3.25 mmol) and CuI (0.6 g, 3.25 mmol). After stirring at 100° C. for 48 hrs, the reaction mixture was cooled to rt and added 30% (w/w) aq. NaOH (20 mL). The resulting mixture was extracted with EtOAc (60 mL×3) and aq. phase was adjusted to pH 7 to 8 by adding concd. aq. HCl. The resulting mixture was concentrated to remove water in vacuo and the residue was purified by silica gel column chromatography (DCM/MeOH=60/1 to 10/1 (v/v)) to give compound 1-3 (18 g, 57% yield) as a brown solid. LC-MS (ESI): m/z 196 [M+H]$^+$.

Step 2. A mixture of compound 1-3 (40.0 g, 20.5 mmol) in polyphosphoric acid (PPA) (100 mL) was mechanically stirred at 90° C. for 3 hrs. The mixture was cooled to 60° C. and ice water (50 mL) was added with stirring for 30 min. Subsequently, the mixture was extracted with EtOAc (120 mL×3). The organic extracts were combined, washed with water (40 mL) and brine (40 mL), and dried over anhydrous $Na_2SO_4$. The solvent was removed and the residue was purified by silica gel column chromatography (DCM/MeOH=100/1 (v/v)) to give compound 1-4 (18 g, 50% yield) as a yellow solid. LC-MS (ESI): m/z 178 [M+H]$^+$.

Step 3. A solution of compound 1-4 (4.00 g, 22.6 mmol) and $Et_3N$ (9.40 mL, 67.8 mmol) in DCM (200 mL) was added MsCl (6.46 g, 56.4 mmol) at 0° C. After stirring at rt for 3 hrs, the reaction was quenched by adding ice water (250 mL) and the aq. phase was extracted with DCM (100 mL×2). The organic extracts were combined, washed with water and brine, and dried over anhydrous $Na_2SO_4$. The solvent was removed that the residue was purified by silica gel column chromatography (DCM/MeOH=400/1 (v/v)) to give compound 1-5 (4.5 g, 78% yield) as a yellow solid. LC-MS (ESI): m/z 256 [M+H]$^+$; $^1$H NMR (500 MHz, $CDCl_3$): δ 8.02 (d, J=9 Hz, 1H), 7.27 (d, J=3.5 Hz, 1H), 6.79 (dd, $J_1$=9 Hz, $J_2$=2 Hz, 1H), 4.19 (t, J=6.5 Hz, 2H), 3.89 (s, 3H), 3.06 (s, 3H), 2.79 (t, J=6.5 Hz, 2H) ppm.

Step 4. To a suspension of $Ph_3PCH_3Br$ (14.0 g, 39.2 mmol) in 130 mL of THF was added n-BuLi (2.5 M in hexane, 15.7 mL, 39.2 mmol) at 0° C. After stirring at 0° C. for 2 hr, a solution of compound 1-5 (4.00 g, 15.7 mmol) in anhydrous THF (30 mL) was added. After stirring at rt overnight, the reaction mixture was quenched by adding aq. $NH_4Cl$ (sat., 20 mL). The mixture was extracted with EtOAc (600 mL×2) and the combined organic extracts were washed with water (100 mL) and brine (100 mL), and dried with anhydrous $Na_2SO_4$. The solvent was removed and the residue was purified by silica gel column chromatography (DCM) to give compound 1-6 (1.2 g, 30% yield). LC-MS (ESI): m/z 254 [M+H]$^+$; $^1$H NMR (500 MHz, $CDCl_3$): δ 7.75 (d, J=9 Hz, 1H), 7.12 (d, J=2.5 Hz, 1H), 6.78 (dd, $J_1$=9 Hz, $J_2$=3 Hz, 1H), 5.59 (s, 1H), 4.91 (s, 1H), 3.76 (s, 3H), 3.73 (t, J=6 Hz, 2H), 3.08 (s, 3H), 2.70 (t, J=6 Hz, 2H) ppm.

Step 5. To a solution of compound 1-6 (2.70 g, 10.7 mmol) in dry toluene (200 mL) was added $ZnEt_2$ (1 M in hexane, 85.4 mL, 85.4 mmol), followed by $CH_2I_2$ (46 g, 171 mmol) at 0° C. After stirring at rt overnight, the reaction mixture was partitioned between EtOAc (100 mL) and 5% HCl (100 mL). The organic layer was dried with anhydrous $Na_2SO_4$ and concentrated and the residue was purified by silica gel column chromatography (DCM) to give compound 1-7 (2.1 g, 72% yield). LC-MS (ESI): m/z 268 [M+H]$^+$; $^1$H NMR (500 MHz, $CDCl_3$): δ 7.33 (d, J=2.5 Hz, 1H), 6.66 (dd, $J_1$=14 Hz, $J_2$=3 Hz, 1H), 6.61 (d, J=9 Hz, 1H), 3.95-3.92 (m, 2H), 3.78 (s, 3H), 2.91 (s, 3H), 1.81-1.83 (m, 2H), 1.01 (dd, $J_1$=6.5 Hz, $J_2$=5 Hz, 2H), 0.85 (dd, $J_1$=6.5 Hz, $J_2$=5 Hz, 2H) ppm.

Step 6. To a solution of compound 1-7 (290 mg, 1.09 mmol) in DCM (10 mL) was added NBS (194 mg, 1.09 mmol) at 0° C. After stirring at rt for 1 hr, the reaction mixture was concentrated and the residue was purified by silica gel column chromatography (Petroleum ether/ethyl acetate=10/1 (v/v)) to give compound 1-8 (220 mg, 59% yield) as a yellow oil. LC-MS (ESI): m/z 346 [M+H]$^+$; $^1$H NMR (500 MHz, $CDCl_3$): δ 7.39 (s, 1H), 6.84 (s, 1H), 3.93 (t, J=5.5 Hz, 2H), 3.88 (s, 3H), 2.90 (s, 3H), 1.81 (t, J=5.5 Hz, 2H), 1.03 (t, J=5 Hz, 2H), 0.89 (t, J=5 Hz, 2H) ppm.

Step 7. To a solution of compound 1-8 (200 mg, 0.58 mmol) in $CH_2Cl_2$ (6 mL) was added $BBr_3$ (4 N in DCM, 0.6 mL, 2.4 mmol) at −20° C. After stirring at 0° C. for 1 hr, the reaction was quenched by adding ice-water (50 mL). The mixture was extracted with DCM (50 mL×2) and the combined extracts were washed with water and brine, and dried with anhydrous $Na_2SO_4$. The solvent was removed and the residue was purified by silica gel column chromatography (Petroleum ether/ethyl acetate=10/1 (v/v)) to give compound 1-9 (120 mg, 63% yield) as a red solid. LC-MS (ESI): m/z 331 [M+H]$^+$; $^1$H NMR (500 MHz, $CDCl_3$): δ 7.44 (s, 1H), 6.77 (s, 1H), 5.47 (br s, 1H), 3.89-3.92 (m, 2H), 2.95 (s, 3H), 2.90 (s, 3H), 1.81 (t, J=5.5 Hz, 2H), 0.89-1.01 (m, 2H), 0.87-0.89 (m, 2H) ppm.

Step 8. To a solution of compound 1-9 (1.60 g, 4.82 mmol) in 30 mL THF was added DMAP (30 mg) and TEA (1.46 g, 14.46 mmol). The resulting mixture was cooled to 0° C. and SEMCl (1.60 g, 9.64 mmol) was added. After stirring at rt for 10 hrs, the reaction mixture was poured into water (50 mL) and extracted with EtOAc (60 mL×3). The combined organic extracts were washed brine (30 mL) and dried with anhydrous $Na_2SO_4$. The solvent was removed and the residue was dried in vacuo to give crude compound 1-10 (2.2 g, 99% yield) as a yellow oil. LC-MS (ESI): m/z 485 [M+Na]$^+$.

Step 9. To a solution of compound 1-10 (1.60 g, 3.47 mmol) in 20 mL of DMF were added 1-11 (0.50 g, 4.16 mmol), CuI (33 mg, 0.17 mmol), $Pd(PPh_3)_2Cl_2$ (244 mg, 0.35 mmol), $P(t-Bu)_3$ (140 mg, 0.69 mmol) and piperidine (1.18 g, 13.9 mmol). The resulting mixture was flushed with Ar and stirred at 80° C. overnight. Subsequently, the reaction mixture was cooled to rt, poured into water (60 mL), and extracted with EtOAc (100 mL×2). The combined organic extracts were washed with water (50 mL×3) and dried with anhydrous $Na_2SO_4$. The solvent was removed and the residue was purified by silica gel column chromatography (Petroleum ether/acetone=10/1 (v/v)) to give compound 1-12 (780 mg, 45% yield) as a yellow oil. LC-MS (ESI): m/z 524 [M+Na]$^+$.

Step 10. To a solution of compound 1-12 (750 mg, 1.50 mmol) in dioxane (10 mL) was added 4 N HCl/dioxane (2 mL). After stirring at rt for 2 hrs, the reaction mixture was concentrated and the residue was dried in vacuo to give crude compound 1-13 (600 mg, quantitative yield) as a yellow oil. LC-MS (ESI): m/z 372 [M+H]$^+$.

Step 11. To a solution of compound 1-13 (600 mg, 1.62 mmol) in MeOH (20 mL) was added NaOAc (265 mg, 3.24 mmol), $K_2CO_3$ (448 mg, 3.24 mmol), $PdCl_2$ (28 mg, 0.16 mmol), and $CuCl_2$ (653 mg, 4.86 mmol). The resulting mixture was flushed with CO and stirred at rt overnight under an atmosphere of CO. The mixture was diluted with EtOAc (80 mL) and filtered through Celite®545. The filtrate was washed with water (30 mL) and brine (30 mL), and dried with anhydrous $Na_2SO_4$. The solvent was removed and the residue was purified by silica gel column chromatography (Petroleum ether/acetone=16/1 (v/v)) to give compound 1-14 (70 mg, 10% yield) as a white solid. LC-MS (ESI): m/z 429 [M+H]$^+$.

Step 12. To a solution of compound 1-14 (70 mg, 0.16 mmol) in MeOH/THF (1 mL/2 mL) was added LiOH (0.65 mmol). After stirring at 70° C. for 2 hr, the reaction mixture was cooled to rt and acidified by adding 1N aq. HCl (7 mL). The resulting mixture was filtered and the solid was dried in vacuo to give compound 1-15 (60 mg, 91% yield) as a white solid. LC-MS (ESI): m/z 454 [M+K]$^+$.

Step 13. To a solution of compound 1-15 (60 mg, 0.14 mmol) in DMF (1.5 mL) was added HATU (66 mg, 0.17 mmol). After stirring at rt for 30 min, the mixture were added DIPEA (181 mg, 1.40 mmol) and $MeNH_2$.HCl (47 mg, 0.70 mmol). The resulting mixture was stirred at rt for 20 min and poured into water (50 mL). The suspension was filtered and the obtained solid was purified by silica gel column chromatography (DCM/MeOH=600/1 (v/v)) to give compound 1-16

(30 mg, 50% yield) as a white solid. LC-MS (ESI): m/z 429 [M+H]+; 1H NMR (500 MHz, CDCl3): δ 7.93 (s, 1H), 7.85 (dd, $J_1$=8.5 Hz, $J_2$=5.5 Hz, 2H), 7.26 (d, J=3 Hz, 1H), 7.19 (t, J=8.5 Hz, 2H), 5.74 (br s, 1H), 3.99 (t, J=6.0 Hz, 2H), 2.98 (d, J=5.0 Hz, 3H), 2.89 (s, 3H), 1.88 (t, J=6.0 Hz, 2H), 1.17-1.19 (m, 2H), 0.90-0.93 (m, 2H) ppm.

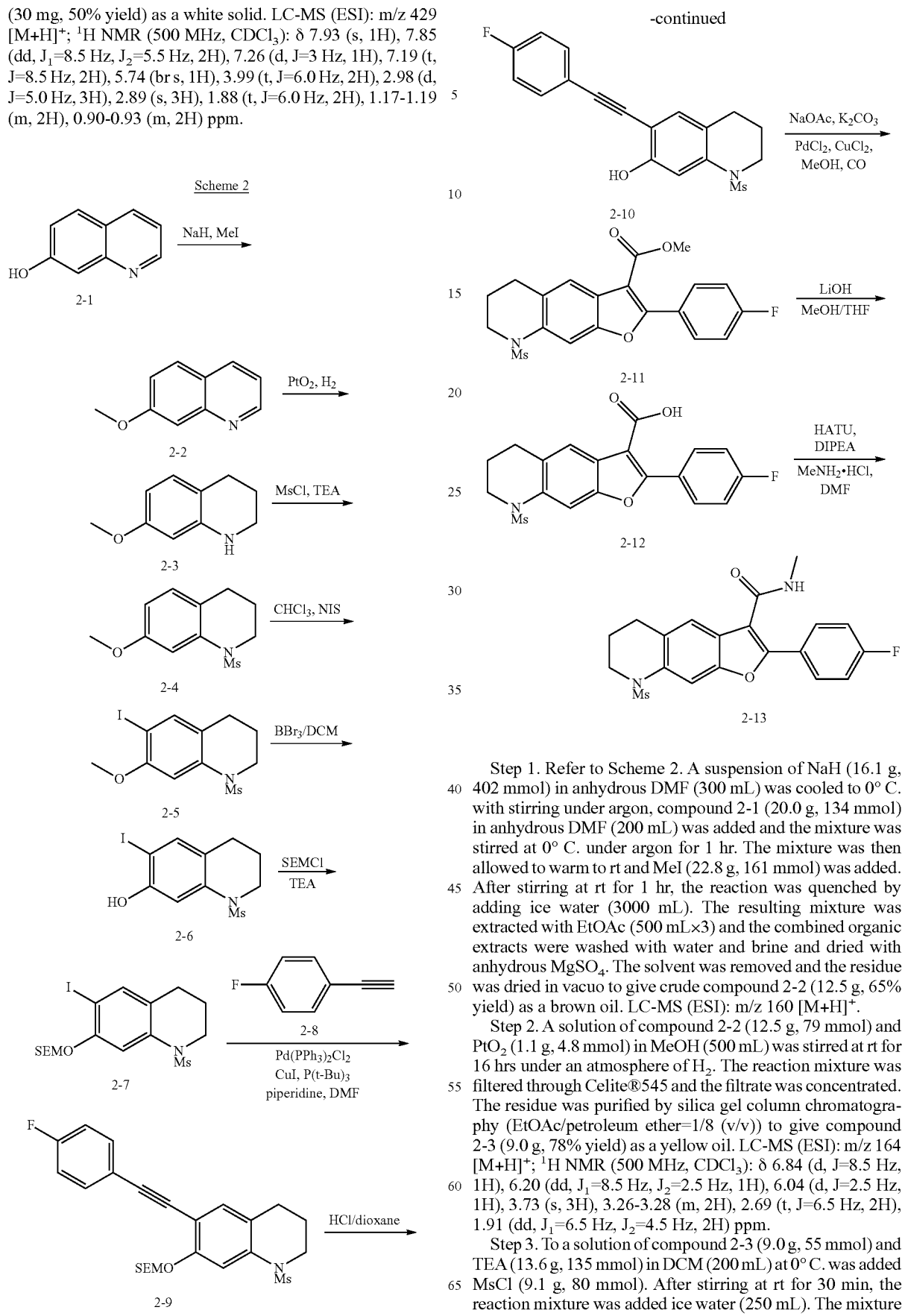

Step 1. Refer to Scheme 2. A suspension of NaH (16.1 g, 402 mmol) in anhydrous DMF (300 mL) was cooled to 0° C. with stirring under argon, compound 2-1 (20.0 g, 134 mmol) in anhydrous DMF (200 mL) was added and the mixture was stirred at 0° C. under argon for 1 hr. The mixture was then allowed to warm to rt and MeI (22.8 g, 161 mmol) was added. After stirring at rt for 1 hr, the reaction was quenched by adding ice water (3000 mL). The resulting mixture was extracted with EtOAc (500 mL×3) and the combined organic extracts were washed with water and brine and dried with anhydrous MgSO4. The solvent was removed and the residue was dried in vacuo to give crude compound 2-2 (12.5 g, 65% yield) as a brown oil. LC-MS (ESI): m/z 160 [M+H]+.

Step 2. A solution of compound 2-2 (12.5 g, 79 mmol) and PtO2 (1.1 g, 4.8 mmol) in MeOH (500 mL) was stirred at rt for 16 hrs under an atmosphere of H2. The reaction mixture was filtered through Celite®545 and the filtrate was concentrated. The residue was purified by silica gel column chromatography (EtOAc/petroleum ether=1/8 (v/v)) to give compound 2-3 (9.0 g, 78% yield) as a yellow oil. LC-MS (ESI): m/z 164 [M+H]+; 1H NMR (500 MHz, CDCl3): δ 6.84 (d, J=8.5 Hz, 1H), 6.20 (dd, $J_1$=8.5 Hz, $J_2$=2.5 Hz, 1H), 6.04 (d, J=2.5 Hz, 1H), 3.73 (s, 3H), 3.26-3.28 (m, 2H), 2.69 (t, J=6.5 Hz, 2H), 1.91 (dd, $J_1$=6.5 Hz, $J_2$=4.5 Hz, 2H) ppm.

Step 3. To a solution of compound 2-3 (9.0 g, 55 mmol) and TEA (13.6 g, 135 mmol) in DCM (200 mL) at 0° C. was added MsCl (9.1 g, 80 mmol). After stirring at rt for 30 min, the reaction mixture was added ice water (250 mL). The mixture was extracted with DCM (100 mL×2) and the combined organic extracts were washed with water and brine and dried with anhydrous $Na_2SO_4$. The solvent was removed and the residue was purified by silica gel column chromatography (EtOAc/Petroleum ether=1/6 (v/v)) to give compound 2-4 (10.6 g, 80% yield) as a yellow oil. LC-MS (ESI): m/z 242 $[M+H]^+$.

Step 4. N-iodosuccinimide (NIS) (19.8 g, 88.0 mmol) was added to a solution of compound 2-4 (10.6 g, 44 mmol) in $CHCl_3$ (200 mL) at 0° C. After stirring at rt for 16 hrs, the reaction mixture was concentrated and the residue was purified by silica gel column chromatography (EtOAc/Petroleum ether=1/6 (v/v)) to give compound 2-6 (12.6 g, 80% yield). LC-MS (ESI): m/z 368 $[M+H]^+$; $^1$H NMR (500 MHz, $CDCl_3$): δ 7.52 (s, 1H), 7.32 (s, 1H), 3.86 (s, 3H), 3.81-3.79 (m, 2H), 2.88 (s, 3H), 2.77 (t, J=6.5 Hz, 2H), 1.95 (t, J=5.5 Hz, 2H) ppm.

Step 5. A solution of $BBr_3$ (13.6 mL/4.0M, 54.4 mmol) in DCM was added to a solution of compound 2-5 (5.04 g, 13.6 mmol) in $CH_2Cl_2$ (100 mL) at −20° C. After stirring at −20° C. for 1 hr, the reaction mixture was added ice water (200 mL). The resulting mixture was extracted with DCM (100 mL×2) and the combined organic extracts were washed water and brine and dried with anhydrous $Na_2SO_4$. The solvent was removed and the residue was purified by silica gel column chromatography (EtOAc/Petroleum ether=1/12 (v/v)) to give compound 2-6 (1.4 g, 25% yield) as a white solid. LC-MS (ESI): m/z 354 $[M+H]^+$; $^1$H NMR (500 MHz, $CDCl_3$): δ 7.42 (s, 2H), 5.31 (s, 1H), 3.78 (t, J=6 Hz, 2H), 2.93 (s, 3H), 2.76 (t, J=6.5 Hz, 2H), 1.95 (t, J=5.5 Hz, 2H) ppm.

Step 6. To a solution of compound 2-6 (1.2 g, 3.4 mmol) in 20 mL THF was added DMAP (20 mg), followed by $Et_3N$ (0.69 g, 6.8 mmol) at rt. The resulting mixture was cooled to 0° C. and SEMCl (0.68 g, 4.08 mmol) was added. After stirring at rt for 3 hrs, the reaction mixture was poured into ice water (50 mL). The resulting mixture was extracted with EtOAc (60 mL×3) and the combined organic extracts were washed with brine (30 mL) and dried with anhydrous $Na_2SO_4$. The solvent was removed and the residue was dried in vacuo to give crude compound 2-7 (1.6 g, quantitative yield) as a yellow oil. LC-MS (ESI): m/z 506 $[M+Na]^+$.

Step 7. To a solution of 2-7 (1.60 g, 3.31 mmol) in 20 mL DMF were added 2-8 (0.48 g, 4.0 mmol), CuI (32 mg, 0.17 mmol), $Pd(PPh_3)_2Cl_2$ (232 mg, 0.330 mmol), P(t-Bu)$_3$ (133 mg, 0.660 mmol) and piperidine (1.13 g, 13.2 mmol). The resulting mixture was flushed with Ar and stirred at 80° C. overnight. The resulting mixture was poured in to ice water (60 mL) and extracted with EtOAc (100 mL×2). The combined organic extracts were washed with water (250 mL ×5) and dried with anhydrous $Na_2SO_4$. The solvent was removed and the residue was purified by silica gel column chromatography (Acetone/petroleum ether=1/10 (v/v)) to give compound 2-9 (1.2 g, 76% yield) as a yellow oil. LC-MS (ESI): m/z 498 $[M+Na]^+$.

Step 8. To a solution of compound 2-9 (1.2 g, 2.52 mmol) in 16 mL dioxane was added 4 N HCl in dioxane (7.6 mL) at rt. After stirring at rt for 30 min, the reaction mixture was concentrated and the residue was dried in vacuo to give crude compound 2-10 (870 mg, quantitative yield) as a yellow oil, which was used directly for the next step without purification. LC-MS (ESI): m/z 346 $[M+H]^+$.

Step 9. To a solution of compound 2-10 (600 mg, 1.74 mmol) in MeOH (17 mL) were added NaOAc (285 mg, 3.48 mmol), $K_2CO_3$ (481 mg, 3.48 mmol), $PdCl_2$ (31.0 mg, 0.17 mmol) and $CuCl_2$ (702 mg, 5.22 mmol) and the resulting mixture was flushed with CO. After stirring at rt overnight, the mixture was concentrated and the residue was diluted with EtOAc (100 mL) and filtered. The filtrate was washed with water (30 mL) and brine (30 mL) and dried with anhydrous $Na_2SO_4$. The solvent was removed and the residue was purified by silica gel column chromatography (Acetone/petroleum ether=1/10 (v/v)) to give compound 2-11 (140 mg, 20% yield) as a yellow solid. LC-MS (ESI): m/z 404 $[M+H]^+$.

Step 10. To a solution of compound 2-11 (140 mg, 0.35 mmol) in MeOH/THF (2 mL/4 mL) was added $LiOH.H_2O$ (58 mg, 1.4 mmol) at rt. After stirring at 70° C. for 1 hr, the reaction mixture was cooled to 0° C. and acidified with 1N aqueous HCl (3 mL). The suspension was filtered and the solid was dried in vacuo to give compound 2-12 (136 mg, quantitative yield) as a white solid, which was used directly for the next step without further purification. LC-MS (ESI): m/z 390 $[M+H]^+$.

Step 11. To a solution of compound 2-12 (60 mg, 0.15 mmol) in DMF (2 mL) was added HATU (68.4 mg, 0.18 mmol). The resulting mixture was stirred at rt for 30 min and then N,N-diisopropylethylamine (DIEA or DIPEA) (194 mg, 1.5 mmol) and $MeNH_2.HCl$ (52 mg, 0.77 mmol) were added. After stirring at rt for 20 min, the reaction mixture was poured into ice water (50 mL). The suspension was filtered and the collected solid was purified by silica gel column chromatography to give compound 2-13 (20 mg, 33% yield). LC-MS (ESI): m/z 403 $[M+H]^+$; $^1$H NMR (500 MHz, $CDCl_3$): δ 7.88-7.93 (m, 3H), 7.60 (s, 1H), 7.19 (t, J=9.0 Hz, 2H), 5.80 (br s, 1H), 3.85-3.89 (m, 2H), 3.00 (d, J=4.5 Hz, 3H), 2.95 (t, J=6.5 Hz, 2H), 2.89 (s, 3H), 2.01-2.06 (m, 2H) ppm.

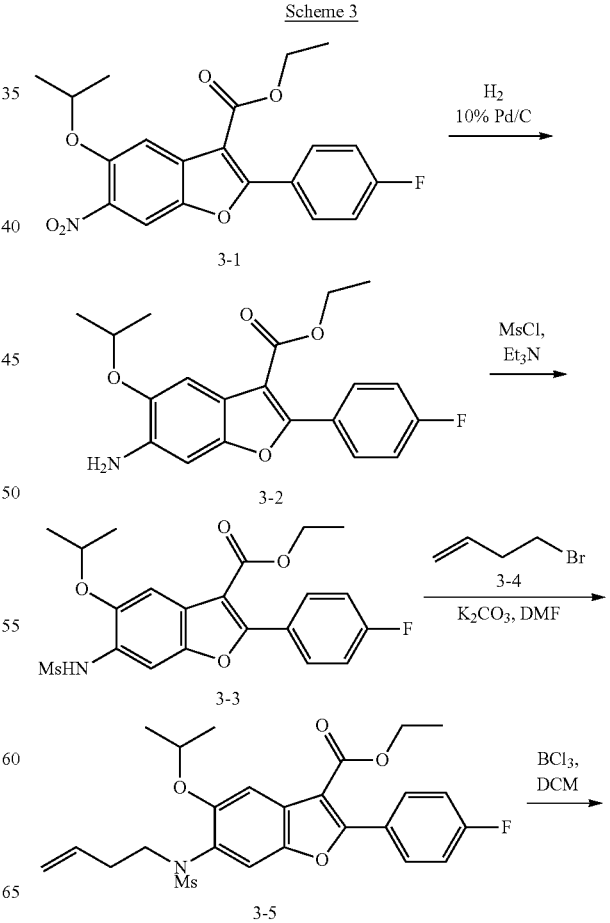

Scheme 3

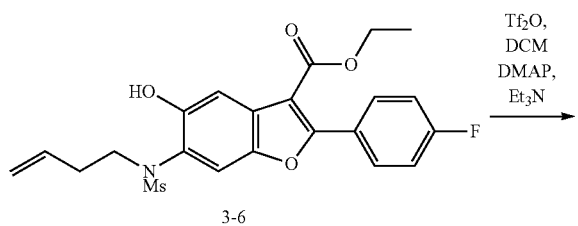

3-6

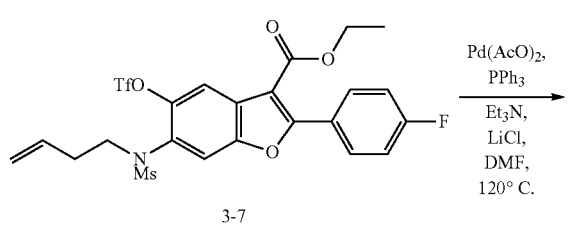

3-7

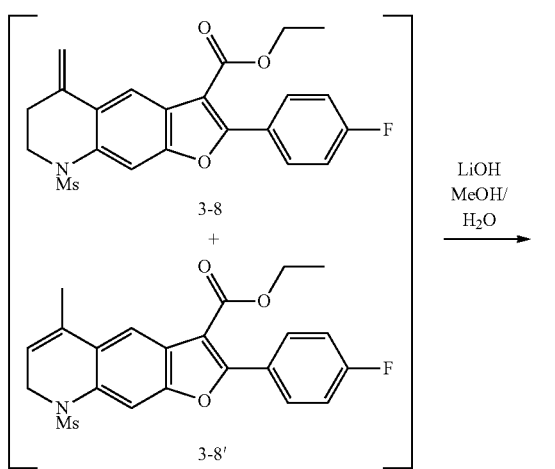

3-8

3-8'

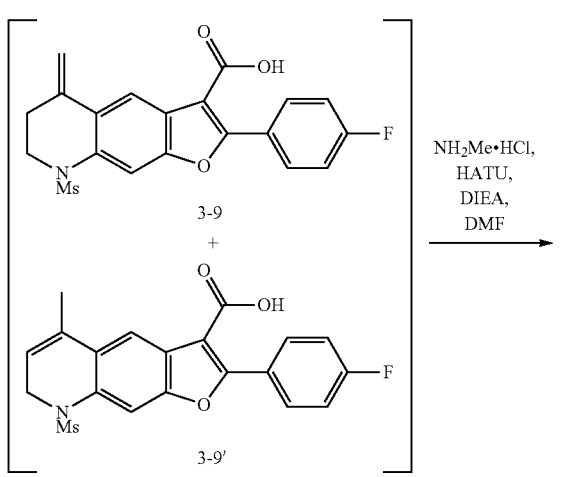

3-9

3-9'

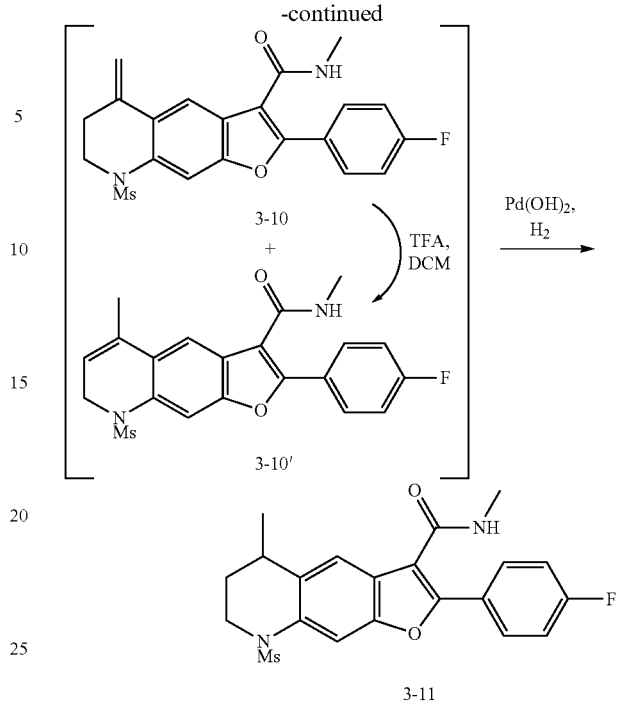

3-10

3-10'

3-11

Step 1. Refer to Scheme 3. A mixture of compound 3-1 (2.00 g, 5.16 mmol) (prepared by following the procedures described in WO200759421 with some modifications) and 10% Pd/C (1.0 g) in EtOAc (40 mL) was stirred at rt for 2 hr under an atmosphere of $H_2$. The reaction mixture was filtered and the filtrate was concentrated to give compound 3-2 (1.7 g, 92% yield). LC-MS (ESI): m/z 358 [M+H]$^+$.

Step 2. To a solution of compound 2 (1.70 g, 4.76 mmol) and TEA (1.32 mL, 9.52 mmol) in DCM (50 mL) was added MSCl (0.660 g, 5.71 mmol) at 0° C. After stirring at rt for 30 min, the reaction mixture was added ice water (250 mL). The mixture was extracted with DCM (100 mL×2) and the combined organic extracts were washed with water and brine and dried with anhydrous $Na_2SO_4$. The solvent was removed and the residue was purified by silica gel column chromatography (Petroleum ether/EtOAc=5/1 (v/v)) to give compound 3-3 (2.07 g, quantitative yield) as a yellow solid. LC-MS (ESI): m/z 436 [M+H]$^+$.

Step 3. To a solution of compound 3-3 (4.00 g, 9.5 mmol) in DMF (50 mL) was added $K_2CO_3$ (5.25 g, 38.0 mmol) and compound 3-4 (1.54 g, 11.4 mmol) at rt. After stirring at 80° C. overnight, the reaction mixture was poured into ice water (60 mL). The resulting mixture was extracted with EtOAc (100 mL×2) and the combined organic extracts were washed with water and dried with anhydrous $Na_2SO_4$. The solvent was removed and the residue was dried in vacuo to give crude compound 3-5 (4.2 g, 92% yield) as a yellow solid. LC-MS (ESI): m/z 512 [M+Na]$^+$.

Step 4. To a solution of compound 3-5 (2.1 g, 4.3 mmol) in $CH_2Cl_2$ (100 mL) was added $BCl_3$ (1 N in DCM, 12.9 mL) at −78° C., the solution was allowed to stirred at −30° C. for 1 hr and then quenched with ice-water (200 mL). The mixture was extracted with DCM (100 mL×2) and the combined organic extracts were washed with water and brine, and dried with anhydrous $Na_2SO_4$. The solvent was removed and the residue was dried in vacuo to give crude compound 3-6 (1.7 g, 86% yield) as a yellow solid. LC-MS (ESI): m/z 448 [M+H]$^+$.

Step 5. To a solution of compound 3-6 (3.30 g, 7.37 mmol) in CH$_2$Cl$_2$ (160 mL) were sequentially added DMAP (45 mg, 0.37 mmol), DIEA (2.58 mL, 14.8 mmol) and Tf$_2$O (1.5 mL, 8.9 mmol) at 0° C. After stirring at 0° C. for 20 min, the reaction mixture was added ice-water (100 mL). The organic layer was washed with water and brine and dried with anhydrous Na$_2$SO$_4$. The solvent was removed and the residue was purified by silica gel column chromatography (Petroleum ether/EtOAc=5/1 (v/v)) to give compound 3-7 (3.2 g, 86% yield) as a yellow solid. LC-MS (ESI): m/z 602 [M+Na]$^+$.

Step 6. To a solution of compound 3-7 (3.00 g, 5.18 mmol) in 20 mL DMF was added Pd(OAc)$_2$ (116 mg, 0.520 mmol), PPh$_3$ (136 mg, 0.520 mmol), LiCl (242 mg, 5.70 mmol) and Et$_3$N (1.44 mL, 10.4 mmol) at rt. The resulting mixture was flushed with Ar and stirred at 120° C. overnight. The mixture was cooled to rt and poured into 60 mL water. The resulting mixture was extracted with EtOAc (100 mL×2) and the combined organic extracts were washed with water (50 mL×3) and dried with anhydrous Na$_2$SO$_4$. The solvent was removed and the residue was purified by silica gel column chromatography (Petroleum ether/EtOAc=6/1 (v/v)) to give a mixture of compounds 3-8 and 3-8' (1.4 g, 63% yield) as a yellow solid. LC-MS (ESI): m/z 430 [M+H]$^+$.

Step 7. To a solution of compounds 3-8 and 3-8' (1.00 g, 2.33 mmol) in MeOH/THF (14 mL/14 mL) was added LiOH (335 mg, 13.97 mmol). The resulting mixture was stirred at 80° C. for 1 hr, cooled to rt and acidified with 1N aq. HCl (5 mL). The suspension was filtered and the solid was washed with water and dried in vacuo to give a mixture of compounds 3-9 and 3-9' (980 mg, 98% yield) as a white solid, which was used directly for the next step. LC-MS (ESI): m/z 402 [M+H]$^+$.

Step 8. To a solution of compounds 3-9 and 3-9' (950 mg, 2.37 mmol) in DMF (5 mL) was added HATU (1.35 g, 3.55 mmol). The resulting mixture was stirred at rt for 30 min and added DIbA (3.30 mL, 19.0 mmol) and MeNH$_2$.HCl (639 mg, 9.47 mmol). After stirring at rt for 20 min, the reaction mixture was poured into ice water (50 mL). The suspension was filtered and the solid was purified by silica gel column chromatography to give a mixture of compounds 3-10 and 3-10' (580 mg, 59% yield). LC-MS (ESI): m/z 415 [M+H]$^+$. Compound 3-10 was readily converted to compound 3-10' in CH$_2$Cl$_2$ in the presence of TFA. LC-MS (ESI): m/z 415 [M+H]$^+$; $^1$H NMR (500 MHz, CDCl$_3$): δ 7.93-7.96 (m, 2H), 7.74 (s, 1H), 7.71 (s, 1H), 7.26-7.29 (m, 2H), 5.96 (s, 1H), 4.38 (br s, 1H), 2.98 (s, 3H), 2.74 (s, 3H), 2.23 (s, 3H) ppm.

Step 9. A mixture of compounds 3-10 and 3-10' (41.4 mg, 0.10 mmol) and Pd(OH)$_2$ (22 mg) in EtOAc (20 mL) and MeOH (2 mL) was stirred at rt for 3 hr under an atmosphere of H$_2$. The reaction mixture was filtered through Celite®545 and the filtrate was concentrated. The residue was purified by re-crystallization (hexane/EtOAc=10/1 (v/v)) to give compound 3-11 (23 mg, 55% yield) as a while solid. LC-MS (ESI): m/z 417 [M+H]$^+$; $^1$H NMR (500 MHz, CDCl$_3$): δ 7.92 (s, 1H), 7.86-7.89 (dd, J$_1$=8.5 Hz, J$_2$=5.5 Hz, 2H), 7.70 (s, 1H), 7.26 (s, 2H), 7.17-7.20 (t, J=8.5 Hz, 2H), 5.93 (br s, 1H), 3.89-3.92 (m, 1H), 3.84-3.86 (m, 1H), 3.03-3.06 (m, 1H), 3.00 (d, 3H), 2.89 (s, 3H), 2.13-2.16 (m, 1H), 1.70-1.73 (m, 1H), 1.42 (d, 3H) ppm.

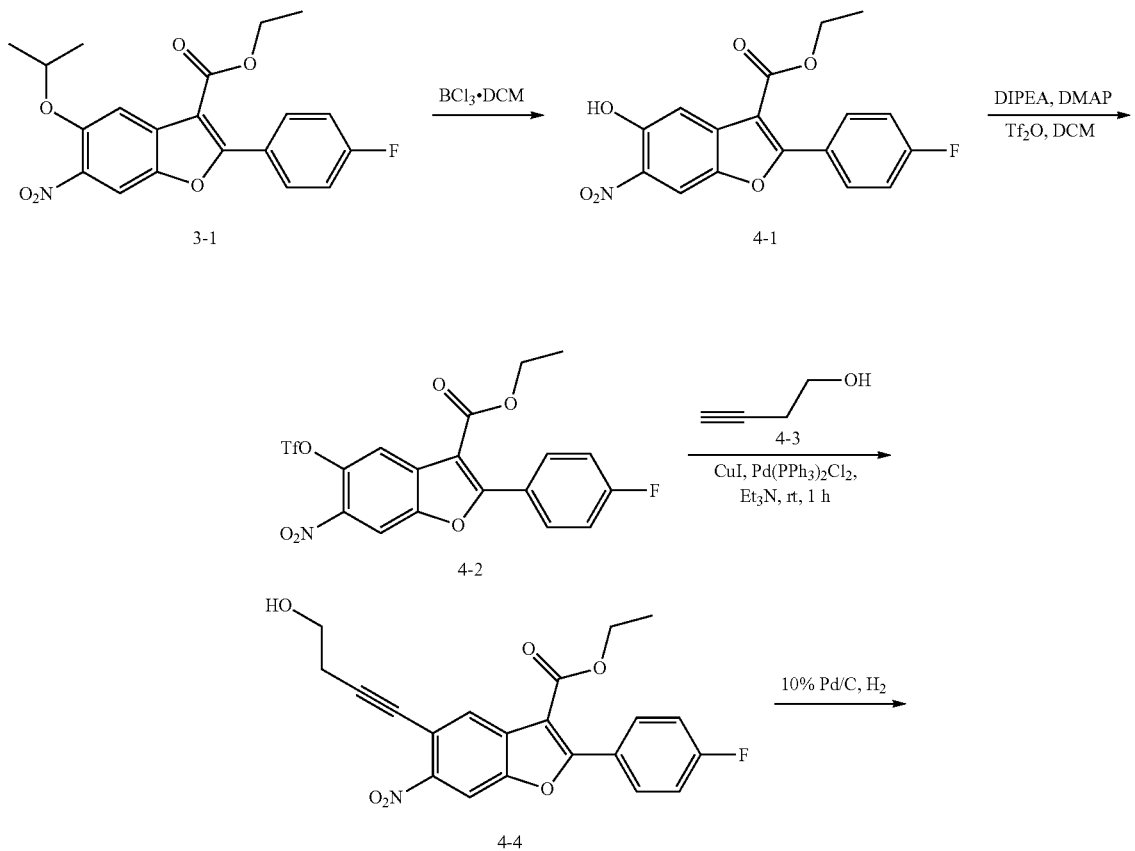

Scheme 4

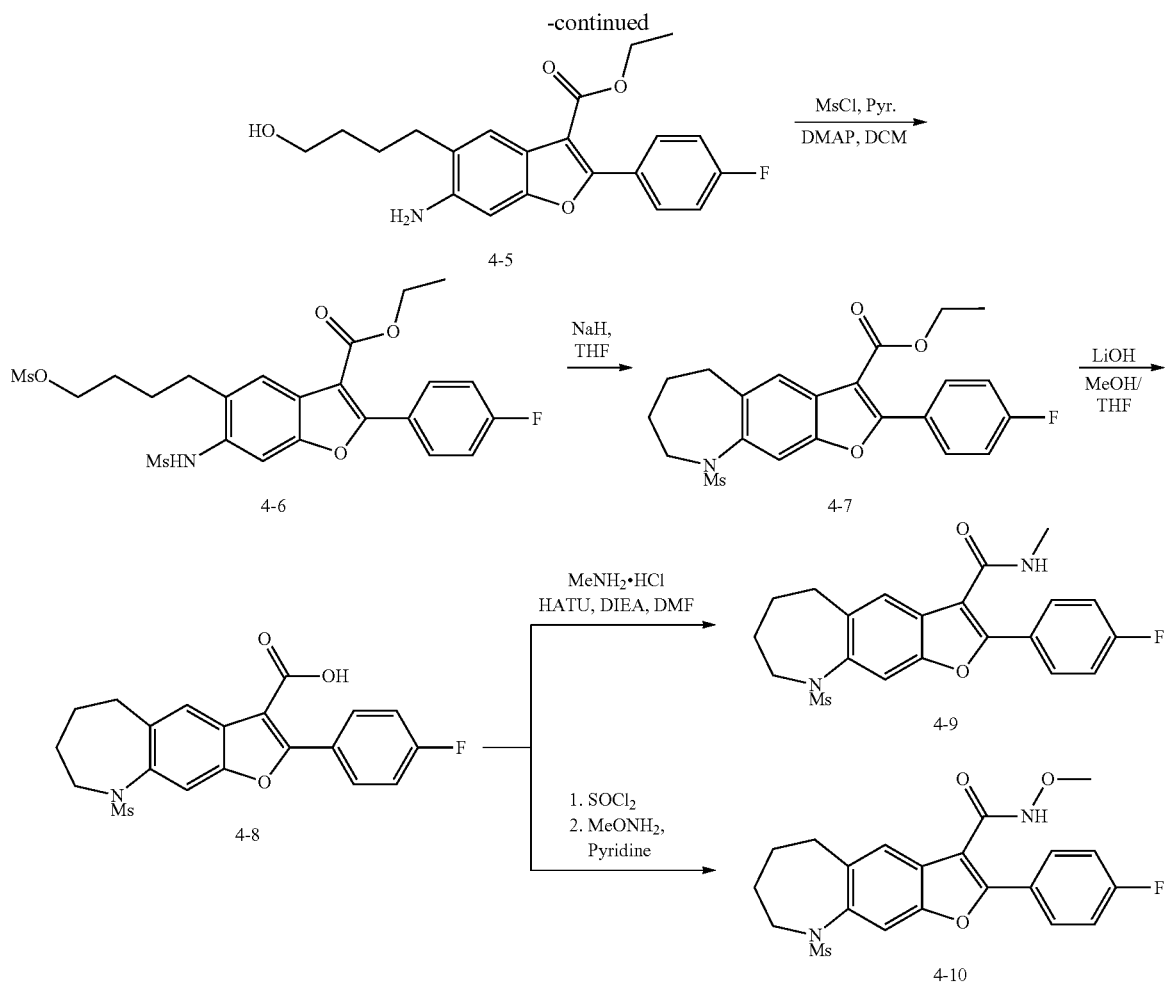

Step 1. Refer to Scheme 4. To a solution of compound 3-1 (4.00 g, 10.3 mmol) in CH$_2$Cl$_2$ (30 mL) was added BCl$_3$ (1 N in CH$_2$Cl$_2$, 20.6 mmol) at 0° C. After stirring at rt for 1 hr, the reaction mixture was added ice water (100 mL). The mixture was extracted with CH$_2$Cl$_2$ (800 mL×2) and the combined organic extracts were washed with water and brine and dried with anhydrous Na$_2$SO$_4$. The solvent was removed and the residue was dried in vacuo to give crude compound 4-1 (3.4 g, 96% yield) as a yellow solid. LC-MS (ESI): m/z 346 [M+H]$^+$.

Step 2. To a solution of compound 4-1 (3.4 g, 9.8 mmol) in CH$_2$Cl$_2$ (100 mL) were added DMAP (120 mg, 0.980 mmol) and DIEA (1.52 g, 11.8 mmol), followed Tf$_2$O (3.20 g, 11.3 mmol) at 0° C. After stirring at 0° C. for 2 hrs, the reaction mixture was added ice water (100 mL). The organic layer was separated, washed with water and brine, and dried with anhydrous Na$_2$SO$_4$. The solvent was removed and the residue was dried in vacuo to give crude compound 4-2 (4.6 g, quantitative yield) as a yellow solid. LC-MS (ESI): m/z 478 [M+H]$^+$.

Step 3. To a solution of 4-2 (2.0 g, 4.2 mmol) in 20 mL DMF was added 4-3 (0.44 g, 6.3 mmol), CuI (0.16 g, 0.84 mmol), Pd(PPh$_3$)$_2$Cl$_2$ (0.29 g, 0.42 mmol) and Et$_3$N (20 mL). The resulting mixture was flushed with Ar, stirred at rt for 1 hr and poured into ice water (100 mL) The mixture was extracted with EtOAc (50 mL×5) and the combined organic extracts were washed with water and dried with anhydrous Na$_2$SO$_4$. The solvent was removed and the residue was purified by silica gel column chromatography (Petroleum ether/acetone=4/1 (v/v) to 3/2 (v/v)) to give compound 4-4 (1.10 g, 69% yield) as a gray solid. LC-MS (ESI): m/z 398 [M+H]$^+$.

Step 4. To a solution of compound 4-4 (2.00 g, 5.03 mmol) in EtOAc (150 mL) was added 10% Pd/C (2.0 g). The resulting mixture was flushed with H$_2$ and stirred at rt for 1.5 hrs. Subsequently, the reaction mixture was filtered through Celite® 545 and the filtrate was concentrated and dried in vacuo to give compound 4-5 (1.8 g, 97% yield). LC-MS (ESI): m/z 372 [M+H]$^+$; $^1$H NMR (500 MHz, CDCl$_3$): δ 7.98-8.01 (m, 2H), 7.70 (s, 1H), 7.12-7.16 (m, 2H), 6.82 (s, 1H), 4.39 (dd, J$_1$=14.5 Hz, J$_2$=7 Hz, 2H), 3.73 (t, J=6 Hz, 3H), 2.66 (t, J=7.5 Hz, 2H), 1.69-1.80 (m, 4H), 1.40 (t, J=7 Hz, 3H) ppm.

Step 5. To a solution of compound 4-5 (1.80 g, 4.85 mmol) in CH$_2$Cl$_2$ (50 mL) was added DMAP (6 mg) and anhydrous pyridine (3.07 g, 38.8 mmol), followed by MsCl (1.60 g, 14.5 mmol) at 0° C. After stirring at rt for 2 hrs, the reaction mixture was added ice water (50 mL). The organic layer was separated, washed with water and brine and dried with anhydrous Na$_2$SO$_4$. The solvent was removed and the residue was purified by silica gel column chromatography (Petroleum ether/acetone=5/1 (v/v)) to give compound 4-6 (1.4 g, 55% yield) as a yellow solid. LC-MS (ESI): m/z 449 [M−Ms+H]$^+$; $^1$H NMR (500 MHz, CDCl$_3$): δ 8.02-8.05(m, 2H), 7.90 (s, 1H), 7.71 (s, 1H), 7.16-7.19 (m, 2H), 6.61 (s, 1H), 4.42 (dd, J$_1$=14 Hz, J$_2$=7.0 Hz, 2H), 4.34 (t, J=5.5 Hz, 2H), 3.04-3.08 (m, 6H), 2.83 (t, J=8.0 Hz, 2H), 1.81-1.92 (m, 4H), 1.41 (t, J=7.0 Hz, 3H) ppm.

Step 6. To a suspension of NaH (0.21 g, 60% in mineral oil, 5.31 mmol) in anhydrous THF (160 mL) was added a solution of compound 4-6 (1.40 g, 2.65 mmol) in anhydrous THF (40 mL) at 0° C. After stirring at rt for 2 hrs, the reaction mixture was added sat. aq. NH$_4$Cl (10 mL) The resulting mixture was concentrated and the residue was diluted with EtOAc (100 mL). The mixture was washed with water and brine and dried with anhydrous Na$_2$SO$_4$. The solvent was removed and the residue was purified by silica gel column chromatography (Petroleum ether/acetone=5/1 (v/v)) to give compound 4-7 (1.1 g, 96% yield) as a yellow solid. LC-MS (ESI): m/z 432 [M+H]$^+$; $^1$H NMR (500 MHz, CDCl$_3$): δ 8.02-8.06 (m, 2H), 7.90 (s, 1H), 7.60 (s, 1H), 7.15-7.20 (m, 2H), 4.42 (dd, J$_1$=14 Hz, J$_2$=6.5 Hz, 2H), 3.69 (t, J=6.0 Hz, 2H), 3.07 (s, 3H), 3.02 (t, J=6.0 Hz, 2H), 1.94 (dd, J$_1$=11 Hz, J$_2$=5.5 Hz, 2H), 1.77 (br s, 2H), 1.40-1.43 (m, 3H) ppm.

Step 7. To a solution of compound 4-7 (50 mg, 0.12 mmol) in MeOH/THF (2 mL/4 mL) was added LiOH (2.0 N, 0.46 mmol). The resulting mixture was stirred at 70° C. for 2 hrs, cooled to rt and acidified with 1 N aq. HCl (5 mL). Subsequently, the suspension was filtered and the solid was washed with waster and dried in vacuo to give crude compound 4-8 (46 mg, 95% yield) as a white solid, which was used directly for the next step without further purification. LC-MS (ESI): m/z 404 [M+H]$^+$.

Step 8. To a solution of compound 4-8 (46 mg, 0.12 mmol) in DMF (2 mL) was added HATU (54 mg, 0.14 mmol). The resulting mixture was stirred at rt for 30 min and added DIEA (154 mg, 1.20 mmol) and MeNH$_2$.HCl (41 mg, 0.60 mmol). After stirring at rt for 20 min, the reaction mixture was poured into ice water (50 mL). The suspension was filtered and the solid was purified by silica gel column chromatography (Petroleum ether/acetone=3/1 (v/v)) to give compound 4-9 (30 mg, 61% yield) as a white solid. LC-MS (ESI): m/z 417 [M+H]$^+$; $^1$H NMR (500 MHz, CDCl$_3$): δ 7.89-7.92 (m, 2H), 7.68 (s, 1H), 7.59 (s, 1H), 7.19 (t, J=9.0 Hz, 2H), 5.80 (d, J=4.0 Hz, 1H), 3.69 (d, J=6.0 Hz, 2H), 3.06 (s, 3H), 2.98-3.03 (m, 5H), 1.93 (dd, J$_1$=11 Hz, J$_2$=5.5 Hz, 2H), 1.75 (d, J=2.5 Hz, 2H) ppm.

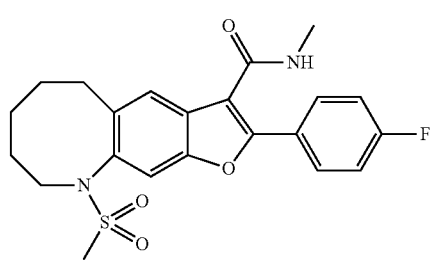

Synthesis of Compound 4-9'. Following Scheme 4 by replacing compound 4-3 (but-3-yn-1-ol) with pen-4-yn-1-ol, compound 4-9' was obtained as a pale yellow solid. LC-MS (ESI): m/z 431 [M+H]$^+$; $^1$H NMR (500 MHz, CDCl$_3$): δ 7.92 (m, 2H), 7.71 (s, 1H), 7.43 (s, 1H), 7.19 (t, J=8.5 Hz, 2H), 5.86 (s, 1H), 3.08 (m, 5H), 3.01 (d, J=4.5 Hz, 3H), 1.59 (m, 6H) ppm.

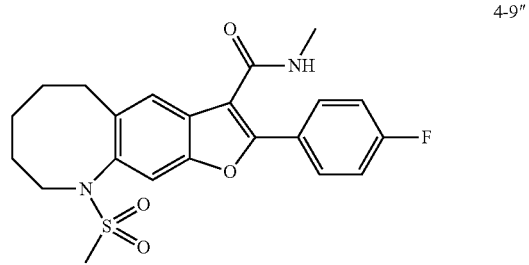 [SMILES: CNC(=O)c1c(-c2ccc(F)cc2)oc2cc3c(cc12)CCCCCN3S(C)(=O)=O]

Synthesis of Compound 4-9". Following Scheme 4 by replacing compound 4-3 (but-3-yn-1-ol) with hex-5-yn-1-ol, compound 4-9" was obtained as a yellow solid. LC-MS (ESI): m/z 447 [M+H]$^+$; $^1$H NMR (500 MHz, CDCl$_3$): δ 7.93 (m, 2H), 7.68 (s, 1H), 7.35 (s, 1H), 7.18 (t, J=8.5 Hz, 2H), 5.86 (s, 1H), 4.05 (m, 1H), 3.47 (m, 1H), 3.37 (m, 1H), 3.00-3.02 (m, 6H), 2.76 (m, 1H), 1.90-1.95 (m, 2H), 1.73-1.79 (m, 1H), 1.26-1.65 (m, 4H), 1.06 (m, 1H) ppm.

Synthesis of Compound 4-10. A mixture of compound 4-8 (50 mg, 0.12 mmol) in SOCl$_2$ (1.5 mL) was stirred at 80° C. for 2 hrs. The solvent was removed and the residue dried in vacuo to give the crude acid chloride, which was used for the next step without further purification. Subsequently, the crude acid chloride was dissolved in anhydrous pyridine (1.5 mL), followed by O-methylhydroxylamine hydrochloride (124 mg, 0.490 mmol). After stirring at 100° C. for 1.5 hrs, the reaction mixture was concentrated and the residue was purified by preparative HPLC to give compound 4-10 (20 mg, 37% yield) as a white powder. LC-MS (ESI): ink 433 [M+H]$^+$; $^1$H NMR (500 MHz, CDCl$_3$): δ 8.31 (s, 1H), 7.90-7.93 (m, 2H), 7.66 (s, 1H), 7.20 (t, J=8.5 Hz, 2H), 3.85 (s, 3H), 3.03 (s, 3H), 2.97-3.00 (m, 2H), 1.93-1.96 (m, 2H), 1.69-1.76 (m, 2H) ppm.

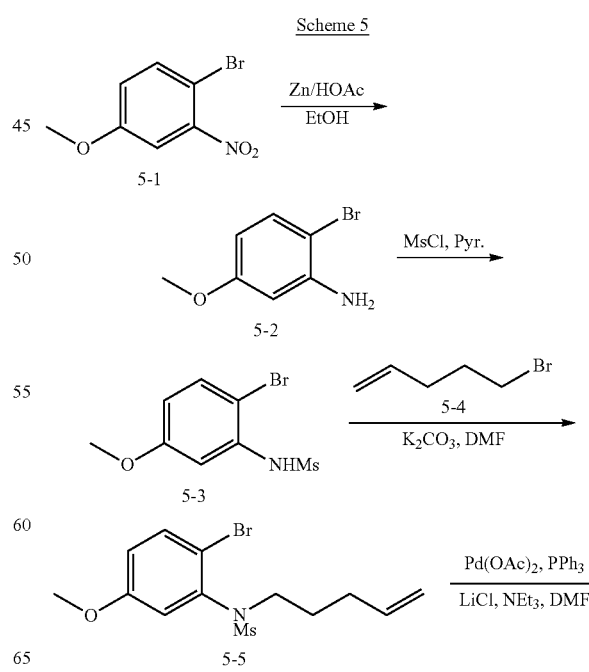

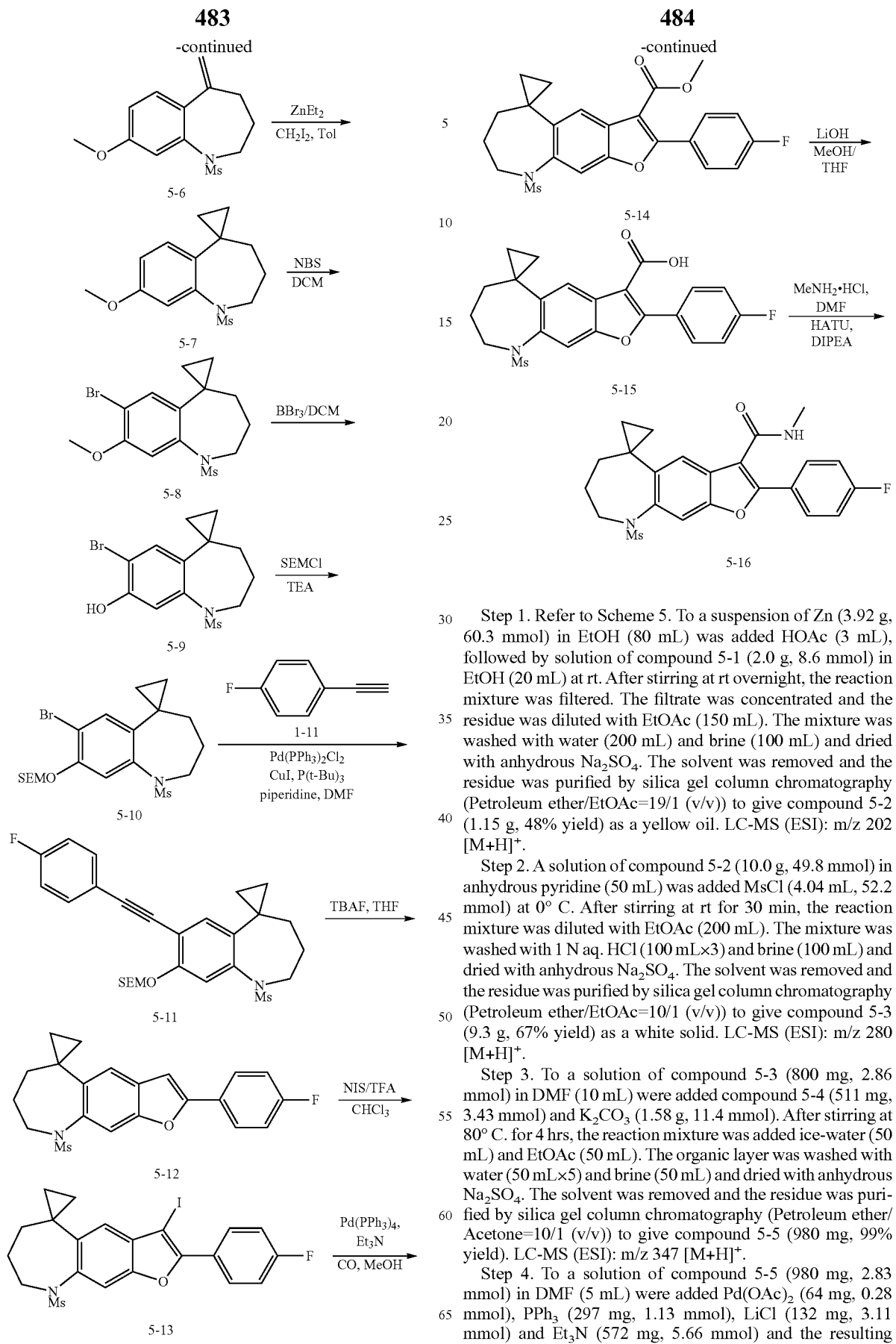

Step 1. Refer to Scheme 5. To a suspension of Zn (3.92 g, 60.3 mmol) in EtOH (80 mL) was added HOAc (3 mL), followed by solution of compound 5-1 (2.0 g, 8.6 mmol) in EtOH (20 mL) at rt. After stirring at rt overnight, the reaction mixture was filtered. The filtrate was concentrated and the residue was diluted with EtOAc (150 mL). The mixture was washed with water (200 mL) and brine (100 mL) and dried with anhydrous $Na_2SO_4$. The solvent was removed and the residue was purified by silica gel column chromatography (Petroleum ether/EtOAc=19/1 (v/v)) to give compound 5-2 (1.15 g, 48% yield) as a yellow oil. LC-MS (ESI): m/z 202 $[M+H]^+$.

Step 2. A solution of compound 5-2 (10.0 g, 49.8 mmol) in anhydrous pyridine (50 mL) was added MsCl (4.04 mL, 52.2 mmol) at 0° C. After stirring at rt for 30 min, the reaction mixture was diluted with EtOAc (200 mL). The mixture was washed with 1 N aq. HCl (100 mL×3) and brine (100 mL) and dried with anhydrous $Na_2SO_4$. The solvent was removed and the residue was purified by silica gel column chromatography (Petroleum ether/EtOAc=10/1 (v/v)) to give compound 5-3 (9.3 g, 67% yield) as a white solid. LC-MS (ESI): m/z 280 $[M+H]^+$.

Step 3. To a solution of compound 5-3 (800 mg, 2.86 mmol) in DMF (10 mL) were added compound 5-4 (511 mg, 3.43 mmol) and $K_2CO_3$ (1.58 g, 11.4 mmol). After stirring at 80° C. for 4 hrs, the reaction mixture was added ice-water (50 mL) and EtOAc (50 mL). The organic layer was washed with water (50 mL×5) and brine (50 mL) and dried with anhydrous $Na_2SO_4$. The solvent was removed and the residue was purified by silica gel column chromatography (Petroleum ether/Acetone=10/1 (v/v)) to give compound 5-5 (980 mg, 99% yield). LC-MS (ESI): m/z 347 $[M+H]^+$.

Step 4. To a solution of compound 5-5 (980 mg, 2.83 mmol) in DMF (5 mL) were added $Pd(OAc)_2$ (64 mg, 0.28 mmol), $PPh_3$ (297 mg, 1.13 mmol), LiCl (132 mg, 3.11 mmol) and $Et_3N$ (572 mg, 5.66 mmol) and the resulting mixture was flushed with Ar and stirred at 120° C. for 1.5 hrs.

Subsequently, the reaction mixture was cooled to rt and poured into water (60 mL). The mixture was extracted with EtOAc (100 mL×2) and the combined organic extracts were washed with water (50 mL×5) and dried with anhydrous $Na_2SO_4$. The solvent was removed and the residue was purified by silica gel column chromatography (Petroleum ether/Acetone=10/1 (v/v)) to give compound 5-6 (600 mg, 79% yield) as a yellow oil. LC-MS (ESI): m/z 268 [M+H]$^+$; $^1$H NMR (500 MHz, CDCl$_3$): δ 7.20 (d, J=8.5 Hz, 1H), 7.04 (d, J=2 Hz, 1H), 6.84 (dd, J$_1$=8.5 Hz, J$_2$=2.5 Hz, 1H), 5.17 (s, 1H), 5.06 (s, 1H), 3.80-3.83 (m, 5H), 2.85 (s, 3H), 2.45 (t, J=6 Hz, 2H), 1.89-1.93 (m, 2H) ppm.

Step 5. To a solution of compound 5-6 (3.60 g, 13.5 mmol) in toluene (60 mL) were added ZnEt$_2$ (1 M in hexane, 108 mmol) and CH$_2$I$_2$ (57.6 g, 216 mmol) at 0° C. After stirring at rt overnight, the reaction mixture was diluted with EtOAc (100 mL) and the resulting mixture was washed with 5% (w/w) aq. HCl (100 mL) and brine and dried with anhydrous Na$_2$SO$_4$. The solvent was removed and the residue was purified by silica gel column chromatography (Petroleum ether/EtOAc=20/1 to 8/1 (v/v)) to give compound 5-7 (2.5 g, 66% yield) as a yellow solid. LC-MS (ESI): m/z 282 [M+H]$^+$; $^1$H NMR (500 MHz, CDCl$_3$) δ 7.18 (d, J=8.5 Hz, 1H), 6.92 (d, J=1.5 Hz, 1H), 6.75 (dd, J$_1$=8.5 Hz, J$_2$=2 Hz, 1H), 3.78 (s, 3H), 3.61 (br s, 2H), 3.06 (s, 3H), 1.92 (br s, 2H), 1.52 (br s, 2H), 0.90 (br s, 2H), 0.73 (br s, 2H) ppm.

Step 6. To a solution of compound 5-7 (1.80 g, 6.43 mmol) in DCM (65 mL) was added NBS (2.28 g, 12.9 mmol) at 0° C. After stirring at rt for 24 hrs, the reaction mixture was concentrated and the residue was purified by silica gel column chromatography (Petroleum ether/EtOAc=15/1 (v/v)) to give compound 5-8 (860 mg, 38% yield) as a white solid. LC-MS (ESI): m/z 360 [M+H]$^+$; $^1$H NMR (500 MHz, CDCl$_3$): δ 7.44 (s, 1H), 6.98 (s, 1H), 3.88 (s, 3H), 3.65 (br s, 2H), 3.09 (s, 3H), 1.90 (br s, 2H), 1.52 (br s, 2H), 0.90 (br s, 2H), 0.75 (br s, 2H) ppm.

Step 7. To a solution of compound 5-8 (800 mg, 2.23 mmol) in CH$_2$Cl$_2$ (30 mL) was added BBr$_3$ (4 N in DCM, 8.91 mmol) at 0° C. After stirring at 0° C. for 20 min, the reaction ixture was poured into ice-water (150 mL) The resulidng mixture was extracted with DCM (50 mL×2) and the combined organic extracts were washed with water and brine and dried with anhydrous Na$_2$SO$_4$. The solvent was removed and the residue was dried in vacuo to give crude compound 5-9 (670 mg, 87% yield) as a white solid. LC-MS (ESI): m/z 346 [M+H]$^+$.

Step 8. To a solution of compound 5-9 (670 mg, 1.94 mmol) in THF (30 mL) were added DMAP (20 mg) and TEA (588 mg, 5.82 mmol). The resulting mixture was cooled to 0° C. and SEMCl (643 mg, 3.87 mmol) was added. After stirring at rt for 1.5 hrs, the reaction mixture was poured into water (50 mL). The mixture was extracted with EtOAc (60 mL×3) and the combined organic extracts were washed with brine (30 mL) and dried anhydrous Na$_2$SO$_4$. The solvent was removed and the residue was purified by silica gel column chromatography (Petroleum ether/EtOAc=10/1 (v/v)) to give compound 5-10 (460 mg, 50% yield) as a white solid. LC-MS (ESI): m/z 498 [M+Na]$^+$.

Step 9. To a solution of compound 5-10 (460 mg, 0.970 mmol) in DMF (6 mL) were added compound 1-11 (139 mg, 1.16 mmol), CuI (9.3 mg, 0.050 mmol), Pd(PPh$_3$)$_2$Cl$_2$ (68 mg, 0.097 mmol), P(t-Bu)$_3$ (39 mg, 0.19 mmol) and piperidine (330 mg, 3.88 mmol). The resulting mixture was flushed with Ar and stirred at 80° C. overnight. Subsequently, the reaction mixture was added into water (60 mL) and extracted with EtOAc (50 mL×2). The combined organic extracts were washed with water (50 mL×5) and dried with anhydrous Na$_2$SO$_4$. The solvent was removed and the residue purified by column chromatography (Petroleum ether/EtOAc=10/1 to 6/1 (v/v)) to give compound 5-11 (300 mg, 60% yield) as a yellow oil. LC-MS (ESI): m/z 538 [M+Na]$^+$.

Step 10. To a solution of compound 5-11 (280 mg, 0.54 mmol) in THF (15 mL) was added TBAF (851 mg, 3.26 mmol) under an atmosphere of Ar. After refluxing overnight, the reaction mixture was concentrated and the residue was purified by silica gel column chromatography (Petroleum ether/EtOAc=8/1 (v/v)) to give compound 5-12 (100 mg, 48% yield) as a yellow solid. LC-MS (ESI): m/z 86 [M+H]$^+$; $^1$H NMR (500 MHz, CDCl$_3$): δ 7.78-7.83 (m, 2H), 7.51 (s, 1H), 7.48 (s, 1H), 7.11-7.16 (m, 2H), 6.89 (s, 1H), 3.64-3.69 (m, 2H), 3.16 (s, 3H), 1.96 (br s, 2H), 1.59 (br s, 2H), 1.01 (br s, 2H), 0.81 (br s, 2H) ppm.

Step 11. To a solution of compound 5-12 (80 mg, 0.21 mmol) in TFA (0.5 mL) and CHCl$_3$ (0.5 mL) was added NIS (70 mg, 0.31 mmol) at rt. After stirring at for 3 hrs, the reaction mixture was concentrated and the residue was purified by silica gel column chromatography (Petroleum ether/EtOAc=6/1 (v/v)) to give compound 5-13 (80 mg, 75% yield) as a yellow solid. LC-MS (ESI): m/z 512 [M+H]$^+$.

Step 12. To a solution of compound 5-13 (80 mg, 0.16 mmol) in DMF (3 mL) and MeOH (3 mL) were added Pd(PPh$_3$)$_4$ (91 mg, 0.080 mmol) and Et$_3$N (64 mg, 0.64 mmol). The resulting mixture was flushed with CO and stirred at 60° C. for 4 hrs under an atmosphere of CO. Subsequently, the mixture was water (20 mL) and extracted with EtOAc (60 mL×2). The combined organic extracts were washed with water (60 mL×5) and dried with anhydrous Na$_2$SO$_4$. The solvent was removed and the residue was purified by silica gel column chromatography (Petroleum ether/EtOAc=8/1 (v/v)) to give compound 5-14 (70 mg, quantitative yield) as a yellow solid. LC-MS (ESI): m/z 444 [M+H]$^+$.

Step 13. To a solution of compound 5-14 (70 mg, 0.16 mmol) in MeOH/THF (1 mL/2 mL) was added LiOH (0.63 mmol). After stirring at 70° C. overnight, the reaction mixture was cooled to 0° C. and acidified with 1 N aq. HCl (7 mL). The suspention was filtered and the solid was washed with water and dried in vacuo to give crude compound 5-15 (60 mg, quantitative yield) as a white solid, which was used for the next step without further purification. LC-MS (ESI): m/z 430 [M+H]$^+$.

Step 14. To a solution of compound 5-15 (60 mg, 0.14 mmol) in DMF (1.5 mL) was added HATU (66 mg, 0.17 mmol). The resulting mixture was stirred at rt for 30 min and then DIPEA (181 mg, 1.40 mmol) and MeNH$_2$.HCl (47 mg, 0.70 mmol) were added. The resulting mixture was stirred at rt for 20 min and poured into water (50 mL). The suspension was filtered and the solid was purified by silica gel column chromatography (Petroleum ether/Acetone=9/1 (v/v)) to give compound 5-16 (10.5 mg, 18% yield) as a white solid. LC-MS (ESI): m/z 443 [M+H]$^+$; $^1$H NMR (500 MHz, CDCl$_3$): δ 7.87 (m, 2H), 7.75 (s, 1H), 7.53 (s, 1H), 7.18 (m, 2H), 5.79 (s, 1H), 3.64 (br s, 2H), 3.15 (s, 3H), 3.01 (d, J=5 Hz, 3H), 1.95 (br s, 2H), 1.61 (br s, 2H), 1.02 (br s, 2H), 0.82 (s, 2H) ppm.

Scheme 6

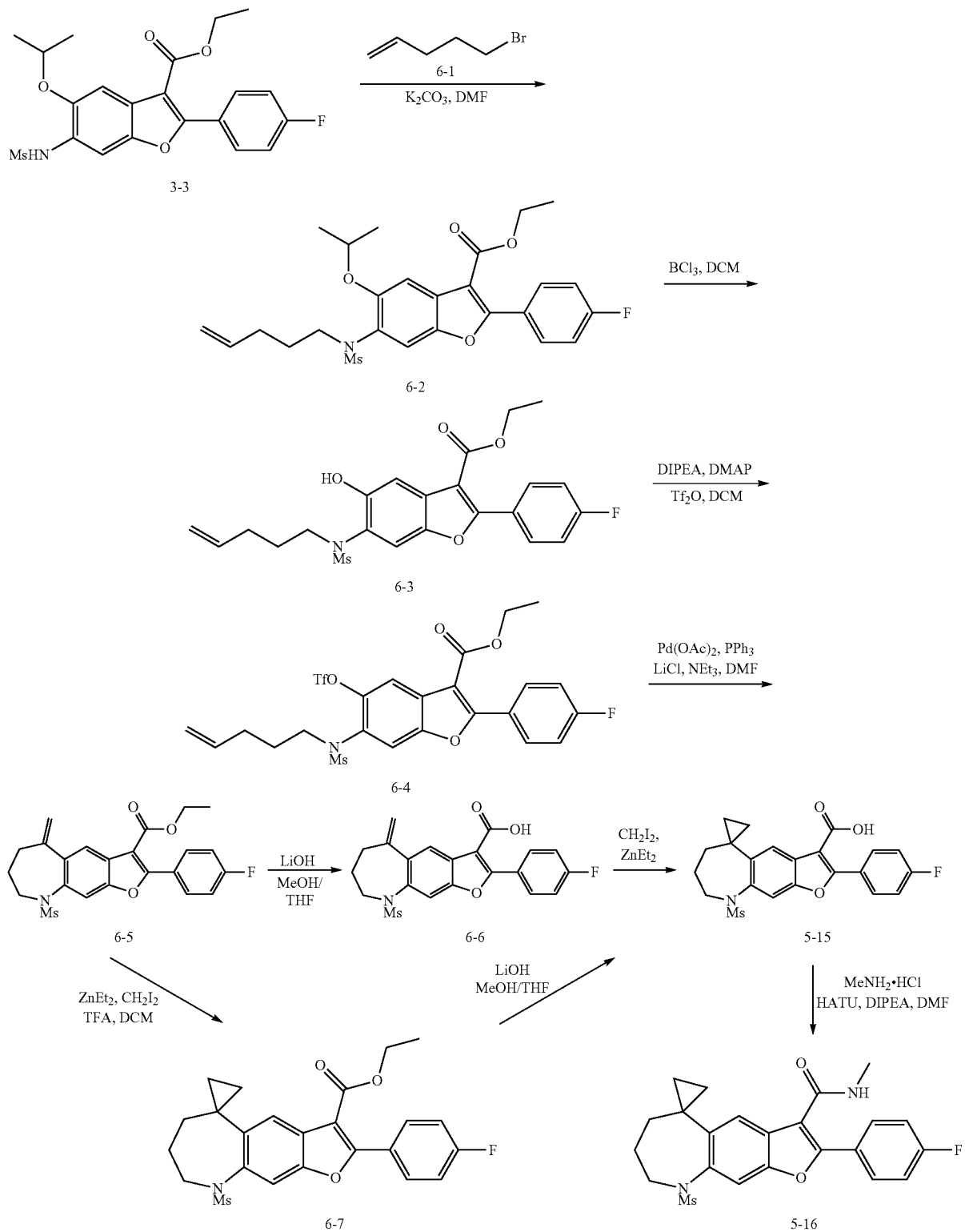

Step 1. Refer to Scheme 6. To a solution of compound 3-3 (4.35 g, 10.0 mmol) in DMF (40 mL) was added K₂CO₃ (5.52 g, 40.0 mmol) and compound 6-1 (1.79 g, 12.0 mmol). After stirring at 80° C. overnight, the reaction mixture was cooled to rt and poured into water (60 mL). The mixture was extracted with EtOAc (100 mL×2) and the combined organic extracts were washed with water and dried with anhydrous Na₂SO₄. The solvent was removed and the residue was purified by silica gel column chromatography (Petroleum ether/acetone=10/1 (v/v)) to give compound 6-2 (4.53 g, 90% yield) as a yellow oil. LC-MS (ESI): m/z 526 [M+Na]$^+$.

Step 2. To a solution of compound 6-2 (2.0 g, 4.0 mmol) in CH$_2$Cl$_2$ (80 mL) was added BCl$_3$ (1 N in DCM, 8.0 mmol) at −30° C. After stirring at −30 to −20° C. for 30 min, the reaction mixture was poured into ice-water (100 mL). The mixture was extracted with DCM (80 mL×2) and combined organic extracts were washed with water and brine and dried with anhydrous Na$_2$SO$_4$. The solvent was removed and the residue was purified by silica gel column chromatography (Petroleum ether/acetone=7/1 (v/v)) to give compound 6-3 (1.4 g, 76% yield) as a yellow solid. LC-MS (ESI): m/z 462 [M+H]$^+$.

Step 3. To a solution of compound 6-3 (1.40 g, 3.04 mmol) in CH$_2$Cl$_2$ (40 mL) were added DMAP (19 mg, 0.15 mmol) and DIEA (0.590 g, 4.56 mmol), followed by Tf$_2$O (1.03 g, 3.64 mmol) at 0° C. After stirring at 0° C. for 20 min, the reaction mixture was added into ice water (50 mL). The organic layer was washed with water and brine and dried with anhydrous Na$_2$SO$_4$. The solvent was removed and the residue was purified by silica gel column chromatography (Petroleum ether/EtOAc=20/1 (v/v)) to give compound 6-4 (1.6 g, 89% yield) as a colorless oil. LC-MS (ESI): m/z 594 [M+H]$^+$.

Step 5. To a solution of compound 6-4 (1.00 g, 1.69 mmol) in 20 mL DMF was added Pd(OAc)$_2$ (38 mg, 0.17 mmol), PPh$_3$ (177 mg, 0.680 mmol), LiCl (79.0 mg, 1.86 mmol) and Et$_3$N (1.00 mL, 6.75 mmol). The resulting mixture was flushed with Ar and stirred at 120° C. overnight. Subsequently, the mixture was cooled to rt and poured into 60 mL water. The resulting mixture was extracted with EtOAc (80 mL×2) and the combined organic extracts was washed with water and dried with anhydrous Na$_2$SO$_4$. The solvent was removed and the residue was purified by silica gel column chromatography (Petroleum ether/EtOAc=15/1 (v/v)) to give compound 6-5 (610 mg, 81% yield) as a yellow solid. LC-MS (ESI): m/z 444 [M+H]$^+$; $^1$H NMR (500 MHz, CDCl$_3$): δ 8.04-8.07 (m, 2H), 7.96 (s, 1H), 7.69 (s, 1H), 7.17-7.20 (m, 2H), 5.30 (s, 1H), 5.21 (d, J=2.0 Hz, 1H), 4.42 (dd, J$_1$=14.5 Hz, J$_2$=7.0 Hz, 2H), 3.85 (br s, 2H), 2.87 (s, 3H), 2.53 (t, J=5.0 Hz, 2H), 1.96 (dd, J$_1$=12 Hz, J$_2$=6.0 Hz, 2H), 1.41 (t, J=6.5 Hz, 3H) ppm.

Step 6. To a solution of compound 6-5 (300 mg, 0.680 mmol) in MeOH/THF (4 mL/8 mL) was added 2.0 N aq. LiOH (2.72 mL, 1.36 mmol). After stirring at 75° C. for 2 hrs, the reaction mixture was colled to rt and acidified with 2 N aq. HCl to pH 5-6. The suspension was filtered and the solid was washed with water and dried in vacuo to give compound 6-6 (260 mg, 92% yield) as a white solid, which was used directly for the next step without further purification. LC-MS (ESI): m/z 416 [M+H]$^+$.

Step 7. To a solution of Et$_2$Zn (1.1 M in toluene, 10 mL, 11 mmol) in 1, 2-dichloroethane (10 mL) was added a solution of CH$_2$I$_2$ (5.87 g, 22 mmol) in 1, 2-dichloroethane (10 mL) at −78° C. under an atmosphere of N$_2$. After stiffing at −15° C. for 30 min, the mixture was cooled to −78° C. Subsequently, a solution of compound 6-6 (200 mg, 0.481 mmol) in 1, 2-dichloroethane (15 mL) was added. The reaction mixture was then stirred at room temperature for 40 hrs and added 1 M aq. HCl at 0° C. The mixture was extracted with DCM (50 mL×2) and the combined organic extracts were concentrated in vacuo. The residue was added THF (20 mL), MeOH (2.5 mL), water (2.5 mL) and LiOH (76 mg). After stirring at 70° C. for 2 hrs, the mixture was treated with 1 M aq. HCl (1.5 mL) at 0° C. The mixture was concentrated and the residue was extracted with DCM (50 mL×4) and the combined organic extracts were dried with anhydrous Na$_2$SO$_4$. The solvent was removed and the residue was purified by silica gel chromatography to give compound 5-15 (113 mg, 55% yield). LC-MS (ESI): m/z 430 [M+H]$^+$; $^1$H NMR (500 MHz, CDCl$_3$): δ 8.04 (m, 3H), 7.57 (s, 1H), 7.20 (m, 2H), 3.68 (br s, 2H), 3.17 (s, 3H), 1.97 (br s, 2H), 1.64 (br s, 2H), 1.06 (br s, 2H). 0.86 (s, 2H) ppm.

Step 8. To a solution of the compound 5-15 (60 mg, 0.14 mmol) in DMF (3.00 mL) was added HATU (64.0 mg, 0.168 mmol). The resulting mixture was stirred at rt for 30 min and 2 M CH$_3$NH$_2$ in THF (1.4 mmol) was added. After stirring at rt for 30 min, the reaction mixture was concentrated and the residue was purified by preparative HPLC to give compound 5-16 (20 mg, 32% yield) as a white powder. LC-MS (ESI): m/z 443 [M+H]$^+$; $^1$HNMR (500 MHz, CDCl$_3$): δ 7.87 (m, 2H), 7.75 (s, 1H), 7.53 (s, 1H), 7.18 (m, 2H), 5.79 (s, 1H), 3.64 (br s, 2H), 3.15 (s, 3H), 3.01 (d, J=5 Hz, 3H), 1.95 (br s, 2H), 1.61 (br s, 2H), 1.02 (br s, 2H), 0.82 (s, 2H) ppm.

Synthesis of Compound 6-7. A solution of Et$_2$Zn (1.1 M in toluene, 0.22 mmol) in DCM (2 mL) was drop-wisely added CH$_2$I$_2$ (117 mg, 0.440 mmol) at −78° C. under an atmosphere of N$_2$. After stirring at −78° C. for 30 min, to the reaction mixture was drop-wisely added a mixture of compound 6-5 (4.43 mg, 0.01 mmol) and TFA (0.01 mL) in DCM (1 mL). Subsequently, the reaction mixture was stirred at 60° C. for 30 min and then cooled to it and diluted with water (25 mL) and DCM (50 mL). The organic layer was separated, washed with brine (25 mL), and dried with anhydrous Na$_2$SO$_4$. The solvent was removed and the residue was dried in vacuo to give compound 6-7. LC-MS (ESI): m/z 458.1 [M+H]$^+$.

Scheme 7

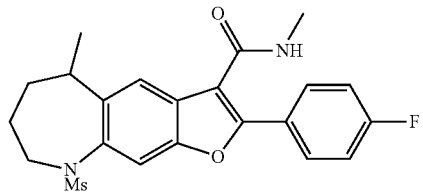

7-3

↑

10% Pd/C, H$_2$

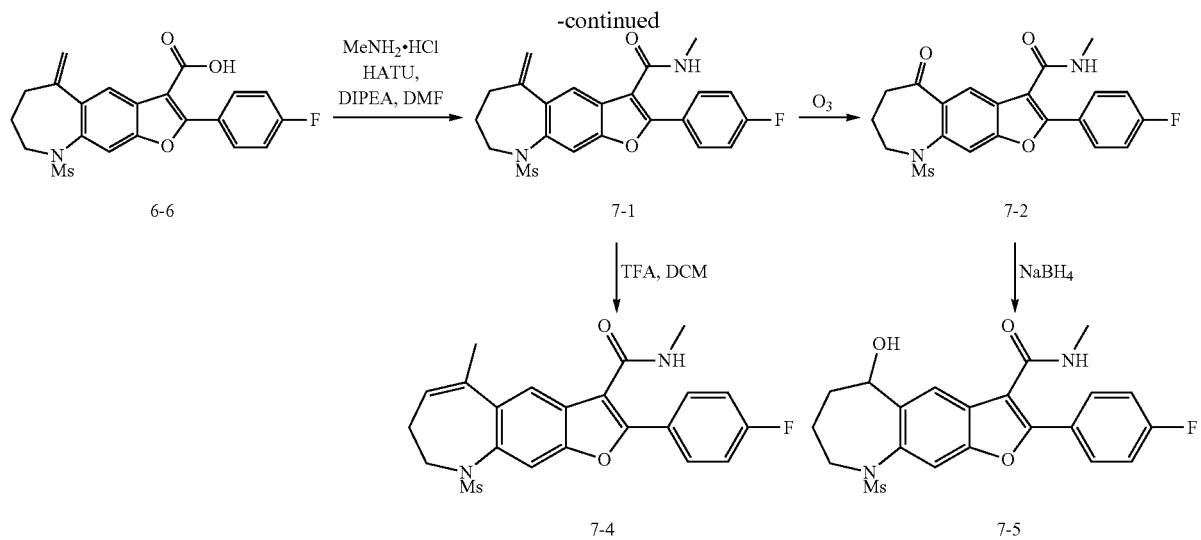

Synthesis of Compound 7-1. Refer to Scheme 7. To a solution of compound 6-6 (250 mg, 0.60 mmol) in DMF (5 mL) was added HATU (275 mg, 0.72 mmol). The resulting mixture was stirred at rt for 30 min before DIEA (154 mg, 1.2 mmol) and MeNH$_2$.HCl (122 mg, 1.8 mmol) were added in. After stirring at rt for 20 min, the reaction mixture was poured into water (50 mL). The suspension was filtered and the solid was washed with water and dried in vacuo. The solid was dissolved in DCM (2 mL) and the resulting solution was added into hexane (80 mL). The suspension was filtered and the solid was dried in vacuo to give compound 7-1 (230 mg, 90% yield) as a white solid. LC-MS (ESI): m/z 429 [M+H]$^+$; $^1$H NMR (500 MHz, CDCl$_3$): δ 7.88-7.91 (m, 2H), 7.74 (s, 1H), 7.67 (s, 1H), 7.19 (t, J=9.0 Hz, 2H), 5.82 (br s, 1H), 5.28 (s, 1H), 5.19 (d, J=1.0 Hz, 1H), 3.83 (br s, 2H), 3.01 (d, J=5.5 Hz, 3H), 2.86 (s, 3H), 2.51 (t, J=5.0 Hz, 2H), 1.92-1.96 (m, 2H) ppm.

Synthesis of Compound 7-2. To a solution of compound 7-1 (40 mg, 0.094 mmol) in DCM (4 mL) was flushed with O$_3$ at −78° C. until compound 7-1 disappeared (about 1 min). Subsequently, the reaction mixture was saturated with N$_2$ and PPh$_3$ (591 mg, 0.26 mmol) was added. After stirring at rt for 3 hrs, the reaction mixture was filtered and the filtrate was concentrated. The residue was purified by silica gel column chromatography to give compound 7-2 (20 mg, 50% yield). LC-MS (ESI): m/z 431 [M+H]$^+$; $^1$H NMR (500 MHz, CDCl$_3$): δ 7.88 (dd, J$_1$=8.5 Hz, J$_2$=6.0 Hz, 2H), 7.71 (s, 1H), 7.54 (s, 1H), 7.19 (t, J=8.5 Hz, 2H), 5.80 (br s, 1H), 4.08-4.13 (m, 1H), 3.25-3.28 (m, 2H), 3.08 (s, 3H), 3.01 (d, J=4.5 Hz, 3H), 1.89-2.04 (m, 2H), 1.67 (br s, 2H), 1.47 (d, J=7.0 Hz, 3H) ppm.

Synthesis of Compound 7-3. To a solution of compound 7-1 (70 mg, 0.16 mmol) in EtOAc (30 mL) was added 10% Pd/C (20 mg). The resulting mixture was flushed with H$_2$ and stirred at rt for 3 hr. The reaction mixture was filtered; the filtrate was concentrated and the residue was purified by silica gel column chromatography (Petroleum ether/EtOAc=5/1 (v/v)) to give compound 7-3 (40 mg, 58% yield) as a white solid. LC-MS (ESI): m/z 431 [M+H]$^+$. $^1$H NMR (500 MHz, CDCl$_3$): δ 8.17 (s, 1H), 7.99 (dd, J$_1$=8.5 Hz, J$_2$=6.0 Hz, 2H), 7.68 (s, 1H), 7.21 (t, J=8.5 Hz, 2H), 5.89 (br s, 1H), 3.90 (t, J=6.0 Hz, 2H), 3.03-3.05 (m, 6H), 2.85 (t, J=6.0 Hz, 2H), 2.04-2.08 (m, 2H) ppm. Compound 7-3 was separated into a pair of enantiomers: enantiomer 7-3_A (t$_R$=9.420 min) and enantiomer 7-3_B (t$_R$=12.173 min) detected by UV absorption at 214 nm on a ChiralPak® IA 4.0 mm×150 mm×5 μm column (eluent: hexane/EtOH=70/30 (v/v) with 0.1% diethylamine (v/v) and flow rate: 1 mL/min).

Synthesis of Compound 7-4. To a solution of compound 7-1 (50 mg, 0.12 mmol) in DCM (4 mL) was added CF$_3$COOH (0.02 mL). After stirring at rt overnight, the reaction mixture was concentrated. The residue was dissolved in DCM (0.5 mL) and the resulting solution was added into hexane (20 mL). The suspension was filtered and the solid was dried in vacuo to give compound 7-4 (30 mg, 58% yield). LC-MS (ESI): m/z 429 [M+H]$^+$; $^1$H NMR (500 MHz, CDCl$_3$): δ 7.89 (dd, J$_1$=8 Hz, J$_2$=5.5 Hz, 2H), 7.82 (s, 1H), 7.67 (s, 1H), 7.22 (t, J=8.5 Hz, 2H), 6.06 (t, J=6.5 Hz, 1H), 5.80 (br s, 1H), 3.75-4.50 (m, 2H), 3.01 (d, J=4.5 Hz, 3H), 2.78 (s, 3H), 2.22 (s, 3H), 2.18 (t, J=6 Hz, 2H) ppm.

Synthesis of Compound 7-5. To a solution of compound 7-2 (40 mg, 0.093 mmol) in MeOH (1 mL) and THF (1 mL) was added NaBH$_4$ (10 mg, 0.28 mmol). After stirring at 0° C. for 10 min, the reaction was quenched by adding several drops of acetone. The solvent was removed and the residue was dissolved in EtOAc (25 mL). The mixture was washed with water and dried with anhydrous Na$_2$SO$_4$. The solvent was removed; the residue was dissolved in DCM (0.5 mL) and the resulting solution was added into hexane (20 mL). The suspension was filtered and the solid was dried in vacuo to give compound 7-5 (10 mg, 25% yield) as a white solid. LC-MS (ESI): m/z 433 [M+H]$^+$; $^1$H NMR (500 MHz, CDCl$_3$): δ 7.92-7.94 (m, 3H), 7.56 (s, 1H), 7.18 (t, J=8.5 Hz, 2H), 5.87 (br s, 1H), 5.15 (br s, 1H), 3.83 (br s, 1H), 3.12 (s, 3H), 3.01-3.02 (m, 4H), 2.32 (br s, 1H), 2.03 (br s, 3H) ppm.

Scheme 8

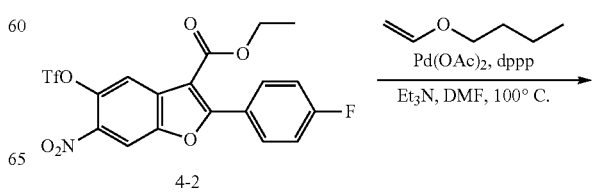

493

-continued

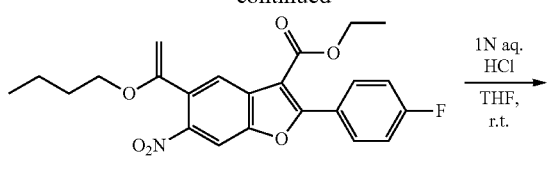

8-1

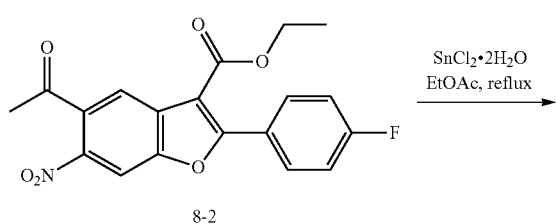

8-2

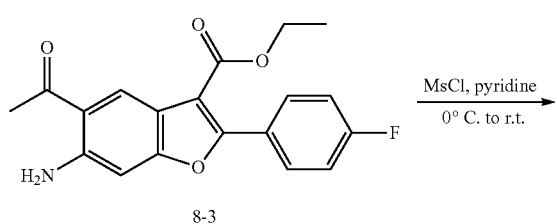

8-3

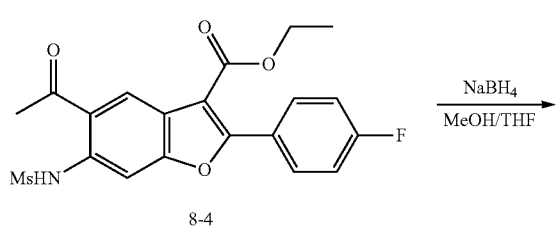

8-4

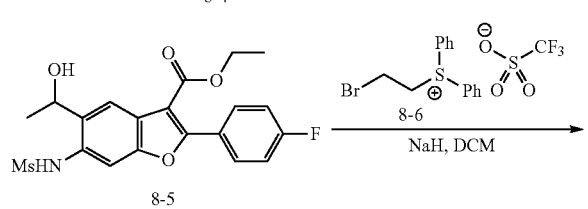

8-5

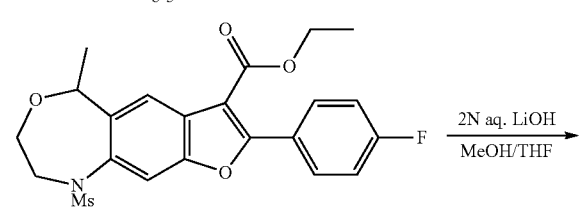

8-7

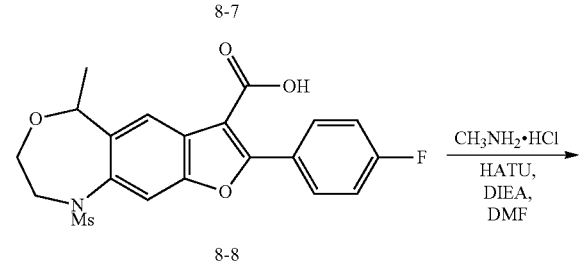

8-8

494

-continued

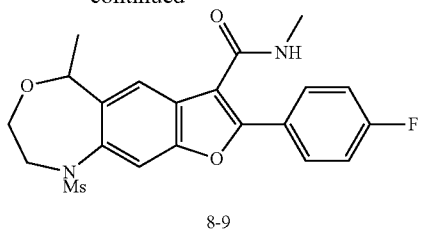

8-9

Step 1. Refer to Scheme 8. To a stirred solution of compound 4-2 (9.00 g, 18.9 mmol) in DMF (100 mL) were added Et$_3$N (7.84 mL, 56.6 mmol), Pd(OAc)$_2$ (212 mg, 0.94 mmol), dppp (469 mg, 1.13 mmol) and butyl vinyl ether (12.1 mL, 94.4 mmol) under an atmosphere of Ar. After stirring at 100° C. for 2 hrs, the reaction mixture was concentrated. The residue was diluted with EtOAc (250 mL) and the resulting mixture was washed with water (100 mL×3) and dried with anhydrous Na$_2$SO$_4$. The solvent was removed and the residue was purified by silica gel column chromatography (Petroleum ether/EtOAc=16/1 (v/v)) to give compound 8-1 (3.9 g, 48% yield) as a yellow solid. LC-MS (ESI): m/z 427 [M+H]$^+$.

Step 2. A solution of compound 8-1 (3.90 g, 9.13 mmol) in THF (60 mL) was added 1 N aq. HCl (10 mL) at rt. After stirring at rt for 15 min, the reaction mixture was concentrated and the residue was diluted with DCM (100 mL). The resulting mixture was washed with brine and dried with anhydrous Na$_2$SO$_4$. The solvent was removed and the residue was dried in vacuo to give crude compound 8-2 (3.27 g, 96% yield) as a yellow solid, which was used for the next step without further purification. LC-MS (ESI): m/z 372 [M+H]$^+$.

Step 3. To a stirred solution of compound 8-2 (2.00 g, 5.38 mmol) in EtOAc (50 mL) was added SnCl$_2$.2H$_2$O (3.47 g, 16.2 mmol). After stirring at 80° C. for 1 hr, the reaction mixture was added sat. aq. NaHCO$_3$ (50 mL) and the resulting mixture was stirred at rt for 30 min. Subsequently, the mixture was filtered through Celite®545 and the filtered cake was washed with EtOAc (50 mL×3). The organic layer of the filtrate was washed with brine and dried with anhydrous Na$_2$SO$_4$. The solvent was removed and the residue was dried in vacuo to give crude compound 8-3 (1.8 g, 98% yield) as a brown solid, which was used for the next step without further purification. LC-MS (ESI): m/z 342 [M+H]$^+$.

Step 4. To a stirred solution of compound 8-3 (900 mg, 2.64 mmol) in anhydrous pyridine (15 mL) was added MSCl (0.25 mL, 3.17 mmol) at 0° C. After stirring at rt for 1 hr, the reaction mixture was diluted with EtOAc (100 mL) and the resulting mixture was washed with 2 N aq. HCl (20 mL×2) and H$_2$O (50 mL×3) and dried with anhydrous Na$_2$SO$_4$. The solvent was removed and the residue was purified by silica gel column chromatography (Petroleum ether/DCM/EtOAc=8/4/1 (v/v)) to compound 8-4 (520 mg, 47% yield) as a yellow solid. LC-MS (ESI): m/z 442 [M+Na]$^+$.

Step 5. To a solution of compound 8-4 (380 mg, 0.91 mmol) in MeOH (10 mL) and THF (10 mL) was added NaBH$_4$ (172 mg, 4.54 mmol) in several portions at 0° C. After stirring at 0° C. for 15 min, the reaction was quenched by adding acetone (1 mL). The mixture was concentrated and the residue was diluted with EtOAc (100 mL) The resulting mixture was washed with 2 N aq. HCl (20 mL) and H$_2$O (50 mL×3) and dried with anhydrous Na$_2$SO$_4$. The solvent was removed and the residue was dried in vacuo to give crude compound 8-5 (240 mg, 63% yield), which was used for the next step without further purification. LC-MS (ESI): m/z 444 [M+Na]$^+$.

Step 6. To a stirring solution of compound 8-5 (50 mg, 0.12 mmol) in THF (15 mL) was added NaH (24 mg, 0.6 mmol) at 0° C. under an atmosphere of Ar. After stirring at rt for 15 min, the mixture was added compound 8-6 (106 mg, 0.24 mmol) (prepared following the procedure described in *Angew. Chem. Intl. Ed.* 2008, 47, 3784) at 0° C. and the resulting mixture was stirred at 0° C. for 3 hrs and rt overnight. Subsequently, saturated aq. NH$_4$Cl (10 mL) was added to quench the reaction and the mixture was concentrated. The residue was diluted with EtOAc (50 mL) and the mixture was washed with brine (10 mL) and dried with anhydrous Na$_2$SO$_4$. The solvent was removed and the residue was purified by silica gel column chromatography (Petroleum ether/Acetone=4/1 (v/v)) to give compound 8-7 (30 mg, 56% yield) as a white solid. LC-MS (ESI): m/z 448 [M+H]$^+$.

Step 7. To a solution of compound 8-7 (40 mg, 0.09 mmol) in MeOH/THF (2 mL/4 mL) was added 2.0 N aq. LiOH (0.18 mmol, 0.36 mmol). After stirring at 75° C. for 3 hrs, the reaction mixture was cooled to 0° C. and acidified with 2N aq. HCl adjust pH value to 5~6. Subsequently, the suspension was filtered and the solid was washed with water and dried in vacuo to give compound 8-8 (38 mg, 97% yield) as a white solid, which was used for the next step without further purification. LC-MS (ESI): m/z 442 [M+Na]$^+$.

Step 8. To a solution of compound 8-8 (40 mg, 0.10 mmol) in DMF (3 mL) was added HATU (43 mg, 0.12 mmol). The resulting mixture was stirred at rt for 60 min and DIEA (0.16 mL, 0.95 mmol) and MeNH$_2$.HCl (20 mg, 0.29 mmol) were added. After stirring at rt for 15 min, the reaction mixture was added into water (30 mL). The suspension was filtered and the solid was washed with water and dried in vacuo. The residue was dissolved in DCM (1.5 mL) and the solution was added into hexane (40 mL). The resulting suspension was filtered and the solid was dried in vacuo to give compound 8-9 (23 mg, 56% yield). LC-MS (ESI): m/z 433 [M+H]$^+$; $^1$H NMR (500 MHz, CDCl$_3$): δ 7.88-7.91 (m, 3H), 7.62 (s, 1H), 7.20 (t, J=8.5 Hz, 2H), 5.80 (br s, 1H), 4.96 (q, J=6.5 Hz, 1H), 4.15-4.18 (m, 1H), 4.02-4.09 (m, 2H), 3.29-3.34 (m, 1H), 3.15 (s, 3H), 3.01 (d, J=5.0 Hz, 3H), 1.74 (d, J=6.5 Hz, 3H) ppm. Compound 8-9 was separated into a pair of enantiomers: enantiomer 8-9_A (t$_R$=3.34 min) and enantiomer 8-9_B (t$_R$=3.89 min) detected by UV absorption at 214 nm on a Daicel CHIRALPAK AS-H column (eluent: MeOH/liquid CO$_2$=10/90 (v/v), flow rate: 60 g/min and back pressure: 100 bar).

Scheme 9

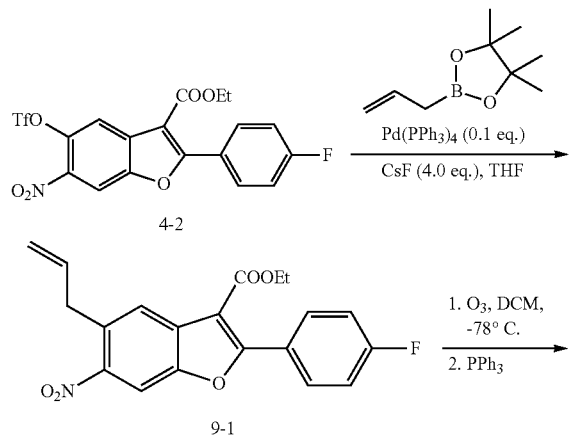

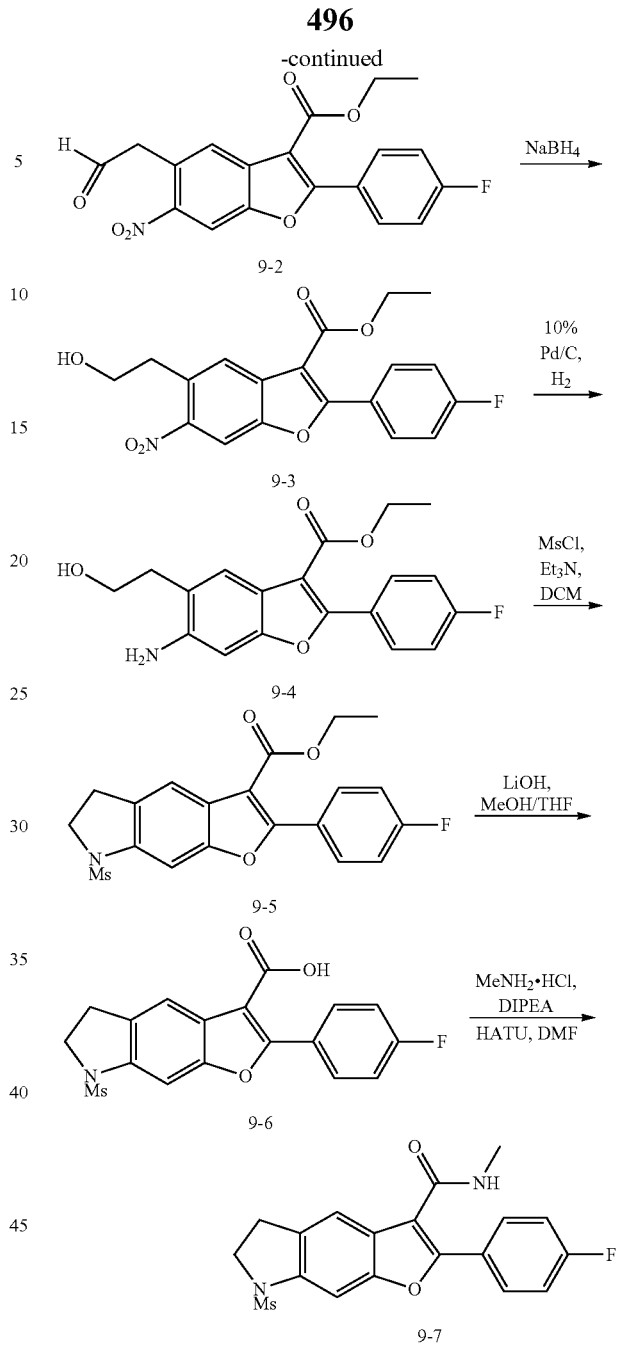

Step 1. Refer to Scheme 9. To a solution of compound 4-2 (2.37 g, 5.00 mmol) in anhydrous THF (70 mL) were added commercially available 2-ally-4,4,5,5-tetramethyl-1,3,2-dioxaborolane (1.09 g, 6.50 mmol), Pd(PPh$_3$)$_4$ (0.58 g, 0.50 mmol) and CsF (3.0 g, 19.87 mmol) under an atmosphere of Ar. The resulting mixture stirred at 80° C. 3 hrs and concentrated. The residue was diluted with water (100 mL) and extracted with EtOAc (50 mL×3). The combined organic extracts were washed with brine and dried with anhydrous Na$_2$SO$_4$. The solvent was removed and the residue was purified by silica gel column chromatography (Petroleum ether/ EtOAc=200/1 (v/v)) to give compound 9-1 (670 mg, 36% yield) as a yellow solid. LC-MS (ESI): m/z 370 [M+H]$^+$.

Step 2. A solution of compound 9-1 (670 mg, 1.82 mmol) in DCM (110 mL) was purged with O$_3$ until reaction solution turned to be light blue at −78° C. Subsequently, PPh$_3$ (1.19 g, 4.5 mmol) was added and the mixture was stirred at rt overnight. The solvent was removed and the residue was purified by silica gel column chromatography (Petroleum ether/EtOAc=20/1 to 10/1 (v/v)) to give compound 9-2 (570 mg, 82% yield) as a yellow solid. LC-MS (ESI): m/z 372 [M+H]⁺.

Step 3. To a solution of compound 9-2 (420 mg, 1.13 mmol) in MeOH (11 mL) and THF (11 mL) was added NaBH₄ (172 mg, 4.53 mmol) at 0° C. After stirring at 0° C. for 30 min, several drops of acetone was added to quench the reaction. The mixture was concentrated and the residue was diluted with water (50 mL) and EtOAc (50 mL) The aq. phase was extracted with EtOAc (50 mL×2) and the combined organic extracts were washed with brine and dried with anhydrous Na₂SO₄. The solvent was removed and the residue was dried in vacuo to give crude compound 9-3 (422 mg, quantitative yield), which was used for the next step without further purification. LC-MS (ESI): m/z 374 [M+H]⁺.

Step 4. To a solution of compound 9-3 (410 mg, 1.10 mmol) in EtOAc (150 mL) was added 10% Pd/C (400 mg). The resulting mixture was flushed with H₂ and stirred at rt overnight under an atmosphere of H₂. Subsequently, the reaction mixture was filtered through Celite®545 and the filtered cake was washed with EtOAc (50 mL×2). The filtrate was concentrated and the residue was dried in vacuo to give crude compound 9-4 (372 mg, 99% yield). LC-MS (ESI): m/z 344 [M+H]⁺.

Step 5. To a solution of compound 9-4 (372 mg, 1.08 mmol) in CH₂Cl₂ (10 mL) were added DMAP (20 mg), Et₃N (654 mg, 6.48 mmol) and MsCl (500 mg, 4.33 mmol) at 0° C. After stirring at 0° C. for 30 min and rt for 1.5 hrs, the reaction mixture was added saturated aq. NaHCO₃ (5 mL). The mixture was diluted with DCM (50 mL) and the organic layer was washed with brine and dried with anhydrous Na₂SO₄. The solvent was removed and the residue was purified by silica gel column chromatography (Petroleum ether/Acetone=4/1 (v/v)) to give compound 9-5 (200 mg, 46% yield) as a yellow solid. LC-MS (ESI): m/z 404 [M+H]⁺.

Step 6. To a solution of compound 9-5 (200 mg, 0.500 mmol) in MeOH/THF (6 mL/12 mL) was added LiOH (2.0 N aq. solution, 2.0 mmol). The resulting mixture was stirred at 70° C. for overnight and then acidified with 1N aq. HCl (aq, 4 mL) at 0° C. The suspension was filtered and the solid was washed with water and dried in vacuo to give crude compound 9-6 (170 mg, 90% yield) as a white solid, which was used for the next step without further purification. LC-MS (ESI): m/z 376 [M+H]⁺.

Step 7. To a solution of compound 9-6 (70 mg, 0.18 mmol) in DMF (4 mL) was added HATU (85 mg, 0.22 mmol). The resulting mixture was stirred at rt for 30 min, followed by adding DIEA (0.33 mL, 1.8 mmol) and MeNH₂.HCl (76.0 mg, 1.12 mmol). After stirring at rt for 20 min, the reaction mixture was added into water (50 mL). The resulting suspension was filtered and the solid was washed with water and dried in vacuo. Subsequently, the residue was dissolved in DCM and the solution was added into hexane to precipitate the product. The resulting suspension was filtered and the solid was dried in vacuo to give compound 9-7 (40 mg, 55% yield) as a white solid. LC-MS (ESI): m/z 389 [M+H]⁺; ¹H NMR (500 MHz, CDCl₃): δ 7.85-7.88 (m, 2H), 7.64 (s, 1H), 7.57 (s, 1H), 7.18 (t, J=8.5 Hz, 2H), 5.82 (br s, 1H), 4.06 (t, J=8.0 Hz, 2H), 3.23 (t, J=8.0 Hz, 2H), 2.99 (d, J=4.5 Hz, 3H), 2.90 (s, 3H) ppm.

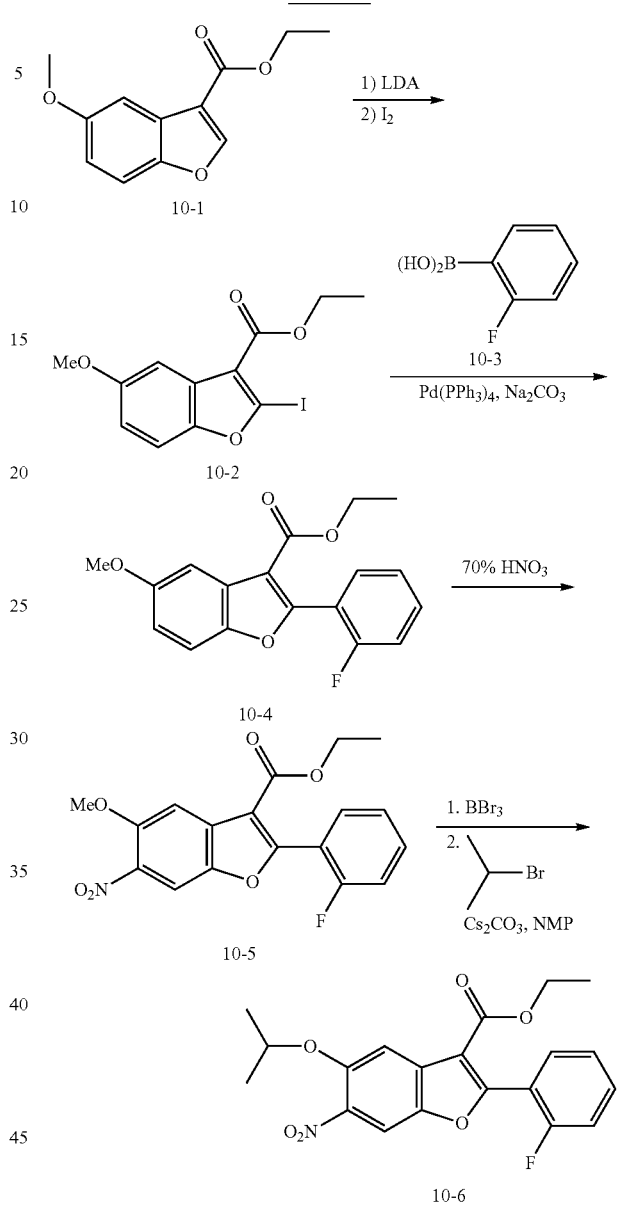

Scheme 10

Step 1. Refer to Scheme 10. To a mixture of iPr₂NH (27 mL, 190.7 mmol) in THF (140 mL) was dropwisely added nBuLi (2.5M in Hexanes, 73 mL, 181.6 mmol) at −78° C. The mixture was stirred at −78° C. for 30 min, then warmed up to rt with stirring for another 20 min. Subsequently, to a mixture of compound 10-1 (10 g, 45.4 mmol) (prepared by following the procedure described in WO2009051306) and I₂ (28.5 g, 114 mmol) in THF (70 mL) was dropwisely added LDA solution freshly prepared at −78° C. Compound 10-1 was consumed when 3.5 equiv of LDA was added and the reaction was quenched by adding sat. aq. NH₄Cl. The mixture was warmed up to rt and concentrated. The residue was diluted with water and extracted by EtOAc (100 mL×3). The organic extracts were combined, washed by brine, and dried with anhydrous Na₂SO₄. The solvent was removed and the residue was purified by silica gel column chromatography (Hexanes/EtOAc=5/1 (v/v)) to give compound 10-2 (13 g, 83% yield) as a yellow solid. $^1$H NMR (300 MHz, CDCl$_3$): δ 7.48 (d, 1H), 7.39 (dd, 1H), 6.84 (dd, 1H), 4.42 (q, 2H), 3.83 (s, 3H), 1.45 (t, 3H) ppm.

Step 2. A mixture of compound 10-1 (3.34 g, 10 mmol), 10-2 (1.40 g, 10 mmol) and Pd(PPh$_3$)$_4$ (0.58 g, 0.5 mmol) in 2 M aq. Na$_2$CO$_3$ (15 mL) and dioxane (75 mL) was degassed and refilled with nitrogen. The process was repeated 3 times.

rt for 2 hrs and at 50° C. for 18 hrs. The reaction mixture was added into ice water (150 mL) and the mixture was extracted with EtOAc (50 mL×3). The combined extracts were washed with brine and dried with anhydrous Na$_2$SO$_4$. The solvent was removed and the residue was dried in vacuo to give crude compound 10-5 (2.15 g, 94% yield). $^1$H NMR (300 MHz, CDCl$_3$): δ 8.04 (s, 1H), 7.78 (s, 1H), 7.68 (m, 1H), 7.57 (m, 1H), 7.18-7.36 (m, 2H), 7.73 (m, 1H), 4.34 (q, J=7.3 Hz, 2H), 1.44 (d, J=7.4 Hz, 6H), 1.27 (t, J=7.3 Hz, 3H) ppm.

Scheme 11

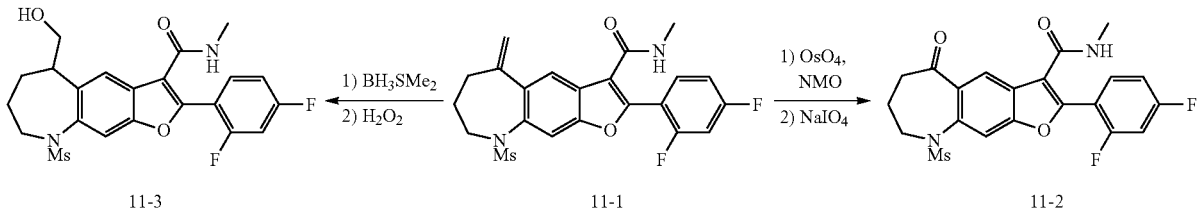

The mixture was then stirred at 90° C. in a sealed flask for 24 hrs. After being cooled down, the reaction mixture was concentrated. The residue was partitioned between DCM and water. The aqueous layer was extracted with DCM several times. The combined organic extracts were dried with anhydrous Na$_2$SO$_4$. The solvent was removed and the residue was purified by silica gel column chromatography (EtOAc/hexanes=1/20 to 1/15 (v/v)) to give compound 10-3 (2.54 g, 88% yield). LC-MS (ESI): m/z 315 [M+H]$^+$; $^1$H NMR (300 MHz, CDCl$_3$): δ 7.68 (m, 1H), 7.57 (d, J=1.3 Hz, 1H), 7.46 (m, 1H), 7.44 (d, J=8.9 Hz, 1H), 7.16-7.30 (m, 2H), 6.98 (dd, J=1.3 and 8.9 Hz, 1H), 4.32 (q, J=7.3 Hz, 2H), 3.92 (s, 3H), 1.27 (t, J=7.3 Hz) ppm.

Step 3. To a solution of compound 10-3 (2.54 g, 8.7 mmol) in chloroform at was slowly added 70% HNO$_3$ (w/w, 4.7 mL, 105 mmol). After completing the addition, the solution was stirred at −20° C. for 30 min and rt overnight. The reaction mixture was diluted with dichloromethane (150 mL), washed with water (50 mL×5), and dried with anhydrous Na$_2$SO$_4$. The solvent was removed and the residue was purified by silica gel column chromatography (EtOAc/hexanes=1/9 to 1/6 (v/v)) to give compound 10-4 (1.98 g, 68% yield). $^1$H NMR (300 MHz, CDCl$_3$): δ 8.10 (s, 1H), 7.79 (s, 1H), 7.69 (m, 1H), 7.56 (m, 1H), 7.20-7.36 (m, 2H), 4.35 (q, J=7.3 Hz, 2H), 4.05 (s, 3H), 1.25 (t, J=7.3 Hz) ppm.

Step 4. To a solution of compound 10-4 (1.98 g, 5.91 mmol) in dichloromethane at −45° C. was slowly added a solution of BBr$_3$ (0.68 mL, 7.1 mmol) in dichloromethane (6 mL). The resulting mixture was stirred at the temperature for 30 min, and then in an ice-water bath for 30 min. Subsequently, the cold reaction mixture was diluted with dichloromethane (100 mL), and ice water (10 mL) was slowly added into the solution to destroy the excess amount of BBr$_3$. The organic layer was washed with water and dried over anhydrous Na$_2$SO$_4$. The solvent was removed and the residue was dried in vacuo to give a crude de-methylated intermediate of compound 10-4, which was used for the next step without further purification. LCMS (ESI): m/z 344 [M−1]$^+$. Subsequently, Cs$_2$CO$_3$ (3.85 g, 12 mmol) was added into a solution of the above crude product in NMP (20 mL). After stirring at rt for 10 min, the reaction mixture was added 2-bromopropane (0.67 mL, 7.1 mmol) and the resulting mixture was stirred at Synthesis of Compound 11-2. Refer to Scheme 11. To a solution of compound 11-1 (100 mg, 0.22 mmol) in THF (6.0 mL) and water (1.5 mL), OsO$_4$ (1.5 mL, 4% in water, 0.23 mmol) was added at rt. The reaction was stirred for 5 min and then NMO (0.028 mL, 0.027 mmol) was added. After stirring for 4 hrs, the reaction was quenched by adding Na$_2$SO$_3$ (454 mg, 3.6 mmol). The reaction was extracted with dichloromethane (25 mL×2) and the extracts were combined, washed with brine, and dried anhydrous Na$_2$SO$_4$. The solvent was removed and the residue was re-dissolved in dichloromethane (5 mL). Subsequently, NaIO$_4$ (103 mg, 0.48 mmol), silica gel (650 mg) and water (0.2 mL) were added to the mixture at rt. After stirring for 4 hrs, the reaction was diluted with dichloromethane (50 mL), washed with brine, and dried with anhydrous Na$_2$SO$_4$. The solvent was removed and the residue was purified by silica gel column chromatography (EtOAc/hexanes=1/10 (v/v)) to give compound 11-2 (70 mg, 70% yield). LC-MS (ESI): m/z 449 [M+H]$^+$; $^1$H NMR (300 MHz, CDCl$_3$): δ 8.23 (s, 1H), 7.68-7.80 (m, 1H), 7.67 (s, 1H), 6.95-7.10 (m, 2H), 5.80-5.81 (m, 1H), 3.89 (t, J=6.3 Hz, 2H), 3.03 (s, 3H), 2.99 (d, J=4.9 Hz, 3H), 2.83-2.97 (m, 2H), 2.02-2.08 (m, 2H) ppm.

Synthesis of Compound 11-3. To a solution of compound 11-1 (65 mg, 0.14 mmol) in THF (6.0 mL), BH$_3$.SMe$_2$ (2M in THF, 0.22 mL, 0.44 mmol) was added at rt. After stirring at rt overnight, 3 N aq. NaOH (0.42 mL, 1.26 mmol) was slowly added. After stirring at rt for 30 min, H$_2$O$_2$ (30% (w/w) in water, 0.42 mL) was added and the resulting mixture was stirred at rt for another 30 min. Subsequently, the reaction mixture was diluted with EtOAc (50 mL) and the organic layer was washed with brine and water and dried with anhydrous Na$_2$SO$_4$. The solvent was removed and the residue was purified by silica gel column chromatography (EtOAc/hexanes=1/10 (v/v)) to give compound 11-3 (50 mg, 77% yield). LC-MS (ESI): m/z 465 [M+H]$^+$; $^1$H NMR (300 MHz, CDCl$_3$): δ 7.64-7.69 (m, 1H), 7.26 (s, 1H), 7.45 (br. s, 1H), 6.85-6.98 (m, 2H), 4.04-4.15 (m, 1H), 3.55-3.80 (m, 3H), 3.83-3.89 (m, 1H), 3.08 (s, 3H), 2.89 (s, 3H), 1.75-1.95 (m, 4H) ppm.

Scheme 12
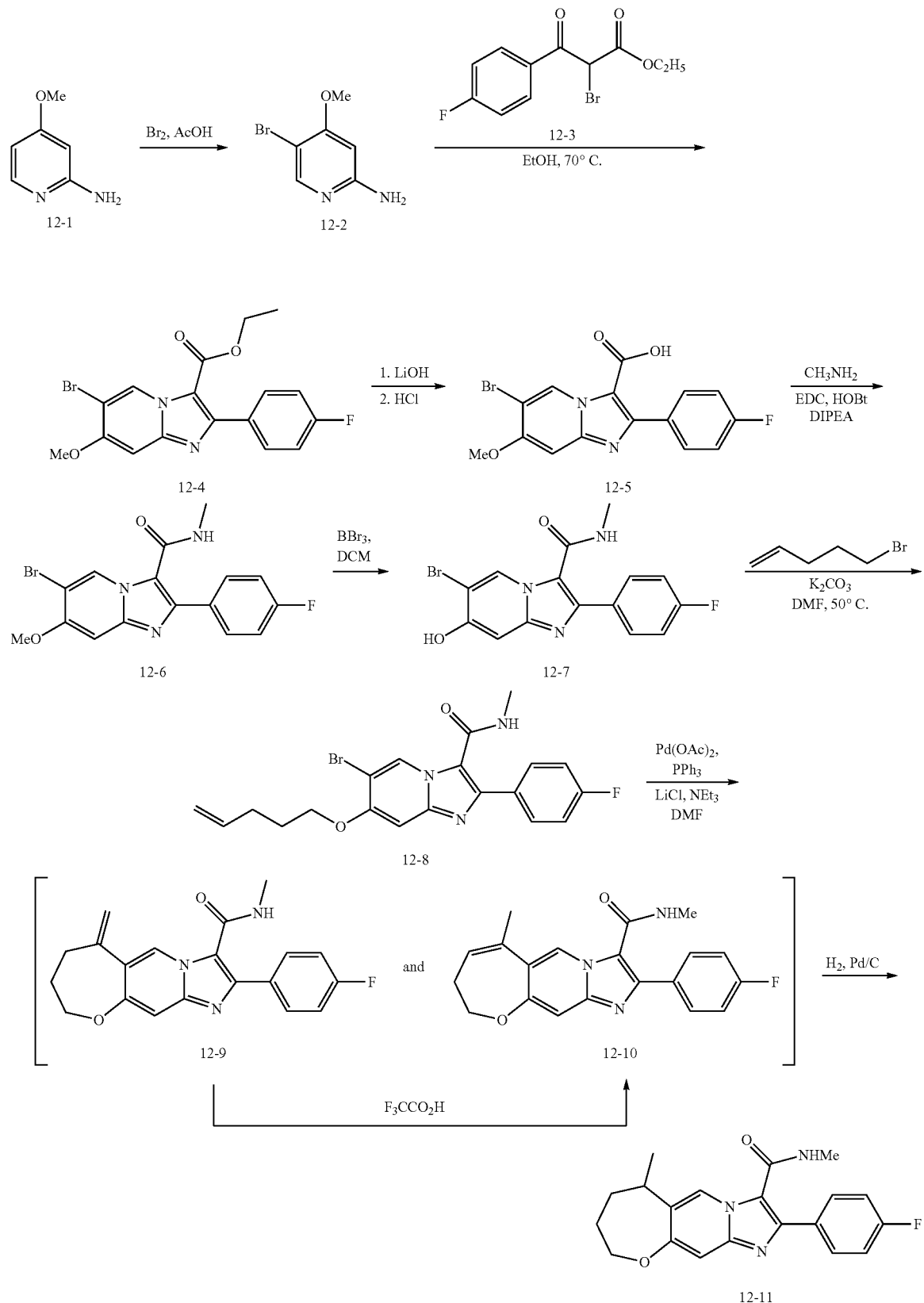

Step 1. Refer to Scheme 12. A solution of $Br_2$ (1 M in AcOH, 10 mL, 10 mmol) was slowly added into a solution commercially available compound 12-1 (1.24 g, 10 mmol) in AcOH (35 mL) at rt. After stirring at rt for 1 hr, the reaction mixture was filtered and the solid was dried in vacuo to give compound 12-2 (1.41 g, 69% yield). $^1$H NMR (300 MHz, $CD_3OD$): δ 7.84 (s, 1H), 6.29 (s, 1H), 3.87 (s, 3H) ppm.

Step 2. A mixture of compound 12-2 (1.41 g, 6.9 mmol) and 2-bromo-3-(4-fluoro-phenyl)-3-oxo-propionic acid ethyl ester (12-3) (1.01 g, 3.5 mmol) in ethanol (100 mL) was stirred at 70° C. for 22 hrs. The solvent was removed and the residue was partitioned between DCM (50 mL) and water (25 mL). The organic layer was washed with sat. aq. $Na_2CO_3$ solution and water and dried with anhydrous $Na_2SO_4$. The solvent was removed and the residue was purified by silica gel column chromatography (EtOAc/DCM=1/10 (v/v)) to give compound 12-4 (0.90 g, 65% yield). $^1$H NMR (300 MHz, $CDCl_3$): δ 9.57 (s, 1H), 7.74-7.78 (m, 2H), 7.09-7.15 (m, 2H), 7.04 (s, 1H), 4.31 (q, J=7.2 Hz, 2H), 4.00 (s, 3H), 1.25 (t, J=7.2 Hz, 3H) ppm.

Step 3. A solution of LiOH (0.25 g, 6.0 mmol) in water (4.5 mL) was added into a solution of compound 12-4 (0.90 g, 2.3 mmol) in THF (9 mL). After stirring at 50° C. for 24 hrs, the reaction mixture was acidified to pH~3.0 by adding 1 N aq. HCl. The solvent was removed and the residue was dried in vacuo to give crude compound 12-5, which was used for the next step without further purification. LC-MS: m/z, 365 $[M+H]^+$.

Step 4. A mixture of compound 12-5 (0.83 g, 2.28 mmol), $CH_3NH_2$·HCl (0.31 g, 4.56 mmol), EDC.HCl (0.66 g, 3.42 mmol), $HOBt·H_2O$ (0.52 g, 3.4 mmol) and DIPEA (1.88 mL, 11.4 mmol) in DMF (22 mL) was stirred at 50° C. for 18 hrs. The reaction mixture was added into ice water (250 L) and filtered. The solid was washed with water and dried in vacuo to give crude compound 12-6. $^1$H NMR (300 MHz, $CDCl_3$): δ 9.70 (s, 1H), 7.66-7.72 (m, 2H), 7.18-7.24 (m, 2H), 6.97 (s, 1H), 5.65 (broad s, 1H, NH), 4.00 (s, 3H), 2.88 (d, J=5.1 Hz, 3H) ppm.

Step 5. $BBr_3$ (1.73 mL, 19 mmol) was slowly added into a solution of compound 12-6 (0.68 g, 1.8 mmol) in DCM (4 mL) at 0° C. The resulting reaction mixture was stirred at rt for 16 hrs under an atmosphere of $N_2$ and treated with ice water (25 mL). After adjusting the pH of the mixture to basic using 5 N aq. NaOH, the mixture was extracted with DCM (25 mL×3). The combined organic extracts dried with anhydrous $Na_2SO_4$. The solvent was removed and the residue was purified by silica gel column chromatography to give compound 12-7 (0.36 g, 55% yield). LC-MS: m/z 366 $[M+H]^+$.

Step 6. A mixture of compound 12-7 (0.36 g, 1.0 mmol), 5-bromo-1-pentene (163 mg, 1.1 mmol) and $K_2CO_3$ (113 mg, 2.0 mmol) in DMF (12 mL) was stirred at 50° C. for 8 hrs. The reaction mixture was poured into water and the precipitate was collected by filtration. The crude product was purified by silica gel column chromatography (EtOAc/DCM=1/7 (v/v)) to give compound 12-8 (0.21 g, 49% yield). LC-MS: m/z 432 $[M+H]^+$; $^1$H NMR (300 MHz, $CDCl_3$): δ 9.67 (s, 1H), 7.66-7.72 (m, 2H), 7.17-7.24 (m, 2H), 6.93 (s, 1H), 5.69-5.97 (m, 1H), 5.68 (br s, 1H), 5.02-5.16 (m, 2H), 4.08 (t, J=6.8 Hz, 2H), 2.88 (d, J=5.2 Hz, 3H), 2.28-2.37 (m, 2H), 1.96-2.06 (m, 2H) ppm.

Step 7. A mixture of compound 12-8 (200 mg, 0.46 mmol), $Pd(OAc)_2$ (10.3 mg, 0.046 mmol), $PPh_3$ (48.5 mg, 0.19 mmol), LiCl (21.5 mg, 0.51 mmol) and $Et_3N$ (0.26 mL, 1.8 mmol) in DMF (6.0 mL) was degassed and refilled with $N_2$. The process was repeated for 3 times. After stirring at 120° C. for 18 hrs, the mixture was added into ice water (100 mL). The suspension was filtered and the solid was purified by silica gel column chromatography (EtOAc/DCM=1/7 (v/v)) to give a mixture of compounds 12-9 and 12-10 (100 mg, 62% yield) at a ratio of 3/1 determined by proton NMR. LC-MS: m/z 352 $[M+H]^+$. Compound 12-9: $^1$H NMR (300 MHz, $CDCl_3$): δ 9.48 (s, 1H), 6.68-7.72 (m, 2H), 7.18-7.24 (m, 2H), 7.13 (s, 1H), 5.65 (br s, 1H), 5.37 (s, 1H), 5.16 (s, 1H), 4.28-4.34 (m, 2H), 2.87 (d, J=5.2 Hz, 3H), 2.58-2.66 (m, 2H), 2.05-2.12 (m, 2H) ppm.

Synthesis of Compound 12-11. A mixture of compounds 12-9 and 12-10 (10 mg, 0.028 mmol) and 10% Pd/C (5 mg) in ethanol (4 mL) was stirred at rt for 6 hrs under an atmosphere of $H_2$. The mixture was filtered through Celite®545 and the filtered cake was washed with DCM (20 mL×2). The filtrate was concentrated and the residue was purified by column chromatography (EtOAc/DCM=1/7 (v/v)) to give compound 13-11 (8 mg, 80% yield). LC-MS: m/z 354 $[M+H]^+$; $^1$H NMR (300 MHz, $CDCl_3$): δ 9.28 (s, 1H), 7.72-7.78 (m, 2H), 7.63 (s, 1H), 7.16-7.28 (m, 2H), 6.06-6.14 (m, 1H), 4.16-4.20 (m, 2H), 3.18-3.28 (m, 1H), 2.91 (d, J=5.2 Hz, 3H), 2.08-2.20 (m, 1H), 1.90-2.05 (m, 2H), 1.68-1.78 (m, 1H), 1.42 (d, J=7.2 Hz, 3H) ppm.

Synthesis of Compound 12-10. A solution of compounds 12-9 and 12-10 (28 mg) in $CF_3CO_2H$ (3 mL) was stirred at 70° C. for 48 hrs. The solvent was removed and the residue was diluted with DCM (25 mL). The mixture was with sat. aq. $NaHCO_3$ and dried with anhydrous $Na_2SO_4$. The solvent was removed and the residue was purified by silica gel column chromatography (EtOAc/DCM=1/7 (v/v)) to give compound 12-10 (22 mg, 79% yield). LC-MS (ESI): m/z 352 $[M+H]^+$; $^1$H NMR (300 MHz, $CDCl_3$): δ 9.63 (s, 1H), 7.65-7.70 (m, 2H), 7.18-7.26 (m, 3H), 6.04-6.08 (m, 1H), 5.66-5.74 (m, 1H), 4.29 (t, J=5.4 Hz, 2H), 2.60 (d, J=4.8 Hz, 3H), 2.64-2.70 (m, 2H), 2.26 (s, 3H) ppm.

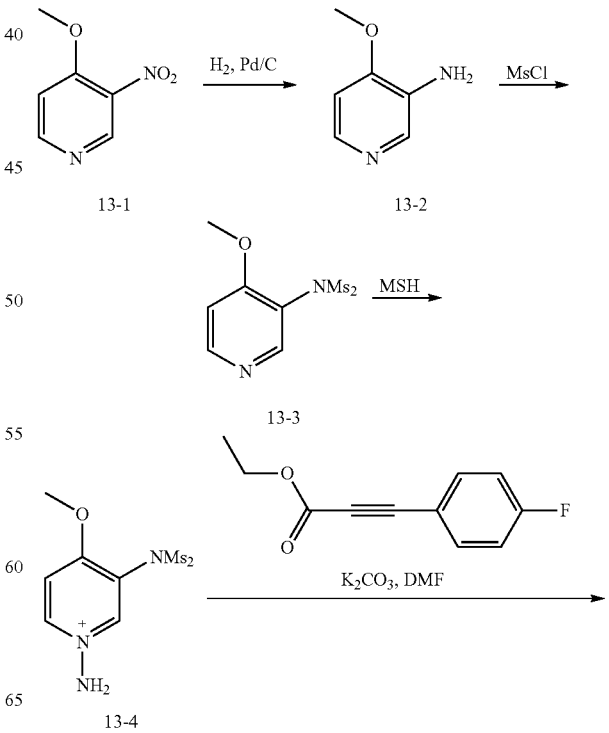

Scheme 13

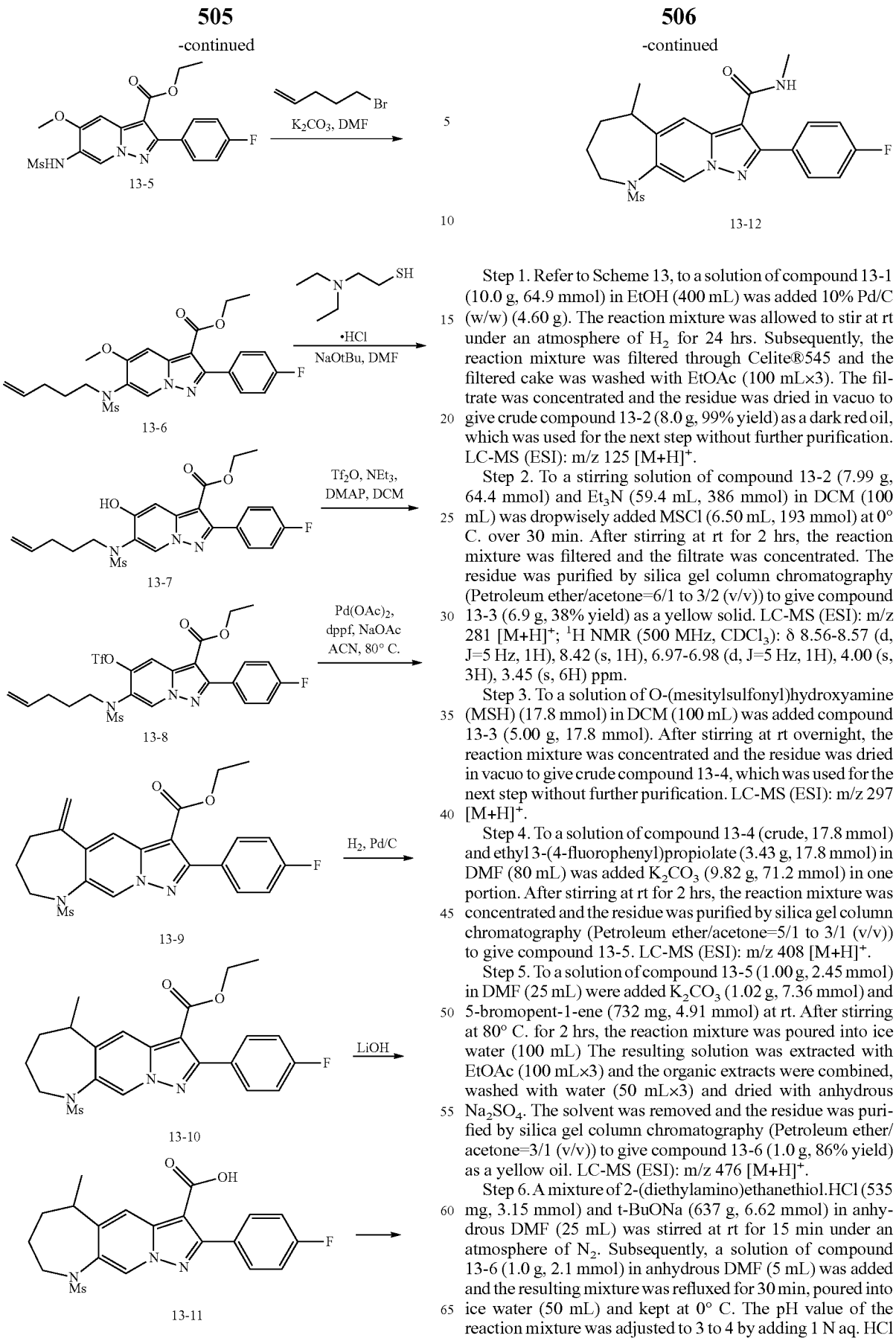

Step 1. Refer to Scheme 13, to a solution of compound 13-1 (10.0 g, 64.9 mmol) in EtOH (400 mL) was added 10% Pd/C (w/w) (4.60 g). The reaction mixture was allowed to stir at rt under an atmosphere of $H_2$ for 24 hrs. Subsequently, the reaction mixture was filtered through Celite®545 and the filtered cake was washed with EtOAc (100 mL×3). The filtrate was concentrated and the residue was dried in vacuo to give crude compound 13-2 (8.0 g, 99% yield) as a dark red oil, which was used for the next step without further purification. LC-MS (ESI): m/z 125 [M+H]$^+$.

Step 2. To a stirring solution of compound 13-2 (7.99 g, 64.4 mmol) and $Et_3N$ (59.4 mL, 386 mmol) in DCM (100 mL) was dropwisely added MSCl (6.50 mL, 193 mmol) at 0° C. over 30 min. After stirring at rt for 2 hrs, the reaction mixture was filtered and the filtrate was concentrated. The residue was purified by silica gel column chromatography (Petroleum ether/acetone=6/1 to 3/2 (v/v)) to give compound 13-3 (6.9 g, 38% yield) as a yellow solid. LC-MS (ESI): m/z 281 [M+H]$^+$; $^1$H NMR (500 MHz, $CDCl_3$): δ 8.56-8.57 (d, J=5 Hz, 1H), 8.42 (s, 1H), 6.97-6.98 (d, J=5 Hz, 1H), 4.00 (s, 3H), 3.45 (s, 6H) ppm.

Step 3. To a solution of O-(mesitylsulfonyl)hydroxyamine (MSH) (17.8 mmol) in DCM (100 mL) was added compound 13-3 (5.00 g, 17.8 mmol). After stirring at rt overnight, the reaction mixture was concentrated and the residue was dried in vacuo to give crude compound 13-4, which was used for the next step without further purification. LC-MS (ESI): m/z 297 [M+H]$^+$.

Step 4. To a solution of compound 13-4 (crude, 17.8 mmol) and ethyl 3-(4-fluorophenyl)propiolate (3.43 g, 17.8 mmol) in DMF (80 mL) was added $K_2CO_3$ (9.82 g, 71.2 mmol) in one portion. After stirring at rt for 2 hrs, the reaction mixture was concentrated and the residue was purified by silica gel column chromatography (Petroleum ether/acetone=5/1 to 3/1 (v/v)) to give compound 13-5. LC-MS (ESI): m/z 408 [M+H]$^+$.

Step 5. To a solution of compound 13-5 (1.00 g, 2.45 mmol) in DMF (25 mL) were added $K_2CO_3$ (1.02 g, 7.36 mmol) and 5-bromopent-1-ene (732 mg, 4.91 mmol) at rt. After stirring at 80° C. for 2 hrs, the reaction mixture was poured into ice water (100 mL) The resulting solution was extracted with EtOAc (100 mL×3) and the organic extracts were combined, washed with water (50 mL×3) and dried with anhydrous $Na_2SO_4$. The solvent was removed and the residue was purified by silica gel column chromatography (Petroleum ether/acetone=3/1 (v/v)) to give compound 13-6 (1.0 g, 86% yield) as a yellow oil. LC-MS (ESI): m/z 476 [M+H]$^+$.

Step 6. A mixture of 2-(diethylamino)ethanethiol.HCl (535 mg, 3.15 mmol) and t-BuONa (637 g, 6.62 mmol) in anhydrous DMF (25 mL) was stirred at rt for 15 min under an atmosphere of $N_2$. Subsequently, a solution of compound 13-6 (1.0 g, 2.1 mmol) in anhydrous DMF (5 mL) was added and the resulting mixture was refluxed for 30 min, poured into ice water (50 mL) and kept at 0° C. The pH value of the reaction mixture was adjusted to 3 to 4 by adding 1 N aq. HCl and the resulting mixture was extracted with EtOAc (50 mL×3). The organic extracts were combined, washed with brine and dried with anhydrous Na₂SO₄. The solvent was removed and the residue was purified by silica gel column chromatography (Hexanes/EtOAc=2/1 (v/v)) to give compound 13-7 (370 mg, 38% yield) as a yellow oil. LC-MS (ESI): m/z 462 [M+H]⁺.

Step 7. To a solution of compound 13-7 (164 mg, 0.35 mmol) and DMAP (2.0 mg, 0.016 mmol) in CH₂Cl₂ (6 mL) was added Et₃N (100 µL, 0.72 mmol), followed by Tf₂O (70 µL, 0.42 mmol) at 0° C. After stirring at 0° C. for 30 min, the reaction mixture was concentrated and the residue was purified by silica gel column chromatography (Petroleum ether/EtOAc=7/1 (v/v)) to give compound 13-8 (102 mg, 48% yield) as a yellow oil. LC-MS (ESI): m/z 594 [M+H]⁺.

Step 8. A solution of compound 13-8 (215 mg, 0.36 mmol), Pd(OAc)₂ (8 mg, 0.036 mmol), dppf (66 mg, 0.12 mmol) and sodium acetate (36 mg, 0.43 mmol) in DMF (20 mL) was heated at 80° C. for 3 hrs under an atmosphere of N₂. The reaction mixture was concentrated and the residue was purified by silica gel column chromatography (Petroleum ether/EtOAc=5/1 (v/v)) to give compound 13-9 (115 mg, 61% yield) as a white solid. LC-MS (ESI): m/z 444 [M+H]⁺; ¹H NMR (500 MHz, CDCl₃): δ 8.70 (s, 1H), 8.12 (s, 1H), 7.78 (m, 2H), 7.15 (m, 2H), 5.38 (s, 1H), 5.37 (s, 1H), 4.32 (q, J=7.0 Hz, 2H), 3.87 (m, 2H), 2.91 (s, 3H), 2.58 (m, 2H), 1.99 (m, 2H), 1.31 (t, J=7.0 Hz, 3H) ppm.

Step 9. To a solution of compound 13-9 (95 mg, 0.21 mmol) in EtOH (40 mL) and THF (10 mL) was added 10% Pd/C (40 mg). The resulting mixture was stirred at rt for 16 hrs under an atmosphere of H₂. The resulting mixture was filtered and the filtrate was concentrated and dried in vacuo to give crude compound 13-10, which was used for the next step without further purification. LC-MS (ESI): m/z 446 [M+H]⁺.

Step 10. A mixture of compound 13-10 (95 mg, 0.213 mmol) and LiOH (2.0 M, 0.852 mmol) in MeOH (4 mL) and THF (8 mL) was stirred at 75° C. for 48 hrs. The mixture was cooled to rt and concentrated. The residue was diluted with water (30 mL) and adjusted its pH value to 5~6 by adding 2 N aq. HCl. The resulting mixture was extracted EtOAc (50 mL×3) and the organic extracts were combined, washed with brine and dried with anhydrous Na₂SO₄. The solvent was removed and the residue was dried in vacuo to give crude compound 13-11 (85 mg, 95% yield) as a white solid, which was used directly for the next step without further purification. LC-MS (ESI): m/z 418 [M+H]⁺.

Step 11. To a solution of compound 13-11 (85.0 mg, 0.20 mmol) in DMF (2 mL) was added HATU (93.0 mg, 0.24 mmol). After stirring at rt for 30 min, the reaction mixture was added DIPEA (53 mg, 0.41 mmol) and MeNH₂·HCl (17 mg, 0.24 mmol) and the resulting mixture was stirred at rt for 30 min. Subsequently, the reaction mixture was poured into ice water and the suspension was filtered. The solid was collected and dried in vacuo to give crude compound 13-12. LC-MS (ESI): m/z 431 [M+H]⁺; ¹H NMR (500 Hz, CDCl₃): δ 8.51 (s, 1H), 8.21 (s, 1H), 7.66 (dd, J₁=5.5 Hz, J₂=8.5 Hz, 2H), 7.23 (t, J=8.5 Hz, 2H), 5.5 (m, 1H), 4.19 (m, 1H), 3.21 (m, 2H), 3.16 (s, 3H), 2.86 (d, J=4.5 Hz, 3H), 1.97-2.06 (m, 2H), 1.63-1.78 (m, 2H), 1.49 (d, J=6.5 Hz, 3H) ppm. Compound 13-12 was separated into a pair of enantiomers: enantiomer 13-12_A (t_R=11.306 min) and enantiomer 13-12_B (t_R=14.966 min) detected by UV absorption at 214 nm on a Daicel CHIRAL-PAK IA 4.0 mm×150 mm×5 µm column (eluent: hexane/EtOH=70/30 (v/v) with 0.1% (v/v) diethylamine and flow rate: 1 mL/min).

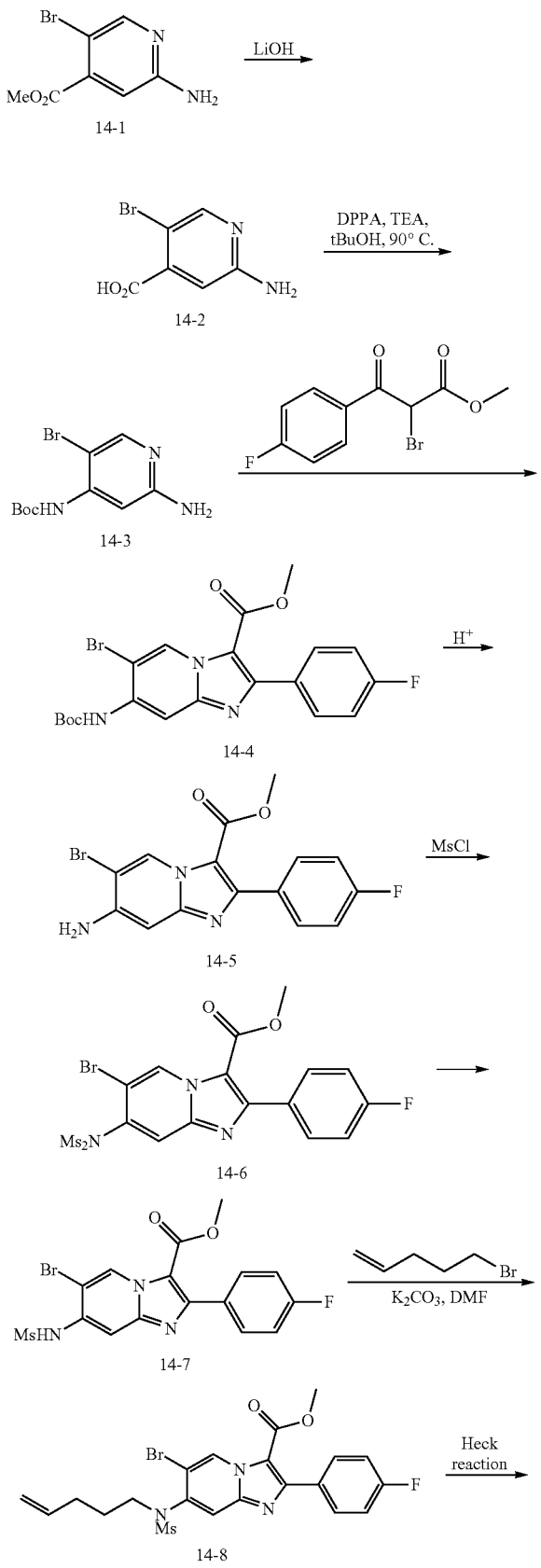

Scheme 14

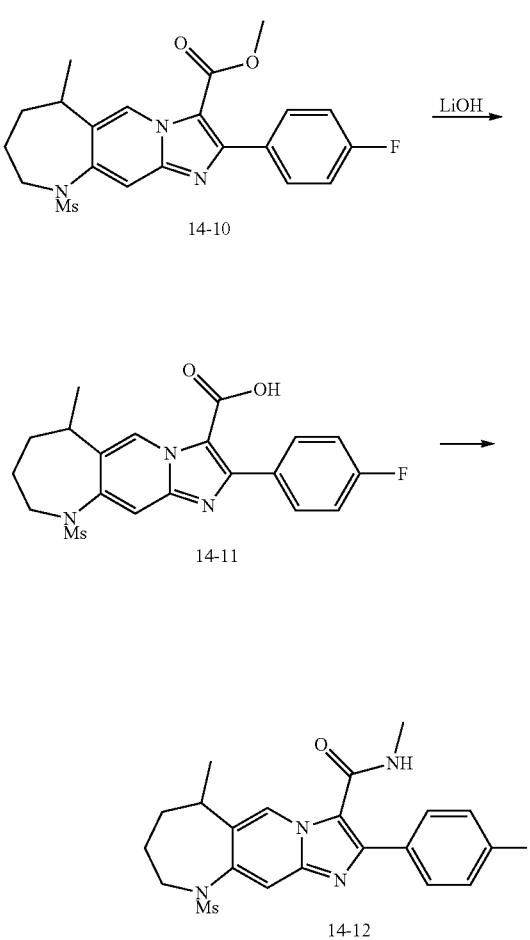

Step 1. Refer to Scheme 14. A mixture of compound 14-1 (10.0 g, 43.28 mmol) and LiOH (5.46 g, 129.8 mmol) in THF (400 mL), MeOH (200 mL) and water (100 mL) was stirred at 70° C. for 2 hrs under an atmosphere of $N_2$. Subsequently, the reaction mixture was cooled to 0° C. and adjusted its pH value to 6 by adding concd. aq. HCl. The resulting suspension was filtered and the solid was dried in vacuo to give compound 14-2 (7.8 g, 83% yield). LC-MS (ESI): m/z 217 [M+H]$^+$.

Step 2. A mixture of compound 14-2 (7.81 g, 35.6 mmol), DPPA (9.40 mL, 43.5 mmol) and $Et_3N$ (5.90 mL, 42.5 mmol) in t-BuOH (300 mL) was stirred at 90° C. for 6 hrs under an atmosphere of $N_2$. The solvent was removed and the residue was purified by silica gel column chromatography (Petroleum ether/EtOAc=5/1 to 4/1 (v/v)) to give compound 14-3 (4.9 g, 47% yield) as a white solid. LC-MS (ESI): m/z 234 [M−56+H]$^+$.

Step 3. A mixture of compound 14-3 (5.10 g, 17.7 mmol) and methyl 2-bromo-3-(4-fluorophenyl)-3-oxopropanoate (5.84 g, 21.2 mmol) in DMF (80 mL) was stirred at 80° C. for 42 hrs under an atmosphere of $N_2$. Subsequently, the reaction mixture was cooled to 0° C., followed by adding a solution of $NaHCO_3$ (1.9 g) in water (20 mL). After stirring at 0° C. for 15 min, the mixture was diluted with water (100 mL) and the resulting suspension was extracted with EtOAc (100 mL×3). The organic extracts were combined, washed with water (10 mL×3) and dried with anhydrous $Na_2SO_4$. The solvent was removed and the residue was purified by silica gel column chromatography (Petroleum ether/EtOAc=40/1 to 20/1 (v/v)) to give compound 14-4 (1.9 g, 23% yield). LC-MS (ESI): m/z 464 [M+H]$^+$.

Step 4. To a solution of compound 14-4 (1.8 g, 3.9 mmol) in dioxane (10 mL) was added 4N HCl in dioxane (10 mL). After stirring at rt for 3 hrs, the reaction mixture was concentrated and the residue was dried in vacuo to give crude compound 14-5, which was used for the next step without further purification. LC-MS (ESI): m/z 364 [M+H]$^+$.

Step 5. To a stirred solution of compound 14-5 (1.4 g, 3.86 mmol) in pyridine (30 ml) was added MsCl (1.33 g, 11.6 mmol) at 0° C. After stirring at rt for 1.5 hrs, the reaction mixture was concentrated and the residue was diluted with water (50 mL). Subsequently, the mixture was adjusted its pH value to 5-6 by adding 2N aq. HCl. The resulting suspension was filtered and the solid was dried in vacuo to give compound 14-6, which was used for the next step without further purification. LC-MS (ESI): m/z 520 [M+H]$^+$.

Step 6. A solution of compound 14-6 (2.00 g, 3.86 mmol) and $K_2CO_3$ (532 mg, 3.86 mmol) in MeOH (100 mL) was stirred at rt for 30 min. The suspension was filtered and the filtrate was concentrated. The residue was purified by silica gel column chromatography (Petroleum ether/acetone=2/1 to 1/2 (v/v)) to give compound 14-7 (970 mg, 56% yield) as a yellow solid. LC-MS (ESI): m/z 442 [M+H]$^+$.

Step 7. To a solution of compound 14-7 (970 mg, 2.19 mmol) in DMF (30 mL) was added $K_2CO_3$ (1.21 g, 8.76 mmol) and 5-bromopent-1-ene (784 mg, 5.26 mmol) at rt. After stirring at 80° C. for 16 hrs and at 90° C. for 24 hrs, the reaction mixture was concentrated and the residue was diluted with water (50 mL). The mixture was extracted with EtOAc (50 mL×2). The organic extracts were combined, washed with water (50 mL×2) and dried with anhydrous $Na_2SO_4$. The solvent was removed and the residue was purified by silica gel column chromatography (Petroleum ether/acetone=5/1 (v/v)) to give compound 14-8 (380 mg, 34% yield) as a yellow solid. LC-MS (ESI): m/z 510 [M+H]$^+$.

Step 8. Following the procedure described for the synthesis of compound 13-11 and replacing compound 13-8 with 14-8, compound 14-12 was obtained. LC-MS (ESI): m/z 431 [M+H]$^+$; $^1$H NMR (500 Hz, $CDCl_3$): δ 9.37 (s, 1H), 7.67 (m, 2H), 7.60 (s, 1H), 7.21 (t, J=8.5 Hz, 2H), 5.72 (m, 1H), 3.24 (m, 2H), 3.16 (s, 3H), 2.87 (d, J=5.0 Hz, 3H), 1.74-2.02 (m, 4H), 1.48 (d, J=7.0 Hz, 3H) ppm.

Scheme 15
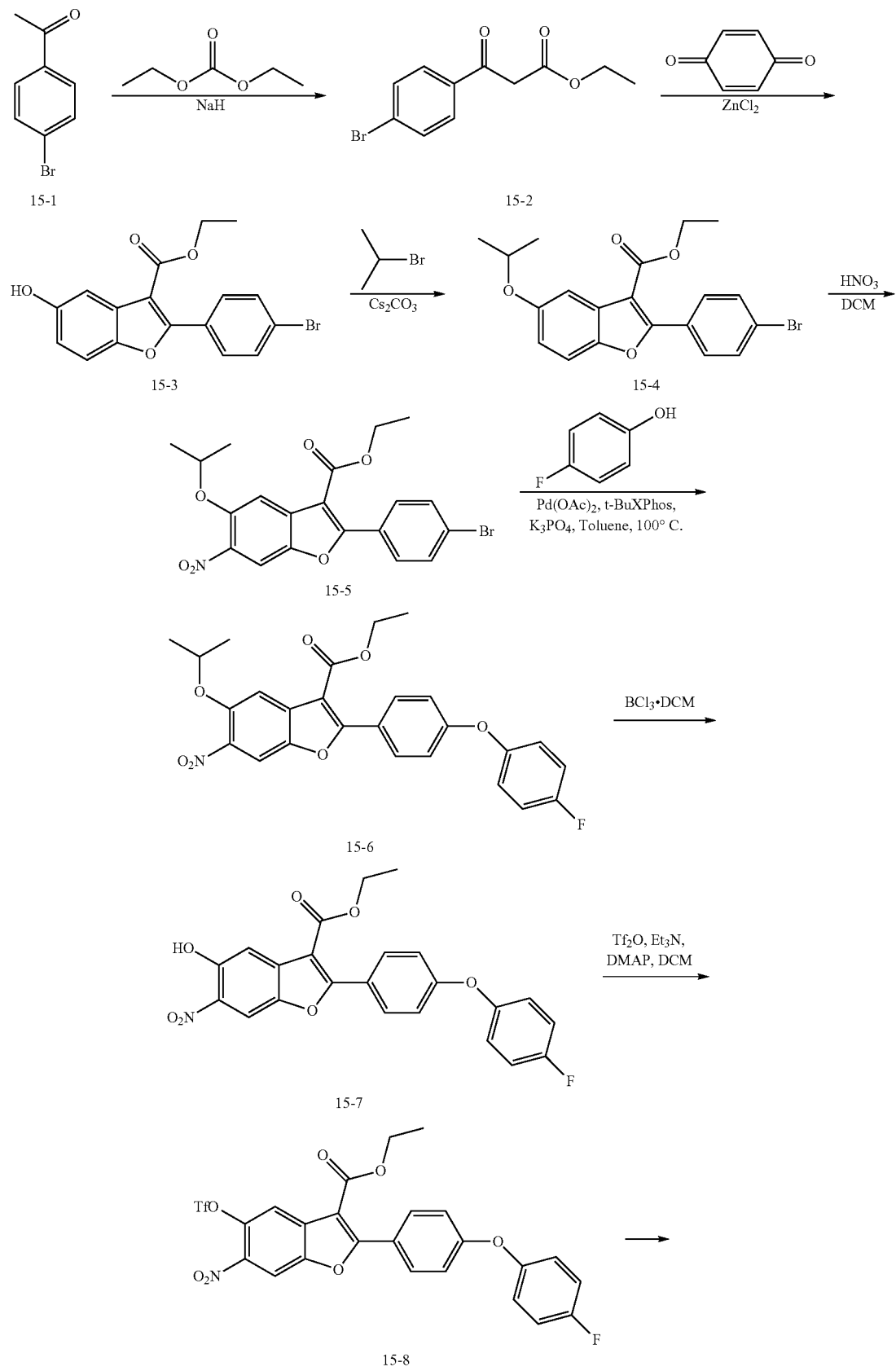

-continued
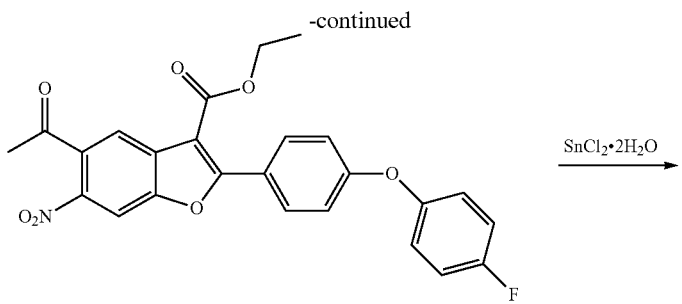
15-9
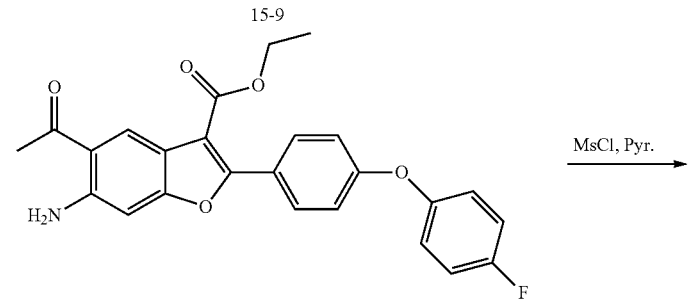
15-10
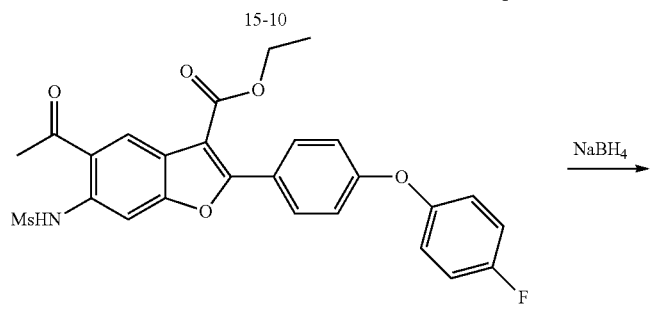
15-11
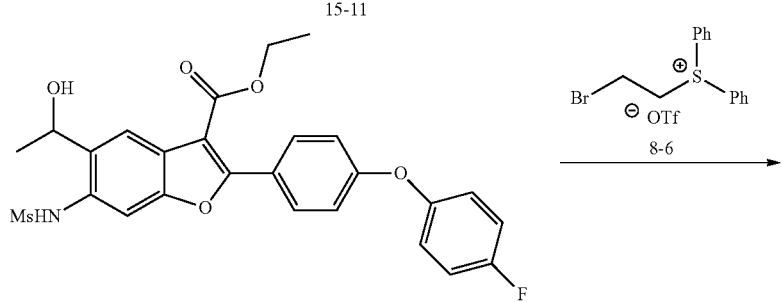
15-12
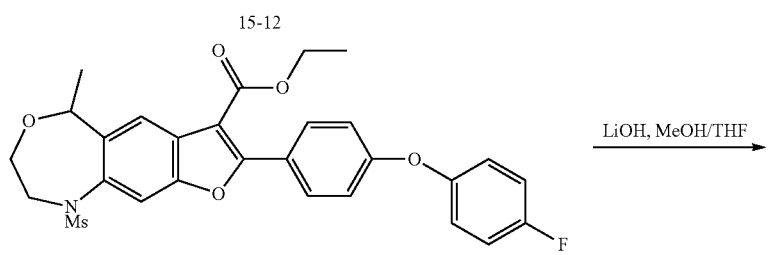
15-13
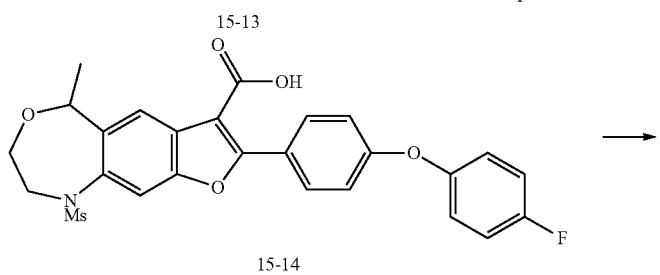
15-14

-continued

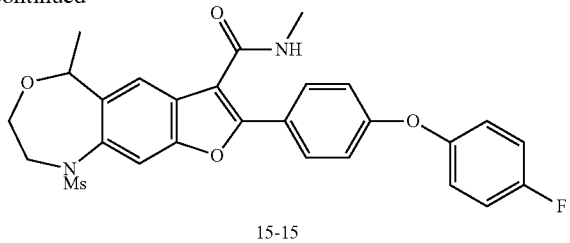

15-15

Step 1. Refer to Scheme 15. To a solution of NaH (80 g, 60% mineral oil dispersion, 2 mol) in toluene (1.2 L) was added diethyl carbonate (295 g, 2.50 mol) at 0° C. After stirring at rt for 2 hrs, the mixture was added drop wise to a solution of compound 15-1 (99 g, 0.50 mol) in toluene (400 mL) at reflux. After refluxing overnight, the reaction mixture was cooled to rt and sequentially treated with HOAc (140 mL) and aq. HCl (2 M, 864 mL). The resulting mixture was extracted with EtOAc (400 mL×3) and the combined organic extracts were washed with water (500 mL×4) and brine (200 mL×2) and dried with anhydrous $Na_2SO_4$. The solvent was removed and the residue was dried in vacuo to give compound 15-2 (122 g, 90% yield) as an oil. LC-MS (ESI): m/z 271.0 $[M+H]^+$.

Step 2. To a solution of compound 15-2 (100 g, 369 mmol) in DMF (70 mL) was added p-benzoquinone (40 g, 369 mmol), followed by $ZnCl_2$ (50 g, 369 mmol) in portions at rt. After stirring at 105° C. for 3.5 hrs, the reaction mixture was partitioned between water (800 mL) and EtOAc (800 mL) and filtered. The aqueous phase was extracted with EtOAc (500 mL×2). The combined organic extracts were washed with water (1000 mL×2) and dried with anhydrous $Na_2SO_4$. The solvent was removed and the residue was purified by silica gel column chromatography (Petroleum ether/Acetone=10/1(v/v)) to give compound 15-3 (26 g, 20% yield) as a yellow solid. LC-MS (ESI): m/z 361.0 $[M+H]^+$.

Step 3. To a solution of compound 15-3 (26 g, 72 mmol) in NMP (200 mL) was added $Cs_2CO_3$ (47.0 g, 144 mmol). After stirring at rt for 20 min, 2-bromopropane (20.0 ml, 216 mmol) was added. The resulting mixture was stirred at 80° C. for 4 hrs, then diluted with ammonia and agitated for 30 min. The mixture was diluted with water (200 mL) and the aqueous phase was extracted with EtOAc (150 mL×3). The combined organic extracts were washed with water (200 mL×3) and dried with anhydrous $Na_2SO_4$. The solvent was removed and the residue was dried in vacuo to give compound 15-4 (27.5 g, 95% yield) as a colorless oil. LC-MS (ESI): m/z 403.0 $[M+H]^+$.

Step 4. To a solution of $HNO_3$ (conc. 66 mL, 0.89 mol) and $CH_2Cl_2$ (300 mL) a solution of compound 15-4 was added drop wise (27.5 g, 68.2 mmol) in $CH_2Cl_2$ (120 mL) at 0° C. over 1 hr. After stirring at rt for 30 min, the reaction mixture was diluted with water (200 mL) and extracted with DCM (150 mL×3). The combined organic extracts were washed with water (200 mL×3) and dried with anhydrous $Na_2SO_4$. The solvent was removed and the residue was re-crystallized in methyl t-butyl ether (MTBE) to give compound 15-5 (24.6 g, 80% yield) as a pale yellow solid. LC-MS (ESI): m/z 448.0 $[M+H]^+$; $^1H$ NMR (500 MHz, $CDCl_3$): δ 7.92 (d, J=8.5 Hz, 2H), 7.87 (m, 2H), 7.76 (s, 1H), 7.65 (d, J=8.5 Hz, 2H), 4.69-4.74 (m, 1H), 4.40-4.44 (m, 2H), 1.54 (s, 6H), 1.41-1.45 (t, 3H) ppm.

Step 5. A mixture of compound 15-5 (5.0 g, 11.2 mmol), 4-fluorophenol (1.7 g, 14.5 mmol), $Pd(OAc)_2$ (250 mg, 1.12 mmol), t-BuXphose (380 mg, 0.9 mmol) and $K_3PO_4$ (4.8 g, 22.4 mmol) in toluene (50 mL) was stirred at 100° C. under an atmosphere of Ar and monitored by LC-MS. After 2 hrs, the reaction mixture was concentrated and the residue was diluted with water (100 mL). The mixture was extracted with EtOAc (100 mL×3) and the combined organic extracts were washed with water (100 mL×2) and dried with anhydrous $Na_2SO_4$. The solvent was removed and the residue was dried in vacuo to give crude compound 15-6 (4.8 g, 90% yield) as a yellow powder. LC-MS (ESI): m/z 480.1 $[M+H]^+$.

Step 6. To a solution of compound 15-6 (2.0 g, 4.2 mmol) in DCM (30 mL) drop wise was added $BCl_3$ (8.4 mL, 8.4 mmol) at −78° C. After stirring at −40° C. for 1 hr, the reaction was quenched by adding sat. aq. $NH_4Cl$ (20 mL). The resulting mixture was extracted with DCM (50 mL×2) and the combined organic extracts were washed with water (50 mL×3) and brine (50 mL) and dried with anhydrous $Na_2SO_4$. The solvent was removed and the residue was dried in vacuo to give crude compound 15-7 (1.6 g, 90% yield) as a yellow solid. LC-MS (ESI): m/z 438.1 $[M+H]^+$.

Step 7. To a solution of compound 15-7 (1.6 g, 3.9 mmol) and DMAP (24 mg, 0.2 mmol) in DCM (30 mL) at 0° C. was added $Et_3N$ (790 mg, 7.8 mmol), followed by $Tf_2O$ (1.6 g, 5.82 mmol). After stirring at rt for 1 hr, LC-MS analysis indicated that the reaction went completion. The mixture was diluted with DCM (100 mL), washed water (50 mL×3) and brine (50 mL) and dried with anhydrous $Na_2SO_4$. The solvent was removed and the residue was dried in vacuo to give crude compound 15-8 (1.8 g, 94% yield) as a yellow solid. LC-MS (ESI): m/z 570.0 $[M+H]^+$.

Step 8. To a solution of compound 15-8 (1.8 g, 3.2 mmol) in $CH_3CN$ (50 mL) was added NaOAc (1.6 g, 16 mmol.), dppf (180 mg, 0.32 mmol), and $Pd(OAc)_2$ (150 mg, 0.64 mmol), and the resulting mixture was saturated with Ar. After 1-(vinyloxy)butane (1.6 g, 16 mmol) was added, the mixture was stirred at 100° C. for 2 hrs under an atmosphere of Ar. Subsequently, the reaction mixture was cooled to rt, concentrated, and diluted with EtOAc (100 mL). The resulting mixture was washed with water (50 mL×2) and brine (100 mL) and dried with anhydrous $Na_2SO_4$. The solvent was removed and the residue was dissolved in THF (50 mL) and aq. HCl (2 N, 12 mL). After refluxing for 1 hr, the mixture was cooled to rt and concentrated to remove most of the organic solvent. The resulting mixture was extracted with EtOAc (50 mL×2). The combined organic extracts were washed with water (50 mL×3) and brine (50 mL) and dried with anhydrous $Na_2SO_4$. The solvent was removed and the residue was dried in vacuo to give crude compound 15-9 (1.4 g, 98% yield). LC-MS (ESI): m/z 464.1 $[M+H]^+$.

Step 9. To a solution of compound 15-9 (1.4 g, 3.4 mmol) in EtOAc (50 mL) was added $SnCl_2.2H_2O$ (2.8 g, 13.6 mmol) at rt and the resulting mixture was stirred at 80° C. for 1 hr.

The mixture was cooled to rt and d its pH value was adjusted to 8~9 by adding sat. aq. NaHCO₃. The mixture was filtered and the filtrate was extracted with EtOAc (50 mL×2). The combined organic extracts were washed with water (50 mL×3) and brine (50 mL) and dried with anhydrous Na₂SO₄. The solvent was removed and the residue was dried in vacuo to give crude compound 15-10 (1.1 g, 85% yield) as a yellow solid. LC-MS (ESI): m/z 434.1 [M+H]⁺.

Step 10. To a solution of compound 15-10 (1.1 g, 2.5 mmol) in anhydrous pyridine (20 mL) was added MsCl (1.8 mL) at 0° C. After the mixture was stirred at 30° C. for 2 hrs, LC-MS analysis indicated that the reaction went to completion. The mixture was diluted with water (100 mL) and EtOAc (50 mL). The aqueous phase was extracted with EtOAc (50 mL×3). The combined organic extracts were washed with sat. aq. NH₄Cl (50 mL×3) and brine (50 mL) and dried with anhydrous Na₂SO₄. The solvent was removed and the residue was dried in vacuo to give crude compound 15-11 (1.1 g, 90% yield) as a yellow solid. LC-MS (ESI): m/z 512.1 [M+H]⁺.

Step 11. To a solution of compound 15-11 (1.1 g, 2.1 mmol) in THF (30 mL) was added NaBH₄ (560 mg, 14.7 mmol) in portions at 0° C. After stirring at 0° C. for 30 min, LC-MS analysis indicated that the reaction went to completion and acetone (2 mL) was added to quench excess amount of NaBH₄. The mixture was concentrated and the residue was diluted with EtOAc (100 mL). The resulting mixture was washed with water (50 mL×3) and brine (50 mL) and dried with anhydrous Na₂SO₄. The solvent was removed and the residue was dried in vacuo to give compound 15-12 (0.9 g, 90% yield) as a yellow solid. LC-MS (ESI): m/z 514.1 [M+H]⁺.

Step 12. To a solution of compound 15-12 (0.9 g, 1.7 mmol) in anhydrous DCM (30 mL) was added NaH (60% in paraoil, 200 mg, 5 mmol) at 0° C., followed by compound 8-6 (1.1 g, 2.55 mmol). After stirring at 0° C. for 3 hrs and at rt for 12 hrs, the reaction was quenched by adding sat. aq. NH₄Cl (10 mL). The resulting mixture was extracted with DCM (30 mL×3) and the combined organic extracts were washed with brine (50 mL) and dried with anhydrous Na₂SO₄. The solvent was removed and the residue was purified by silica gel column chromatography (Petroleum ether/EtOAc=6/1(v/v)) to give compound 15-13 (520 mg, 55% yield) as a white solid. LC-MS (ESI): m/z 540.1 [M+H]⁺.

Step 13. To a solution of compound 15-13 (520 mg, 0.96 mmol) in MeOH/THF (4 mL/8 mL) was added aq. LiOH (2.0 M, 2 mL) at rt. After stirring at 80° C. for 12 hrs, the reaction mixture was cooled to rt and adjusted its pH value to 2~3 by adding aq. HCl (2.0 M). The organic solvent was removed and the residue was diluted with EtOAc (50 mL). The organic layer was isolated, washed with brine (25 mL) and dried with anhydrous Na₂SO₄. The solvent was removed and the residue was dried in vacuo to give crude compound 15-14 (442 mg, 90% yield) as a white solid. LC-MS: (ESI): m/z 512.1 [M+H]⁺.

Step 14. Compound 15-14 (442 mg, 0.86 mmol) was dissolved in DMF (5 mL), followed by addition of HATU (450 mg, 1.17 mmol). After stirring at rt for 1 hr, the reaction mixture was added DIPEA (503 mg, 3.9 mmol) and MeNH₂.HCl (157 mg, 2.34 mmol). The resulting mixture was stirred at rt for another 1 hr before being concentrated. The residue was diluted with water (25 mL) and EtOAc (50 mL). The organic layer was isolated, washed with brine (25 mL), and dried with anhydrous Na₂SO₄. The solvent was removed and the residue was purified by silica gel column chromatography (Petroleum ether/EtOAc=5/1(v/v)) to give compound 15-15 (360 mg, 80% yield) as a white solid. LC-MS (ESI): m/z 525.1 [M+H]⁺; ¹H NMR (500 MHz, CDCl₃): δ 7.89 (s, 1H), 7.82-7.84 (m, 2H), 7.26 (s, 1H), 7.04-7.12 (m, 6H), 5.85 (m, 1H), 4.94-4.98 (m, 1H), 4.14-4.18 (m, 1H), 4.02-4.06 (m, 2H), 3.31 (m, 1H), 3.15 (d, J=8.5 Hz, 3H), 3.00 (d, J=5.0 Hz, 3H), 2.07-1.73 (d, J=6.5 Hz, 3H) ppm. Compound 15-15 was separated into a pair of enantiomers: enantiomer 15-15a (t_R=3.66 min) and enantiomer 15-15b (t_R=4.25 min) detected by UV absorption at 214 nm on a 4.6 mm×250 mm×5 μm Daicel CHIRALPAK AS-H column (column temperature: 39.7° C.; eluent: MeOH/liquid CO₂=20/80 (v/v); CO₂ flow rate: 2.4 g/min and co-solvent flow rate: 0.6 g/min; front pressure: 198 bar and back pressure: 150 bar).

Scheme 16

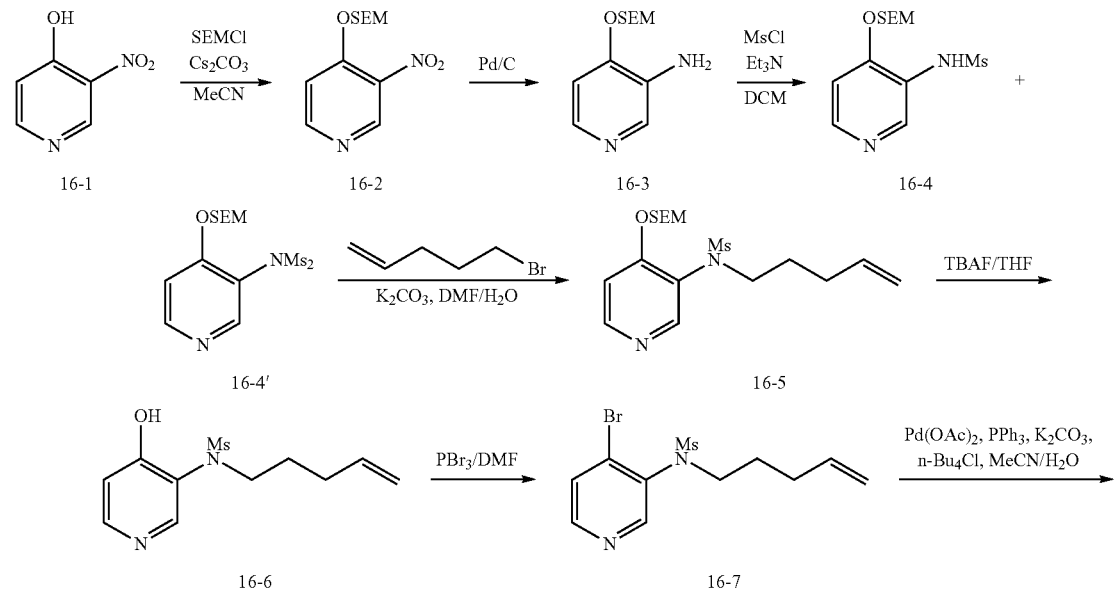

-continued

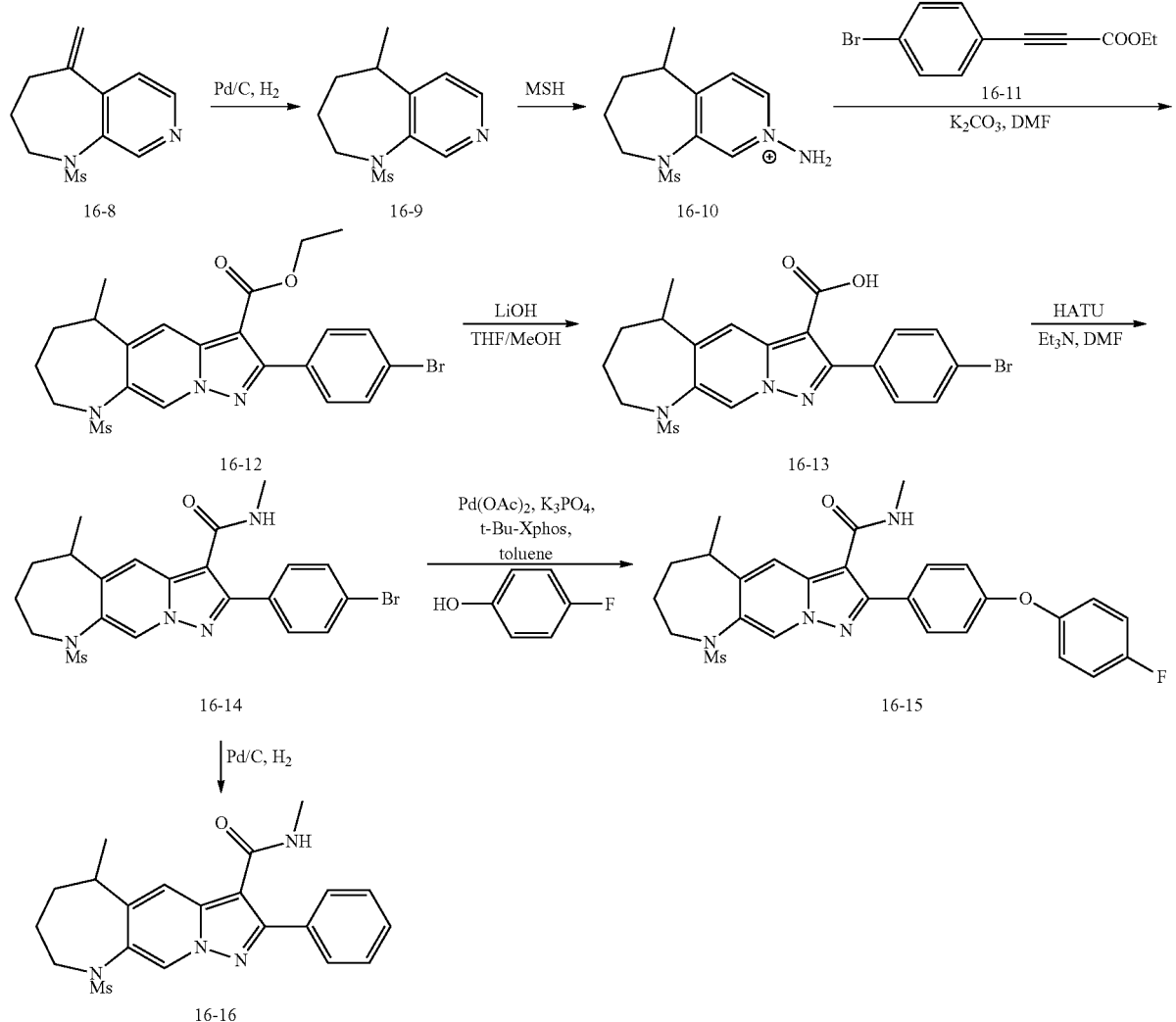

Step 1. Refer to Scheme 16. To a solution of compound 16-1 (1.00 g, 7.14 mmol) and SEMCl (0.670 mL, 7.14 mmol) in CH$_3$CN (10 mL) was slowly added Cs$_2$CO$_3$ (1.57 g, 7.86 mmol). After stirring at rt for 3 hrs, the reaction mixture was concentrated and the residue was purified by silica gel column chromatography (Petroleum ether/EtOAc=3/1 to 1/1 (v/v)) to give compound 16-2 (1.35 g, 70% yield) as a yellow solid. LC-MS (ESI): m/z 271.1 [M+H]$^+$.

Step 2. To a solution of compound 16-2 (1.25 g, 4.61 mmol) in EtOH (20 mL) was added 10% Pd/C (311 mg), the reaction mixture was stirred at rt overnight under an atmosphere of hydrogen. The mixture was filtered through Celite® 545 and the filtered cake was washed with EtOH (20 mL×2). The filtrate was concentrated and the residue was dried in vacuo to give compound 16-3 (1.10 g, 99% yield) as a yellow oil. LC-MS (ESI): m/z 241.1 [M+H]$^+$.

Step 3. To a solution of compound 16-3 (1.10 g, 4.58 mmol) and Et$_3$N (3.72 mL, 26.7 mmol) in DCM (15 mL) was added drop-wise a solution of MsCl (0.63 mL, 8.0 mmol) in DCM (30 mL) over 30 min at 0° C. After stirring at rt overnight, the reaction mixture was filtered through Celite® 545 and the filtered cake was washed with DCM (30 mL×2). The filtrate was concentrated and the residue was dried in vacuo to give a mixture of compounds 16-4 and 16-4' (2.30 g) as a yellow oil, which was used directly for next step without further purification. LC-MS (ESI): m/z 319.1 [M+H]$^+$and 397.1 [M+H]$^+$ for compounds 16-4 and 16-4', respectively.

Step 4. To a solution of compounds 16-4 and 16-4' (2.30 g, 5.81 mmol) in DMF (20 mL) and H$_2$O (4 mL) were added K$_2$CO$_3$ (2.94 g, 21.3 mmol) and 5-bromopent-1-ene (1.31 g, 8.83 mmol) at rt. After stirring at 80° C. for 3 hrs, the reaction mixture was concentrated and the residue was purified by silica gel column chromatography (Petroleum ether/Acetone=4/1 to 1/1(v/v)) to give compound 16-5 (1.60 g, 90% yield, two steps from compound 16-3) as a white solid. LC-MS (ESI): m/z 387.2 [M+H]$^+$.

Step 5. To a solution of compound 16-5 (1.15 g, 2.98 mmol) in THF (25 mL) was added tetrabutylammonium floride (TBAF) (2.33 g, 8.93 mmol) at rt. After stirring at 45° C. overnight, the reaction mixture was concentrated and the residue was purified by silica gel column chromatography (Petroleum ether/Acetone=3/1 to1/1 (v/v)) to give compound 16-6 (564 mg, 74% yield) as a white solid. LC-MS (ESI): m/z 257.1 [M+H]$^+$.

Step 6. To a solution of compound 16-6 (564 mg, 2.20 mmol) in DMF (30 mL) was added PBr$_3$ (1.77 g, 6.61 mmol) and the resulting mixture was stirred at rt for 30 min under an atmosphere of Ar. Subsequently, the reaction was quenched by adding sat. aq. NaHCO₃ (100 mL). The mixture was extracted with EtOAc (100 mL×3) and the combined organic extracts were washed with water (100 mL×5) and brine (50 mL) and dried with anhydrous Na₂SO₄. The solvent was removed and the residue was dried in vacuo to give crude compound 16-7 (350 mg, 50% yield) as a yellow powder. LC-MS (ESI): m/z 319.0 [M+H]⁺.

Step 7. A mixture of compound 16-7 (400 mg, 1.26 mmol), Pd(OAc)₂ (30 mg, 0.13 mmol), PPh₃ (66 mg, 0.25 mmol), n-Bu₄Cl (350 mg, 1.26 mmol) and K₂CO₃ (442 mg, 3.20 mmol) in MeCN/H₂O (10 mL/1 mL) was stirred at 80° C. overnight under an atmosphere of N₂. The mixture was cooled to rt and concentrated. The residue was purified by silica gel column chromatography (Petroleum ether/Acetone=5/1 to 2/1(v/v)) to give compound 16-8 (135 mg, 45% yield) as a yellow solid. LC-MS (ESI): m/z 239.1 [M+H]⁺; ¹H NMR (500 MHz, CDCl₃): δ 8.68 (s, 1H), 8.50-8.51 (d, J=5 Hz, 1H), 7.23-7.24 (d, J=5 Hz, 1H), 5.35 (s, 1H), 5.27 (s, 1H), 3.79 (br, 2H), 2.91 (s, 3H), 2.49-2.51 (m, 2H), 1.96-1.99 (m, 2H) ppm.

Step 8. A mixture of compound 16-8 (130 mg, 0.544 mmol) and 10% Pd/C (50 mg) in MeOH (30 mL) was stirred at rt for 24 hrs under an atmosphere of H₂. The reaction mixture was filtered through Celite® 545 and the filtered cake was washed with MeOH (30 mL×2). The filtrate was concentrated and the residue was dried in vacuo to give compound 16-9 (120 mg, 92% yield) as an off-white solid. LC-MS (ESI): m/z 241.1 [M+H]⁺.

Step 9. To a solution of O-(mesitylsulfonyl)hydroxylamine (MSH) (0.498 mmol) in DCM (10 mL) was added compound 16-9 (120 mg, 0.498 mmol). After stirring at rt overnight, the reaction mixture was concentrated and the residue was dried in vacuo to give crude compound 16-10 as a pale-yellow solid, which was used directly for the next reaction without further purification. LC-MS (ESI): m/z 257.1 [M+H]⁺.

Step 10. To a solution of compounds 16-10 (0.50 mmol) and 16-11 (128 mg, 0.50 mmol) in DMF (6 mL) was added K₂CO₃ (275 mg, 2.0 mmol) in one portion. After stirring at rt for 24 hrs, the reaction mixture was concentrated and the residue was partitioned between EtOAc (100 mL) and water (100 mL). The organic layer was washed with water (50 mL×3) and brine (50 mL) and dried with anhydrous Na₂SO₄. The solvent was removed and the residue was purified by silica gel column chromatography (Petroleum ether/Acetone=10/1 to 6/1 (v/v)) to give compound 16-12 (90 mg, 35% yield) as a yellow solid. LC-MS (ESI): m/z 506.1 [M+H]⁺.

Step 11. To a mixture of compound 16-12 (80 mg, 0.16 mmol) in MeOH (1 mL) and THF (2 mL) was added aq. LiOH (2.0 M, 1.3 mmol). After stirring at 70° C. for 24 hrs, the mixture was cooled to rt and adjusted its pH value to 5~6 by adding 2 M aq. HCl. Subsequently, H₂O (30 mL) was added and the resulting mixture was extracted with DCM (50 mL×3). The combined organic extracts were washed with water (50 mL×2) and dried with anhydrous Na₂SO₄. The solvent was removed and the residue was dried in vacuo to give crude compound 16-13 (80 mg) as a yellow solid, which was used directly for the next step without further purification. LC-MS (ESI): m/z 478.0 [M+H]⁺.

Step 12. To a solution of compound 16-13 (80 mg, 0.16 mmol) in DMF (2 mL) was added HATU (71 mg, 0.19 mmol). After stirring at rt for 10 min, to the reaction mixture was added Et₃N (81 mg, 0.80 mmol), followed by MeNH₂.HCl (13 mg, 0.19 mmol). The resulting mixture was stirred at rt for 30 min and then partitioned between EtOAc (25 mL) and water (25 mL). The organic layer was isolated, washed with water (25 mL×3) and brine (25 mL) and dried with anhydrous Na₂SO₄. The solvent was removed and the residue was purified by silica gel column chromatography (Petroleum ether/Acetone=10/1 to 6/1(v/v)) to give compound 16-14 (65 mg, 83% yield) as a yellow solid. LC-MS (ESI): m/z 491.1 [M+H]⁺; ¹H NMR (500 MHz, CDCl₃): δ 8.53 (s, 1H), 8.21 (s, 1H), 7.68 (dd, J₁=2.0 Hz, J₂=6.8 Hz, 2H), 7.57 (dd, J₁=1.5 Hz, J₂=6.5 Hz, 2H), 5.51 (m, 1H), 4.18 (m, 1H), 3.23 (m, 2H), 3.11 (s, 3H), 2.89 (d, J=5.0 Hz, 3H), 1.99-2.09 (m, 2H), 1.81 (m, 2H), 1.50 (d, J=7.0 Hz, 3H) ppm.

Step 13. A mixture of compound 16-14 (60.0 mg, 0.122 mmol), 4-fluorophenol (16.4 mg, 0.146 mmol), Pd(OAc)₂ (2.7 mg, 0.012 mmol), t-BuXphos (2.6 mg, 0.0061 mmol) and K₃PO₄ (51.7 mg, 0.244 mmol) in toluene (4 mL) was stirred at 80° C. for 4 hrs under an atmosphere of N₂. The mixture was concentrated and the residue was diluted with EtOAc (25 mL) and filtered through Celite® 545. The filtrate was concentrated and the residue was purified by preparative HPLC to give compound 16-15 (13 mg, 20% yield) as a white solid. LC-MS (ESI): m/z 523.2 [M+H]⁺; ¹H NMR (500 MHz, CDCl₃): δ 8.46 (s, 1H), 8.19 (s, 1H), 7.61-7.63 (m, 2H), 7.58-7.60 (m, 6H), 7.19-7.49 (m, 3H), 5.50-5.51 (d, J=5.0 Hz, 1H), 4.11 (br, 1H), 3.14-3.17 (m, 2H), 3.03 (s, 3H), 2.76-2.77 (d, J=5.0 Hz, 3H), 1.99 (m, 2H), 1.72-1.91 (m, 2H), 1.42-1.44 (d, J=7.0 Hz, 3H) ppm.

Syntheses of Analogs of Compound 16-15. Following the same procedure as described in Step 12 and replacing 4-fluorophenol with the respective substituted phenols (ArOH), the following analogs of compound 16-15 were obtained.

| ArOH | Target Compound | [M + H]⁺ | ¹H NMR (500 MHz, CDCl₃) (δ, ppm) |
|---|---|---|---|
| 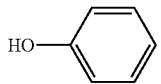 | 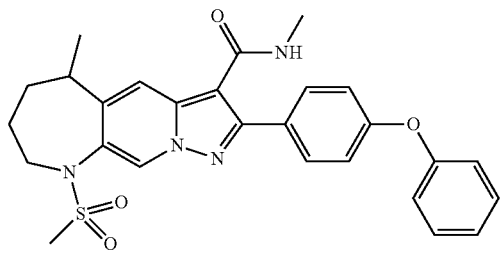 [SMILES: CNC(=O)c1c(-c2ccc(Oc3ccccc3)cc2)nn2cc3c(cc12)C(C)CCCN3S(C)(=O)=O] | 505.2 | 8.45 (s, 1H), 8.16 (s, 1H), 7.55 (d, J = 8.5 Hz, 2H), 7.33 (t, J = 8.0 Hz, 2H), 7.02-7.13 (m, 5H), 5.58 (m, 1H), 4.12 (m, 1H), 3.13 (m, 2H), 3.03 (s, 3H), 2.80 (d, J = 5.0 Hz, 3H), 1.89-2.02 (m, 2H), 1.71 (m, 2H), 1.42 (d, J = 7.0 Hz, 3H) |

16-17

-continued

| ArOH | Target Compound | [M + H]+ | 1H NMR (500 MHz, CDCl3) (δ, ppm) |
|---|---|---|---|
| 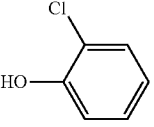 | 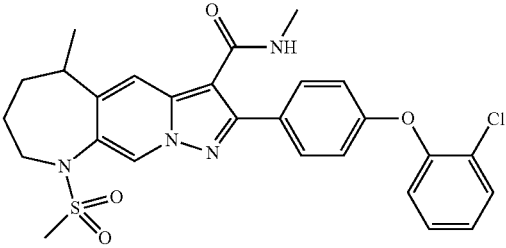 [SMILES: CNC(=O)c1c(-c2ccc(Oc3ccccc3Cl)cc2)nn2cc3c(cc12)C(C)CCCN3S(C)(=O)=O]<br>16-18 | 539.1 | 8.45 (s, 1H), 8.16 (s, 1H), 7.55 (d, J = 8.5 Hz, 2H), 7.44 (d, J = 1.5 Hz, 1H), 7.01-7.23 (m, 5H), 5.56 (m, 1H), 4.10 (m, 1H), 3.14 (m, 2H), 3.03 (s, 3H), 2.79 (d, J = 4.5 Hz, 3H), 1.96 (m, 2H), 1.72 (m, 2H), 1.44 (d, J = 6.5 Hz, 3H) |
| 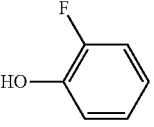 | 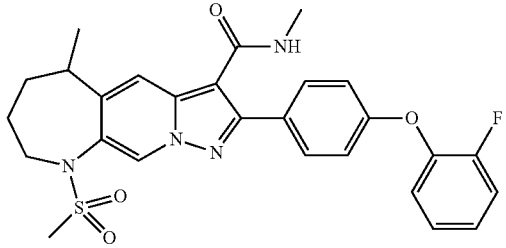 [SMILES: CNC(=O)c1c(-c2ccc(Oc3ccccc3F)cc2)nn2cc3c(cc12)C(C)CCCN3S(C)(=O)=O]<br>16-19 | 523.2 | 8.51 (s, 1H), 8.23 (s, 1H), 7.61 (d, J = 8.5 Hz, 2H), 7.17-7.23 (m, 4H), 7.11 (d, J = 8.5 Hz, 2H), 5.63 (m, 1H), 4.21 (m, 1H), 3.21 (m, 2H), 3.10 (s, 3H), 2.86 (d, J = 5.0 Hz, 3H), 1.96 (m, 2H), 1.79 (m, 2H), 1.49 (d, J = 6.5 Hz, 3H) |
| 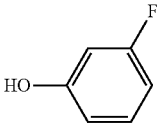 | 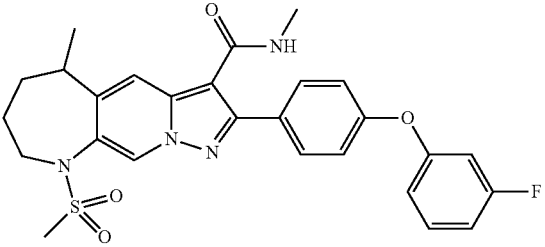 [SMILES: CNC(=O)c1c(-c2ccc(Oc3cccc(F)c3)cc2)nn2cc3c(cc12)C(C)CCCN3S(C)(=O)=O]<br>16-20 | 523.2 | 8.45 (s, 1H), 8.15 (s, 1H), 7.59 (d, J = 8.5 Hz, 2H), 7.26 (m, 1H), 7.10 (d, J = 8.5 Hz, 2H), 6.79 (m, 2H), 6.73 (dd, J1 = 2.0 Hz, J2 = 10.3 Hz, 1H), 5.54 (m, 1H), 4.12 (m, 1H), 3.14 (m, 2H), 3.30 (s, 3H), 2.81 (d, J = 4.5 Hz, 3H), 1.91-1.99 (m, 2H), 1.71 (m, 1H), 1.51 (m 1H), 1.42 (d, J = 7.0 Hz, 3H) |
| 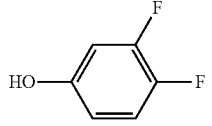 | 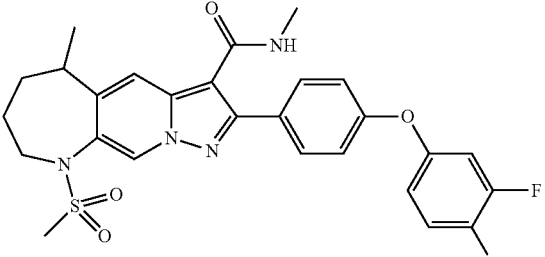<br>16-21 | 541.2 | 8.52 (s, 1H), 8.22 (s, 1H), 7.66 (d, J = 9.0 Hz, 2H), 7.18 (dd, J1 = 9.0 Hz, J2 = 18.5 Hz, 1H), 7.13 (d, J = 9.0 Hz, 2H), 6.89 (m, 1H), 6.82 (m, 1H), 5.61 (m, 1H), 4.17 (m, 1H), 3.21 (m, 2H), 3.10 (s, 3H), 2.88 (d, J = 4.5 Hz, 3H), 2.03-2.08 (m, 2H), 1.98 (m, 1H), 1.59 (m, 1H), 1.49 (d, J = 7.0 Hz, 3H) |
| 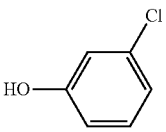 | 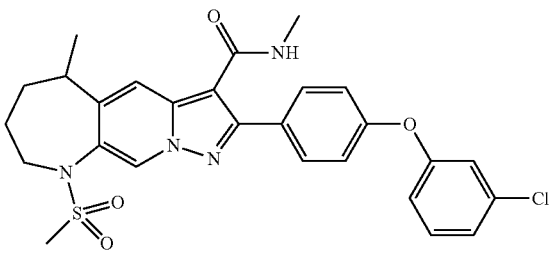 [SMILES: CNC(=O)c1c(-c2ccc(Oc3cccc(Cl)c3)cc2)nn2cc3c(cc12)C(C)CCCN3S(C)(=O)=O]<br>16-22 | 539.1 | 8.45 (s, 1H), 8.16 (s, 1H), 7.59 (d, J = 8.5 Hz, 2H), 7.24 (t, J = 7.5 Hz, 1H), 7.07-7.10 (m, 3H), 7.00 (t, J = 2.5 Hz, 1H), 6.91 (dd, J1 = 2.0 Hz, J2 = 8.0 Hz, 1H), 5.55 (m, 1H), 4.13 (m, 1H), 3.14 (m, 2H), 3.30 (s, 3H), 2.81 (d, J = 5.0 Hz, 3H), 1.91-1.98 (m, 2H), 1.71 (m, 1H), 1.51 (m, 1H), 1.42 (d, J = 7.0 Hz, 3H) |

-continued
| ArOH | Target Compound | [M + H]+ | 1H NMR (500 MHz, CDCl3) (δ, ppm) |
|---|---|---|---|
| 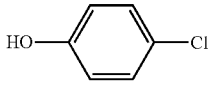 | 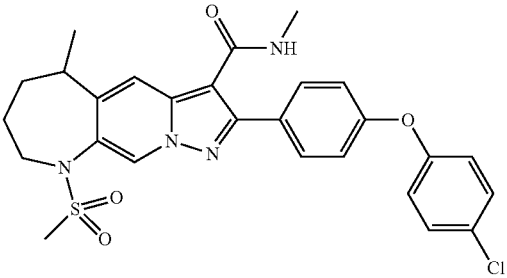 [SMILES: CNC(=O)c1c(-c2ccc(Oc3ccc(Cl)cc3)cc2)nn2cc3c(cc12)C(C)CCCN3S(C)(=O)=O]<br>16-23 | 539.1 | 8.44 (s, 1H), 8.15 (s, 1H), 7.57 (d, J = 9.0 Hz, 2H), 7.29 (m, 2H), 7.06 (d, J = 8.5 Hz, 2H), 6.96 (d, J = 9.0 Hz, 2H), 5.55 (m, 1H), 4.11 (m, 1H), 3.14 (m, 2H), 3.30 (s, 3H), 2.80 (d, J = 5.0 Hz, 3H), 1.93-2.00 (m, 2H), 1.72 (m, 1H), 1.51 (m, 1H), 1.42 (d, J = 7.0 Hz, 3H) |
Synthesis of Compound 16-16. Compound 16-16 was obtained as a white solid from the hydrogenation of compound 16-14 in the presence of 5% Pd/C in EtOH. LC-MS (ESI): m/z 413.2 [M+H]+; 1H NMR (500 MHz, CDCl3): δ 8.45 (s, 1H), 8.19 (s, 1H), 7.58-7.59 (m, 2H), 7.45-7.49 (m, 3H), 5.51 (m, 1H), 4.11 (m, 1H), 3.16 (m, 2H), 3.14 (s, 3H), 2.76 (d, J=4.5 Hz, 3H), 1.90-1.99 (m, 2H), 1.73 (m, 1H), 1.48 (m, 1H), 1.43 (d, J=6.5 Hz, 3H) ppm.
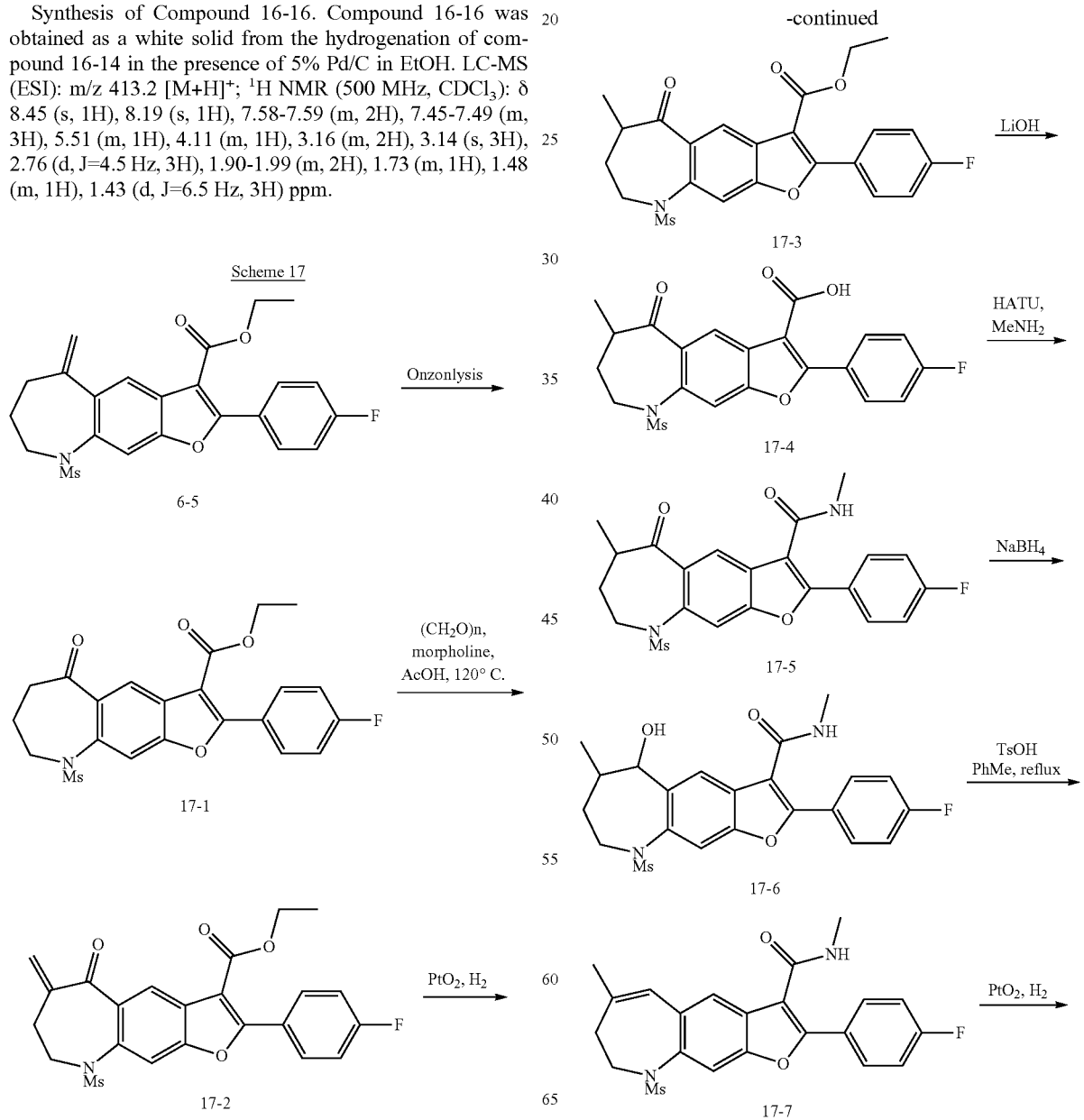
Scheme 17

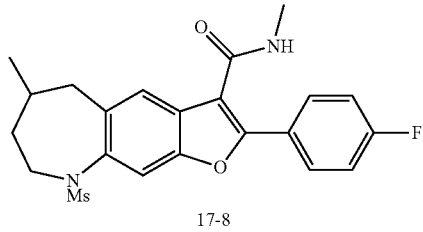

17-8

Step 1. Refer to Scheme 17. A mixture of compound 17-1 (100 mg, 0.225 mmol) (readily prepared by onzonlysis of compound 6-5), paraformaldehyde (20 mg, 0.67 mmol) and morpholine (2 μL, 0.02 mmol) in acetic acid (2 mL) was heated at 120° C. for 2 hrs under an atmosphere of $N_2$. The reaction mixture was concentrated and the residue was dissolved in THF/EtOH (10 mL/10 mL) and $PtO_2$ (22 mg) was added. After stirring at rt overnight under an atmosphere of $H_2$, the reaction mixture was filtered through Celite® 545 and the filtered cake was washed with EtOH (20 mL×2). The filtrate was concentrated and the residue was purified by silica gel column chromatography (Petroleum ether/EtOAc=4/1 (v/v)) to give compound 17-3 (45 mg, 33% yield, two steps from 17-1) as a white solid. LC-MS (ESI): m/z 460.1 [M+H]$^+$; $^1$H NMR (500 MHz, CDCl$_3$): δ 8.40 (s, 1H), 8.12 (m, 2H), 7.71 (s, 1H), 7.20 (m, 2H), 4.45 (q, J=7.0 Hz, 2H), 4.15 (m, 1H), 3.62 (m, 1H), 3.07 (s+m, 3+1H), 2.33 (m, 1H), 1.79 (m, 1H), 1.45 (t, J=7.0 Hz, 3H), 1.32 (d, J=7.0 Hz, 3H) ppm.

Step 2. A mixture of compound 17-3 (182 mg, 0.396 mmol) and LiOH (50 mg, 1.19 mmol) in THF (20 mL), MeOH (5 mL), and water (5 mL) was refluxed and monitored by LC-MS. After the reaction went completion, the reaction mixture was cooled to 0° C. and adjusted its pH value to 7 by adding 1 M aq. HCl. The organic solvent was removed and the residue was triturated with water (15 mL) and then filtered. The solid was washed with water (10 mL×3) and dried in vacuo to give compound 17-4, which was used in the next step without further purification. LC-MS (ESI): ink 432.1 [M+H]$^+$.

Step 3. To a solution of compound 17-4 (about 0.396 mmol, crude) and HATU (181 mg, 0.475 mmol) in DMF (4 mL) was added DIPEA (131 μL, 0.792 mmol). After stirring at rt for 15 min, the mixture was added to DIPEA (196 μl, 1.19 mmol), followed by methylamine hydrochloride (80 mg, 1.19 mmol) and the resulting mixture was stirred at rt for 2 hrs. Subsequently, the mixture was concentrated and the residue was diluted with water and filtered. The solid was collected and purified by preparative HPLC to give compound 17-5 as a white solid. LC-MS (ESI): ink 445.1 [M+H]$^+$; $^1$H NMR (500 MHz, CDCl$_3$): δ 8.13 (s, 1H), 8.00 (m, 2H), 7.21 (m, 2H), 7.71 (s, 1H), 5.90 (brs, 1H), 4.15 (m, 1H), 3.64 (m, 1H), 3.08 (s, 3H), 3.05 (d, J=5.0 Hz, 3H), 3.03 (m, 1H), 2.32 (m, 1H), 1.80 (m, 1H), 1.32 (d, J=6.5 Hz, 3H) ppm.

Step 4. To a solution of compound 17-5 (40 mg, 0.090 mmol) in MeOH (4 mL) was added NaBH$_4$ (10 mg, 0.27 mmol) at 0° C. After stirring at 0° C. for 30 min, the reaction was quenched by adding several drops of acetone. The solvent was removed and the residue was diluted with water (25 mL) and extracted with DCM (25 mL×2). The combined organic extracts were washed with brine (25 mL) and dried with anhydrous Na$_2$SO$_4$. The solvent was removed and the residue was purified by preparative HPLC to give compound 17-6 as a white solid and as a mixture of cis- and trans-isomers. LC-MS (ESI): m/z 447.1 [M+H]$^+$; $^1$H NMR (500 MHz, CDCl$_3$, major isomer): δ 7.93 (s, 2H), 7.87 (s, 1H), 7.58 (s, 1H), 7.20 (m, 2H), 5.93 (brs, 1H), 4.78 (d, J=7.0 Hz, 1H), 3.70 (m, 1H), 3.11 (s, 3H), 3.02 (d, J=5.0 Hz, 3H), 2.08 (brs, 1H), 1.61 (brs, 1H), 1.03 (brs, 3H) ppm.

Step 5. A mixture of compound 17-6 (88 mg, 0.20 mmol) and TsOH (8 mg, 0.04 mmol) in toluene (6 mL) was refluxed for 2 hrs under an atmosphere of $N_2$. The solvent was removed and the residue was purified by preparative HPLC to give compound 17-7 as a white solid. LC-MS (ESI): m/z 429.1 [M+H]$^+$; $^1$H NMR (500 MHz, CDCl$_3$): δ 7.90 (m, 2H), 7.71 (m, 1H), 7.67 (s, 1H), 7.19 (m, 2H), 6.44 (s, 1H), 5.81 (brs, 1H), 3.87 (brs, 2H), 3.01 (d, J=5.0 Hz, 3H), 2.74 (s, 3H), 2.68 (m, 2H), 2.00 (s, 3H) ppm.

Step 6. A mixture of compound 17-7 (56 mg, 0.13 mmol) and PtO$_2$ (23 mg) in THF (4 mL) and MeOH (4 mL) was stirred at rt overnight under an atmosphere of H$_2$. The mixture was filtered through Celite® 545 and the filtered cake was washed with MeOH (25 mL×2). The filtrate was concentrated and the residue was purified by preparative HPLC to give compound 17-8 as a white solid. LC-MS (ESI): m/z 431.1 [M+H]$^+$; $^1$H NMR (500 MHz, CDCl$_3$): δ 7.90 (s, 2H), 7.67 (s, 1H), 7.58 (s, 1H), 7.19 (m, 2H), 5.79 (brs, 1H), 4.10 (brs, 1H), 3.31 (brs, 1H), 3.06 (s, 3H), 3.01 (d, J=5.0 Hz, 3H), 2.87 (m, 2H), 1.68-1.90 (m, 3H), 1.04 (d, J=6.0 Hz, 3H) ppm.

Scheme 18

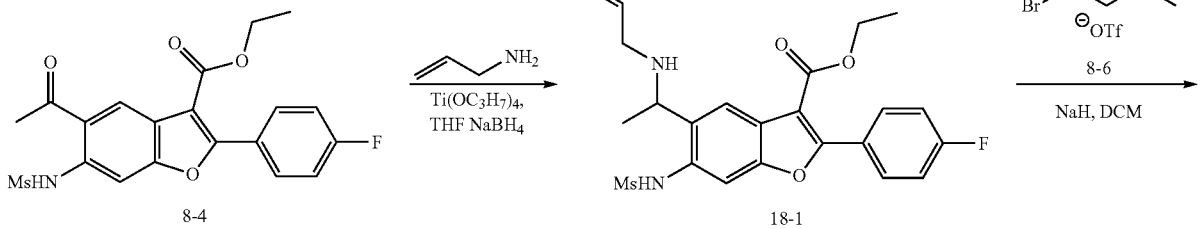

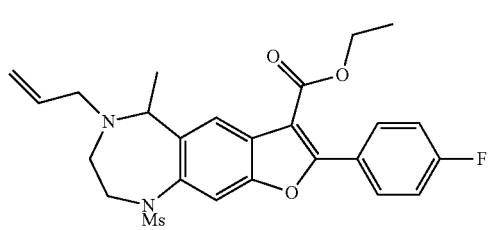

18-2

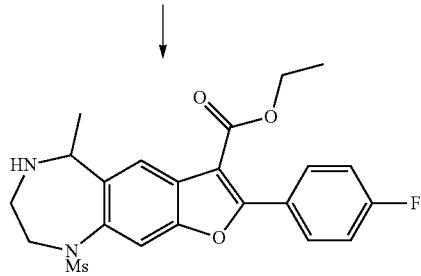

18-4

1. LiOH·H₂O, MeOH/THF
2. HATU, MeNH₂·HCl 18-3

18-5

Step 1. Refer to Scheme 18. A solution of compound 8-4 (656 mg, 1.57 mmol) and aminopropene (3.70 mL, 50.0 mmol) in THF (dry) was slowly added Ti(O^iPr)₄ (16.5 mL, 20.0 mmol) and the resulting mixture was stirred at rt for 4 hrs. Subsequently, EtOH (30 mL) and NaBH₄ (760 mg, 20.0 mmol) were added and the mixture was stirred at rt overnight. Subsequently, the mixture was poured into ice-water (100 mL) and the suspension was filtered. The filtrate was concentrated and the residue was diluted with EtOAc (200 mL) and dried with anhydrous Na₂SO₄. The solvent was removed and the residue was purified by silica gel column chromatography (Petroleum ether/EtOAc=6/1 (v/v)) to give compound 18-1 (7.0 g, 87% yield) as a yellow solid. LC-MS (ESI): m/z 459.2 [M+H]⁺.

Step 2. To a solution of compound 18-1 in anhydrous DCM (30 mL) was added NaH (172 mg, 43.0 mmol) at 0° C. After stirring at 0° C. for 30 min, compound 8-6 (640 mg, 1.44 mmol) was added and the resulting mixture was stirred at 0° C. for 3 hrs and at rt overnight. Subsequently, sat. aq. NH₄Cl (10 mL) was added and the aqueous phase was extracted with DCM (25 mL×3). The combined organic extracts were washed with brine (25 mL) and dried with anhydrous Na₂SO₄. The solvent was removed and the residue was purified by silica gel column chromatography (Petroleum ether/EtOAc=6/1 (v/v)) to give compound 18-2 (200 mg, 71% yield) as a white solid. LC-MS (ESI): m/z 487.1 [M+H]⁺.

Step 3. To a solution of compound 18-2 (100 mg, 0.100 mmol) in MeOH/THF (1 mL/2 mL) was added aq. LiOH (2.0 M, 0.5 mL). After stirring at 80° C. for 12 hrs, the reaction mixture was acidified to pH 2~3 by adding aq. HCl (2.0 M), and then concentrated. The residue was dissolved in EtOAc (25 mL) and dried with anhydrous Na₂SO₄. The solvent was removed and the residue was dried in vacuo to give crude acid, which was used in the next step without further purification. LC-MS (ESI): m/z 459.1 [M+H]⁺. Subsequently, the crude acid was dissolved in DMF (3 mL) and HATU (74 mg, 0.25 mmol) was added. The mixture was stirred at rt for 1 hr and then DIPEA (0.40 mL, 2.02 mmol) and MeNH₂·HCl (82 mg, 1.2 mmol) were added. After stirring at rt for 1 hr, the reaction mixture was concentrated and the residue was diluted with EtOAc (50 mL) The solution was washed with brine (25 mL) and dried with anhydrous Na₂SO₄. The solvent was removed and the residue was purified by silica gel column chromatography (Petroleum ether/EtOAc=5/1(v/v)) to give compound 18-3 (70 mg, 55% yield) as a white solid. LC-MS (ESI): m/z 472.1 [M+H]⁺.

Step 4. To a solution of compound 18-3 (42 mg) in THF (1 mL) were added polymethylhydrosiloxane (PMHS) (0.18 mmol), ZnCl₂ (3.0 mg, 0.02 mmol) and Pd[PPh₃]₄ (1.04 mg, 0.009 mmol), the mixture was stirred at 25° C. for 12 hrs under an atmosphere of N₂. The solvent was removed and the residue was purified by preparative HPLC to give compound 18-5 (9 mg, 23% yield) as a white solid. LC-MS (ESI): m/z 432.1 [M+H]⁺; ¹H NMR (500 MHz, d⁶-DMSO): δ 8.49 (m, 1H), 7.94 (dd, J₁=5.0 Hz, J₂=8.3 Hz, 2H), 7.74 (s, 1H), 7.50 (s, 1H), 7.39 (t, J=9.0 Hz, 2H), 4.13 (m, 1H), 3.25 (m, 5H), 3.04 (m, 2H), 2.84 (d, J=4.5 Hz, 3H), 1.49 (d, J=6.5 Hz, 3H) ppm.

Synthesis of Compound 18-4. Following the same procedure as described in Step 4 and replacing compound 18-3 with 18-2, compound 18-4 was obtained. LC-MS (ESI): m/z 447.1 [M+H]⁺.

18-6

Synthesis of Compound 18-6. Method A. To a solution of compound 18-4 (120 mg, 0.248 mmol) and NaHCO₃ (42 mg, 0.50 mmol) in DMF (3 mL) was added CF₃CH₂OTf (69 mg, 0.30 mmol). The resulting mixture was stirred at rt overnight. The solvent was removed and the residue was diluted with EtOAc (50 mL). The mixture was washed with brine (25 mL) and dried with anhydrous Na₂SO₄. The solvent was removed and the residue was dried in vacuo to give an ester, LC-MS (ESI): m/z 529.1 [M+H]$^+$, which was subsequently hydrolyzed and performed methyl amide formation, following the conditions described in Step 3, to give compound 18-6. LC-MS (ESI): m/z 514.1 [M+H]$^+$; $^1$H NMR (500 MHz, d$^6$-DMSO): δ 8.51 (m, 1H), 7.97 (m, 2H), 7.80 (s, 1H), 7.58 (s, 1H), 7.40 (m, 2H), 4.44 (m, 1H), 3.85 (m, 1H), 3.33-3.38 (m, 6H), 2.99 (m, 2H), 2.86 (d, J=5.0 Hz, 3H), 1.51 (d, J=5.5 Hz, 3H) ppm.

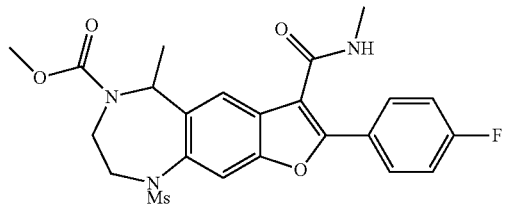

18-7

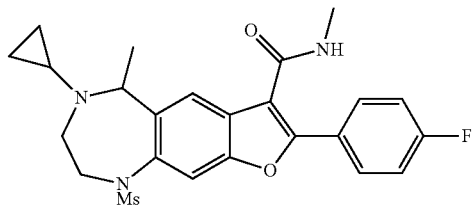

18-9

Synthesis of Compound 18-9. Following the same procedure as described in Method C and replacing 37% aq. HCHO with (1-ethoxycyclopropoxy)trimethylsilane, compound 18-9 was obtained. LC-MS (ESI): m/z 472.1 [M+H]$^+$.

Synthesis of Compound 18-7. Method B. To a solution of compound 18-4 (100 mg, 0.224 mmol) and pyridine (106 mg, 1.34 mmol) in DCM (5 mL) was added methyl chloroformate (37 mg, 0.47 mmol) at 0° C. and the resulting mixture was stirred at rt for 30 min. The reaction was quenched by adding several drops of sat. aq. NaHCO$_3$ and the mixture was concentrated. The residue was diluted with DCM (60 mL) and the mixture was washed with brine (25 mL) and dried with anhydrous Na$_2$SO$_4$. The solvent was removed and the residue was dried in vacuo to give an ester, LC-MS (ESI): m/z 505.1 [M+H]$^+$, which was subsequently hydrolyzed and performed methyl amide formation, following the conditions described in Step 3, to give compound 18-7. LC-MS (ESI): m/z 490.1 [M+H]$^+$; $^1$H NMR (500 MHz, CD$_3$CN): δ 7.96 (m, 2H), 7.71 (s, 1H), 7.55 (s, 1H), 7.28 (m, 2H), 6.78 (br, 1H), 5.45-5.54 (m, 1H), 4.14 (m, 2H), 3.99-4.04 (m, 4H), 3.24-3.28 (m, 4H), 2.91 (d, J=4.5 Hz, 3H), 1.68 (br, 3H) ppm.

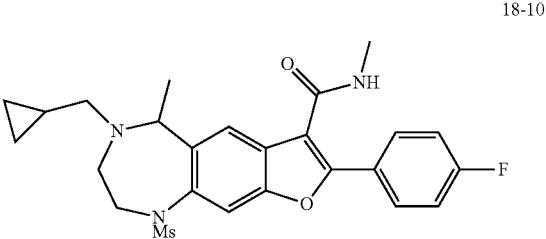

18-10

Synthesis of Compound 18-10. Following the same procedure as described in Method C and replacing 37% aq. HCHO with cyclopropanecarbaldehyde, compound 18-10 was obtained. LC-MS (ESI): m/z 486.2 [M+H]$^+$.

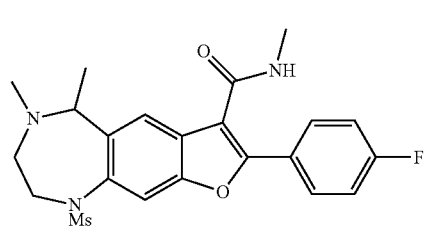

18-8

Synthesis of Compound 18-8. Method C. To a solution of compound 18-4 (70 mg, 0.16 mmol) in MeOH (5 mL) were added 37% aq. HCHO (0.050 mL, 0.63 mmol) and HOAc (0.020 mL, 0.31 mmol). The reaction mixture was stirred at 40° C. for 2 hrs and then cooled to rt. Subsequently, NaBH$_4$ (50 mg, 0.79 mmol) was slowly added and the mixture was stirred at rt for 30 min. The solvent was removed and the residue was diluted with EtOAc (25 mL). The mixture was washed with brine (10 mL) and dried with anhydrous Na$_2$SO$_4$. The solvent was removed and the residue was dried in vacuo to give a crude ester (70 mg) as a yellow solid, LC-MS: (ESI) m/z 461.1 [M+H]$^+$, which was subsequently hydrolyzed and performed methyl amide formation, following the conditions described in Step 3, to give compound 18-8. LC-MS (ESI): m/z 446.1 [M+H]$^+$; $^1$H NMR (300 MHz, d$^6$-DMSO): δ 7.92 (m, 2H), 7.66 (s, 1H), 7.49 (s, 1H), 7.33 (m, 2H), 4.20 (m, 1H), 3.50-3.53 (m, 2H), 3.42 (br, 3H), 3.29-3.30 (m, 2H), 2.84 (d, J=4.5 Hz, 3H), 2.10 (br, 3H), 1.49 (d, J=7.2 Hz, 3H) ppm.

Scheme 18a

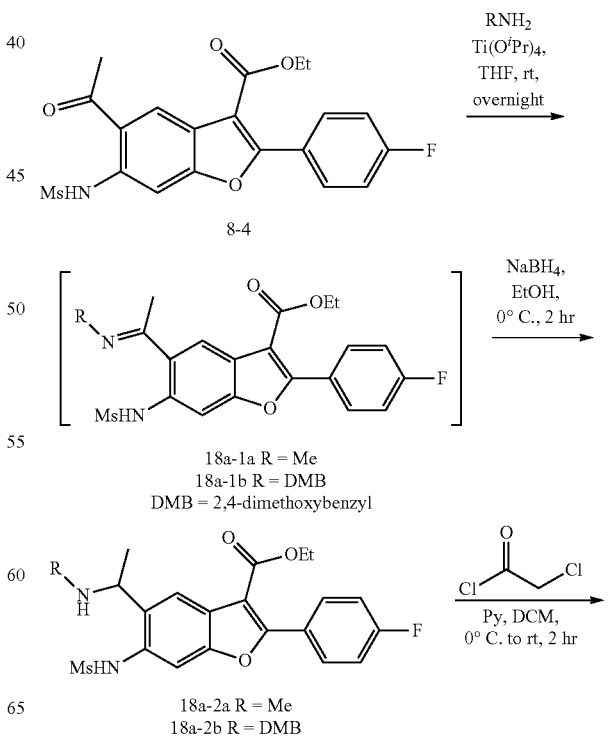

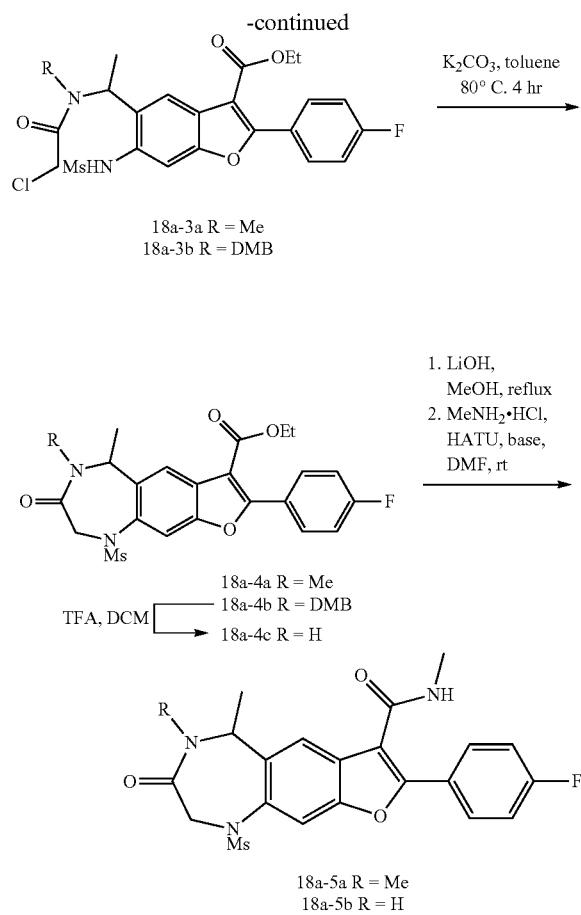

18a-3a R = Me
18a-3b R = DMB 18a-4a R = Me
18a-4b R = DMB
18a-4c R = H 18a-5a R = Me
18a-5b R = H

Step 1. Refer to Scheme 18a. To a solution of compound 8-4 (2.1 g, 5 mmol) in dry THF (20 mL) was added MeNH$_2$ (2 M in THF, 20 mL, 40 mmol), followed by Ti(O$^i$Pr)$_4$ (6 mL, 20 mmol) under an atmosphere of N$_2$. After stirring at rt overnight, the reaction mixture was cooled to 0° C. and sequentially added EtOH (20 mL) and NaBH$_4$ (945 mg, 25 mmol). The reaction mixture was stirred at 0° C. for 2 hrs and slowly added H$_2$O (20 mL). The suspension was filtered and the filtrate was extracted with DCM (100 mL×3). The combined organic extracts were washed with brine (50 mL) and dried over anhydrous Na$_2$SO$_4$. The solvent was removed and the residue was dried in vacuo to give crude compound 18a-2a (2.17 g) as a yellow solid, which was used directly for the next step without further purification. LC-MS (ESI): m/z 435.1 [M+H]$^+$.

Step 2. To a solution of compound 18a-2a (2.17 g, 5.0 mmol) in DCM (40 mL) at 0° C. was added anhydrous pyridine (0.8 mL, 10 mmol), followed by 2-chloroacetyl chloride (0.75 mL, 10 mmol). After stirring at 0° C. for 2 hrs, the reaction mixture was warmed to rt and treated with 1 M aq. HCl (10 mL). The mixture was extracted with EtOAc (100 mL×3) and the combined organic extracts were washed with H$_2$O (50 mL) and brine (50 mL) and dried over anhydrous Na$_2$SO$_4$. The solvent was removed and the residue was purified by silica gel column chromatography (PE/EtOAc=1/1 (v/v)) to give compound 18a-3a (1.8 g, 71% yield) as a light yellow solid. LC-MS (ESI): m/z 511.1 [M+H]$^+$.

Step 3. To a solution of compound 18a-3a (2.55 g, 5.0 mmol) in toluene (50 mL) was added K$_2$CO$_3$ (1.38 g, 10 mmol). After stirring at 80° C. stirred for 4 hrs, the reaction mixture was cooled to rt and filtered. The filtrate was concentrated and the residue was dried in vacuo to give crude compound 18a-4a (2.4 g) as a yellow solid, which was used for the next step without further purification. LC-MS (ESI): m/z 475.1 [M+H]$^+$.

Step 4. Following the same procedure as that for the preparation of compound 18-3 described in Scheme 18 and replacing compound 18-2 with 18a-4a, compound 18a-5a (1.1 g, 57% yield) was obtained as a white solid. LC-MS (ESI): m/z 460.1 [M+H]$^+$; $^1$H NMR (500 MHz, CD$_3$OD): δ 7.82 (br, 2H), 7.63 (s, 1H), 7.59 (s, 1H), 7.14 (t, J=7 Hz, 2H). 4.69 (q, J=6 Hz, 1H), 4.59 (d, J=18 Hz, 1H), 3.96 (d, J=18 Hz, 1H), 3.27 (s, 3H), 3.06 (s, 3H), 2.82 (s, 3H), 1.66 (d, J=6 Hz, 3H) ppm. Compound 18a-5a was separated into a pair of enantiomers: enantiomer 18a-5a_A (t$_R$=2.48 min) and enantiomer 18a-5a_B (t$_R$=3.28 min) detected by UV absorption at 214 nm on a 4.6 mm×250 mm×5 μm Daicel CHIRALPAK® OD-H column (column temperature: 39.3° C.; eluent: MeOH/liquid CO$_2$=50/50 (v/v); CO$_2$ flow rate: 1.5 g/min and co-solvent flow rate: 1.5 g/min; front pressure: 235 bar and back pressure: 152 bar).

Synthesis of Compound 18b-2b. Following the same procedure as that for the synthesis of compound 18a-2a described in Scheme 18a and replacing methylamine with 2,4-dimethoxybenzylamine, compound 18a-2b (6.5 g crude product) was obtained as a yellow solid. LC-MS (ESI): m/z 571.2 [M+H]$^+$.

Synthesis of Compound 18b-3b. Following the same procedure as that for the synthesis of compound 18a-3a described in Scheme 18a and replacing compound 18a-2a with 18a-2b, compound 18a-3b (4.9 g, 75% yield) was obtained as a light yellow solid. LC-MS (ESI): m/z 647.2 [M+H]$^+$.

Synthesis of Compound 18a-4b. Following the same procedure as that for the synthesis of compound 18a-4a described in Scheme 18a and replacing compound 18a-3a with 18a-3b, compound 18a-4b (3.4 g crude product) was obtained as a yellow solid. LC-MS (ESI): m/z 611.2 [M+H]$^+$.

Synthesis of Compound 18a-4c. To a stirred solution of compound 18a-4b (3.4 g, 7.3 mmol) in DCM (10 mL) was added TFA (20 mL). After stirring at rt overnight, the reaction mixture was concentrated and the residue was purified by column chromatography to give compound 18a-4c as a pale yellow solid. LC-MS (ESI): m/z 461.1 [M+H]$^+$.

Synthesis of Compound 18a-5b. Following the same procedure as that for the preparation of compound 18-3 described in Scheme 18 and replacing compound 18-2 with 18a-4c, compound 18a-5b (700 mg, 40% yield) was obtained as a white solid. LC-MS (ESI): m/z 446.1 [M+H]$^+$; $^1$H NMR (500 MHz, CDCl$_3$): δ 7.91 (s, 1H), 7.84-7.87 (m, 2H). 7.59 (s, 1H), 7.22 (t, J=8 Hz, 2H), 5.95 (s, 1H), 5.79 (br, 1H), 5.24-5.26 (m, 1H), 4.92 (d, J=18 Hz, 1H), 3.93 (d, J=18 Hz, 1H), 3.20 (s, 3H), 2.99 (d, J=5 Hz, 3H), 1.74 (d, J=7 Hz, 3H) ppm. Compound 18a-5a was separated into a pair of enantiomers: enantiomer 18a-5b_A (t$_R$=3.67 min) and enantiomer 18a-5b_B (t$_R$=4.53 min) detected by UV absorption at 214 nm on a 4.6 mm×250 mm×5 μm M ChiralPak® OD-H column (column temperature: 39.7° C.; eluent: MeOH/liquid CO$_2$=30/70 (v/v); CO$_2$ flow rate: 2.1 g/min and co-solvent flow rate: 0.9 g/min; front pressure: 207 bar and back pressure: 150 bar).

Scheme 19

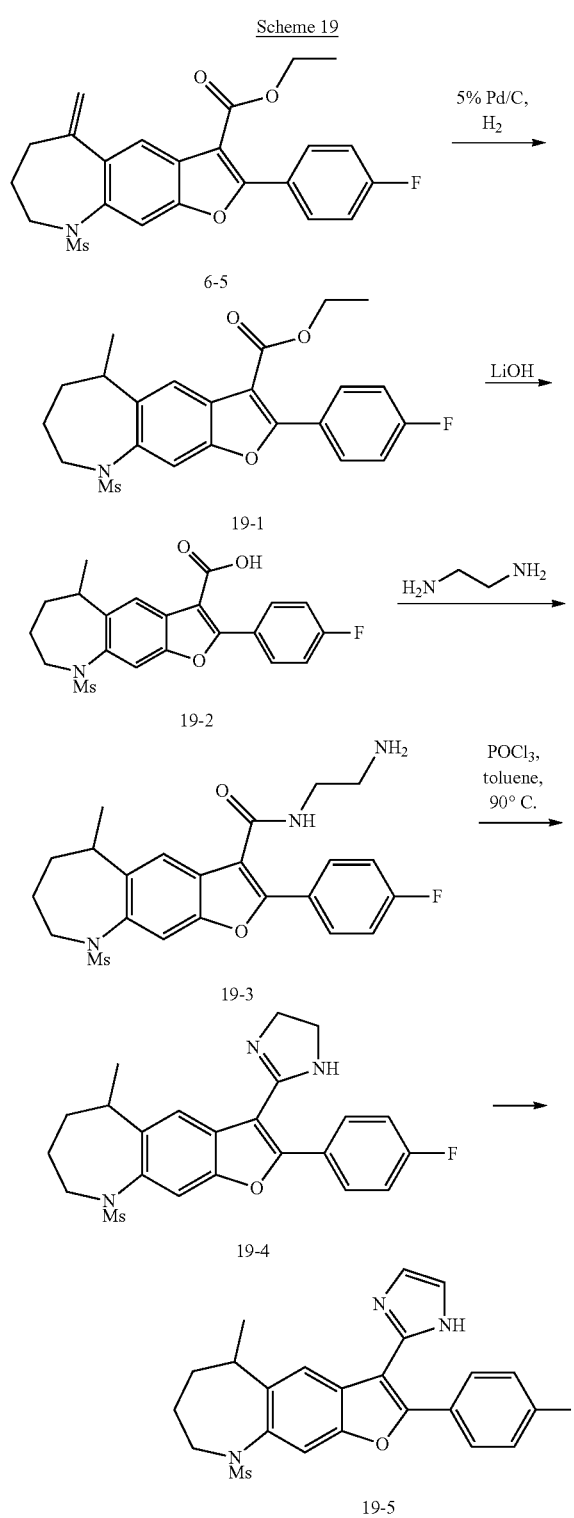

Step 1. Refer to Scheme 19. A mixture of compound 6-5 (1.00 g, 2.25 mmol) and 5% Pd/C (1.0 g) in THF/MeOH (50 mL/50 mL) was stirred at rt overnight under an atmosphere of H₂. The mixture was filtered through Celite® 545 and the filtered cake was washed with MeOH (25 mL×2). The filtrate was concentrated and the residue was dried in vacuo to give compound 19-1 (970 mg, 97% yield). LC-MS (ESI): m/z 446.1 [M+H]⁺.

Step 2. To a solution of compound 19-1 (970 mg, 2.18 mmol) in MeOH/THF (10 mL/10 mL) was added aq. LiOH (2.0 N, 4.36 mmol, 8.72 mmol). After stirring at 75° C. for 2 hrs, the reaction mixture was cooled to rt and adjusted to pH 5~6 by adding aq. HCl (2.0 N). The mixture was concentrated and the residue was diluted with EtOAc (100 mL) and H₂O (25 mL). The organic layer was dried with anhydrous Na₂SO₄. The solvent was removed and the residue was dried in vacuo to give compound 19-2 (880 mg, 96% yield) as a white solid. LC-MS (ESI): m/z 418.1 [M+H]⁺.

Step 3. To a solution of compound 19-2 (830 mg, 2.0 mmol) in DCM (50 ml) was added (COCl)₂ (379 mg, 3.0 mmol) at rt and the resulting mixture was stirred at rt for 1 hr. Subsequently, the mixture was cooled to 0° C. and ethylenediamine was added (359 mg, 6.0 mmol). The resulting mixture was stirred at rt for 30 min and then concentrated to give crude compound 19-3, which was used for the next step without further purification. LC-MS (ESI): m/z 460.2 [M+H]⁺.

Step 4. A solution of compound 19-3 (900 mg, 1.96 mmol) and POCl₃ (1.20 g, 7.84 mmol) in toluene (30 mL) was stirred at 90° C. overnight under an atmosphere of N₂. The reaction mixture was concentrated and the residue was added sat. aq. NaHCO₃ to adjust to pH 7~8. The resulting suspension was filtered and the solid was dried in vacuo to give crude compound 19-4 as a white solid. LC-MS (ESI): m/z 442.2 [M+H]⁺.

Step 5. A solution of compound 19-4 (250 mg, 0.57 mmol), PhI(OAc)₂ (201 mg, 0.62 mmol) and K₂CO₃ (86 mg, 0.62 mmol) in DMSO (5 mL) was stirred at 25° C. for 24 hrs. The mixture was concentrated and the residue was purified by preparative HPLC to give compound 19-5 (30 mg, 12% yield) as a white solid. LC-MS (ESI): m/z 440.1 [M+H]⁺; ¹H NMR (500 MHz, d⁶-DMSO): δ 12.43 (br, 1H), 7.95-7.98 (m, 2H), 7.48 (s, 1H), 7.34 (m, 3H), 7.20 (s, 1H), 4.08 (br, 2H), 3.21 (s, 3H), 3.04 (s, 1H), 1.92 (br, 4H), 1.36 (d, 2H, J=7.0 Hz) ppm.

Synthesis of Compound 19-6. Following the same procedure as described in the synthesis of compound 19-5 and replacing compound 19-2 with the corresponding de-methylated analog, compound 19-6 was obtained. LC-MS (ESI): m/z 426.1 [M+H]⁺.

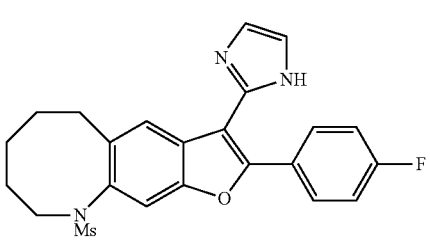

19-7

Synthesis of Compound 19-7. Following the same procedure as described in the synthesis of compound 19-5 and replacing compound 19-2 with the corresponding de-methylated eight-member ring analog, compound 19-7 was obtained. LC-MS (ESI): m/z 440.1 [M+H]$^+$.

Scheme 19a

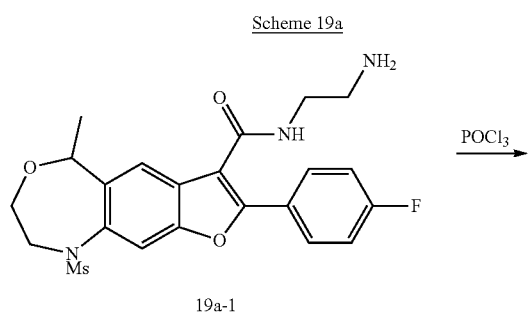

19a-1

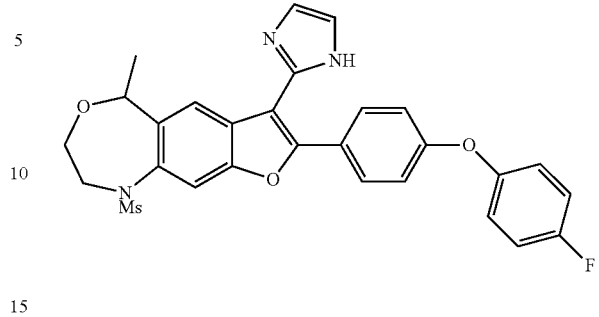

19-9

Synthesis of Compound 19-9. Following the same procedure as described in the preparation of compound 19-5 described in Scheme 19, replacing compound 19-2 with 15-14, and taking the modified condition for dihydroimidazole formation shown in Scheme 19a, compound 19-8 was obtained. LC-MS (ESI): m/z 534.1 [M+H]$^+$; $^1$H NMR (500 MHz, d$^6$-DMSO): δ 12.46 (s, 1H), 7.95 (d, J=8.5 Hz, 2H), 7.84 (s, 1H), 7.60 (s, 1H), 7.36 (s, 1H), 7.26-7.30 (m, 2H), 7.15-7.19 (m, 3H), 7.06 (d, J=8.5 Hz, 2H), 4.87 (m, 1H), 4.00-4.03 (m, 1H), 3.88-3.93 (m, 2H), 3.38 (s, 3H), 3.18-3.19 (m, 1H), 1.58 (d, J=6.5 Hz, 3H) ppm.

19a-2

Synthesis of Compound 19a-2. Refer to Scheme 19a. A solution of compound 19a-1 (250 mg, 0.54 mmol) (prepared from compound 8-8 by following the procedure for the conversion of compound 19-2 to 19-3 described in Scheme 19) in POCl$_3$ (5 mL) was stirred at 75° C. for 3 hrs under an atmosphere of N$_2$ and then was concentrated to remove POCl$_3$ under a reduced pressure. Subsequently, the residue was added sat. aq. NaHCO$_3$ (25 mL) and the resulting suspension was extracted with EtOAc (40 mL×3). The combined organic extracts were washed with brine (50 mL) dried over anhydrous Na$_2$SO$_4$. The solvent was removed and the residue was dried in vacuo to give crude compound 19a-2 (100 mg) as a white solid, which was used for the next aromatization step without further purification. LC-MS (ESI): m/z 444.1 [M+H]$^+$.

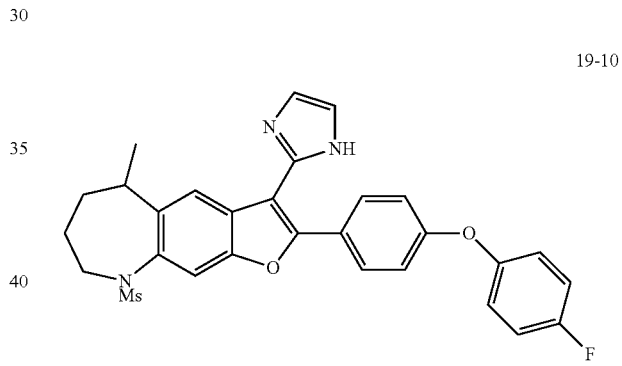

19-10

Synthesis of Compound 19-10. Following the same procedure as described in the preparation of compound 19-5 described in Scheme 19, replacing compound 19-2 with the full carbon analog of compound 15-14 (prepared from compound 23-6 shown in Scheme 23 by hydrogenation of the terminal alkene residue and hydrolysis of the ethyl ester moiety), and taking the modified condition for dihydroimidazole formation shown in Scheme 19a, compound 19-10 was obtained. LC-MS (ESI): m/z 532.2 [M+H]$^+$.

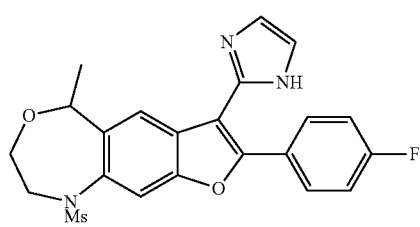

19-8

Synthesis of Compound 19-8. Following the same procedure as described in the preparation of compound 19-5 described in Scheme 19 and replacing compound 19-4 with 19a-2, compound 19-8 was obtained. LC-MS (ESI): m/z 442.1 [M+H]$^+$; $^1$H NMR (500 MHz, d$^6$-DMSO): δ 12.46 (d, J=10 Hz, 1H), 8.01-8.03 (m, 2H), 7.85 (s, 1H), 7.61 (d, J=7.5 Hz, 1H), 7.33-7.37 (m, 3H), 7.20 (s, 1H), 4.87-4.88 (m, 1H), 3.87-4.06 (m, 4H), 3.38 (s, 3H), 1.59 (d, J=7.0 Hz, 3H) ppm.

Scheme 20

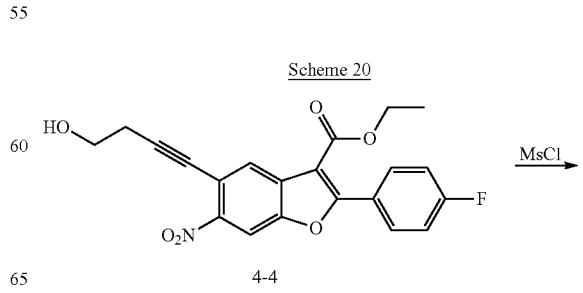

4-4

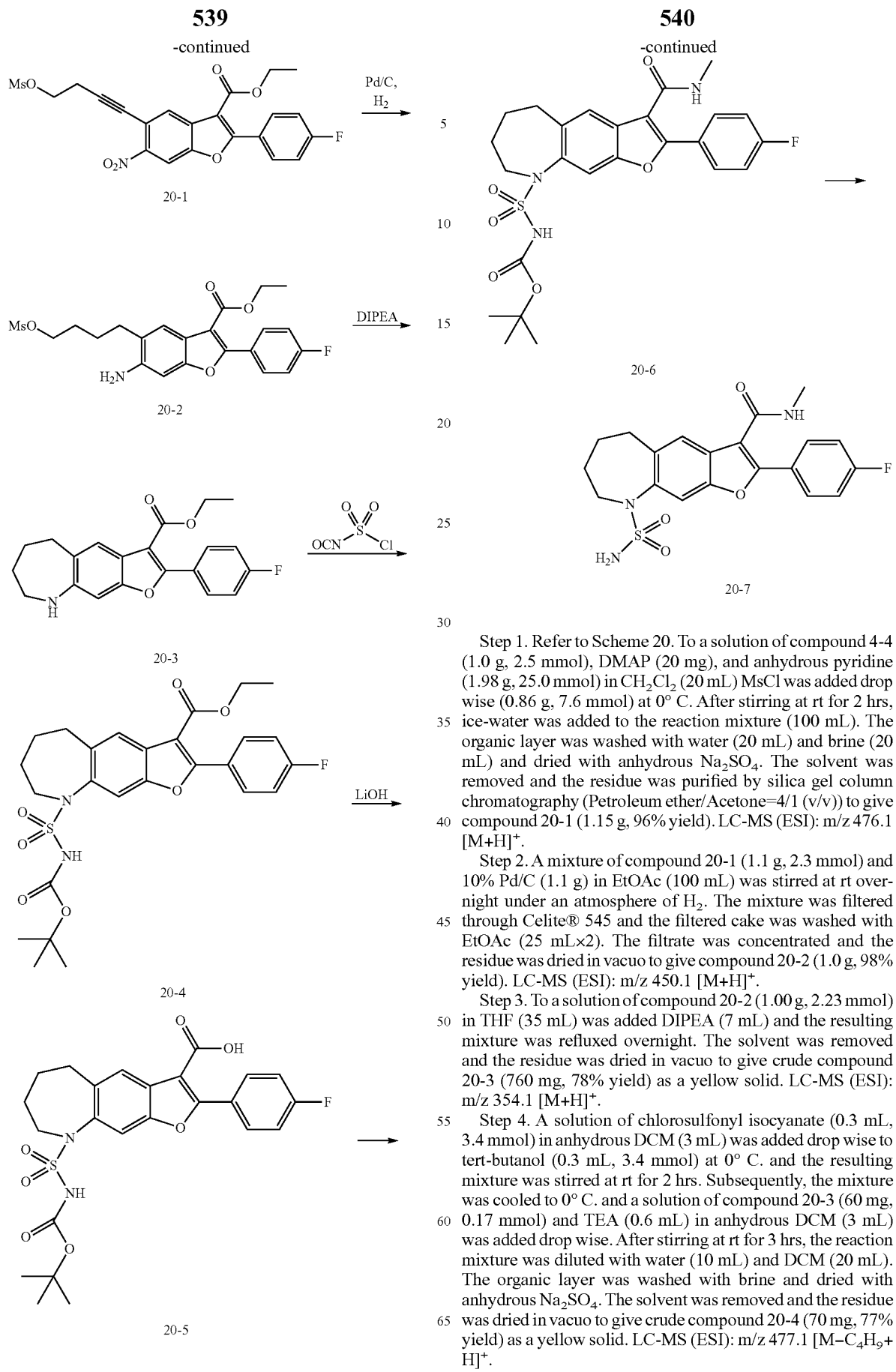

Step 1. Refer to Scheme 20. To a solution of compound 4-4 (1.0 g, 2.5 mmol), DMAP (20 mg), and anhydrous pyridine (1.98 g, 25.0 mmol) in CH$_2$Cl$_2$ (20 mL) MsCl was added drop wise (0.86 g, 7.6 mmol) at 0° C. After stirring at rt for 2 hrs, ice-water was added to the reaction mixture (100 mL). The organic layer was washed with water (20 mL) and brine (20 mL) and dried with anhydrous Na$_2$SO$_4$. The solvent was removed and the residue was purified by silica gel column chromatography (Petroleum ether/Acetone=4/1 (v/v)) to give compound 20-1 (1.15 g, 96% yield). LC-MS (ESI): m/z 476.1 [M+H]$^+$.

Step 2. A mixture of compound 20-1 (1.1 g, 2.3 mmol) and 10% Pd/C (1.1 g) in EtOAc (100 mL) was stirred at rt overnight under an atmosphere of H$_2$. The mixture was filtered through Celite® 545 and the filtered cake was washed with EtOAc (25 mL×2). The filtrate was concentrated and the residue was dried in vacuo to give compound 20-2 (1.0 g, 98% yield). LC-MS (ESI): m/z 450.1 [M+H]$^+$.

Step 3. To a solution of compound 20-2 (1.00 g, 2.23 mmol) in THF (35 mL) was added DIPEA (7 mL) and the resulting mixture was refluxed overnight. The solvent was removed and the residue was dried in vacuo to give crude compound 20-3 (760 mg, 78% yield) as a yellow solid. LC-MS (ESI): m/z 354.1 [M+H]$^+$.

Step 4. A solution of chlorosulfonyl isocyanate (0.3 mL, 3.4 mmol) in anhydrous DCM (3 mL) was added drop wise to tert-butanol (0.3 mL, 3.4 mmol) at 0° C. and the resulting mixture was stirred at rt for 2 hrs. Subsequently, the mixture was cooled to 0° C. and a solution of compound 20-3 (60 mg, 0.17 mmol) and TEA (0.6 mL) in anhydrous DCM (3 mL) was added drop wise. After stirring at rt for 3 hrs, the reaction mixture was diluted with water (10 mL) and DCM (20 mL). The organic layer was washed with brine and dried with anhydrous Na$_2$SO$_4$. The solvent was removed and the residue was dried in vacuo to give crude compound 20-4 (70 mg, 77% yield) as a yellow solid. LC-MS (ESI): m/z 477.1 [M−C$_4$H$_9$+H]$^+$.

Step 5. A mixture of compound 20-4 (70 mg, 0.13 mmol) and LiOH.H₂O (28 mg, 0.66 mmol) in EtOH/THF/H₂O (1.5 mL/3 mL/1.5 mL) was stirred at 70° C. for 2 hrs. Subsequently, the mixture was added 2 N aq. HCl to adjust the pH value to 3 and the resulting suspension was filtered. The solid was washed with water and dried in vacuo to give compound 20-5 (60 mg, 90% yield) as a yellow solid. LC-MS (ESI): m/z 449.1 [M−C₄H₉+H]⁺.

Step 6. To a solution of compound 20-5 (60 mg, 0.12 mmol) in DMF (2 mL) was added HATU (90 mg, 0.24 mmol). The resulting mixture was stirred at rt for 1 hr before DIPEA (154 mg, 1.19 mmol) and MeNH₂.HCl (40 mg, 0.60 mmol) were added. After stirring at rt for 1 hr, the reaction mixture was added into ice-water (30 mL) and the resulting suspension was filtered. The solid was washed with water and dried in vacuo to give crude compound 20-6 (60 mg, 97% yield). LC-MS (ESI): m/z 462.1 [M−C₄H₉+H]⁺.

Step 7. To a solution of compound 20-6 (60 mg, 0.12 mmol) in MeOH (1 mL) was added 3.5 M HCl in dioxane (20 mL). After stirring at rt overnight, the mixture was concentrated and the residue was purified by preparative HPLC to give compound 20-7 (35 mg, 72% yield). LC-MS (ESI): m/z 418.1 [M+H]⁺; ¹H NMR (500 MHz, MeOD): δ 7.95-7.92 (m, 2H), 7.73 (s, 1H), 7.52 (s, 1H), 7.26 (t, J=9.0 Hz, 2H), 3.63 (br, 2H), 3.05 (s, 2H), 2.97 (s, 3H), 1.96 (d, J=6.5 Hz, 2H), 1.76 (br, 2H) ppm.

Syntheses of Analogs of Compound 20-7. Following the same synthetic strategy by treating compound 20-3 with various acyl chlorides or sulfonyl chlorides instead of chlorosulfonyl isocyanate, followed by hydrolyzation and methyl amide formation, the following analogs of compound 20-7 were obtained.

| RCOCl or RSO₂Cl | Target | [M + H]⁺ | ¹H NMR (500 MHz, CDCl₃) (δ, ppm) |
|---|---|---|---|
| MeOCOCl | 20-8 | 397.1 | 7.91 (d, J = 5.5 Hz, 2H), 7.63 (s, 1H), 7.31 (s, 1H), 7.18 (t, J = 5.5 Hz, 2H), 5.81 (br s, 1H), 4.46 (t, J = 2.5 Hz, 1H) 3.82 (s, 1H), 3.67 (s, 2H), 3.01 (d, J = 4.5 Hz, 3H), 2.79 (t, J = 1.5 Hz, 2H), 2.02-1.74 (m, 3H), 1.37 (br s, 1H) |
| CH₃COCl | 20-9 | 381.2 | 7.93-7.90 (m, 2H), 7.72 (s, 1H), 7.30 (s, 1H), 7.22-7.17 (m, 2H), 5.82 (br, 1H), 4.73 (d, J = 13 Hz, 1H), 3.02 (t, J = 5 Hz, 3H), 2.88-2.80 (m, 2H), 2.70-2.65 (m, 1H), 2.05-2.00 (m, 2H), 1.90 (s, 3H), 1.80-1.77 (m, 1H), 1.45-1.27 (m, 1H) |
| Me₂NSO₂Cl | 20-10 | 446.1 | 8.53 (br s, 1H), 7.96-7.94 (m, 2H), 7.62 (s, 1H), 7.54 (s, 1H), 7.28-7.25 (m, 2H), 3.62-3.58 (m, 2H), 3.08 (s, 2H), 3.02 (s, 3H), 2.90 (s, 5H), 1.95 (br s, 2H), 1.71 (br s, 2H) |

| RCOCl or RSO₂Cl | Target | [M + H]⁺ | ¹H NMR (500 MHz, CDCl₃) (δ, ppm) |
|---|---|---|---|
| c-PrSO₂Cl | 20-11 | 443.2 | 7.92-7.88 (m, 2H), 7.66 (s, 1H), 7.64 (s, 1H), 7.21-7.16 (m, 2H), 5.82 (br, 1H), 3.67 (br , 2H), 3.02 (d, J = 12 Hz, 2H), 3.00 (s, 3H), 2.54-2.49 (m, 2H), 1.94 (d, J = 5.5 Hz, 2H), 1.74 (br s, 2H), 1.12 (d, J = 4.0 Hz, 2H), 0.99-0.98 (m, 2H) |

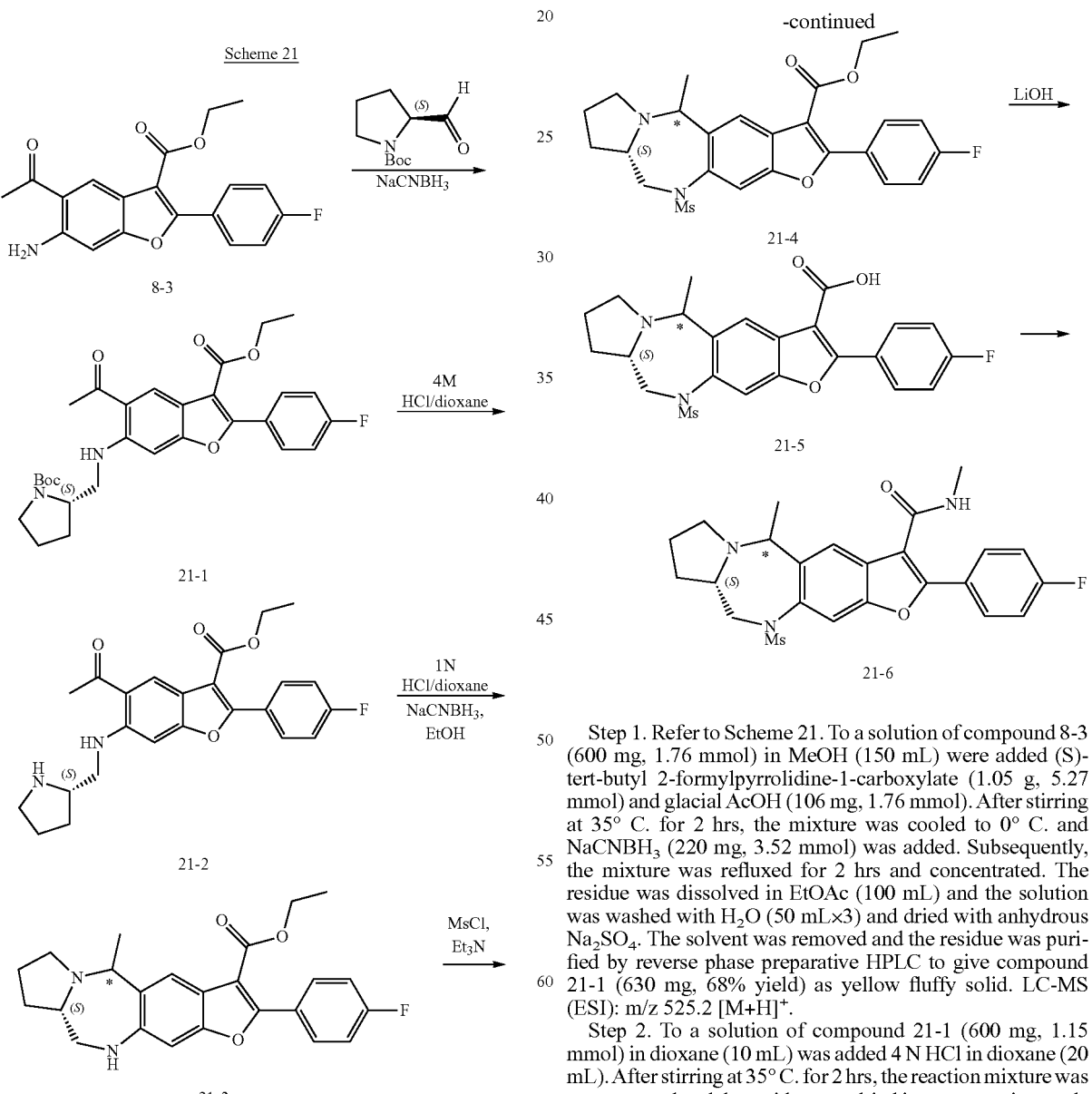

Step 1. Refer to Scheme 21. To a solution of compound 8-3 (600 mg, 1.76 mmol) in MeOH (150 mL) were added (S)-tert-butyl 2-formylpyrrolidine-1-carboxylate (1.05 g, 5.27 mmol) and glacial AcOH (106 mg, 1.76 mmol). After stirring at 35° C. for 2 hrs, the mixture was cooled to 0° C. and NaCNBH₃ (220 mg, 3.52 mmol) was added. Subsequently, the mixture was refluxed for 2 hrs and concentrated. The residue was dissolved in EtOAc (100 mL) and the solution was washed with H₂O (50 mL×3) and dried with anhydrous Na₂SO₄. The solvent was removed and the residue was purified by reverse phase preparative HPLC to give compound 21-1 (630 mg, 68% yield) as yellow fluffy solid. LC-MS (ESI): m/z 525.2 [M+H]⁺.

Step 2. To a solution of compound 21-1 (600 mg, 1.15 mmol) in dioxane (10 mL) was added 4 N HCl in dioxane (20 mL). After stirring at 35° C. for 2 hrs, the reaction mixture was concentrated and the residue was dried in vacuo to give crude compound 21-2 (500 mg, quantitative yield) as a yellow solid. LC-MS (ESI): m/z 425.2 [M+H]⁺.

Step 3. To a stirred solution of compound 21-2 (500 mg, 1.2 mmol) in EtOH (30 mL) was added 1 N HCl in dioxane (2 mL). After stirring at 35° C. for 2 hrs, the reaction mixture was cooled to 0° C. and NaCNBH₃ (148 mg, 2.4 mmol) was added. The mixture was stirred at rt for 2 hrs and concentrated. The residue was dissolved in EtOAc (100 mL) and the solution was washed with brine (25 mL) and dried with anhydrous Na₂SO₄. The solvent was removed and the residue was purified by reverse phase preparative HPLC to give compound 21-3 (420 mg, 87% yield) as a yellow foam. LC-MS (ESI): m/z 409.2 [M+H]⁺. Long column (30 min) HPLC and Chiral HPLC showed there was only one diastereomer formed during the reductive-elimination step; however, the chirality of the benzylic carbon in compound 21-3 was not determined.

Step 4. To a solution of compound 21-3 (300 mg, 0.73 mmol) and Et₃N (0.3 mL) in DCM (30 mL) was added MsCl drop wise (85 mg, 0.73 mmol) at 0° C. After stirring at rt for 30 min, the reaction mixture was washed with H₂O (20 mL×3) and dried with anhydrous Na₂SO₄. The solvent was removed and the residue was purified by reverse phase preparative HPLC to give compound 21-4 (186 mg, 52% yield) as a yellow solid. LC-MS (ESI): m/z 487.2 [M+H]⁺.

Step 5. A mixture of compound 21-4 (180 mg, 0.371 mmol) and LiOH.H₂O (47 mg, 1.1 mmol) in MeOH/THF/H₂O (2 mL/4 mL/1 mL) was stirred at 75° C. for 30 min. The resulting mixture was acidified to pH 5~6 by adding 2 N aq. HCl. The suspension was filtered and the solid was dried in vacuo to give compound 21-5 (150 mg, 93% yield) as a white solid. LC-MS (ESI): m/z 459.1 [M+H]⁺.

Step 6. To a solution of compound 21-5 (150 mg, 0.327 mmol) in DMF (5 mL) was added HATU (187 mg, 0.491 mmol). After stirring at rt for 30 min, the mixture was added DIPEA (127 mg, 0.982 mmol) and MeNH₂.HCl (66 mg, 0.98 mmol). Subsequently, the mixture was stirred at rt for 30 min and poured into ice-water (50 mL). The suspension was filtered and the solid was purified by preparative HPLC to give compound 21-6 (32 mg, 21% yield) as a white solid. LC-MS (ESI): m/z 472.2 [M+H]⁺.

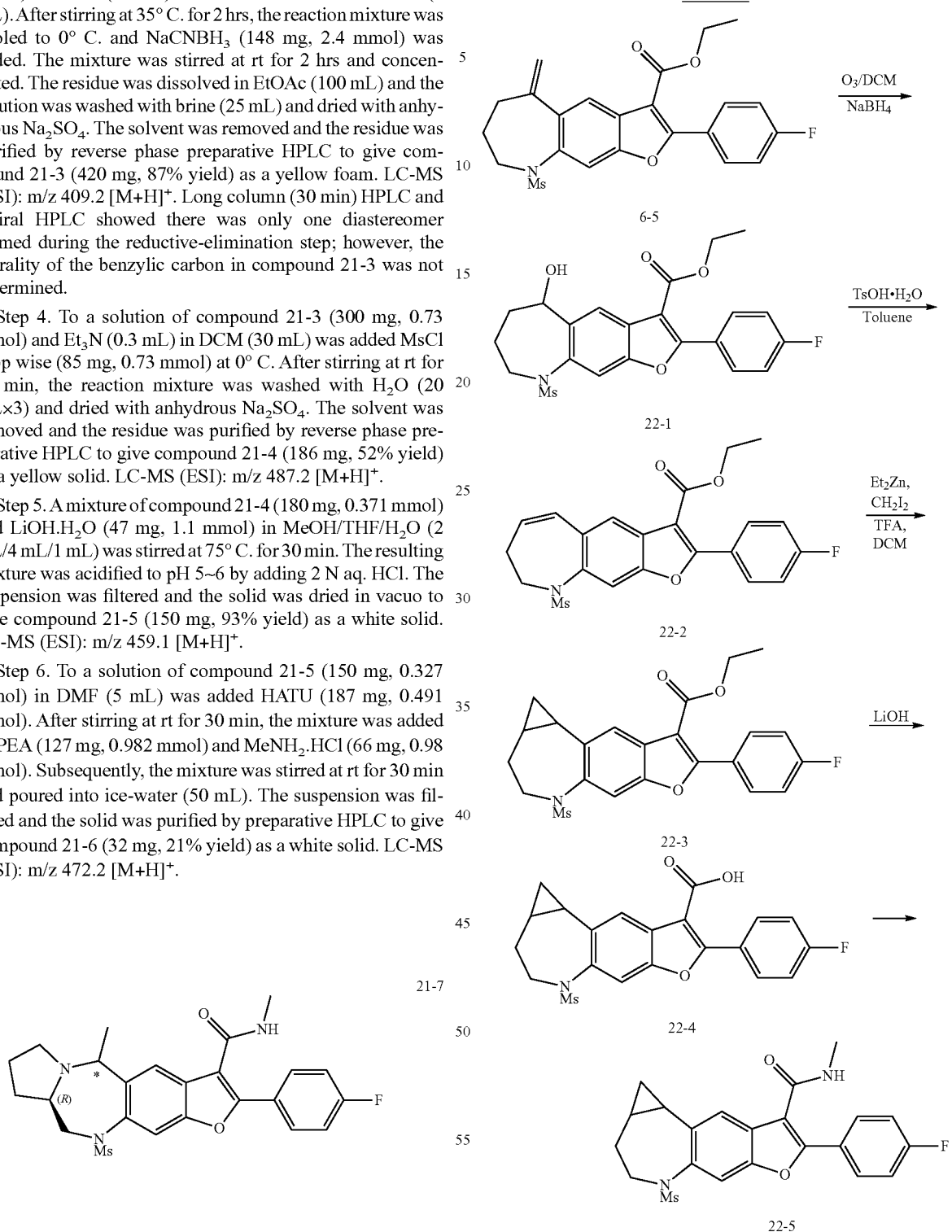

Synthesis of Compound 21-7. Following the same scheme and replacing (S)-tert-butyl 2-formylpyrrolidine-1-carboxylate with its (R)-enantiomer, compound 21-7 was obtained. LC-MS (ESI): m/z 472.2 [M+H]⁺. Long column (30 min) HPLC and Chiral HPLC showed there was only one diastereomer formed during the reductive-elimination step; however, the chirality of the benzylic carbon in compound 21-7 was not determined.

Step 1. Refer to Scheme 22. A solution of compound 6-5 (1.0 g, 2.28 mmol) in DCM (200 mL) was cooled to −78° C. and O₃ was flushed through until the starting material disappeared as monitored by TLC. Excessive O₃ was removed completely by flushing the reaction mixture with N₂. Subsequently, NaBH₄ (866 mg, 22.8 mmol) and MeOH (40 mL)

were added to the mixture. After stirring at −78° C. for 3 hrs, the reaction mixture was warmed to rt and water (200 mL) was added. The aqueous phase was extracted with DCM (50 mL×3) and the combined organic extracts were washed with water (100 mL×2) and brine (50 mL) and dried with anhydrous $Na_2SO_4$. The solvent was removed and the residue was dried in vacuo to give compound 22-1 (958 mg, 94% yield) as a white solid. LC-MS (ESI): m/z 430.1 [M−$H_2O$]$^+$.

Step 2. A mixture of compound 22-1 (1.0 g, 2.24 mmol) and TsOH.$H_2O$ (170 mg, 0.90 mmol) in toluene (40 mL) was refluxed overnight. The solvent was removed and the residue was purified by silica gel column chromatography (Petroleum ether/Acetone=10/1) to give compound 22-2 (600 mg, 63% yield) as a white solid. LC-MS (ESI): m/z 430.1 [M+H]$^+$.

Step 3. A solution of $Et_2Zn$ (1.1 M in hexane, 27.5 mL, 27.5 mmol) was added into DCM (30 mL) dropwise at −78° C. under an atmosphere of $N_2$, followed by addition of $CH_2I_2$ (4.4 mL, 55.0 mmol). After the reaction mixture was stirred at −78° C. for 30 min, a solution of compound 22-2 (536 mg, 1.25 mmol) and TFA (0.5 mL) in DCM (10 mL) was added. The resulting mixture was stirred at −78° C. for 3 hrs and then partitioned between water (80 mL) and DCM (80 mL). The aqueous phase was extracted with DCM (50 mL×3). The combined organic extracts were washed with water (100 mL×3) and brine (50 mL) and dried with anhydrous $Na_2SO_4$. The solvent was removed and the residue was purified by silica gel column chromatography (Petroleum ether/EtOAc=10/1 (v/v)) to give compound 22-3 (190 mg, 35% yield) as a yellow solid. LCMS (ESI): m/z 444.1 [M+H]$^+$; $^1$H NMR (500 MHz, CDCl$_3$): δ 8.11 (m, 1H), 8.02-8.04 (m, 2H), 7.53 (s, 1H), 7.16-7.20 (m, 2H), 4.41-4.44 (m, 2H), 4.11 (m, 1H), 3.40 (m, 1H), 3.02 (s, 3H), 2.28 (m, 1H), 2.18 (m, 2H), 1.42 (t, 3H), 1.20 (m, 2H), 0.63 (m, 1H), 0.41 (m, 1H) ppm.

Step 4. To a solution of compound 22-3 (190 mg, 0.429 mmol) in MeOH/THF (5 mL/5 mL) was added 2 N aq. LiOH (0.857 mL, 1.761 mmol). The resulting mixture was stirred at 75° C. overnight, then cooled to rt, acidified with 2 N aq. HCl to pH 5~6, and extracted with EtOAc (30 mL×2). The combined organic extracts were washed with $H_2O$ (25 mL) and brine (25 mL) and dried with anhydrous $Na_2SO_4$. The solvent was removed and the residue was dried in vacuo to give compound 22-4 (178 mg, 99% yield) as a white solid, which was used directly in the next step without further purification. LC-MS (ESI): m/z 337.1 [M−Ms]$^+$.

Step 5. To a solution of compound 22-4 (138 mg, 0.33 mmol) in DMF (3 mL) was added HATU (152 mg, 0.40 mmol) at rt. The resulting mixture was stirred for 30 min and then added DIPEA (86 mg, 0.67 mmol) and $CH_3NH_2$.HCl (45 mg, 0.67 mmol). After stirring at rt for 20 min, the reaction mixture was poured into water and the suspension was filtered. The solid was washed with water, dried in vacuo, and re-crystallized in EtOAc and hexane to give compound 22-5 as white solid (120 mg, 84% yield). LC-MS (ESI): m/z 429.1 [M+H]$^+$; $^1$H NMR (500 MHz, DMSO): δ 8.49 (s, 1H), 7.94-7.97 (m, 2H), 7.63 (s, 1H), 7.57 (s, 1H), 7.39 (t, J=9.0 Hz, 2H), 3.95-4.00 (m, 1H), 3.26-3.29 (m, 1H), 3.14 (s, 3H), 2.84 (d, J=4.5 Hz, 3H), 2.14-2.23 (m, 2H), 1.11-1.22 (m, 2H), 0.44-0.52 (m, 1H), 0.30-0.33 (m, 1H) ppm. Compound 22-5 was separated to give a pair of enantiomers: enantiomer 22-5_A ($t_R$=2.48 min) and enantiomer 22-5_B ($t_R$=4.90 min) detected by UV absorption at 214 nm on a 4.6 mm×250 mm×5 μm Lux Amylose-2 column (column temperature: 40.2° C.; eluent: MeOH/liquid $CO_2$=40/60 (v/v); $CO_2$ flow rate: 1.8 g/min and co-solvent flow rate: 1.2 g/min; front pressure: 207 bar and back pressure: 151 bar).

Scheme 23

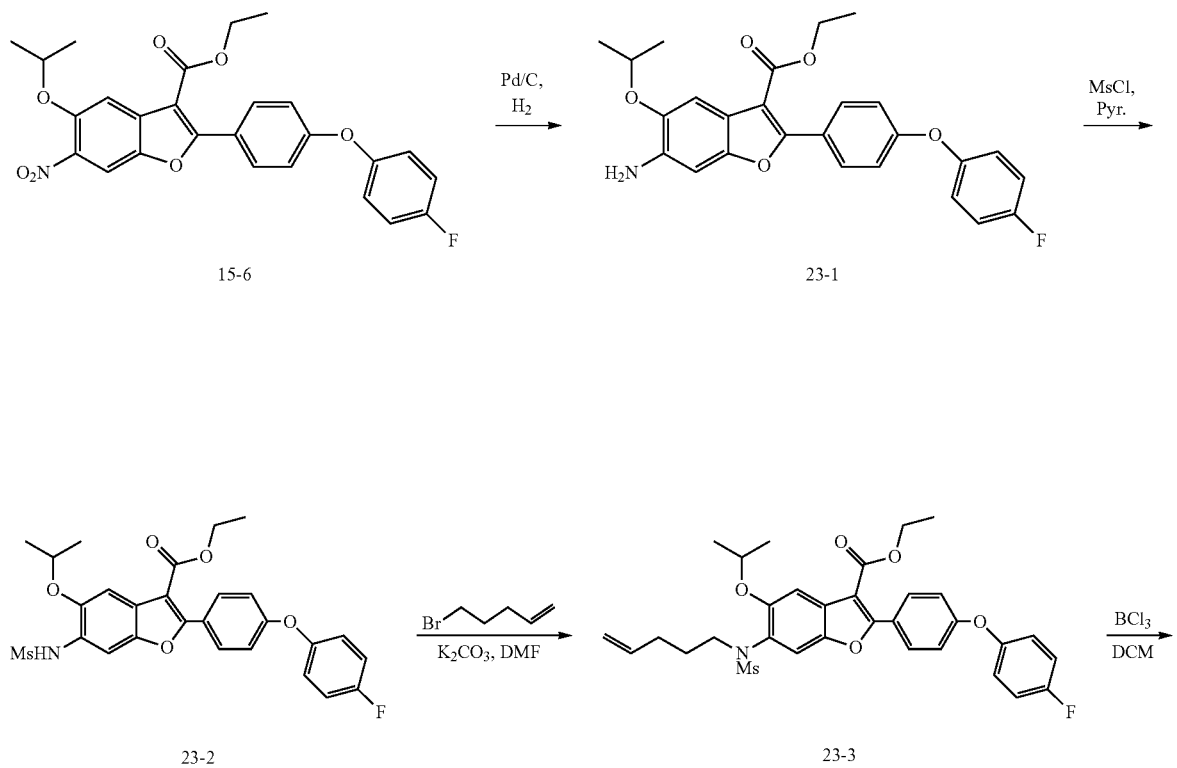

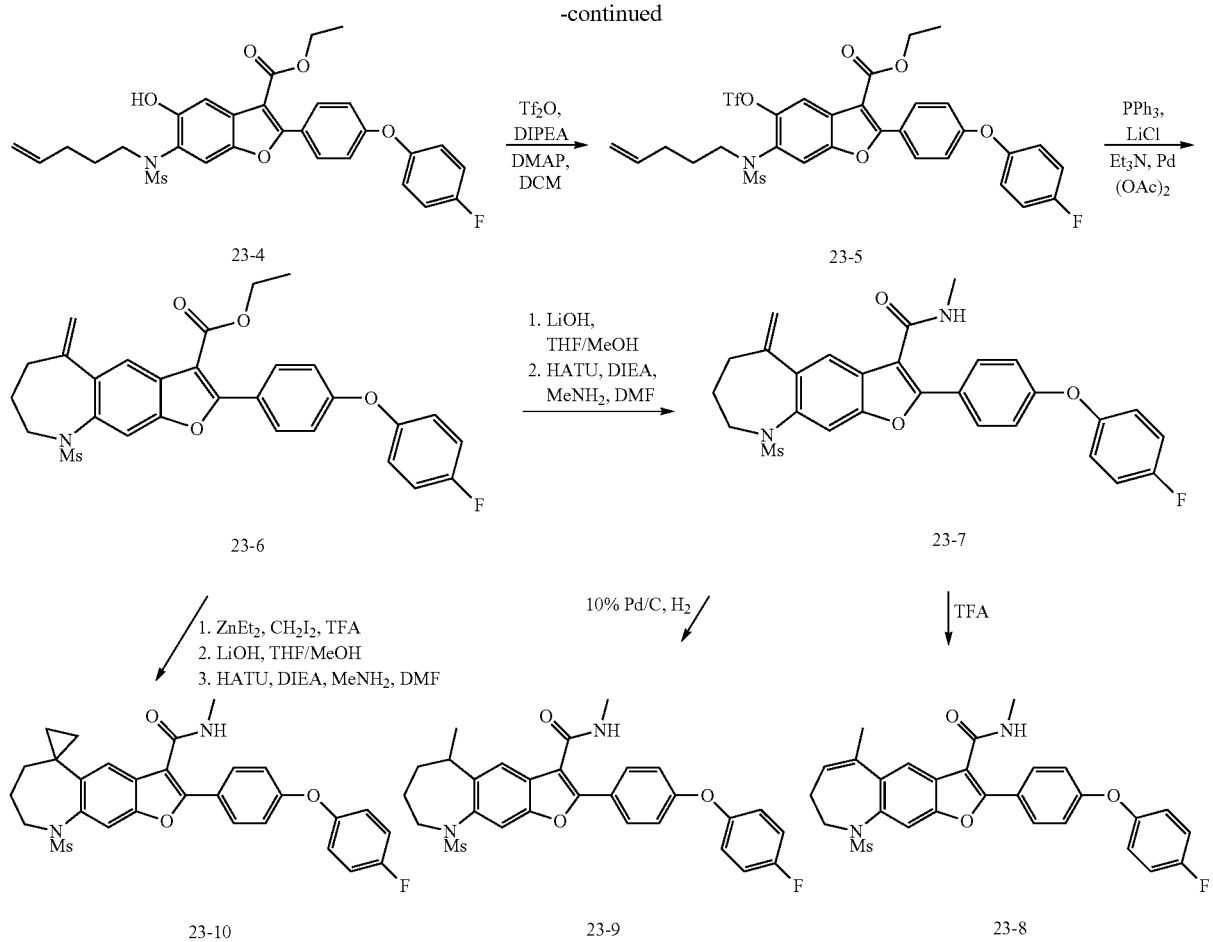

Step 1. Refer to Scheme 23. A mixture of compound 15-6 (8.0 g, 16.7 mmol) and 10% Pd/C (4.0 g) in EtOAc (200 mL) was stirred at rt for 3 hrs under an atmosphere of $H_2$. The reaction mixture was filtered through a Celite® 545 pad and the filtered cake was washed with EtOAc (50 mL×2). The filtrate was concentrated and the residue was dried in vacuo to give compound 23-1 (7.5 g, quantitative yield as a yellow solid. LC-MS (ESI): m/z 450.2 [M+H]$^+$.

Step 2. To a solution of compound 23-1 (7.5 g, 16.7 mmol) in anhydrous pyridine (100 mL) was added dropwise a solution of MsCl (1.4 mL, 17.54 mmol) in anhydrous DCM (20 mL) at 0° C. After stirring at 0° C. for 3 hrs, the reaction mixture was diluted with EtOAc (500 mL). The resulting mixture was washed with 1 M aq. HCl (200 mL×3) and brine (100 mL×2) and dried with anhydrous $Na_2SO_4$. The solvent was removed and the residue was re-crystallized in EtOAc to give compound 23-2 (7.9 g, 90% yield) as a pale brown solid. LC-MS (ESI): m/z 528.1 [M+H]$^+$.

Step 3. To a solution of compound 23-2 (7.9 g, 15.0 mmol) in DMF (150 mL) was added $K_2CO_3$ (8.3 g, 60.0 mmol), followed by 5-bromo-1-pentene (2.68 g, 18.0 mmol). After stirring at 80° C. for 2 hrs, the reaction mixture was concentrated. The residue was diluted with EtOAc (200 mL) and water (200 mL). The aqueous phase was extracted with EtOAc (150 mL×3). The combined organic extracts were washed with (250 mL) and brine (250 mL) and dried with anhydrous $Na_2SO_4$. The solvent was removed and the residue was dried in vacuo to give compound 23-3 (7.9 g, 93% yield) as a yellow solid. LC-MS (ESI): m/z 618.2 [M+Na]$^+$.

Step 4. To a solution of compound 23-3 (7.6 g, 12.8 mmol) in DCM (100 mL) was added dropwise $BCl_3$ in DCM (31.9 g, 31.9 mmol.) at −30° C. under an atmosphere of $N_2$. After stirring at −30° C. for 2 hrs, the reaction mixture was poured into ice-water (300 mL) and the resulting mixture was extracted with DCM (150 mL×3). The combined organic extracts were washed with water (100 mL×3) and brine (100 mL) and dried with anhydrous $Na_2SO_4$. The solvent was removed and the residue was dried in vacuo to give crude compound 23-4 (7.2 g, 98% yield) as a yellow solid. LC-MS (ESI): m/z 554.2 [M+H]$^+$.

Step 5. To a solution of compound 23-4 (7.5 g, 13.6 mmol) in DCM (100 mL) were added DIPEA (5.25 g, 40.7 mmol) and DMAP (165 mg, 1.4 mmol), followed by a solution of $Tf_2O$ (5.0 g, 17.6 mmol) in DCM (25 mL) at 0° C. After stirring at rt overnight, the reaction mixture was diluted with DCM (300 mL) and water (300 mL). The aqueous phase was extracted with DCM (300 mL×2). The combined organic extracts were washed with water (250 mL×3) and brine (250 mL) and dried with anhydrous $Na_2SO_4$. The solvent was removed and the residue was purified by silica gel column chromatography (Petroleum ether/Acetone=20/1 (v/v)) to give compound 23-5 (8.0 g, 90% yield) as a yellow solid. LC-MS (ESI): m/z 686.1 [M+H]$^+$.

Step 6. A mixture of compound 23-5 (8.0 g, 11.7 mmol), LiCl (539 mg, 12.8 mmol), $Et_3N$ (3.24 mL, 23.3 mmol), Pd(OAc)$_2$ (392 mg, 1.8 mmol), and PPh$_3$ (1.22 g, 4.7 mmol) in DMF (80 mL) was stirred at 120° C. for 2 hrs under an atmosphere of Ar. Subsequently, the reaction mixture was concentrated and the residue was partitioned between water (200 mL) and EtOAc (200 mL). The aqueous phase was extracted with EtOAc (150 mL×3) and the combined organic extracts were washed with water (250 mL×3) and brine (250 mL) and dried with anhydrous $Na_2SO_4$. The solvent was removed and the residue was purified by silica gel column chromatography (Petroleum ether/Acetone=10/1 (v/v)) to give compound 23-6 (4.0 g, 64% yield) as a yellow solid. LC-MS (ESI): m/z 536.1 [M+H]$^+$; $^1$H NMR (500 MHz, CDCl$_3$): δ 8.02-8.04 (m, 2H), 7.95 (s, 1H), 7.68 (s, 1H), 7.07-7.10 (m, 4H), 7.03-7.05 (m, 2H), 5.30 (m, 1H), 5.20 (d, 1H), 4.40-4.44 (t, 2H), 3.85 (m, 2H), 2.87 (s, 3H), 2.52 (m, 2H), 1.95 (m, 2H), 1.42 (t, J=5.5 Hz, 3H) ppm.

Synthesis of Compound 23-7. Following the same procedures of hydrolyzation and methylamide formation as described in the synthesis of compounds 6-6 and 7-1, respectively, compound 23-7 was obtained. LC-MS (ESI): m/z 521.1 [M+H]$^+$; $^1$H NMR (300 MHz, CDCl$_3$): δ 7.83 (dd, $J_1$=1.6 Hz, $J_2$=6.2 Hz, 2H), 7.75 (s, 1H), 7.65 (s, 1H), 7.02-7.10 (m, 6H), 5.86 (m, 1H), 5.29 (s, 1H), 5.17 (d, J=1.8 Hz, 1H), 3.82 (m, 2H), 2.99 (d, J=5.7 Hz, 3H), 2.85 (3, 3H), 2.47 (m, 2H), 1.93 (m, 2H) ppm.

Synthesis of Compound 23-8. Following the same procedure of isomerization as described in the synthesis of compound 7-4, compound 23-8 was obtained. LC-MS (ESI): m/z 521.1 [M+H]$^+$; $^1$H NMR (300 MHz, CDCl$_3$): δ 7.81 (dd, $J_1$=1.8 Hz, $J_2$=5.9 Hz, 2H), 7.63 (s, 1H), 7.26 (s, 1H), 70.3-7.10 (m, 6H), 6.04 (m, 1H), 5.85 (m, 1H), 4.15 (m, 2H), 2.98 (d, J=5.1 Hz, 3H), 2.76 (s, 3H), 2.20 (s, 3H), 2.17 (m, 2H) ppm.

Synthesis of Compound 23-9. Following the same procedure of hydrogenation as described in the synthesis of compound 7-3, compound 23-9 was obtained. LC-MS (ESI): m/z 523.2 [M+H]$^+$; $^1$H NMR (300 MHz, CDCl$_3$): δ 7.82 (d, J=8.7 Hz, 2H), 7.72 (s, 1H), 7.54 (s, 1H), 7.03-7.10 (m, 6H), 5.84 (m, 1H), 4.10 (m, 1H), 3.24 (m, 2H), 3.08 (s, 3H), 3.00 (d, J=5.2 Hz, 3H), 1.92-2.02 (m, 4H), 1.46 (d, J=6.7 Hz, 3H) ppm. Compound 23-9 was separated into a pair of enantiomers: enantiomer 23-9_A ($t_R$=3.82 min) and enantiomer 23-9_B ($t_R$=4.99 min) detected by UV absorption at 214 nm on a ChiralPak® IB column (column temperature: 40.3° C.; eluent: MeOH/liquid $CO_2$=30/70 (v/v); $CO_2$ flow rate: 2.1 g/min and co-solvent flow rate: 0.9 g/min; front back pressure: 152 bar).

Synthesis of Compound 23-10. Following the same procedure of cyclopropanation as described in the synthesis of compound 6-7, followed by hydrolyzation and methyl amide formation, compound 23-10 was obtained. LC-MS (ESI): m/z 535.2 [M+H]$^+$; $^1$H NMR (500 MHz, CDCl$_3$): δ 7.82 (dd, $J_1$=2.0 Hz, $J_2$=5.0 Hz, 2H), 7.79 (d, J=3.0 Hz, 1H), 7.52 (s, 1H), 6.97-7.10 (m 6H), 5.84 (m, 1H), 3.58-3.71 (m, 2H), 3.15 (s, 3H), 3.00 (d, J=4.5 Hz, 3H), 1,94 (m, 2H), 1.61 (m, 2H), 1.04 (m, 2H), 0.92 (m, 2H) ppm.

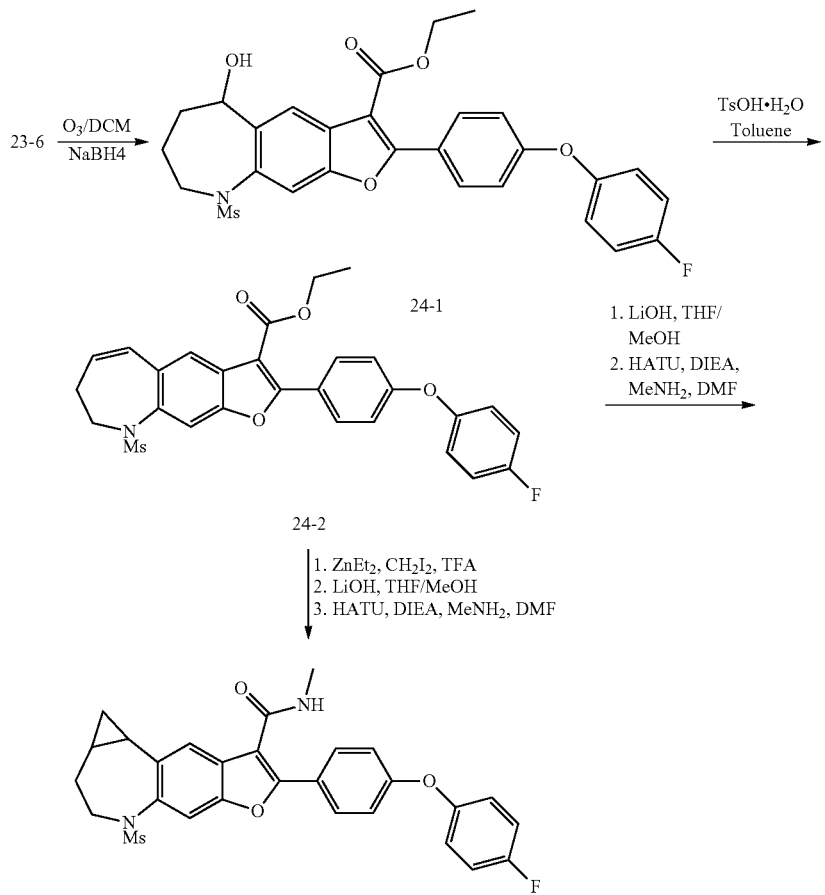

Scheme 24

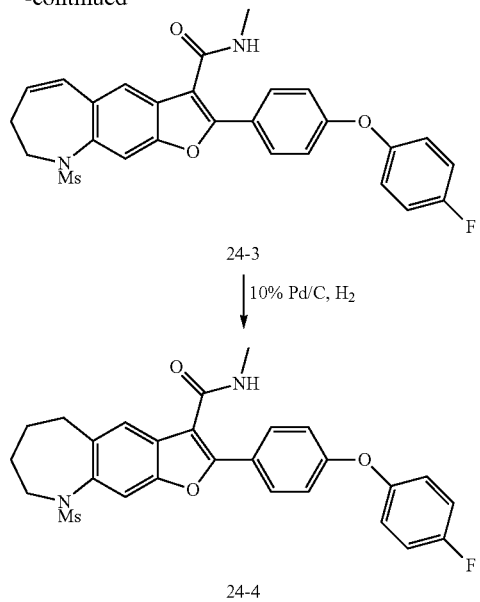

24-3

↓ 10% Pd/C, H₂

24-4

Step 1. Refer to Scheme 24. Following the same procedure as described in the synthesis of compound 22-1, compound 24-1 was obtained as a yellow solid in 80% yield. LC-MS (ESI): m/z=540.1 [M+H]⁺.

Step 2. Following the same procedure as described in the synthesis of compound 22-2, compound 24-2 was obtained as a yellow solid in 57% yield. LC-MS (ESI): m/z=522.1 [M+H]⁺; ¹H NMR (500 MHz, CDCl₃): δ 8.03-8.06 (m, 2H), 7.77 (s, 1H), 7.07-7.09 (m, 4H), 7.03-7.05 (m, 2H), 6.63 (d, 1H), 6.01(d, 1H), 4.41-4.45 (m, 2H), 3.85-3.91 (brs, 2H), 2.80 (brs, 2H), 2.76 (s, 3H), 1.43 (t, J=7.0 Hz, 3H) ppm.

Synthesis of Compound 24-3. Following the same procedure as described in the synthesis of compound 23-7, compound 24-3 was obtained as a white solid in 88% yield. LC-MS (ESI): m/z 507.1 [M+H]⁺; ¹H NMR (500 MHz, CDCl₃): δ 7.84 (d, J=9.0 Hz, 2H), 7.77 (d, J=12.0 Hz, 2H), 7.04-7.10 (m, 6H), 6.60 (d, J=12.5 Hz, 1H), 5.97-5.99 (m, 1H), 5.81 (br, 1H), 3.26-3.29 (m, 1H), 3.89 (br, 2H), 2.99 (d, J=5.0 Hz, 3H), 2.78 (br, 2H), 2.75 (s, 3H) ppm.

Synthesis of Compound 24-4. Following the same procedure as described in the synthesis of compound 23-9, compound 24-4 was obtained as a white solid in 50% yield. LC-MS (ESI): m/z 509.1 [M+H]⁺; ¹H NMR (500 MHz, CDCl₃): δ 7.84 (d, J=9.0 Hz, 2H), 7.69 (s, 1H), 7.57 (s, 1H), 7.03-7.11 (m, 6H), 5.83 (br, 1H), 3.69 (br, 2H), 3.06 (s, 3H), 2.97-3.00 (m, 5H), 1.92-1.94 (m, 2H), 1.74 (br, 2H) ppm.

Synthesis of Compound 24-5. Following the same procedure as described for the synthesis of compound 23-10, compound 24-5 was obtained. LC-MS (ESI): m/z 521.1 [M+H]⁺; ¹H NMR (500 MHz, CDCl₃): δ 7.91 (s, 1H), 7.84 (d, J=8.0 Hz, 2H), 7.50 (s, 1H), 7.05-7.11 (m, 6H), 5.84 (m, 1H), 4.10 (dt, J₁=5.0 Hz, J₂=15.0 Hz, 1H), 3.39 (dd, J₁=5.0 Hz, J₂=13.0 Hz, 1H), 3.00 (s and d, J=3.5 Hz, 6H), 2.25 (m, 1H), 2.14 (m, 1H), 1.15 (m, 2H), 0.63 (m, 1H), 0.39 (m, 1H) ppm. Compound 24-5 was separated into a pair of enantiomers: enantiomer 24-5_A (t_R=7.237 min) and enantiomer 24-5_B (t_R=10.044 min) detected by UV absorption at 214 nm on a 4.6 mm×250 mm×5 μm ChiralPak® AS-H column (column temperature: 40° C.; eluent: n-Hexane/EtOH/DEA=70/30/0.1 (v/v/v); flow rate: 1.0 mL/min).

Scheme 25

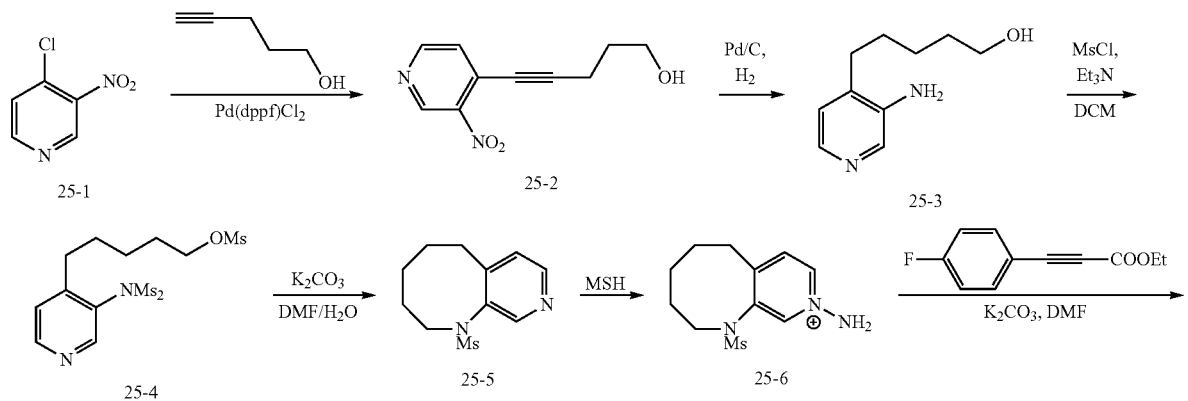

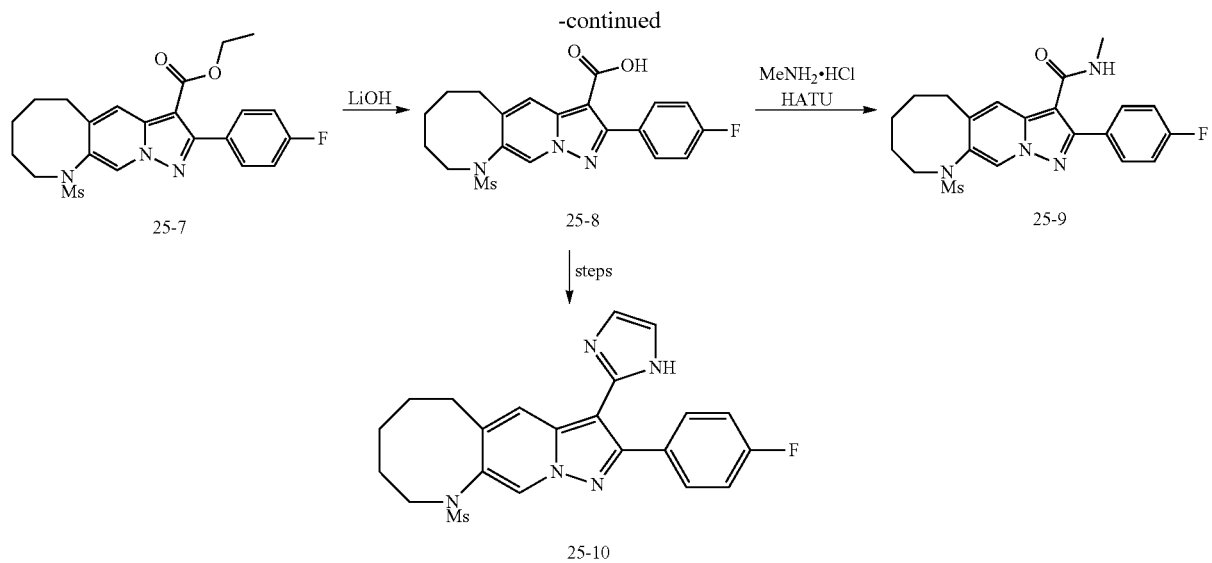

Step 1. Refer to Scheme 25. A mixture of compound 25-1 (600 mg, 3.8 mmol), 4-pentyn-1-ol (620 mg, 7.4 mmol), CuI (141 mg, 0.74 mmol), $Et_3N$ (1.57 g, 11.4 mmol), and Pd(dppf)$Cl_2$ (266 mg, 0.38 mmol) in DMF (30 mL) was stirred at rt overnight under an atmosphere of $N_2$. The solvent was removed and the residue was purified by silica gel column chromatography (Petroleum ether/Acetone=4/1 to 2/1 (v/v)) to give compound 25-2 (250 mg, 32% yield) as a yellow oil. LC-MS: (ESI) m/z 207.1 $[M+H]^+$.

Step 2. A mixture of compound 25-2 (250 mg, 1.2 mmol) and 10% Pd/C (150 mg) in MeOH (20 mL) was stirred at rt overnight under an atmosphere of $H_2$. The mixture was filtered through a Celite® 545 pad and the filtered cake was washed with MeOH (25 mL×2). The filtrate was concentrated and the residue was dried in vacuo to give compound 25-3 (200 mg, 91% yield) as a yellow oil. LC-MS: (ESI) m/z 181.1 $[M+H]^+$.

Step 3. To a solution of compound 25-3 (200 mg, 1.1 mmol) and $Et_3N$ (0.90 mL, 6.6 mmol) in DCM (10 mL) was added dropwise a solution of MsCl (376 mg, 3.3 mmol) in DCM (5 mL) over 10 min at 0° C. After stirring at rt for 1 hr, the reaction mixture was filtered through a Celite® 545 pad and the filtered cake was washed with DCM (25 mL×2). The filtrate was concentrated and the residue was dried in vacuo to give crude compound 25-4 (495 mg) as yellow solid, which was used for the next step without further purification. LC-MS: (ESI) m/z 415.1 $[M+H]^+$.

Step 4. A mixture of compound 25-4 (495 mg, 1.1 mmol) and $K_2CO_3$ (607 mg, 4.4 mmol) in DMF (10 mL) and $H_2O$ (2 mL) was stirred at 80° C. overnight. The solvent was removed and the residue was purified by silica gel column chromatography (Petroleum ether/Acetone=3/1 to 1/1 (v/v)) to give compound 25-5 (100 mg, 37% yield, two steps from compound 25-3) as a white oil. LC-MS (ESI): m/z 241.1 $[M+H]^+$; $^1H$ NMR (500 MHz, $CDCl_3$): δ 8.40 (s, 1H), 8.34-8.35 (d, J=5.0 Hz, 1H), 7.29-7.30 (d, J=5.0 Hz, 1H), 3.52 (br, 2H), 3.06 (s, 3H), 2.81 (br, 2H), 1.63 (br, 2H), 1.50 (br, 2H), 1.40 (br, 2H) ppm.

Synthesis of Compound 25-7. Following the same procedure as described in the synthesis of compound 13-5 from 13-3, compound 25-7 was obtained as a yellow solid in 33% yield (two steps from 25-5). LC-MS: (ESI) m/z 446.1 $[M+H]^+$.

Synthesis of Compound 25-9. Following the same procedure as described in the synthesis of compound 13-12 from 13-10, compound 25-9 was obtained as a yellow solid in 62% yield (two steps from 25-7). LC-MS: (ESI) m/z 431.1 $[M+H]^+$; $^1H$ NMR (500 MHz, $CDCl_3$): δ 8.44 (s, 1H), 8.23 (s, 1H), 7.65-7.68 (m, 2H), 7.21-7.25 (m, 2H), 5.48 (br, 1H), 3.65 (br, 2H), 3.09 (s, 3H), 2.95 (br, 2H), 2.85-2.86 (d, J=5.0 Hz, 3H), 1.54-1.65 (m, 6H) ppm.

Synthesis of Compound 25-10. Following the same procedure as described in the synthesis of compound 19-5 from 19-2, compound 25-10 was obtained as a white solid. LC-MS: (ESI) m/z, 440.1 $[M+H]^+$; $^1H$ NMR (500 MHz, $d^6$-DMSO): δ 9.04 (s, 1H,), 7.70 (s, 2H), 7.69 (s, 3H), 7.59-7.62 (m, 2H), 7.25 (t, J=8.5 Hz, 2H), 3.71 (br, 2H), 3.24 (s, 3H), 3.01 (br, 2H), 1.70 (br, 6H) ppm.

Scheme 26

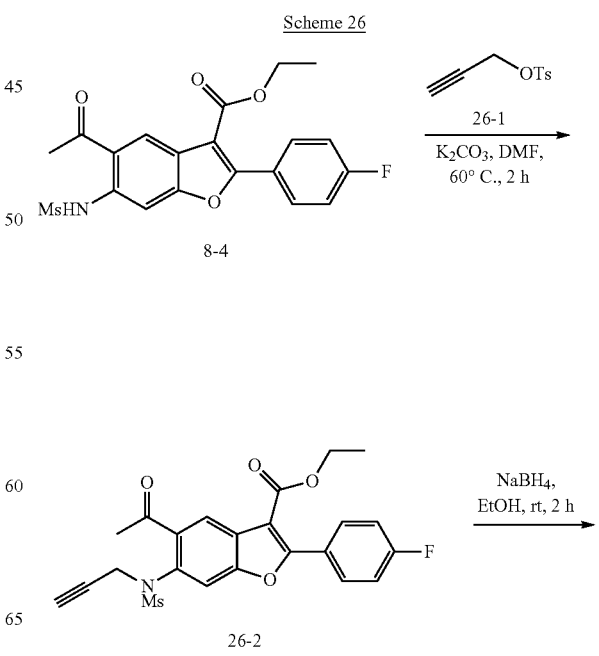

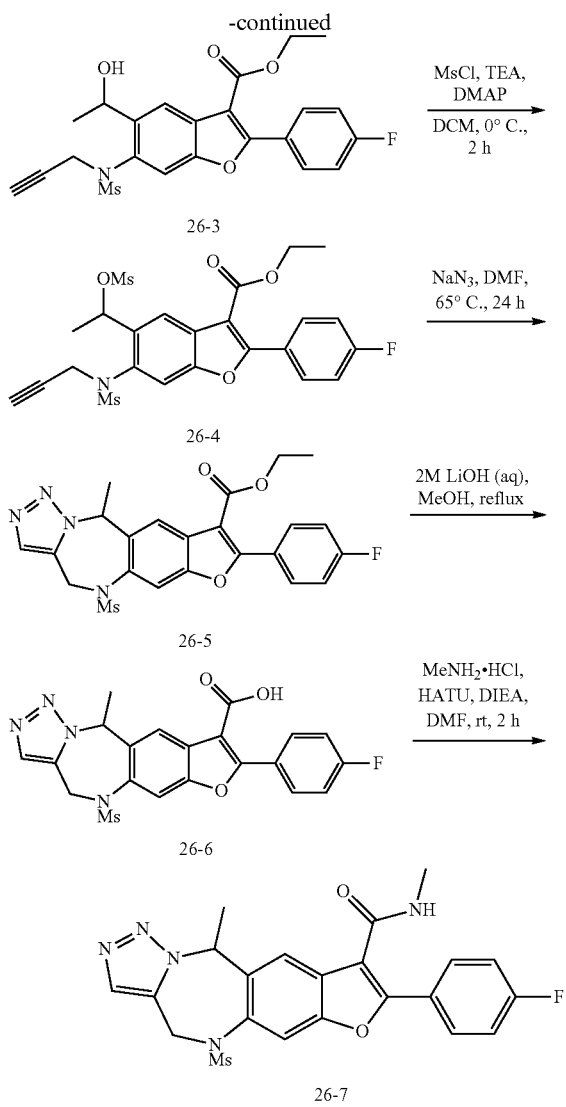

anhydrous Na₂SO₄. The solvent was removed and the residue was dried in vacuo to give compound 26-2 (700 mg, 90% yield) as a yellow solid. LC-MS (ESI): m/z 458.1 [M+H]⁺.

Step 3. To a solution of compound 26-2 (685 mg, 1.5 mmol) in EtOH (20 mL) was added NaBH₄ (114 mg, 3 mmol) in portions at 0° C. After stirring at 0° C. for 2 hrs, the reaction was quenched by adding several drops of acetone. The mixture was concentrated and the residue was partitioned between EtOAc (25 mL) and water (25 mL). The aqueous phase was extracted with EtOAc (25 mL×3) and the combined organic extracts were washed with brined (25 mL) and dried with anhydrous Na₂SO₄. The solvent was removed and the residue was dried in vacuo to give compound 26-3 (640 mg, 93% yield) as a colorless oil. LC-MS (ESI): m/z 460.1 [M+H]⁺.

Step 4. To a solution of compound 26-3 (640 mg, 1.4 mmol) and DMAP (10 mg, 0.075 mmol) in DCM (50 mL) was added Et₃N (0.83 mL, 6 mmol) at 0° C., followed by MsCl (0.5 mL, 3 mmol). After stirring at 0° C. for 2 hrs, the reaction mixture was diluted with DCM (50 mL). The mixture was washed with sat. aq. NH₄Cl (25 mL) and brine (25 mL) and dried with anhydrous Na₂SO₄. The solvent was removed and the residue was purified by silica gel column chromatography (Petroleum ether/EtOAc=2/1 (v/v)) to give compound 26-4 (450 mg, 95% yield) as a yellow solid. LC-MS (ESI): m/z 538.1 [M+H]⁺.

Step 5. To a solution of NaN₃ (390 mg, 6 mmol) in DMF (5 mL) at 65° C. was added compound 26-4 (322 mg, 0.6 mmol). After stirring at 65° C. for 24 hrs, the reaction mixture was concentrated. The residue was partitioned between EtOAc (25 mL0 and water (25 mL). The aqueous phase was extracted with EtOAc (25 mL×3) and the combined organic extracts were washed with brine (50 mL) and dried with anhydrous Na₂SO₄. The solvent was removed and the residue was purified by silica gel column chromatography (Petroleum ether/EtOAc=2/1 (v/v)) to give compound 26-5 (121 mg, 41% yield) as a yellow solid. LC-MS (ESI): m/z 485.1 [M+H]⁺.

Synthesis of Compound 26-7. Following the same procedure as described in the synthesis of compound 25-9 from 25-7, compound 26-7 was obtained as a white solid in 43% yield (two steps from compound 26-5). LC-MS: (ESI) m/z 470.1 [M+H]⁺; ¹H NMR (500 MHz, CDCl₃): δ 7.99 (s, 1H), 7.87-7.90 (m, 2H), 7.70 (s, 1H), 7.51 (s, 1H), 7.22 (t, J=7.5 Hz, 2H), 6.21 (m, 1H), 5.85 (br, 1H), 4.97 and 5.17 (AB, $J_{AB}$=16.0 Hz, 2H), 3.20 (s, 3H), 3.01 (d, J=4.5 Hz, 3H), 2.14 (d, J=6.5 Hz, 3H) ppm.

Step 1. Refer to Scheme 26. To a solution of prop-2-yn-1-ol (2.24 g, 40 mmol) in DME (80 mL) was added KOH (2.7 g, 48 mmol) at 0° C. After stirring at 0° C. for 30 min, the mixture was drop-wisely added a solution of TsCl (8.36 g, 44 mmol) in DME (40 mL) and the resulting mixture was stirred at 0° C. for 4 hrs. Subsequently, the reaction mixture was concentrated and the residue was added DCM (50 mL) and water (50 mL). The aqueous phase was extracted with DCM (100 mL×3) and the combined organic extracts were washed with water (100 mL) and brine (100 mL) and dried with anhydrous Na₂SO₄. The solvent was removed and the residue was purified by silica gel column chromatography to give compound 26-1 (4.3 g, 51% yield) as a colorless oil. LC-MS (ESI): m/z 211.0 [M+H]¹.

Step 2. To a solution of compound 8-4 (712 mg, 1.7 mmol) in DMF (30 mL) was added K₂CO₃ (414 mg, 3 mmol) under an atmosphere of argon. After stirring at rt for 1 hr, the reaction mixture was added 26-1 (714 mg, 3.4 mmol) and the resulting mixture was stirred at 60° C. for 2 hrs. The mixture was concentrated and the residue was partitioned between EtOAc (100 mL) and water (100 mL). The aqueous phase was extracted with EtOAc (50 mL×3) and the combined organic extracts were washed with water (50 mL×2) and dried with Scheme 26a

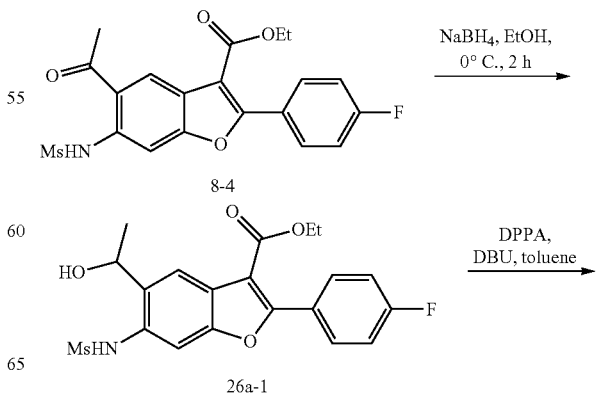

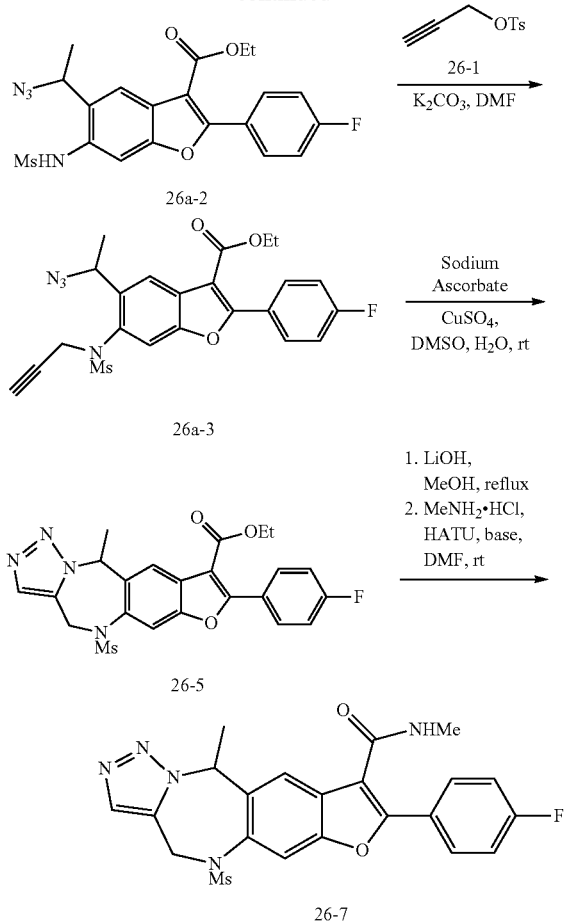

was purified by silica gel column chromatography (PE/EtOAc=2/1 (v/v)) to give compound 26a-3 (3.3 g, 78% yield) as a yellow solid. LC-MS (ESI): m/z 485.1 [M+H]⁺.

Step 4. To a solution of compound 26a-3 (3 g, 6.2 mmol) in DMSO/H$_2$O (60 mL/20 mL) were added Sodium Ascorbate (2.32 g, 9.3 mmol) and CuSO$_4$·5H$_2$O (1.55 g, 6.2 mmol). After stirring at rt overnight, the reaction mixture was poured into H$_2$O (100 mL). The resulting mixture was extracted with EtOAc (100 mL×3) and the combined organic extracts were washed with water (50 mL×3) and brine (50 mL) and dried over anhydrous Na$_2$SO$_4$. The solvent was removed and the residue was purified by silica gel column chromatography (DCM/MeOH=40/1 (v/v)) to give compound 26-5 (2.1 g, 66% yield) as a yellow solid. LC-MS (ESI): m/z 485.1 [M+H]⁺.

Step 5. Following the same procedure as that for the preparation of 1-16 described in Scheme 1 and replacing compound 1-14 with 26-5, compound 26-7 (1.3 g, 67% yield) was obtained as a white solid. LC-MS (ESI): m/z 470.1 [M+H]⁺; $^1$H NMR (500 MHz, d$^6$-DMSO): δ 8.53 (q, J=4.8 Hz, 1H), 8.04 (s, 1H), 7.97-7.99 (m, 2H), 7.96 (s, 1H), 7.60 (s, 1H), 7.42 (t, J=8.5 Hz, 2H), 6.34 (q, J=7.0 Hz, 1H), 5.39 and 4.72 (AB, J$_{AB}$=17.5 Hz, 2H), 3.56 (s, 1H), 2.86 (d, J=4.5 Hz, 3H), 1.89 (d, J=7.5 Hz, 3H) ppm. Compound 26-7 was separated into a pair of enantiomers: enantiomer 26-7_A (t$_R$=8.596 min) and enantiomer 26-7_B (t$_R$=11.887 min) detected by UV absorption at 214 nm on a 4.6 mm×250 mm×5 μm ChiralPak® AS column (column temperature: 40° C.; eluent: n-Hexane/EtOH/DEA=70/30/0.1 (v/v/v); flow rate: 1.0 mL/min).

Step 1. Refer to Scheme 26a. To a solution of compound 8-4 (4.6 g, 11 mmol) in a mixed solvent of DCM (20 mL) and EtOH (60 mL) at 0° C. was added NaBH$_4$ (756 mg, 20 mmol) in small portions. After stirring at 0° C. for 2 hrs, the reaction mixture was slowly added H$_2$O (20 mL) and then concentrated. The residue was extracted with DCM (100 mL×3) and the combined organic extracts were washed with water (50 mL×3) and brine (50 mL) and dried over anhydrous Na$_2$SO$_4$. The solvent was removed and the residue was purified by silica gel column chromatography (PE/EtOAc=2/1 (v/v)) to give compound 26a-1 (4.3 g, 92% yield) as a yellow solid. LC-MS (ESI): m/z 404.1 [M−H$_2$O+H]⁺.

Step 2. To a solution of compound 26a-1 (4.3 g, 10 mmol) in toluene (120 mL) were added DPPA (4.3 mL, 20 mmol) and DBU (3 mL, 20 mmol). The reaction mixture was stirred at 50° C. for 4 hrs. Subsequently, the mixture was concentrated and the residue was purified by silica gel column chromatography (PE/EtOAc=2/1 (v/v)) to give compound 26a-2 (4.0 g, 85% yield) as a yellow solid. LC-MS (ESI): m/z 447.1 [M+H]⁺.

Step 3. To a solution of compound 26a-2 (3.95 g, 8.8 mmol) in DMF (50 mL) was added K$_2$CO$_3$ (1.38 g, 10 mmol) and the mixture was stirred at rt for 30 min. Next, a solution of compound 26-1 (2.52 g, 12 mmol) in 20 mL DMF was added. After stirring at rt overnight, the reaction mixture was poured into H$_2$O (150 mL). The mixture was extracted with EtOAc (100 mL×3) and the combined organic extracts were washed with water (100 mL×3) and brine (50 mL) and dried over anhydrous Na$_2$SO$_4$. The solvent was removed and the residue Scheme 26b

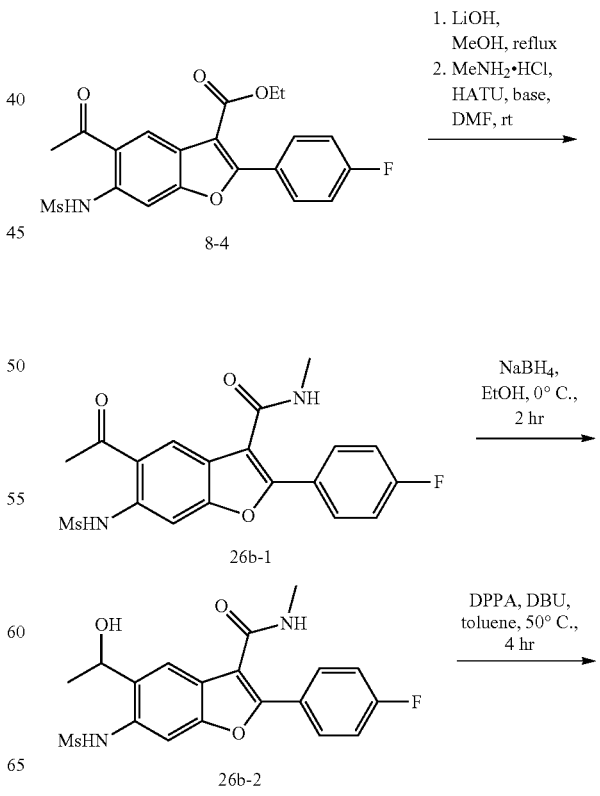

-continued

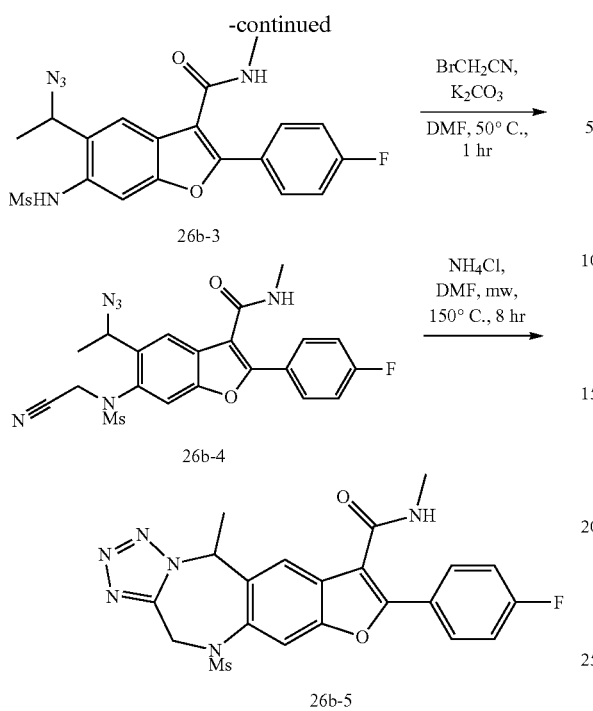

Step 1. Refer to Scheme 26b. Following the same procedure as that for the synthesis of compound 26-7 described in Scheme 26 and replacing compound 26-5 with 8-4, compound 26b-1 was obtained. LC-MS (ESI): m/z 405.1 [M+H]+.

Step 2. Following the same procedure as that for the synthesis of compound 26a-1 described in Scheme 26a and replacing compound 8-4 with 26b-1, compound 26b-2 was obtained. LC-MS (ESI): m/z 407.1 [M+H]+.

Step 3. Following the same procedure as that for the synthesis of compound 26a-2 described in Scheme 26a and replacing compound 26a-1 with 26b-2, compound 26b-3 was obtained as a yellow solid. LC-MS (ESI): m/z 390.1 [M−N$_3$+H]+.

Step 4. To a solution of compound 26b-3 (43 mg, 0.1 mmol) in DMF (2 mL) was added K$_2$CO$_3$ (28 mg, 0.2 mmol) and the resulting mixture was stirred at rt for 30 min. Next, a solution of 2-bromoacetonitrile (24 mg, 0.2 mmol) in 1 mL DMF was added. After stirring at rt for 4 hrs, the mixture was poured into H$_2$O (20 mL). The mixture was extracted with EtOAc (20 mL×3) and the combined organic extracts were washed with water (15 mL×3) and brine (10 mL) and dried over anhydrous Na$_2$SO$_4$. The solvent was removed and the residue was purified by silica gel column chromatography (PE/EtOAc=2/1 (v/v)) to give compound 26b-4 (42 mg, 89% yield) as a yellow solid. LC-MS (ESI): m/z 429.1 [M−N$_3$+H]+.

Step 5. To a solution of compound 26b-4 (24 mg, 0.05 mmol) in DMF (2 mL) was added NH$_4$Cl (26, 0.5 mmol). After being heated at 150° C. in a microwave reactor for 8 hrs, the reaction mixture was cooled to rt and poured into H$_2$O (30 mL). The suspension was extracted with EtOAc (20 mL×3) and the combined organic extracts were washed with water (15 mL×3) and brine (10 mL×1) and dried over anhydrous Na$_2$SO$_4$. The solvent was removed and the residue was purified by preparative HPLC to give compound 26b-5 (15 mg, 63% yield) as a yellow solid. LC-MS (ESI): m/z 471.1 [M+H]+; $^1$H NMR (500 MHz, CD$_3$OD): δ 7.95-7.97 (m, 2H), 7.93 (s, 1H), 7.90 (s, 1H), 7.27 (t, J=9 Hz, 2H), 6.34 (q, J=7 Hz, 1H), 5.48 (m, 1H), 5.07 (m, 1H), 3.50 (s, 3H), 2.97 (s, 3H), 2.08 (br s, 3H) ppm.

Scheme 26c

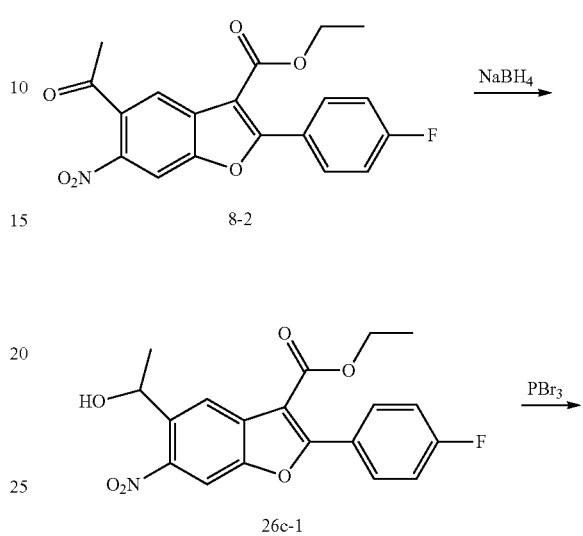

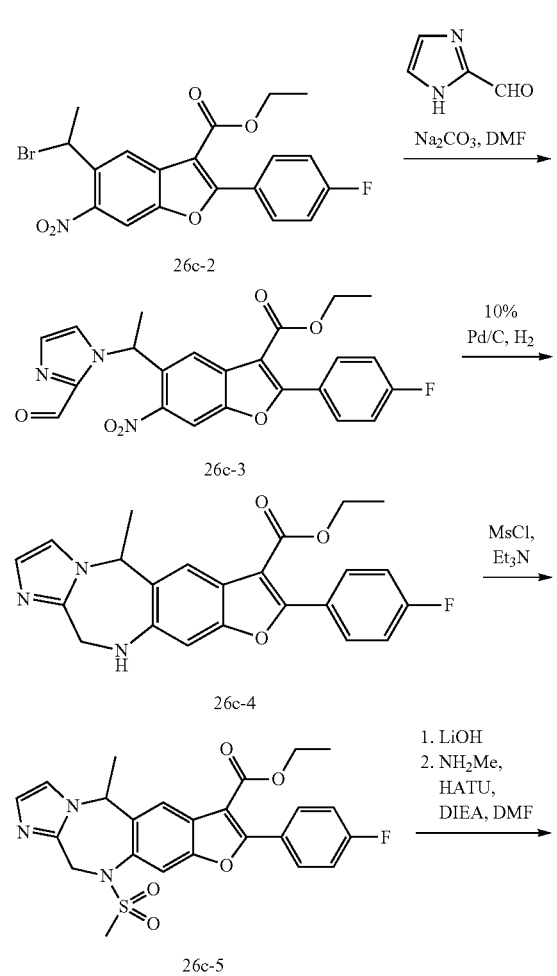

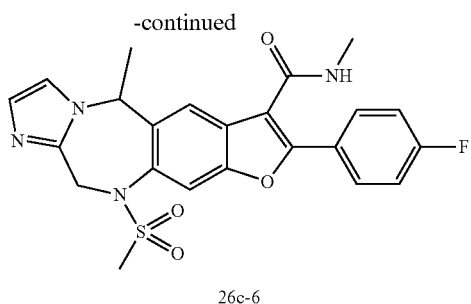

26c-6

Step 1. Refer to Scheme 26c. To a solution of compound 8-2 (5.0 g, 13.5 mmol) in EtOH (150 mL) was added NaBH$_4$ (921 mg, 24.3 mmol) at rt. After stirring at rt for 4 hrs, the reaction mixture was added several drops of acetone and concentrated. The residue was diluted with water (20 mL) and EtOAc (100 mL). The organic layer was washed with water (25 mL×2) and brine (25 mL), dried over anhydrous Na$_2$SO$_4$, and concentrated. The residue was purified by silica gel column chromatography (PE/EtOAc=2/1 (v/v)) to give compound 26c-1 (4.3 g, 85% yield) as a yellow solid. LC-MS (ESI): m/z 356.2 [M−H$_2$O+H]$^+$.

Step 2. To a solution of compound 26c-1 (1.0 g, 2.7 mmol) in DMF (20 mL) at 0° C. was added dropwise a solution of PBr$_3$ (0.78 mL, 8.1 mmol) in DMF (3 mL). After stirring at 0° C. for 10 min, the reaction mixture was added water (20 mL). The mixture was extracted with EtOAc (20 mL×3). The combined organic extracts were washed with brine (50 mL), dried over anhydrous Na$_2$SO$_4$, and concentrated. The residue was purified by silica gel column chromatography (PE/EtOAc=10/1 (v/v)) to give compound 26c-2 (500 mg, 43% yield) as a yellow solid. LC-MS (ESI): m/z 356.1 [M−Br+H]$^+$.

Step 3. To a solution of compound 26c-2 (1.0 g, 2.7 mmol) and 1H-imidazole-2-carbaldehyde (220 mg, 2.3 mmol) in DMF (5 mL) was added Na$_2$CO$_3$ (366 mg, 3.45 mmol). After stirring at 80° C. for 2 hrs, the reaction mixture was diluted with water (20 mL). The resulting mixture was extracted with EtOAc (20 mL×3). The combined organic extracts were washed with water (20 mL×2) and brine (20 mL), dried over anhydrous Na$_2$SO$_4$, and concentrated. The residue was purified by silica gel column chromatography (PE/EtOAc=10/1 (v/v)) to give compound 26c-3 (300 mg, 58% yield) as a yellow solid. LC-MS (ESI): m/z 452.1 [M+H]$^+$.

Step 4. To a solution of compound 26c-3 (300 mg, 0.67 mmol) in EtOAc (10 mL) was added 10% Pd/C (150 mg), and the resulting mixture was stirred at rt for 12 hrs under an atmosphere of H$_2$. at the completion of the reaction, the reaction mixture was filtered through Celite®545 and the filtered cake was washed with EtOAc (20 mL×2). The filtrate was concentrated and the residue was purified by silica gel column chromatography (DCM/MeOH=50/1 (v/v)) to give compound 26c-4 (150 mg, 56% yield) as a yellow solid. LC-MS (ESI): m/z 406.1 [M+H]$^+$.

Step 5. To a solution of compound 26c-4 (150 mg, 0.37 mmol) in DCM (3 mL) was added Et$_3$N (0.1 mL, 0.74 mmol), followed by MsCl (43 µL, 0.56 mmol). After stirring at rt for 2 hrs, the reaction mixture was diluted with DCM (35 mL) and washed with water (15 mL×2) and brine (15 mL), dried over anhydrous Na$_2$SO$_4$, and evaporated. The residue was purified by silica gel column chromatography (DCM/MeOH=50/1 (v/v)) to give compound 26c-5 (60 mg, 34% yield) as a yellow solid. LC-MS (ESI): m/z 484.1 [M+H]$^+$.

Step 6. Following the same procedure as that used for the preparation of 1-16 described in Scheme 1 and replacing compound 1-14 with 26c-5, compound 26c-6 was obtained as a white solid. LC-MS (ESI): m/z 469.1 [M+H]$^+$; $^1$H NMR (500 MHz, CDCl$_3$): δ 7.92 (s, 1H), 7.83-7.86 (m, 2H), 7.64 (s, 1H), 7.21 (t, J=8 Hz, 2H), 6.96 (d, J=11.5 Hz, 2H), 5.82 (d, J=4.5 Hz, 1H), 5.67-5.68 (m, 1H), 5.05 (s, 2H), 3.21 (s, 3H), 2.98 (d, J=5.5 Hz, 3H), 2.05 (d, J=7.5 Hz, 3H) ppm.

Scheme 27

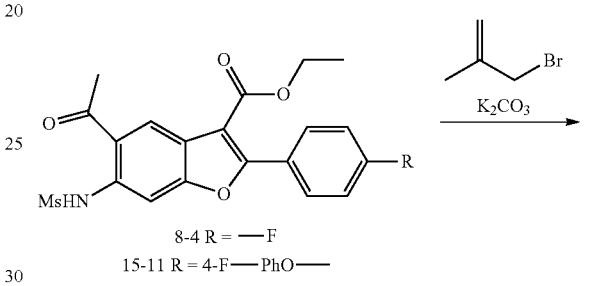

8-4 R = —F
15-11 R = 4-F—PhO—

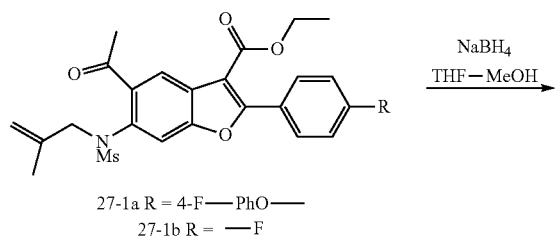

27-1a R = 4-F—PhO—
27-1b R = —F

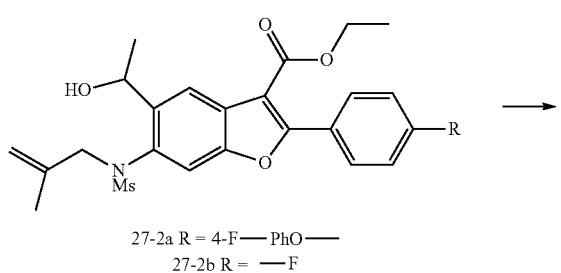

27-2a R = 4-F—PhO—
27-2b R = —F

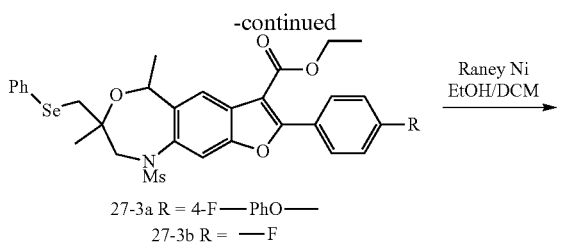

27-3a R = 4-F—PhO—
27-3b R = —F

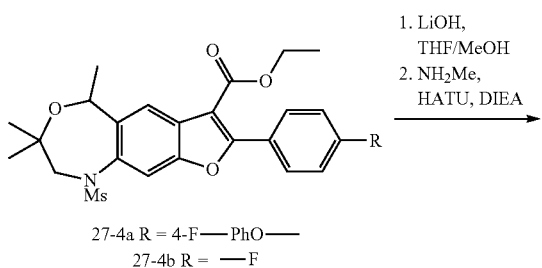

27-4a R = 4-F—PhO—
27-4b R = —F

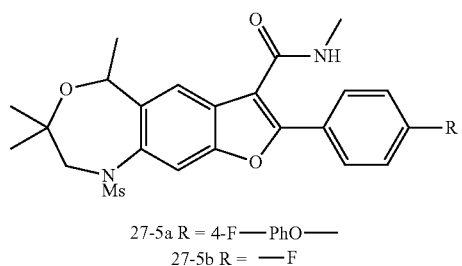

27-5a R = 4-F—PhO—
27-5b R = —F

Step 1. Refer to Scheme 27. To a stirred solution of compound 15-11 (1.0 g, 2.0 mmol) in DMF (25 mL) was added $K_2CO_3$ (1.1 g, 8.0 mmol) at rt, followed by 3-bromo-2-methylpropene (324 mg, 2.4 mmol). After stirring at 80° C. for 2 hrs, the reaction mixture was cooled to rt and partitioned between water (60 mL) and EtOAc (50 mL). The aqueous layer was extracted with EtOAc (40 mL×3). The combined organic extracts were washed with water (60 mL×3) and brine (60×2 mL) and dried over anhydrous $Na_2SO_4$. The solvent was removed and the residue was purified by silica gel column chromatography (PE/EtOAc=10/1 (v/v)) to give compound 27-1a (760 mg, 67% yield) as a yellow solid. LC-MS (ESI): m/z 588.1 $[M+Na]^+$.

Step 2. To a stirred solution of compound 27-1a (375 mg, 0.66 mmol) in a mixed solvent of THF (6 mL) and MeOH (6 mL) was added $NaBH_4$ (75.5 mg, 2.0 mmol) in portions at 0° C. After stirring at 0° C. for 2 hrs, the reaction was quenched by adding several drops of acetone and the resulting mixture was concentrated. The residue was partitioned with water (20 mL) and EtOAc (20 mL) and the aqueous layer was extracted with EtOAc (30 mL×3). Subsequently, the combined organic extracts were washed with water (30 mL×3) and brine (10 mL) and dried over anhydrous $Na_2SO_4$. The solvent was removed and the residue was purified by silica gel column chromatography (PE/EtOAc=3/1 (v/v)) to give compound 27-2a (369 mg, 98% yield) as a yellow solid. LC-MS (ESI): m/z 590.2 $[M+Na]^+$.

Step 3. To a stirred solution of compound 27-2a (320 mg, 0.56 mmol) in DCM (20 mL) were added phenylselenophtalimide (255 mg, 0.85 mmol) and (±)-camphorsulfonic acid (26 mg, 0.11 mmol) at 0° C. After stirring at rt overnight, the reaction mixture was concentrated and the residue was purified by silica gel column chromatography (PE/EtOAc=3/1 (v/v)) to give compound 27-3a (290 mg, 71% yield) as a white solid. LC-MS (ESI): m/z 746.1 $[M+Na]^+$.

Step 4. To a stirred solution of compound 27-3a (320 mg, 0.44 mmol) in a mixed solvent of $CH_2Cl_2$ (30 mL) and EtOH (50 mL) was added Raney nickel (160 mg). After refluxing for 2 hrs, the reaction mixture was filtered through a pad of Celite® 545 and the filtrate was concentrated. The residue was purified by silica gel column chromatography (PE/EtOAc=4/1 (v/v)) to give compound 27-4a (120 mg, 48% yield) as a yellow solid. LC-MS (ESI): m/z 590.2 $[M+Na]^+$.

Step 5. Following the same procedure as that for the preparation of compound 1-16 described in Scheme 1 and replacing compound 1-14 with 27-4a, compound 27-5a was obtained as a white solid. LC-MS (ESI): m/z 553.2 $[M+H]^+$; $^1$H NMR (500 MHz, $CDCl_3$): δ 7.82-7.87 (m, 4H), 7.04-7.11 (m, 6H), 5.80-5.85 (m, 1H), 5.15 (q, J=6.4 Hz, 1H), 4.14 (d, J=14.0 Hz, 1H), 3.11 (s, 3H), 2.99 (d, J=5.0 Hz, 3H), 2.98 (d, J=14.0 Hz, 1H), 1.67 (d, J=7.0 Hz, 3H), 1.53 (s, 3H), 1.14 (s, 3H) ppm. Compound 27-5a was separated into a pair of enantiomers: enantiomer 27-5a_A ($t_R$=3.93 min) and enantiomer 27-5a_B ($t_R$=4.66 min) detected by UV absorption at 214 nm on a 4.6 mm×250 mm×5 μm ChiralPak® IA column (column temperature: 40.2° C.; eluent: MeOH (0.1% DEA)/liquid $CO_2$=30/70 (v/v); $CO_2$ flow rate: 2.1 g/min and co-solvent flow rate: 0.9 g/min; back pressure: 152 bar).

Synthesis of Compound 27-5b. Following the same procedure as that for the synthesis of compound 27-5a described in Scheme 27 and replacing compound 15-11 with 8-4, compound 27-5b was obtained as a white solid. LC-MS (ESI): m/z 461.1 $[M+H]^+$; $^1$H NMR (500 MHz, $CDCl_3$): δ 7.91 (dd, $J_1$=3.5 Hz, $J_2$=6.2 Hz, 2H), 7.89 (s, 1H), 7.86 (s, 1H), 7.19 (t, J=8.5 Hz, 2H), 5.80 (m, 1H), 5.15 (q, J=6.5 Hz, 1H), 4.14 (d, J=14.5 Hz, 1H), 3.12 (s, 3H), 3.00 (d, J=5.5 Hz, 3H), 2.89 (d, J=14.5 Hz, 1H), 1.66 (d, J=6.5 Hz, 3H), 1.54 (s, 3H), 1.15 (s, 3H) ppm. Compound 27-5b was separated into a pair of enantiomers: enantiomer 27-5b_A ($t_R$=2.31 min) and enantiomer 27-5b_B ($t_R$=3.38 min) detected by UV absorption at 214 nm on a 4.6 mm×250 mm, 5 μm ChiralPak® AD-H column (column temperature: 39.6° C.; eluent: MeOH/liquid $CO_2$=30/70 (v/v); $CO_2$ flow rate: 2.1 g/min and co-solvent flow rate: 0.9 g/min; back pressure: 151 bar).

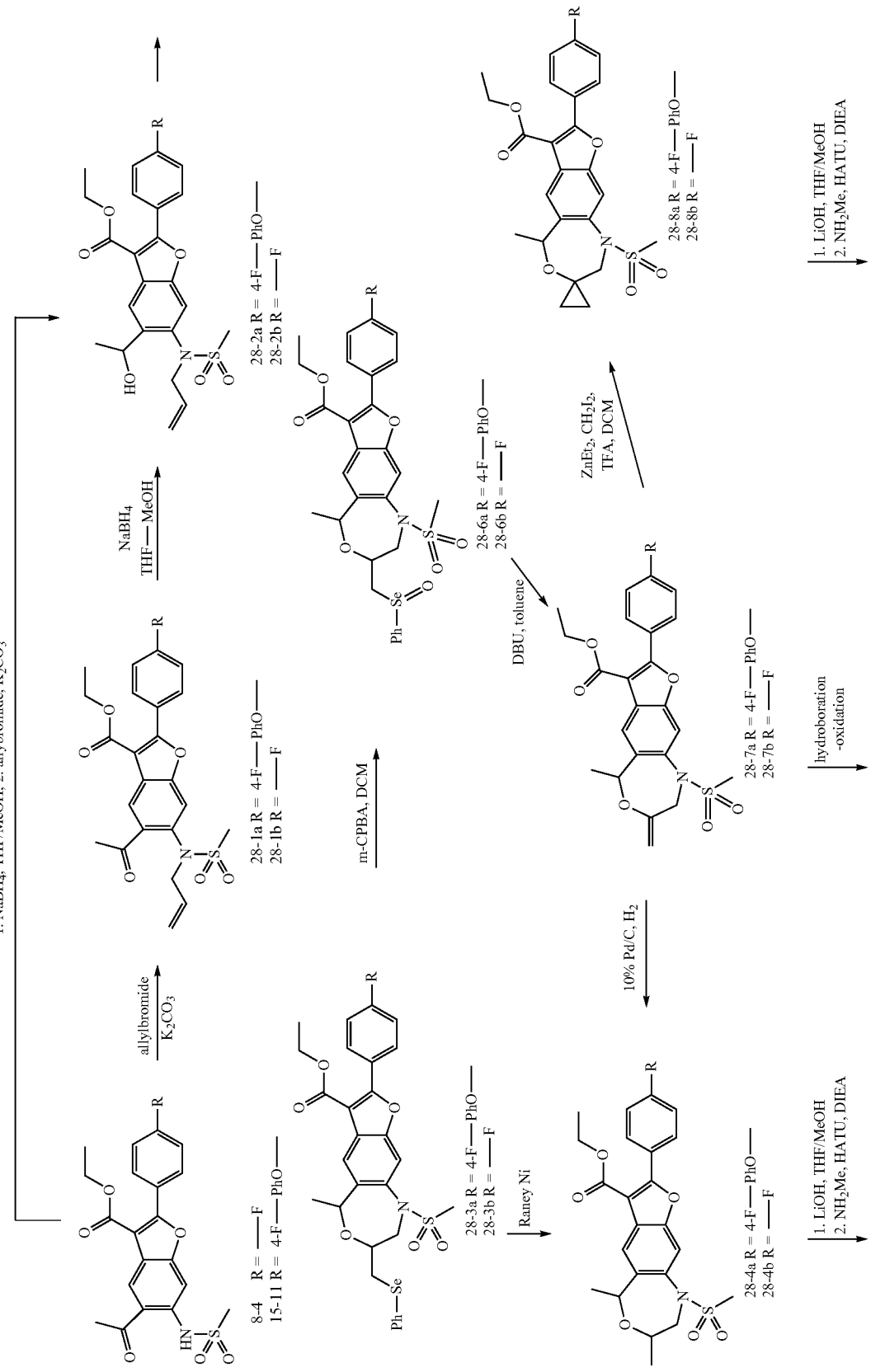

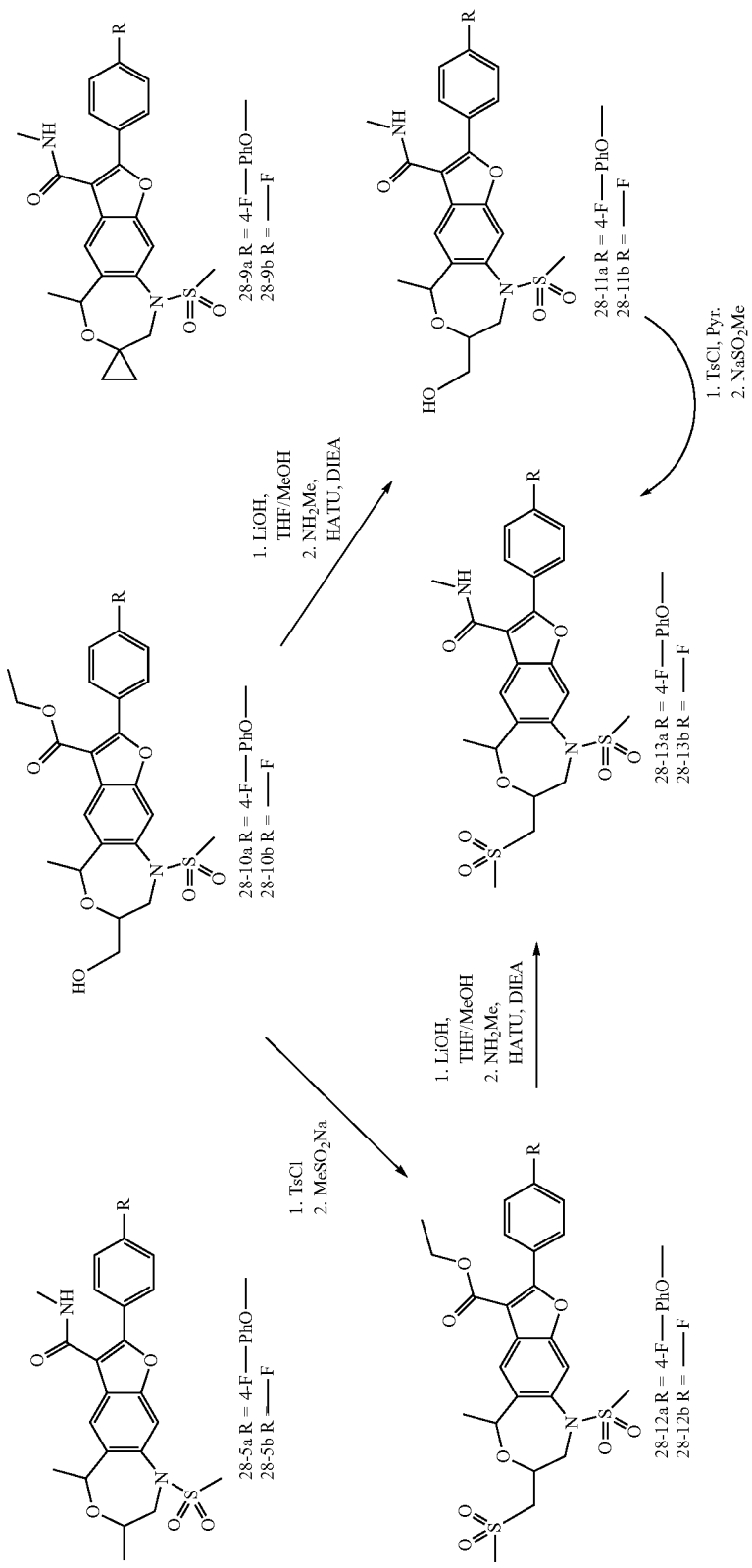

Synthesis of Compound 28-3a. Refer to Scheme 28. Following the same procedure as that for the preparation of compound 27-3a from 15-11 described in Scheme 27 and replacing 3-bromo-2-methylpropene with allyl bromide, compound 28-3a was obtained as a white solid. LC-MS (ESI): m/z 732.1 [M+Na]$^+$.

Synthesis of Compound 28-5a. Following the same procedure as that for the preparation of compound 27-5a from 27-3a described in Scheme 27 and replacing compound 27-3a with 28-3a, compound 28-5a was obtained as a white solid. LC-MS (ESI): m/z 539.2 [M+H]$^+$; $^1$H NMR (500 MHz, CDCl$_3$): δ 7.89 and 7.78 (s, s, 1H), 7.83 (dd, J$_1$=6.5 Hz, J$_2$=8.5 Hz, 2H), 7.61 and 7.58 (br s, s, 1H), 7.04-7.12 (m, 6H), 5.83 (d, J=4.0 Hz, 1H), 5.18 and 4.98 (dd, dd, J$_1$=13.5 Hz, J$_2$=6.5 Hz, 1H), 4.13-4.16 and 3.78-3.81 (m, m, 2H), 3.15 and 3.12 (s, s, 3H), 3.12 and 2.85 (m, m, 1H), 3.00 (d, J=5.0 Hz, 3H), 1.73 (t, J=6.5 Hz, 3H), 1.23 and 1.17 (d, d, J=6.5 Hz, 3H) ppm. Alternatively, compound 28-5a can be obtained using compound 28-7a as the starting material described in Scheme 28.

Synthesis of Compound 28-5b. Following the same procedure as that for the preparation of compound 28-5a described in Scheme 27 and replacing compound 27-3a with 28-3b, compound 28-5b was obtained as a white solid. LC-MS (ESI): m/z 447.1 [M+H]$^+$; $^1$H NMR (500 MHz, CDCl$_3$): δ 7.89-7.92 (m, 2H), 7.87 (s, 1H), 7.59 (s, 1H), 7.20 (t, J=8.5 Hz, 2H), 5.78 (m, 1H), 4.98 (m, 1H), 4.14 (m, 2H), 3.15 and 3.12 (s, s, 3H), 3.01 (d, J=4.5 Hz, 3H), 2.83 (m, 1H), 1.73 and 1.71 (d, d, J=7.0 Hz, 3H), 1.23 and 1.18 (d, d, J=6.5 Hz, 3H) ppm. Alternatively, compound 28-5b can be obtained using compound 28-7b as the starting material described in Scheme 28.

Synthesis of Compound 28-6a. To a solution of compound 28-3a (2.1 g, 3.0 mmol) in DCM (200 mL) was added m-CPBA (563 mg, 3.3 mmol) at 0° C. After stirring at 0° C. for 30 min, the reaction mixture was washed with saturated aq. NaHCO$_3$ solution and water. The organic layer was dried over anhydrous Na$_2$SO$_4$ and concentrated to dryness to give crude compound 28-6a as a red solid, which was used in the next step without further purification. LC-MS (ESI): m/z 748.1 [M+Na]$^+$.

Synthesis of Compound 28-7a. Compound 28-6a (375 mg, 0.52 mmol) was dissolved in dry toluene (300 mL) and the resulting solution was added DBU (4.2 mL, 28.1 mmol) at 0° C. After stirring at 100° C. for 45 min under an atmosphere of N$_2$, the reaction mixture was concentrated and the residue was purified by silica gel column chromatography (PE/EtOAc=5/1 to 3/1 (v/v)) to give compound 28-7a (248 mg, 87% yield) as an off white solid. LC-MS (ESI): m/z 552.1 [M+H]$^+$; $^1$H NMR (500 MHz, d$^6$-DMSO): δ 8.05 (d, J=9.0 Hz, 2H), 8.00 (s, 1H), 7.79 (s, 1H), 7.31 (m, 2H), 7.21-7.23 (m, 2H), 7.12 (d, J=9.0 Hz, 2H), 5.46 (q, J=6.0 Hz, 1H), 4.67 (d, J=14.0 Hz, 1H), 4.46 (s, 1H), 4.40 (s, 1H), 4.36 (q, J=7.0 Hz, 2H), 4.20 (d, J=14.0 Hz, 1H), 3.24 (s, 3H), 1.72 (d, J=6.0 Hz, 3H), 1.36 (t, J=7.0 Hz, 3H) ppm.

Synthesis of Compound 28-8a. Under an atmosphere of N$_2$, ZnEt$_2$ (1M in hexane, 7.40 mL, 7.40 mmol) was added to dry DCM (20 mL) at −78° C., followed by CH$_2$I$_2$ (1.2 mL, 14.8 mmol) over 10 min. The resulting mixture was stirred at −78° C. for 30 min and then at −10° C. for 30 min. The mixture was cooled to −78° C. and a solution of TFA (137 μL, 1.9 mmol) in DCM (1 mL) was added dropwise. After stirring at −78° C. for 30 min, the mixture was added dropwise a solution of compound 28-7a (340 mg, 0.62 mmol) in DCM (2 mL) at −78° C. The resulting mixture was stirred at −78° C. for 10 min, 0° C. for 1 hr, and 25° C. for 4 hrs. Subsequently, saturated aq. NH$_4$Cl solution (10 mL) was added and the mixture was concentrated. The residue was extracted with DCM (20 mL×3). The combined organic extracts were washed with saturated aq. NaHCO$_3$ solution and water and dried over anhydrous Na$_2$SO$_4$. The solvent was removed and the residue was purified by silica gel column chromatography (PE/EtOAc=10/1 to 4/1 (v/v)) to give compound 28-8a (230 mg, 66% yield) as a white solid. LC-MS (ESI): m/z 566.2 [M+H]$^+$; $^1$H NMR (500 MHz, d$^6$-DMSO): δ 8.06-8.08 (m, 2H), 8.01 (s, 1H), 7.88 (s, 1H), 7.30-7.34 (m, 2H), 7.21-7.24 (m, 2H), 7.12-7.14 (m, 2H), 5.09 (q, J=6.0 Hz, 1H), 4.36 (q, J=7.5 Hz, 2H), 3.69 (d, J=15.0 Hz, 1H), 3.57 (d, J=15.0 Hz, 1H), 3.32 (s, 3H), 1.57 (d, J=6.0 Hz, 3H), 1.35 (t, J=7.5 Hz, 3H), 0.71-0.96 (m, 4H) ppm.

Synthesis of Compound 28-9a. Following the same procedure as that for the preparation of 1-16 described in Scheme 1 and replacing compound 1-14 with 28-8a, compound 28-9a was obtained as a white solid. LC-MS (ESI): m/z 551.2 [M+H]$^+$; $^1$H NMR (500 MHz, d$^6$-DMSO): δ 8.50 (d, J=4.5 Hz, 1H), 7.92 (d, J=9 Hz, 2H), 7.83 (s, 1H), 7.56 (s, 1H), 7.28-7.32 (m, 2H), 7.17-7.20 (m, 2H), 7.12 (d, J=8.5 Hz, 2H), 5.06 (dd, J$_1$=12.5 Hz, J$_2$=6.5 Hz, 1H), 3.67 (d, J=15.5 Hz, 1H), 3.56 (d, J=14.5 Hz, 1H), 3.31 (s, 3H), 2.84 (d, J=4.5 Hz, 3H), 1.54 (d, J=6 Hz, 3H), 0.70-0.93 (m, 4H) ppm. Compound 28-9a was separated into a pair of enantiomers: enantiomer 28-9a_A (t$_R$=4.13 min) and enantiomer 28-9a_B (t$_R$=5.05 min) detected by UV absorption at 214 nm on a 4.6 mm×250 mm×5 μm Regis (R,R)-Whelk-ol column (column temperature: 39.3° C.; eluent: MeOH/liquid CO$_2$=50/50 (v/v); CO$_2$ flow rate: 1.5 g/min and co-solvent flow rate: 1.5 g/min; front pressure: 218 bar and back pressure: 152 bar).

Synthesis of Compound 28-9b. Following the same procedure as that for the preparation of compound 28-9a described in Scheme 28 and replacing compound 15-11 with 8-4, compound 28-9b was obtained as a white solid. LC-MS (ESI): m/z 459.1 [M+H]$^+$; $^1$H NMR (500 MHz, d$^6$-DMSO): δ 8.53 (m, 1H), 7.97 (dd, J$_1$=5.5 Hz, J$_2$=8.7 Hz, 2H), 7.85 (s, 1H), 7.58 (s, 1H), 7.41 (t, J=8.5 Hz, 2H), 5.06 (q, J=6.5 Hz, 1H), 3.68 (d, J=14.5 Hz, 1H), 3.57 (d, J=14.5 Hz, 1H), 3.32 (s, 3H), 2.84 (d, J=4.5 Hz, 3H), 1.54 (d, J=6.5 Hz, 3H), 0.93 (m, 1H), 0.84-0.86 (m, 2H), 0.70 (m, 1H) ppm. Compound 28-9b was separated into a pair of enantiomers: enantiomer 28-9b_A (t$_R$=4.36 min) and enantiomer 28-9b_B (t$_R$=6.09 min) detected by UV absorption at 214 nm on a 4.6 mm×250 mm 5 μm ChiralPak® AD-H column (column temperature: 39.8° C.; eluent: MeOH/liquid CO$_2$=30/70 (v/v); CO$_2$ flow rate: 2.1 g/min and co-solvent flow rate: 0.9 g/min; back pressure: 150 bar).

Synthesis of Compound 28-10a. To a solution of compound 28-7a (680 mg, 1.2 mmol) in THF (10 mL) was added BH$_3$.THF (7.4 mL, 7.4 mmol) at 0° C. After stirring at rt for 3 hrs, the reaction mixture was added 3 N aq. NaOH (7 mL) at 0° C., followed by 30% aq. H$_2$O$_2$ (7 mL). The reaction mixture was stirred at rt overnight and the added iced water (30 mL). The mixture was extracted with EtOAc (25 mL×2). The combined organic extracts were washed with water (20 mL×2), dried over anhydrous Na$_2$SO$_4$, and concentrated. The residue was purified by silica gel column chromatography (DCM/Acetone=50/1 (v/v)) to give compound 28-10a (560 mg, 80% yield) as a white solid. LC-MS (EST): m/z 592.2 [M+Na]$^+$.

Synthesis of Compound 28-10b. Following the same procedure as that for the preparation of compound 28-10a and replacing compound 28-7a with 28-7b, compound 28-10b was obtained as a white solid. LC-MS (ESI): m/z 500.1 [M+Na]$^+$.

Synthesis of Compound 28-11a. Following the same procedure as that for the preparation of compound 1-16 described in Scheme 1 and replacing compound 1-14 with 28-10a, compound 28-11a was obtained as a white solid. LC-MS (EST): m/z 555.2 [M+H]⁺; ¹H NMR (500 MHz, d⁶-DMSO): δ 8.42-8.50 (m, 1H), 7.90-7.93 (m, 2H), 7.82 and 7.77 (s, s, 1H), 7.56 and 7.54 (s, s, 1H), 7.27-7.31 (m, 2H), 7.17-7.19 (m, 2H), 7.11 (d, J=8.5 Hz, 2H), 5.17 and 4.88 (m, m, 1H), 4.78 (m, 1H), 4.18 and 3.99 (m, m, 1H), 3.93 (m, 1H), 3.45 (m, 1H), 3.47 (m, 1H), 3.38 and 3.36 (s, s, 3H), 2.84 (d, J=4.5 Hz, 3H), 2.83 (m, 1H), 1.62 and 1.60 (d, d, J=6.5 Hz, 3H) ppm.

Synthesis of Compound 28-11b. Following the same procedure as that for the preparation of compound 28-11a described in Scheme 28 and replacing compound 28-10a with 28-10b, compound 28-11b was obtained as a white solid. LC-MS (ESI): m/z 463.1 [M+H]⁺; ¹H NMR (500 MHz, d⁶-DMSO): δ 8.52 (m, 1H), 7.95-7.98 (m, 2H), 7.83 and 7.79 (s, s, 1H), 7.58 and 7.57 (s, s, 1H), 7.40 (t, J=9.0 Hz, 2H), 4.88 (q, J=6.5 Hz, 1H), 4.78 (t, J=5.5 Hz, 1H), 4.19 (d, J=15 Hz, 1H), 3.92 (m, 1H), 3.43-3.48 (m, 1H), 3.39 (s, 3H), 3.26-3.31 (m, 1H), 2.84 (d, J=4.5 Hz, 3H), 2.83 (m, 1H), 1.62 and 1.60 (d, d, J=6.0 Hz, 3H) ppm.

Synthesis of Compound 28-12a. To a solution of compound 28-10a (200 mg, 0.35 mmol), DMAP (21 mg, 0.18 mmol) and Et₃N (0.15 mL, 1.1 mmol) in CH₂Cl₂ (5 mL) was added TsCl (100 mg, 0.53 mmol) at 0° C. After stirring it for 2 hrs, the reaction mixture was added ice water (10 mL) and DCM (25 mL). The organic layer was washed with saturated aq. NaHCO₃ (10 mL×2), water (10 mL×2) and brine (10 mL), dried over anhydrous Na₂SO₄, and concentrated. The residue was purified by silica gel column chromatography (PE/EtOAc=6/1 to 2/1 (v/v)) to give the tosylate as a white solid (230 mg, 91% yield). LC-MS (ESI): m/z 746.2 [M+Na]⁺. Subsequently, a mixture of the tosylate (140 mg, 0.19 mmol), MeSO₂Na (59 mg, 0.58 mmol) and KI (964 mg, 0.581 mmol) in DMF (2 mL) was stirred at 120° C. for 2 hrs. The mixture was then poured into water (15 mL). The resulting precipitate was filtered and the white was washed with water (15 mL×3) and dried in vacuo to give compound 28-12a (100 mg, 82% yield). LC-MS (ESI): m/z 654.1 [M+Na]⁺.

Synthesis of Compound 28-12b. Following the same procedure as that for the preparation of compound 28-12a described in Scheme 28 and replacing compound 28-10a with 28-10b, compound 28-12b was obtained as a white solid. LC-MS (ESI): m/z 562.1 [M+H]⁺.

Synthesis of Compound 28-13a. Following the same procedure as that for the preparation of compound 1-16 described in Scheme 1 and replacing compound 1-14 with 28-12a, compound 28-13a was obtained as a white solid. LC-MS (ESI): m/z 617.1 [M+H]⁺; ¹H NMR (500 MHz, CDCl₃): δ 7.94 (s, 1H), 7.81 (dd, J₁=2.5 Hz, J₂=8.5 Hz, 2H), 7.61 (s, 1H), 7.05-7.13 (m, 6H), 5.82 (m, 1H), 5.09 (q, J=8.5 Hz, 1H), 4.59 (t, J=11.5 Hz, 1H), 4.24 (d, J=18.5 Hz, 1H), 3.16 (s, 3H), 3.05-3.13 (m, 3H), 3.07 (s, 3H), 2.98 (d, J=6.0 Hz, 3H), 1.78 (d, J=8.5 Hz, 3H) ppm. Alternatively, compound 28-13a can be obtained using compound 28-11a as the starting material as described in Scheme 28.

Synthesis of Compound 28-13b. Following the same procedure as that for the preparation of compound 28-13a described in Scheme 28 and replacing compound 28-12a with 28-12b, compound 28-13b was obtained as a white solid. LC-MS (ESI): m/z 525.1 [M+H]⁺; ¹H NMR (500 MHz, d⁶-DMSO): δ 8.52 (m, 1H), 7.95-7.99 (m, 2H), 7.87 (s, 1H), 7.61 (s, 1H), 7.40 (t, J=8.5 Hz, 2H), 4.98 (q, J=6.0 Hz, 1H), 4.39 (t, J=9.0 Hz, 1H), 4.20 (d, J=14.0 Hz, 1H), 3.37 (s, 3H), 3.29-3.32 (m, 2H), 3.04 (s, 3H), 2.89 (m, 1H), 2.85 (d, J=4.5 Hz, 3H), 1.66 (d, J=6.5 Hz, 3H) ppm. Alternatively, compound 28-13b can be obtained using compound 28-11b as the starting material as described in Scheme 28.

Scheme 29

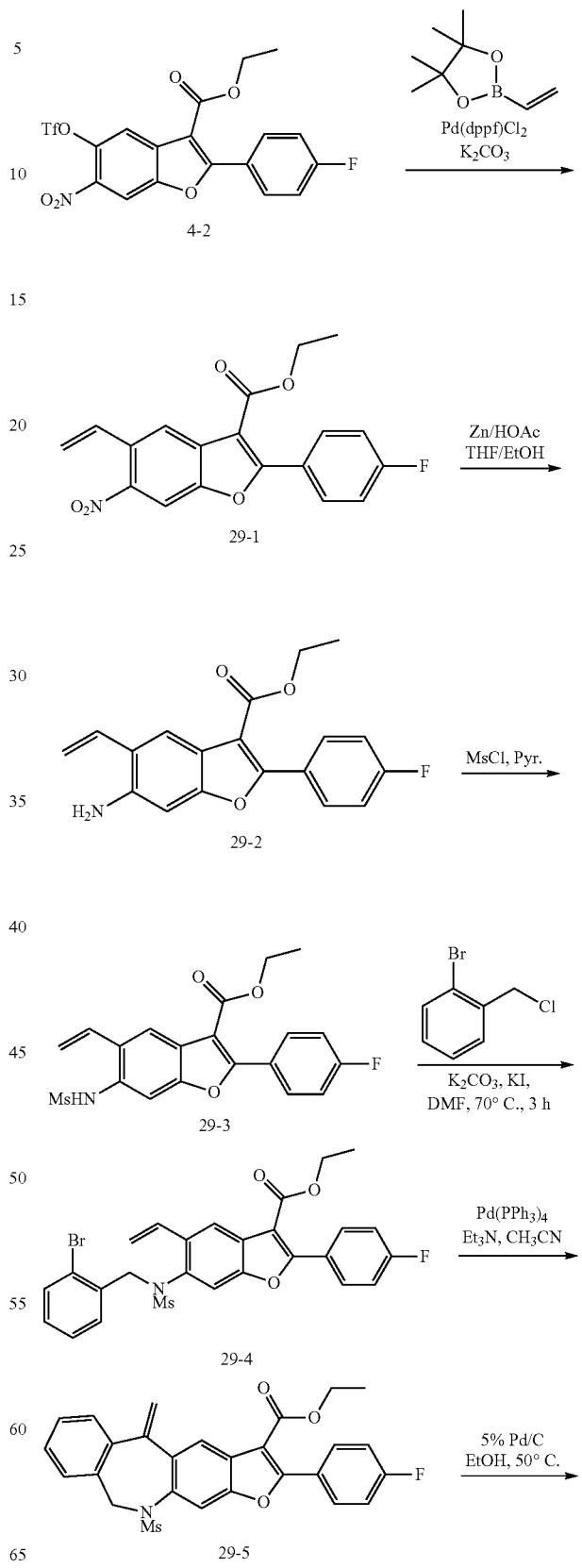

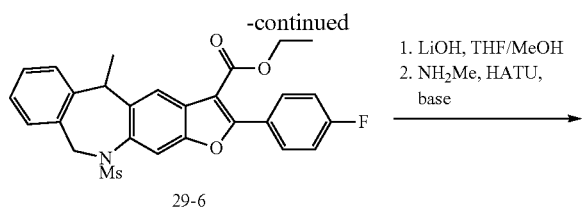

1. LiOH, THF/MeOH
2. NH₂Me, HATU, base 29-6

29-7

Step 1. Refer to Scheme 29. To a solution of compound 4-2 (9.0 g, 18.9 mmol) in DME (200 mL) and H₂O (400 mL) were added K₂CO₃ (7.8 g, 56.6 mmol), Pd(dppf)Cl₂ (1.5 g, 1.9 mmol) and 4,4,5,5-tetramethyl-2-vinyl-1,3,2-dioxaborolane (4.4 g, 28.3 mmol). After stirring at 60° C. for 2 hrs under an atmosphere of Ar, the reaction mixture was concentrated and the residue was partitioned between water (150 mL) and EtOAc (150 mL). The aqueous phase was extracted with EtOAc (100 mL×3) and the combined organic extracts were washed with water (100 mL×3) and brine (100 mL) and dried over anhydrous Na₂SO₄. The solvent was removed and the residue was purified by silica gel column chromatography (PE/EtOAc=15/1 (v/v)) to give compound 29-1 (5.0 g, 75% yield) as a yellow solid. LCMS (ESI): m/z 356.1 [M+H]⁺.

Step 2. To a solution of compound 29-1 (1.2 g, 3.4 mmol) in THF (50 mL), EtOH (20 mL) and HOAc (40 mL) was slowly added Zn (1.3 g, 20.1 mmol) at 0° C. After stirring at rt for 2 hrs, the reaction mixture was filtered and the filtrate was concentrated. The residue was partitioned between water (80 mL) and EtOAc (80 mL) and the organic layer was extracted with EtOAc (60 mL×3). The organic extracts were combined and washed with water (80 mL×2), sat. aq. NaHCO₃ (80 mL) and brine (80 mL) and dried over anhydrous Na₂SO₄. The solvent was concentrated and the residue was dried in vacuo to give crude compound 29-2 (1.0 g, 91% yield) as a yellow solid. LC-MS (ESI): m/z 326.1 [M+H]⁺.

Step 3. To a solution of compound 29-2 (1.0 g, 3.1 mmol) in anhydrous pyridine (5 mL) was treated with DMAP (20 mg), followed by a solution of MsCl (1.1 g, 9.2 mmol) in DCM (3 mL) at 0° C. After stirring at rt for 3 hrs, the reaction mixture was concentrated and the residue was partitioned between water (20 mL) and EtOAc (20 mL). The aqueous layer was extracted with DCM (30 mL×3) and the combined organic extracts were washed with water (60 mL×2) and brine (60 mL) and dried over anhydrous Na₂SO₄. The solvent was removed and the residue was dried in vacuo to give crude compound 29-3 (1.1 g, 88% yield) as a yellow solid. LC-MS (ESI): m/z 404.1 [M+H]⁺.

Step 4. To a solution of compound 29-3 (700 mg, 1.7 mmol) in DMF (30 mL) were added K₂CO₃ (719 mg, 5.2 mmol) and KI (144 mg, 0.87 mmol), followed by 2-bromobenzyl chloride (534 mg, 2.6 mmol). After stirring at 70° C. for 3 hrs, the reaction mixture was concentrated and the residue was partitioned between water (50 mL) and EtOAc (50 mL). The aqueous layer was extracted with EtOAc (3×40 mL) and the combined organic extracts were washed with water (80 mL×3) and brine (50 mL) and dried over anhydrous Na₂SO₄. The solvent was removed and the residue was purified by silica gel column chromatography (Petroleum ether/ EtOAc=15/1 (v/v)) to give compound 29-4 (800 mg, 87% yield) as a yellow solid. LC-MS (ESI): m/z 574.0 [M+H]⁺.

Step 5. To a solution of compound 29-4 (770 mg, 1.34 mmol) in CH₃CN (25 ml) were added Et₃N (4.6 mL), and Pd(PPh₃)₄ (1.55 g, 1.34 mmol). After stirring at 80° C. for several hours under an atmosphere of Ar, the reaction mixture was concentrated and the residue was purified by silica gel column chromatography (Petroleum ether/EtOAc=10/1 (v/v)) to give compound 29-5 (260 mg, 40% yield) as a yellow solid. LC-MS (ESI): m/z 492.1 [M+H]⁺.

Step 6. To a solution of compound 29-5 (150 mg, 0.31 mmol) in EtOH (30 mL) was added 5% Pd/C (w/w, 200 mg). After stirring at 50° C. for several hours under an atmosphere of H₂, the reaction mixture was filtered through a pad of Celite® 545. The filtered cake was washed with EtOH (15 mL×2). The filtrate was concentrated and the residue was dried in vacuo to give crude compound 29-6 (149 mg, 99% yield) as a yellow solid. LC-MS (ESI): m/z 494.1 [M+H]⁺.

Step 7. Following the same procedure as that for the preparation of compound 1-16 described in Scheme 1 and replacing compound 1-14 with 29-6, compound 29-7 was obtained (130 mg, 90% yield) as a pale brown solid. LC-MS (ESI): m/z 479.1 [M+H]⁺; ¹H NMR (500 MHz, CDCl₃): δ 7.85-7.88 (m, 2H), 7.78 (s, 1H), 7.71 (s, 1H), 7.30 (d, 2H), 7.15-7.24 (m, 5H), 5.76 (brs, 2H), 5.12 (d, J=16 Hz, 2H), 4.95 (d, J=16 Hz, 5H), 4.57-4.62 (dd, J₁=15 Hz, J₂=7 Hz, 1H), 2.72 (d, J=5 Hz, 3H), 2.73 (s, 3H), 1.80 (d, J=8 Hz, 3H) ppm. Compound 29-7 was separated into a pair of enantiomers: enantiomer 29-7_A (t_R=4.16 min) and enantiomer 29-7_B (t_R=6.05 min) detected by UV absorption at 214 nm on a 4.6 mm×250 mm 5 μm ChiralPak® OD-H column (column temperature: 40.4° C.; eluent: MeOH/liquid CO₂=30/70 (v/v); CO₂ flow rate: 2.1 g/min and co-solvent flow rate: 0.9 g/min; front pressure: 205 bar and back pressure: 148 bar).

Scheme 30

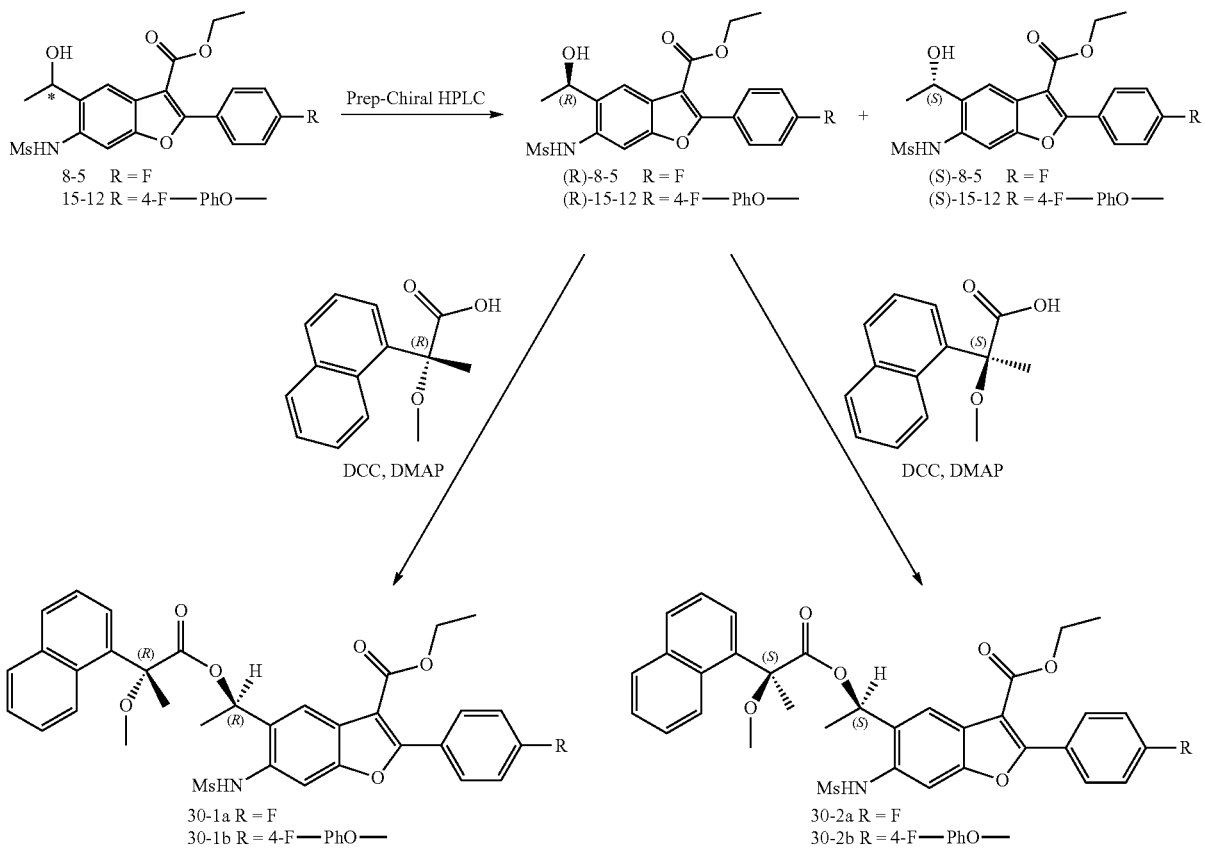

Chiral Separation of Compound 8-5. Compound 8-5 (3.8 g) was separated into a pair of enantiomers: (R)-8-5 ($t_R$=2.61 min, 1.6 g, 84% yield) and (S)-8-5 ($t_R$=3.14 min, 1.6 g, 84% yield) detected by UV absorption at 214 nm on a 4.6 mm×250 mm×5 µm ChiralPak® AD-H column (column temperature: 40.2° C.; eluent: MeOH (0.1% DEA)/liquid $CO_2$=30/70 (v/v); $CO_2$ flow rate: 2.1 g/min and co-solvent flow rate: 0.9 g/min; front pressure: 206 bar and back pressure: 149 bar).

Chiral Separation of Compound 15-12. Using the same prep-chiral HPLC condition as that used for separating compound 8-5, Compound 15-12 (5.6 g) was separated into a pair of enantiomers: (R)-15-12 ($t_R$=5.71 min, 1.1 g, 39% yield) and (S)-15-12 ($t_R$=6.58 min, 1.0 g, 36% yield).

Synthesis of Compound 30-1a. To a solution of the enantiomer came out first from the chiral separation of compound 8-5 ($t_R$=2.61 min) (30 mg, 0.07 mmol) and (R)-MαNP (18.4 mg, 0.08 mmol) in $CH_2Cl_2$ (2 mL) was added DCC (72.1 mg, 0.35 mmol), followed by DMAP (17.1 mg, 0.14 mmol). After stirring at rt for 20 hrs, the reaction mixture was concentrated and the residue was diluted with EtOAc (45 mL). The solution was washed with water (20 mL) and brine (20 mL), dried with anhydrous $Na_2SO_4$, and concentrated. The residue was purified by prep-HPLC to give compound 30-1a (15 mg) as a white powder. LC-MS: (ESI) m/z=656.2 [M+Na]+; 1H NMR (500 MHz, $CDCl_3$): δ 8.11-8.13 (m, 2H), 7.74-7.77 (m, 2H), 7.60 (d, J=7.0 Hz, 2H), 7.47 (t, J=8.0 Hz, 1H), 7.45 (s, 1H), 7.22 (t, J=9.0 Hz, 2H), 7.08 (s, 1H), 7.00 (t, J=7.0 Hz, 1H), 6.76 (t, J=8.0 Hz, 1H), 6.07 (q, J=7.0 Hz, 1H), 4.23-4.36 (m, 2H), 3.05 (s, 3H), 2.98 (s, 3H), 2.03 (s, 3H), 1.49 (d, J=7.0 Hz, 3H), 1.27 (t, J=7.0 Hz, 3H) ppm.

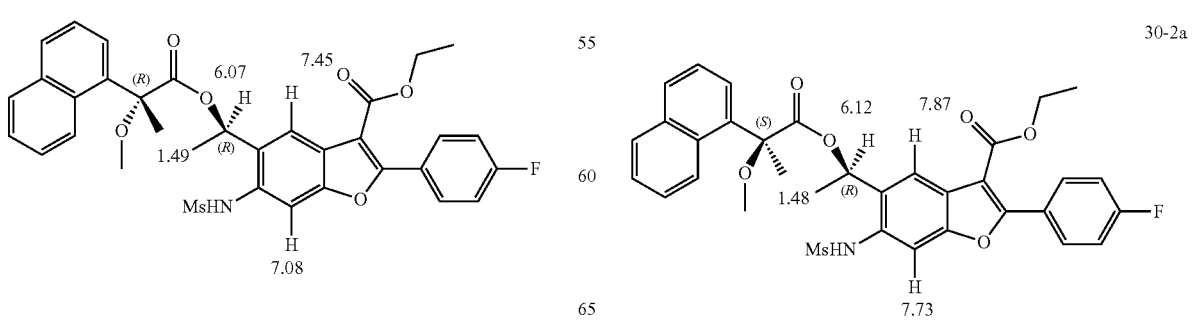

Synthesis of Compound 30-2a. Following the same procedure as that used for preparing compound 30-1a and replacing (R)-MαNP with (S)-MαNP, compound 30-2a was obtained. LC-MS: (ESI) m/z=656.2 [M+Na]⁺; ¹H NMR (500 MHz, CDCl₃): δ 8.06-8.09 (m, 2H), 7.95 (d, J=8.5 Hz, 1H), 7.87 (s, 1H), 7.82 (d, J=8.0 Hz, 1H), 7.78 (d, J=8.0 Hz, 1H), 7.73 (s, 1H), 7.67 (s, 1H), 7.64 (d, J=7.0 Hz, 1H), 7.47 (t, J=8.0 Hz, 1H), 7.28 (t, J=7.5 Hz, 1H), 7.20 (t, J=7.5 Hz, 2H), 7.06 (t, J=7.5 Hz, 1H), 6.12 (q, J=6.5 Hz, 1H), 4.35-4.41 (m, 2H), 3.12 (s, 3H), 3.00 (s, 3H), 2.00 (s, 3H), 1.48 (d, J=6.5 Hz, 3H), 1.27 (t, J=7.0 Hz, 3H) ppm.

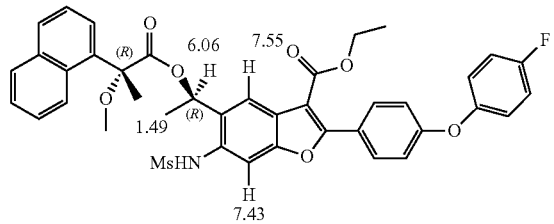

30-1b

Synthesis of Compound 30-1b. Following the same procedure as that used for preparing compound 30-1a and using the enantiomer came out first from the chiral separation of compound 15-12 (t$_R$=5.71 min), compound 30-1b was obtained. LC-MS: (ESI) m/z=748.2 [M+Na]⁺; ¹H NMR (500 MHz, CD₃Cl): δ 8.08-8.10 (m, 2H), 7.06-7.11 (m, 7H), 6.99 (t, J=7.0 Hz, 1H), 6.75 (dt, J₁=1.0 Hz, J₂=8.0 Hz, 1H), 6.06 (q, J=7.0 Hz, 1H), 4.24-4.35 (m, 2H), 3.05 (s, 3H), 2.98 (s, 3H), 2.03 (s, 3H), 1.49 (d, J=7.0 Hz, 3H), 1.27 (t, J=7.0 Hz, 3H) ppm.

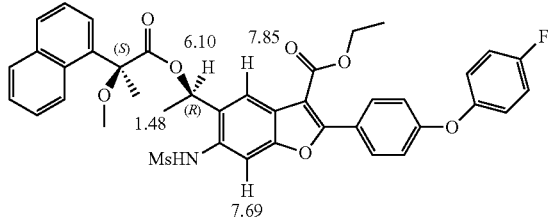

30-2b

Synthesis of Compound 30-2b. Following the same procedure as that used for preparing compound 30-1b and replacing (R)-MαNP with (S)-MαNP, compound 30-2b was obtained. LC-MS: (ESI) m/z=748.2 [M+Na]⁺; ¹H NMR (500 MHz, CD₃Cl): δ 8.06 (d, J=7.0 Hz, 2H), 7.93 (d, J=8.5 Hz, 1H), 7.85 (s, 1H), 7.83 (d, J=8.0 Hz, 1H), 7.78 (d, J=8.0 Hz, 1H), 7.69 (s, 1H), 7.63-7.66 (m, 2H), 7.46 (t, J=8.0 Hz, 1H), 7.29 (t, J=8.0 Hz, 1H), 7.04-7.10 (m, 7H), 6.10 (q, J=7.0 Hz, 1H), 4.36-4.39 (m, 2H), 3.13 (s, 3H), 2.99 (s, 3H), 1.91 (s, 3H), 1.48 (d, J=7.0 Hz, 3H), 1.36 (t, J=7.0 Hz, 3H) ppm.

Scheme 31

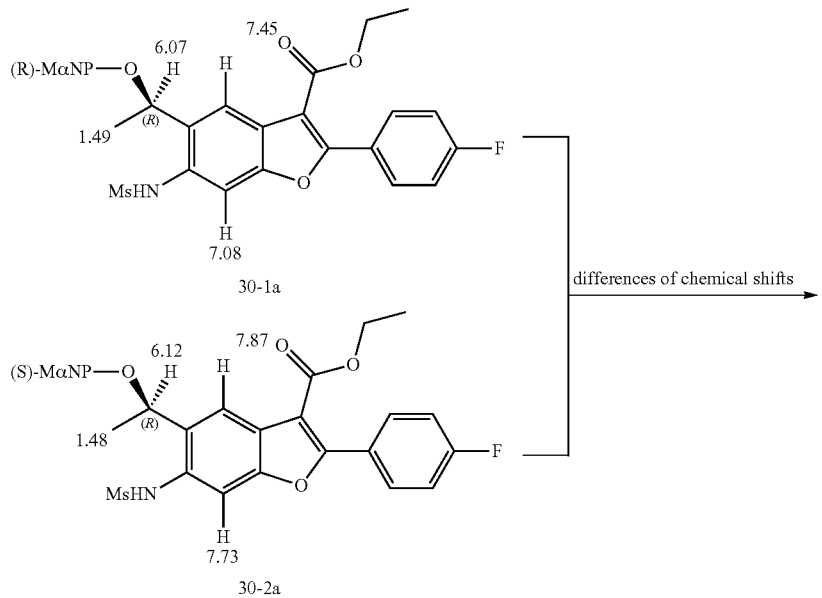

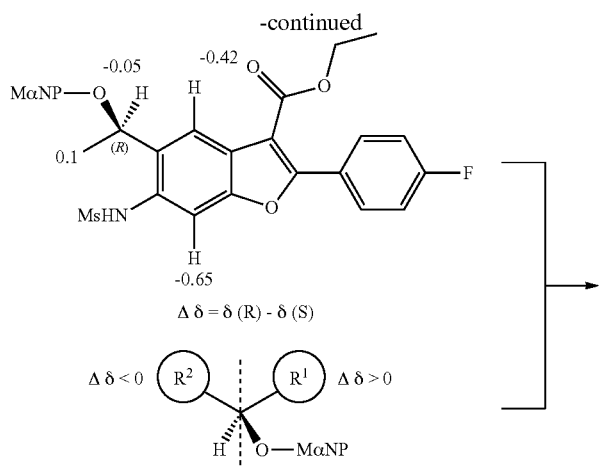

$\Delta\delta = \delta(R) - \delta(S)$

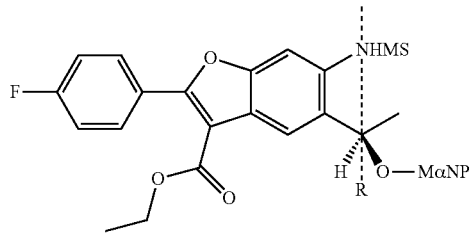

*Tetrahedron:Asymmetry* 2000, 11, 1249
*Chirality* 2002, 14, 81

Determination of Chirality. Refer to Scheme 31. Based on the general rule of chemical shifts of a pair of diastereomeric esters derived from an alcohol with (R)-MαNP and (S)-MαNP, the chirality of the benzylic carbon in the enantiomer came out first ($t_R$=2.61 min) from the chiral separation of compound 8-5 was determined as R. Accordingly, the chirality of the benzylic carbon in the enantiomer came out first ($t_R$=5.71 min) from the chiral separation of compound 15-12 was determined as R.

Scheme 32

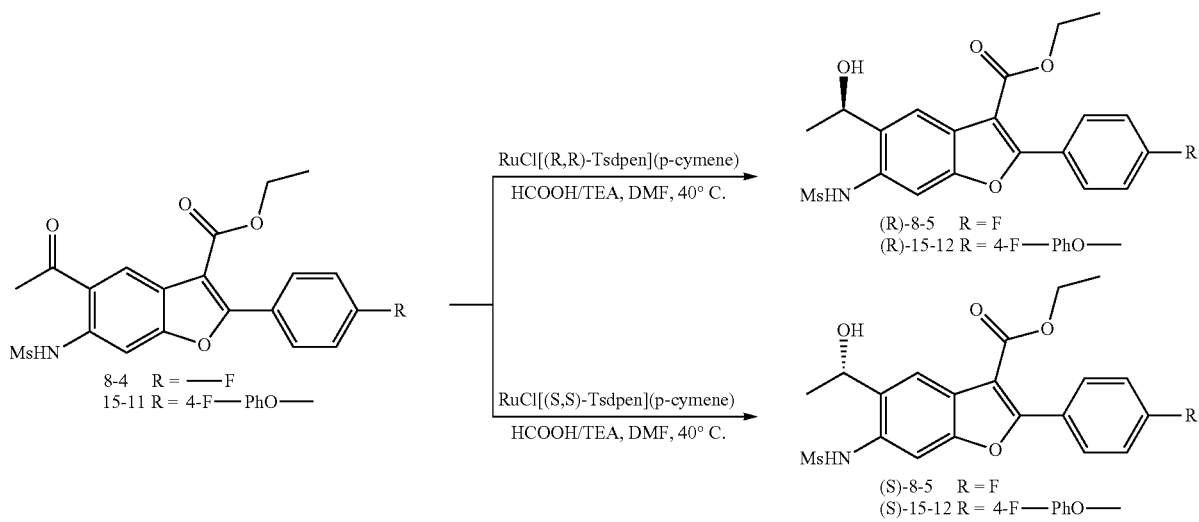

Synthesis of Compound (R)-8-5. Refer to scheme 32. A 25 mL flask was charged with triethylamine (76 mg, 0.75 mmol, 7 eq.) in an ice bath, followed by adding formic acid (35 mg, 0.75 mmol, 7 eq.) dropwise. After stirring at rt for 20 min, a solution of compound 8-4 (45 mg, 0.107 mmol, 1 equiv.) in DMF (6 mL) and RuCl[(R,R)-Tsdpen](p-cymene) (1.6 mg, 0.0029 mmol 0.024 equiv.) were added. The resulting dark red reaction mixture was stirred at 40° C. overnight and then concentrated. The residue was purified by silica column chromatography (EtOAc/PE=1:1 (v/v)) to give compound (R)-8-5 (30 mg, 66% yield, 95.5% ee) as a white solid. The absolute configuration of the sample ($t_R$=2.59 min) was determined as R by taking chiral HPLC along with compound 8-5 following chiral HPLC the condition in Scheme 30.

Synthesis of Compound (S)-8-5. Following the same procedure as described for the preparation of compound (R)-8-5 and replacing RuCl[(R,R)-Tsdpen](p-cymene) with RuCl[S,S)-Tsdpen](p-cymene), compound (S)-8-5 (28 mg, 66% yield, 94.0% ee, $t_R$=3.12 min, S configuration) was obtained from compound 8-4 (42 mg, 0.1 mmol).

Synthesis of Compound (R)-15-12. Following the same procedure as described for the preparation of compound (R)-8-5 and replacing compound 8-4 with compound 15-11 (50 mg, 0.1 mmol), compound (S)-8-12 (38 mg, 75% yield, 95.9% ee, $t_R$=5.76 min, R configuration).

Synthesis of Compound (S)-15-12. Following the same procedure as described for the preparation of compound (R)-15-12 and replacing RuCl[(R,R)-Tsdpen](p-cymene) with RuCl[(S,S)-Tsdpen](p-cymene), compound (S)-15-12 (70 mg, 70% yield, 96.6% ee, $t_R$=6.70 min, S configuration) was obtained from compound 15-11 (100 mg, 0.2 mmol).

Synthesis of Compound (R)-8-9. Using compound (R)-8-5 as the starting material and following the same procedure for the preparation of compound 8-9 described in Scheme 8, compound (R)-8-9 was obtained. Chiral HPLC analysis determined that compound (R)-8-9 and enantiomer 8-9_A obtained from chiral separation of compound 8-9 are identical.

Synthesis of Compound (R)-15-15. Using compound (R)-15-12 as the starting material and following the same procedure for the preparation of compound 15-15 described in Scheme 15, compound (R)-15-15 was obtained. Chiral HPLC analysis determined that compound (R)-15-15 and enantiomer 15-15_A obtained from chiral separation of compound 15-15 are identical.

Syntheses of diastereomers of compounds 28-11a and -13a. Using either compounds (R)-15-12 or (S)-15-12 as the starting material and following the procedure for the preparation of compounds 28-11a and -13a described in Scheme 28, those diastereomers of compounds 28-11a and -13a were obtained, respectively. The absolute configurations of those diastereomers were determined by 2D-COSY and NOESY spectra.

Syntheses of diastereomers of compounds 28-11b and -13b. Using either compounds (R)-8-5 or (S)-8-5 as the starting material and following the procedure for the preparation of compounds 28-11b and -13b described in Scheme 28, those diastereomers of compounds 28-11b and -13b were obtained, respectively. The absolute configurations of those diastereomers were determined by 2D-COSY and NOESY spectra.

Scheme 33

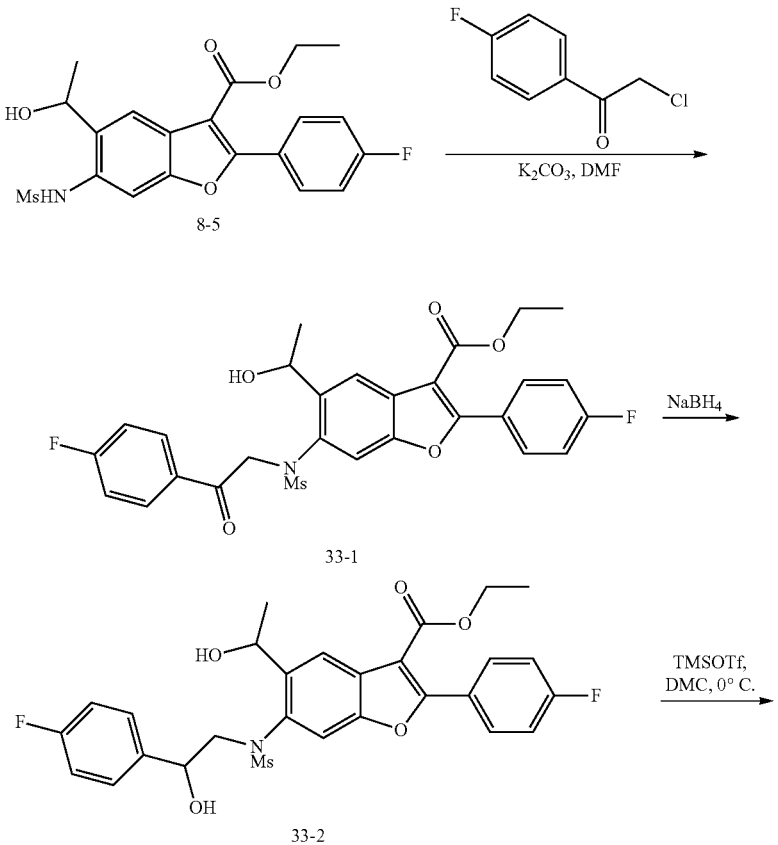

-continued

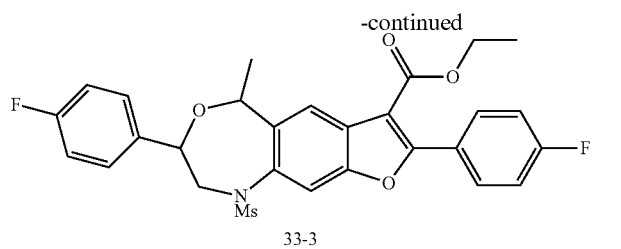

33-3

1. LiOH
2. NH₂Me, HATU, DIEA, DMF

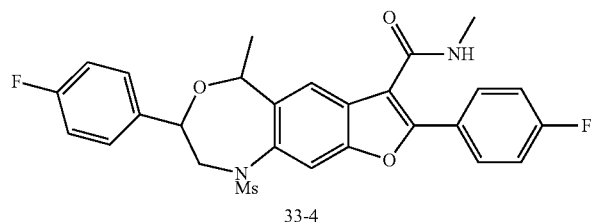

33-4

Step 1. Refer to Scheme 33. A mixture of compound 8-5 (500 mg, 1.2 mmol), 2-chloro-1-(4-fluorophenyl)ethanone (266 mg, 1.5 mmol) and K₂CO₃ (492 mg, 3.6 mmol) in DMF (4 mL) was stirred at 50° C. for 2 hrs. Subsequently, the reaction mixture was poured into water (100 mL) and the suspension was filtered. The solid obtained was purified by silica gel column chromatography (PE/EtOAc=4/1 (v/v)) to give compound 33-1 (500 mg, 76% yield) as a yellow solid. LC-MS (ESI): m/z 461.1 [M–H₂O–Ms+H]⁺.

Step 2. To a solution of compound 33-1 (300 mg, 0.54 mmol) in THF/EtOH (5 mL/5 mL) was added NaBH₄ (102 mg, 2.7 mmol) at 0° C. After stirring at rt for 2 hrs, the reaction mixture was added several drops of acetone and the concentrated. The residue was diluted with water (25 mL) and extracted with DCM (25 mL×3). The combined extracts were washed with water (25 mL) and brine (25 mL), dried over anhydrous Na₂SO₄, and concentrated. The residue was dried in vacuo to give compound 33-2 (300 mg, 99% yield) as a yellow solid. LC-MS (ESI): m/z 463.2 [M–H₂O–Ms+H]⁺.

Step 3. To a solution of compound 33-2 (180 mg, 0.322 mmol) in CH₂Cl₂ (2 mL) was added TMSOTf (143 mg, 0.64 mmol) at 0° C. After stirring at 0° C. for 10 min, the reaction mixture was added saturated aq. NaHCO₃ (25 mL) and the resulting mixture was extracted with DCM (25 mL×2). The combined organic extracts were washed with water (25 mL) and brine (25 mL), dried over anhydrous Na₂SO₄, and concentrated. The residue was dried in vacuo to give compound 33-3 (160 mg, 92% yield) as a yellow solid. LC-MS (ESI): m/z 564.0 [M+Na]⁺.

Step 4. Following the same procedure as that for the preparation of compound 1-16 described in Scheme 1 and replacing compound 1-14 with 33-3, compound 33-4 was obtained (100 mg, 65% yield) as a white solid. LC-MS (ESI): m/z 527.1 [M+H]⁺; ¹H NMR (500 MHz, d⁶-DMSO): δ 8.50-8.56 (m, 1H), 7.95-7.99 (m, 2H), 7.89 and 7.84 (s, s, 1H), 7.66 (m, 1H), 7.32-7.42 (m, 4H), 7.16-7.21 (m, 2H), 5.35 and 5.08 (q, q, J=6.5 Hz, 1H), 5.01 (d, J=10 Hz, 0.5 H), 4.20 (d, J=14 Hz, 0.5 Hz), 4.06 and 3,45 (m, m, 1H), 3.46 and 3.44 (s, s, 3H), 3.28 and 2.99 (m, m, 1H), 2.85-2.87 (m, 3H), 1.67-1.70 (m, 3H) ppm.

Scheme 34

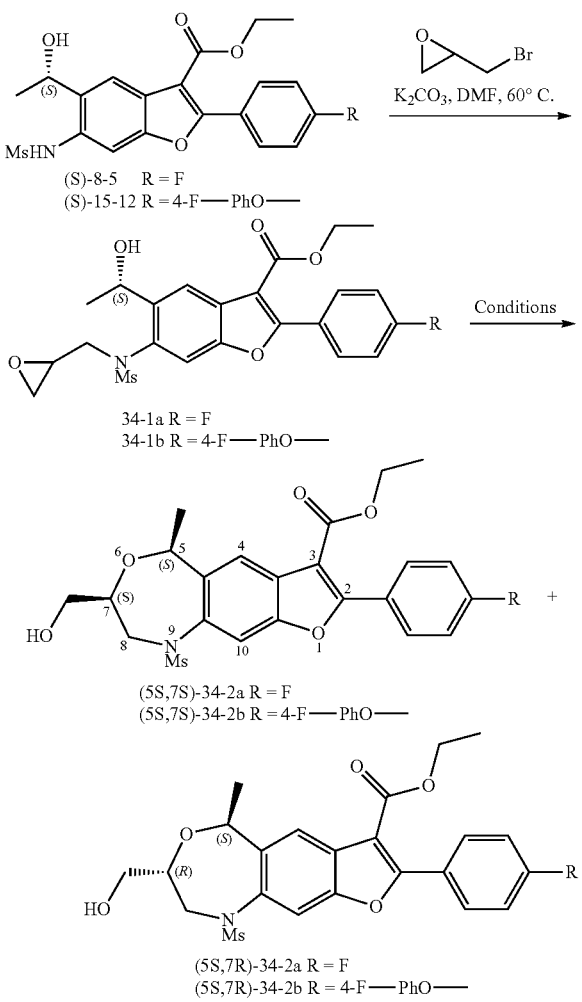

dropwise added to the mixture. After stirring at 60° C. overnight, the reaction mixture was concentrated. The residue was diluted with H₂O (100 mL) and EtOAc (150 mL). The aqueous layer was extracted with EtOAc (150 mL×2). The combined organic extracts were washed with H₂O (100 mL×2) and brine (100 mL), dried over anhydrous Na₂SO₄, filtrated and concentrated. The residue was purified by silica gel column chromatography (Petroleum ether/EtOAc=1/1 (v/v)) to give compound 34-1b (4.8 g, 84% yield) as a white solid. LC-MS (ESI): m/z 570.1 [M+H]⁺.

Step 2. To a solution of TsOH (91 mg, 0.53 mmol) in DCM (10 mL) at rt was added compound 34-1b (150 mg, 0.26 mmol). After stirring at rt overnight, the reaction mixture was concentrated and the residue was dissolved in DCM (50 mL). The mixture was washed with sat. aq. NaHCO₃ (25 mL×2) and brine (25 mL), dried over anhydrous Na₂SO₄, filtered, and concentrated. The residue was purified by silica gel column chromatography (Petroleum ether/EtOAc=1/1 (v/v)) to give a mixture of compounds (5S,7S)-34-2b and (5S,7R)-34-2b (120 mg, 81% yield) as white solid in a ratio of 1/1 as determined by comparing the integrations of the benzylic carbons at 5.08 ppm for compound (5S,7S)-34-2b and 5.20 ppm for compound (5S,7R)-34-2b, respectively. LC-MS (ESI): m/z 570.1 [M+H]⁺. Compound (5S,7S)-34-2b: ¹H NMR (500 MHz, CDCl₃): δ 8.14 (s, 1H), 8.04 (m, 2H), 7.58 (s, 1H), 7.03-7.11 (m, 6H), 5.08 (q, J=6.5 Hz, 1H), 4.42 (q, J=7.0 Hz, 2H), 4.13-4.19 (m, 2H), 3.73 (dd, J₁=3.5 Hz, J₂=11.5 Hz, 1H), 3.53 (dd, J₁=6.0 Hz, J₂=11.8 Hz, 1H), 3.18 (s, 1H), 3.12 (m, 1H), 1.92 (bs, 1H), 1.77 (d, J=7.0 Hz, 3H), 1.44 (t, J=6.5 Hz, 3H) ppm. Compound (5S,7R)-34-2b: ¹H NMR (500 MHz, CDCl₃): δ 7.94-7.97 (m, 3H), 7.52 (s, 1H), 6.96-7.03 (m, 6H), 5.20 (q, J=6.5 Hz, 1H), 4.35 (q, J=7.0 Hz, 2H), 3.94 (brm, 1H), 3.71 (dd, J₁=4.5 Hz, J₂=11.8 Hz, 1H), 3.58-3.66 (m, 4H), 3.08 (s, 3H), 1.92 (bs, 1H), 1.67 (d, J=7.0 Hz, 3H), 1.36 (t, J=7.0 Hz, 3H) ppm. Further chiral HPLC analyses showed that although better ratios were achieved when performing the cyclization at elevated temperatures, racemization of the chirality at the benzylic carbon was observed and a racemic syn/anti mixture of the cyclized products was obtained.

Comparison of the stereo-selectivity of the acid catalyzed epoxide-opening-ring-formation step

| Starting material | Acid | Solvent | Temperature and reaction time | ratio of compound 34-2 |
|---|---|---|---|---|
| 34-1a | TsOH (0.3 eq.) | DCM | 0° C., overnight | 1.0/3.0 ((5S,7S)-34-2a/(5S,7R)-34-2a) |
| 34-1a | TsOH (2.0 eq.) | DCM | rt, overnight | 1.0/1.0 ((5S,7S)-34-2a/(5S,7R)-34-2a) |
| 34-1a | TsOH (2.0 eq.) | DCE | 60° C., 4 hr | 4.0/1.0 ((±)-syn-34-2a/(±)-anti-34-2a) |
| 34-1b | TsOH (0.3 eq.) | DCM | 0° C., overnight | 1.0/3.0 ((5S,7S)-34-2b/(5S,7R)-34-2b) |
| 34-1b | TsOH (2.0 eq.) | DCM | rt, overnight | 1.0/1.0 ((5S,7S)-34-2b/(5S,7R)-34-2b) |
| 34-1b | TsOH (2.0 eq.) | DCE | 60° C., 4 hr | 6.5/1.0 ((±)-syn-34-2b/(±)-anti-34-2b) |
| 34-1b | TsOH (2.0 eq.) | Toluene | 100° C., 4 hr | 7.5/1.0 ((±)-syn-34-2b/(±)-anti-34-2b) |
| 34-1b | TsOH (2.0 eq.) | DMF | 150° C., 2 hr | 3.0/2.0 ((±)-syn-34-2b/(±)-anti-34-2b) |

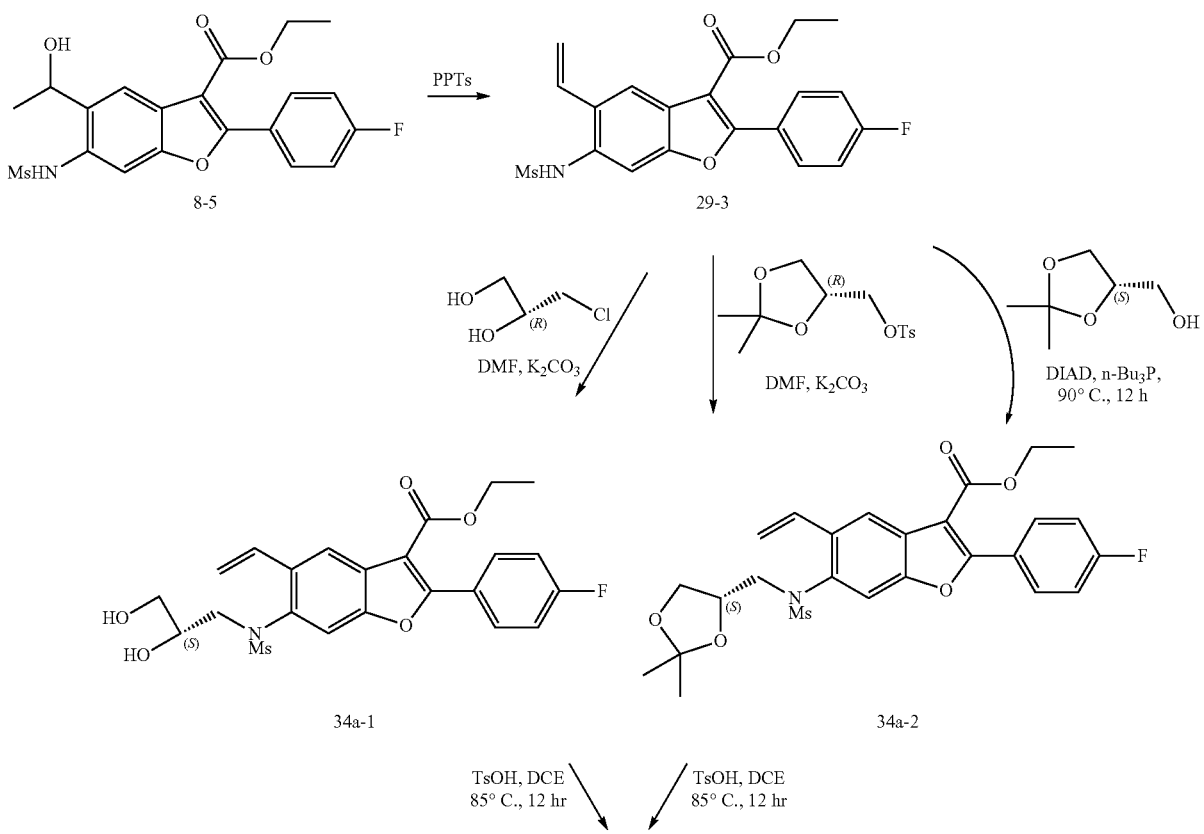

Scheme 34a

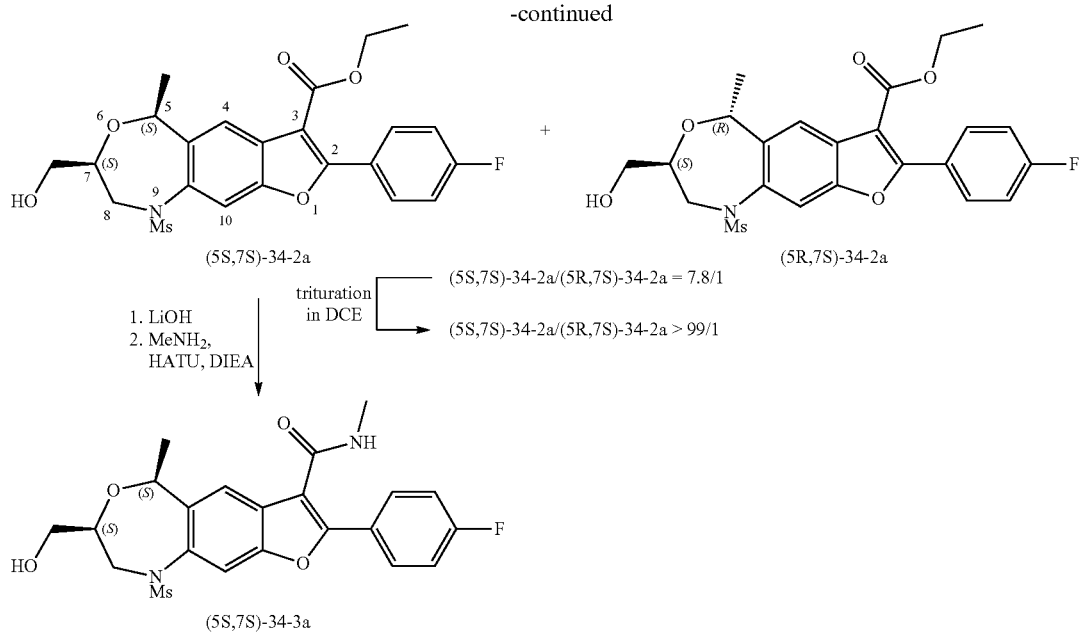

(5S,7S)-34-2a (5R,7S)-34-2a

1. LiOH
2. MeNH₂, HATU, DIEA trituration in DCE (5S,7S)-34-2a/(5R,7S)-34-2a = 7.8/1

(5S,7S)-34-2a/(5R,7S)-34-2a > 99/1

(5S,7S)-34-3a

Step 1. Refer to Scheme 34a. To a stirred solution of compound 8-5 (15.0 g, 35.6 mmol) in toluene (250 mL) at 70° C. was added PPTs (3.56 g, 14.2 mol). After refluxing overnight, the reaction mixture was concentrated and the residue was dissolved in DCM (200 mL). The resulting mixture was washed with sat. aq. NaHCO₃ (300 mL) and brine (200 mL), and dried over anhydrous Na₂SO₄. The solvent was removed and the residue was purified by silica gel column chromatography (Petroleum ether/Acetone=10/1 (v/v)) to give compound 29-3 (10.0 g, 70% yield) as a pale yellow solid. LC-MS (ESI): m/z 404.1 [M+H]⁺; ¹H NMR (500 MHz, CDCl₃): δ 8.14 (s, 1H), 8.07-8.04 (m, 2H), 7.72 (s, 1H), 7.18 (t, J=8.5 Hz, 2H), 6.97 (dd, J₁=11 Hz, J₂=17 Hz, 1H), 6.60 (s, 1H), 5.78 (d, J=17 Hz, 1H), 5.53 (d, J=11 Hz, 1H), 4.42 (q, J=7.0 Hz, 2H), 3.02 (s, 3H), 1.42 (t, J=7.0 Hz, 3H) ppm.

Step 2. To a solution of compound 29-3 (100 mg, 0.25 mmol) in DMF (2 mL) were added K₂CO₃ (103 mg, 0.75 mmol) and (R)-3-chloropropane-1,2-diol (82 mg, 0.744 mmol). After stirring at 110° C. overnight, the reaction mixture was cooled to rt and poured into water (50 mL). The suspension was filtered; the solid was washed with water (20 mL), dried, and purified by silica gel column chromatography (DCM/MeOH=100/1 (v/v)) to give compound 34a-1 (100 mg, 84% yield) as a white solid. LC-MS (ESI): m/z 500.1 [M+Na]⁺.

Step 3. To a stirred solution of compound 34a-1 (94.0 mg, 0.20 mmol) in DCE (20 mL) at 85° C. was added TsOH (94 mg, 0.49 mmol). After refluxing overnight, the reaction mixture was concentrated. The residue was diluted with DCM (50 mL) and the resulting mixture was washed with sat. aq. NaHCO₃ (50 mL) and brine (50 mL), and dried over anhydrous Na₂SO₄. The solvent was removed and the residue was purified by silica gel column chromatography (Petroleum ether/EtOAc=2/1 (v/v)) to give a mixture of compounds (5S,7S)-34-2a and (5R,7S)-34-2a with a ratio of 7.8/1 (75 mg, 80% yield) as a white solid. LC-MS (ESI): m/z 500.1 [M+Na]⁺.

Synthesis of Compound 34a-2. Method A. To a solution of compound 29-3 (1.0 g, 2.5 mmol) in DMF (25 mL) were added K₂CO₃ (1.04 g, 7.5 mmol) and (R)-(2,2-dimethyl-1,3-dioxolan-4-yl)methyl 4-methylbenzenesulfonate (1.42 g, 5.0 mmol). After stirring at 90° C. for 48 hr, the reaction mixture was cooled, diluted with EtOAc (100 mL), and filtered through Celite®545. The filtered cake was washed with EtOAc (100 mL). The filtrate was concentrated and the residue was diluted with EtOAc (100 mL). The mixture was washed with water (50 mL×2) and brine (50 mL), and dried with anhydrous Na₂SO₄. The solvent was removed and the residue was purified by silica gel column chromatography (Petroleum ether/EtOAc=5/1 (v/v)) to give compound 34a-2 (0.95 g, 74% yield) as a yellow solid. LC-MS (ESI): m/z 540.2 [M+Na]⁺.

Synthesis of Compound 34a-2. Method B. To a solution of compound 29-3 (1.2 g, 3.0 mmol) in dry toluene (20 mL) were added n-Bu₃P (1.4 mL, 6 mmol) and DIAD (1.2 mL, 6 mmol) under an atmosphere of N₂. After stirring at 0° C. for 30 min, the reaction mixture was added a solution of (S)-(2,2-dimethyl-1,3-dioxolan-4-yl)methanol (0.56 mL, 4.5 mmol) in toluene (5 mL). The resulting reaction mixture was stirred at 90° C. overnight and then concentrated. The residue was diluted with DCM (200 mL), washed with water (50 mL×2) and brine (50 mL), and dried over anhydrous Na₂SO₄. The solvent was removed and the residue was purified by silica gel column chromatography (Petroleum ether/EtOAc=4/1 (v/v)) to give compound 34a-2 (1.3 g, 83% yield) as a yellow solid. LC-MS (ESI): m/z 540.2 [M+Na]⁺.

Synthesis of Compound (5S,7S)-34-2a from Compound 34a-2. To a stirred solution of compound 34a-2 (0.95 g, 1.8 mmol) in DCE (40 mL) at 85° C. was added TsOH (0.86 g, 4.5 mmol). After refluxing overnight, the reaction mixture was concentrated. The residue was diluted with DCM (200 mL) and the resulting mixture was washed with sat. aq. NaHCO₃ (50 mL×2) and brine (50 mL), and dried over anhydrous Na₂SO₄. The solvent was removed and the residue was purified by silica gel column chromatography (Petroleum ether/EtOAc=2/1 (v/v)) to give a mixture of compounds (5S,7S)-34-2a and (5R,7S)-34-2a with a ratio of 7.8/1 (0.64 g, 74% yield) as a white solid. LC-MS (ESI): m/z 500.1 [M+Na]⁺. The mixture was dissolved in DCE at reflux and slowly cooled to rt. The resulting suspension was filtered. The solid was washed with cold DCE and dried in vacuo to give compound (5S,7S)-34-2a with a diastereomeric purity of >99% in 75% yield.

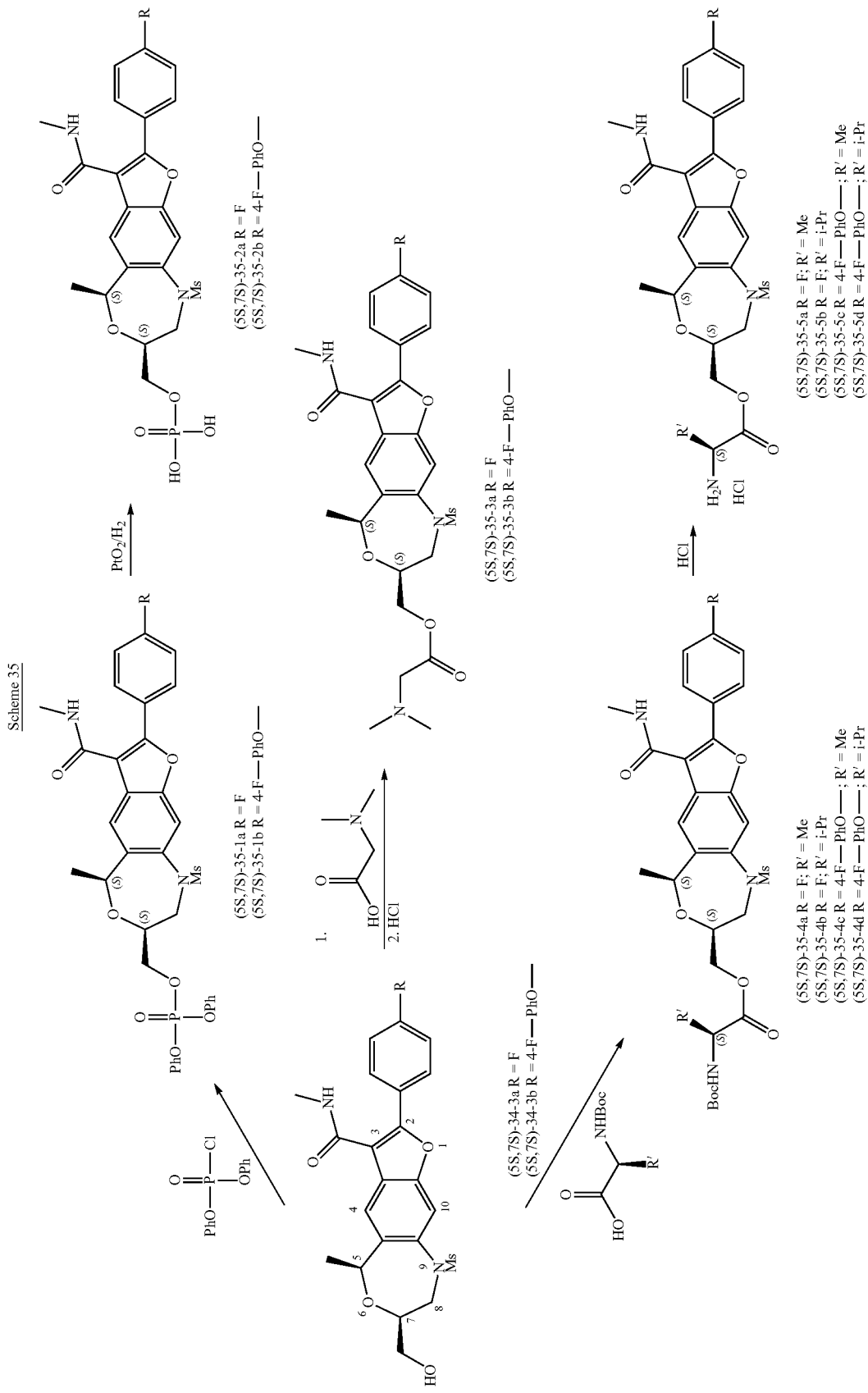

Synthesis of Compound (5S,7S)-35-1b. Refer to Scheme 35. To a solution of compound (5S,7S)-34-3b (120 mg, 0.22 mmol) and DMAP (159 mg, 1.3 mmol) in DCM (2 mL) was added diphenyl phosphorochloridate (291 mg, 1.08 mmol) at 0° C. under an atmosphere of Ar. After stirring rt overnight, the reaction mixture was added ice water (10 mL) and DCM (10 mL). The organic layer was washed with saturated aq. $NaHCO_3$ (10 mL×3) and water (10 mL×3), dried over anhydrous $Na_2SO_4$, filtered and concentrated. The residue was dried in vacuo to give crude compound (5S,7S)-35-1b (120 mg, 71% yield) as a white solid. LC-MS (ESI): m/z 787.2 [M+H]$^+$.

Synthesis of Compound (5S,7S)-35-2b. To a solution of compound (5S,7S)-35-1b (120 mg, 0.15 mmol) in THF (5 mL) was added $PtO_2$ (50 mg). The resulting mixture was flushed with $H_2$ and stirred at rt overnight. Subsequently, the mixture was diluted with THF (25 mL) and filtered through Celite®545. The filtrate was concentrated and the residue was diluted with water (25 mL). The suspension was filtered; the solid was washed with water (10 mL) and $CH_3CN$ (10 mL) and dried in vacuo to give compound (5S,7S)-35-2b (50 mg, 52% yield) as a white solid. LC-MS (EST): m/z 635.2 [M+H]$^+$. $^1$H NMR (500 MHz, d$^6$-DMSO): δ 8.50 (d, J=4.5 Hz, 1H), 7.91 (d, J=8.5 Hz, 2H), 7.81 (s, 1H), 7.56 (s, 1H), 7.29 (d, J=8.5 Hz, 2H), 7.15-7.18 (m, 2H), 7.10 (d, J=8.5 Hz, 2H), 4.89 (d, J=5.5 Hz, 1H), 4.10-4.16 (m, 1H), 4.03 (br, 1H), 3.77 (br, 1H), 3.58-3.60 (m, 1H), 3.47 (br, 2H), 3.36 (s, 3H), 2.89 (br, 1H), 2.83 (d, J=4.5 Hz, 3H), 1.60 (d, J=5.5 Hz, 3H) ppm.

Synthesis of Compound (5S,7S)-35-3b. To a solution of N,N-dimethylglycine (45 mg, 0.43 mmol), DCC (149 mg, 0.72 mmol) and compound (5S,7S)-34-3b (80 mg, 0.14 mmol) in $CH_2Cl_2$ (2 mL) was added DMAP (89 mg, 0.72 mmol) at rt. After stirring at rt overnight, the reaction mixture was filtered and the filtrated was concentrated. The residue was purified by preparative HPLC and product was converted to its HCl salt to give compound (5S,7S)-35-3b (50 mg, 54% yield) as a white solid. LC-MS (ESI): m/z 640.2 [M+H]$^+$. $^1$H NMR (500 MHz, d$^6$-DMSO): δ 10.32 (br, 1H), 8.51 (d, J=5.0 Hz, 1H), 7.91 (d, J=9.0 Hz, 2H), 7.86 (s, 1H), 7.57 (s, 1H), 7.30 (t, J=8.5 Hz, 2H), 7.17-7.20 (m, 2H), 7.12 (d, J=9.0 Hz, 2H), 4.92 (q, J=6.5 Hz, 1H), 4.19-4.26 (m, 6H), 3.04 (s, 1H), 3.00 (br, 1H), 2.83 (s, 9H), 1.64 (d, J=6.0 Hz, 3H) ppm.

Synthesis of Compound (5S,7S)-35-4c. To a solution of N-Boc-L-Alanine (68 mg, 0.36 mmol), DCC (149 mg, 0.72 mmol) and compound (5S,7S)-34-3b (100 mg, 0.18 mmol) in $CH_2Cl_2$ (2 mL) was added DMAP (89 mg, 0.72 mmol) at rt. After stirring at rt overnight, the reaction mixture was filtered; the filtrate was concentrated and the residue was dried in vacuo to give crude compound (5S,7S)-35-4c (105 mg, 80% yield) as a white solid. LC-MS (ESI): m/z 626.1 [M−Boc+2H]$^+$.

Synthesis of Compound (5S,7S)-35-5c. A mixture of compound (5S,7S)-35-4c (100 mg, 0.14 mmol) in 4.0 N HCl in 1,4-dioxane (3 mL) was stirred at rt for 2 hr. The solvent was removed and the residue was purified by prep-HPLC to give compound (5S,7S)-35-5c (50 mg, 58% yield) as a white solid. LC-MS (ESI): m/z 626.1 [M+H]$^+$. $^1$H NMR (500 MHz, d$^6$-DMSO): δ 8.48-8.51 (m, 1H), 8.40 (s, 2H), 7.90 (d, J=8.5 Hz, 2H), 7.81 (s, 1H), 7.56 (s, 1H), 7.31 (t, J=8.5 Hz, 2H), 7.16-7.20 (m, 2H), 7.12 (d, J=9.0 Hz, 2H), 4.91 (q, J=6.5 Hz, 1H), 4.09-4.26 (m, 5H), 4.00 (s, 3H), 2.95 (br, 1H), 2.83 (d, J=6.5 Hz, 1H), 1.61 (d, J=4.5 Hz, 3H), 1.40 (d, J=7.0 Hz, 3H) ppm.

Synthesis of Compound (5S,7S)-35-5d. Following the same procedure as that used for preparing compound (5S,7S)-35-5c and replacing N-Boc-L-Alanine with N-Boc-L-Valine, compound (5S,7S)-35-5d was obtained as a white solid in 69% yield. LC-MS (ESI): m/z 654.2 [M+H]$^+$. $^1$H NMR (500 MHz, d$^6$-DMSO): δ 8.49-8.51(m, 1H), 8.08 (br, 2H), 7.91 (d, J=9.0 Hz, 2H), 7.86 (s, 1H), 7.57 (s, 1H), 7.30 (t, J=9.0 Hz, 2H), 7.17-7.20 (m, 2H), 7.12 (d, J=9.0 Hz, 2H), 4.93 (d, J=6.5 Hz, 1H), 4.15-4.20 (m, 4H), 3.87 (s, 1H), 3.36 (s, 3H), 2.95 (br, 1H), 2.84 (d, J=4.0 Hz, 3H), 2.13-2.16 (m, 1H), 2.16 (d, J=6.5 Hz, 3H), 1.00 (d, J=6.5 Hz, 3H), 0.95 (d, J=6.5 Hz, 3H) ppm.

Synthesis of analogs of compound (5S,7S)-35-2, -3, and -5. Following the same synthetic strategy described in Scheme 35, the following analogs were readily obtained.

| Acylator | Product | [M + H]$^+$ | $^1$H NMR (500 MHz, d$^6$-DMSO) (δ, ppm) |
|---|---|---|---|
| (pivalic acid) | (pivaloyl ester product) | 639.2 | 8.49 (q, J = 4.0 Hz, 1H), 7.92 (d, J = 9.5 Hz, 2H), 7.84 (s, 1H), 7.57 (s, 1H), 7.29 (t, J = 9.0 Hz, 2H), 7.17-7.20 (m, 2H), 7.12 (d, J = 9.0 Hz, 2H), 4.90 (q, J = 6.0 Hz, 1H), 3.96-4.17 (m, 4H), 3.38 (s, 3H), 2.86 (t, J = 11.0 Hz, 1H), 2.84 (d, J = 5.0 Hz, 3H), 1.62 (d, J = 6.5 Hz, 3H), 1.15 (s, 9H) |
| (nicotinic acid) | (nicotinoyl ester product) | 660.2 | 9.12 (s, 1H), 8.86 (d, J = 5.0 Hz, 1H), 8.50 (q, J = 4.5 Hz, 1H), 8.35 (d, J = 6.5 Hz, 1H), 7.92 (d, J = 7.0 Hz, 2H), 7.86 (s, 1H), 7.65 (t, J = 5.5 Hz, 1H), 7.58 (s, 1H), 7.30 (t, J = 8.0 Hz, 2H), 7.17-7.20 (m, 2H), 7.12 (d, J = 8.0 Hz, 2H), 4.90 (q, J = 6.5 Hz, 1H), 4.21-4.38 (m, 5H), 3.41 (s, 3H), 3.06 (t, J = 4.5 Hz, 1H), 2.83 (d, J = 5.0 Hz, 1H), 1.63 (d, J = 6.5 Hz, 3H) |

| Acylator | Product | [M + H]+ | 1H NMR (500 MHz, d6-DMSO) (δ, ppm) |
|---|---|---|---|
| 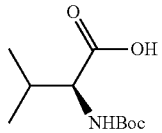 | 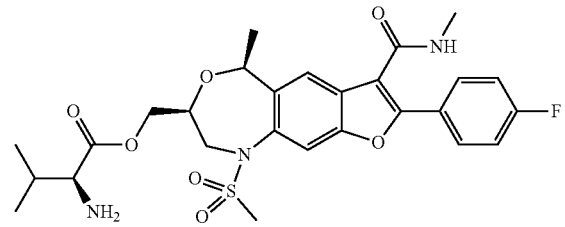 [SMILES: CNC(=O)c1c(-c2ccc(F)cc2)oc2cc3c(cc12)[C@H](C)O[C@H](COC(=O)[C@@H](N)C(C)C)CN3S(C)(=O)=O] | 562.1 | 8.47-8.54 (m, 4H), 7.94-7.98 (m, 2H), 7.88 (s, 1H), 7.60 (s, 1H), 7.41 (t, J = 9.0 Hz, 2H), 4.93 (q, J = 6.0 Hz, 1H), 4.16-4.25 (m, 4H), 3.92 (s, 1H), 3.41 (s, 3H), 2.96 (t, J = 11.5 Hz, 1H), 2.84 (d, J = 4.5 Hz, 3H), 2.16-2.20 (m, 1H), 1.63 (d, J = 7.0 Hz, 3H), 1.03 (d, J = 8.0 Hz, 3H), 0.95 (d, J = 8.0 Hz, 3H) |
| 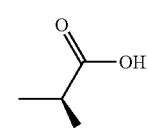 | 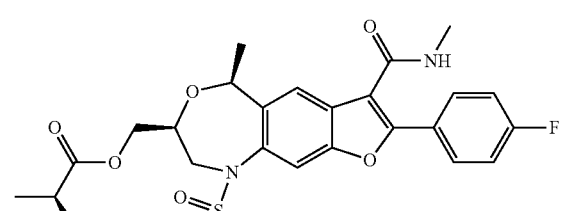 | 534.2 | 8.53 (q, J = 4.0 Hz, 1H), 8.42 (br, 3H), 7.95 (q, J = 5.0 Hz, 2H), 7.88 (s, 1H), 7.59 (s, 1H), 7.41 (t, J = 8.5 Hz, 2H), 4.92 (q, J = 6.0 Hz, 1H), 4.10-4.27 (m, 5H), 3.40 (s, 3H), 2.97 (t, J = 10.5 Hz, 1H), 2.84 (d, J = 4.5 Hz, 3H), 1.63 (d, J = 6.5 Hz, 3H), 1.41 (d, J = 7 Hz, 3H) |
| 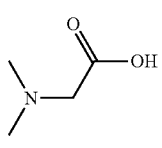 | 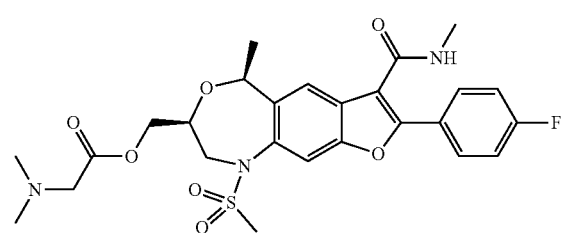 [SMILES: CNC(=O)c1c(-c2ccc(F)cc2)oc2cc3c(cc12)[C@H](C)O[C@H](COC(=O)CN(C)C)CN3S(C)(=O)=O] | 548.2 | 10.43 (br, 1H), 8.53 (q, J = 4.5 Hz, 1H), 7.96 (t, J = 4.5 Hz, 2H), 7.87 (s, 1H), 7.60 (s, 1H), 7.41 (t, J = 9.0 Hz, 2H), 4.93 (q, J = 6.5 Hz, 1H), 4.18-4.26 (m, 6H), 3.41 (s, 3H), 2.97 (t, J = 9.0 Hz, 1H), 2.80-2.85 (m , 9H), 2.54 (s, 1H), 1.64 (d, J = 6.5 Hz, 3H) |
| 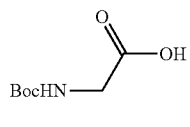 [SMILES: CC(C)(C)OC(=O)NCC(=O)O] | 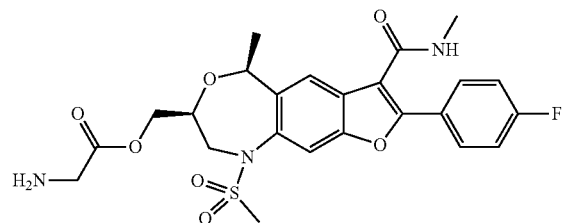 [SMILES: CNC(=O)c1c(-c2ccc(F)cc2)oc2cc3c(cc12)[C@H](C)O[C@H](COC(=O)CN)CN3S(C)(=O)=O] | 520.1 | 8.54 (q, J = 4.0 Hz, 1H), 8.38 (br, 3H), 7.95 (q, J = 5.5 Hz, 2H), 7.87 (s, 1H), 7.60 (s, 1H), 7.41 (t, J = 8.5 Hz, 2H), 4.92 (q, J = 6.0 Hz, 1H), 4.17-4.24 (m, 4H), 3.82 (d, J = 5.5 Hz, 2H), 3.41 (s, 3H), 2.98 (t, J = 12.5 Hz, 1H), 2.84 (d, J = 4.5 Hz, 3H), 1.65 (d, J = 6.5 Hz, 3H) |
| 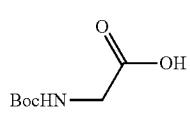 | 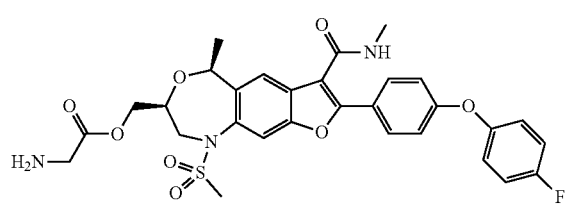 [SMILES: CNC(=O)c1c(-c2ccc(Oc3ccc(F)cc3)cc2)oc2cc3c(cc12)[C@H](C)O[C@H](COC(=O)CN)CN3S(C)(=O)=O] | 612.2 | 8.54 (q, J = 3.5 Hz, 1H), 7.88 (d, J = 8.5 Hz, 2H), 7.80 (s, 1H), 7.61 (s, 1H), 7.30 (t, J = 9.0 Hz, 2H), 7.17-7.19 (m, 2H), 7.13 (d, J = 9.0 Hz, 2H), 4.93 (q, J = 6.5 Hz, 1H), 4.24-4.30 (m, 2H), 3.76 (s, 2H), 3.36 (s, 3H), 3.00-3.03 (m, 1H), 2.86 (d, J = 4.0 Hz, 3H), 1.65 (d, J = 6.5 Hz, 3H) |
| 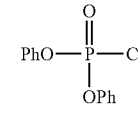 | 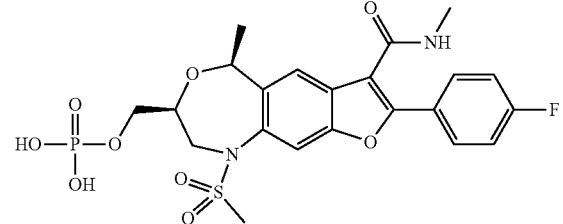 [SMILES: CNC(=O)c1c(-c2ccc(F)cc2)oc2cc3c(cc12)[C@H](C)O[C@H](COP(=O)(O)O)CN3S(C)(=O)=O] | 543.1 | 8.54 (q, J = 4.5 Hz, 1H), 7.98 (q, J = 5.5 Hz, 2H), 7.85 (s, 1H), 7.60 (s, 1H), 7.40 (t, J = 9 Hz, 2H), 4.92 (q, J = 6.5 Hz, 1H), 4.10-4.20 (m, 2H), 3.74-3.87 (m, 3H), 2.92 (br, 2H), 2.85 (d, J = 4.5 Hz, 1H), 2.08 (s, 1H), 1.64 (d, J = 6.5 Hz, 3H), 1.16 (t, J = 7 Hz, 3H) |

-continued

| Acylator | Product | [M + H]⁺ | ¹H NMR (500 MHz, d⁶-DMSO) (δ, ppm) |
|---|---|---|---|
| (structure) | (structure) | 623.2 | 8.53 (q, J = 3.5 Hz, 1H), 7.97 (t, J = 5.5 Hz, 2H), 7.86 (s, 1H), 7.59 (s, 1H), 7.40 (t, J = 8.5 Hz, 2H), 4.91 (q, J = 6.0 Hz, 1H), 4.11-4.18 (m, 6H), 3.48-3.51 (m, 2H), 3.39-3.41 (m, 7H), 3.24 (s, 1H), 3.22 (s, 3H), 2.93 (t, J = 4.5 Hz, 1H), 2.84 (t, J = 4.5 Hz, 1H), 1.63 (d, J = 6.5 Hz, 3H) |
| (structure) | (structure) | 667.2 | 8.52 (q, J = 3.5 Hz, 1H), 7.97 (t, J = 5.5 Hz, 2H), 7.85 (s, 1H), 7.60 (s, 1H), 7.40 (t, J = 9.5 Hz, 2H), 4.91 (q, J = 6.5 Hz, 1H), 4.18-4.11 (m, 6H), 3.59-3.57 (m, 2H), 3.48-3.51 (m, 8H), 3.40-3.41 (m, 2H), 3.39 (s, 3H), 3.22 (s, 3H), 2.94 (t, J = 9 Hz, 1H), 2.84 (d, J = 4.5 Hz, 3H), 1.63 (d, J = 6.5 Hz, 3H) |
| (structure) | (structure) | 711.3 | 8.52 (q, J = 3.5 Hz, 1H), 7.97 (t, J = 5.5 Hz, 2H), 7.86 (s, 1H), 7.60 (s, 1H), 7.40 (t, J = 9.5 Hz, 2H), 4.90 (q, J = 6.5 Hz, 1H), 4.11-4.18 (m, 6H), 3.57-3.59 (m, 2H), 3.48-3.51 (m, 12H), 3.39-3.44 (m, 2H), 3.38 (s, 3H), 3.23 (s, 3H), 2.93 (t, J = 9.0 Hz, 1H), 2.84 (d, J = 4.5 Hz, 3H), 1.63 (d, J = 6.5 Hz, 3H) |
| (structure) | (structure) | 547.2 | In CDCl₃: 7.88-7.91 (m, 3H), 7.60 (s, 1H), 7.20 (t, J = 8.0 Hz, 2H), 5.78 (m 1H), 4.99 (q, J = 7.0 Hz, 1H), 4.18-4.25 (m, 3H), 3.96-3.99 (m, 1H), 3.15 (s, 3H), 3.00 (d, J = 5.0 Hz, 3H), 2.99-3.01 (m, 1H), 1.73 (d, J = 6.0 Hz, 3H), 1.22 (s, 9H) |
| (structure) | (structure) | 568.1 | 9.09 (d, J = 2.5 Hz, 1H), 8.82 (dd, J₁ = 5.0 Hz, J₂ = 1.5 Hz, 1H), 8.53 (q, J = 4.0 Hz, 1H), 8.29 (dt, J₁ = 8.5 Hz, J₂ = 1.5 Hz, 1H), 7.97 (dd, J₁ = 8.0 Hz, J₂ = 5.5 Hz, 1H), 7.88 (s, 1H), 7.60 (s, 1H), 7.58 (dd, J₁ = 8.5 Hz, J₂ = 5.5 Hz, 1H), 7.41 (t, J = 9.0 Hz 1H), 4.96 (q, J = 6.0 Hz, 1H), 4.27-4.37 (m, 4H), 3.42 (s, 3H), 3.06 (m, 1H), 2.84 (d, J = 4.5 Hz, 3H), 1.63 (d, J = 6.5 Hz, 3H) |
| (structure) | (structure) | 588.2 | 8.69 (m, 1H), 8.53 (q, J = 5.5 Hz, 1H), 8.39 (m, 1H), 7.56 (dd, J₁ = 10.5 Hz, J₂ = 6.0 Hz, 1H), 7.86 (s, 1H), 7.59 (s, 1H), 7.41 (t, J = 10.5 Hz, 2H), 4.91 (q, J = 8.5 Hz, 1H), 4.03-4.17 (m, 4H), 3.19-3.23 (m, 2H), 2.84-2.89 (m, 9H), 2.31 (d, J = 8.5 Hz, 3H), 1.96 (m, 1H), 1.78-1.82 (m, 2H), 1.62 (d, J = 8.5 Hz, 2H), 1.29-1.38 (m, 2H) |

-continued

| Acylator | Product | [M + H]⁺ | ¹H NMR (500 MHz, d⁶-DMSO) (δ, ppm) |
|---|---|---|---|
| 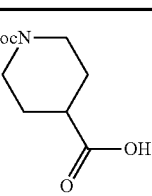 | 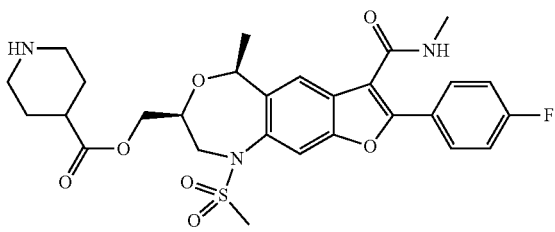 [SMILES: CNC(=O)c1c(-c2ccc(F)cc2)oc2cc3c(cc12)[C@H](C)O[C@H](COC(=O)C1CCNCC1)CN3S(C)(=O)=O] | 574.2 | 8.81 (m, 1H), 8.59 (m, 1H), 8.54 (q, J = 5.5 Hz, 1H), 7.49-7.98 (m, 2H), 7.87 (s, 1H), 7.60 (s, 1H), 7.41 (t, J = 11.0 Hz, 2H), 4.90 (q, J = 6.0 Hz, 1H), 4.08-4.18 (m, 4H), 2.89-2.94 (m, 2H), 2.83-2.94 (m, 9H), 2.70-2.73 (m, 1H), 1.97 (m, 2H), 1.68-1.77 (m, 2H), 1.63 (d, J = 7.5 Hz, 3H) |
| 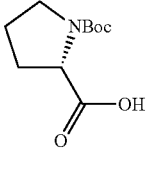 [SMILES: CC(C)(C)OC(=O)N1CCC[C@H]1C(=O)O] | 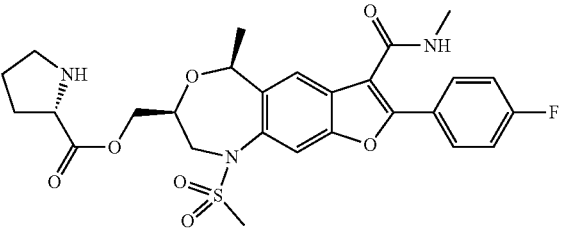 [SMILES: CNC(=O)c1c(-c2ccc(F)cc2)oc2cc3c(cc12)[C@H](C)O[C@H](COC(=O)[C@@H]1CCCN1)CN3S(C)(=O)=O] | 560.2 | In CDCl₃: 8.55 (m, 1H), 7.96 (m, 2H), 7.88 (s, 1H), 7.60 (s, 1H), 7.43 (t, J = 10.0 Hz, 2H), 4.93 (m, 1H), 4.39 (m, 1H), 4.30-4.50 (m, 4 H), 3.41 (s, 3H), 3.25-3.50 (m, 2H), 2.97 (m, 1H), 2.84 (d, J = 4.5 Hz, 3H), 2.52 (m 1H), 1.97 (m, 1H), 1.90 (m, 2H), 1.63 (d, J = 7.5 Hz, 3H) |
| 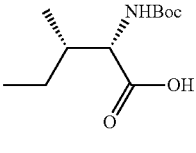 [SMILES: CC[C@H](C)[C@H](NC(=O)OC(C)(C)C)C(=O)O] | 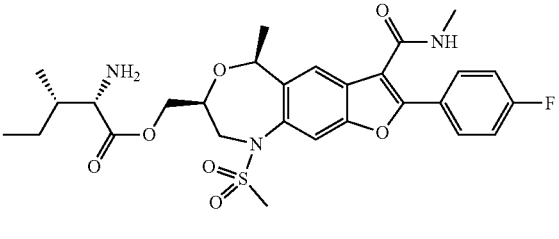 [SMILES: CC[C@H](C)[C@H](N)C(=O)OC[C@@H]1CN(S(C)(=O)=O)c2cc3oc(-c4ccc(F)cc4)c(C(=O)NC)c3cc2[C@H](C)O1] | 576.2 | 8.53 (q, J = 4.5 Hz, 1H), 8.39 (brs, 2H), 7.95-7.98 (m, 2H), 7.88 (s, 1H), 7.59 (d, J = 4.0 Hz, 1H), 7.41 (t, J = 9.0 Hz, 2H), 4.94 (q, J = 6.5 Hz, 1H), 4.16-4.23 (m, 4H), 4.03 (m, 1H), 3.41 (s, 3H), 2.93-2.96 (m, 1H), 2.84 (d, J = 4.5 Hz, 3H), 1.87-1.89 (m, 1H), 1.62 (d, J = 7.0 Hz, 3H), 1.49-1.53 (m, 1H), 1.33-1.37 (m, 1H), 0.89-0.92 (m, 6H) |
| 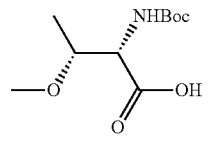 [SMILES: CO[C@H](C)[C@H](NC(=O)OC(C)(C)C)C(=O)O] | 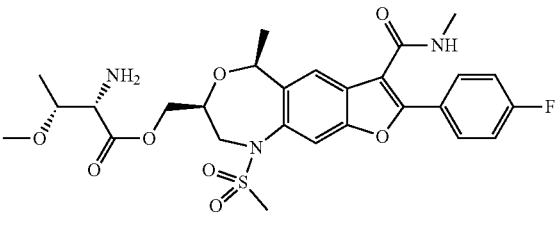 [SMILES: CNC(=O)c1c(-c2ccc(F)cc2)oc2cc3c(cc12)[C@H](C)O[C@H](COC(=O)[C@@H](N)[C@@H](C)OC)CN3S(C)(=O)=O] | 578.2 | 8.54 (q, J = 4.5 Hz, 1H), 8.42 (brs, 2H), 7.95 (dd, J₁ = 9.0 Hz, J₂ = 5.0 Hz, 2H), 7.88 (s, 1H), 7.60 (s, 1H), 7.41 (t, J = 9.0 Hz, 2H), 4.93 (q, J = 6.0 Hz, 1H), 4.19-4.25 (m, 4H), 4.12 (d, J = 3.5 Hz, 1H), 3.41 (s, 3H), 3.20 (s, 3H), 2.97-3.01 (m, 1H), 2.83 (d, J = 5.0 Hz, 3H), 1.64 (d, J = 6.0 Hz, 3H), 1.21 (d, J = 6.5 Hz, 3H) |
| 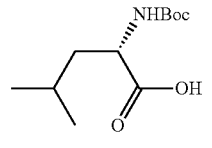 [SMILES: CC(C)C[C@H](NC(=O)OC(C)(C)C)C(=O)O] | 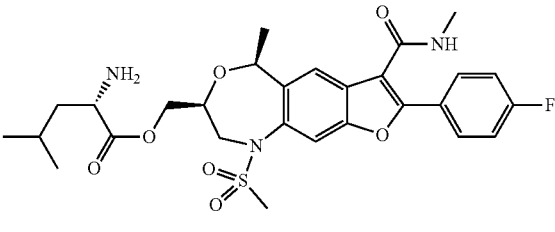 [SMILES: CNC(=O)c1c(-c2ccc(F)cc2)oc2cc3c(cc12)[C@H](C)O[C@H](COC(=O)[C@@H](N)CC(C)C)CN3S(C)(=O)=O] | 576.2 | 8.53-8.56 (m, 3H), 7.96 (dd, J₁ = 9.0 Hz, J₂ = 5.5 Hz, 2H), 7.88 (s, 1H), 7.60 (s, 1H), 7.41 (t, J = 8.5 Hz, 2H), 4.92 (q, J = 6.5 Hz, 1H), 4.15-4.22 (m, 4H), 3.97 (m, 1H), 3.41 (s, 3H), 2.93-2.98 (m, 1H), 2.83 (d, J = 4.5 Hz, 3H), 1.78 (m, 1H), 1.63-1.67 (m, 5 H), 0.89-0.92 (m, 6H) |
| 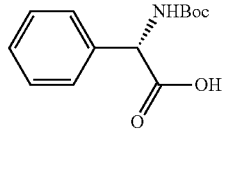 [SMILES: CC(C)(C)OC(=O)N[C@H](C(=O)O)c1ccccc1] | 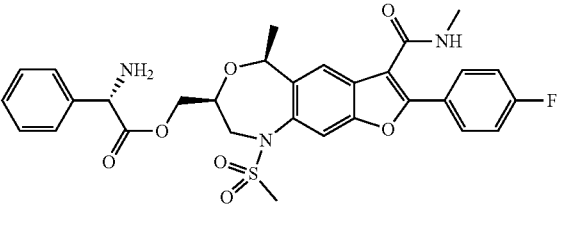 [SMILES: CNC(=O)c1c(-c2ccc(F)cc2)oc2cc3c(cc12)[C@H](C)O[C@H](COC(=O)[C@@H](N)c1ccccc1)CN3S(C)(=O)=O] | 596.2 | In CDCl₃: 8.90-8.97 (m, 3H), 8.54 (m, 1H), 7.94-7.97 (m, 2H), 7.81 (s, 1H), 7.32-7.53 (m, 8H), 5.33 (m, 1H), 4.77 (q, J = 4.5 Hz, 1H), 4.00-4.39 (m, 4 H), 3.35 (s, 3H), 2.84 (d, J = 4.5 Hz, 3H), 2.73-2.78 (m, 1H), 1.44-1.50 (m, 3H) |

-continued

| Acylator | Product | [M + H]+ | 1H NMR (500 MHz, d6-DMSO) (δ, ppm) |
|---|---|---|---|
| 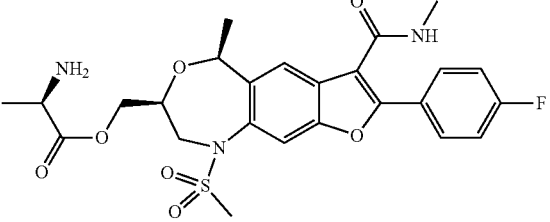 | 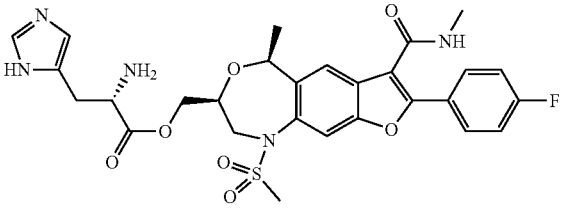 [SMILES: CNC(=O)c1c(-c2ccc(F)cc2)oc2cc3c(cc12)[C@H](C)O[C@H](COC(=O)[C@@H](N)Cc1cnc[nH]1)CN3S(C)(=O)=O] | 534.2 | 8.52 (q, J = 4.5 Hz, 1H), 8.38 (br, 3H), 7.95 (dd, J1 = 8.8 Hz, J2 = 5.0 Hz, 2H), 7.88 (s, 1H), 7.59 (s, 1H), 7.41 (t, J = 9.0 Hz, 2H), 4.89 (q, J = 4.5 Hz, 1H), 4.10-4.31 (m, 5H), 3.40 (s, 3H), 2.98 (m, 1H), 2.84 (d, J = 4.5 Hz, 3H), 1.63 (d, J = 6.5 Hz, 3H), 1.39 (d, J = 6.5 Hz, 3H) |
| 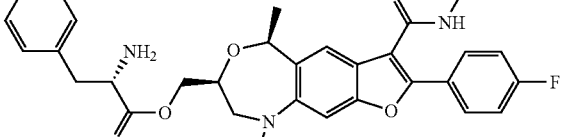 | 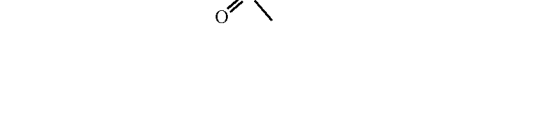 | 600.2 | 9.03 (m, 1H), 8.71 (brs, 2H), 8.56 (s, 1H), 7.94 (m, 2H), 7.86 (s, 1H), 7.60 (s, 1H), 7.50 (s, 1H), 7.43 (t, J = 8.5 Hz, 2H), 4.87 (m, 1H), 4.44 (m, 1H), 4.10-4.25 (m, 4H), 3.26 (m, 2H), 2.84 (d, J = 4.5 Hz, 3H), 2.62 (d, J = 6.5 Hz, 3H) |
| 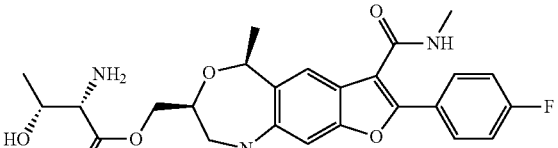 |  | 610.2 | 8.62 (brs, 3H), 8.55 (q, J = 4.5 Hz, 1H), 7.97 (dd, J1 = 9.0 Hz, J2 = 5.0 Hz, 2H), 7.89 (s, 1H), 7.59 (s, 1H), 7.42 (t, J = 9.0 Hz, 2H), 7.25-7.31 (m, 5H), 4.89 (q, J = 6.0 Hz, 1H), 4.28 (t, J = 6.5 Hz, 1H), 4.16 (d, J = 10.0 Hz, 2H), 4.08 (dd, J1 = 12.0 Hz, J2 = 6.5 Hz, 2H), 3.92 (d, J = 15.0 Hz, 1H), 3.41 (s, 3H), 3.19 (dd, J1 = 14.0 Hz, J2 = 5.5 Hz, 1H), 3.50 (dd, J1 = 14.0 Hz, J2 = 7.5 Hz, 1H), 2.85 (d, J = 5.0 Hz, 3H), 2.85 (m, 1H), 1.63 (d, J = 6.5 Hz, 3H) |
| 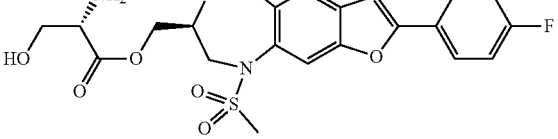 | 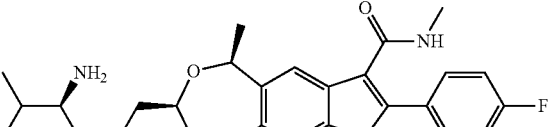 | 564.2 | 8.53 (q, J = 4.5 Hz, 1H), 8.27 (brs, 2H), 7.95 (dd, J1 = 8.8 Hz, J2 = 5.0 Hz, 2H), 7.88 (s, 1H), 7.59 (s, 1H), 7.41 (t, J = 9.0 Hz, 2H), 6.61 (d, J = 4.5 Hz, 1H), 4.91 (q, J = 6.0 Hz, 1H), 4.17-4.25 (m, 4H), 4.04 (m, 1H), 3.95 (m, 1H), 3.40 (s, 3H), 2.98 (m, 1H), 2.84 (d, J = 4.5 Hz, 3H), 1.63 (d, J = 7.0 Hz, 3H), 1.20 (d, J = 6.5 Hz, 3H) |
| 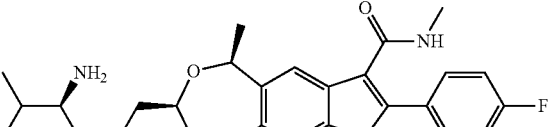 | 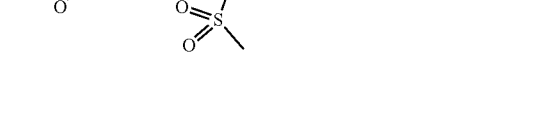 | 550.2 | 8.53 (q, J = 4.5 Hz, 1H), 8.46 (brs, 2H), 7.94-7.97 (m, 2H), 7.88 (s, 1H), 7.59 (s, 1H), 7.41 (t, J = 9.0 Hz, 2H), 5.60 (brs, 1H), 4.92 (q, J = 6.0 Hz, 1H), 4.13-4.24 (m 5H), 3.79 (m, 2H), 3.41 (s, 3H), 2.98 (m, 1H), 2.84 (d, J = 4.5 Hz, 3H), 1.64 (d, J = 6.5 Hz, 3H) |
| 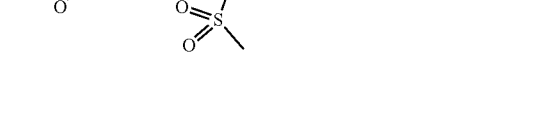 |  | 562.2 | 8.54 (m, 4H), 7.96 (dd, J1 = 9.0 Hz, J2 = 5.0 Hz, 2H), 7.89 (s, 1H), 7.60 (s, 1H), 7.42 (t, J = 9.0 Hz, 2H), 4.92 (q, J = 6.0 Hz, 1H), 4.36 (d, J = 11.5 Hz, 1H), 4.20-4.22 (m, 2H), 3.91-4.12 (m, 5H), 3.42 (s, 3H), 2.98 (m, 1H), 2.85 (d, J = 4.5 Hz, 3H), 2.18 (m, 1H), 1.63 (d, J = 6.5 Hz, 3H), 0.98 (d, J = 7.0 Hz, 3H), 0.96 (d, J = 7.0 Hz, 3H) |

-continued

| Acylator | Product | [M + H]+ | 1H NMR (500 MHz, d6-DMSO) (δ, ppm) |
|---|---|---|---|
| ![Acylator structure with NHBoc, OMe, OH] | ![Product structure with NH2, methylsulfonyl, fluorophenyl furan] | 564.2 | 8.61 (brs, 3H), 8.54 (m, 1H), 7.97 (dd, J₁ = 8.5 Hz, J₂ = 5.5 Hz, 2H), 7.88 (s, 1H), 7.60 (s, 1H), 7.42 (t, J = 8.0 Hz), 2H), 4.94 (m, 1H), 4.17-4.36 (m, 5H), 3.74 (m, 2H), 3.55 (s, 3H), 3.41 (s, 3H), 2.97 (m, 1H), 2.85 (d, J = 5.0 Hz, 3H), 1.65 (d, J = 6.5 Hz) |

Scheme 35a

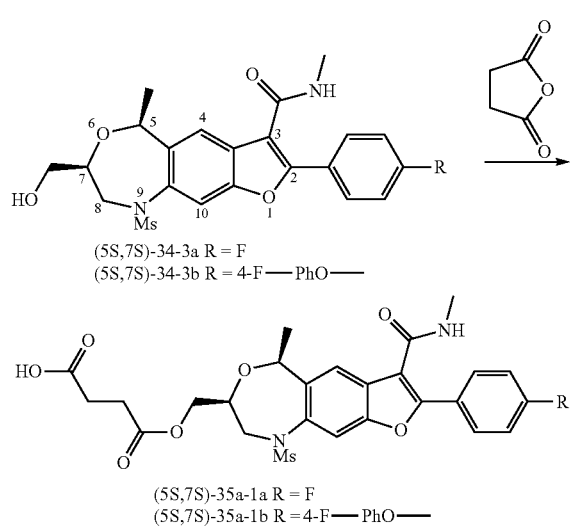

(5S,7S)-34-3a R = F
(5S,7S)-34-3b R = 4-F—PhO—

(5S,7S)-35a-1a R = F
(5S,7S)-35a-1b R = 4-F—PhO—

Synthesis of Compound (5S,7S)-35a-1b. Refer to Scheme 35a. To a solution of compound (5S,7S)-34-3b (60 mg, 0.11 mmol), DMAP (10 mg) and Et₃N (0.5 mL) in DCM (2 mL) at 0° C. was added dihydrofuran-2,5-dione (108 mg, 1.1 mmol). After stifling at rt for 2 hr, the reaction mixture was concentrated and the residue was purified by preparative HPLC to give compound (5S,7S)-35a-1b (40 mg, 56.5% yield) as a white solid. LC-MS (ESI): m/z 655.1 [M+H]+; ¹H NMR (500 MHz, d⁶-DMSO): δ 12.29 (br, 1H), 8.51 (q, J=5.5 Hz, 1H), 7.92 (t, J=4.5 Hz, 2H), 7.84 (s, 1H), 7.57 (s, 1H), 7.30 (t, J=8.5 Hz, 2H), 7.20-7.17 (m ,2H), 7.12 (d, J=8.0 Hz, 2H), 4.90 (q, J=6.5 Hz, 1H), 4.12-4.15 (m, 2H), 4.04 (s, 2H), 3.39 (s, 3H), 2.90 (t, J=4.5 Hz, 1H), 2.84 (d, J=4.0 Hz, 3H), 2.46-2.50 (m, 4 H), 1.63 (d, J=6.5 Hz, 3H) ppm.

Synthesis of Compound (5S,7S)-35a-1a. Following the same procedure as that used to prepare compound (5S,7S)-35a-1b and replacing compound (5S,7S)-34-3b with (5S,7S)-34-3a, compound (5S,7S)-35a-1a was obtained as a white solid. LC-MS (ESI): m/z 563.1 [M+H]+; ¹H NMR (500 MHz, d⁶-DMSO): δ 8.55 (q, J=5.0 Hz, 1H), 7.97 (dd, J₁=9.0 Hz, J₂=5.5 Hz, 2H), 7.86 (s, 1H), 7.59 (s, 1H), 7.41 (t, J=9.0 Hz, 2H), 4.90 (q, J=6.5 Hz, 1H), 4.13-4.16 (m, 2H), 4.40 (m, 2H), 3.39 (s, 3H), 2.89-2.94 (m, 1H), 2.84 (d, J=4.5 Hz, 3H), 2.43-2.48 (m, 4H), 1.63 (d, J=6.0 Hz) ppm.

Scheme 35b

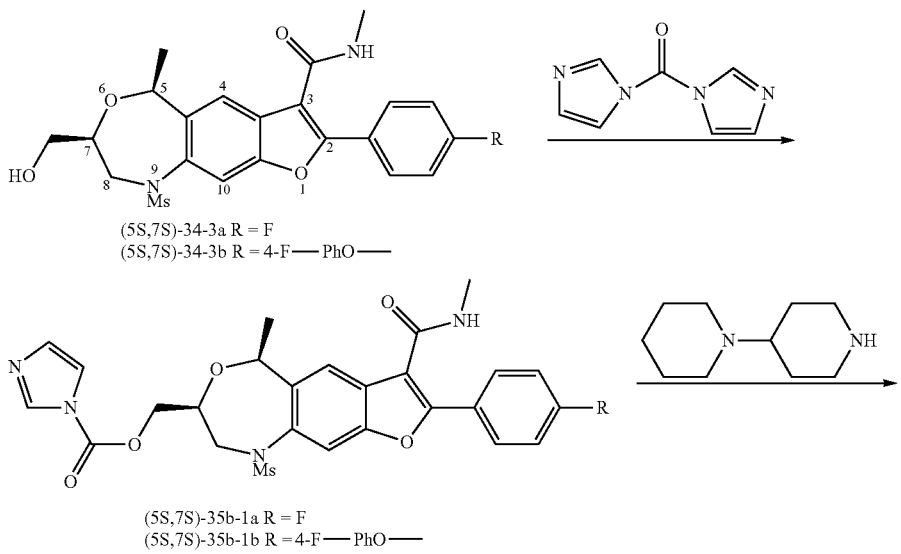

(5S,7S)-34-3a R = F
(5S,7S)-34-3b R = 4-F—PhO—

(5S,7S)-35b-1a R = F
(5S,7S)-35b-1b R = 4-F—PhO—

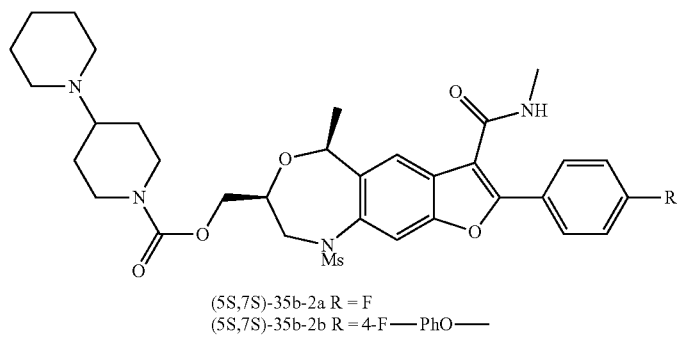

(5S,7S)-35b-2a R = F
(5S,7S)-35b-2b R = 4-F—PhO—

Synthesis of Compound (5S,7S)-35b-2a. Refer to Scheme 35b. To a stirred solution of compound (5S,7S)-34-3a (60 mg, 0.13 mmol) in THF (5 mL) was added 1,1'-carbonyldiimidazole (CDI) (63 mg, 0.39 mmol) at rt. After stirring at rt overnight, compound (5S,7S)-34-3a was completely converted to compound (5S,7S)-35b-1a determined by LC-MS. Subsequently, 1,4'-bipiperidine (327 mg, 1.95 mmol) was added into the reaction mixture. After stirring at rt for 10 hrs, the reaction mixture was concentrated and the residue was dissolved in DCM (25 mL). The mixture was washed with brine and dried with anhydrous $Na_2SO_4$. The solvent was removed and the residue was purified by preparative HPLC to give compound (5S,7S)-35b-2a (50 mg, 59% yield) as a white solid. LC-MS (ESI): m/z 657.1 [M+H]$^+$; $^1$H NMR (500 MHz, d$^6$-DMSO): δ 8.52 (q, J=4.0 Hz, 1H), 7.95-7.98 (m, 2H), 7.84 (s, 1H), 7.85 (s, 1H), 7.40 (t, J=8.5 Hz, 2H), 4.90 (q, J=6.5 Hz, 1H), 3.95-4.14 (m, 6H), 3.38 (s, 3H), 2.91 (br, 1H), 2.84 (d, J=5.0 Hz, 3H), 2.80 (br, 2H), 2.37 (br, 5H), 1.62-1.68 (m, 5H), 1.27-1.46 (m, 8H) ppm.

Scheme 36a

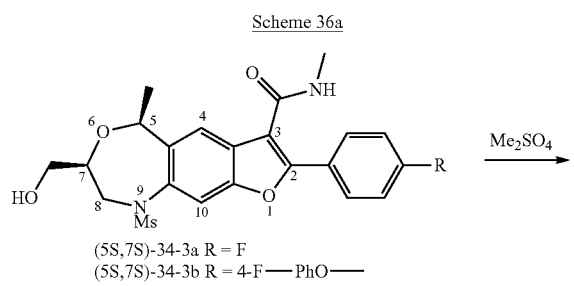

(5S,7S)-34-3a R = F
(5S,7S)-34-3b R = 4-F—PhO—

$\xrightarrow{Me_2SO_4}$

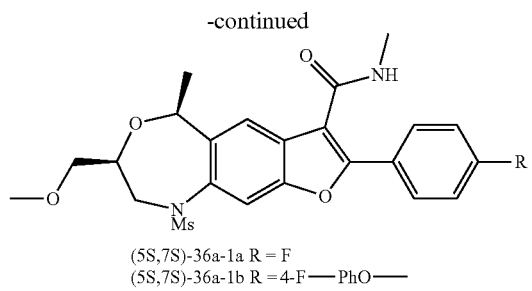

(5S,7S)-36a-1a R = F
(5S,7S)-36a-1b R = 4-F—PhO—

Synthesis of Compound (5S,7S)-36a-1b. Refer to Scheme 36a. To a solution of compound (5S,7S)-34-3b (40 mg, 0.0724 mmol), and NaOH (0.5 mL, 40% (w/w) in $H_2O$) in acetone (3 mL) was added dimethyl sulfate (0.6 mL) at rt. After stirring at rt overnight, the reaction mixture was concentrated and the residue was diluted with DCM (50 mL). The organic layer was washed with brine and dried over anhydrous $Na_2SO_4$. The solvent was removed that the residue was purified by preparative HPLC to give compound (5S,7S)-36a-1b (20 mg, 49% yield) as a white solid. LC-MS (ESI): m/z 569.2 [M+H]$^+$; $^1$H NMR (500 MHz, d$^6$-DMSO): δ 8.50 (q, J=4.5 Hz, 1H), 7.92 (d, J=15.0 Hz, 2H), 7.82 (s, 1H), 7.56 (s, 1H), 7.29 (t, J=17.5 Hz, 2H), 7.17-7.20 (m, 2H), 7.12 (d, J=17.5 Hz, 2H), 4.89 (q, J=6.5 Hz, 1H), 4.13 (d, J=10.5 Hz, 1H), 4.07 (t, J=4.5 Hz, 1H), 3.37-3.40 (m, 1H), 3.37 (s, 3H), 3.27-3.30 (m, 1H), 3.25 (s, 3H), 2.84 (d, J=4.5 Hz, 3H), 1.62 (d, J=6.5 Hz, 3H) ppm.

Synthesis of Compound (5S,7S)-36a-1a. Following the same procedure as that used to prepare compound (5S,7S)-36a-1b and replacing compound (5S,7S)-34-3b with (5S,7S)-34-3a, compound (5S,7S)-36a-1a was obtained as a white solid. LC-MS (ESI): m/z 477.1 [M+H]$^+$; $^1$H NMR (500 MHz, d$^6$-DMSO): δ 8.52 (q, J=3.5 Hz, 1H), 7.97 (dd, $J_1$=8.8 Hz, $J_2$=5.5 Hz, 2H), 7.84 (s, 1H), 7.59 (s, 1H), 7.40 (t, J=8.0 Hz, 2H), 4.90 (q, J=6.0 Hz, 1H), 4.07-4.16 (m, 2H), 3.39 (s, 3H), 3.27-3.38 (m, 2H), 3.27 (s, 3H), 2.84-2.88 (m, 1H), 2.84 (d, J=4.5 Hz, 3H), 1.62 (d, J=6.5 Hz, 3H) ppm.

Scheme 36b
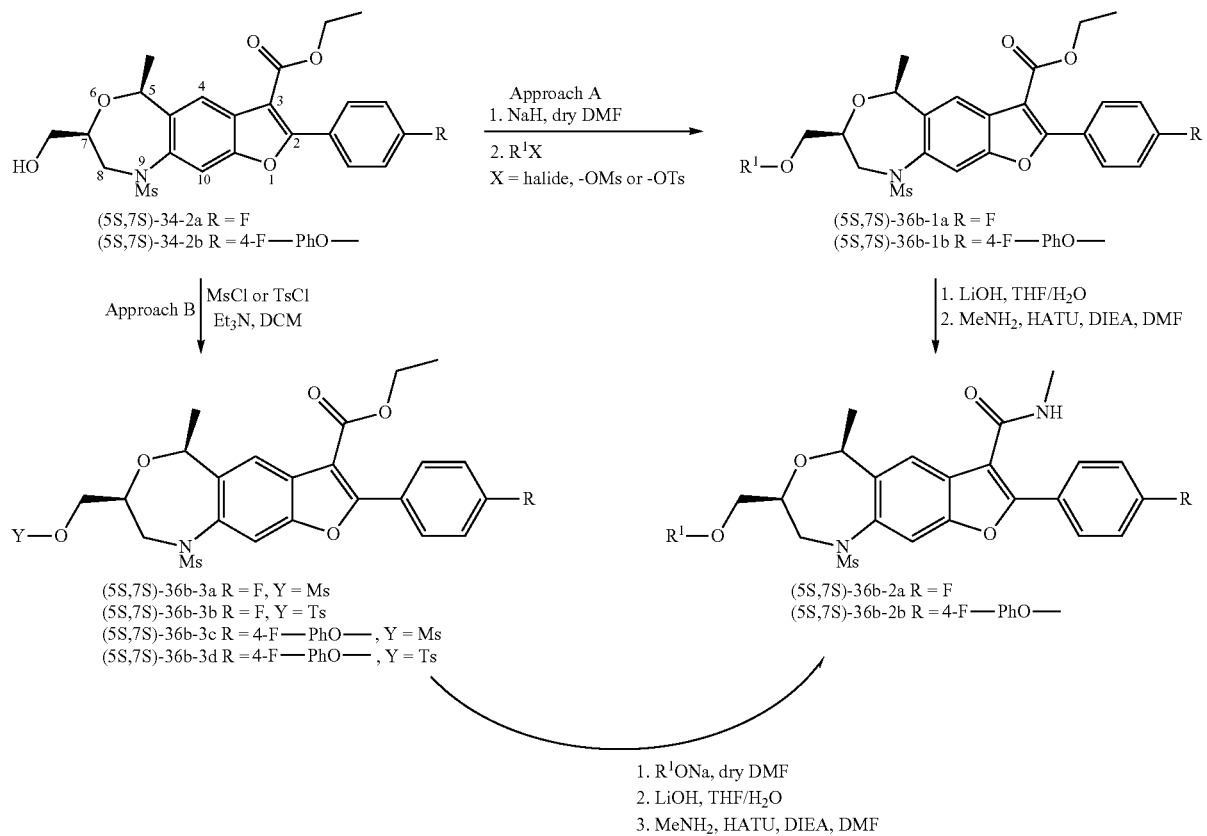
Following either Approach A or B described in Scheme 36b, the following analogs were readily obtained:
| Method | R¹X or R¹ONa | Product | [M + H]⁺ | $^1$H NMR (500 MHz, d$^6$-DMSO) (δ, ppm) |
|---|---|---|---|---|
| A | (methoxyethyl OTs) | (structure) | 521.2 | 8.54 (q, J = 4.5 Hz, 1H), 7.97-7.99 (m 2H), 7.85 (s, 1H), 7.60 (s, 1H), 7.41 (m, 2H), 4.91 (q, J = 6.5 Hz, 1H), 4.24-4.17 (m, 1H), 4.08 (m, 1H), 3.39-3.54 (m, 6H), 3.39 (s, 3H), 3.38 (s, 3H), 2.86-2.89 (m, 1H), 2.85 (d, J = 4.5 Hz, 3H), 1.63 (d, J = 6.5 Hz, 3H) |
| A | (bis-methoxyethoxy OTs) | (structure) | 565.2 | 8.54 (q, J = 4.5 Hz, 1H), 7.97-7.99 (m 2H), 7.84 (s, 1H), 7.60 (s, 1H), 7.40 (m, 2H), 4.91 (q, J = 6.5 Hz, 1H), 4.14-4.17 (m, 1H), 4.08 (m, 1H), 3.32-3.54 (m, 11H), 3.22 (s, 3H), 2.86-2.89 (m, 1H), 2.83 (d, J = 4.5 Hz, 3H), 1.62 (d, J = 6.5 Hz, 3H) |

-continued

| Method | R¹X or R¹ONa | Product | [M + H]⁺ | ¹H NMR (500 MHz, d⁶-DMSO) (δ, ppm) |
|---|---|---|---|---|
| A | (structure with dioxolane-CH₂-OTs) | (product with dimethyl dioxolane ether side chain) | 577.2 | 8.52 (q, J = 4.5 Hz, 1H), 7.95-7.98 (m 2H), 7.84 (s, 1H), 7.59 (s, 1H), 7.40 (t, J = 8.5 Hz, 2H), 4.90 (q, J = 7.0 Hz, 1H), 4.08-4.17 (m, 1H), 3.99 (m, 1H), 3.95-3.98 (m, 1H), 3.57-3.60 (m, 1H), 4.24-4.17 (m, 1H), 3.57-3.60 (m, 1H), 3.38-3.51 (m, 3H0, 3.39 (s, 3H), 2.86-2.89 (m, 1H), 2.84 (d, J = 4.0 Hz, 3H), 1.62 (d, J = 6.5 Hz, 3H), 1.31 (s, 3H), 1.25 (s, 3H) |
| A | (structure with dioxolane-CH₂-OTs) | (product with diol side chain) obtained by treating the compound shown above with aq. HCl | 537.2 | 8.53 (q, J = 4.5 Hz, 1H), 7.97 (dd, J1 = 9.0 Hz, J2 = 5.5 Hz, 2H), 7.84 (s, 1H), 7.59 (s, 1H), 7.40 (t, J = 9.0 Hz, 2H), 4.90 (q, J = 6.5 Hz, 1H), 4.15-4.18 (m, 1H), 4.07-4.08 (m, 1H), 3.29-3.60 (m, 8H), 2.86-2.89 (m, 1H), 2.84 (d, J = 5.0 Hz, 3H), 1.62 (d, J = 6.0 Hz, 3H) |
| B | (tetrahydrofuran-3-ONa) | (product with tetrahydrofuranyloxy side chain) | 533.2 | In CDCl₃: 7.88 (m, 2H), 7.87 (s, 1H), 7.58 (s, 1H), 7.20 (m, 2H), 5.79 (m, 1H), 5.00 (q, J = 6.5 Hz, 1H), 4.25 (m, 1H), 4.14-4.17 (m, 2H), 3.89 (m, 1H), 3.74-3.85 (m, 3H), 3.57 (dd, J₁ = 10.8 Hz, J₂ = 5.0 Hz, 1H), 3.39 (dd, J₁ = 10.0 Hz, J₂ = 5.5 Hz, 1H), 3.17 (s, 3H), 3.12 (m, 3H), 3.09 (d, J = 5.0 Hz, 3H), 1.91-1.99 (m, 2H), 1.73 (d, J = 6.5 Hz, 3H) |
| B | (tetrahydrofuran-3-ONa) | (product with tetrahydrofuranyloxy side chain) | 533.2 | In CDCl₃: 7.89 (m, 2H), 7.87 (s, 1H), 7.58 (s, 1H), 7.20 (m, 2H), 5.78 (m, 1H), 5.00 (q, J = 4.5 Hz, 1H), 4.29 (m, 1H), 4.14-4.24 (m, 2H), 3.76-3.86 (m, 4H), 3.54 (dd, J₁ = 10.0 Hz, J₂ = 5.5 Hz, 1H), 3.42 (dd, J₁ = 10.0 Hz, J₂ = 5.5 Hz, 1H), 3.17 (s, 3H), 2.99-3.15 (m, 3H), 3.00 (d, J = 5.0 Hz, 3H), 1.91-1.99 (m, 2H), 1.73 (d, J = 6.0 Hz, 3H) |

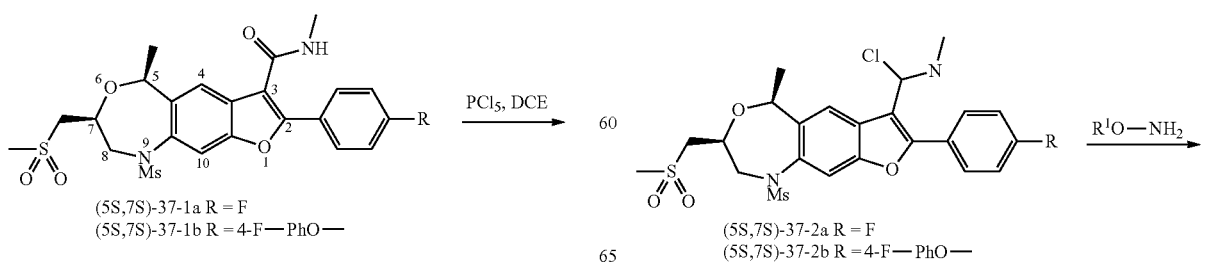

Scheme 37

(5S,7S)-37-1a R = F
(5S,7S)-37-1b R = 4-F—PhO—

→ PCl₅, DCE →

(5S,7S)-37-2a R = F
(5S,7S)-37-2b R = 4-F—PhO—

→ R¹O—NH₂ →

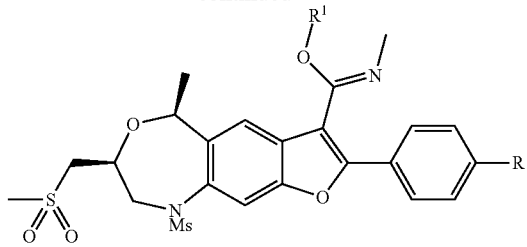

(5S,7S)-37-3a-1 R = F, R¹ = H
(5S,7S)-37-3a-2 R = F, R¹ = Me
(5S,7S)-37-3b-1 R = 4-F—PhO—, R¹ = H
(5S,7S)-37-3b-2 R = 4-F—PhO—, R¹ =Me

Synthesis of Compound (5S,7S)-37-3a-1. Refer to Scheme 37. To a stirred solution of compound (5S,7S)-37-1a (60 mg, 0.115 mmol) in DCE (3 mL) was added PCl₅ (72 mg, 0.344 mmol) at rt. After refluxing for 3 hrs, the reaction mixture was cooled to rt. Subsequently, NH₂OH.HCl (23 mg, 0.344 mmol) and DIPEA (369 mg, 2.86 mmol) were added and the resulting mixture was refluxed for 3 hrs. The mixture was concentrated and the residue was purified by preparative HPLC to give compound (5S,7S)-37-3a-1 (40 mg, 65% yield) as a white solid. LC-MS (ESI): m/z 540.1 [M+H]⁺; ¹H NMR (500 MHz, d⁶-DMSO): δ 9.81 (s, 1H), 8.40 (s, 1H), 7.94-7.97 (m, 2H), 7.90 (s, 1H), 7.46 (s, 1H), 7.37-7.44 (t, 2H), 6.25 (q, J=5.0 Hz, 1H), 4.99 (q, J=6.5 Hz, 1H), 4.40 (t, J=6.5 Hz, 1H), 4.20-4.22 (m, 1H), 3.40 (s, 3H), 3.23 (br, 1H), 3.04 (s, 3H), 2.92-2.97 (br, 1H), 2.48 (d, J=5.5 Hz, 3H), 1.64 (d, J=6.5 Hz, 3H) ppm.

Synthesis of Compound (5S,7S)-37-3a-2. Following the same procedure as that used for the preparation of compound (5S,7S)-37-3a-1 and replacing NH₂OH.HCl with NH₂OMe.HCl, compound (5S,7S)-37-3a-2 (45 mg, 71% yield) was obtained as a white solid. LC-MS (ESI): m/z 554.1 [M+H]⁺; ¹H NMR (500 MHz, d⁶-DMSO): δ 7.94 (m, 2H), 7.89 (s, 1H), 7.47 (s, 1H), 7.43 (m, 2H), 6.48 (q, J=4.5 Hz, 1H), 4.98 (m, 1H), 4.39 (m, 1H), 4.20 (m, 1H), 3.72 (s, 3H), 3.39 (s, 3H), 3.23-3.30 m, 2H), 3.04 (s, 3H), 2.93 (m, 1H), 2.45 (d, J=6.5 Hz, 3H), 1.64 (d, J=6.5 Hz, 3H) ppm.

Scheme 38

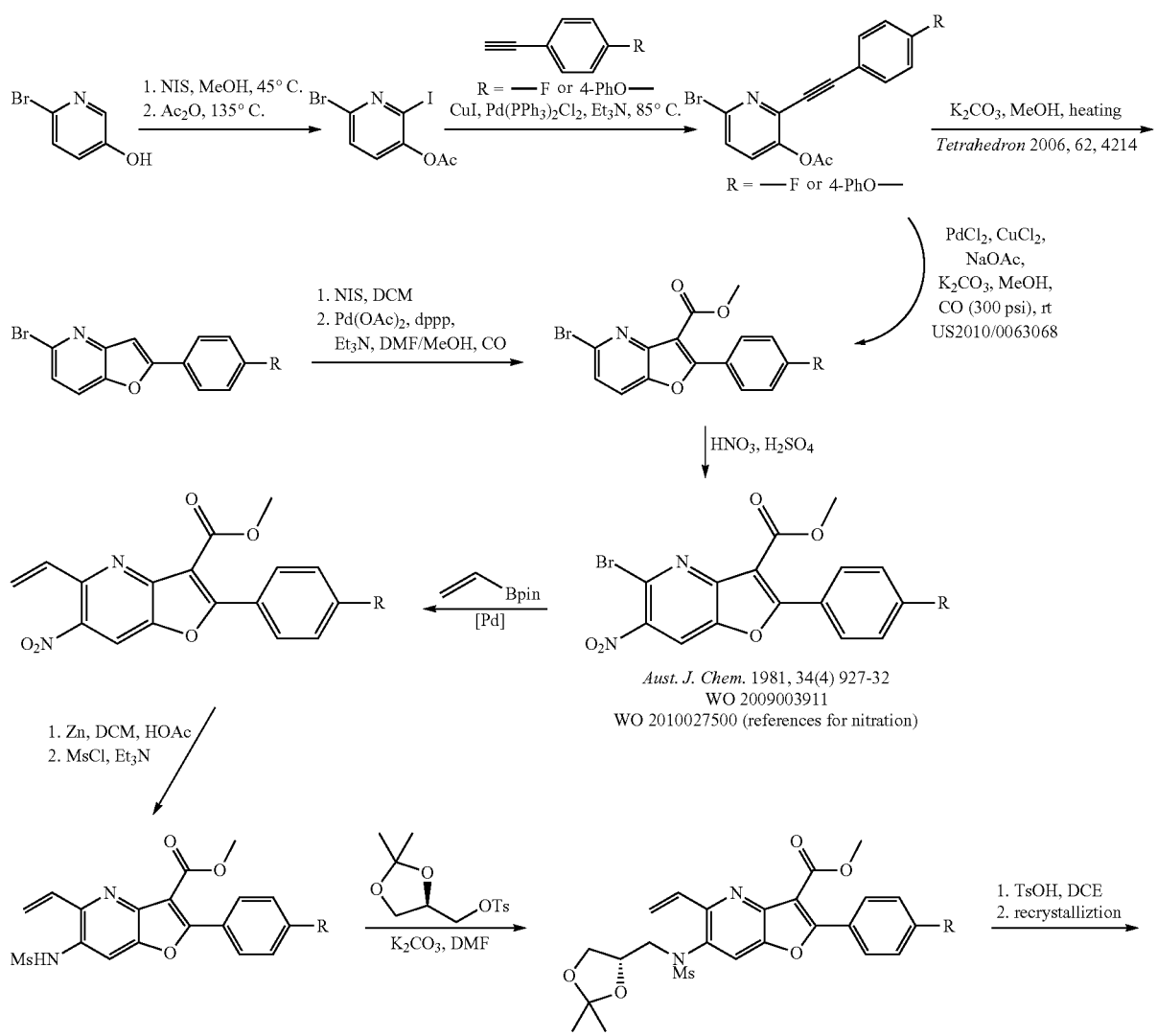

613    614
-continued
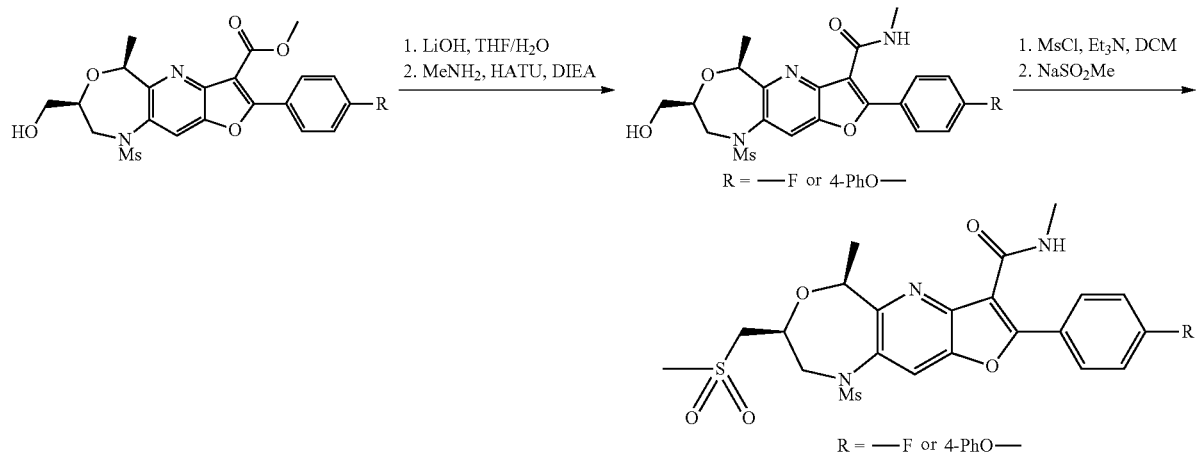
Scheme 39
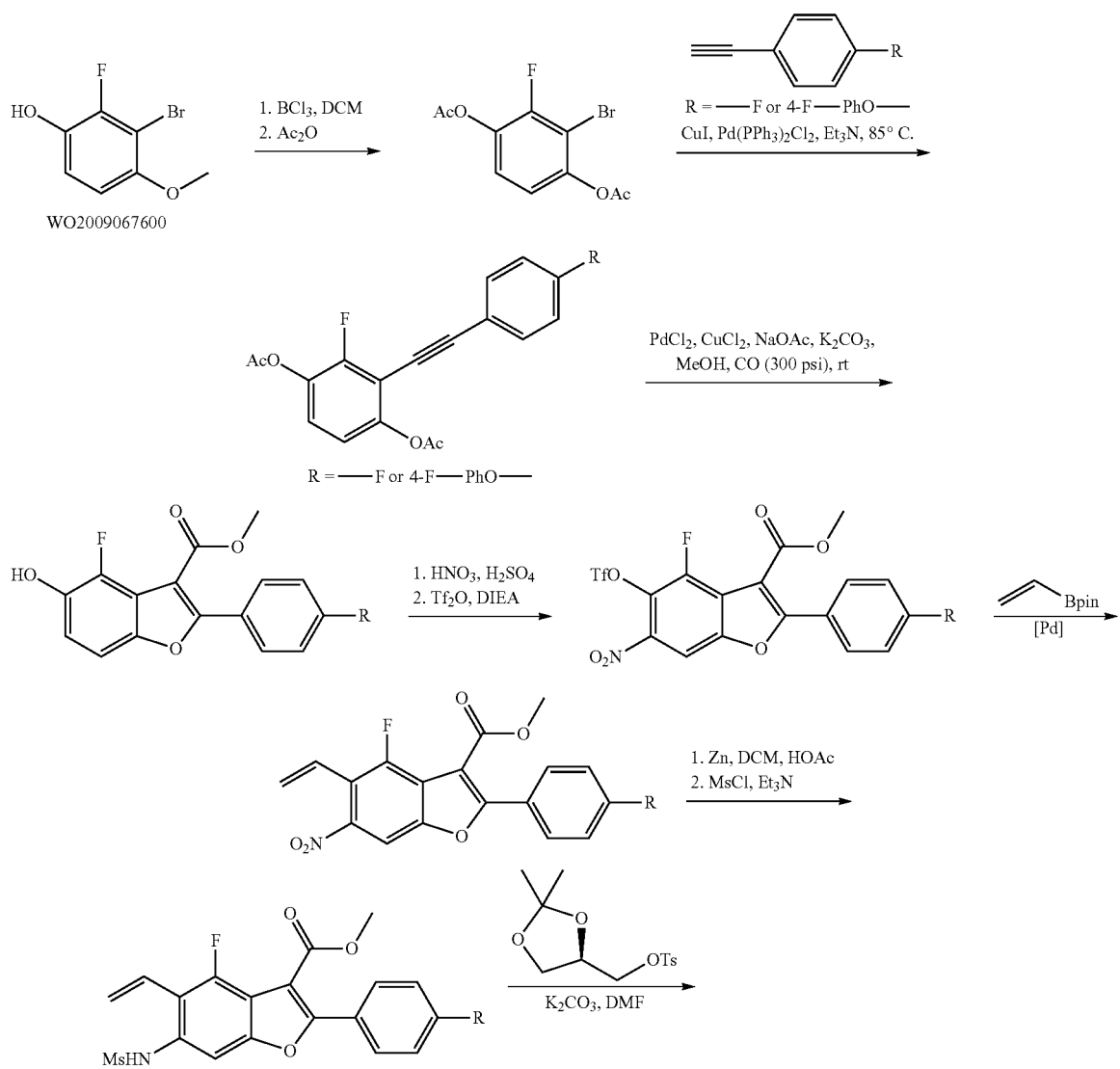

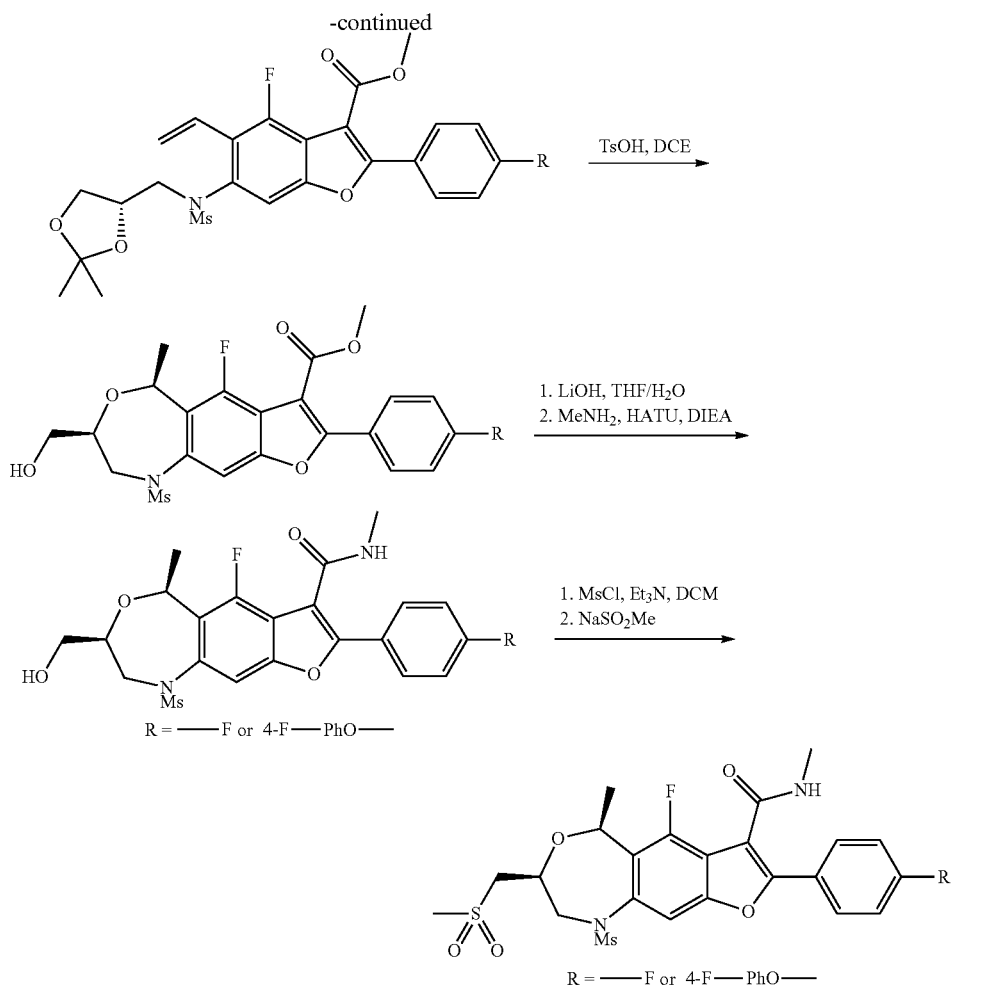
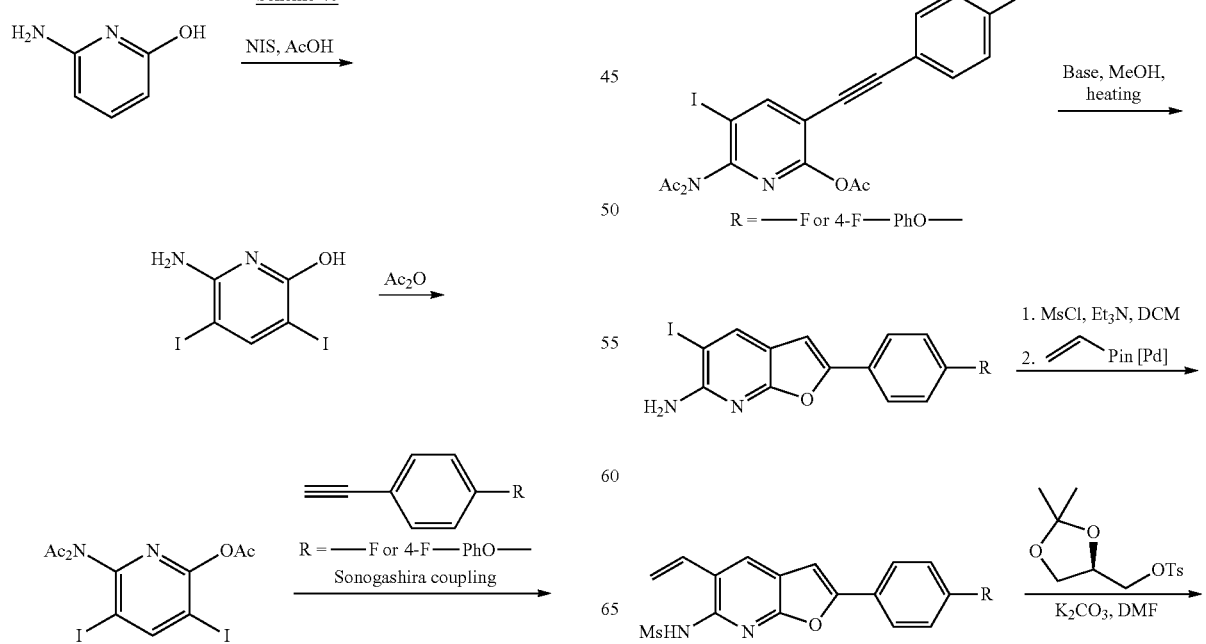
Scheme 40

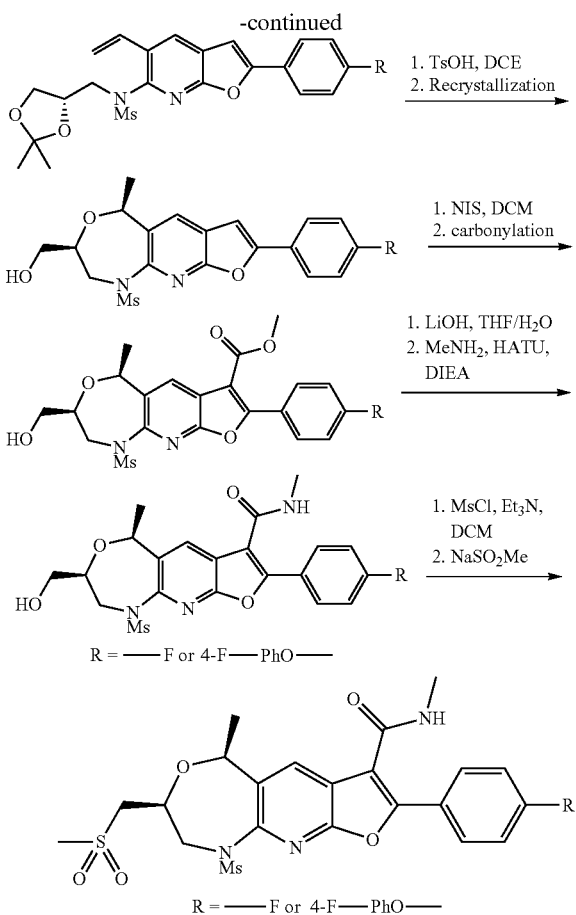

Biological Activity

Biological activity of the compounds of the invention was determined using an HCV replicon assay. The 1b_Huh-Luc/Neo-ET cell line persistently expressing a bicistronic genotype 1b replicon in Huh 7 cells was obtained from ReBLikon GMBH. This cell line was used to test compound inhibition using luciferase enzyme activity readout as a measurement of compound inhibition of replicon levels.

On Day 1 (the day after plating), each compound was added in triplicate to the cells. Plates were incubated for 72 hours prior to running the luciferase assay. Enzyme activity was measured using a Bright-Glo Kit (cat. number E2620) manufactured by Promega Corporation. The following equation was used to generate a percent control value for each compound.

% Control=(Average Compound Value/Average Control)*100

The $EC_{50}$ value was determined using GraphPad Prism and the following equation:

$Y$=Bottom+(Top-Bottom)/(1+10^((Log $IC50$−$X$)*Hill-Slope))

$EC_{50}$ values of compounds were repeated several times in the replicon assay.

Compounds of the invention can inhibit multiple genotypes of HCV selected but not limited to 1a, 1b, 2a, 3a, and 4a. The $EC_{50}$s are measured in the corresponding replicon assays that are similar to HCV 1b replicon assay as described above.

Exemplary compounds of the disclosed invention are illustrated in the Tables attached as Appendix A and Appendix B.

Apendix A shows inhibitory activity of the compound with respect to HCV 1b, 1a, or 2a and HCV NS5B C316Y or S365A mutant as indicated. The biological activity against HCV 1b, 1a, or 2a is indicated as being *, , *, or ****, which corresponds to $EC_{50}$ ranges of $EC_{50}$>1000 nM, 100 nM<$EC_{50}$≤1000 nM, 10 nM<$EC_{50}$≤100 nM, or $EC_{50}$≤10 nM, respectively. The biological activity against HCV NS5B C316Y or S365A mutant is indicated as being †, ††, or \\\, which corresponds to $EC_{50}$ ranges of $EC_{50}$>1000 nM, 200 nM<$EC_{50}$≤1000 nM, 200 nM≤$EC_{50}$, respectively.

Appendix A shows structures of 289 compounds of the invention identified by ID NOD B1-B289, and $EC_{50}$ values determined for 289 of the compounds. Of these, the 191 compounds with the highest measured activity can be divided into two groups. Group 1 compound are those having a measured $EC_{50}$ value, as determined by the concentration of the compound effective to produce a half-maximal inhibition of HCV 1b replication ($EC_{50}$) in a 1b_Huh-Luc/Neo-ET cell line, in accordance with the method above, of 10 nM or less. This group includes the compounds identified in Appendix A by ID NOS: B5, B15, B20, B33, B35, B45, B67, B85, B92, B94, B107, B118, B120, B121, B127, B128, B130, B131, B132, B138, B139, B145, B148, B158, B163, B168, B169, B171, B187, B190, B191, B192, B196, B197, B198, B201, B207, B208, B212, B214, B218, B221, B226, B232, B233, B236, B237, B238, B239, B240, B243, B244, B245, B246, B247, B248, B249, B252, B253, B254, B255, B256, B257, B258, B259, B260, B261, B263, B265, B266, B267, B268, B269, B270, B271, B272, B273, B275, B276, B277, B278, B280, B281, B282, B285, and B286. Group 2 includes those compounds that have a measured $EC_{50}$ of between 10 and 100 nM, and includes compounds identified in Appendix A by ID NOS: B2, B3, B4, B6, B7, B9, B16, B18, B19, B22, B29, B31, B32, B34, B36, B47, B48, B54, B55, B57, B60, B63, B71, B84, B93, B100, B101, B106, B108, B109, B111, B112, B113, B115, B116, B119, B123, B124, B134, B136, B137, B142, B144, B146, B147, B150, B151, B153, B154, B155, B156, B157, B159, B160, B161, B162, B164, B165, B166, B167, B170, B172, B173, B174, B175, B176, B178, B179, B180, B181, B183, B184, B186, B188, B189, B193, B195, B199, B200, B202, B203, B204, B205, B210, B215, B216, B217, B219, B220, B222, B223, B224, B225, B227, B228, B229, B230, B231, B234, B235, B241, B262, B264, B279, and B287.

Pharmaceutical Compositions

Provided herein is a pharmaceutical composition comprising one or more compounds of the invention. The compounds described herein may be formulated in a pharmaceutical composition comprising one or more compounds, optionally together with one or more pharmaceutically acceptable excipients or vehicles, and optionally other therapeutic and/or prophylactic ingredients. Such excipients are known to those of skill in the art. Pharmaceutically acceptable salts can be used in the compositions of the present invention and include, for example, mineral acid salts such as hydrochlorides, hydrobromides, phosphates, sulfates and the like; and the salts of organic acids such as acetates, propionates, malonates, benzoates and the like. A thorough discussion of pharmaceutically acceptable excipients and salts is available in Remington's Pharmaceutical Sciences, 18th Edition (Easton, Pa.: Mack Publishing Company, 1990), and in Handbook of Pharmaceutical Excipients, $6^{th}$ Edition, Ed. R. C. Rowe, P. J. Sheskey, and M. E. Quinn (American Pharmacists Association, 2009).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The compound comprised within the pharmaceutical composition includes isomers, racemic or non-racemic mixtures of isomers, or pharmaceutically acceptable salts or solvates thereof, together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

In yet another aspect, provided herein is the use of the compounds of the invention in the manufacture of a medicament, e.g., for the treatment of hepatitis C.

Also provided is a method of treating hepatitis C. The method comprises administering to a subject in need thereof, a therapeutically effective amount of a compound of the invention, optionally contained in a pharmaceutical composition. A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined and optimized by routine experimentation. The subject may be administered as many doses as is required to reduce and/or alleviate the signs, symptoms or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease.

A treatment regimen using one or more of the compounds provided herein, optionally in combination with one or more anti-HCV agents, will generally involve administering a therapeutically effective dose of the compound, which can readily be determined by one skilled in the art taken into account variables as previously described. A typical dose of a compound as provided herein will generally range from about 10 mg to 1000 mg a day. Representative dosage ranges include from about 10 mg to 900 mg a day, or from about 30 mg to about 700 mg a day, from about 50 mg to about 600 mg a day. A therapeutically effective dosage amount will typically range from 0.1 mg/kg body weight to about 30 mg/kg body weight, or from about 0.1 mg/kg body weight to about 15 mg/kg body weight. The compound may be administered once or multiple times (two to three times) daily, once a week, twice a week, three times a week, etc., over a time course effective to achieve a positive virologic response. Representative courses of treatment include but are not limited to 10 weeks, 12 weeks, 24 weeks, 36 weeks, 48 weeks, and the like. A positive virologic response generally refers to undetectable HCV RNA in serum as measured by PCR and a biochemical response (normalization of aminotransferase levels). Although one may gauge success of treatment by a histologic response (e.g., pathology of liver biopsy), post-treatment biopsies are generally less preferable to an assessment based upon a virologic response.

Generally, treatment by administering a compound as provided herein is effective to result in at least a 2 log reduction in HCV RNA levels over the course of treatment. In some cases HCV RNA will still remain positive (detectable) after a course of treatment, although ideally, treatment is effective to achieve undetectable HCV RNA after completing a round of therapy. Subjects may also be assessed following completion of therapy to confirm maintenance of a positive and sustained virologic response (undetectable HCV RNA levels). Follow-up assessments may be carried out over the course of months or even years following treatment.

Combination Therapy

The compounds of the present invention and their isomeric forms and pharmaceutically acceptable salts thereof are useful in treating and preventing HCV infection alone or when used in combination with other compounds targeting viral or cellular elements or functions involved in the HCV life cycle. Classes of compounds useful in the invention may include, without limitation, all classes of HCV antivirals, both direct-acting and indirect-acting ('cell-targeted' inhibitors of HCV replication). For combination therapies, mechanistic classes of agents that may be useful when combined with the compounds of the present invention include, for example, nucleoside and non-nucleoside inhibitors of the HCV protease inhibitors, helicase inhibitors, NS5A inhibitors, NS4B inhibitors and medicinal agents that functionally inhibit the internal ribosomal entry site (IRES), other NS5B inhibitors and other medicaments that inhibit HCV cell attachment or virus entry, HCV RNA translation, HCV RNA transcription, replication or HCV maturation, assembly or virus release.

Specific compounds in these classes and useful in the invention include, but are not limited to, linear, macrocyclic, and heterocyclic HCV protease inhibitors such as telaprevir (VX-950), boceprevir (SCH-503034), narlaprevir (SCH-900518), ITMN-191 (R-7227), TMC-435350 (a.k.a. TMC-435), MK-7009, MK-5172, BI-201335, BMS-650032, ACH-1625, ACH-2784, ACH-1095 (HCV NS4A protease co-factor inhibitor), AVL-181, AVL-192, VX-813, PHX-1766, PHX-2054, IDX-136, IDX-316, IDX-320, GS-9256, GS-9265, GS-9451, ABT-450, EP-013420 (and congeners) and VBY-376; the nucleosidic HCV polymerase (replicase) inhibitors useful in the invention include, but are not limited to, R7128, PSI-7851, PSI-7977 (GS-7977), PSI-938, PSI-879, PSI-6130, IDX-184, IDX-102, INX-189, R1479, R1626, UNX-08189, and various other nucleoside and nucleotide analogs and HCV inhibitors including, but not limited to, those derived from 2'-C-methyl modified nucleos(t)ides, 4'-aza modified nucleos(t)ides, and 7'-deaza modified nucleos(t)ides. NS5A inhibitors useful in the invention, include, but are not limited to, PPI-461, PPI-668, BMS-790052, BMS-824393, GS-5885, EDP-239, ACH-2928, AZD-7295, IDX-719, IDX-380, ABT-267, GSK-2336805, CF-102, A-831 and ITMN-9916. Non-nucleosidic HCV polymerase (replicase) inhibitors useful in the invention, include, but are not limited to, VCH-759, VCH-916, VCH-222, ANA-598, MK-3281, ABT-333, ABT-072, PF-00868554 (filibuvir), BI-207127, GS-9190, A-837093, GSK-625433, JKT-109, GL-59728 and GL-60667. HCV P7 inhibitors useful in the present invention include BIT-225 and other P7 inhibitors, as well as HCV NS4B inhibitors including but not limited to histamine agents that antagonize HCV NS4B function.

In addition, NS5B inhibitors of the present invention may be used in combination with cyclophyllin and immunophyllin antagonists (eg, without limitation, DEBIO compounds, NM-811, SCY-635, EP-CyP282, as well as cyclosporine and its derivatives), kinase inhibitors, inhibitors of heat shock proteins (e.g., HSP90 and HSP70), other immunomodulatory agents that may include, without limitation, interferons (-alpha, -beta, -omega, -gamma, -lambda or synthetic) such as Intron A™, Roferon-A™, Canferon-A300™, Advaferon™, Infergen™, Humoferon™, Sumiferon MP™, Alfaferone™, IFN-β™, Feron™ and the like; polyethylene glycol derivatized (pegylated) interferon compounds, such as PEG interferon-α-2a (Pegasys™) PEG interferon-α-2b (PEGIntron™), pegylated IFN-α-con1 and the like; long acting formulations and derivatizations of interferon compounds such as the albumin-fused interferon, Albuferon™ Locteron™ and the like; interferons with various types of controlled delivery systems (e.g. ITCA-638, omega-interferon delivered by the DUROS™ subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773, SD-101, IMO-2125, and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as GI-5005, TG-4040, InnoVac C, HCV E1E2/MF59 and the like. In addition, any of the above-described methods involving administering an NS5B inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL™, REMICADE™ and HUMIRA™.

NS5B inhibitors of the present invention may also be used with alternative forms of interferons and pegylated interferons, ribavirin or its analogs (e.g., tarabavarin, levoviron), microRNA, small interfering RNA compounds (e.g., SIR-PLEX-140-N and the like) and microRNA agents (such as micro-RNA-122), nucleotide or nucleoside analogs, multifunction inhibitors such as nitazoxanide, immunoglobulins, hepatoprotectants, anti-inflammatory agents and other direct and indirect inhibitors of HCV replication. Inhibitors of other targets in the HCV life cycle include NS3 helicase inhibitors; NS4A co-factor inhibitors; antisense oligonucleotide inhibitors, such as ISIS-14803, ISIS-11, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors.

Other illustrative HCV inhibitor compounds include those disclosed in the following publications: U.S. Pat. Nos. 5,807, 876; 6,498,178; 6,344,465; 6,054,472; 7,759,495; 7,704,992; 7,741,347; WO 02/04425; WO 03/007945; WO 03/010141; WO 03/000254; WO 03/037895; WO 02/100851; WO 02/100846; EP 1256628; WO 02/18369; WO 05/073216; WO 05/073195; WO 08/021,927; US 20080050336; US 20080044379; US 2009004716; US 20090043107; US 20090202478; US 20090068140; WO 10/096302; US 20100068176; WO 10/094977; WO 07/138242; WO 10/096462; US 2010091413; WO 10/075380; WO 10/062821; WO 10/09677; WO 10/065681 and WO 10/065668.

Additionally, combinations of, for example, ribavirin a NS3 protease inhibitor, a replicase inhibitor and interferon, may be administered as multiple combination therapy with at least one of the compounds of the present invention. The present invention is not limited to the aforementioned classes or compounds and contemplates known and new compounds and combinations of biologically active agents (see, for example, Klebl et al. "Host cell targets in HCV therapy: novel strategy or proven practice, *Antiviral Chemistry & Chemotherapy* 16:69-90, which is incorporated by reference herein). It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

APPENDIX A

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B1 | 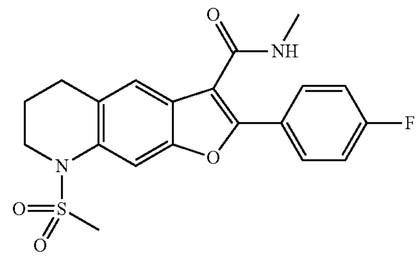 [SMILES: CNC(=O)c1c(-c2ccc(F)cc2)oc2cc3c(cc12)CCCN3S(C)(=O)=O] | ** (100 nM < EC$_{50}$ ≤ 1000 nM) | ††† (EC$_{50}$ ≤ 200 nM) | ††† (EC$_{50}$ ≤ 200 nM) | 403.1 |
| B2 | 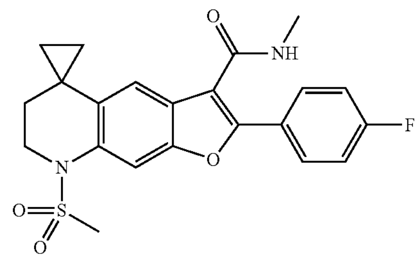 [SMILES: CNC(=O)c1c(-c2ccc(F)cc2)oc2cc3c(cc12)C1(CCN3S(C)(=O)=O)CC1] | *** (10 nM < EC50 ≤ 100 nM) | | | 429.1 |
| B3 | 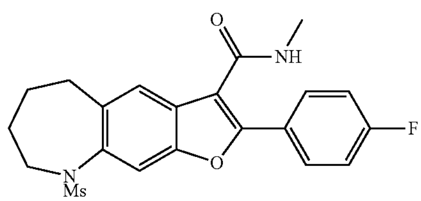 | *** | | | 417.1 |
| B4 | 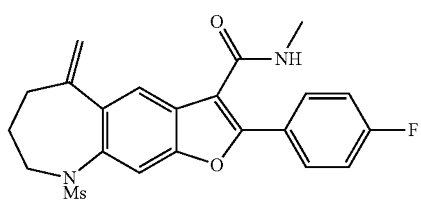 | *** | | | 429.1 |
| B5 | 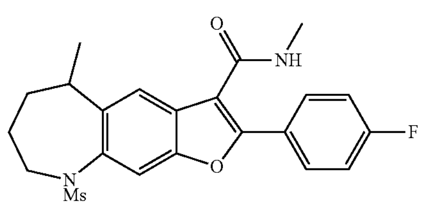 | **** (EC$_{50}$ ≤ 10 nM) | | | 431.1 |
| B6 | 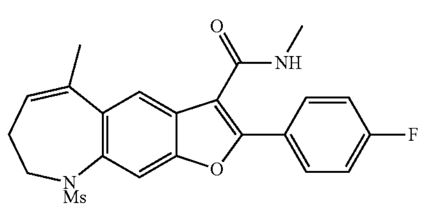 | *** | | | 429.1 |
| B7 | 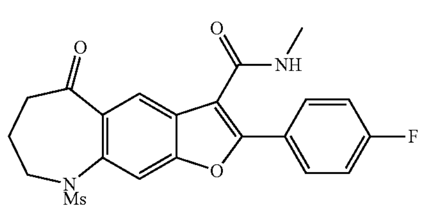 | *** | | | 431.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B8 | 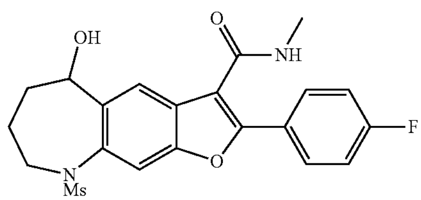 | EC$_{50}$ = 106.5 nM | | | 433.1 |
| B9 | 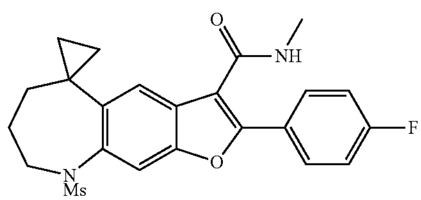 | *** | | | 443.1 |
| B10 | 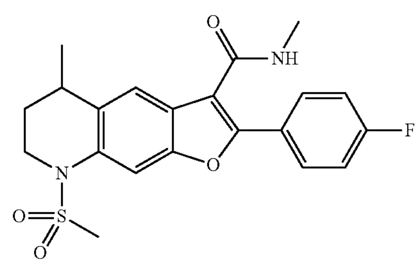 [SMILES: CNC(=O)c1c(-c2ccc(F)cc2)oc2cc3c(cc12)C(C)CCN3S(C)(=O)=O] | ** (HCV genotype 2a replicon assay) | | | 417.1 |
| B11 | 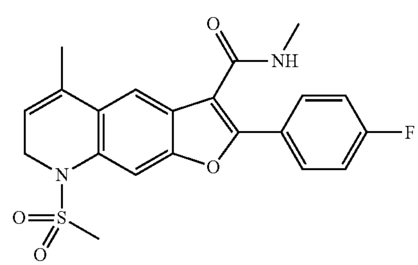 [SMILES: CNC(=O)c1c(-c2ccc(F)cc2)oc2cc3c(cc12)C(C)=CCN3S(C)(=O)=O] | * (EC$_{50}$ > 1000 nM) (HCV genotype 2a replicon) | | | 415.1 |
| B12 | 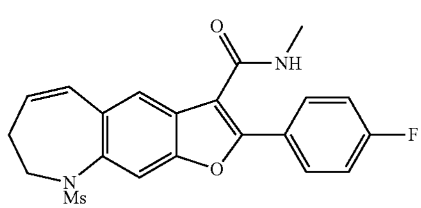 | ** (HCV genotype 2a replicon) | | | 415.1 |
| B13 | 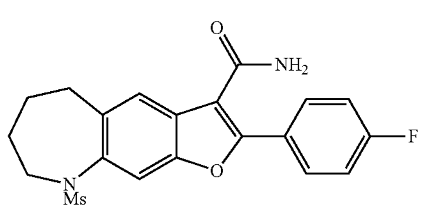 | * (HCV genotype 2a replicon) | | | 403.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B14 | 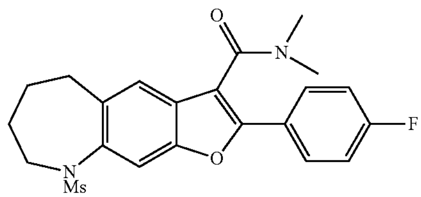 | * (HCV genotype 2a replicon) | | | 431.1 |
| B15 | Chirality was tentatively assigned | 5.5 nM | ††† | ††† | 431.1 |
| B16 | Chirality was tentatively assigned | 45.7 nM | | | 431.1 |
| B17 | 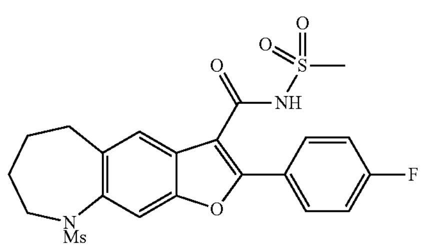 | | | | 481.1 |
| B18 | 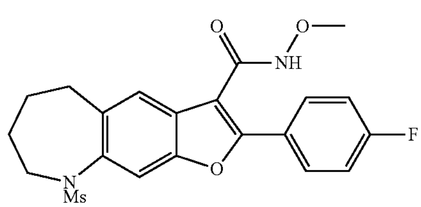 | *** | | | 433.1 |
| B19 | 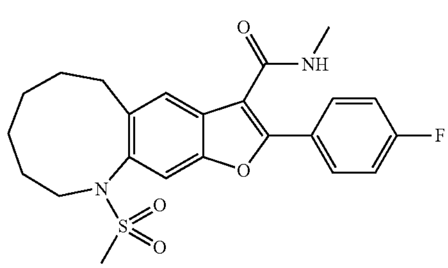 [SMILES: CNC(=O)c1c(-c2ccc(F)cc2)oc2cc3c(cc12)CCCCCCN3S(C)(=O)=O] | *** | | | 445.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B20 | 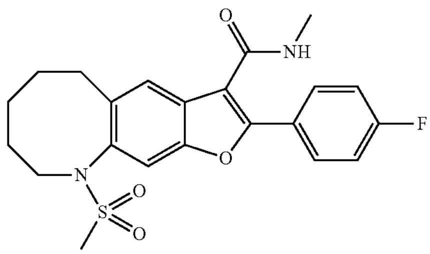 [SMILES: CNC(=O)c1c(-c2ccc(F)cc2)oc2cc3c(cc12)CCCCCN3S(C)(=O)=O] | **** | | | 431.1 |
| B21 | 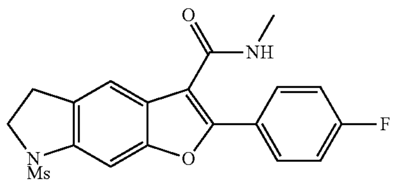 | ** | | | 389.1 |
| B22 | 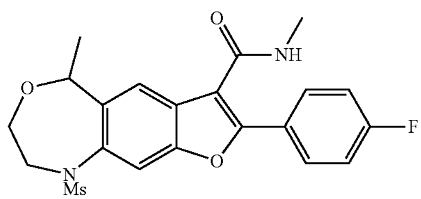 | *** | | | 433.1 |
| B23 | 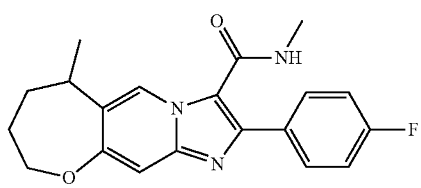 [SMILES: CNC(=O)c1c(-c2ccc(F)cc2)nc2cc3c(cn12)C(C)CCCO3] | | | | 354.2 |
| B24 | 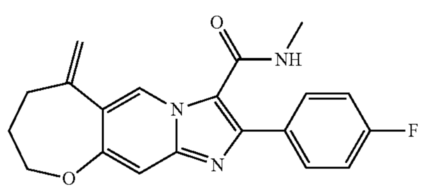 [SMILES: C=C1CCCOc2cc3nc(-c4ccc(F)cc4)c(C(=O)NC)n3cc21] | | | | 352.1 |
| B25 | 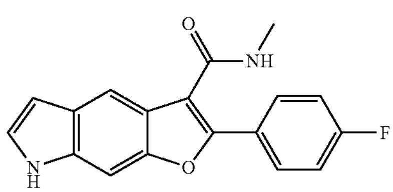 [SMILES: CNC(=O)c1c(-c2ccc(F)cc2)oc2cc3[nH]ccc3cc12] | * | | | 309.1 |
| B26 | 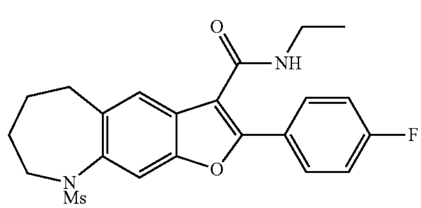 | | | | 431.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B27 | 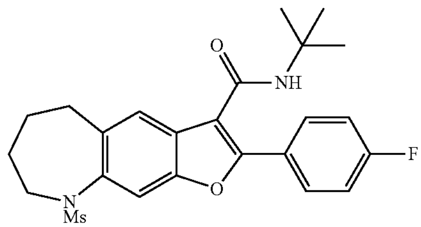 | | | | 459.2 |
| B28 | 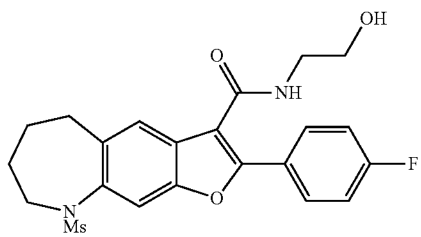 | | | | 447.1 |
| B29 | 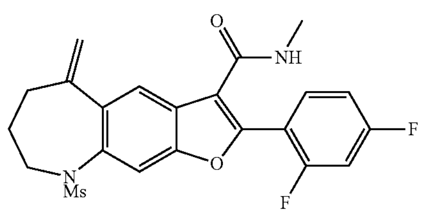 | EC$_{50}$ = 56.1 nM | | | 447.1 |
| B30 | 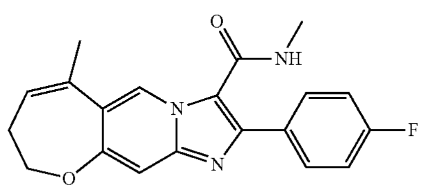 [SMILES: CNC(=O)c1c(-c2ccc(F)cc2)nc2cc3c(cn12)C(C)=CCCO3] | * | | | 352.1 |
| B31 | 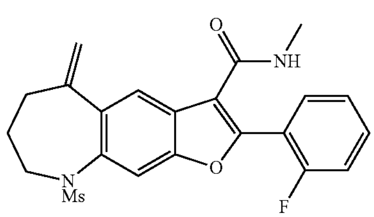 | *** | | | 429.1 |
| B32 | 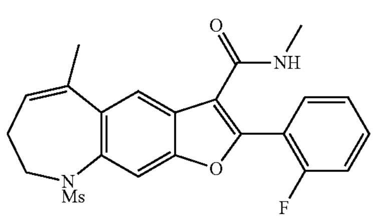 | *** | | | 429.1 |
| B33 | 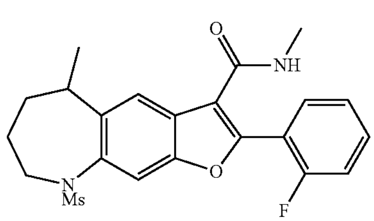 | **** | | | 431.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]⁺ |
|---|---|---|---|---|---|
| B34 | 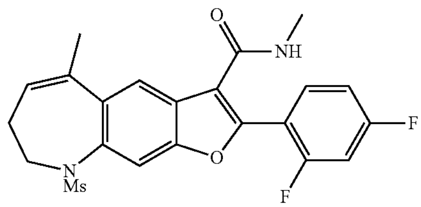 | *** | | | 447.1 |
| B35 | 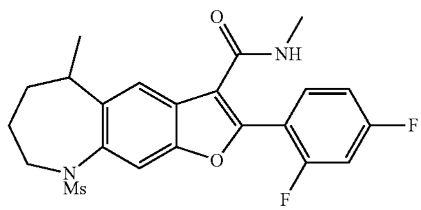 | **** | | | 449.1 |
| B36 | 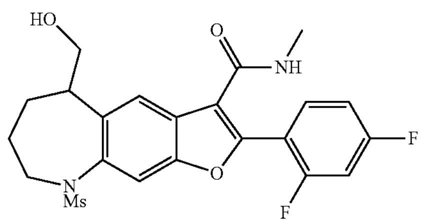 | *** | | | 465.1 |
| B37 | 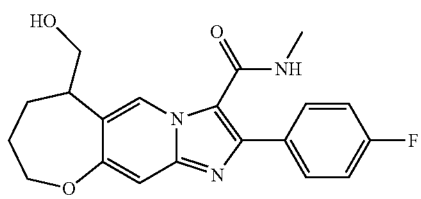 [SMILES: CNC(=O)c1c(-c2ccc(F)cc2)nc2cc3c(cn12)C(CO)CCCO3] | | | | 370.1 |
| B38 | 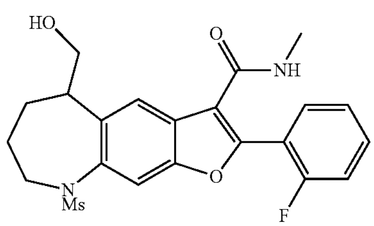 | | | | 447.1 |
| B39 | 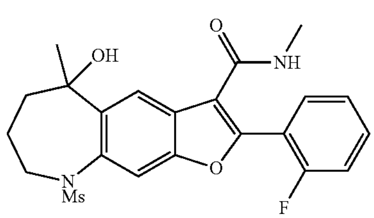 | | | | 447.1 |
| B40 | 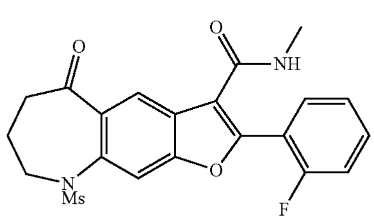 | | | | 431.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B41 | 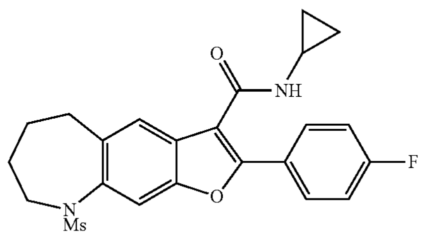 | * (HCV genotype 2a replicon) | | | 443.1 |
| B42 | 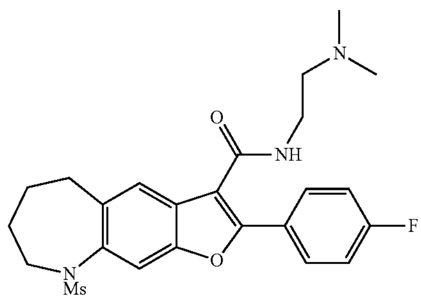 | * (HCV genotype 2a replicon) | | | 474.2 |
| B43 | 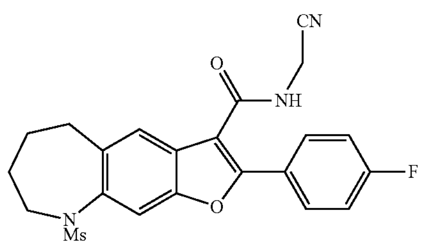 | * (HCV genotype 2a replicon) | | | 442.1 |
| B44 | (absolute configuration) | ** (HCV genotype 2a replicon) | | | 433.1 |
| B45 | (absolute configuration) | 3.0 nM | ††† | ††† | 433.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B46 | 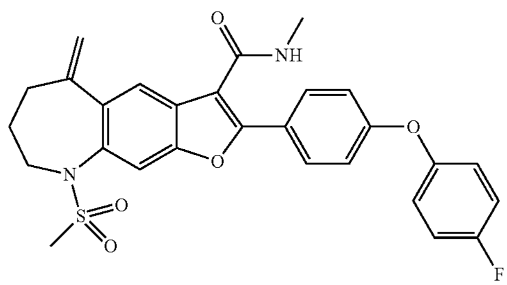 [SMILES: C=C1CCCN(S(C)(=O)=O)c2cc3oc(-c4ccc(Oc5ccc(F)cc5)cc4)c(C(=O)NC)c3cc21] | ** | | | 521.1 |
| B47 | 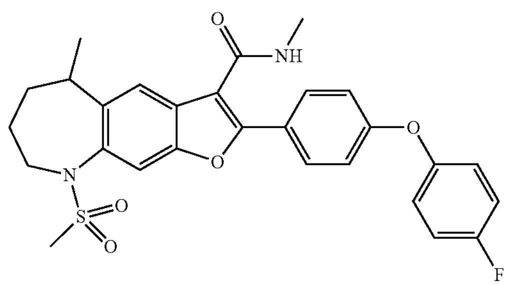 | *** | | | 523.2 |
| B48 | 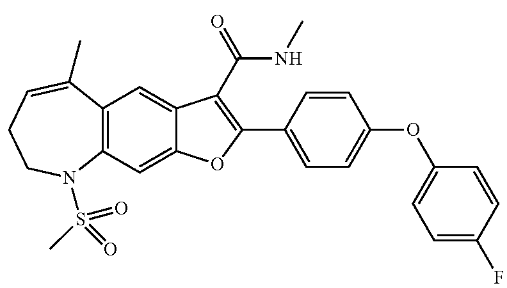 [SMILES: CNC(=O)c1c(-c2ccc(Oc3ccc(F)cc3)cc2)oc2cc3c(cc12)C(C)=CCCN3S(C)(=O)=O] | *** | | | 521.1 |
| B49 | 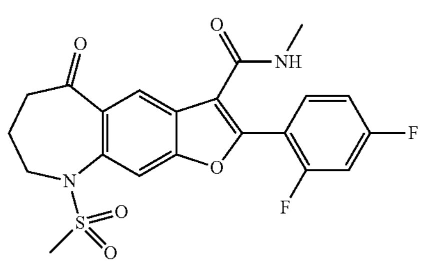 [SMILES: CNC(=O)c1c(-c2ccc(F)cc2F)oc2cc3c(cc12)C(=O)CCCN3S(C)(=O)=O] | ** | | | 449.1 |
| B50 | 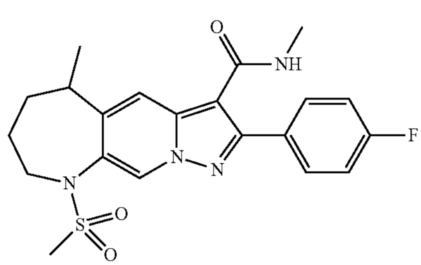 [SMILES: CNC(=O)c1c(-c2ccc(F)cc2)nn2cc3c(cc12)C(C)CCCN3S(C)(=O)=O] | ** | | | 431.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B51 | Chirality was tentatively assigned | * | | | 431.1 |
| B52 | Chirality was tentatively assigned | ** | | | 431.1 |
| B53 | 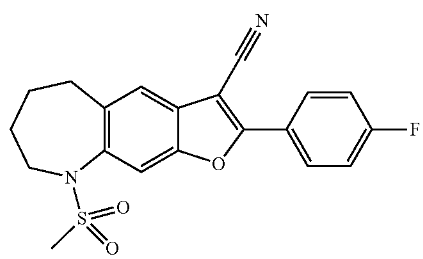 [SMILES: CS(=O)(=O)N1CCCCc2cc3c(C#N)c(-c4ccc(F)cc4)oc3cc21] | * | | | 385.1 |
| B54 | 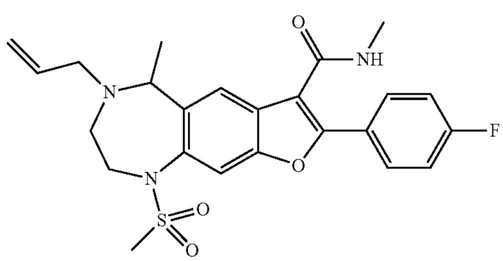 [SMILES: C=CCN1CCN(S(C)(=O)=O)c2cc3oc(-c4ccc(F)cc4)c(C(=O)NC)c3cc2C1C] | *** | | | 472.2 |
| B55 | 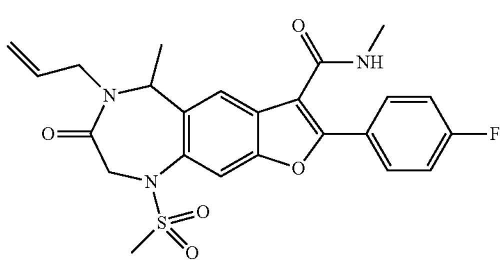 [SMILES: C=CCN1C(=O)CN(S(C)(=O)=O)c2cc3oc(-c4ccc(F)cc4)c(C(=O)NC)c3cc2C1C] | *** | | | 486.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B56 | 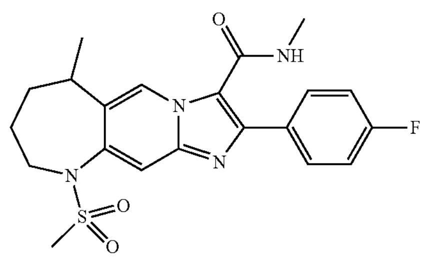 [SMILES: CNC(=O)c1c(-c2ccc(F)cc2)nc2cc3c(cn12)C(C)CCCN3S(C)(=O)=O] | ** | | | 431.1 |
| B57 | 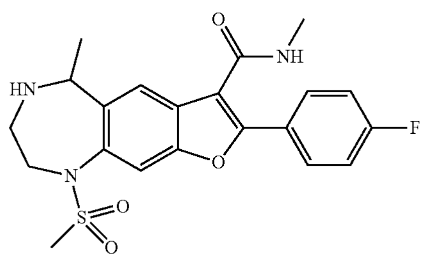 [SMILES: CNC(=O)c1c(-c2ccc(F)cc2)oc2cc3c(cc12)C(C)NCCN3S(C)(=O)=O] | *** | | | 432.1 |
| B58 | 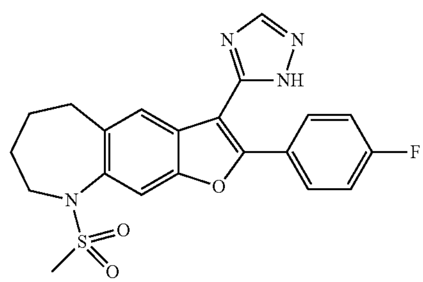 [SMILES: CS(=O)(=O)N1CCCCc2cc3c(-c4ncn[nH]4)c(-c4ccc(F)cc4)oc3cc21] | ** | | | 427.1 |
| B59 | 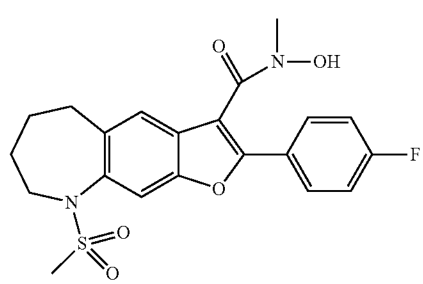 [SMILES: CN(O)C(=O)c1c(-c2ccc(F)cc2)oc2cc3c(cc12)CCCCN3S(C)(=O)=O] | ** | | | 433.1 |
| B60 | 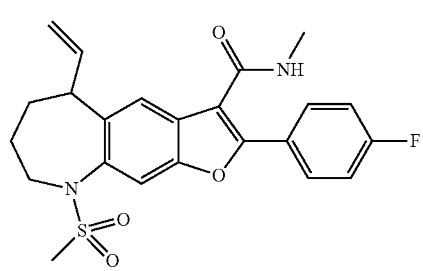 [SMILES: C=CC1CCCN(S(C)(=O)=O)c2cc3oc(-c4ccc(F)cc4)c(C(=O)NC)c3cc21] | *** (HCV genotype 2a replicon) | | | 443.1 |

APPENDIX A-continued
| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B61 | 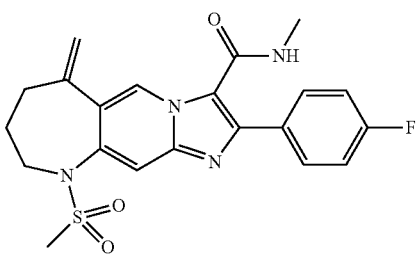 [SMILES: C=C1CCCN(S(C)(=O)=O)c2cc3nc(-c4ccc(F)cc4)c(C(=O)NC)n3cc21] | *<br>(HCV genotype 2a replicon) | | | 429.1 |
| B62 | 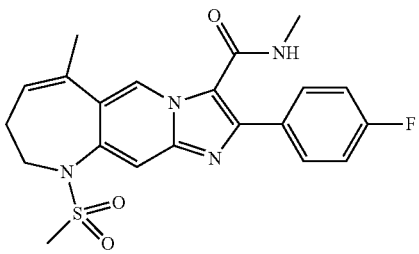 [SMILES: CNC(=O)c1c(-c2ccc(F)cc2)nc2cc3c(cn12)C(C)=CCCN3S(C)(=O)=O] | *<br>(HCV genotype 2a replicon) | | | 429.1 |
| B63 | 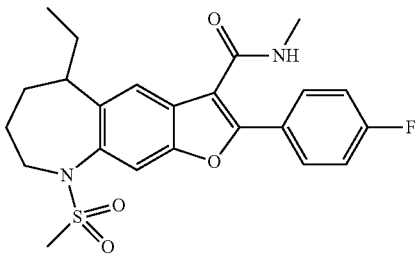 [SMILES: CCC1CCCN(S(C)(=O)=O)c2cc3oc(-c4ccc(F)cc4)c(C(=O)NC)c3cc21] | ***<br>(HCV genotype 2a replicon) | | | 445.2 |
| B64 | 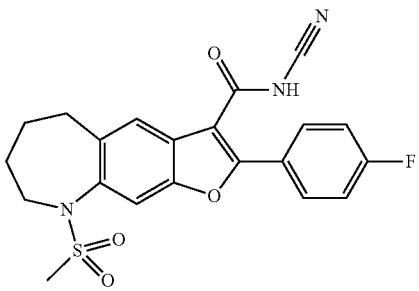 [SMILES: CS(=O)(=O)N1CCCCc2cc3c(C(=O)NC#N)c(-c4ccc(F)cc4)oc3cc21] | *<br>(HCV genotype 2a replicon) | | | 428.1 |
| B65 | 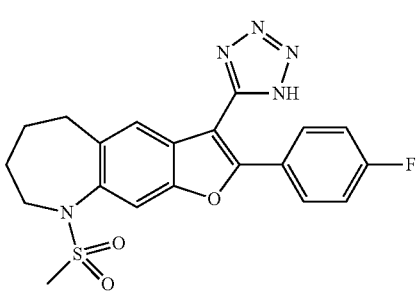 [SMILES: CS(=O)(=O)N1CCCCc2cc3c(-c4nnn[nH]4)c(-c4ccc(F)cc4)oc3cc21] | *<br>(HCV genotype 2a replicon) | | | 428.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B66 | 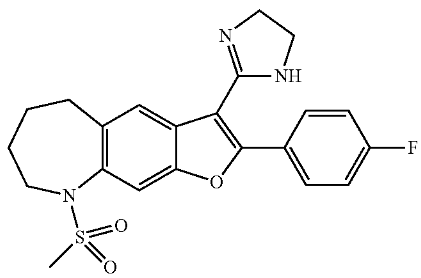 [SMILES: CS(=O)(=O)N1CCCCc2cc3c(C4=NCCN4)c(-c4ccc(F)cc4)oc3cc21] | * (HCV genotype 2a replicon) | | | 428.1 |
| B67 | 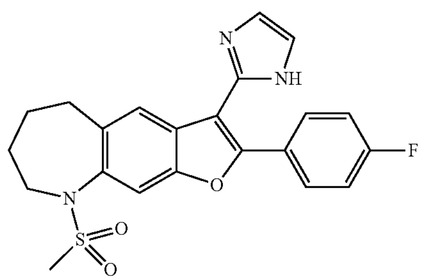 [SMILES: CS(=O)(=O)N1CCCCc2cc3c(-c4ncc[nH]4)c(-c4ccc(F)cc4)oc3cc21] | 5.2 nM | ††† | †† (200 nM < EC$_{50}$ < 1000 nM) | 426.1 |
| B68 | 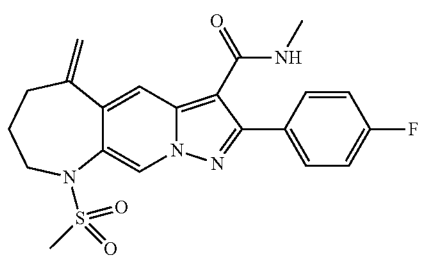 [SMILES: C=C1CCCN(S(C)(=O)=O)c2cn3nc(-c4ccc(F)cc4)c(C(=O)NC)c3cc21] | * (HCV genotype 2a replicon) | | | 429.1 |
| B69 | 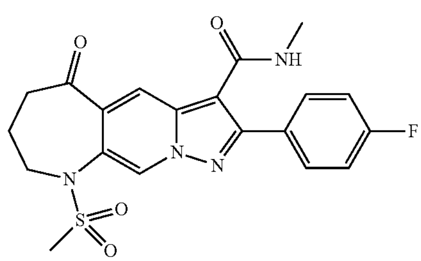 [SMILES: CNC(=O)c1c(-c2ccc(F)cc2)nn2cc3c(cc12)C(=O)CCCN3S(C)(=O)=O] | * (HCV genotype 2a replicon) | | | 431.1 |
| B70 | 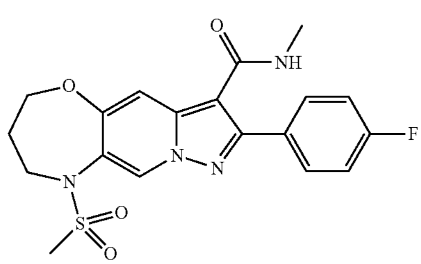 [SMILES: CNC(=O)c1c(-c2ccc(F)cc2)nn2cc3c(cc12)OCCCN3S(C)(=O)=O] | * (HCV genotype 2a replicon) | | | 419.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]⁺ |
|---|---|---|---|---|---|
| B71 | 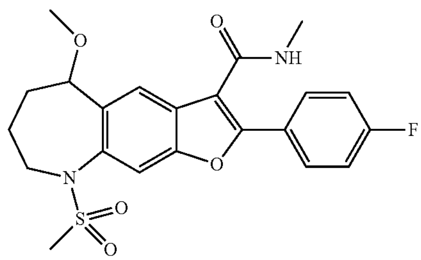 [SMILES: CNC(=O)c1c(-c2ccc(F)cc2)oc2cc3c(cc12)C(OC)CCCN3S(C)(=O)=O] | *** (HCV genotype 2a replicon) | | | 447.1 |
| B72 | 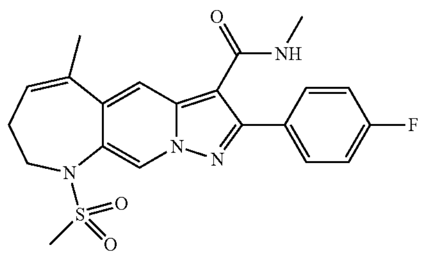 [SMILES: CNC(=O)c1c(-c2ccc(F)cc2)nn2cc3c(cc12)C(C)=CCCN3S(C)(=O)=O] | * (HCV genotype 2a replicon) | | | 429.1 |
| B73 | 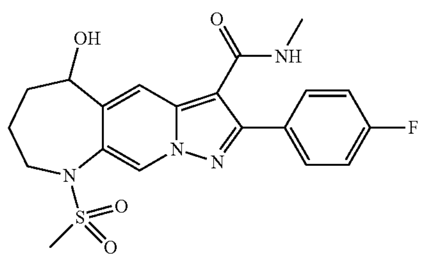 [SMILES: CNC(=O)c1c(-c2ccc(F)cc2)nn2cc3c(cc12)C(O)CCCN3S(C)(=O)=O] | * (HCV genotype 2a replicon) | | | 433.1 |
| B74 | 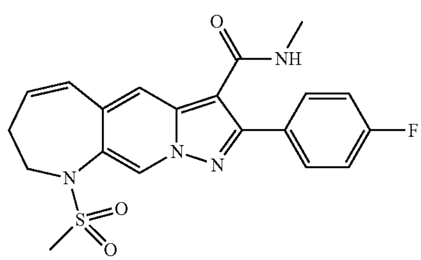 [SMILES: CNC(=O)c1c(-c2ccc(F)cc2)nn2cc3c(cc12)C=CCCN3S(C)(=O)=O] | * (HCV genotype 2a replicon) | | | 415.1 |
| B75 | 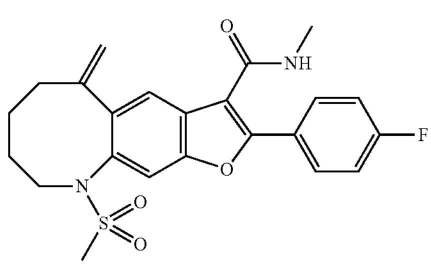 [SMILES: C=C1CCCCN(S(C)(=O)=O)c2cc3oc(-c4ccc(F)cc4)c(C(=O)NC)c3cc21] | ** (HCV genotype 2a replicon) | | | 443.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B76 | 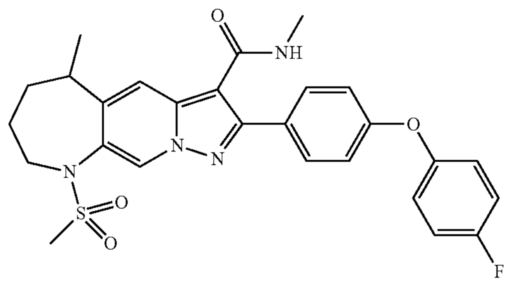 [SMILES: CNC(=O)c1c(-c2ccc(Oc3ccc(F)cc3)cc2)nn2cc3c(cc12)C(C)CCCN3S(C)(=O)=O] | ** (HCV genotype 2a replicon) | | | 523.2 |
| B77 | 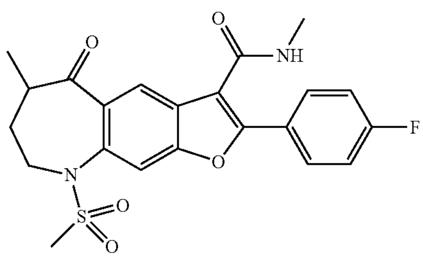 [SMILES: CNC(=O)c1c(-c2ccc(F)cc2)oc2cc3c(cc12)C(=O)C(C)CCN3S(C)(=O)=O] | ** (HCV genotype 2a replicon) | | | 445.1 |
| B78 | 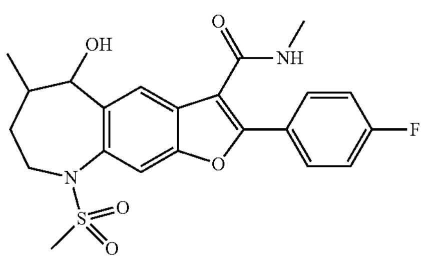 [SMILES: CNC(=O)c1c(-c2ccc(F)cc2)oc2cc3c(cc12)C(O)C(C)CCN3S(C)(=O)=O] | ** (HCV genotype 2a replicon) | | | 447.1 |
| B79 | 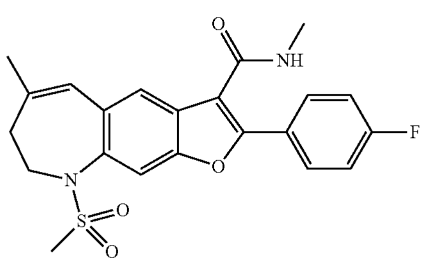 [SMILES: CNC(=O)c1c(-c2ccc(F)cc2)oc2cc3c(cc12)C=C(C)CCN3S(C)(=O)=O] | * (HCV genotype 2a replicon) | | | 429.1 |
| B80 | 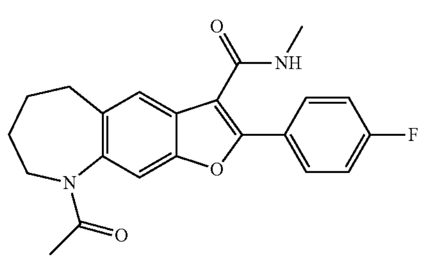 [SMILES: CNC(=O)c1c(-c2ccc(F)cc2)oc2cc3c(cc12)CCCCN3C(C)=O] | * (HCV genotype 1a replicon) | | | 381.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B81 | 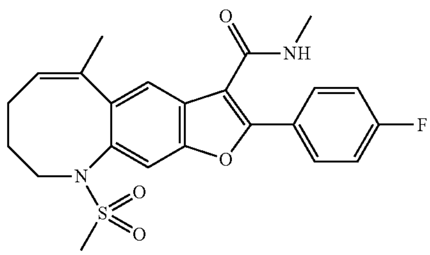 [SMILES: CNC(=O)c1c(-c2ccc(F)cc2)oc2cc3c(cc12)/C(C)=C\CCCN3S(C)(=O)=O] | ** (HCV genotype 1a replicon) | | | 443.1 |
| B82 | 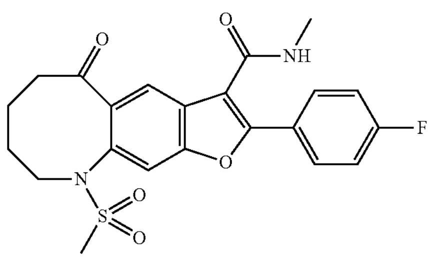 [SMILES: CNC(=O)c1c(-c2ccc(F)cc2)oc2cc3c(cc12)C(=O)CCCCN3S(C)(=O)=O] | ** (HCV genotype 1a replicon) | | | 445.1 |
| B83 | 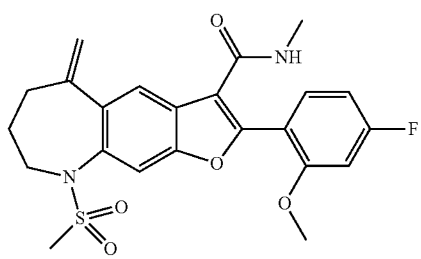 [SMILES: C=C1CCCN(S(C)(=O)=O)c2cc3oc(-c4ccc(F)cc4OC)c(C(=O)NC)c3cc21] | * | | | 459.1 |
| B84 | 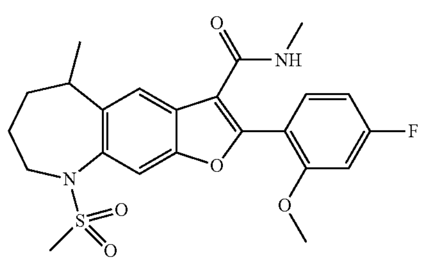 [SMILES: CNC(=O)c1c(-c2ccc(F)cc2OC)oc2cc3c(cc12)C(C)CCCN3S(C)(=O)=O] | *** | | | 461.1 |
| B85 | 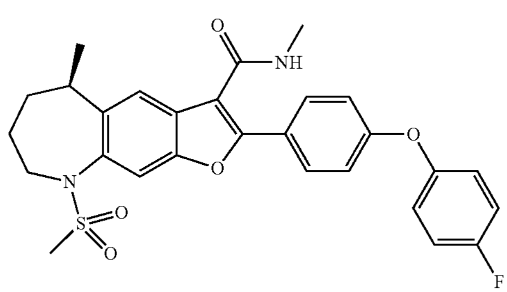 [SMILES: CNC(=O)c1c(-c2ccc(Oc3ccc(F)cc3)cc2)oc2cc3c(cc12)[C@H](C)CCCN3S(C)(=O)=O] | 3.0 nM | ††† | ††† | 523.2 |

Chirality was tentatively assigned

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B86 | *Chirality was tentatively assigned* | ** | | | 523.2 |
| B87 | 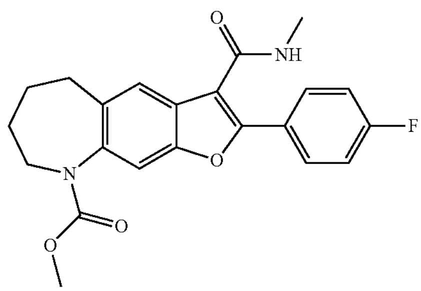 [SMILES: CNC(=O)c1c(-c2ccc(F)cc2)oc2cc3c(cc12)CCCCN3C(=O)OC] | ** | | | 397.1 |
| B88 | 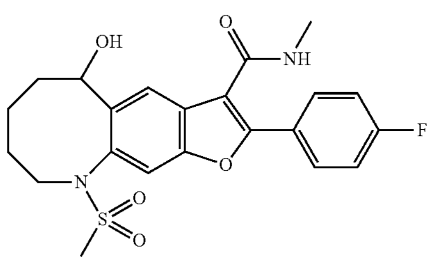 [SMILES: CNC(=O)c1c(-c2ccc(F)cc2)oc2cc3c(cc12)C(O)CCCCN3S(C)(=O)=O] | ** | | | 447.1 |
| B89 | 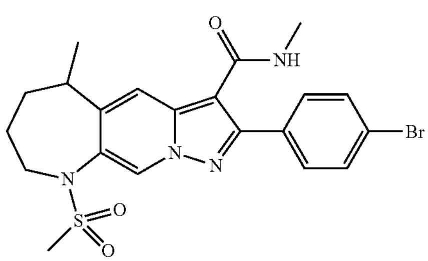 [SMILES: CNC(=O)c1c(-c2ccc(Br)cc2)nn2cc3c(cc12)C(C)CCCN3S(C)(=O)=O] | *** | | | 491.1 |
| B90 | 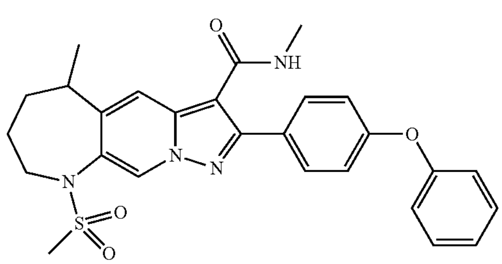 [SMILES: CNC(=O)c1c(-c2ccc(Oc3ccccc3)cc2)nn2cc3c(cc12)C(C)CCCN3S(C)(=O)=O] | ** | | | 505.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B91 | 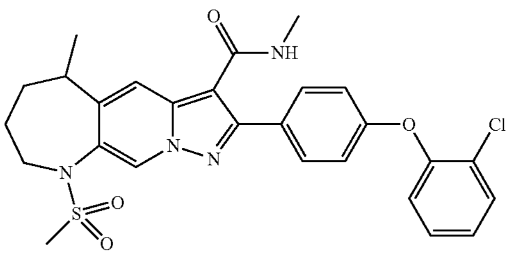 [SMILES: CNC(=O)c1c(-c2ccc(Oc3ccccc3Cl)cc2)nn2cc3c(cc12)C(C)CCCN3S(C)(=O)=O] | | ** | | 539.1 |
| B92 | 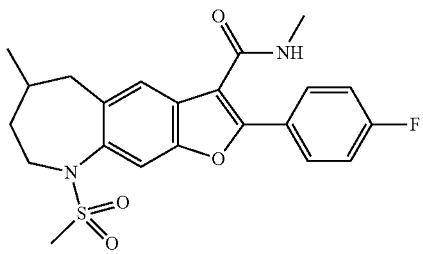 [SMILES: CNC(=O)c1c(-c2ccc(F)cc2)oc2cc3c(cc12)CC(C)CCN3S(C)(=O)=O] | | **** | | 431.1 |
| B93 | 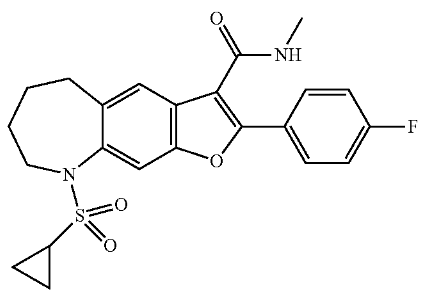 [SMILES: CNC(=O)c1c(-c2ccc(F)cc2)oc2cc3c(cc12)CCCCN3S(=O)(=O)C1CC1] | | *** | | 443.1 |
| B94 | 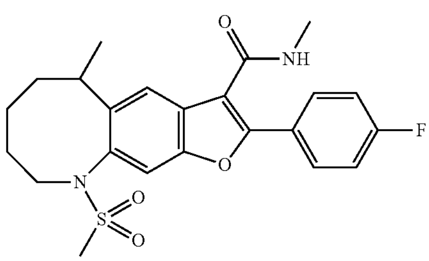 [SMILES: CNC(=O)c1c(-c2ccc(F)cc2)oc2cc3c(cc12)C(C)CCCCN3S(C)(=O)=O] | | **** | | 445.2 |
| B95 | 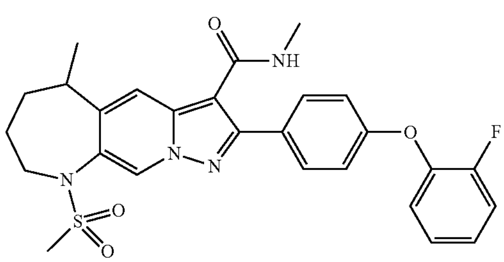 [SMILES: CNC(=O)c1c(-c2ccc(Oc3ccccc3F)cc2)nn2cc3c(cc12)C(C)CCCN3S(C)(=O)=O] | | ** | | 523.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B96 | 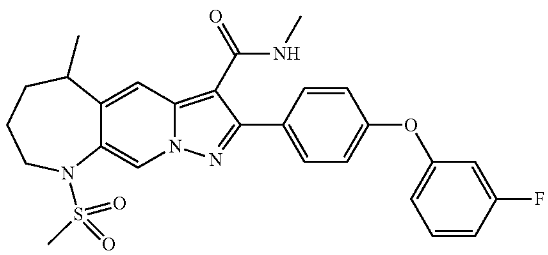 [SMILES: CNC(=O)c1c(-c2ccc(Oc3cccc(F)c3)cc2)nn2cc3c(cc12)C(C)CCCN3S(C)(=O)=O] | *** | | | 523.2 |
| B97 (3) | 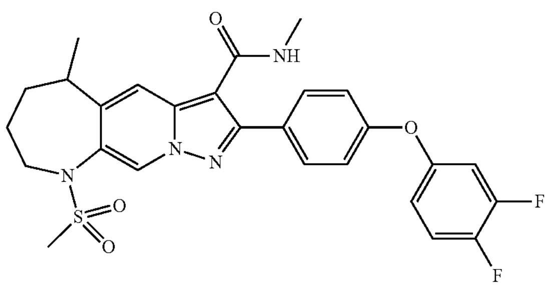 [SMILES: CNC(=O)c1c(-c2ccc(Oc3ccc(F)c(F)c3)cc2)nn2cc3c(cc12)C(C)CCCN3S(C)(=O)=O] | *** | | | 541.2 |
| B98 | 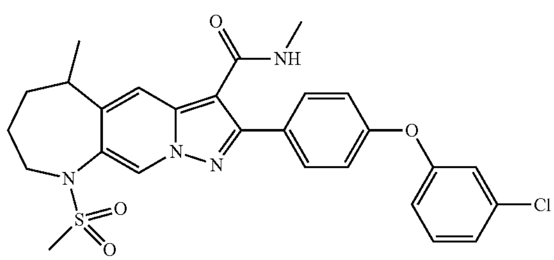 [SMILES: CNC(=O)c1c(-c2ccc(Oc3cccc(Cl)c3)cc2)nn2cc3c(cc12)C(C)CCCN3S(C)(=O)=O] | | ** (HCV genotype 2a replicon) | | 539.1 |
| B99 | 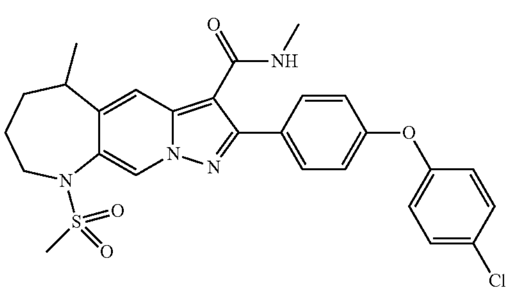 [SMILES: CNC(=O)c1c(-c2ccc(Oc3ccc(Cl)cc3)cc2)nn2cc3c(cc12)C(C)CCCN3S(C)(=O)=O] | | ** (HCV genotype 2a replicon) | | 539.1 |
| B100 | 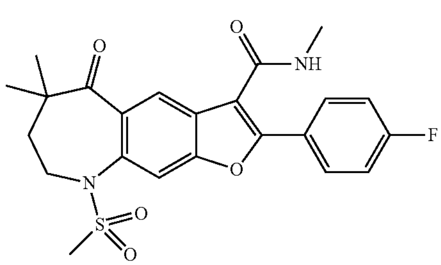 [SMILES: CNC(=O)c1c(-c2ccc(F)cc2)oc2cc3c(cc12)C(=O)C(C)(C)CCN3S(C)(=O)=O] | | *** (HCV genotype 2a replicon) | | 459.1 |

APPENDIX A-continued

| compound ID | Structure | Inhibition of HCV genotype 1b replicon | Inhibition of HCV NS5B C316Y mutant | Inhibition of HCV NS5B S365A mutant | MS [M + 1]$^+$ |
|---|---|---|---|---|---|
| B101 | 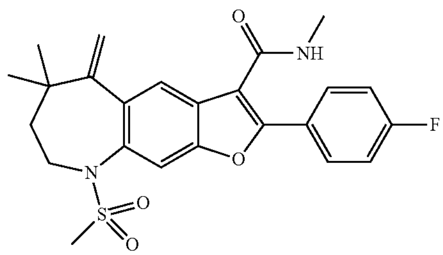 [SMILES: C=C1c2cc3c(C(=O)NC)c(-c4ccc(F)cc4)oc3cc2N(S(C)(=O)=O)CCC1(C)C] | *** (HCV genotype 2a replicon) | | | 457.2 |
| B102 | 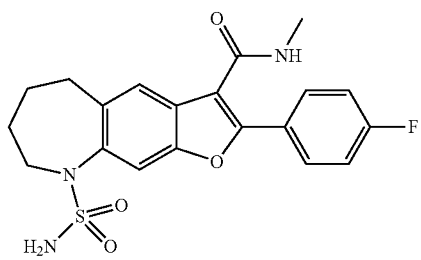 [SMILES: CNC(=O)c1c(-c2ccc(F)cc2)oc2cc3c(cc12)CCCCN3S(N)(=O)=O] | ** (HCV genotype 1a replicon) | | | 418.1 |
| B103 | 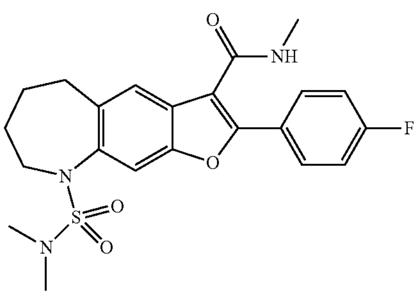 [SMILES: CNC(=O)c1c(-c2ccc(F)cc2)oc2cc3c(cc12)CCCCN3S(=O)(=O)N(C)C] | ** (HCV genotype 1a replicon) | | | 446.1 |
| B104 | 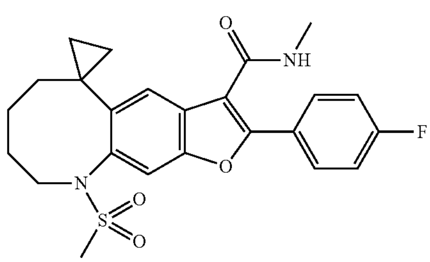 [SMILES: CNC(=O)c1c(-c2ccc(F)cc2)oc2cc3c(cc12)C1(CCCCN3S(C)(=O)=O)CC1] | ** (HCV genotype 1a replicon) | | | 457.2 |
| B105 | 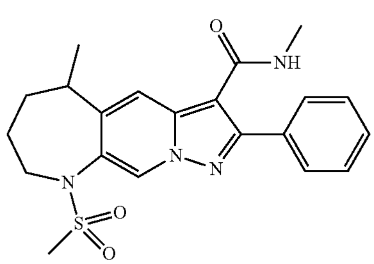 [SMILES: CNC(=O)c1c(-c2ccccc2)nn2cc3c(cc12)C(C)CCCN3S(C)(=O)=O] | ** (HCV genotype 1a replicon) | | | 413.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B106 | 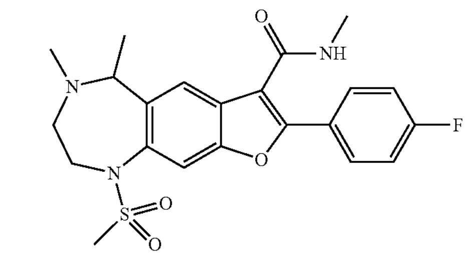 [SMILES: CNC(=O)c1c(-c2ccc(F)cc2)oc2cc3c(cc12)C(C)N(C)CCN3S(C)(=O)=O] | *** (HCV genotype 1a replicon) | | | 446.1 |
| B107 | 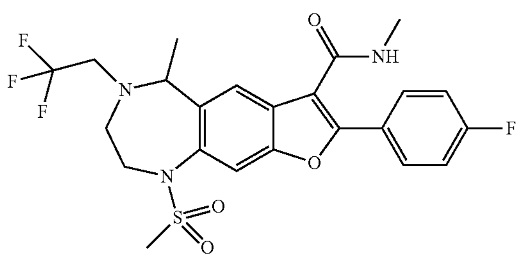 [SMILES: CNC(=O)c1c(-c2ccc(F)cc2)oc2cc3c(cc12)C(C)N(CC(F)(F)F)CCN3S(C)(=O)=O] | **** | | | 514.1 |
| B108 | 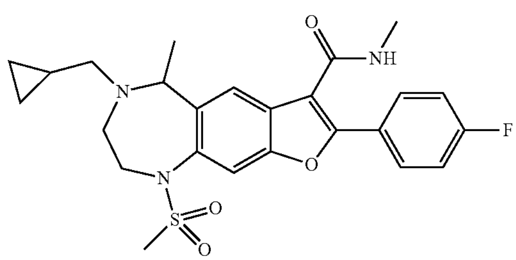 [SMILES: CNC(=O)c1c(-c2ccc(F)cc2)oc2cc3c(cc12)C(C)N(CC1CC1)CCN3S(C)(=O)=O] | *** (HCV genotype 1a replicon) | | | 486.2 |
| B109 | 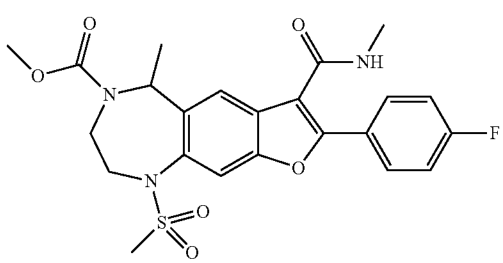 [SMILES: CNC(=O)c1c(-c2ccc(F)cc2)oc2cc3c(cc12)C(C)N(C(=O)OC)CCN3S(C)(=O)=O] | *** (HCV genotype 1a replicon) | | | 490.1 |
| B110 | 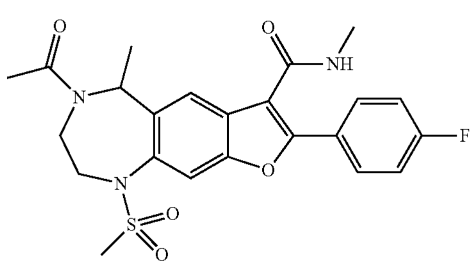 [SMILES: CNC(=O)c1c(-c2ccc(F)cc2)oc2cc3c(cc12)C(C)N(C(C)=O)CCN3S(C)(=O)=O] | ** (HCV genotype 1a replicon) | | | 474.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B111 | 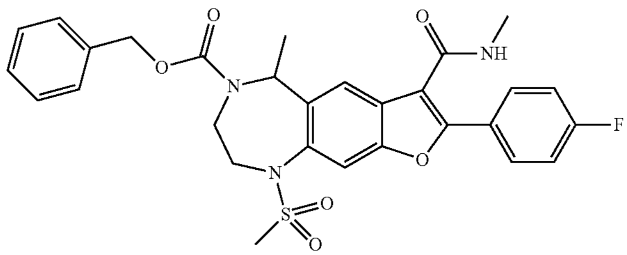 [SMILES: CNC(=O)c1c(-c2ccc(F)cc2)oc2cc3c(cc12)C(C)N(C(=O)OCc1ccccc1)CCN3S(C)(=O)=O] | *** (HCV genotype 1a replicon) | | | 566.2 |
| B112 | 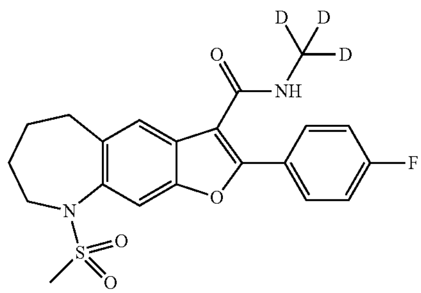 [SMILES: [2H]C([2H])([2H])NC(=O)c1c(-c2ccc(F)cc2)oc2cc3c(cc12)CCCCN3S(C)(=O)=O] | *** (HCV genotype 1a replicon) | | | 420.1 |
| B113 | 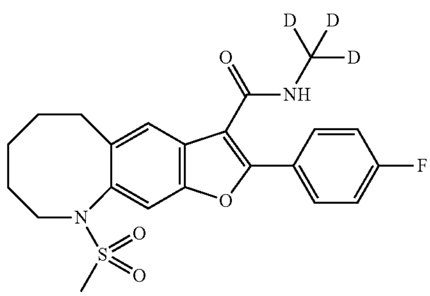 [SMILES: [2H]C([2H])([2H])NC(=O)c1c(-c2ccc(F)cc2)oc2cc3c(cc12)CCCCCN3S(C)(=O)=O] | *** (HCV genotype 1a replicon) | | | 434.2 |
| B114 | 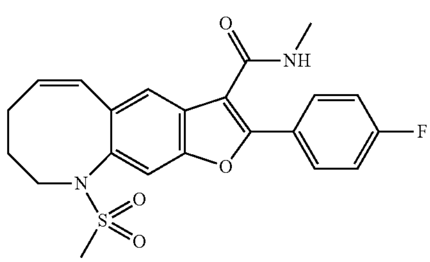 [SMILES: CNC(=O)c1c(-c2ccc(F)cc2)oc2cc3c(cc12)/C=C\CCCN3S(C)(=O)=O] | ** (HCV genotype 1a replicon) | | | 429.1 |
| B115 | 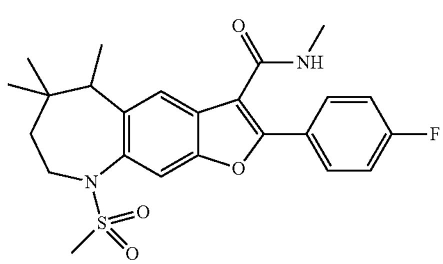 [SMILES: CNC(=O)c1c(-c2ccc(F)cc2)oc2cc3c(cc12)C(C)C(C)(C)CCN3S(C)(=O)=O] | *** (HCV genotype 1a replicon) | | | 459.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B116 | 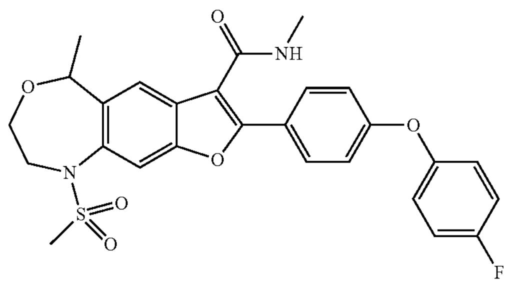 | *** (HCV genotype 1a replicon) | | | 525.1 |
| B117 | absolute configuration | ** (HCV genotype 1a replicon) | | | 525.1 |
| B118 | absolute configuration | 3.1 nM | ††† | ††† | 525.1 |
| B119 | 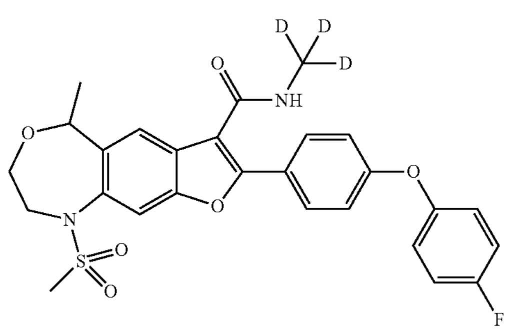 [SMILES: [2H]C([2H])([2H])NC(=O)c1c(-c2ccc(Oc3ccc(F)cc3)cc2)oc2cc3c(cc12)C(C)OCCN3S(C)(=O)=O] | *** (HCV genotype 1a replicon) | | | 528.2 |
| B120 | 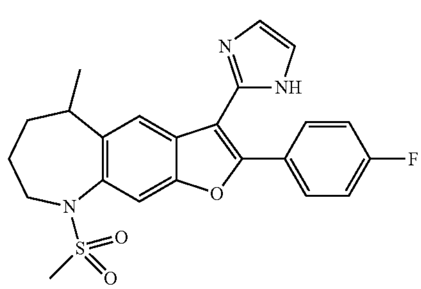 [SMILES: CC1CCCN(S(C)(=O)=O)c2cc3oc(-c4ccc(F)cc4)c(-c4ncc[nH]4)c3cc21] | **** (HCV genotype 1a replicon) | ††† | ††† | 440.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B121 | 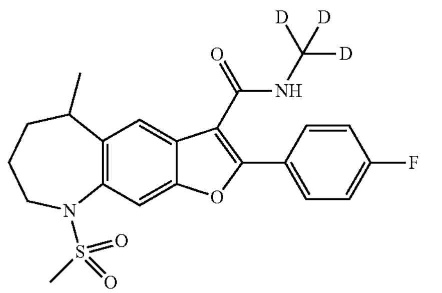 [SMILES: [2H]C([2H])([2H])NC(=O)c1c(-c2ccc(F)cc2)oc2cc3c(cc12)C(C)CCCN3S(C)(=O)=O] | **** (HCV genotype 1a replicon) | | | 434.2 |
| B122 | Chirality was tentatively assigned | * (HCV genotype 1a replicon) | | | 472.2 |
| B123 | 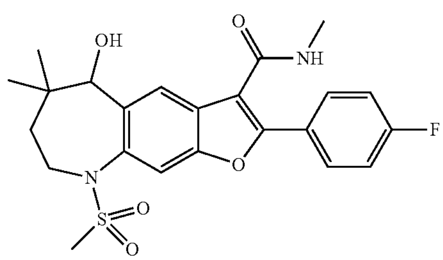 [SMILES: CNC(=O)c1c(-c2ccc(F)cc2)oc2cc3c(cc12)C(O)C(C)(C)CCN3S(C)(=O)=O] | *** | | | 461.1 |
| B124 | 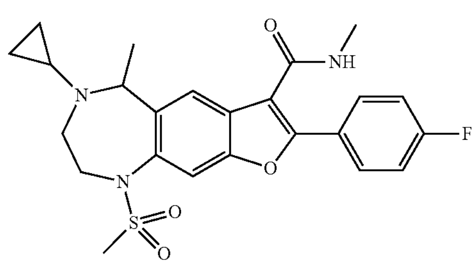 [SMILES: CNC(=O)c1c(-c2ccc(F)cc2)oc2cc3c(cc12)C(C)N(C1CC1)CCN3S(C)(=O)=O] | *** | | | 472.2 |
| B125 | 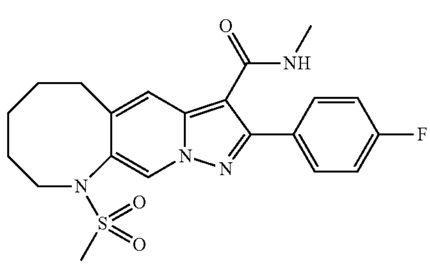 [SMILES: CNC(=O)c1c(-c2ccc(F)cc2)nn2cc3c(cc12)CCCCCN3S(C)(=O)=O] | *** | | | 431.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B126 | 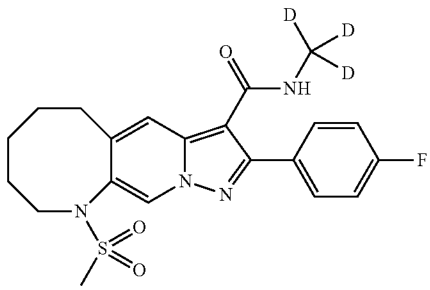 [SMILES: [2H]C([2H])([2H])NC(=O)c1c(-c2ccc(F)cc2)nn2cc3c(cc12)CCCCCN3S(C)(=O)=O] | *** | | | 434.2 |
| B127 | 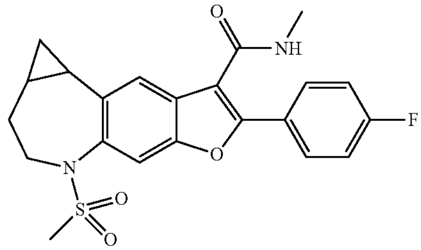 [SMILES: CNC(=O)c1c(-c2ccc(F)cc2)oc2cc3c(cc12)C1CC1CCN3S(C)(=O)=O] | **** | | | 429.1 |
| B128 | 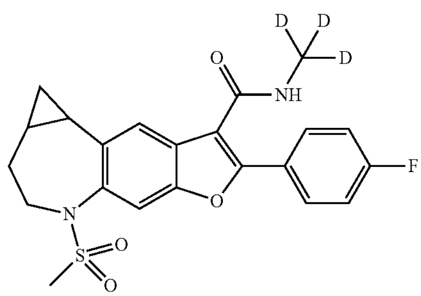 [SMILES: [2H]C([2H])([2H])NC(=O)c1c(-c2ccc(F)cc2)oc2cc3c(cc12)C1CC1CCN3S(C)(=O)=O] | **** | | | 432.1 |
| B129 | 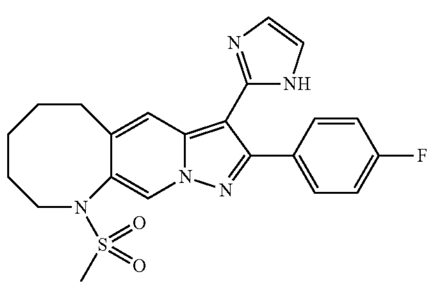 [SMILES: CS(=O)(=O)N1CCCCCc2cc3c(-c4ncc[nH]4)c(-c4ccc(F)cc4)nn3cc21] | *** | | | 440.1 |
| B130 | 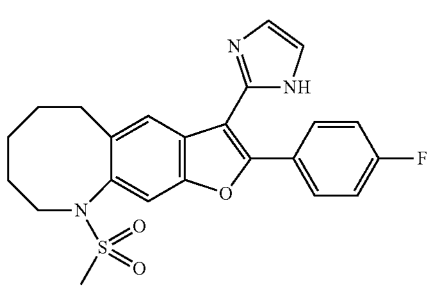 [SMILES: CS(=O)(=O)N1CCCCCc2cc3c(-c4ncc[nH]4)c(-c4ccc(F)cc4)oc3cc21] | **** | | | 440.1 |

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B131 | Chirality was tentatively assigned | **** | | | 472.2 |
| B132 | Chirality was tentatively assigned | **** | ††† | ††† | 429.1 |
| B133 | Chirality was tentatively assigned | * | | | 429.1 |
| B134 | 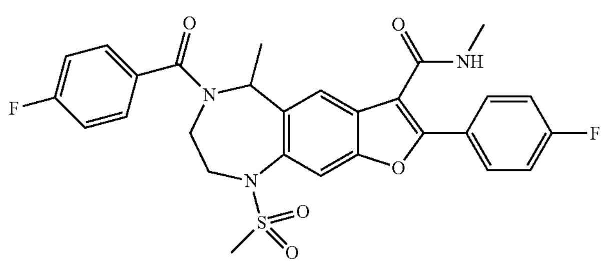 [SMILES: CNC(=O)c1c(-c2ccc(F)cc2)oc2cc3c(cc12)C(C)N(C(=O)c1ccc(F)cc1)CCN3S(C)(=O)=O] | *** | | | 554.1 |
| B135 | 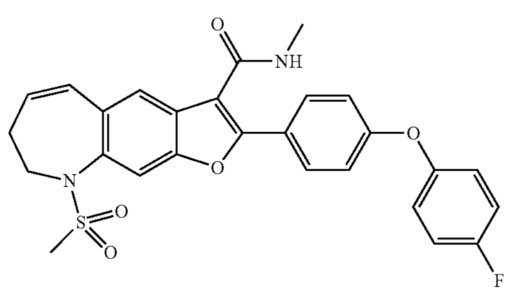 [SMILES: CNC(=O)c1c(-c2ccc(Oc3ccc(F)cc3)cc2)oc2cc3c(cc12)C=CCCN3S(C)(=O)=O] | ** | | | 507.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
| --- | --- | --- | --- | --- | --- |
| B136 | 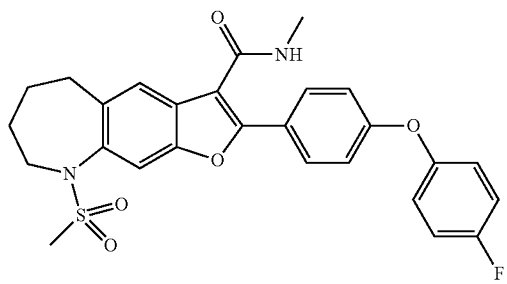 [SMILES: CNC(=O)c1c(-c2ccc(Oc3ccc(F)cc3)cc2)oc2cc3c(cc12)CCCCN3S(C)(=O)=O] | | *** | | 509.1 |
| B137 | 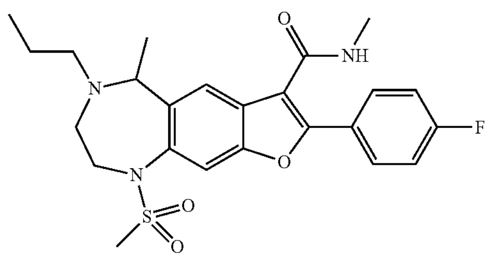 [SMILES: CCCN1CCN(S(C)(=O)=O)c2cc3oc(-c4ccc(F)cc4)c(C(=O)NC)c3cc2C1C] | *** (HCV genotype 1a replicon) | | | 474.2 |
| B138 | 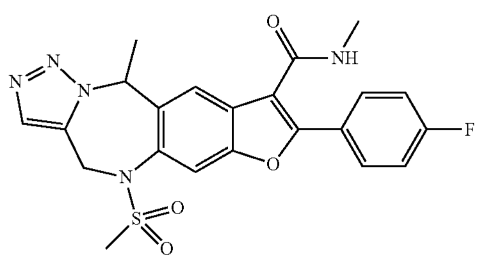 | | **** | | 470.1 |
| B139 | 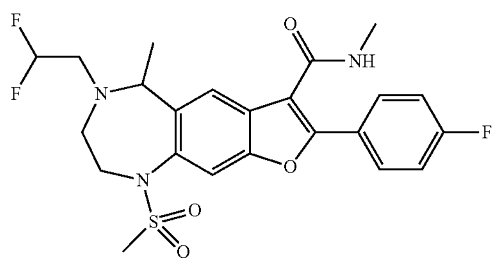 [SMILES: CNC(=O)c1c(-c2ccc(F)cc2)oc2cc3c(cc12)C(C)N(CC(F)F)CCN3S(C)(=O)=O] | | **** | | 496.1 |
| B140 | 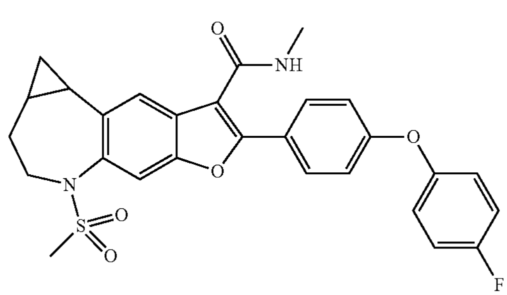 [SMILES: CNC(=O)c1c(-c2ccc(Oc3ccc(F)cc3)cc2)oc2cc3c(cc12)C1CC1CCN3S(C)(=O)=O] | ** (HCV genotype 1a replicon) | | | 521.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B141 | 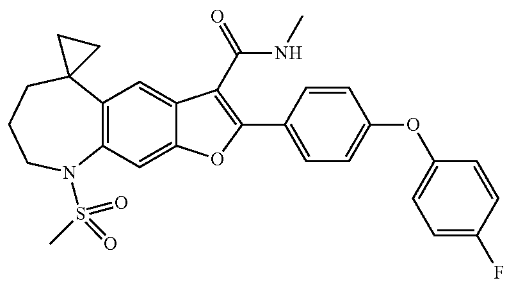 [SMILES: CNC(=O)c1c(-c2ccc(Oc3ccc(F)cc3)cc2)oc2cc3c(cc12)C1(CCCN3S(C)(=O)=O)CC1] | ** (HCV genotype 1a replicon) | | | 535.2 |
| B142 | 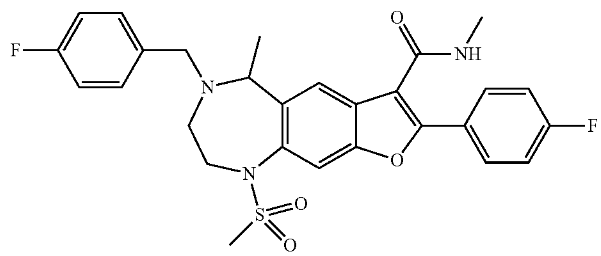 [SMILES: CNC(=O)c1c(-c2ccc(F)cc2)oc2cc3c(cc12)C(C)N(Cc1ccc(F)cc1)CCN3S(C)(=O)=O] | *** | | | 540.2 |
| B143 | Chirality was tentatively assigned | ** (HCV genotype 1a replicon) | | | 521.1 |
| B144 | 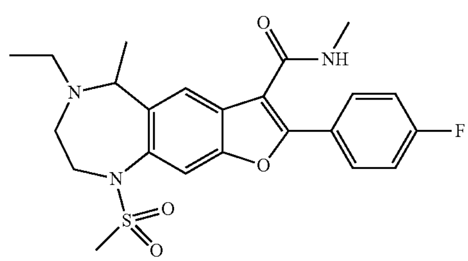 [SMILES: CCN1CCN(S(C)(=O)=O)c2cc3oc(-c4ccc(F)cc4)c(C(=O)NC)c3cc2C1C] | *** | | | 460.2 |
| B145 | 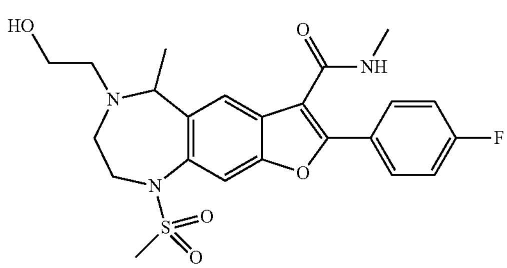 [SMILES: CNC(=O)c1c(-c2ccc(F)cc2)oc2cc3c(cc12)C(C)N(CCO)CCN3S(C)(=O)=O] | **** | ††† | †† | 476.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B146 | Chirality was tentatively assigned | *** (HCV genotype 1a replicon) | | | 521.1 |
| B147 | 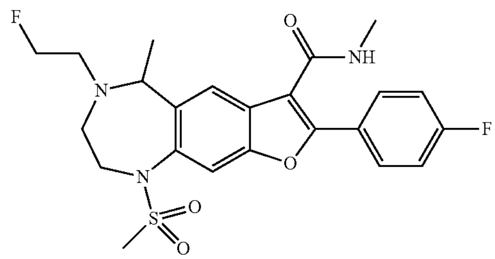 [SMILES: CNC(=O)c1c(-c2ccc(F)cc2)oc2cc3c(cc12)C(C)N(CCF)CCN3S(C)(=O)=O] | *** | | | 478.2 |
| B148 | 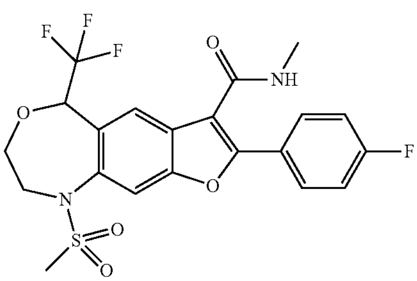 [SMILES: CNC(=O)c1c(-c2ccc(F)cc2)oc2cc3c(cc12)C(C(F)(F)F)OCCN3S(C)(=O)=O] | **** | | | 487.1 |
| B149 | 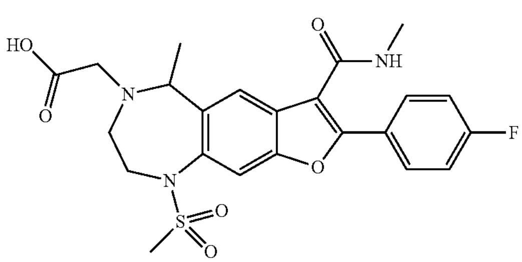 [SMILES: CNC(=O)c1c(-c2ccc(F)cc2)oc2cc3c(cc12)C(C)N(CC(=O)O)CCN3S(C)(=O)=O] | * | | | 490.1 |
| B150 | 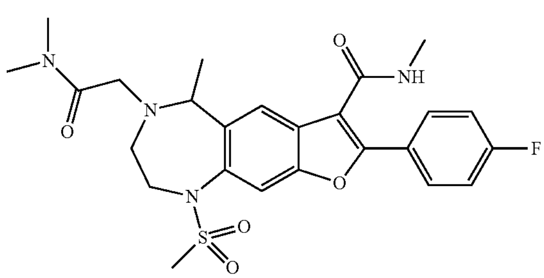 [SMILES: CNC(=O)c1c(-c2ccc(F)cc2)oc2cc3c(cc12)C(C)N(CC(=O)N(C)C)CCN3S(C)(=O)=O] | *** (HCV genotype 1a replicon) | | | 517.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B151 | 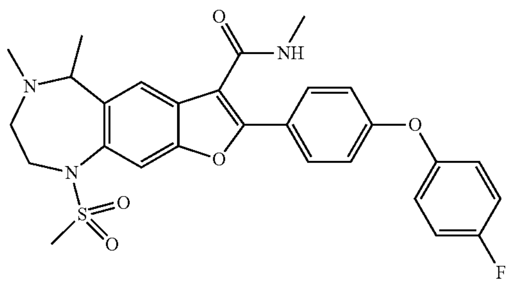 [SMILES: CNC(=O)c1c(-c2ccc(Oc3ccc(F)cc3)cc2)oc2cc3c(cc12)C(C)N(C)CCN3S(C)(=O)=O] | *** (HCV genotype 1a replicon) | | | 538.2 |
| B152 | 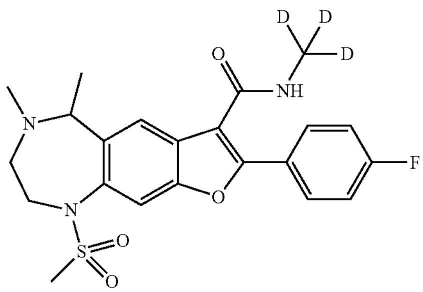 [SMILES: [2H]C([2H])([2H])NC(=O)c1c(-c2ccc(F)cc2)oc2cc3c(cc12)C(C)N(C)CCN3S(C)(=O)=O] | ** (HCV genotype 1a replicon) | | | 449.2 |
| B153 | 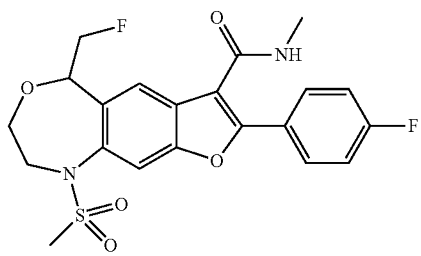 [SMILES: CNC(=O)c1c(-c2ccc(F)cc2)oc2cc3c(cc12)C(CF)OCCN3S(C)(=O)=O] | *** (HCV genotype 1a replicon) | | | 451.1 |
| B154 | 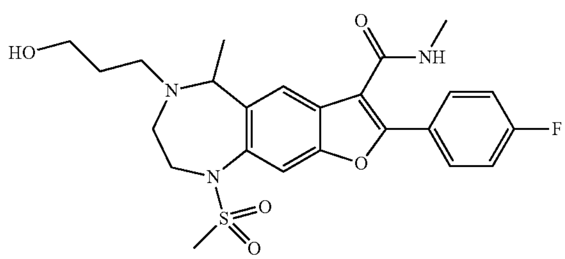 [SMILES: CNC(=O)c1c(-c2ccc(F)cc2)oc2cc3c(cc12)C(C)N(CCCO)CCN3S(C)(=O)=O] | *** (HCV genotype 1a replicon) | | | 490.2 |
| B155 | 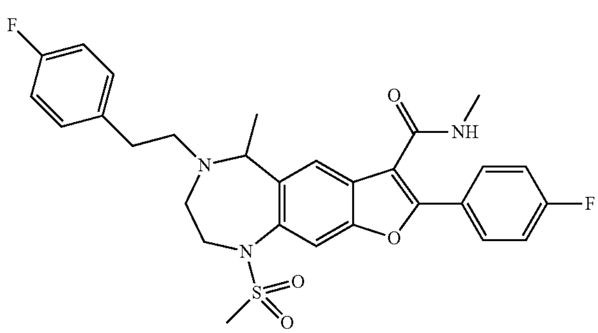 [SMILES: CNC(=O)c1c(-c2ccc(F)cc2)oc2cc3c(cc12)C(C)N(CCc1ccc(F)cc1)CCN3S(C)(=O)=O] | *** (HCV genotype 1a replicon) | | | 554.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B156 | 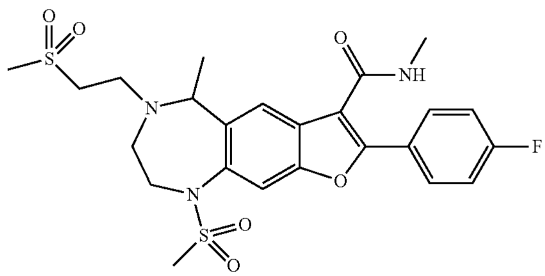 [SMILES: CNC(=O)c1c(-c2ccc(F)cc2)oc2cc3c(cc12)C(C)N(CCS(C)(=O)=O)CCN3S(C)(=O)=O] | *** | ††† | ††† | 538.1 |
| B157 | 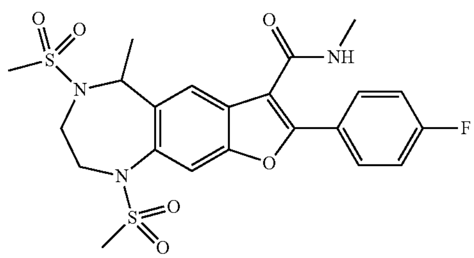 [SMILES: CNC(=O)c1c(-c2ccc(F)cc2)oc2cc3c(cc12)C(C)N(S(C)(=O)=O)CCN3S(C)(=O)=O] | *** | | | 510.1 |
| B158 | 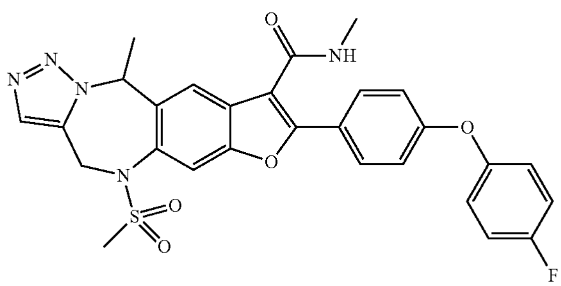 | **** | | | 562.1 |
| B159 | 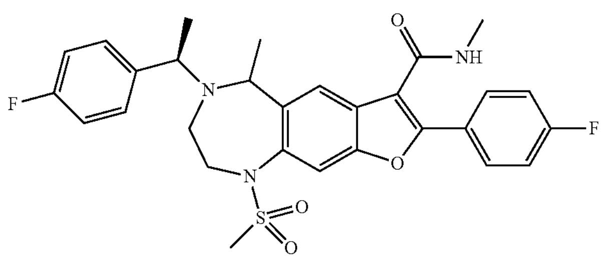 [SMILES: CNC(=O)c1c(-c2ccc(F)cc2)oc2cc3c(cc12)C(C)N([C@H](C)c1ccc(F)cc1)CCN3S(C)(=O)=O] | *** | | | 554.2 |
| B160 | 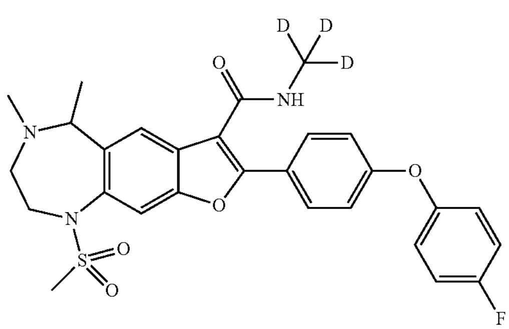 [SMILES: [2H]C([2H])([2H])NC(=O)c1c(-c2ccc(Oc3ccc(F)cc3)cc2)oc2cc3c(cc12)C(C)N(C)CCN3S(C)(=O)=O] | *** | | | 541.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
| --- | --- | --- | --- | --- | --- |
| B161 | 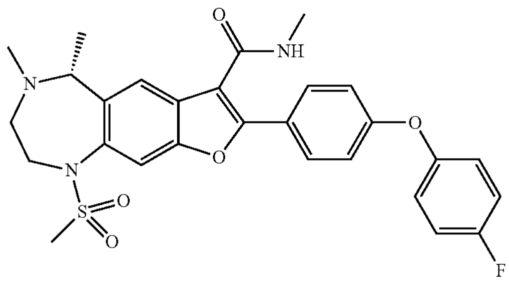 [SMILES: CNC(=O)c1c(-c2ccc(Oc3ccc(F)cc3)cc2)oc2cc3c(cc12)[C@@H](C)N(C)CCN3S(C)(=O)=O] | *** | | | 541.2 |
| B162 | 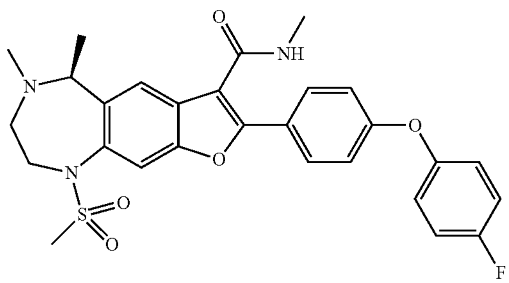 | *** | | | 541.2 |
| B163 | Chirality was tentatively assigned | **** | ††† | ††† | 562.1 |
| B164 | Chirality was tentatively assigned | *** | | | 562.1 |
| B165 | 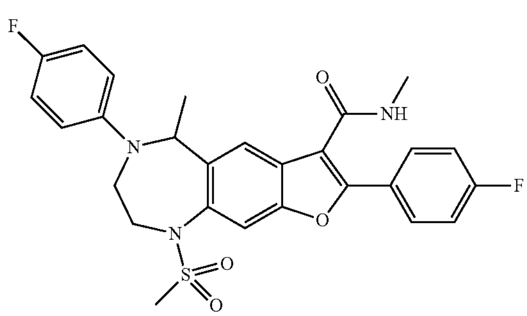 [SMILES: CNC(=O)c1c(-c2ccc(F)cc2)oc2cc3c(cc12)C(C)N(c1ccc(F)cc1)CCN3S(C)(=O)=O] | *** | | | 526.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B166 | 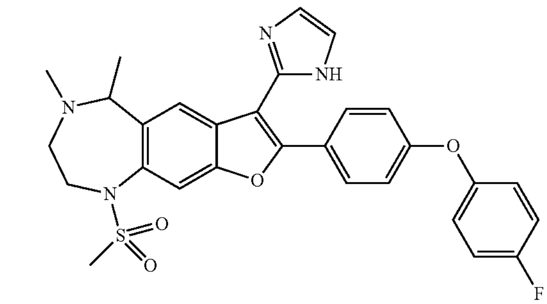 [SMILES: CC1c2cc3c(-c4ncc[nH]4)c(-c4ccc(Oc5ccc(F)cc5)cc4)oc3cc2N(S(C)(=O)=O)CCN1C] | *** | | | 547.2 |
| B167 | 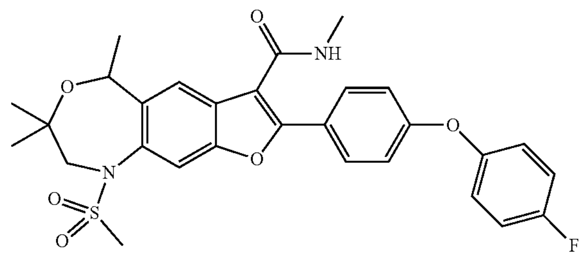 | *** | | | 553.2 |
| B168 | 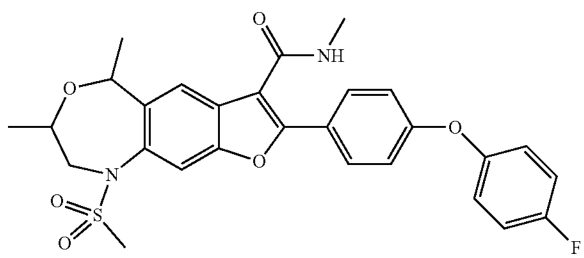 [SMILES: CNC(=O)c1c(-c2ccc(Oc3ccc(F)cc3)cc2)oc2cc3c(cc12)C(C)OC(C)CN3S(C)(=O)=O] | **** | | | 539.2 |
| B169 | 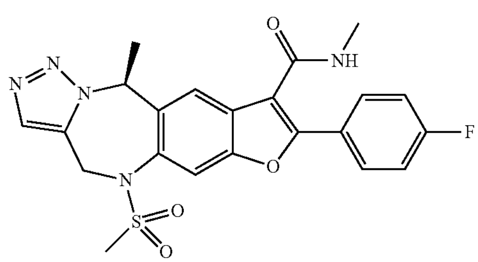 [SMILES: CNC(=O)c1c(-c2ccc(F)cc2)oc2cc3c(cc12)[C@H](C)n1nncc1CN3S(C)(=O)=O] | **** | ††† | ††† | 470.1 |
| | Chirality was tentatively assigned | | | | |
| B170 | 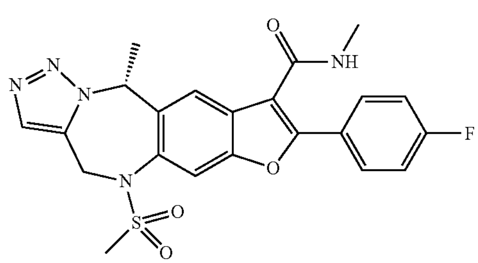 [SMILES: CNC(=O)c1c(-c2ccc(F)cc2)oc2cc3c(cc12)[C@@H](C)n1nncc1CN3S(C)(=O)=O] | *** | | | 470.1 |
| | Chirality was tentatively assigned | | | | |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
| --- | --- | --- | --- | --- | --- |
| B171 | 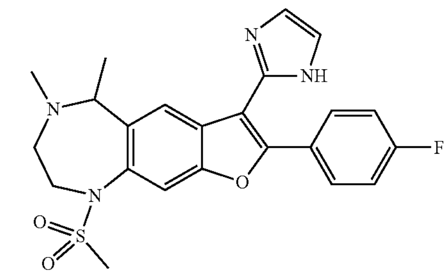 [SMILES: CC1c2cc3c(-c4ncc[nH]4)c(-c4ccc(F)cc4)oc3cc2N(S(C)(=O)=O)CCN1C] | **** | ††† | †† | 455.1 |
| B172 | 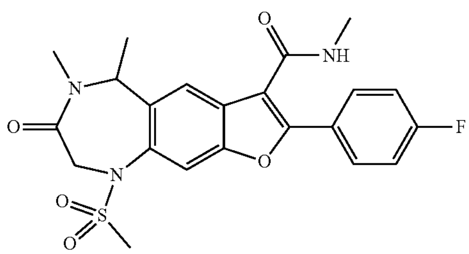 [SMILES: CNC(=O)c1c(-c2ccc(F)cc2)oc2cc3c(cc12)C(C)N(C)C(=O)CN3S(C)(=O)=O] | *** | | | 460.1 |
| B173 | 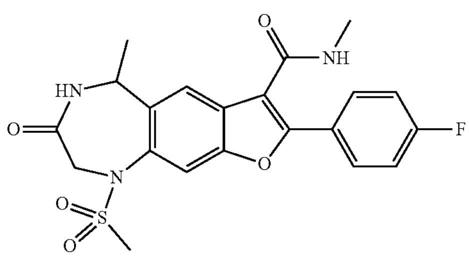 [SMILES: CNC(=O)c1c(-c2ccc(F)cc2)oc2cc3c(cc12)C(C)NC(=O)CN3S(C)(=O)=O] | *** | | | 446.1 |
| B174 | 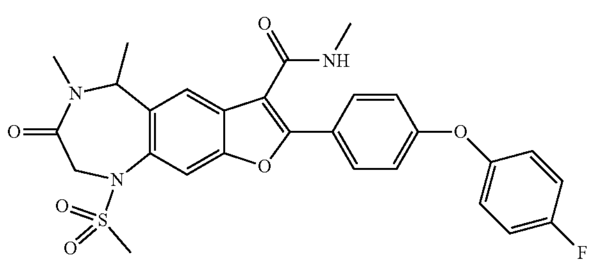 [SMILES: CNC(=O)c1c(-c2ccc(Oc3ccc(F)cc3)cc2)oc2cc3c(cc12)C(C)N(C)C(=O)CN3S(C)(=O)=O] | *** | | | 552.2 |
| B175 | 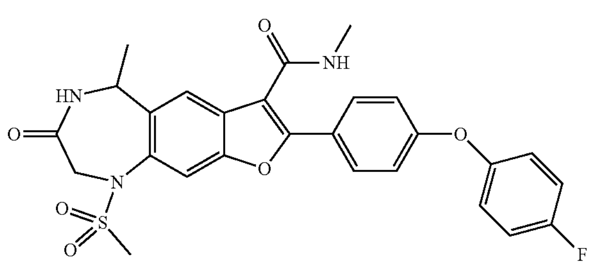 [SMILES: CNC(=O)c1c(-c2ccc(Oc3ccc(F)cc3)cc2)oc2cc3c(cc12)C(C)NC(=O)CN3S(C)(=O)=O] | *** | | | 538.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B176 | *Chirality was tentatively assigned* | 13.6 nM | †† (200 nM < EC$_{50}$ < 1000 nM) | †† | 553.2 |
| B177 | *Chirality was tentatively assigned* | ** | | | 553.2 |
| B178 | 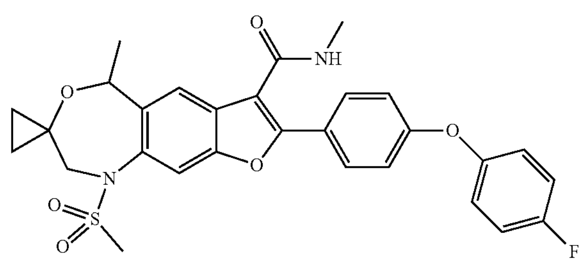 [SMILES: CNC(=O)c1c(-c2ccc(Oc3ccc(F)cc3)cc2)oc2cc3c(cc12)C(C)OC1(CC1)CN3S(C)(=O)=O] | *** | | | 551.2 |
| B179 | *Chirality was tentatively assigned* | *** | ††† | †† | 460.1 |
| B180 | *Chirality was tentatively assigned* | *** | | | 460.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B181 | Chirality was tentatively assigned | *** | | | 552.2 |
| B182 | Chirality was tentatively assigned | ** | | | 552.2 |
| B183 | 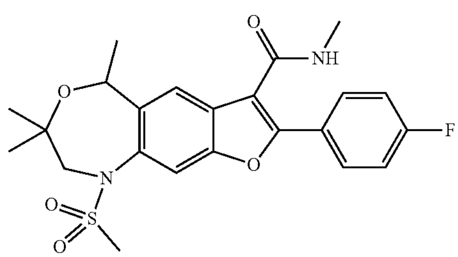 [SMILES: CNC(=O)c1c(-c2ccc(F)cc2)oc2cc3c(cc12)C(C)OC(C)(C)CN3S(C)(=O)=O] | *** | | | 461.1 |
| B184 | Chirality was tentatively assigned | 16.5 nM | † (EC$_{50}$ ≥ 1000 nM) | †† | 461.1 |
| B185 | Chirality was tentatively assigned | * | | | 461.1 |

APPENDIX A-continued
| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B186 | 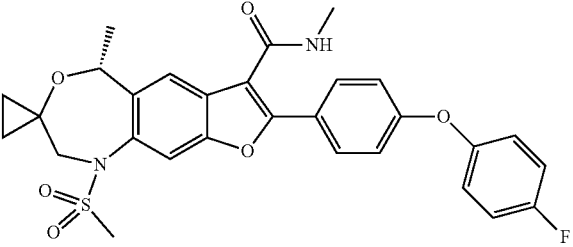 [SMILES: CNC(=O)c1c(-c2ccc(Oc3ccc(F)cc3)cc2)oc2cc3c(cc12)[C@@H](C)OC1(CC1)CN3S(C)(=O)=O] Chirality was tentatively assigned | *** | | | 551.2 |
| B187 | 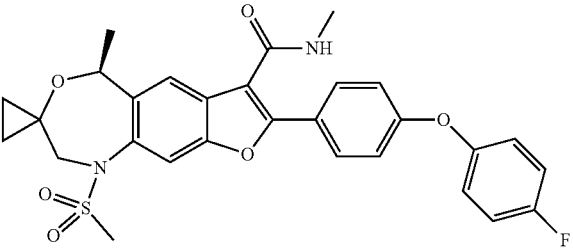 [SMILES: CNC(=O)c1c(-c2ccc(Oc3ccc(F)cc3)cc2)oc2cc3c(cc12)[C@H](C)OC1(CC1)CN3S(C)(=O)=O] Chirality was tentatively assigned | **** | † | † (EC$_{50}$ ≥ 1000 nM) | 551.2 |
| B188 | 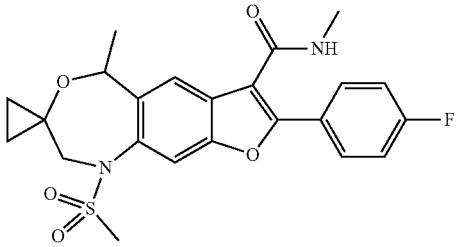 [SMILES: CNC(=O)c1c(-c2ccc(F)cc2)oc2cc3c(cc12)C(C)OC1(CC1)CN3S(C)(=O)=O] | *** | | | 459.1 |
| B189 | 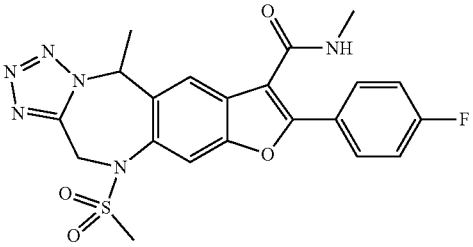 [SMILES: CNC(=O)c1c(-c2ccc(F)cc2)oc2cc3c(cc12)C(C)n1nnnc1CN3S(C)(=O)=O] | *** | | | 471.1 |
| B190 | 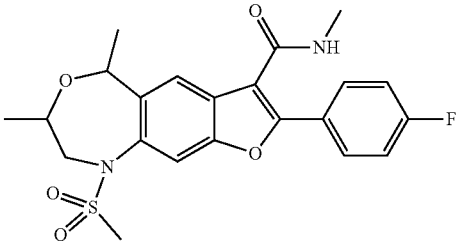 [SMILES: CNC(=O)c1c(-c2ccc(F)cc2)oc2cc3c(cc12)C(C)OC(C)CN3S(C)(=O)=O] | **** | | | 447.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B191 | 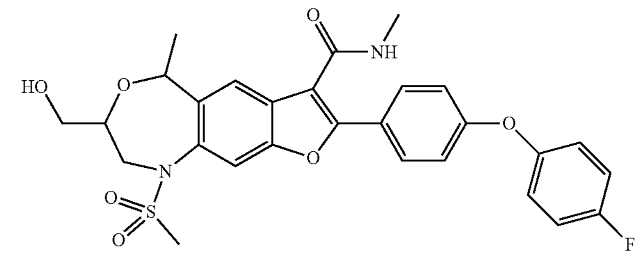 [SMILES: CNC(=O)c1c(-c2ccc(Oc3ccc(F)cc3)cc2)oc2cc3c(cc12)C(C)OC(CO)CN3S(C)(=O)=O] | **** | | | 555.2 |
| B192 | 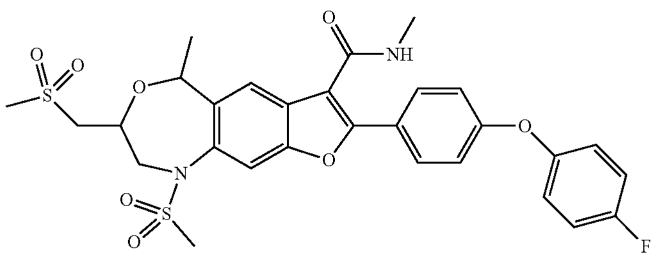 [SMILES: CNC(=O)c1c(-c2ccc(Oc3ccc(F)cc3)cc2)oc2cc3c(cc12)C(C)OC(CS(C)(=O)=O)CN3S(C)(=O)=O] | **** | | | 617.1 |
| B193 | 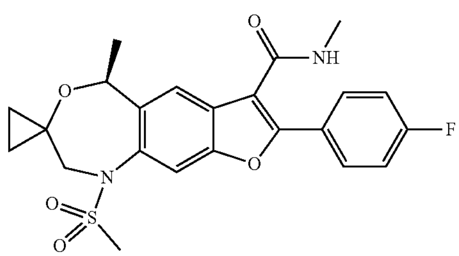 [SMILES: CNC(=O)c1c(-c2ccc(F)cc2)oc2cc3c(cc12)[C@H](C)OC1(CC1)CN3S(C)(=O)=O] | *** | †† | †† | 459.1 |
| | Chirality was tentatively assigned | | | | |
| B194 | 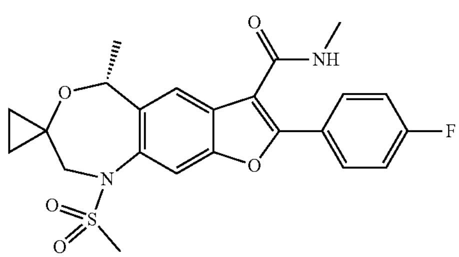 [SMILES: CNC(=O)c1c(-c2ccc(F)cc2)oc2cc3c(cc12)[C@@H](C)OC1(CC1)CN3S(C)(=O)=O] | ** | | | 459.1 |
| | Chirality was tentatively assigned | | | | |
| B195 | 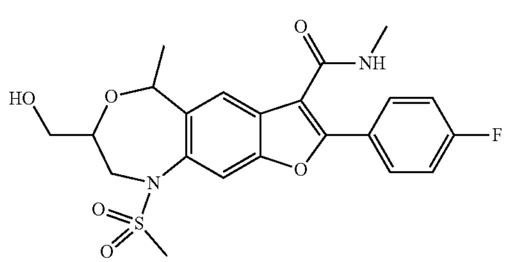 [SMILES: CNC(=O)c1c(-c2ccc(F)cc2)oc2cc3c(cc12)C(C)OC(CO)CN3S(C)(=O)=O] | *** | | | 463.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]⁺ |
|---|---|---|---|---|---|
| B196 | 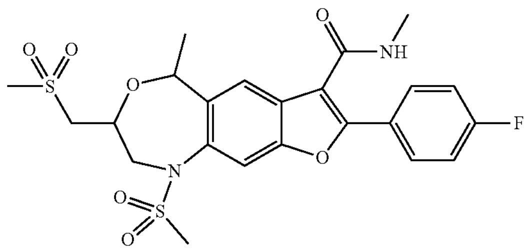 [SMILES: CNC(=O)c1c(-c2ccc(F)cc2)oc2cc3c(cc12)C(C)OC(CS(C)(=O)=O)CN3S(C)(=O)=O] | **** | | | 525.1 |
| B197 | 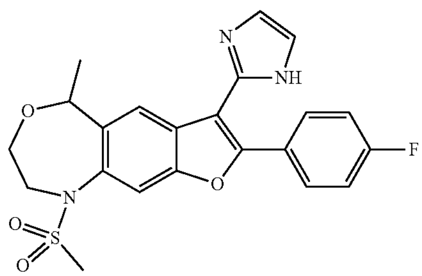 [SMILES: CC1OCCN(S(C)(=O)=O)c2cc3oc(-c4ccc(F)cc4)c(-c4ncc[nH]4)c3cc21] | **** | ††† | †† | 442.1 |
| B198 | 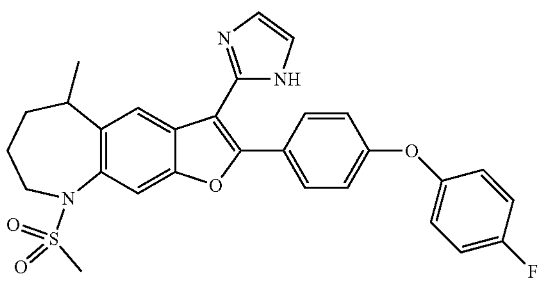 [SMILES: CC1CCCN(S(C)(=O)=O)c2cc3oc(-c4ccc(Oc5ccc(F)cc5)cc4)c(-c4ncc[nH]4)c3cc21] | **** | | | 532.2 |
| B199 | 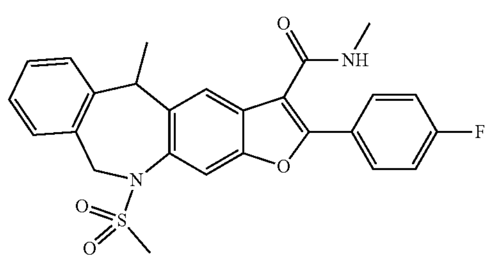 [SMILES: CNC(=O)c1c(-c2ccc(F)cc2)oc2cc3c(cc12)C(C)c1ccccc1CN3S(C)(=O)=O] | *** | | | 479.1 |
| B200 | 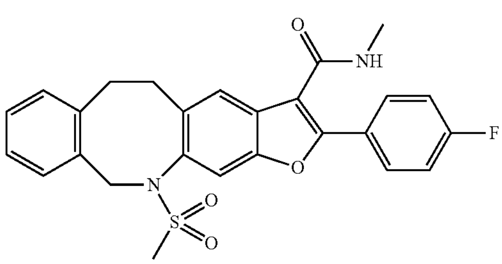 [SMILES: CNC(=O)c1c(-c2ccc(F)cc2)oc2cc3c(cc12)CCc1ccccc1CN3S(C)(=O)=O] | *** | | | 479.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B201 | 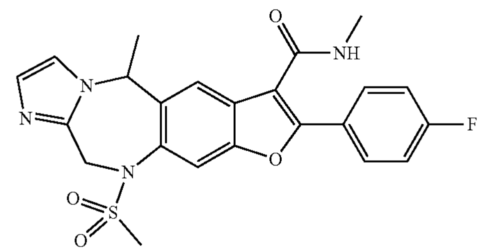 [SMILES: CNC(=O)c1c(-c2ccc(F)cc2)oc2cc3c(cc12)C(C)n1ccnc1CN3S(C)(=O)=O] | **** | ††† | †† | 532.2 |
| B202 | 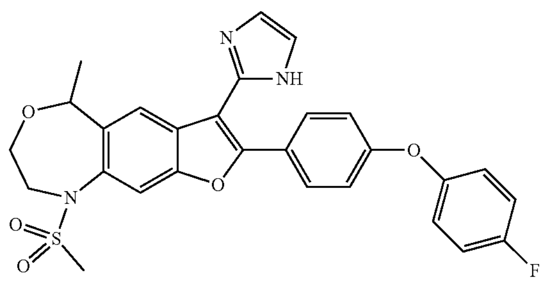 [SMILES: CC1OCCN(S(C)(=O)=O)c2cc3oc(-c4ccc(Oc5ccc(F)cc5)cc4)c(-c4ncc[nH]4)c3cc21] | *** | | | 534.1 |
| B203 | Chirality was tentatively assigned | *** | | | 479.1 |
| B204 | Chirality was tentatively assigned | *** | | | 479.1 |
| B205 | 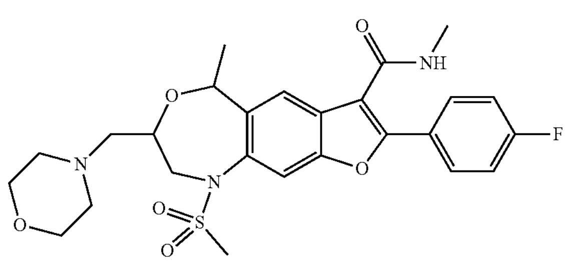 [SMILES: CNC(=O)c1c(-c2ccc(F)cc2)oc2cc3c(cc12)C(C)OC(CN1CCOCC1)CN3S(C)(=O)=O] | *** | | | 532.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B206 | absolute configuration | ** | | | 617.1 |
| B207 | absolute configuration | **** | ††† | ††† | 617.1 |
| B208 | Chirality was tentatively assigned | **** | ††† | ††† | 446.1 |
| B209 | Chirality was tentatively assigned | ** | | | 446.1 |
| B210 | 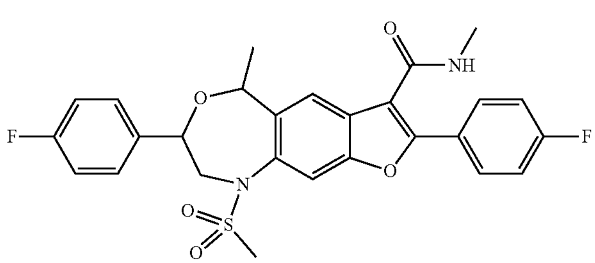 [SMILES: CNC(=O)c1c(-c2ccc(F)cc2)oc2cc3c(cc12)C(C)OC(c1ccc(F)cc1)CN3S(C)(=O)=O] | *** | | | 527.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B211 | absolute configuration | * | | | 463.1 |
| B212 | absolute configuration | **** | ††† | ††† | 463.1 |
| B213 | absolute configuration | * | | | 525.1 |
| B214 | absolute configuration | **** | ††† | ††† | 525.1 |
| B215 | absolute configuration | *** | | | 525.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B216 | absolute configuration | *** | | | 617.1 |
| B217 | absolute configuration | *** | | | 463.1 |
| B218 | 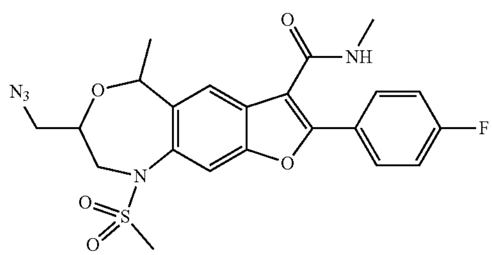 [SMILES: CNC(=O)c1c(-c2ccc(F)cc2)oc2cc3c(cc12)C(C)OC(CN=[N+]=[N-])CN3S(C)(=O)=O] | **** | | | 488.1 |
| B219 | 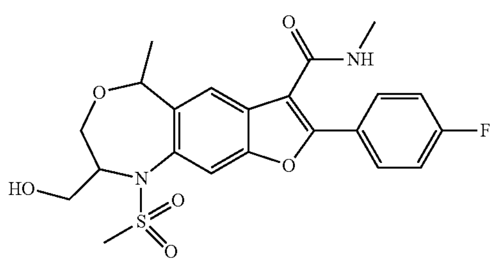 [SMILES: CNC(=O)c1c(-c2ccc(F)cc2)oc2cc3c(cc12)C(C)OCC(CO)N3S(C)(=O)=O] | *** | | | 463.1 |
| B220 | 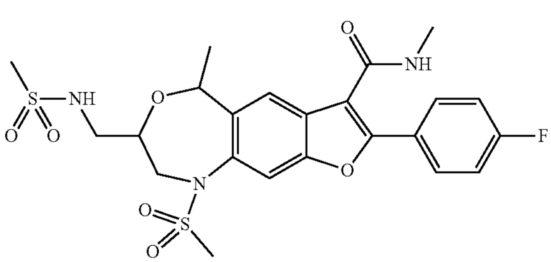 [SMILES: CNC(=O)c1c(-c2ccc(F)cc2)oc2cc3c(cc12)C(C)OC(CNS(C)(=O)=O)CN3S(C)(=O)=O] | *** | | | 540.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B221 | 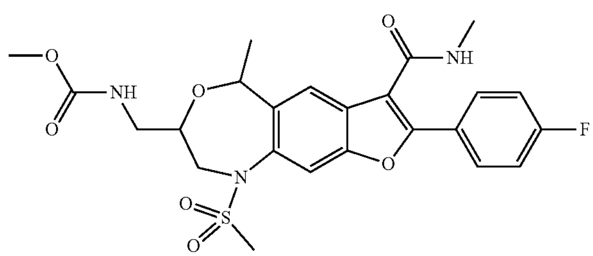 [SMILES: CNC(=O)c1c(-c2ccc(F)cc2)oc2cc3c(cc12)C(C)OC(CNC(=O)OC)CN3S(C)(=O)=O] | **** | | | 520.1 |
| B222 | 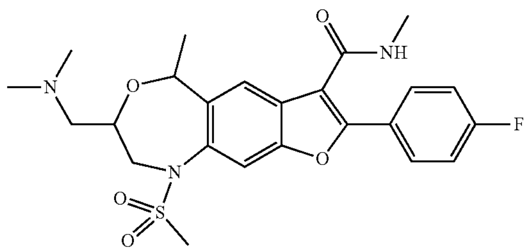 [SMILES: CNC(=O)c1c(-c2ccc(F)cc2)oc2cc3c(cc12)C(C)OC(CN(C)C)CN3S(C)(=O)=O] | *** | | | 490.2 |
| B223 | 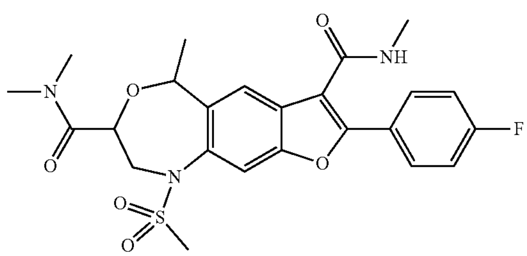 [SMILES: CNC(=O)c1c(-c2ccc(F)cc2)oc2cc3c(cc12)C(C)OC(C(=O)N(C)C)CN3S(C)(=O)=O] | *** | | | 504.2 |
| B224 | (absolute configuration) | *** | | | 617.1 |
| B225 | 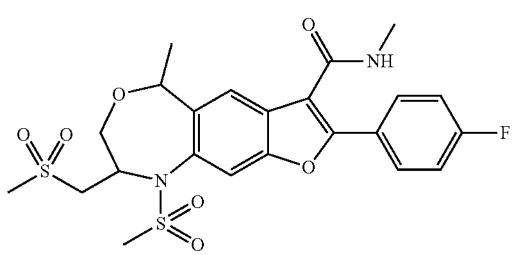 [SMILES: CNC(=O)c1c(-c2ccc(F)cc2)oc2cc3c(cc12)C(C)OCC(CS(C)(=O)=O)N3S(C)(=O)=O] | *** | | | 525.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B226 | 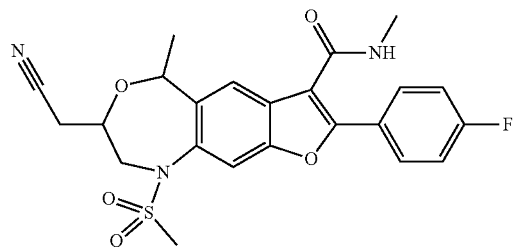 [SMILES: CNC(=O)c1c(-c2ccc(F)cc2)oc2cc3c(cc12)C(C)OC(CC#N)CN3S(C)(=O)=O] | **** | | | 472.1 |
| B227 | 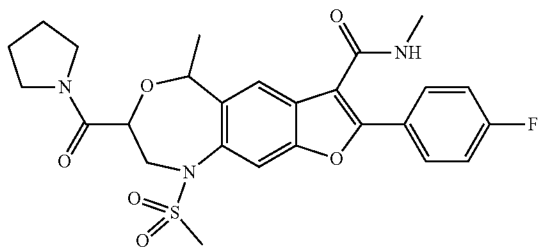 [SMILES: CNC(=O)c1c(-c2ccc(F)cc2)oc2cc3c(cc12)C(C)OC(C(=O)N1CCCC1)CN3S(C)(=O)=O] | *** | | | 530.2 |
| B228 | 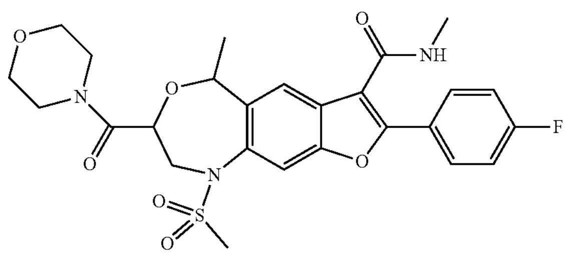 [SMILES: CNC(=O)c1c(-c2ccc(F)cc2)oc2cc3c(cc12)C(C)OC(C(=O)N1CCOCC1)CN3S(C)(=O)=O] | *** | | | 546.2 |
| B229 | 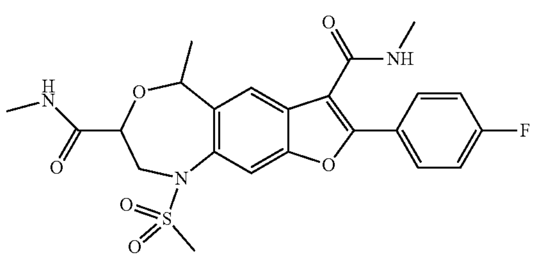 [SMILES: CNC(=O)c1c(-c2ccc(F)cc2)oc2cc3c(cc12)C(C)OC(C(=O)NC)CN3S(C)(=O)=O] | *** | | | 490.1 |
| B230 | a pair of syn- isomers | *** | | | 477.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B231 | a pair of anti- isomers | *** | | | 477.1 |
| B232 | absolute configuration | **** | ††† | ††† | 555.2 |
| B233 | a pair of syn- isomers | **** | | | 539.1 |
| B234 | a pair of anti- isomers | *** | | | 539.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B235 | 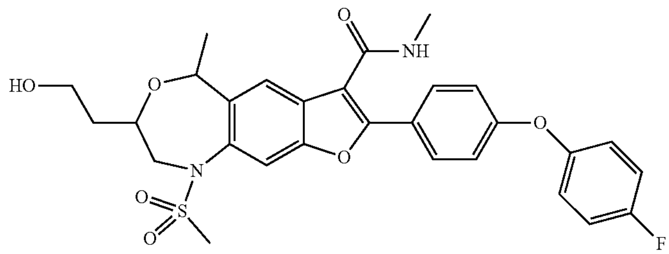 [SMILES: CNC(=O)c1c(-c2ccc(Oc3ccc(F)cc3)cc2)oc2cc3c(cc12)C(C)OC(CCO)CN3S(C)(=O)=O] | *** | | | 569.2 |
| B236 | 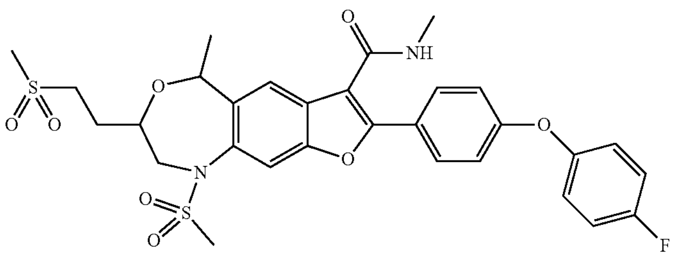 [SMILES: CNC(=O)c1c(-c2ccc(Oc3ccc(F)cc3)cc2)oc2cc3c(cc12)C(C)OC(CCS(C)(=O)=O)CN3S(C)(=O)=O] | **** | | | 631.2 |
| B237 | absolute configuration | **** | | | 654.2 |
| B238 | absolute configuration | **** | | | 626.2 |
| B239 | absolute configuration | **** | | | 640.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B240 | absolute configuration | **** | | | 635.1 |
| B241 | absolute configuration | *** | | | 555.2 |
| B242 | 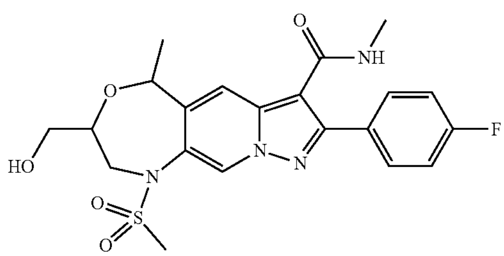 [SMILES: CNC(=O)c1c(-c2ccc(F)cc2)nn2cc3c(cc12)C(C)OC(CO)CN3S(C)(=O)=O] | ** | | | 463.1 |
| B243 | absolute configuration | **** | | | 569.2 |
| B244 | absolute configuration | **** | | | 639.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B245 | absolute configuration | **** | | | 655.2 |
| B246 | absolute configuration | **** | | | 660.2 |
| B247 | 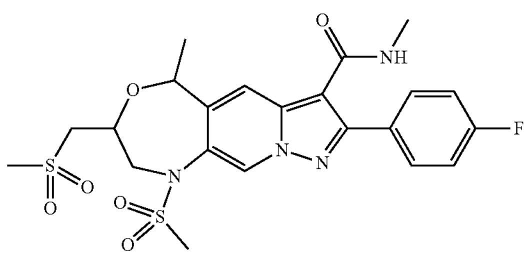 [SMILES: CNC(=O)c1c(-c2ccc(F)cc2)nn2cc3c(cc12)C(C)OC(CS(C)(=O)=O)CN3S(C)(=O)=O] | *** | | | 525.1 |
| B248 | absolute configuration | **** | | | 562.1 |
| B249 | absolute configuration | **** | | | 534.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B250 | 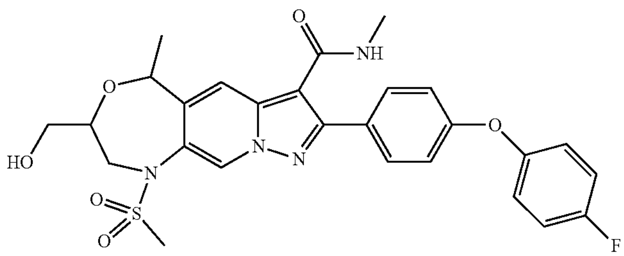 [SMILES: CNC(=O)c1c(-c2ccc(Oc3ccc(F)cc3)cc2)nn2cc3c(cc12)C(C)OC(CO)CN3S(C)(=O)=O] | *** | | | 555.2 |
| B251 | 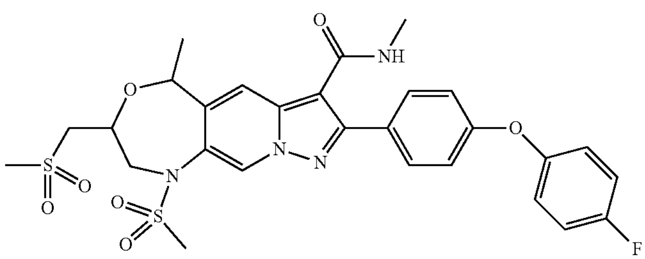 [SMILES: CNC(=O)c1c(-c2ccc(Oc3ccc(F)cc3)cc2)nn2cc3c(cc12)C(C)OC(CS(C)(=O)=O)CN3S(C)(=O)=O] | *** | | | 617.1 |
| B252 | absolute configuration | **** | | | 548.2 |
| B253 | absolute configuration | **** | | | 520.1 |
| B254 | absolute configuration | **** | | | 612.2 |

APPENDIX A-continued
| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B255 | 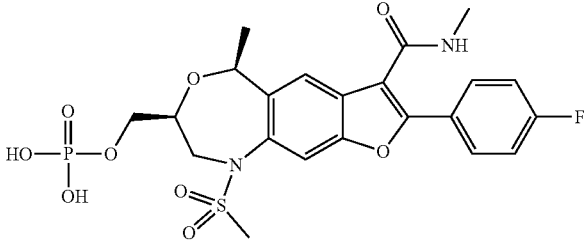 [SMILES: CNC(=O)c1c(-c2ccc(F)cc2)oc2cc3c(cc12)[C@H](C)O[C@H](COP(=O)(O)O)CN3S(C)(=O)=O] absolute configuration | **** | | | 543.1 |
| B256 | 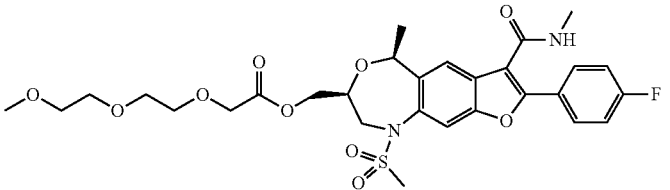 [SMILES: CNC(=O)c1c(-c2ccc(F)cc2)oc2cc3c(cc12)[C@H](C)O[C@H](COC(=O)COCCOCCOC)CN3S(C)(=O)=O] absolute configuration | **** | | | 623.2 |
| B257 | 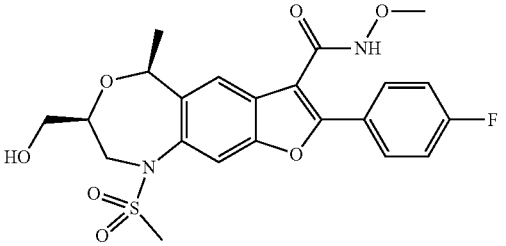 [SMILES: CONC(=O)c1c(-c2ccc(F)cc2)oc2cc3c(cc12)[C@H](C)O[C@H](CO)CN3S(C)(=O)=O] absolute configuration | **** | | | 479.1 |
| B258 | 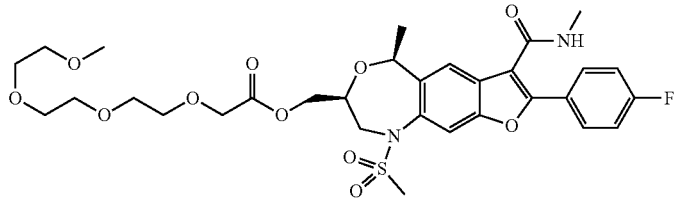 [SMILES: CNC(=O)c1c(-c2ccc(F)cc2)oc2cc3c(cc12)[C@H](C)O[C@H](COC(=O)COCCOCCOCCOC)CN3S(C)(=O)=O] absolute configuration | **** | | | 667.2 |
| B259 | 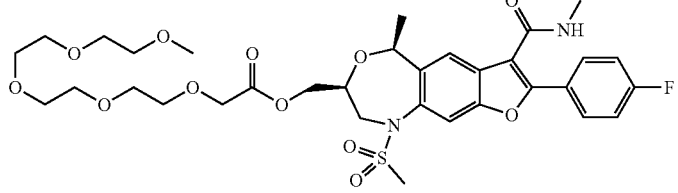 absolute configuration | **** | | | 711.3 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]⁺ |
|---|---|---|---|---|---|
| B260 | absolute configuration | **** | | | 477.1 |
| B261 | absolute configuration | **** | | | 547.2 |
| B262 | absolute configuration | *** | | | 563.1 |
| B263 | absolute configuration | **** | | | 568.1 |
| B264 | absolute configuration | *** | | | 588.2 |

APPENDIX A-continued

| compound ID | Structure | Inhibition of HCV genotype 1b replicon | Inhibition of HCV NS5B C316Y mutant | Inhibition of HCV NS5B S365A mutant | MS [M + 1]+ |
|---|---|---|---|---|---|
| B265 | absolute configuration | **** | | | 574.2 |
| B266 | absolute configuration | **** | | | 560.2 |
| B267 | absolute configuration | **** | | | 521.2 |
| B268 | absolute configuration | **** | | | 565.2 |
| B269 | absolute configuration | **** | | | 576.2 |

APPENDIX A-continued

| compound ID | Structure | Inhibition of HCV genotype 1b replicon | Inhibition of HCV NS5B C316Y mutant | Inhibition of HCV NS5B S365A mutant | MS [M + 1]+ |
|---|---|---|---|---|---|
| B270 | absolute configuration | **** | | | 578.2 |
| B271 | absolute configuration | **** | | | 576.2 |
| B272 | absolute configuration | **** | | | 596.2 |
| B273 | absolute configuration | **** | | | 534.2 |
| B274 | absolute configuration | *** | | | 463.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]⁺ |
|---|---|---|---|---|---|
| B275 | absolute configuration | **** | | | 577.2 |
| B276 | absolute configuration | **** | | | 657.3 |
| B277 | absolute configuration | **** | | | 600.2 |
| B278 | absolute configuration | **** | | | 610.2 |
| B279 | absolute configuration | *** | | | 537.2 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B280 | absolute configuration | | **** | | 564.2 |
| B281 | absolute configuration | | **** | | 550.2 |
| B282 | absolute configuration | | **** | | 562.2 |
| B283 | absolute configuration | | ** | | 540.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B284 | absolute configuration | ** | | | 554.1 |
| B285 | absolute configuration | **** | | | 533.2 |
| B286 | absolute configuration | **** | | | 533.2 |
| B287 | absolute configuration | *** | | | 525.1 |
| B288 | 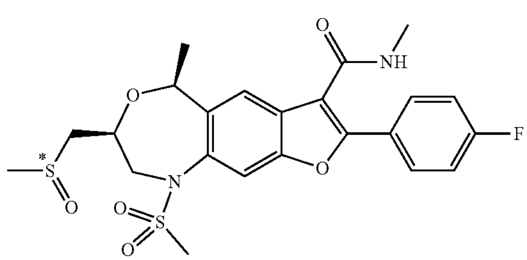 [SMILES: CNC(=O)c1c(-c2ccc(F)cc2)oc2cc3c(cc12)[C@H](C)O[C@H](CS(C)=O)CN3S(C)(=O)=O] | | | | 509.1 |

APPENDIX A-continued

| compound ID | Structure | Inhibition of HCV genotype 1b replicon | Inhibiton of HCV NS5B C316Y mutant | Inhibiton of HCV NS5B S365A mutant | MS [M + 1]+ |
|---|---|---|---|---|---|
| B289 | absolute configuration | | | | 564.2 |

APPENDIX B

| compound ID | Structure | Inhibition of HCV genotype 1b replicon | MS [M + 1]+ |
|---|---|---|---|
| D1 | 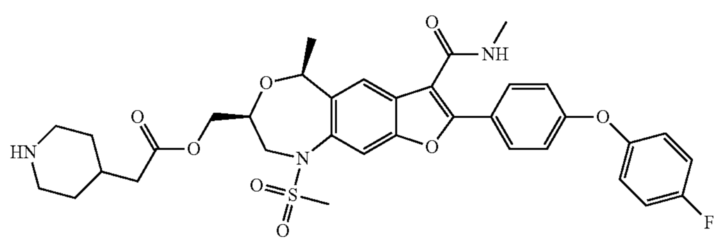 [SMILES: CNC(=O)c1c(-c2ccc(Oc3ccc(F)cc3)cc2)oc2cc3c(cc12)[C@H](C)O[C@H](COC(=O)CC1CCNCC1)CN3S(C)(=O)=O] | | |
| D2 | 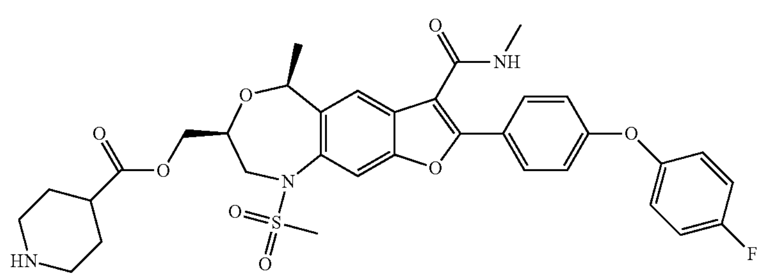 [SMILES: CNC(=O)c1c(-c2ccc(Oc3ccc(F)cc3)cc2)oc2cc3c(cc12)[C@H](C)O[C@H](COC(=O)C1CCNCC1)CN3S(C)(=O)=O] | | |
| D3 | 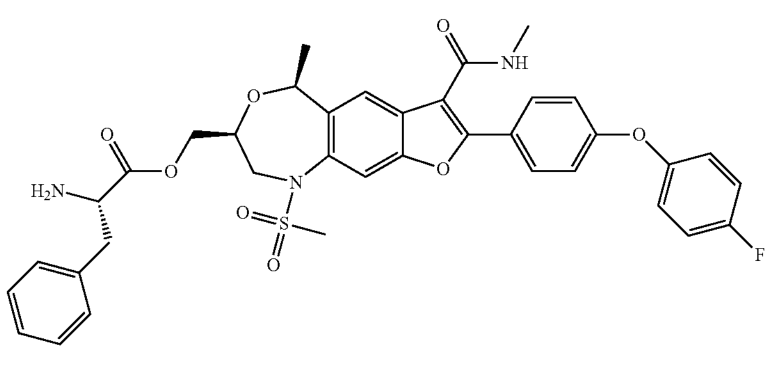 [SMILES: CNC(=O)c1c(-c2ccc(Oc3ccc(F)cc3)cc2)oc2cc3c(cc12)[C@H](C)O[C@H](COC(=O)[C@@H](N)Cc1ccccc1)CN3S(C)(=O)=O] | | |

APPENDIX B-continued

| compound ID | Structure | Inhibition of HCV genotype 1b replicon | MS [M + 1]+ |
|---|---|---|---|
| D4 | 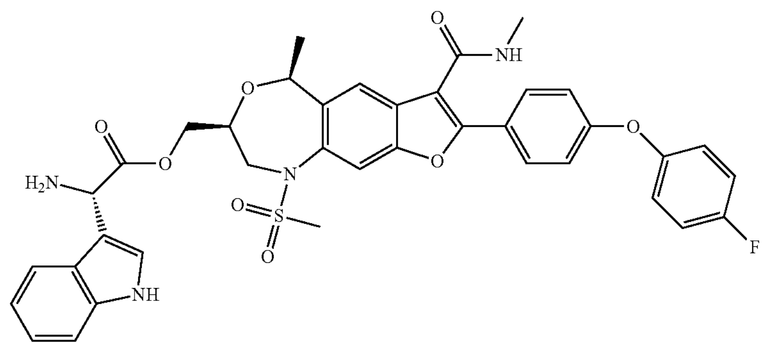 [SMILES: CNC(=O)c1c(-c2ccc(Oc3ccc(F)cc3)cc2)oc2cc3c(cc12)[C@H](C)O[C@H](COC(=O)[C@@H](N)c1c[nH]c2ccccc12)CN3S(C)(=O)=O] | | |
| D5 | 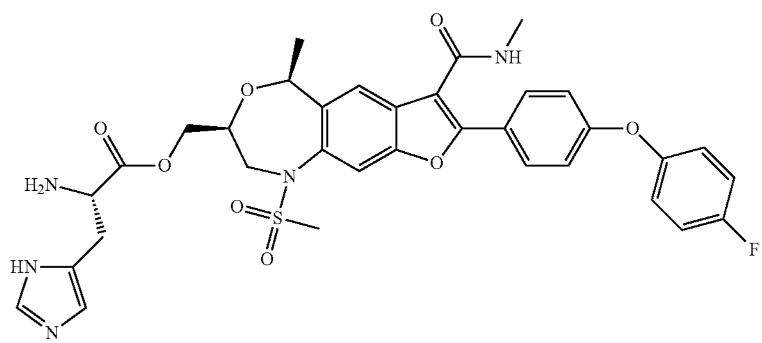 [SMILES: CNC(=O)c1c(-c2ccc(Oc3ccc(F)cc3)cc2)oc2cc3c(cc12)[C@H](C)O[C@H](COC(=O)[C@@H](N)Cc1cnc[nH]1)CN3S(C)(=O)=O] | | |
| D6 | 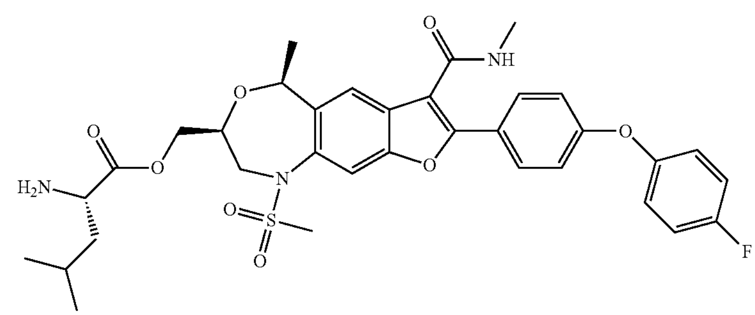 [SMILES: CNC(=O)c1c(-c2ccc(Oc3ccc(F)cc3)cc2)oc2cc3c(cc12)[C@H](C)O[C@H](COC(=O)[C@@H](N)CC(C)C)CN3S(C)(=O)=O] | | |
| D7 | 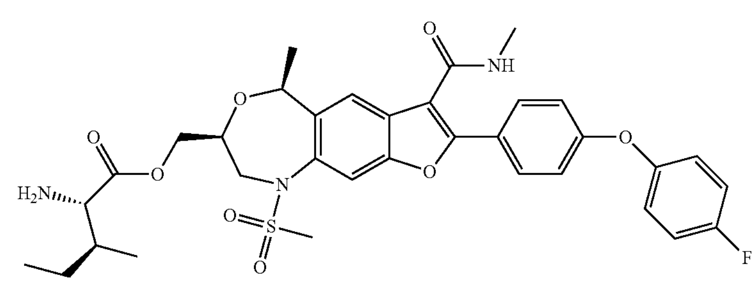 [SMILES: CC[C@H](C)[C@H](N)C(=O)OC[C@@H]1CN(S(C)(=O)=O)c2cc3oc(-c4ccc(Oc5ccc(F)cc5)cc4)c(C(=O)NC)c3cc2[C@H](C)O1] | | |

APPENDIX B-continued

| compound ID | Structure | Inhibition of HCV genotype 1b replicon | MS [M + 1]+ |
|---|---|---|---|
| D8 | 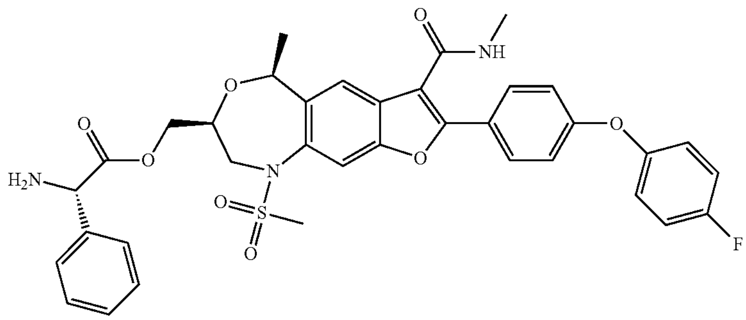 [SMILES: CNC(=O)c1c(-c2ccc(Oc3ccc(F)cc3)cc2)oc2cc3c(cc12)[C@H](C)O[C@H](COC(=O)[C@@H](N)c1ccccc1)CN3S(C)(=O)=O] | | |
| D9 | 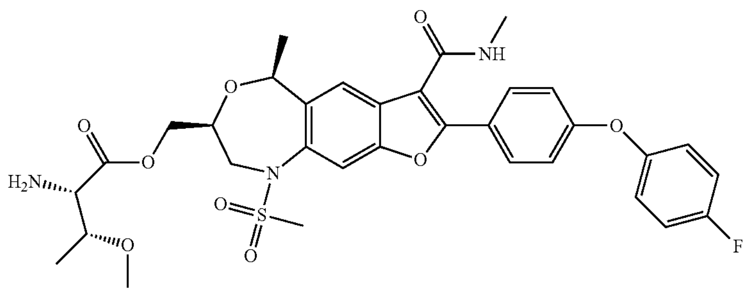 [SMILES: CNC(=O)c1c(-c2ccc(Oc3ccc(F)cc3)cc2)oc2cc3c(cc12)[C@H](C)O[C@H](COC(=O)[C@@H](N)[C@@H](C)OC)CN3S(C)(=O)=O] | | |
| D10 | 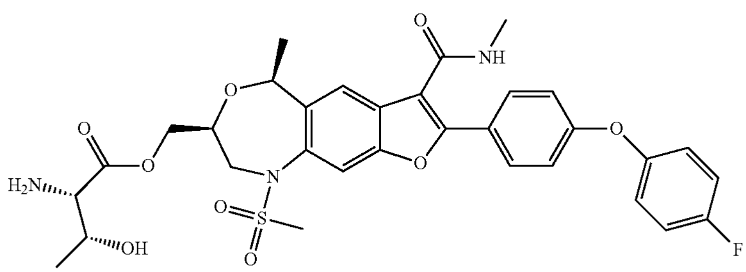 [SMILES: CNC(=O)c1c(-c2ccc(Oc3ccc(F)cc3)cc2)oc2cc3c(cc12)[C@H](C)O[C@H](COC(=O)[C@@H](N)[C@@H](C)O)CN3S(C)(=O)=O] | | |
| D11 | 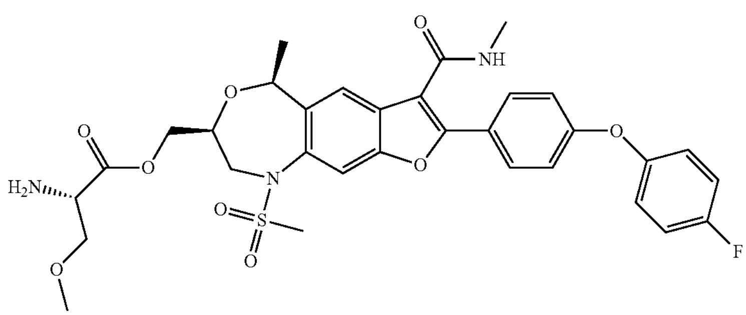 [SMILES: CNC(=O)c1c(-c2ccc(Oc3ccc(F)cc3)cc2)oc2cc3c(cc12)[C@H](C)O[C@H](COC(=O)[C@@H](N)COC)CN3S(C)(=O)=O] | | |
| D12 | 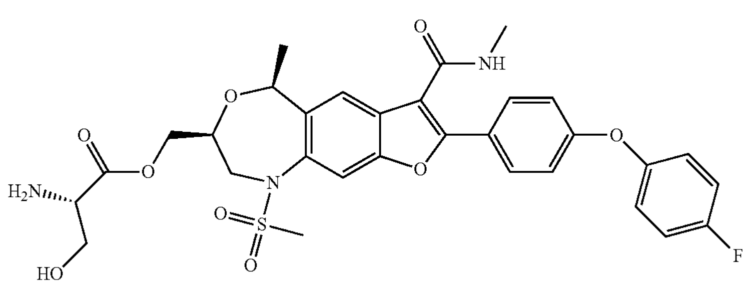 [SMILES: CNC(=O)c1c(-c2ccc(Oc3ccc(F)cc3)cc2)oc2cc3c(cc12)[C@H](C)O[C@H](COC(=O)[C@@H](N)CO)CN3S(C)(=O)=O] | | |

APPENDIX B-continued

| compound ID | Structure | Inhibition of HCV genotype 1b replicon | MS [M + 1]+ |
|---|---|---|---|
| D13 | 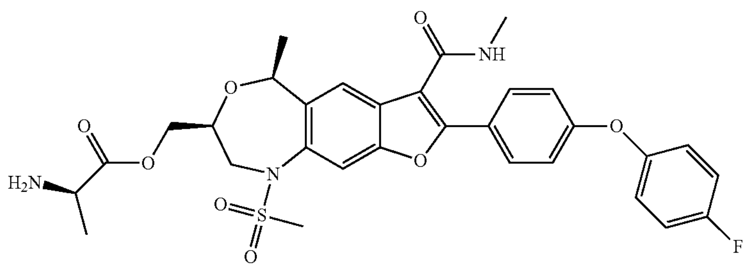 [SMILES: CNC(=O)c1c(-c2ccc(Oc3ccc(F)cc3)cc2)oc2cc3c(cc12)[C@H](C)O[C@H](COC(=O)[C@@H](C)N)CN3S(C)(=O)=O] | | |
| D14 | 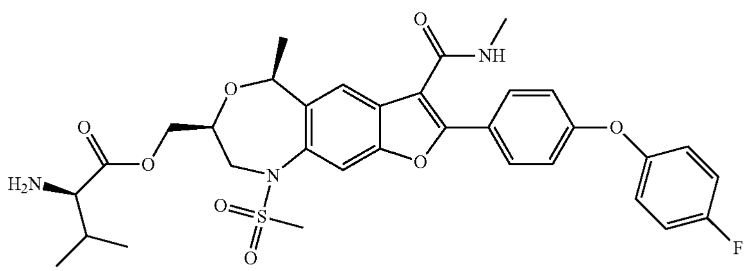 [SMILES: CNC(=O)c1c(-c2ccc(Oc3ccc(F)cc3)cc2)oc2cc3c(cc12)[C@H](C)O[C@H](COC(=O)[C@H](N)C(C)C)CN3S(C)(=O)=O] | | |
| D15 | 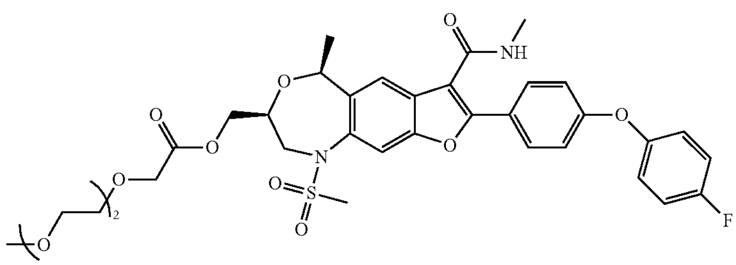 | | |
| D16 | 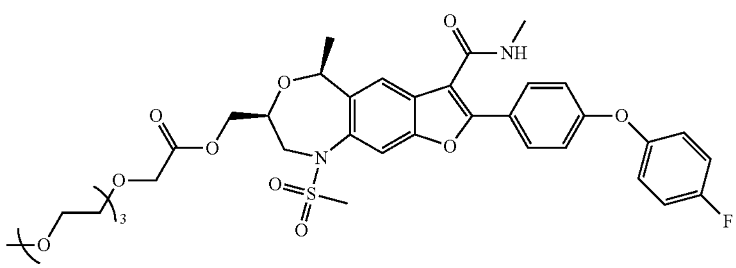 | | |
| D17 | 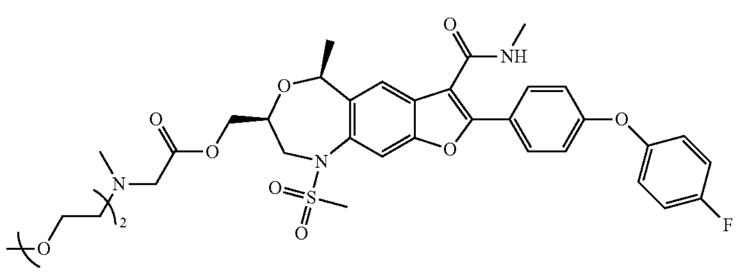 | | |

APPENDIX B-continued

| compound ID | Structure | Inhibition of HCV genotype 1b replicon | MS [M + 1]+ |
|---|---|---|---|
| D18 | 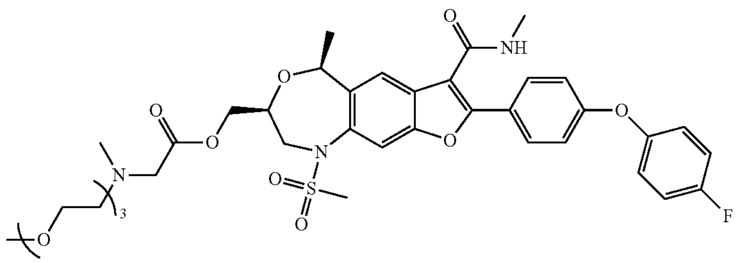 | | |
| D19 | 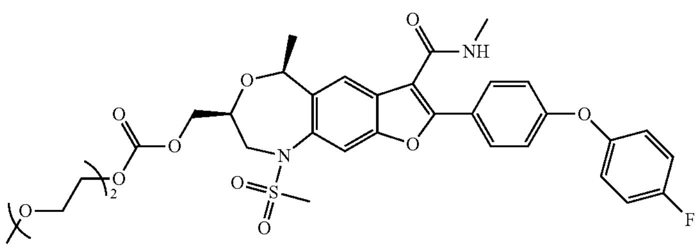 | | |
| D20 | 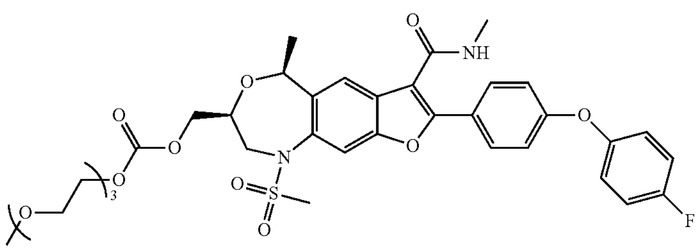 | | |
| D21 | 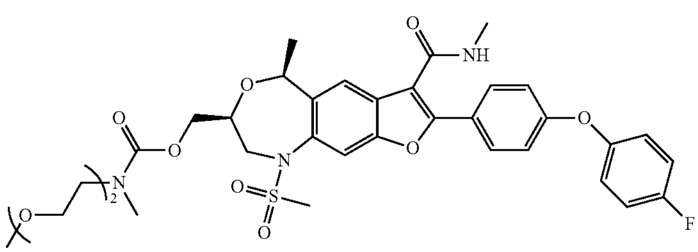 | | |
| D22 | 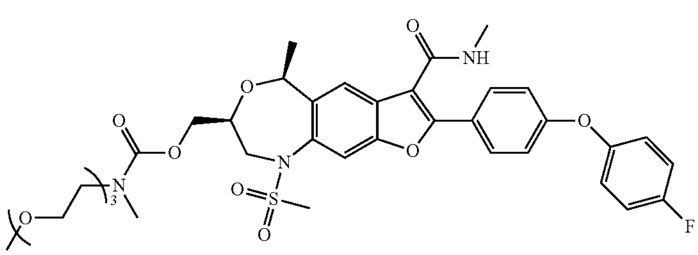 | | |

APPENDIX B-continued

| compound ID | Structure | Inhibition of HCV genotype 1b replicon | MS [M + 1]+ |
|---|---|---|---|
| D23 | 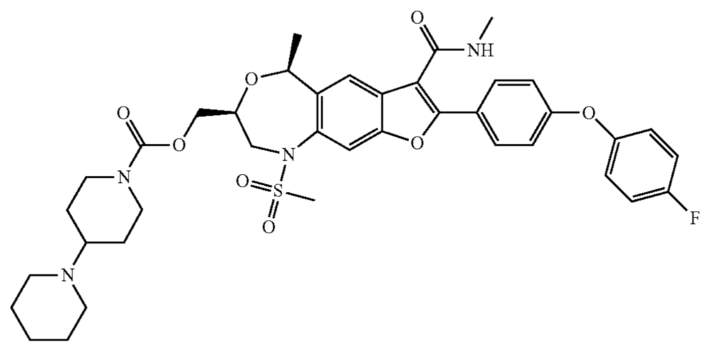 [SMILES: CNC(=O)c1c(-c2ccc(Oc3ccc(F)cc3)cc2)oc2cc3c(cc12)[C@H](C)O[C@H](COC(=O)N1CCC(N2CCCCC2)CC1)CN3S(C)(=O)=O] | | |
| D24 | 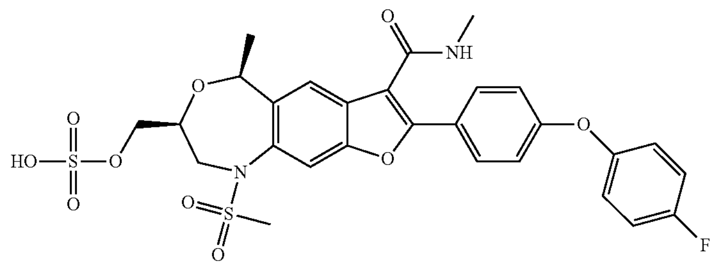 [SMILES: CNC(=O)c1c(-c2ccc(Oc3ccc(F)cc3)cc2)oc2cc3c(cc12)[C@H](C)O[C@H](COS(=O)(=O)O)CN3S(C)(=O)=O] | | |
| D25 | 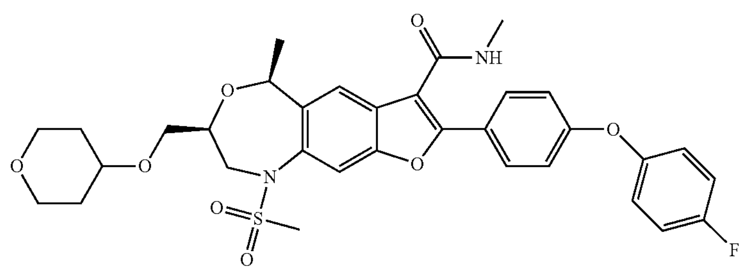 [SMILES: CNC(=O)c1c(-c2ccc(Oc3ccc(F)cc3)cc2)oc2cc3c(cc12)[C@H](C)O[C@H](COC1CCOCC1)CN3S(C)(=O)=O] | | |
| D26 | 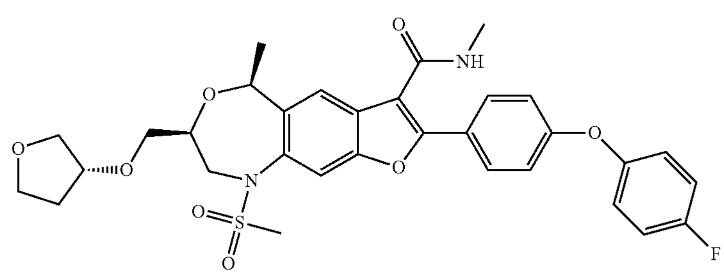 [SMILES: CNC(=O)c1c(-c2ccc(Oc3ccc(F)cc3)cc2)oc2cc3c(cc12)[C@H](C)O[C@H](CO[C@@H]1CCOC1)CN3S(C)(=O)=O] | | |
| D27 | 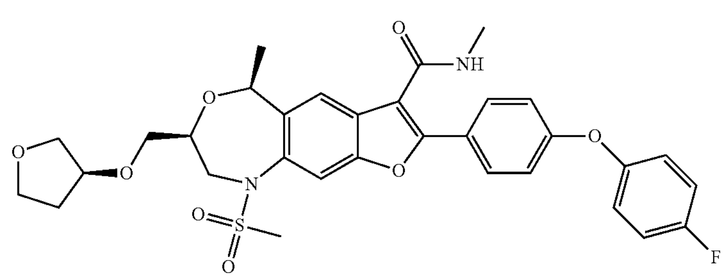 [SMILES: CNC(=O)c1c(-c2ccc(Oc3ccc(F)cc3)cc2)oc2cc3c(cc12)[C@H](C)O[C@H](CO[C@H]1CCOC1)CN3S(C)(=O)=O] | | |

APPENDIX B-continued

| compound ID | Structure | Inhibition of HCV genotype 1b replicon | MS [M + 1]+ |
|---|---|---|---|
| D28 | 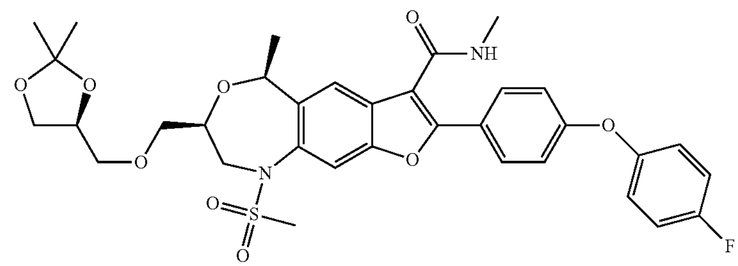 [SMILES: CNC(=O)c1c(-c2ccc(Oc3ccc(F)cc3)cc2)oc2cc3c(cc12)[C@H](C)O[C@H](COC[C@H]1COC(C)(C)O1)CN3S(C)(=O)=O] | | |
| D29 | 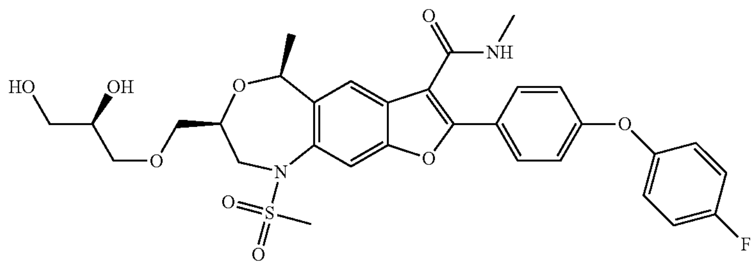 [SMILES: CNC(=O)c1c(-c2ccc(Oc3ccc(F)cc3)cc2)oc2cc3c(cc12)[C@H](C)O[C@H](COC[C@H](O)CO)CN3S(C)(=O)=O] | | |
| D30 | 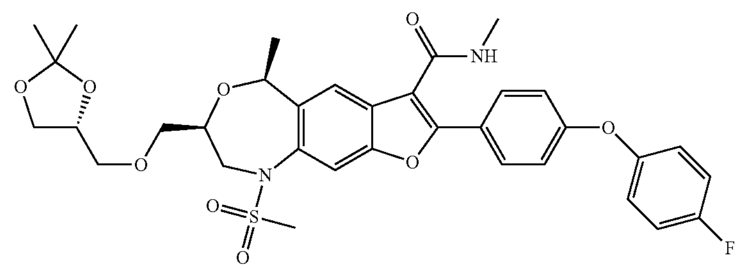 [SMILES: CNC(=O)c1c(-c2ccc(Oc3ccc(F)cc3)cc2)oc2cc3c(cc12)[C@H](C)O[C@H](COC[C@@H]1COC(C)(C)O1)CN3S(C)(=O)=O] | | |
| D31 | 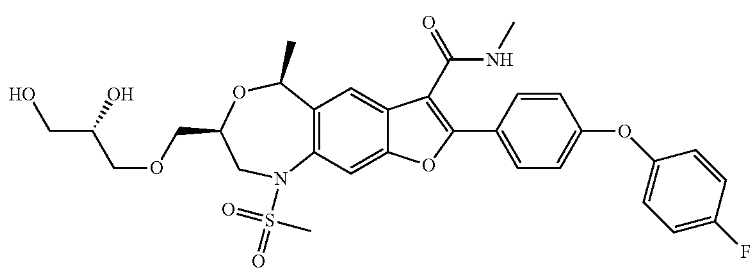 [SMILES: CNC(=O)c1c(-c2ccc(Oc3ccc(F)cc3)cc2)oc2cc3c(cc12)[C@H](C)O[C@H](COC[C@@H](O)CO)CN3S(C)(=O)=O] | | |
| D32 | 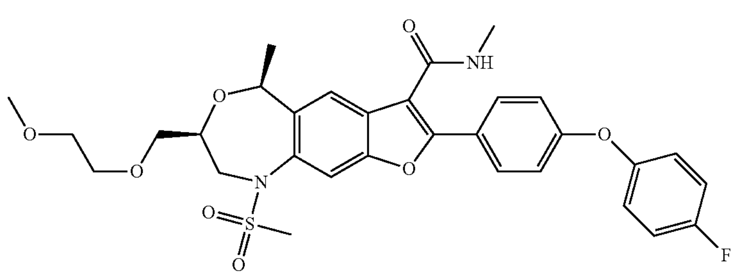 [SMILES: CNC(=O)c1c(-c2ccc(Oc3ccc(F)cc3)cc2)oc2cc3c(cc12)[C@H](C)O[C@H](COCCOC)CN3S(C)(=O)=O] | | |

APPENDIX B-continued

| compound ID | Structure | Inhibition of HCV genotype 1b replicon | MS [M + 1]+ |
|---|---|---|---|
| D33 | 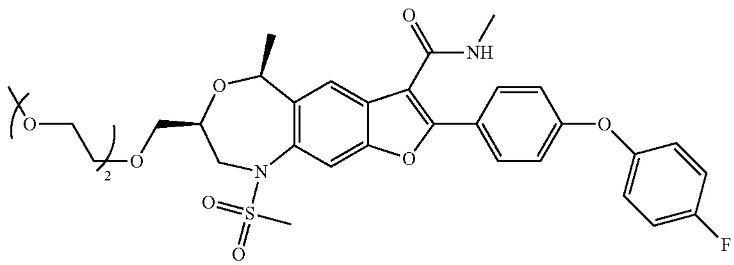 | | |
| D34 | 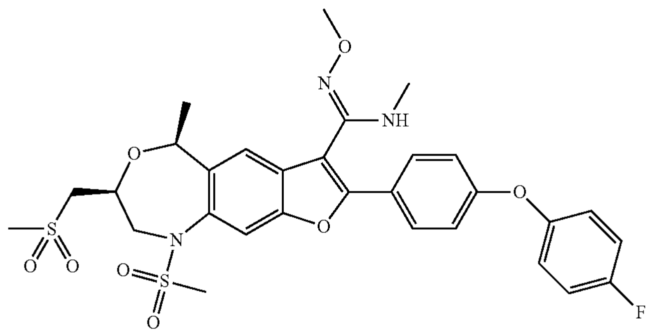 [SMILES: CN/C(=N\OC)c1c(-c2ccc(Oc3ccc(F)cc3)cc2)oc2cc3c(cc12)[C@H](C)O[C@H](CS(C)(=O)=O)CN3S(C)(=O)=O] | | |
| D35 | 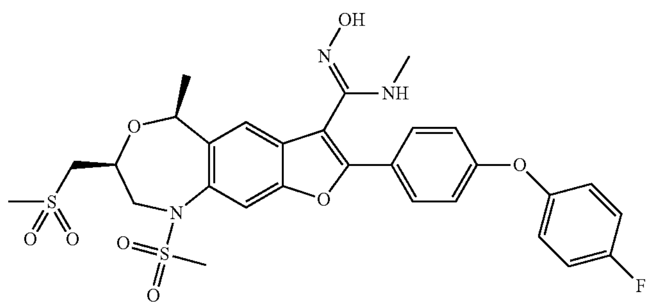 [SMILES: CN/C(=N\O)c1c(-c2ccc(Oc3ccc(F)cc3)cc2)oc2cc3c(cc12)[C@H](C)O[C@H](CS(C)(=O)=O)CN3S(C)(=O)=O] | | |
| D36 | 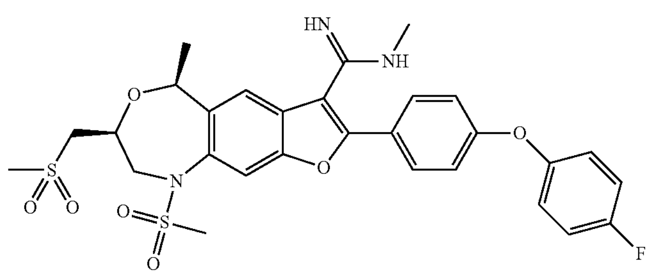 [SMILES: CNC(=N)c1c(-c2ccc(Oc3ccc(F)cc3)cc2)oc2cc3c(cc12)[C@H](C)O[C@H](CS(C)(=O)=O)CN3S(C)(=O)=O] | | |
| D37 | 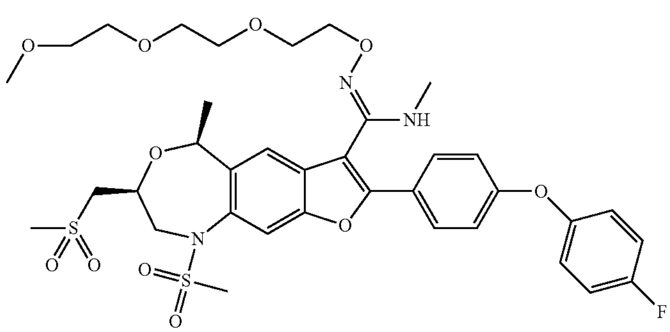 [SMILES: CN/C(=N\OCCOCCOCCOC)c1c(-c2ccc(Oc3ccc(F)cc3)cc2)oc2cc3c(cc12)[C@H](C)O[C@H](CS(C)(=O)=O)CN3S(C)(=O)=O] | | |

APPENDIX B-continued

| compound ID | Structure | Inhibition of HCV genotype 1b replicon | MS [M + 1]+ |
|---|---|---|---|
| D38 | 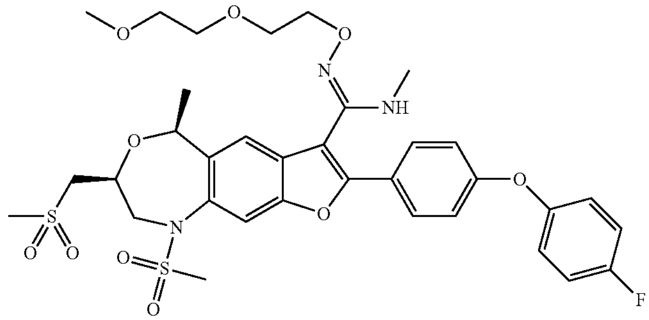 [SMILES: CN/C(=N\OCCOCCOC)c1c(-c2ccc(Oc3ccc(F)cc3)cc2)oc2cc3c(cc12)[C@H](C)O[C@H](CS(C)(=O)=O)CN3S(C)(=O)=O] | | |
| D39 | 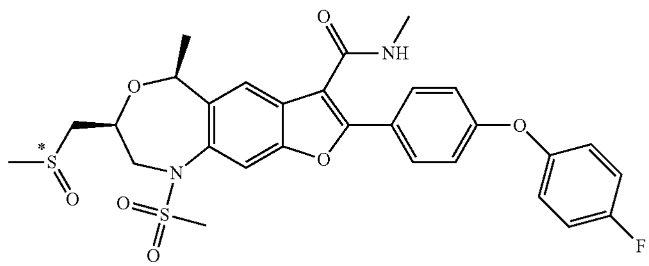 [SMILES: CNC(=O)c1c(-c2ccc(Oc3ccc(F)cc3)cc2)oc2cc3c(cc12)[C@H](C)O[C@H](CS(C)=O)CN3S(C)(=O)=O] | | |
| D40 | 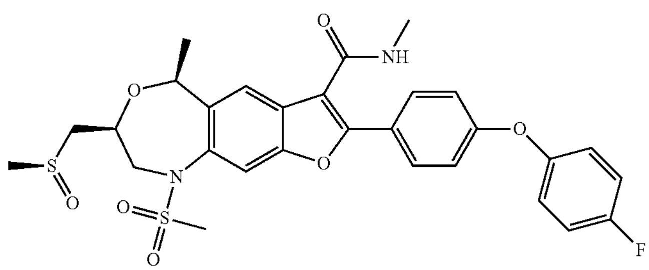 [SMILES: CNC(=O)c1c(-c2ccc(Oc3ccc(F)cc3)cc2)oc2cc3c(cc12)[C@H](C)O[C@H](C[S@](C)=O)CN3S(C)(=O)=O] | | |
| D41 | 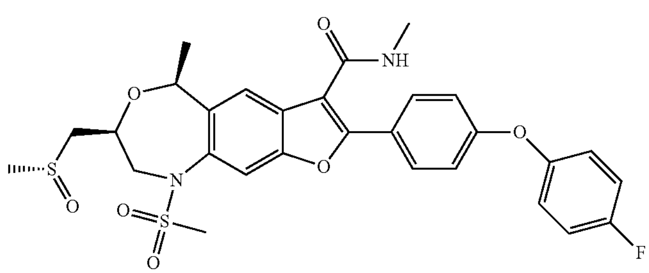 [SMILES: CNC(=O)c1c(-c2ccc(Oc3ccc(F)cc3)cc2)oc2cc3c(cc12)[C@H](C)O[C@H](C[S@@](C)=O)CN3S(C)(=O)=O] | | |
| D42 | 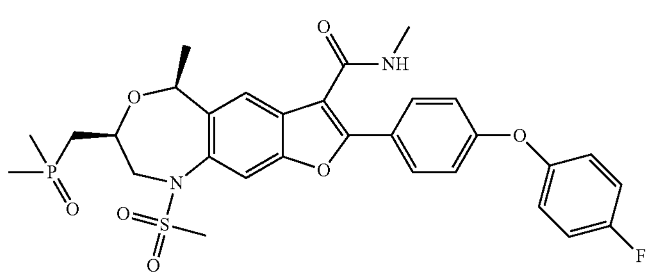 [SMILES: CNC(=O)c1c(-c2ccc(Oc3ccc(F)cc3)cc2)oc2cc3c(cc12)[C@H](C)O[C@H](CP(C)(C)=O)CN3S(C)(=O)=O] | | |

APPENDIX B-continued

| compound ID | Structure | Inhibition of HCV genotype 1b replicon | MS [M + 1]+ |
|---|---|---|---|
| D43 | 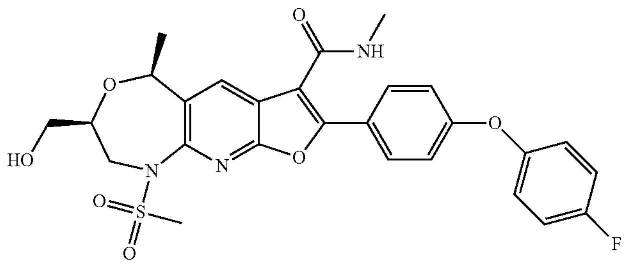 [SMILES: CNC(=O)c1c(-c2ccc(Oc3ccc(F)cc3)cc2)oc2nc3c(cc12)[C@H](C)O[C@H](CO)CN3S(C)(=O)=O] | | |
| D44 | 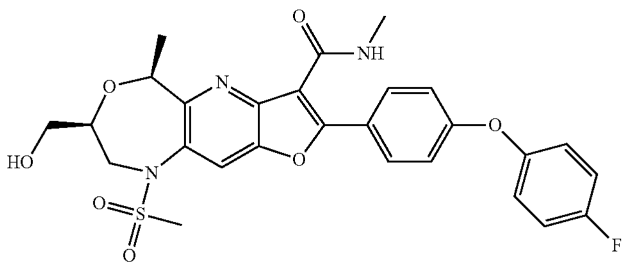 [SMILES: CNC(=O)c1c(-c2ccc(Oc3ccc(F)cc3)cc2)oc2cc3c(nc12)[C@H](C)O[C@H](CO)CN3S(C)(=O)=O] | | |
| D45 | 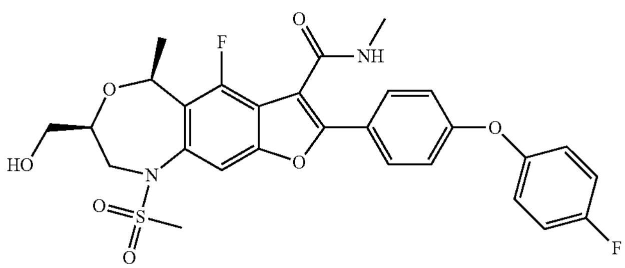 [SMILES: CNC(=O)c1c(-c2ccc(Oc3ccc(F)cc3)cc2)oc2cc3c(c(F)c12)[C@H](C)O[C@H](CO)CN3S(C)(=O)=O] | | |
| D46 | 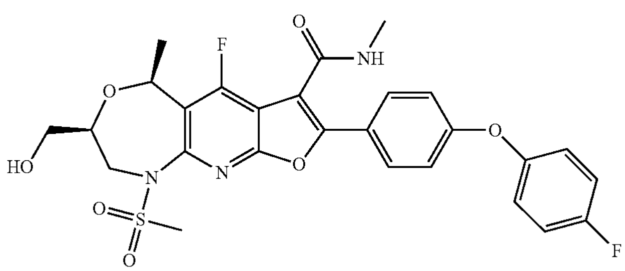 [SMILES: CNC(=O)c1c(-c2ccc(Oc3ccc(F)cc3)cc2)oc2nc3c(c(F)c12)[C@H](C)O[C@H](CO)CN3S(C)(=O)=O] | | |
| D47 | 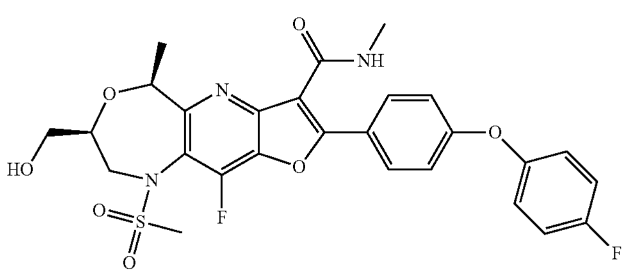 [SMILES: CNC(=O)c1c(-c2ccc(Oc3ccc(F)cc3)cc2)oc2c(F)c3c(nc12)[C@H](C)O[C@H](CO)CN3S(C)(=O)=O] | | |

APPENDIX B-continued

| compound ID | Structure | Inhibition of HCV genotype 1b replicon | MS [M + 1]+ |
|---|---|---|---|
| D48 | 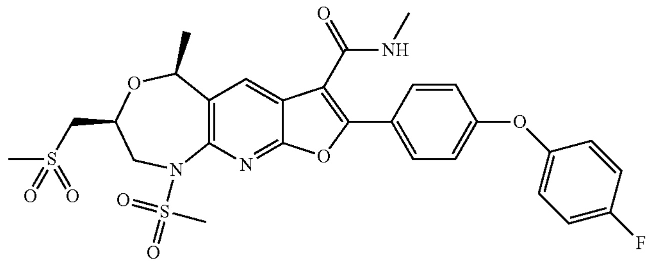 [SMILES: CNC(=O)c1c(-c2ccc(Oc3ccc(F)cc3)cc2)oc2nc3c(cc12)[C@H](C)O[C@H](CS(C)(=O)=O)CN3S(C)(=O)=O] | | |
| D49 | 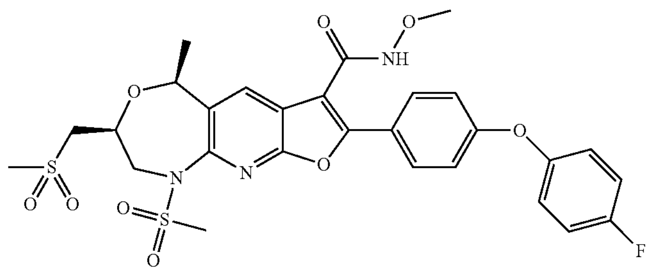 [SMILES: CONC(=O)c1c(-c2ccc(Oc3ccc(F)cc3)cc2)oc2nc3c(cc12)[C@H](C)O[C@H](CS(C)(=O)=O)CN3S(C)(=O)=O] | | |
| D50 | 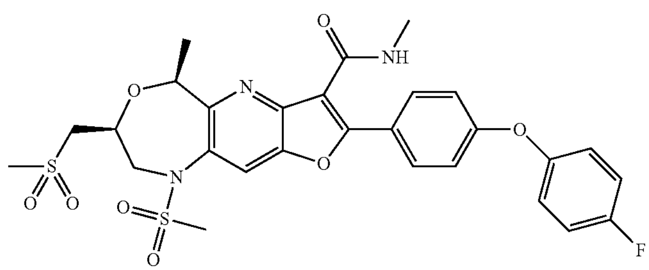 [SMILES: CNC(=O)c1c(-c2ccc(Oc3ccc(F)cc3)cc2)oc2cc3c(nc12)[C@H](C)O[C@H](CS(C)(=O)=O)CN3S(C)(=O)=O] | | |
| D51 | 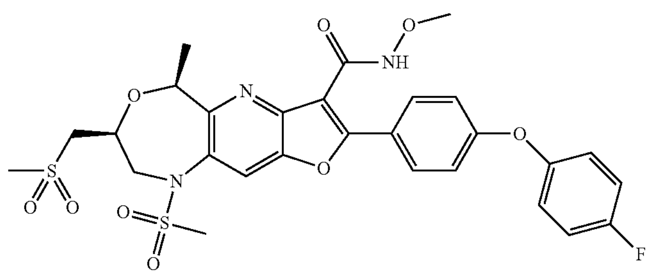 [SMILES: CONC(=O)c1c(-c2ccc(Oc3ccc(F)cc3)cc2)oc2cc3c(nc12)[C@H](C)O[C@H](CS(C)(=O)=O)CN3S(C)(=O)=O] | | |
| D52 | 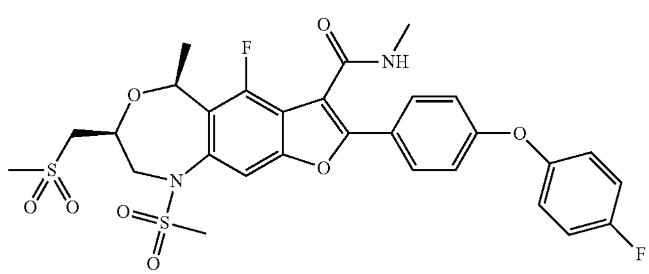 [SMILES: CNC(=O)c1c(-c2ccc(Oc3ccc(F)cc3)cc2)oc2cc3c(c(F)c12)[C@H](C)O[C@H](CS(C)(=O)=O)CN3S(C)(=O)=O] | | |

APPENDIX B-continued

| compound ID | Structure | Inhibition of HCV genotype 1b replicon | MS [M + 1]+ |
|---|---|---|---|
| D53 | 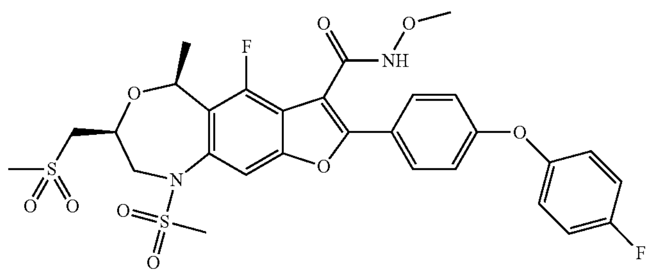 [SMILES: CONC(=O)c1c(-c2ccc(Oc3ccc(F)cc3)cc2)oc2cc3c(c(F)c12)[C@H](C)O[C@H](CS(C)(=O)=O)CN3S(C)(=O)=O] | | |
| D54 | 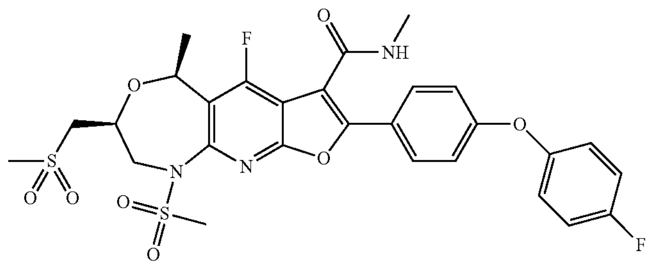 [SMILES: CNC(=O)c1c(-c2ccc(Oc3ccc(F)cc3)cc2)oc2nc3c(c(F)c12)[C@H](C)O[C@H](CS(C)(=O)=O)CN3S(C)(=O)=O] | | |
| D55 | 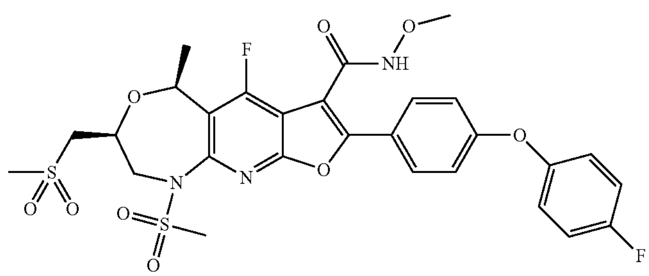 [SMILES: CONC(=O)c1c(-c2ccc(Oc3ccc(F)cc3)cc2)oc2nc3c(c(F)c12)[C@H](C)O[C@H](CS(C)(=O)=O)CN3S(C)(=O)=O] | | |
| D56 | 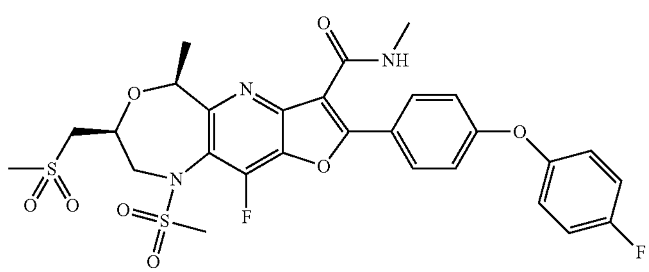 [SMILES: CNC(=O)c1c(-c2ccc(Oc3ccc(F)cc3)cc2)oc2c(F)c3c(nc12)[C@H](C)O[C@H](CS(C)(=O)=O)CN3S(C)(=O)=O] | | |
| D57 | 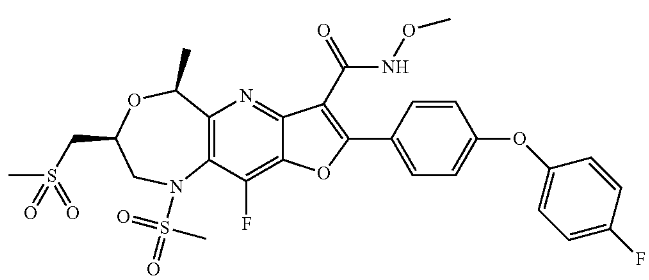 [SMILES: CONC(=O)c1c(-c2ccc(Oc3ccc(F)cc3)cc2)oc2c(F)c3c(nc12)[C@H](C)O[C@H](CS(C)(=O)=O)CN3S(C)(=O)=O] | | |

APPENDIX B-continued

| compound ID | Structure | Inhibition of HCV genotype 1b replicon | MS [M + 1]+ |
|---|---|---|---|
| D58 | 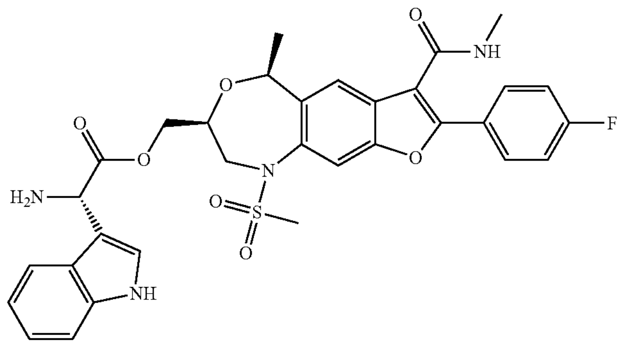 [SMILES: CNC(=O)c1c(-c2ccc(F)cc2)oc2cc3c(cc12)[C@H](C)O[C@H](COC(=O)[C@@H](N)c1c[nH]c2ccccc12)CN3S(C)(=O)=O] | | |
| D59 | 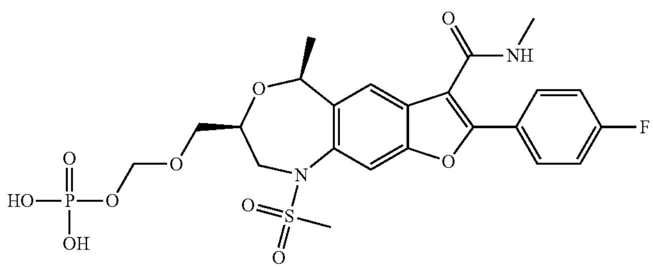 [SMILES: CNC(=O)c1c(-c2ccc(F)cc2)oc2cc3c(cc12)[C@H](C)O[C@H](COCOP(=O)(O)O)CN3S(C)(=O)=O] | | |
| D60 | 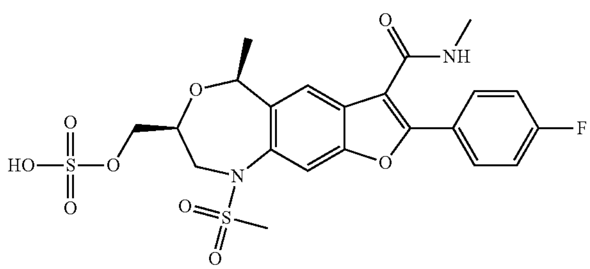 [SMILES: CNC(=O)c1c(-c2ccc(F)cc2)oc2cc3c(cc12)[C@H](C)O[C@H](COS(=O)(=O)O)CN3S(C)(=O)=O] | | |
| D61 | 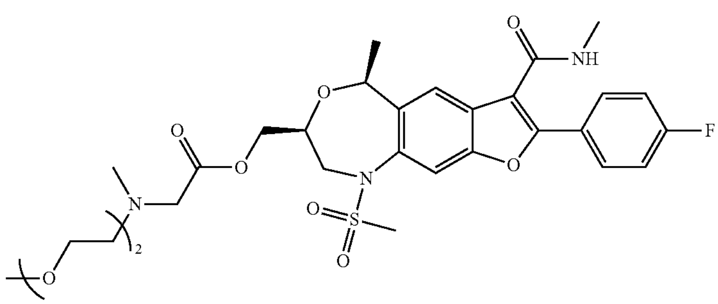 | | |
| D62 | 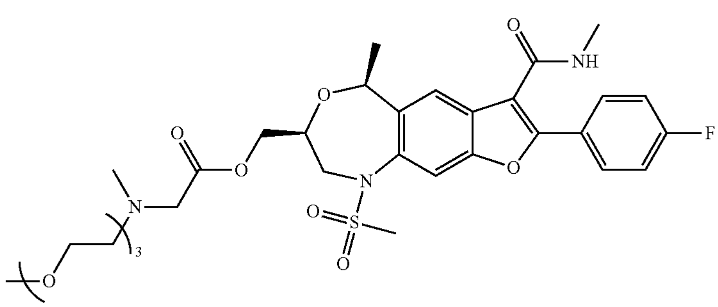 | | |

APPENDIX B-continued

| compound ID | Structure | Inhibition of HCV genotype 1b replicon | MS [M + 1]+ |
|---|---|---|---|
| D63 | 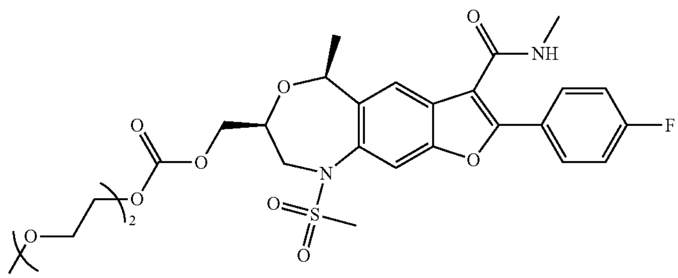 | | |
| D64 | 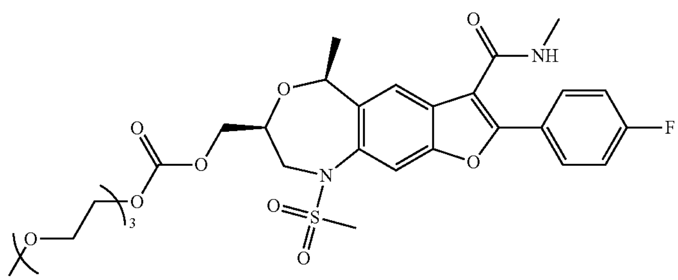 | | |
| D65 | 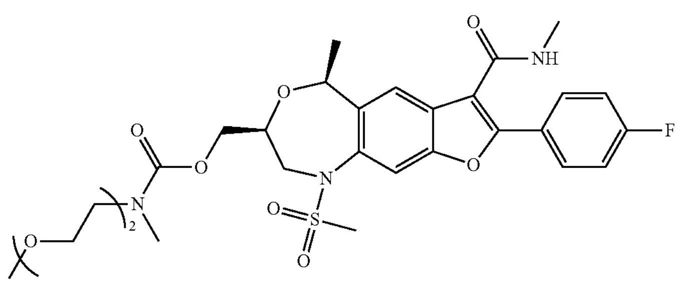 | | |
| D66 | 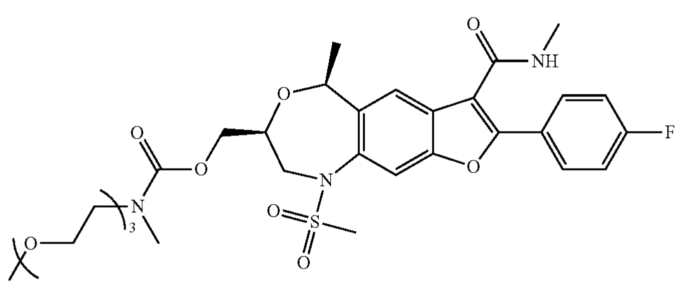 | | |
| D67 | 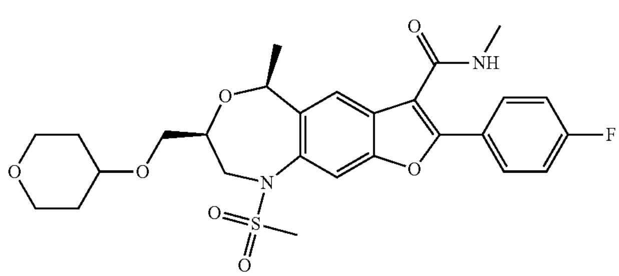 [SMILES: CNC(=O)c1c(-c2ccc(F)cc2)oc2cc3c(cc12)[C@H](C)O[C@H](COC1CCOCC1)CN3S(C)(=O)=O] | | |

APPENDIX B-continued

| compound ID | Structure | Inhibition of HCV genotype 1b replicon | MS [M + 1]+ |
|---|---|---|---|
| D68 | 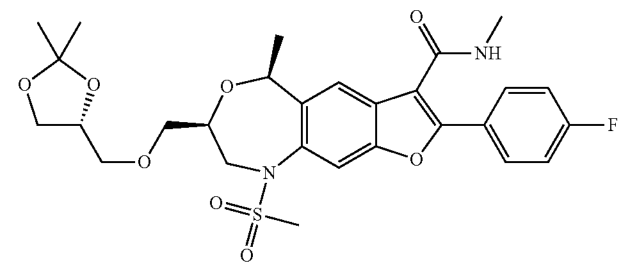 [SMILES: CNC(=O)c1c(-c2ccc(F)cc2)oc2cc3c(cc12)[C@H](C)O[C@H](COC[C@@H]1COC(C)(C)O1)CN3S(C)(=O)=O] | | |
| D69 | 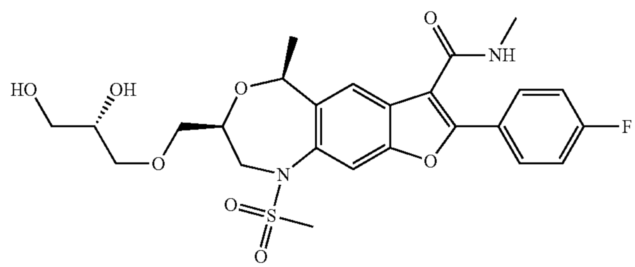 [SMILES: CNC(=O)c1c(-c2ccc(F)cc2)oc2cc3c(cc12)[C@H](C)O[C@H](COC[C@@H](O)CO)CN3S(C)(=O)=O] | | |
| D70 | 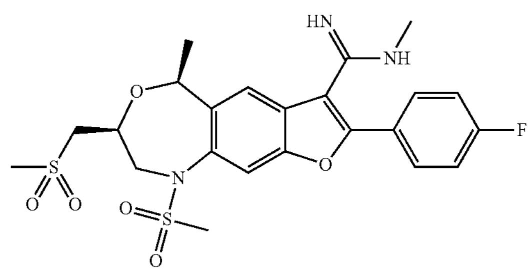 [SMILES: CNC(=N)c1c(-c2ccc(F)cc2)oc2cc3c(cc12)[C@H](C)O[C@H](CS(C)(=O)=O)CN3S(C)(=O)=O] | | |
| D71 | 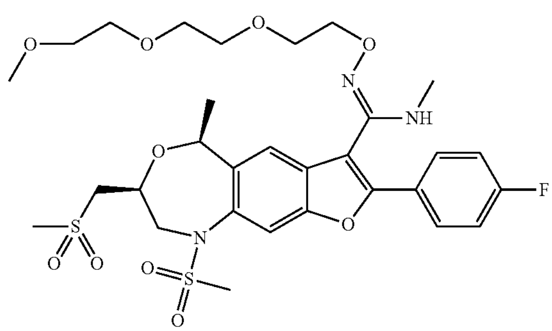 [SMILES: CN/C(=N\OCCOCCOCCOC)c1c(-c2ccc(F)cc2)oc2cc3c(cc12)[C@H](C)O[C@H](CS(C)(=O)=O)CN3S(C)(=O)=O] | | |
| D72 | 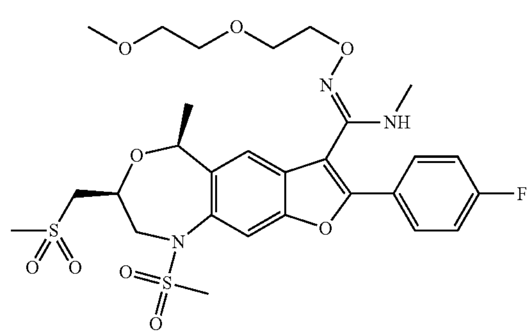 [SMILES: CN/C(=N\OCCOCCOC)c1c(-c2ccc(F)cc2)oc2cc3c(cc12)[C@H](C)O[C@H](CS(C)(=O)=O)CN3S(C)(=O)=O] | | |

APPENDIX B-continued

| compound ID | Structure | Inhibition of HCV genotype 1b replicon | MS [M + 1]+ |
|---|---|---|---|
| D73 | 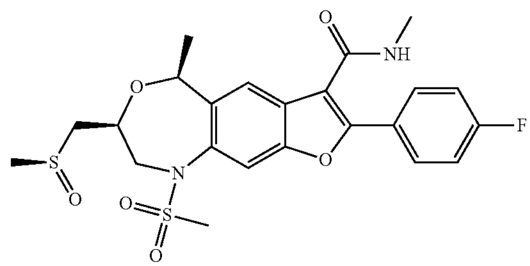 [SMILES: CNC(=O)c1c(-c2ccc(F)cc2)oc2cc3c(cc12)[C@H](C)O[C@H](C[S@](C)=O)CN3S(C)(=O)=O] | | |
| D74 | 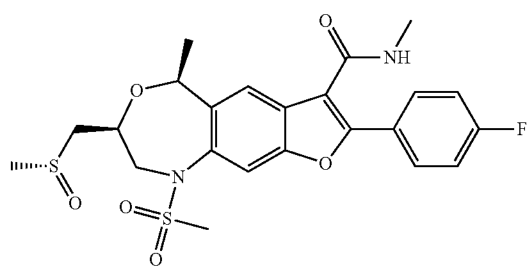 [SMILES: CNC(=O)c1c(-c2ccc(F)cc2)oc2cc3c(cc12)[C@H](C)O[C@H](C[S@@](C)=O)CN3S(C)(=O)=O] | | |
| D75 | 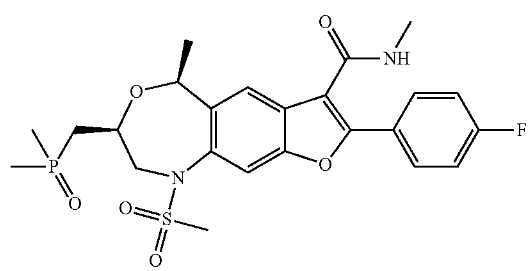 [SMILES: CNC(=O)c1c(-c2ccc(F)cc2)oc2cc3c(cc12)[C@H](C)O[C@H](CP(C)(C)=O)CN3S(C)(=O)=O] | | |
| D76 | 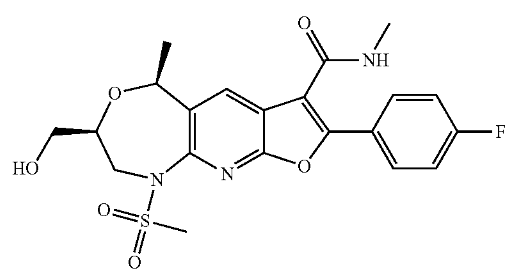 [SMILES: CNC(=O)c1c(-c2ccc(F)cc2)oc2nc3c(cc12)[C@H](C)O[C@H](CO)CN3S(C)(=O)=O] | | |
| D77 | 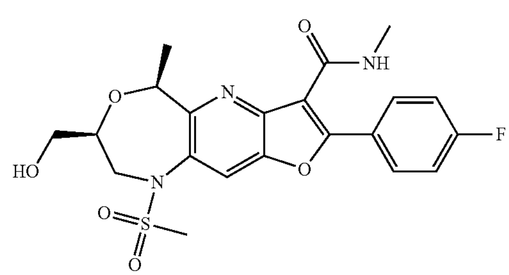 [SMILES: CNC(=O)c1c(-c2ccc(F)cc2)oc2cc3c(nc12)[C@H](C)O[C@H](CO)CN3S(C)(=O)=O] | | |

APPENDIX B-continued

| compound ID | Structure | Inhibition of HCV genotype 1b replicon | MS [M + 1]+ |
|---|---|---|---|
| D78 | 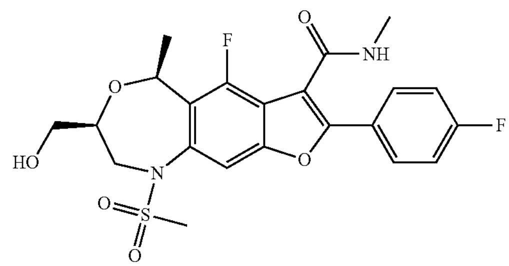 [SMILES: CNC(=O)c1c(-c2ccc(F)cc2)oc2cc3c(c(F)c12)[C@H](C)O[C@H](CO)CN3S(C)(=O)=O] | | |
| D79 | 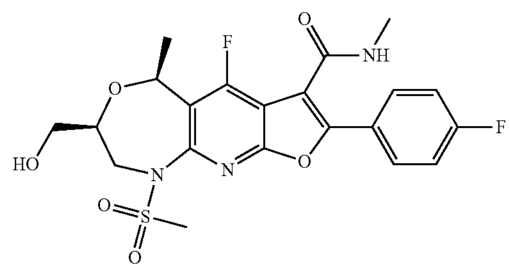 [SMILES: CNC(=O)c1c(-c2ccc(F)cc2)oc2nc3c(c(F)c12)[C@H](C)O[C@H](CO)CN3S(C)(=O)=O] | | |
| D80 | 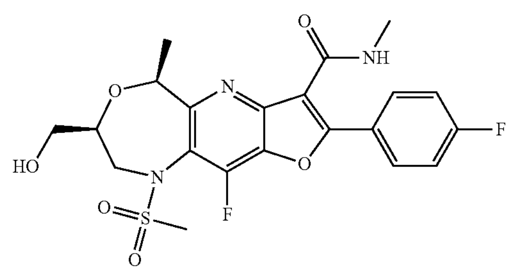 [SMILES: CNC(=O)c1c(-c2ccc(F)cc2)oc2c(F)c3c(nc12)[C@H](C)O[C@H](CO)CN3S(C)(=O)=O] | | |
| D81 | 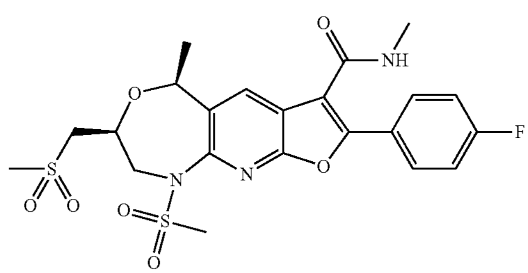 [SMILES: CNC(=O)c1c(-c2ccc(F)cc2)oc2nc3c(cc12)[C@H](C)O[C@H](CS(C)(=O)=O)CN3S(C)(=O)=O] | | |
| D82 | 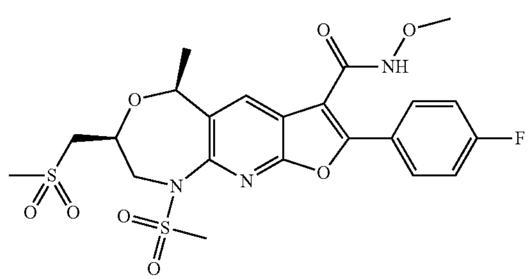 [SMILES: CONC(=O)c1c(-c2ccc(F)cc2)oc2nc3c(cc12)[C@H](C)O[C@H](CS(C)(=O)=O)CN3S(C)(=O)=O] | | |

APPENDIX B-continued

| compound ID | Structure | Inhibition of HCV genotype 1b replicon | MS [M + 1]+ |
|---|---|---|---|
| D83 | 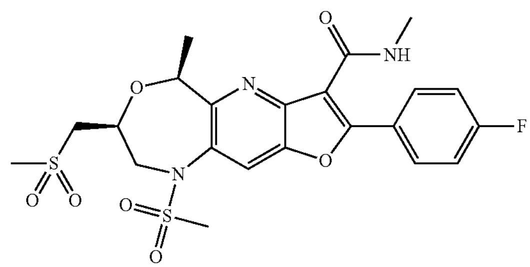 [SMILES: CNC(=O)c1c(-c2ccc(F)cc2)oc2cc3c(nc12)[C@H](C)O[C@H](CS(C)(=O)=O)CN3S(C)(=O)=O] | | |
| D84 | 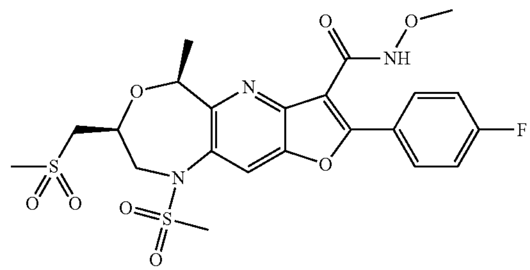 [SMILES: CONC(=O)c1c(-c2ccc(F)cc2)oc2cc3c(nc12)[C@H](C)O[C@H](CS(C)(=O)=O)CN3S(C)(=O)=O] | | |
| D85 | 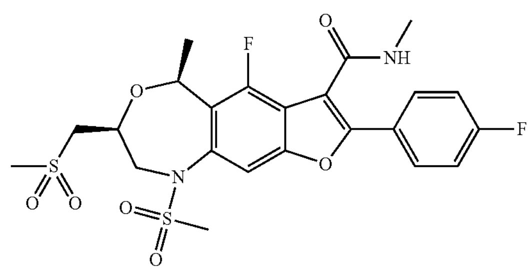 [SMILES: CNC(=O)c1c(-c2ccc(F)cc2)oc2cc3c(c(F)c12)[C@H](C)O[C@H](CS(C)(=O)=O)CN3S(C)(=O)=O] | | |
| D86 | 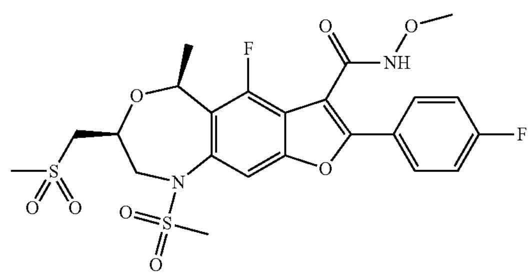 [SMILES: CONC(=O)c1c(-c2ccc(F)cc2)oc2cc3c(c(F)c12)[C@H](C)O[C@H](CS(C)(=O)=O)CN3S(C)(=O)=O] | | |
| D87 | 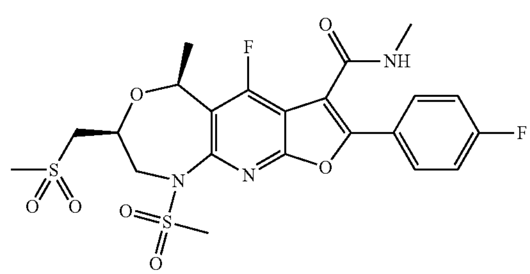 [SMILES: CNC(=O)c1c(-c2ccc(F)cc2)oc2nc3c(c(F)c12)[C@H](C)O[C@H](CS(C)(=O)=O)CN3S(C)(=O)=O] | | |

APPENDIX B-continued
| compound ID | Structure | Inhibition of HCV genotype 1b replicon | MS [M + 1]+ |
|---|---|---|---|
| D88 | 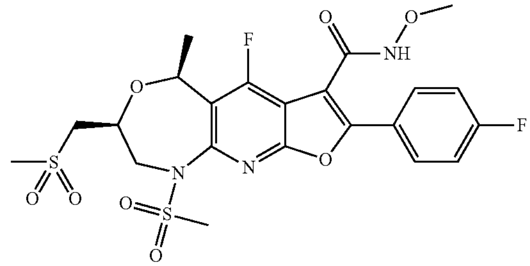 [SMILES: CONC(=O)c1c(-c2ccc(F)cc2)oc2nc3c(c(F)c12)[C@H](C)O[C@H](CS(C)(=O)=O)CN3S(C)(=O)=O] | | |
| D89 | 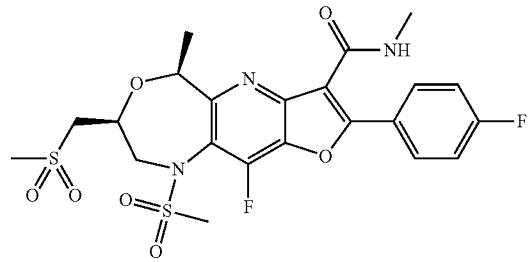 [SMILES: CNC(=O)c1c(-c2ccc(F)cc2)oc2c(F)c3c(nc12)[C@H](C)O[C@H](CS(C)(=O)=O)CN3S(C)(=O)=O] | | |
| D90 | 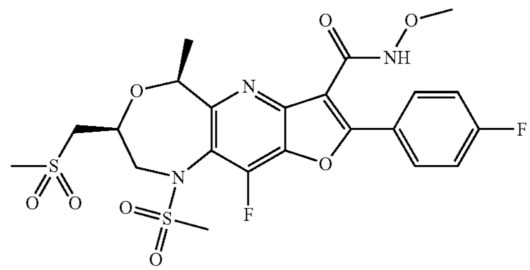 [SMILES: CONC(=O)c1c(-c2ccc(F)cc2)oc2c(F)c3c(nc12)[C@H](C)O[C@H](CS(C)(=O)=O)CN3S(C)(=O)=O] | | |
It is claimed:
1. A compound selected from the group consisting of:
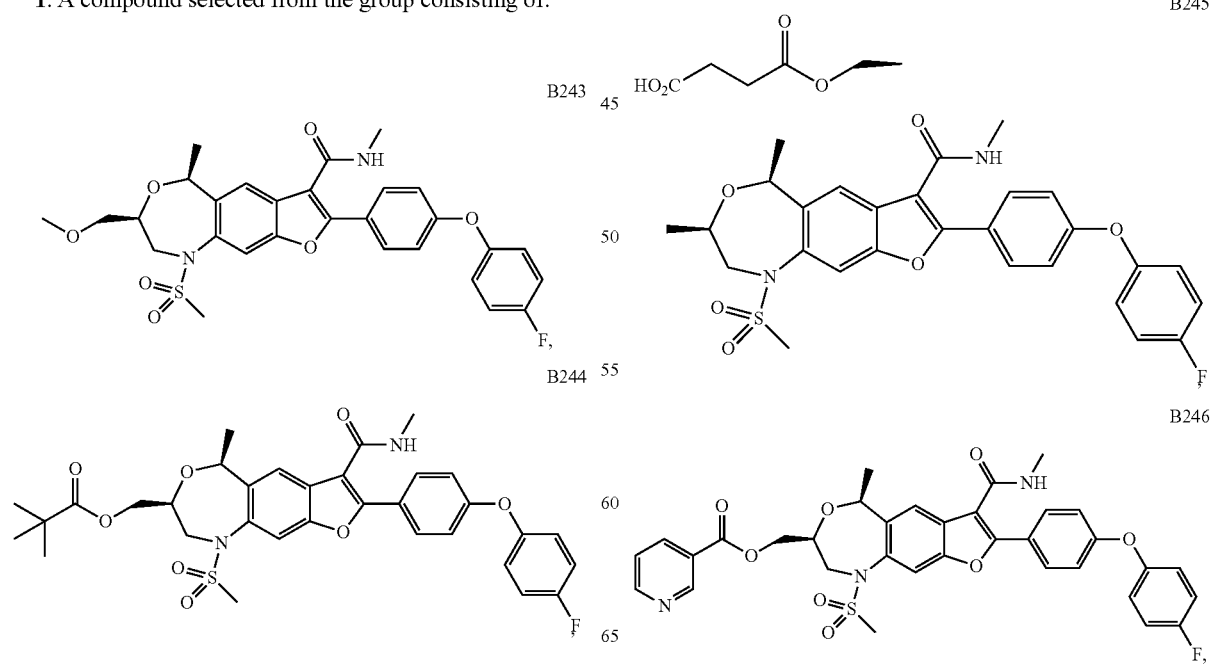

B248
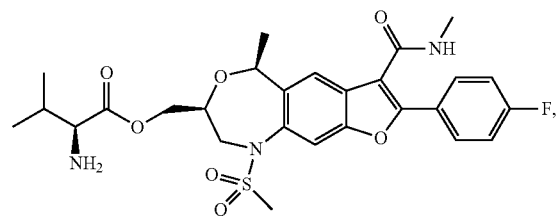
B249
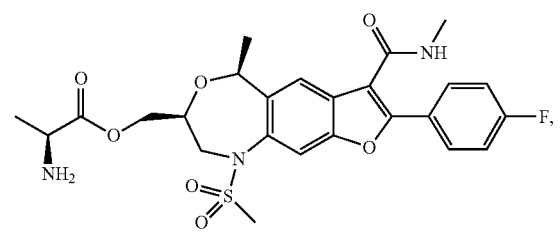
B252
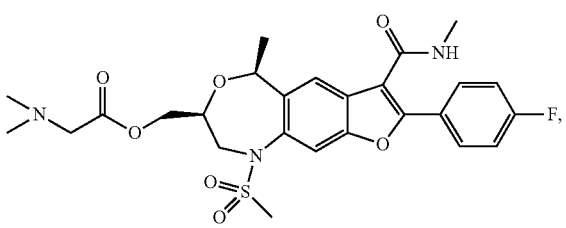
B254
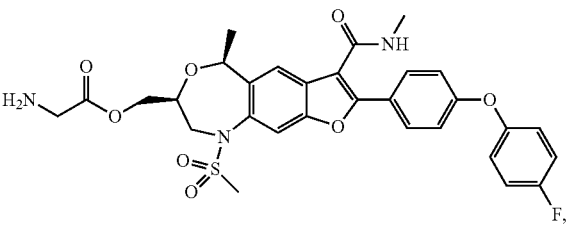
B255
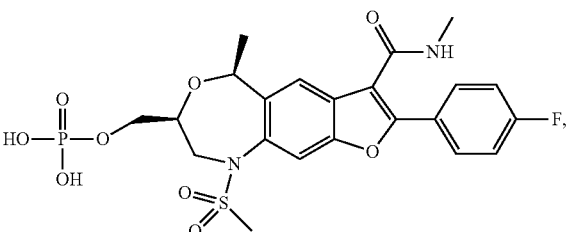
B256
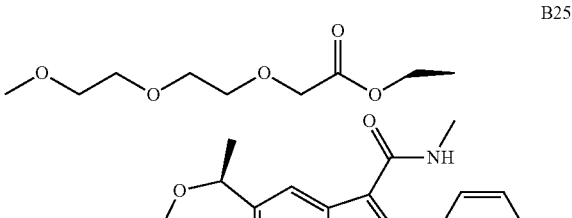
B257
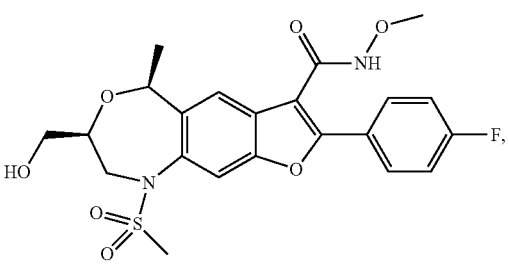
B258
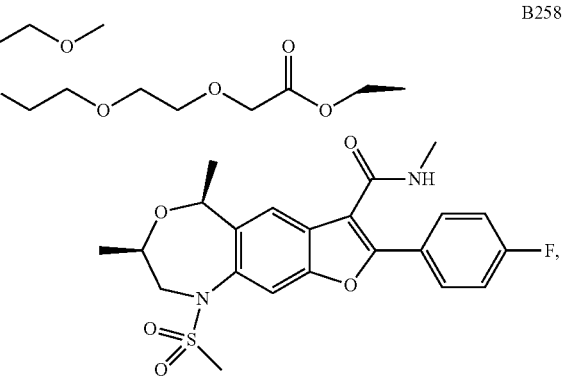
B259
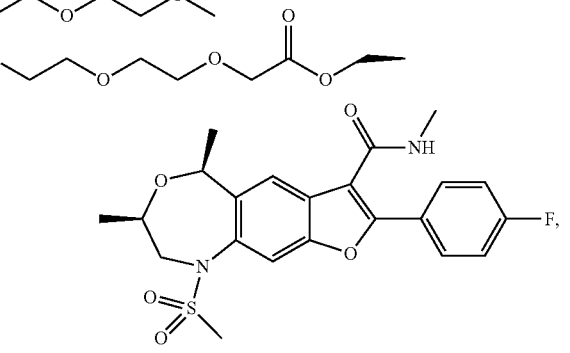
B260
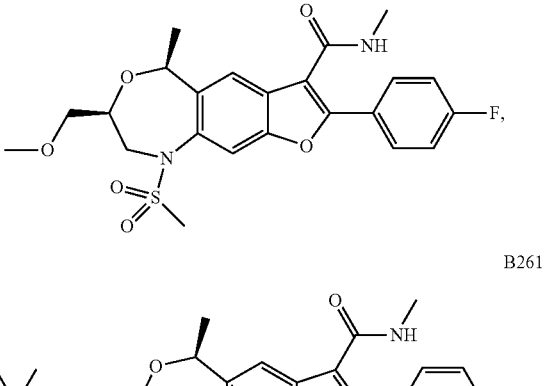
B261
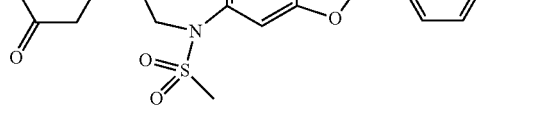

775
-continued
B262
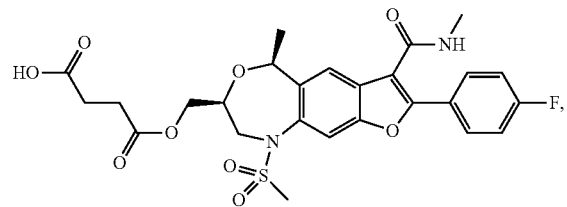
B263
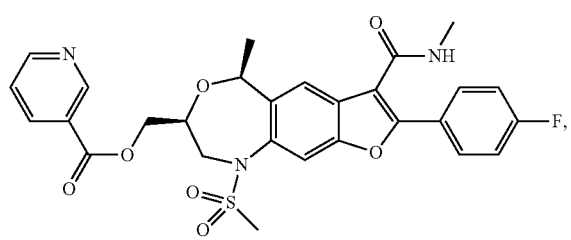
B264
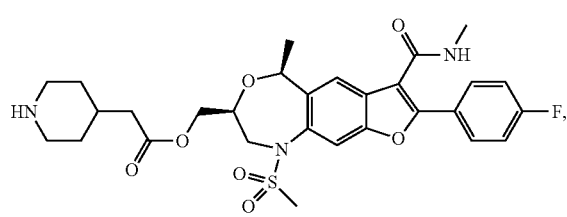
B265
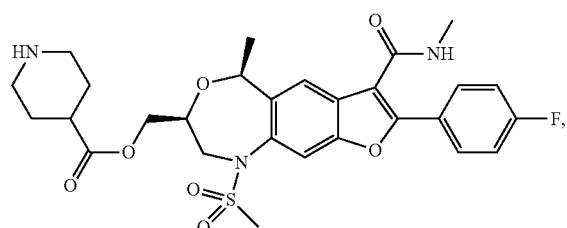
B266
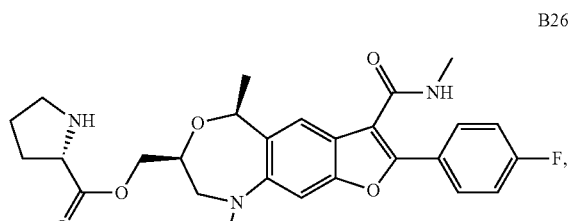
B267
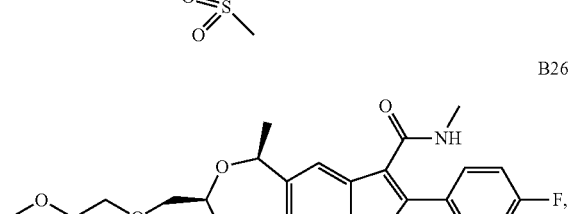
776
-continued
B268
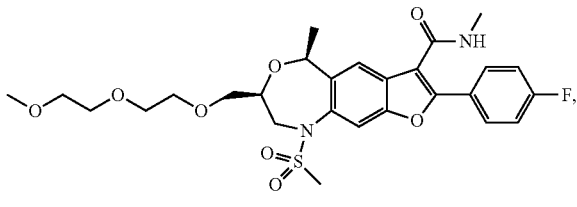
B269
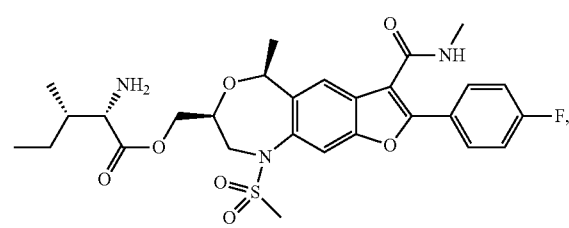
B270
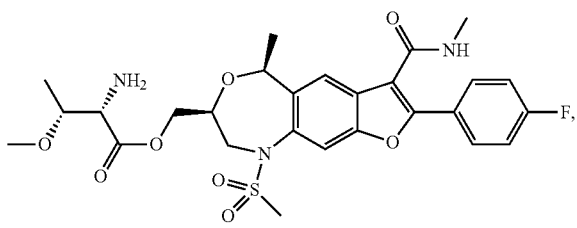
B271
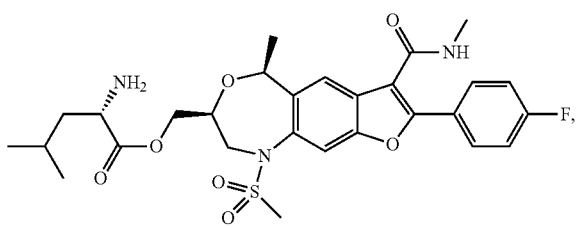
B272
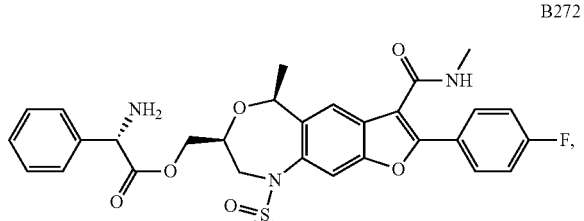
B273
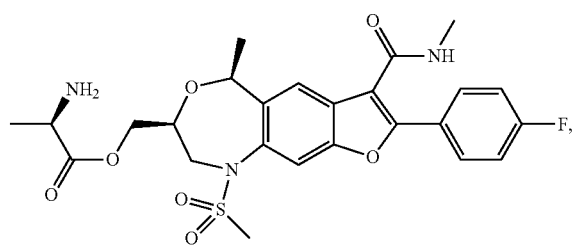

B274
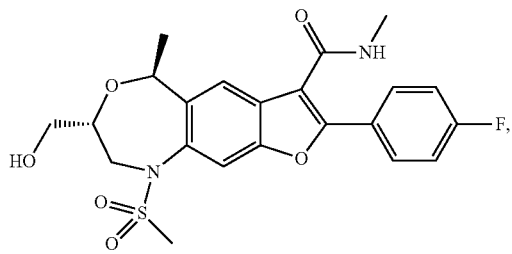
B280
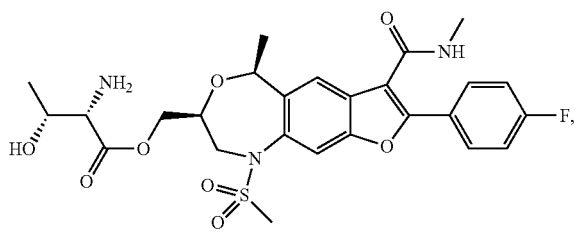
B275
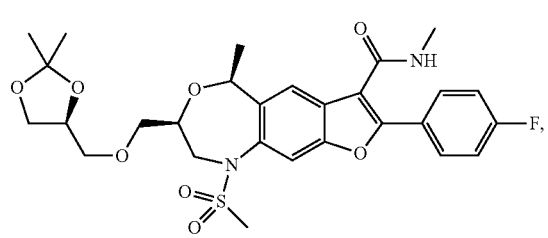
B281
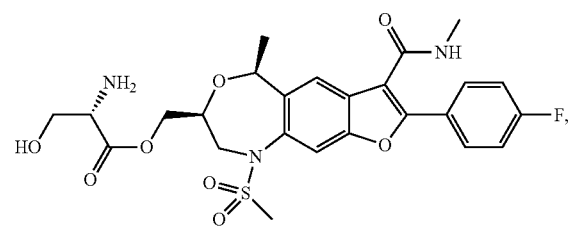
B276
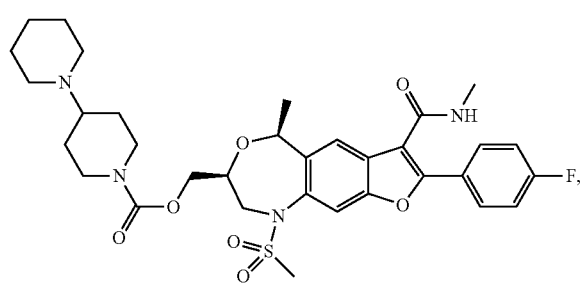
B282
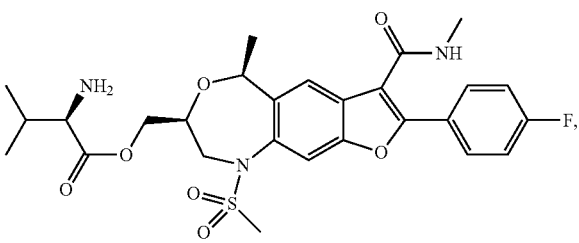
B277
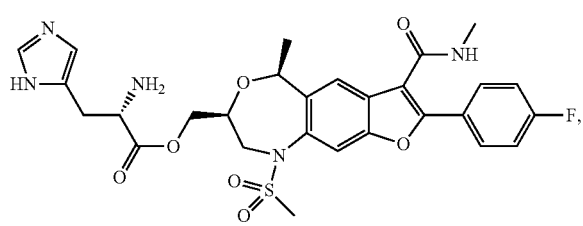
B283
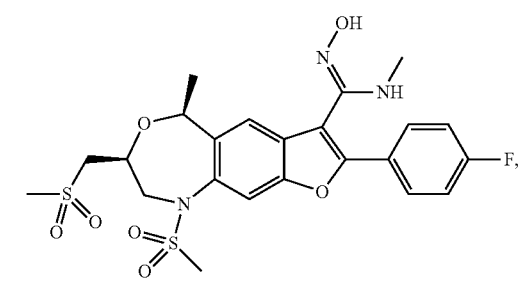
B278
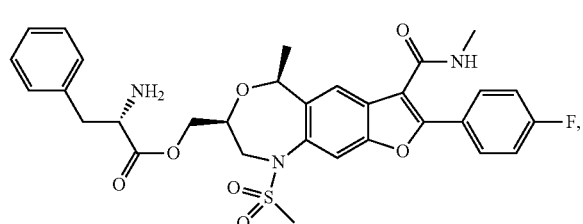
B284
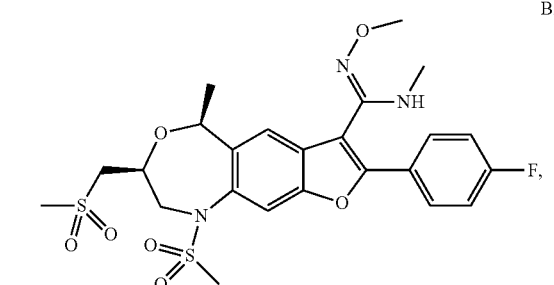
B279
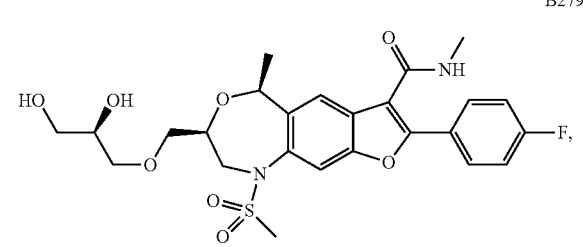
B285
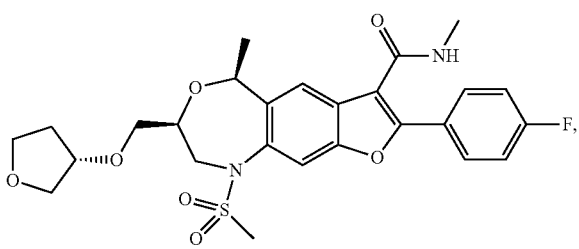

779
-continued
B286
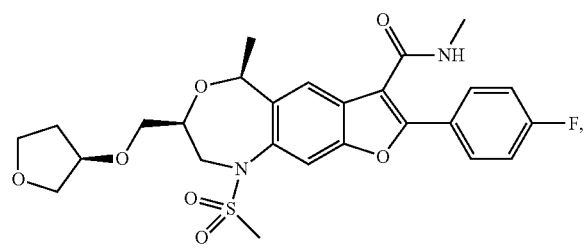
B287
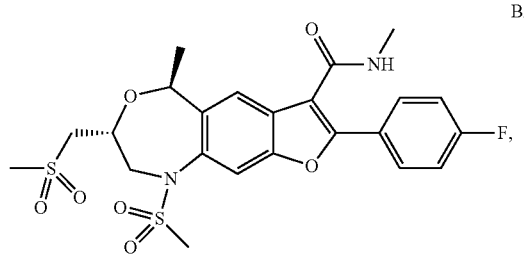
B288
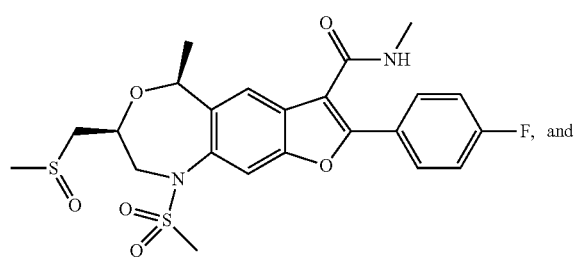
B289
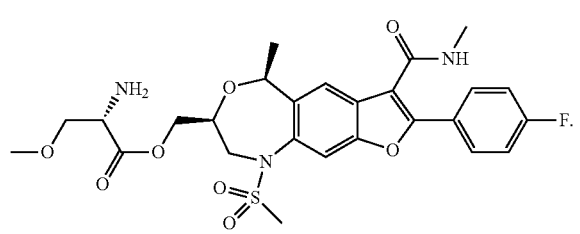
2. The compound of claim 1 having the structure:
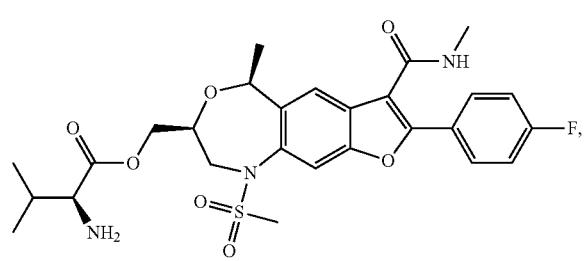
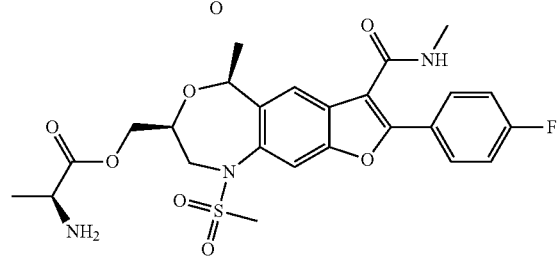
780
-continued
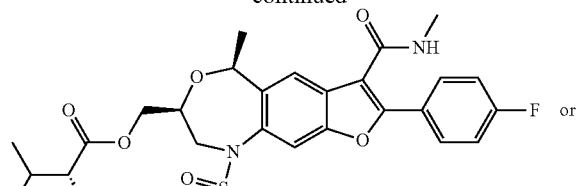
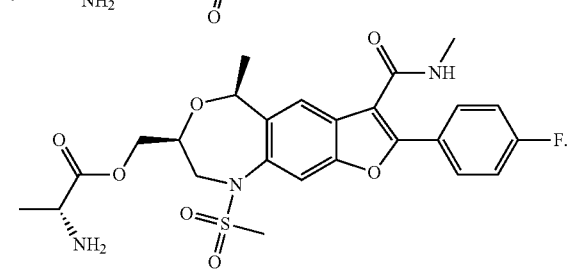
3. A pharmaceutical composition comprising a compound of claim 1 together with one or more pharmaceutically acceptable excipients or vehicles, and optionally other therapeutic and/or prophylactic ingredients.
4. A pharmaceutical compound of claim 3, wherein the compound is
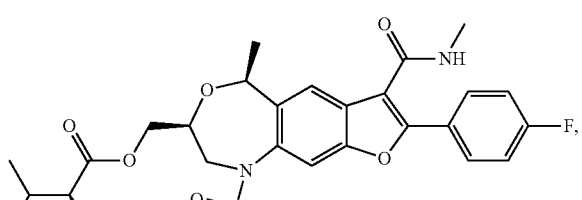
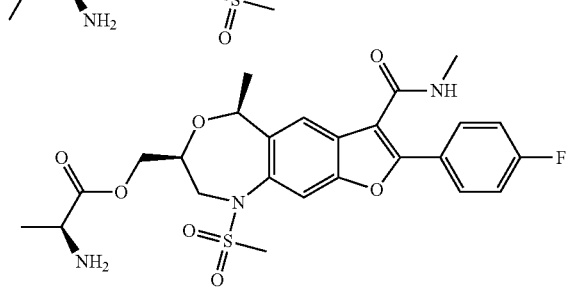
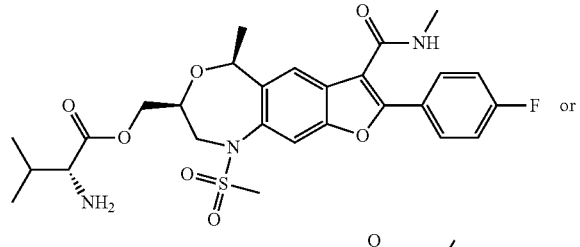
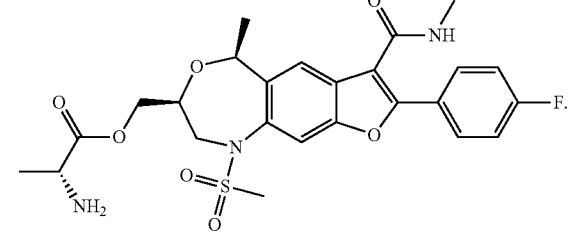

5. A method of treating HCV infection in a subject comprising administering to the subject, a pharmaceutically acceptable dose of the compound of claim 1, and continuing the administering until a selected reduction in the subject's HCV titer is achieved.

6. The method of claim 5, wherein the administering is by oral administration.

7. The method of claim 5 wherein the compound is

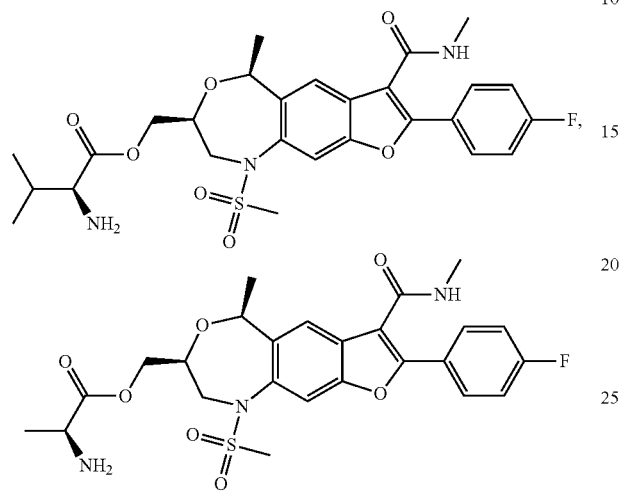

-continued

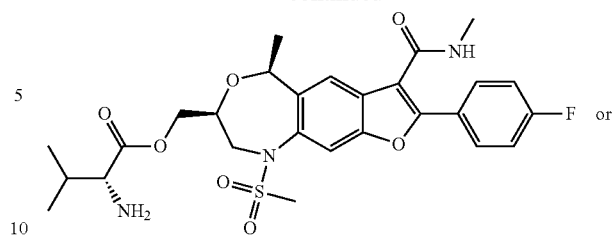

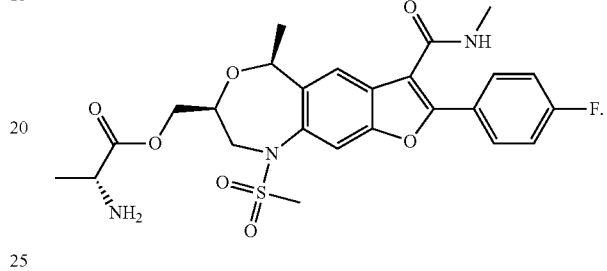

8. The method of claim 7, wherein the administering is by oral administration.

* * * * *